United States Patent [19]

Attardo et al.

[11] Patent Number: 5,593,970
[45] Date of Patent: Jan. 14, 1997

[54] HETEROCYCLIC ANTHRACYCLINE ANALOGS

[75] Inventors: Giorgio Attardo, Laval, Canada; Jean-Louis Kraus, Marseilles, France; Marc Courchesne, Laval-des-Rapides, Canada; Serge Lamonthe, Boisbriand, Canada; Jean-François Lavallée, Laval, Canada; Elaine Lebeau, Kamloops, Canada; Dieu Nguyen, Chomedey, Canada; Rabindra Rej; Yves St-Denis, both of Montreal, Canada; Wuyi Wang, St-Laurent, Canada; Yao-Chang Xu, Indianapolis, Ind.; France Barbeau, Ste-Thérèse; Bernard Belleau, deceased, late of Westmount, both of Canada, by Pierette Belleau, executrix

[73] Assignee: Biochem Pharma Inc., Laval, Canada

[21] Appl. No.: 263,925

[22] Filed: Jun. 20, 1994

Related U.S. Application Data

[63] Continuation-in-part of Ser. No. 2,766, Jan. 13, 1993, abandoned, which is a continuation-in-part of Ser. No. 859,244, Mar. 26, 1992, abandoned, which is a continuation-in-part of Ser. No. 536,107, Jun. 11, 1990, abandoned.

[51] Int. Cl.$^6$ .......................... C07M 15/24; A61K 31/70
[52] U.S. Cl. ........................ 514/34; 536/6.4; 536/18.1; 514/25
[58] Field of Search .................... 536/6.4, 18.1; 549/24, 208; 546/77; 514/25, 34, 80, 96, 300

[56] References Cited

U.S. PATENT DOCUMENTS

| | | | |
|---|---|---|---|
| 4,259,776 | 3/1981 | Kende et al. | 536/18.1 |
| 4,585,760 | 4/1986 | Lee . | |
| 5,348,946 | 9/1994 | Attardo et al. | 514/34 |

FOREIGN PATENT DOCUMENTS

| | | |
|---|---|---|
| 0251361 | 1/1988 | European Pat. Off. . |
| 2067552 | 7/1981 | United Kingdom . |

OTHER PUBLICATIONS

Koch et al, *Heterocycles*, 26 (2), pp. 341–345 (1927).
Koch et al, *Heterocycles*, 26 (4), pp. 879–882 (1987).
Bycroft, B. W. "Dictionary of antibiotics . . . " 1988, Chapman & Hall (London, GB), p. 76, A–00427, Antibiotica DC44A.
Mitscher, L. A. "Total chemical synthesis . . . " J. Med. Chem., vol. 29 (1986), Amer Chem Soc (US), pp. 1277–1281.
Chemical Abstracts #24828t, vol. 94 No. 2 (2 Feb. 1981), Goldstein et al. "The blockade of alpha 2– . . . ", pp. 305–308.
Chemical Abstracts #186527d, vol. 108 No. 21 (23 May 1988) Kubo et al "A facile synthesis of . . . " pp. 824–827.
Chemical Abstracts #38804f, vol. 97 No. 5 (2 Aug. 1982), Retamal et al "Studies on quinones. IX . . . ", pp. 279–285.
Giles et al "An investigation into the formation of Benzo–and . . . " J. Chem J. Chem Soc (1984) p. 2390.
Chemical Abstracts #88435, vol. 104 No. 11 (17 Mar. 1986), p. 647.
Chemical Abstracts #177028x, vol. 112 No. 19 (7 May 1990), pp. 592–593.
Chemical Abstracts #180684y, vol. 94 No. 22 (1 Jun. 1981), pp. 380–381.
Dufat–Trinh Van, "Total synthesis of 7–hydroxy–'9–oxa . . . " Heterocycles, vol. 26 No. 4, 1987, pp. 879–882.

*Primary Examiner*—Elli Peselev
*Attorney, Agent, or Firm*—Nixon & Vanderhye

[57] ABSTRACT

Novel pyrano heterocyclic anthracycline derivatives are described, which are useful in the treatment of cancer and tumors, such as breast cancer, leukemia, lung cancer, colon cancer, ovarian cancer, renal cancer, and melanoma. As well, these compounds may be used ex vivo for the treatment of cancerous bone marrow before retransplanting said marrow in a patient. Pharmaceutical compositions and methods of preparing the compounds are also described.

34 Claims, No Drawings

HETEROCYCLIC ANTHRACYCLINE ANALOGS

This application is a continuation-in-part of application Ser. No. 08/002,766, filed Jan. 13, 1993, now abandoned, which is a continuation-in-part of application Ser. No. 07/859,244 filed Mar. 26, 1992, now abandoned, which is a continuation-in-part of application Ser. No. 07/536,107 filed Jun. 11, 1990, now abandoned.

This invention relates to improved anthracycline derivatives, to processes and to intermediates for preparing the derivatives, to pharmaceutical compositions containing them and to the use of these derivatives as antitumor agents in mammals. More specifically, the present invention relates to 8-heteroanthracycline derivatives.

BACKGROUND OF THE INVENTION

Anthracycline antibiotics including doxorubicin and daunorubicin are important chemotherapeutic agents in the treatment of a broad spectrum of neoplastic conditions. While daunorubicin (1) is clinically used mainly against acute childhood and adult leukemias, doxorubicin (2), also known as adriamycin, has the widest spectrum of antitumor activity of all chemotherapeutic agents (Weiss, R. B., Sarosy, G., Clagett-Carr, K., Russo, M. and Leyland-Jones, B., Cancer Chemother. Pharmacol., 18, 185–197, 1986; Arcamone, F., Doxorubicin, Academic Press, New York, 1980).

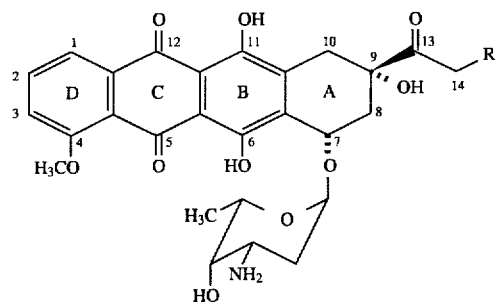

(1) daunorubicin R = H
(2) doxorubicin R = OH

The usefulness of known anthracycline antibiotics is compromised by dose limiting toxicities such as myelosuppression (Crooke, S. K., Anthracyclines; Current Status and New Developments, Academic Press, New York 1980) and cardiotoxicity (Olson, R. D. et al, Proc. Natl. Acad. Sci., USA 85 3585–3589, 1988 and references therein) as well as the resistance from treated tumors (Mimnaugh, E. G. et al, Cancer Research, 49, 8–15, 1989; McGrath, T. et al, Biochemical Pharmacology, 38 497–501, 1989). In view of the proven effectiveness of known anthracyclines in the treatment of cancer, efforts have been undertaken to develop anthracycline analogs with either an improved therapeutic index or with reduced cross-resistance.

Several thousands of anthracycline derivatives have been obtained either from streptomyces biosynthesis or via the semisynthetic modification of known natural anthracycline antibiotics (Arcamone, F., Doxorubicin, Academic Press, New York 1980; Thomson, R. H., Naturally Occurring Quinones III: Recent Advances, Chapman and Hall, New York 1987; Anthracyclines: Current Status and New Developments, Academic Press, New York, 1980; Brown, J. R. and Iman, S. H., Recent Studies on Doxorubicin and its Analogues, Prog. Med. Chem. 21 170–236, 1984; Brown, J. R. Adriamycin and Related Anthracycline Antibiotics, Prog. Med. Chem., 15, 125–164, 1978). The majority of known anthracyclines show two types of structural differences: (i) the substitution pattern of the aglycone tetracyclic ring system, and (ii) the structure and number of glycosides attached at C-7 or C-10 (doxorubicin numbering). Some examples of the structural diversity of anthracycline antibiotics are shown in FIG. 1.

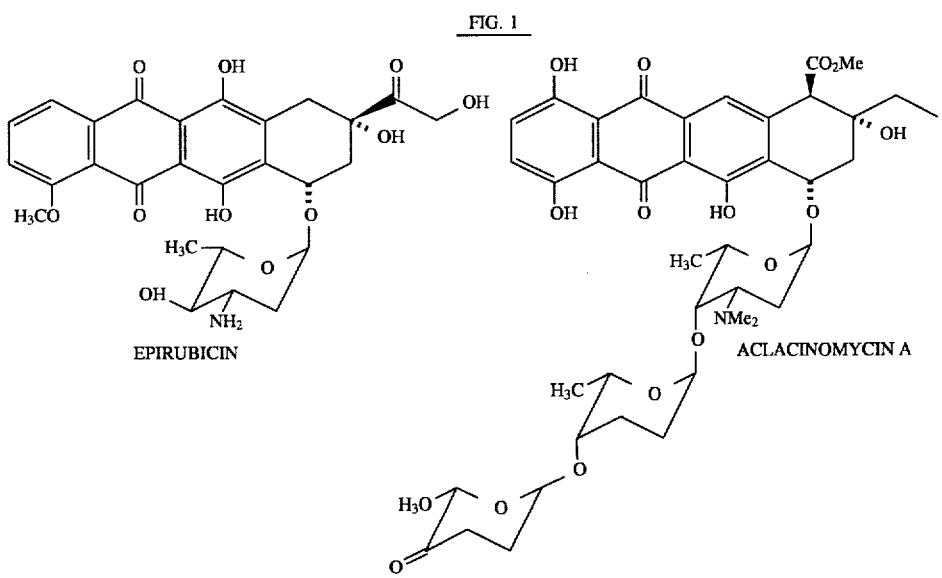

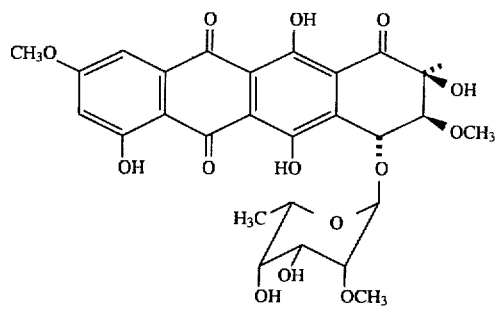

STEFFIMYCIN B

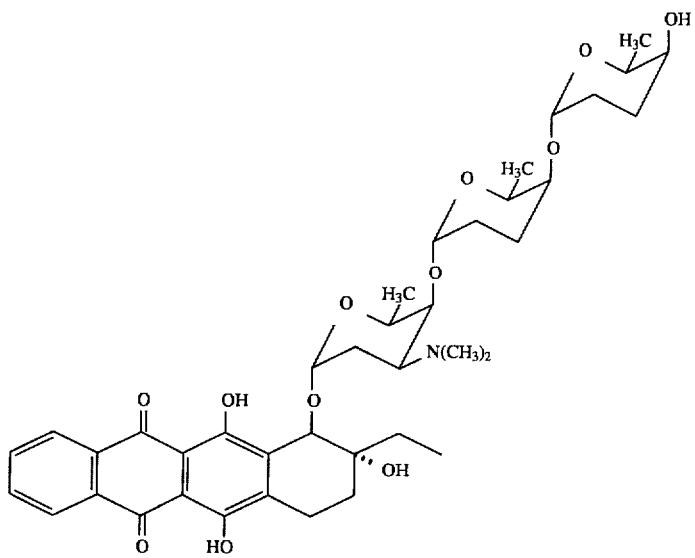

COSMOMYCIN A

In contrast to the great number of derivatives obtained from these two kinds of structural modifications, there has been little effort towards the synthesis and biological evaluation of ring-A heteroanthracycline derivatives. Some 9-oxa-heteroanthracyclines (3–5) were prepared by Koch et al but antitumor activity was not significant (Heterocycles, 26(2), 341–5, 1987; Heterocycles 26(4), 879–82, 1987). Mitsher et al found that N-(trifluoroacetyl)-4-demethoxy-9-azadaunorubicin (6) had no antitumor activity (J. Med. Chem., 29(7), 1277–81, 1986).

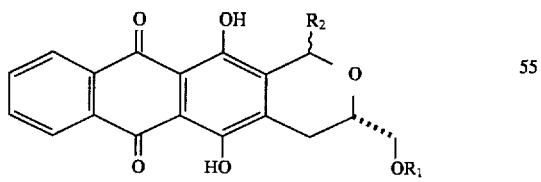

-continued

3  $R_1 = H; R_2 = H, CH_3$
4  $R_1 = sugar; R_2 = H, CH_3$

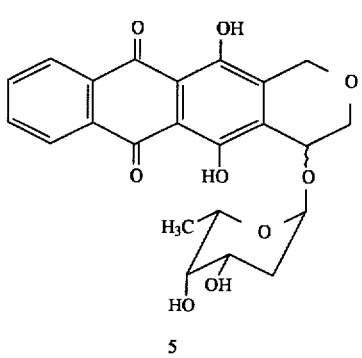

5

5
-continued

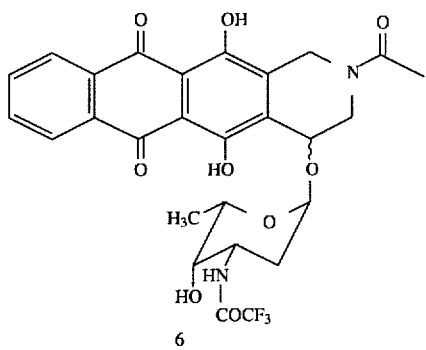

6

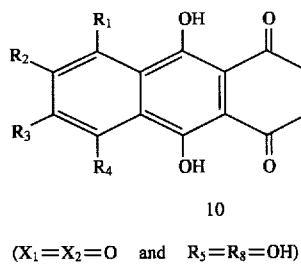

Pyranonaphthoquinones such as nanaomycin A (7) and kalafungin (8) occur naturally and show potent antibacterial as well as antifungal activity (Moore, H. W. and Czerniak, R., Medicinal Research Reviews, 1(3), 249–280, 1981 and references therein). Granaticin (9) has been reported to show antitumor activity (Chang, C. J., Floss, H. G., Soong, P. and Chang, C. T., J. Antibiot., 28, 156, 1975).

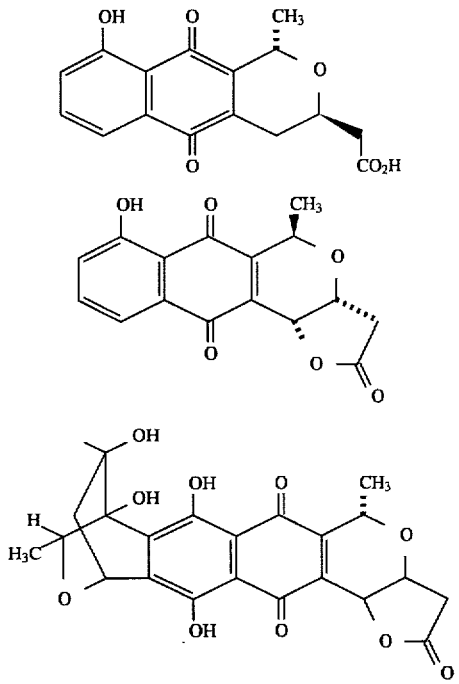

7

8

9

SUMMARY OF THE INVENTION

Therefore, the invention provides a compound of formula (10):

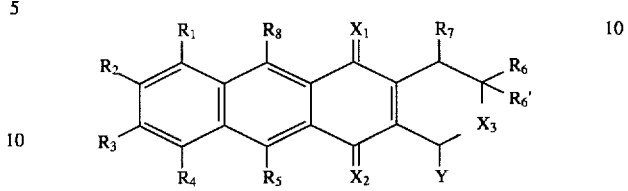

10 wherein $X_1$ and $X_2$ are independently O; S; or substituted or unsubstituted amino.

$X_3$ is selected from the group consisting of: O; S; SO; $SO_2$; and substituted or unsubstituted amino.

$R_1$, $R_2$, $R_3$, $R_4$, $R_5$, & $R_8$ are each independently selected from the group consisting of: hydrogen; hydroxy; $C_{1-16}$ alkyl; $C_{1-16}$ acyl; halogen; silane; sulfonate; ureido; and unsubstituted or substituted amino.

$R_6$ is hydrogen; $C_{1-16}$ alkyl or alkoxy, $C_{1-16}$ acyl or acyloxy, $C_{7-20}$ aryl or aryloxy; squaric acid and salts thereof; phosphonate; or a 5 or 6 membered heterocycle.

$R_6'$ is hydrogen; halogen; $C_{1-16}$ alkyl or alkoxy; substituted or unsubstituted amino; hydroxy; thiol; cyano; sulfide; and $C_{1-16}$ acyl or acyloxy.

Y and $R_7$ are independently selected from the group consisting of: hydrogen; halogen; hydroxy; $C_{1-16}$ alkyl; cyano; amino; $C_{1-16}$ acyl or acyloxy; and a saccharide.

It will be appreciated by those skilled in the art that when $R_5=R_8=$hydroxy and $X_1=X_2=$O, that compounds of formula (10) exist in the form of the thermodynamically favored tautomers of formula (11). Therefore, compounds of formula (11) are included within the scope of the invention.

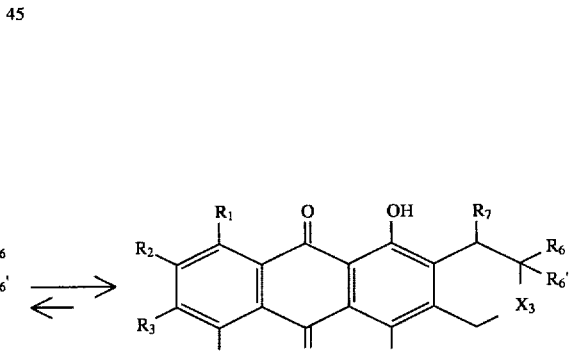

10     11

($X_1=X_2=$O  and  $R_5=R_8=$OH)

This invention also includes all the possible isomers and mixtures thereof, including diastereoisomeric mixtures and racemic mixtures, resulting from the possible combination of R or S stereochemical centers, when pertinent, at C-7, C-9 and C-10 as well as in all the chiral centers present in the sugar moiety.

The term "alkyl" as employed herein includes both straight and branched chain radicals of up to 16 carbons, for example methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl; a cycloalkyl group having 3 to 8 carbons, for example cyclopropyl, cyclobutyl, cyclopentyl, cyclohexyl, cyclopentylmethyl, cyclohexylmethyl, cyclohexylethyl, cycloheptyl and cyclooctyl, or substituted with halogen such as F, Cl, Br, I or $CF_3$, or an alkoxy or hydroxyl, an aryl substituent, an alkyl-aryl substituent, a haloaryl substituent, a cycloalkyl substituent, the various branched chain isomers thereof. As well the term "alkyl" includes carbon chains interrupted by one or more heteroatom such as oxygen to form an alkoxy, sulfur such as S, SO, or $SO_2$, amino to form an alkylamine, etc..

The term "acyl" as employed herein refers to a alkyl as defined above linked to a substituent through a carbonyl group.

The term "aryl" as employed herein refers to monocyclic or bicyclic aromatic groups containing from 6 to 10 carbons in the ring portion, such as phenyl, naphthyl, substituted phenyl or substituted naphthyl, wherein the substituent on either the phenyl or naphthyl may be for example $C_{1-4}$ alkyl such as aralkyl, halogen, $C_{1-4}$ alkoxy such as aralkoxy, carboxy such as aroyl, or nitro. The term also include heterocycle containing one or more heteroatom such as oxygen, sulfur, or amino.

The term "substituted amino" refers to an amino group mono- or disubstituted by alkyl groups, acyl groups, aryl groups, or other amino groups.

The term "halogen" as used herein means chlorine, bromine, fluorine or iodine.

The term "saccharide" means a 5 or 6 sugar ring of natural or unnatural configuration linked to the heteroanthracycline through an carbon chain such as an alkyl, or through a heteroatom such as oxygen sulfur, or amino.

DETAILED DESCRIPTION OF THE INVENTION

The present invention provides heteroanthracyclines which are structurally distinguished from the prior art compounds by the nature of ring A of the anthracyclinone moiety. More specifically, the compounds of the present invention are structurally distinguished from the prior art compounds by having an hetero atom at position 8 of the ring A of the anthracyclinone. This structurally distinct class of compounds exhibits therapeutic activity, in particular anticancer and antitumor activity, are active against some adriamycin-resistant tumor cells, and also may potentially display less myelosupression.

In one aspect of the invention, there is provided a compound of the formula (10):

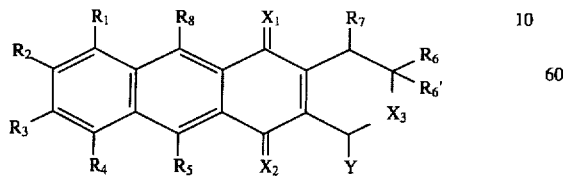

wherein, preferably, $X_1$ and $X_2$ are independently selected from the group consisting of:

O, S, and $N(R_{20})$, wherein $R_{20}$ is selected from the group consisting of:
hydrogen; hydroxyl; $C_{1-16}$ alkyl; $C_{1-16}$ acyl; and $C_{1-16}$ alkylamine.

$X_3$ is selected from the group consisting of O; S; SO; $SO_2$; and
$NR_{21}$, wherein $R_{21}$ is selected from the group consisting of hydroxyl, $C_{2-16}$ acyl, $C_{1-16}$ alkyl, $C_{7-16}$ aryl, $C_{2-16}$ haloacyl, and hydrogen.

$R_1$, $R_2$, $R_3$, $R_4$, $R_5$ and $R_8$ are independently selected from the group consisting of hydrogen; hydroxyl; $C_{1-16}$ alkyl; $C_{1-16}$ alkoxyl; $C_{3-8}$ cycloalkyl; $C_{3-16}$ alkyl silane; tosyl; triflate; trifluoroacetate; halogen; thiol; nitro; cyano; $C_{2-16}$ acyl; $C_{7-16}$ arylacyl; $C_{3-16}$ alkoxy silane; amino; aminoalkylhalide of formula $NH(CH_2)_{1-4} NH(CH_2)_{1-4}$ OH; aminoalkylaminoalkylhalide of formula $NH(CH_2)_{1-4} NH(CH_2)_{1-4}$ X where X is a halogen;

amino which may be unsubstituted or mono- or di-substituted by $C_{1-8}$ alkyl, $C_{3-8}$ cycloalkyl, $C_{1-16}$ acyl, $C_{1-16}$ trifluoroacyl, $C_{7-16}$ aralkyl or $C_{7-4}$ aryl, $C_{2-8}$ alkenyl, $C_{2-8}$ alkynyl;

haloalkylnitrosoureido of the formula $NH(CO)N(NO)(CH_2)_{0-4} CH_2X$, wherein X is a halogen; and a group of the formula $-O-C(R_{22})=O$ wherein $R_{22}$ is selected from the group consisting of hydrogen, $C_{1-16}$ alkyl, $C_{3-8}$ cycloalkyl, $C_{2-16}$ alkoxyalkyl, $C_{7-16}$ aralkyl, $C_{8-16}$ araloxyalkyl, $C_{8-16}$ aryloxyalkyl and $C_{6-14}$ aryl.

$R_6$ is selected from the group consisting of cyano; hydrogen. acetoxy; $C_{6-14}$ aryl; $C_{2-8}$ alkenyl; $C_{2-8}$ alkynyl; $C_{1-16}$ hydroxyalkyl; phenyl; phenylsulfone; $C_{6-14}$ aryl sulfone; methylsulfone; $C_{1-16}$ alkyl; $C_{1-16}$ dihydroxyalkyl; $C_{3-8}$ cycloalkyl; squaric acid; $C_{1-16}$ alkyl squarate; dimethylphosphonate; acyl of the formula $-C(R_{23})=O$, or its dioxolane or dioxane ketal wherein $R_{23}$ is selected from the group consisting of hydrogen, $C_{1-16}$ alkyl, thiomethyl, $C_{3-8}$ cycloalkyl, fluoromethyl, difluoromethyl, $C_{1-16}$ hydroxyalkyl, squaric acid, $C_{1-4}$ alkyl squarate, $C_{2-16}$ alkoxyalkyl, $C_{8-16}$ araloxyalkyl, $C_{3-6}$ acyloxyalkyl, $C_{3-16}$ acetoxymethyl, bromomethyl, amino which may be unsubstituted or mono-or di-substituted by $C_{1-8}$ alkyl, $C_{3-8}$ cycloalkyl, $C_{2-8}$ acyl, $C_{2-8}$ trifluoroacyl, $C_{7-16}$ aralkyl or $C_{7-16}$ aryl, and an amino acid selected from the group consisting of alanine, arginine, asparagine, aspartic acid, cysteine, glutamine, glutamic acid, glycine, histidine, isoleucine, leucine, lysine, methionine ornithine, phenylalanine, proline, serine, threonine, tryptophan, tyrosine, and valine.

$R_6$ may also be a group of the formula $-C(R_{23})(OC_{1-5}$ alkyl$)_2$ where $R_{23}$ is as defined above;

a group of the formula $-C(OR_{24})=O$, wherein $R_{24}$ is selected from the group consisting of hydrogen, $C_{1-16}$ alkyl, $C_{3-8}$ cycloalkyl, $C_{1-16}$ hydroxyalkyl, $C_{2-16}$ alkoxyalkyl, $C_{7-16}$ aryloxyalkyl, $C_{8-16}$ araloxyalkyl, $C_{6-14}$ aryl, and $C_{7-16}$ aralkyl.

$R_6$ may also be a group of the formula $-CR_{25}R_{26}C(R_{27})=O$, wherein $R_{25}$ and $R_{26}$ are independently selected from the group consisting of hydrogen, fluorine, chlorine, and bromine, and wherein $R_{27}$ is selected from the group consisting of hydrogen, hydroxy, $C_{1-16}$ alkyl, $C_{1-8}$ alkoxy, $C_{3-8}$ cycloalkyl, $C_{1-16}$ hydroxyalkyl, $C_{2-16}$ alkoxyalkyl, $C_{7-16}$ aryloxyalkyl, $C_{8-16}$ araloxyalkyl, $C_{6-14}$ aryl, $C_{7-16}$ aralkyl, and amino which may be unsubstituted, mono- or di-substituted by $C_{1-8}$ alkyl, $C_{3-8}$ cycloalkyl, $C_{2-8}$ acyl, $C_{1-16}$ trifluoroacyl, $C_{7-16}$ aralkyl or $C_{6-16}$ aryl.

$R_6$ may also be a 5 or 6 membered aromatic or non aromatic heterocycle containing one or more heteroatoms selected from the group consisting of O, S, N, SO, $SO_2$, P, PO, and $NR_{28}$ wherein $R_{28}$ is selected from the group consisting of hydrogen, oxygen, hydroxyl, $C_{2-8}$ acyl, $C_{1-4}$ alkyl,, and $C_{6-41}$ aryl;

said heterocycle being optionally substituted with one or more halogens, hydroxy, $C_{-16}$ alkoxy, nitro, $C_{1-16}$ alkyl, $C_{1-6}$ hydroxyalkyl, amino which may be unsubstituted or mono- or disubstituted by $C_{1-8}$ alkyl, $C_{3-8}$ cycloalkyl, $C_{2-8}$ acyl, $C_{2-8}$ trifluoroacyl, $C_{7-16}$ aralkyl, $C_{6-14}$ aryl, $C_{2-8}$ alkenyl, $C_{2-8}$ alkynyl, and hydroxy.

$R_6'$ is selected from the group consisting of hydrogen; $C_{1-6}$ alkyl; halogen; amino; hydroxy; $C_{1-16}$ alkoxy; thiol; cyano; sulfide; acyl of the formula —$C(R_{29})=O$, wherein $R_{29}$ is selected from the group consisting of: hydrogen, $C_{1-16}$ alkyl, $C_{3-8}$ cycloalkyl, $C_{1-16}$ hydroxyalkyl, $C_{2-16}$ araloxyalkyl, $C_{2-16}$ alkoxyalkyl, $C_{3-16}$ acyloxyalkyl, squaric acid, $C_{5-10}$ alkyl squarate, amino which may be unsubstituted or mono- or di-substituted by $C_{1-8}$ alkyl, $C_{3-8}$ cycloalkyl, $C_{2-8}$ acyl, cyano, trifluoroacyl, $C_{7-16}$ aralkyl or $C_{6-14}$ aryl, and an amino acid as defined in $R_6$.

$R_6'$ may also be a group of the formula —$C(OR_{30})=O$, wherein $R_{30}$ is selected from the group consisting of hydrogen, $C_{1-16}$ alkyl, $C_{3-8}$ cycloalkyl, $C_{1-16}$ hydroxyalkyl, $C_{2-16}$ alkoxyalkyl, $C_{7-16}$ aryloxyalkyl, $C_{8-16}$ araloxyalkyl, $C_{6-14}$ aryl, $C_{7-16}$ aralkyl; and $C_{2-16}$ alkenyl.

Y and $R_7$ are independently selected from the group consisting of hydrogen; halogen; hydroxyl; $C_{2-16}$ trihydroxyalkyl; $C_{1-16}$ dihydroxyalkyl; $C_{1-16}$ alkoxyl; $C_{1-16}$ alkyl; $C_{2-16}$ alkoxyamino; $C_{2-16}$ acetylenyl; $C_{3-8}$ cycloalkyl; $C_{2-16}$ alkenyl; cyano; amino which may be unsubstituted or mono- or di-substituted by $C_{1-8}$ alkyl, $C_{3-8}$ cycloalkyl, $C_{2-8}$ acyl, cyano, trifluoroacyl, $C_{7-16}$ aralkyl, $C_{6-14}$ aryl, and an amino acid as defined in $R_6$.

Y and $R_7$ may also be a group of the formula —O—$C(R_{31})=O$, wherein $R_{31}$ is selected from the group consisting of hydrogen, $C_{1-16}$ alkyl, $C_{3-8}$ cycloalkyl, $C_{2-16}$ alkoxyalkyl, and $C_{6-14}$ aryl.

Y and $R_7$ may also be an acyl of the formula —$C(R_{32})=O$, wherein $R_{32}$ is selected from the group consisting of hydrogen, thiol, $C_{1-16}$ thioalkyl, $C_{1-16}$ alkyl, $C_{3-8}$ cycloalkyl, $C_{1-16}$ hydroxyalkyl, $C_{2-16}$ alkoxyalkyl, $C_{8-16}$ araloxyalkyl, and $C_{3-16}$ acyloxyalkyl.

Y and $R_7$ may also be a group of the formula —$C(OR_{33})=O$, wherein $R_{33}$ is selected from the group consisting of hydrogen, $C_{1-16}$ alkyl, and $C_{3-8}$ cycloalkyl.

Y and $R_7$ may also be a saccharide of the formula:

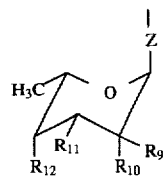

wherein

Z is selected from O; S; SO; $SO_2$; $C_{1-6}$ alkyl; or amino unsubstituted or monosubstituted with $C_{1-16}$ alkyl or acyl.

$R_9$ and $R_{10}$ are independently selected from the group consisting of hydrogen; halogen; hydroxyl; acetoxy; $C_{1-6}$ alkoxy; $C_{1-16}$ alkyl; $C_{3-8}$ cycloalkyl; thiol; amino; cyano; trifluoroacetamido; chloroethylnitrosoureido; chloroethylureido; ethylnitrosoureido; and ethylureido.

$R_{11}$ is amino, which may be unsubstituted or mono or di-substituted by $C_{1-8}$ acetoxy, $C_{1-8}$ alkyl, $C_{3-8}$ cycloalkyl, $C_{2-8}$ acyl, t-butylacyl, t-butyloxycarbonyl, trifluoroacyl, $C_{7-16}$ aralkyl or $C_{6-16}$ aryl and an amino acid as defined in $R_6$.

$R_{11}$ may also be selected from the group consisting of mono or dibenzylated amino; $C_{2-8}$ acylated amino; trifluoroacylated amino; morpholino; cyano-substituted morpholino; mono-, di-, tri- or tetra-methoxy-substituted morpholino; mono-, di, tri- or tetra-acetoxy-substituted morpholino; hydroxyl; hydrogen; halogen; acetoxy; $C_{1-16}$ alkoxyl; $C_{3-8}$ cycloalkyl; thiol; and sulfide.

$R_{11}$ may also be a group of the formula $NH(CH_2)_{0-5}CH(OR_{34})_2$, wherein $R_{34}$ is independently selected from the group consisting of a $C_{1-16}$ alkyl, $C_{1-16}$ acyl or $C_{7-16}$ aroyl.

$R_{11}$ may also be $NH(CH_2)_2OCH_2CH(OAc)_2$; or a chloroalkylnitrosoureido of the formula $NH(CO)N(NO)(CH_2)_{0-4}CH_2Cl$.

$R_{12}$ is selected from the group consisting of hydrogen; hydroxyl or its tetrahydropropyl ether (—OTHP); halogen; mono, bi, or tri-saccharide; amino; $C_{1-16}$ mono or dialkylated amino; trifluoroacetamido; $C_{1-16}$ alkoxy; $C_{3-8}$ cycloalkyl; benzoate which may be unsubstituted or substituted with nitro; acetoxy; trifluoroacetoxy; $NH(CH_2)_2OCH_2CH(OAC)_2$; and a chloroalkylnitrosoureido of the formula $NH(CO)N(NO)(CH_2)_{0-4}CH_2Cl$.

Still, preferably, the invention further seeks to provide a compound of formula (10) wherein $X_1$, and $X_2$ are independently O; and NH.

$X_3$ is selected from the group consisting of O; S; SO; $SO_2$; NH; and NOH.

$R_1, R_2, R_3, R_4, R_5$ and $R_8$ are independently selected from the group consisting of: hydrogen; hydroxyl; $C_{1-4}$ alkoxyl; tosyl; triflate; fluorine; chlorine; $C_{3-9}$ alkoxy silane; amino; aminoalkylaminoalcohol of formula $NH(CH_2)_{1-3}$ $NH(CH_2)_{1-3}$ OH; aminoalkylaminoalkylchloride of formula NH $(CH_2)_{1-3}$ NH $(CH_2)_{1-3}$ Cl; chloroalkylnitrosoureido of the formula $NH(CO)N(NO)$ $(CH_2)_{0-4}$ $CH_2$ Cl,; and a group of the formula —O—$C(R_{22})=O$, wherein $R_{22}$ is selected from the group consisting of hydrogen, $C_{1-6}$ alkyl, and $C_{6-10}$ aryl.

$R_6$ is preferably selected from the group consisting of hydrogen; cyano; acetoxy; phenylsulfone; $C_{1-8}$ hydroxyalkyl, $C_{1-8}$ dihydroxyalkyl; squaric acid; $C_{1-16}$ alkyl squarate; $C_{1-4}$ alkyl; acyl of the formula —$C(R_{23})=O$, wherein $R_{23}$ is selected from the group consisting of hydrogen, $C_{1-8}$ alkyl, $C_{1-8}$ hydroxyalkyl, squaric acid, $C_{1-4}$ alkyl squarate, $C_{2-8}$ alkoxyalkyl, $C_{3-8}$ acyloxyalkyl, bromomethyl, $C_{3-8}$ acetoxymethyl, and amino which may be unsubstituted or mono-or di-substituted with $C_{1-8}$ alkyl, $C_{3-8}$ cycloalkyl, $C_{2-8}$ acyl, trifluoroacyl, $C_{7-16}$ aralkyl or $C_{7-16}$ aryl.

$R_6$ may also be preferably a group of the formula —$C(OR_{24})=O$, wherein $R_{24}$ is selected from the group consisting of hydrogen, $C_{1-8}$ alkyl, $C_{6-14}$ aryl, $C_{7-16}$ aralkyl.

$R_6$ may further be preferably a group of the formula —$CH_2C(R_{27})$=O, wherein $R_{27}$ is selected from the group consisting of hydrogen, hydroxy, straight or branched $C_{1-8}$ alkyl, $C_{1-8}$ alkoxy, or amino which may be unsubstituted or mono- or di-substituted with $C_{1-8}$ alkyl, $C_{3-8}$ cycloalkyl, $C_{2-8}$ acyl, $C_{1-8}$ trifluoroacyl, $C_{7-16}$ aralkyl or $C_{7-14}$ aryl.

Furthermore, $R_6$ may be preferably a 5 or 6 membered aromatic or non-aromatic heterocycle containing one or more heteroatoms selected from the group consisting of O, S, N, and NH; said heterocycle being optionally substituted with one or more halogen, hydroxy, $C_{1-8}$ alkoxy, $C_{1-8}$ alkyl, $C_{1-8}$ hydroxyalkyl, amino which may be unsubstituted or mono- or disubstituted by $C_{1-4}$ alkyl, $C_{3-5}$ cycloalkyl, acyl, trifluoroacyl, $C_{6-14}$ aryl, and hydroxy. Preferably, $R_6'$ is selected from the group consisting of hydrogen, fluorine, $C_{1-4}$ alkyl, $C_{1-4}$ alkoxy, cyano, acyl of the formula —$C(R_{29})$=O, wherein $R_{29}$ is selected from the group consisting of hydrogen, $C_{1-8}$ alkyl, $C_{1-8}$ hydroxyalkyl, $C_{3-8}$ acylcoxyalkyl, and amino.

$R_6'$ may also be preferably a group of the formula —$C(OR_{30})$=O, wherein $R_{30}$ is selected from the group consisting of hydrogen, $C_{1-8}$ alkyl, $C_{6-10}$ aryl, and $C_{1-8}$ alkenyl. Preferably, Y and $R_7$ are independently selected from the group consisting of hydrogen; halogen; hydroxyl; $C_{1-8}$ alkoxy; $C_{2-8}$ acetylenyl; $C_{2-8}$ alkenyl; cyano; a group of the formula —O—$C(R_{31})$=O, wherein $R_{31}$ is selected from the group consisting of hydrogen, and $C_{1-8}$ alkyl.

An acyl of the formula —$C(R_{32})$=O, wherein $R_{32}$ is selected from the group consisting of hydrogen, thiol, $C_{1-8}$ alkyl, hydroxyalkyl, and amino.

A group of the formula —$C(OR_{33})$=O, wherein $R_{33}$ is selected from the group consisting of hydrogen, $C_{1-8}$ alkyl, and a saccharide of formula:

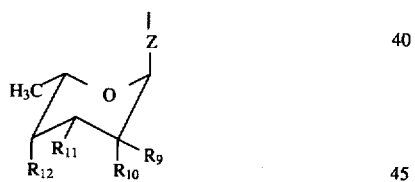

wherein, preferably,

Z is O; or $C_{1-6}$ alkyl;.

$R_9$ and $R_{10}$ are independently selected from the group consisting of hydrogen; iodine; fluorine; chlorine; hydroxyl; amino; trifluoroacetamido; chloroethylnitrosoureido; and chloroethylureido.

$R_{11}$ is preferably selected from the group consisting of amino which may be unsubstituted or mono- or di-substituted with $C_{1-8}$ acetoxy, $C_{1-8}$ alkyl, $C_{3-8}$ cycloalkyl, $C_{2-8}$ acyl, trifluoroacyl, $C_{7-11}$ aralkyl or $C_{7-11}$ aryl; morpholino; cyano-substituted morpholino; mono-, di-, tri-, or tetra-methoxy-substituted morpholino; hydroxyl; $C_{1-16}$ mono or dialkylated amino; azido; iodine; acetoxy; fluorine; and $C_{1-8}$ alkoxyl.

$R_{11}$ is also preferably a group of the formula NH$(CH_2)_{1-5}$CH$(OR)_2$ wherein R is independently selected from a group consisting of $C_{1-8}$ alkyl, $C_{2-8}$ acyl, and $C_{7-12}$ aroyl; NH$_2(CH_2)_2OCH_2CH(OAc)_2$; and chloroalkylnitrosoureido of the formula NH(CO)N(NO) $(CH_2)_{0-4}$CH$_2$Cl.

$R_{12}$ is preferably selected from the group consisting of hydrogen; hydroxyl or its tetrahydropyranyl ether; thiol; halogen; mono-, bi-, or tri-saccharide selected from the group consisting of rhodosamine, cinerulose-B, L-cinerulose, D-cinerulose, cinerulose A, amicetose, aculose, rednose, rhodinose, 2-deoxyfucose, daunosamine and trifluoroacetyldaunosamine; amino; trifluoroacetamido; mono or dimethylated amino; $C_{1-8}$ alkoxy; benzoate; p-nitrobenzoate; chloroalkylnitrosourea; acetoxy; and trifluoroacetoxy.

The invention further seeks to provide a compound of formula (10) wherein, more preferably, $X_1$, and $X_2$, are independently selected from the group consisting of O, and NH.

More preferably, $X_3$ is selected from the group consisting of O; S; and SO.

More preferably, $R_1$, $R_2$, $R_3$, $R_4$, $R_5$ and $R_8$ are independently selected from the group consisting of hydrogen; hydroxy; methoxy; $C_{1-6}$ alkyl silane; aminoethylaminoethanol; aminoethylaminoethylchloride; chloroalkylnitrosoureido of the formula NH(CO)N(NO)$(CH_2)_{0-2}$CH$_2$Cl; amino; and fluorine. More preferably, $R_6$ is selected from the group consisting of hydrogen; $C_{1-4}$ alkyl; $C_{1-4}$ hydroxyalkyl; $C_{1-4}$ dihydroxyalkyl; cyano; acetoxy; phenylsulfone; acyl of the formula —$C(R_{23})$=O, wherein $R_{23}$ is selected from the group consisting of methyl, hydroxymethyl, bromomethyl, acyloxymethyl, and amino;

a group of the formula —$C(OR_{24})$=O, wherein $R_{24}$ is selected from the group consisting of hydrogen, methyl, and ethyl;

a group of the formula —$CH_2C(R_{27})$=O, wherein $R_{27}$ is selected from the group consisting of hydrogen, methyl, and ethyl;

a 5 or 6 membered aromatic or non-aormatic heterocycle containing one or more heteroatoms selected from the group consisting of O, S, N, and NH, said heterocycle being optionally substituted with one or more halogens, hydroxy, $C_{1-4}$ alkoxy, $C_{1-4}$ alkyl, $C_{1-4}$ hydroxyalkyl, amino which may be unsubstituted or mono- or disubstituted by methyl, cyclopropyl, $C_{2-8}$ acyl, and hydroxy. More preferably, $R_6'$ is selected from the group consisting of hydrogen, fluorine; methyl; methoxy; cyano; an acyl of the formula —$C(R_{29})$=O, wherein $R_{29}$ is selected from the group consisting of hydrogen, $C_{1-5}$ alkyl, $C_{1-4}$ hydroxyalkyl, and amino;

a group of the formula —$C(OR_{30})$=O, wherein $R_{30}$ is selected from the group consisting of hydrogen, $C_{1-5}$ alkyl, $C_{6-10}$ aryl, and $C_{-4}$ alkenyl.

Preferably, $R_7$ is selected from the group consisting of hydrogen; hydroxy; methoxy; fluorine; cyano; acetate; and acetyl.

Preferably, Y is selected from the group consisting of hydrogen, halogen, hydroxy, methoxy, cyano, acetate, acetyl and a saccharide of formula:

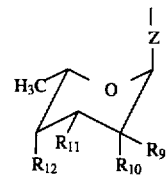

wherein, more preferably,

Z is O; or $CH_2$;

$R_9$ and $R_{10}$ are independently selected from the group consisting of hydrogen; amino; chloroethylnitroso; ureido; fluorine; and iodine.

More preferably, $R_{11}$ is selected from the group consisting of hydroxyl; acetoxy; amino; dimethylamino; trifluoroacetamido; morpholino; cyano-substituted morpholino; mono-, di-, tri-, or tetra-methoxy-substituted morpholino; fluorine; a group of the formula $NH(CH_2)_{2-5}CH(OR)_2$ wherein R is selected from a group consisting of $C_{1-4}$ alkyl, $C_{1-4}$ acyl, or $C_{7-8}$ aroyl; $NH(CH_2)_2OCH(OAc)_2$; and chloroalkylnitrosoureido of the formula $NH(CO)N(NO)(CH_2)_{0-4}CH_2Cl$.

More preferably, $R_{12}$ is selected from the group consisting of hydroxyl or its tetrahydopyranyl ether; benzoate; acetoxy; p-nitrobenzoate; amino; trifluoroacetoamido; chloroethylnitrosoureido; fluorine; and iodine.

The invention seeks to provide a compound of formula (10) wherein, most preferably, $X_1$ and $X_2$ are both oxygen.

Most preferably, $X_3$ is selected from O; or S.

Most preferably, $R_1$, $R_2$, $R_3$ and $R_4$ each are independently selected from the group consisting of hydrogen; fluorine; methoxy; and hydroxy.

Most preferably, $R_5$ and $R_8$ are independently selected from the group consisting of hydrogen; hydroxyl; amino; and fluorine.

Most preferably, $R_6$ is selected from the group consisting of methyl; ethyl; hydroxymethyl; 1,2-dihydroxyethyl; cyano; phenylsulfone; methyl carboxylate ($-CO_2CH_3$); ethyl carboxylate; methyl homo carboxylate ($-CH_2CO_2CH_3$); acyl of the formula $-C(R_{23})=O$, wherein $R_{23}$ is selected from the group consisting of methyl, fluromethyl, difluoromethyl, hydroxymethyl, acetoxymethyl, and bromomethyl; a 5 or 6 membered aromatic or non-aromatic heterocycle containing one or more heteroatom selected from the group consisting of O, S, N, NH, said heterocycle being optionally substituted with one or more fluorine, hydroxy, methoxy, methyl, hydroxymethyl, amino, and acylamino groups.

Most preferably, $R_6'$ is selected from the group consisting of hydrogen; fluorine; methyl; and cyano.

Most preferably, $R_7$ is selected from the group consisting of hydrogen; hydroxy; and fluorine.

Y is most preferably selected from the group consisting of hydrogen; hydroxyl; bromine; chlorine; cyano; acetate; acetyl; and a saccharide of formula:

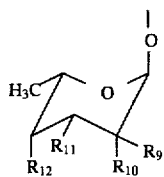

wherein, most preferably, $R_9$ and $R_{10}$ are independently selected from hydrogen; fluorine; and iodine.

Most preferably, $R_{11}$ is selected from amino, hydroxy; dimethylamino, acetoxy; trifluoroacetamido; morpholino; cyano-substituted morpholino; methoxymorpholino; and a group of the formula $NH(CH_2)_4CH(OR_{34})_2$ wherein $R_{34}$ is selected from a group consisting of methyl, acyl, and benzoyl; $NH(CH_2)OCH_2CH(OAc)_2$; and chloroalkylnitrosoureido of the formula $NH(CO)N(NO)(CH_2)CH_2Cl$.

Most preferably, $R_{12}$ is selected from hydroxy; or iodine.

This invention also comprises novel compounds which are prepared as intermediates or precursors of compounds of formulas (10) and (11). Such intermediate compounds are described hereinafter in connection with processes of preparing compounds of formulas (10) and (11).

The compounds of formula (10) can be prepared by the process illustrated in Reaction Scheme I.

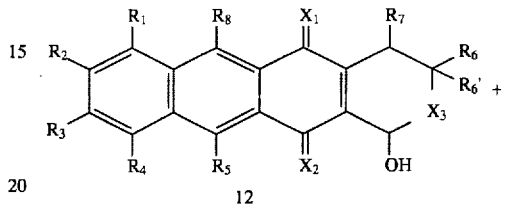

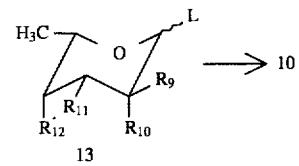

(MOL-7)

Heteroanthracyclines of general formula (10) in which Y is a saccharide are best prepared by using Scheme I. With reference to Reaction Scheme I, an aglycone of formula (12) in which $R_1$ to $R_8$ are as defined herein is reacted with a sugar derivative of formula (13) in which $R_9$ to $R_{12}$ are as defined herein and L is a displaceable atom or group. Suitable groups L include halogen, for example iodine, bromine or chlorine, an unsubstituted or substituted benzoyl group such as p-nitrobenzoyl, and $-OR$ or $-SR$, where R is an unsubstituted or substituted alkyl group, for example a $C_{1-16}$ alkyl group such as methyl, ethyl or butyl, or R is an unsubstituted or substituted acyl group such as a $C_{1-16}$ acyl group such as acetyl, or R is an unsubstituted or substituted aryl group. Such sugars are obtained by derivatizing known saccharides of the family of anthracycline antibiotics which are available from commercial or natural sources, (see for example, Monneret, C., Martini, A., Pais, M., Carbohydrate Research, 166, 59–70, 1987 and references therein; Acton, E. M., Tong, G. L., Mosher, C. W., and Wolgemuth, R. L., J. Med. Chem. 27, 638–645, 1984 and references therein; Arcamone Cancer Research, 45, 5995–5999, 1985 and references therein).

The aglycone of formula (12) is typically reacted with the appropriate sugar derivative of formula (13) in a compatible solvent such as methylene chloride using a Lewis acid such as titanium tetrachloride, stannic chloride, of trimethylsilyl-trifluoromethane-sulfonate. Alternatively, as it is known in the art of anthracycline chemistry, when the leaving group of the sugar moiety is a halogen, the Koenigs-Knorr glycosidation or its modification may be used.

A method of preparing the compounds of formula (12) in which $X_1$, $X_2$, $X_3$=O and $R_6'$=hydrogen, is illustrated in Reaction Scheme II.

Reaction Scheme II

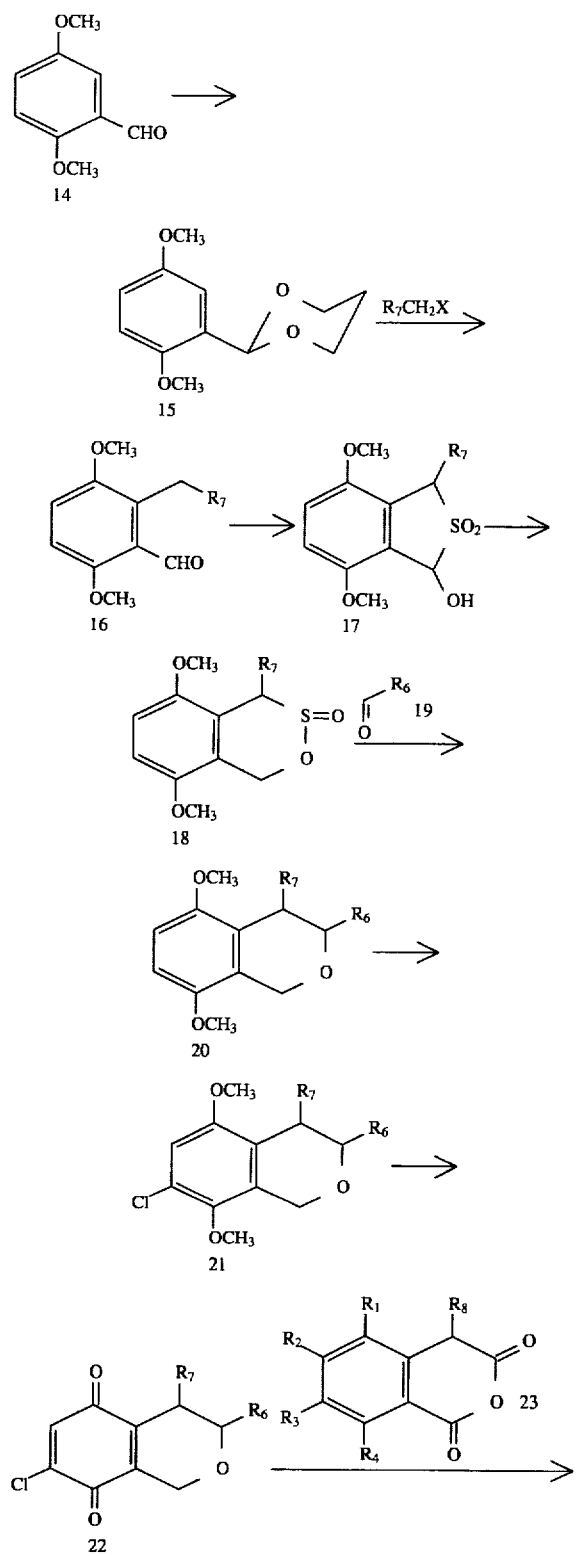

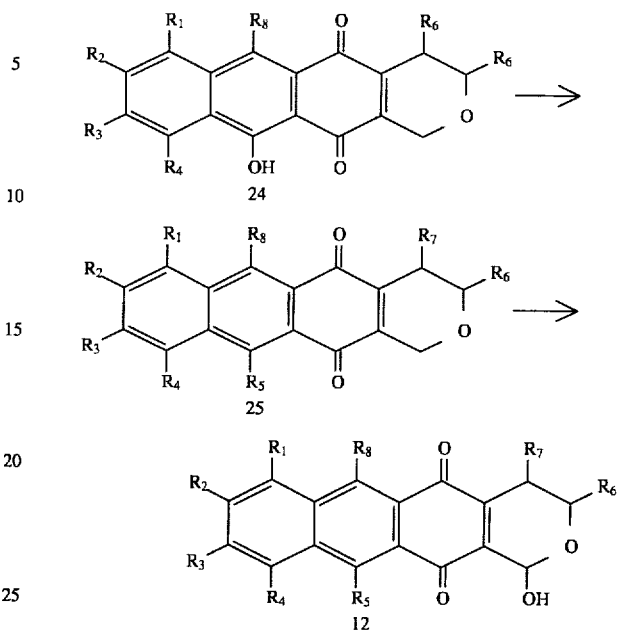

With reference to Reaction Scheme II, 2,5-dimethoxybenzaldehyde dioxane acetal (15) can be prepared by treating at reflux 2,5-dimethoxybenzaldehyde (14) with 1,3-propanediol in benzene or any other suitable solvent and with an acid catalyst such as p-toluenesulfonic acid. The dioxane acetal (15) can then be treated with an alkyl lithium such as n-butyllithium and the lithio salt reacted with an appropriate alkyl halide of the formula $R_7CH_2X$, wherein X is halogen and $R_7$ is as defined above, but compatible with the necessary reaction conditions. In the event that $R_7$ is not compatible, functional group interconversion can be carried out at a latter step by using methods which are well known by one familiar with the art of organic synthesis.

Subsequent aqueous acidic treatment can lead to an appropriate 2,5-dimethoxy-6-alkylbenzaldehyde such as (16). Photochemical irradiation of an intermediate such as (16) in a solution of $SO_2$ in an aryl solvent such as benzene can give a dihydrothiophene-2,2-dioxide of formula (17) which can then be reduced with a borohydride. Following acidic treatment, a d-sultine of formula (18) can be obtained. This intermediate can then be coupled via cyclocondensation with an appropriately functionalized aldehyde (19) and consequently yield dimethoxyisochroman intermediates such as (20). The intermediates (20) can subsequently be chlorinated with an hypochlorite such as t-butylhypochlorite to give compounds of formula (21). Oxidative demethylation of (21) with an adequate oxidant such as ceric ammonium nitrate can give chloropyranoquinones of formula (22). These quinones can then be coupled under basic conditions with adequately functionalized homophthalic anhydrides such as (23) to give pyranoquinone tetracyclic derivatives of formula (24). The free phenol can then be protected to give tetracyclic compounds of the general formula (25). Tetracyclic derivative (25) can then be brominated with a free radical brominating agent such as n-bromosuccinimide in the presence of an initiator such as UV light and in a chlorinated solvent such as carbon tetrachloride. The resulting unstable bromides can then be treated directly with an aqueous-ethereal solvent system to yield the pyrano-tetracyclic aglycones of formula (12). The aglycones of formula (12) can further be transformed to a variety of structures by using synthetic methodologies well understood in the art of anthracycline synthesis. Any functional group interconversion or removal of protecting groups is preferentially carried out under neutral or basic conditions at this stage or later in the synthesis, as convenient.

A variation for preparing the compounds of formula (12) is illustrated in Reaction Scheme III.

Reaction Scheme III

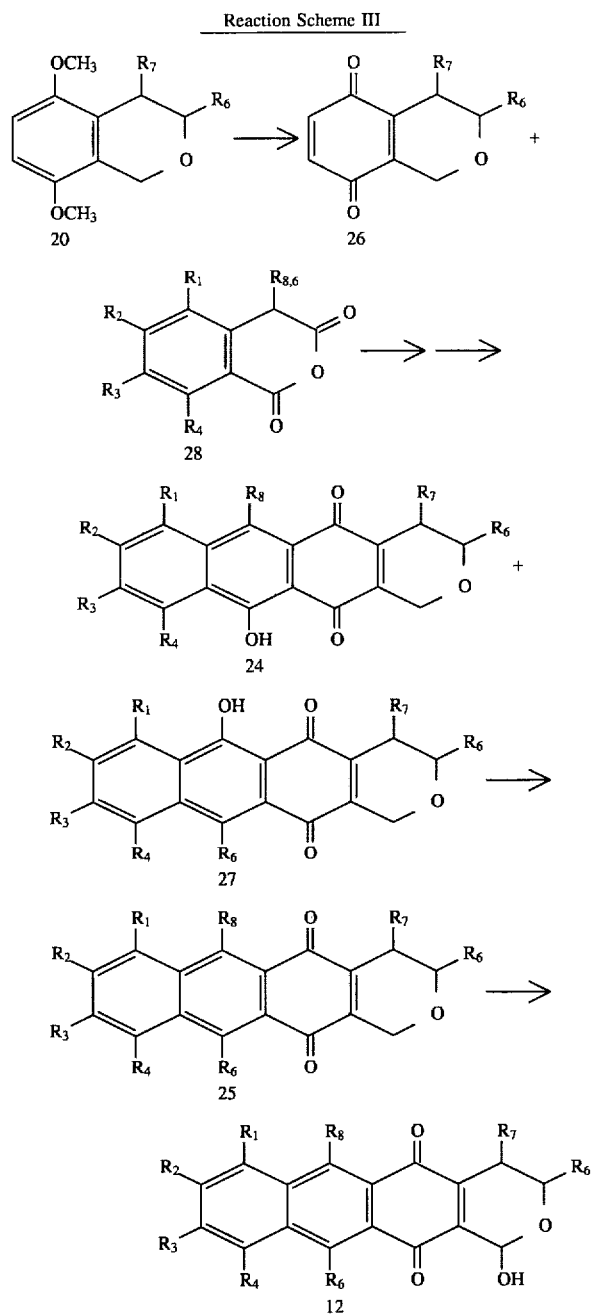

With reference to Reaction Scheme III, dimethoxy-isochroman intermediates such as (20) can be directly oxidatively demethylated with an oxidizing reagent such as ceric ammonium nitrate in a polar solvent system such as acetonitrile in water. The resulting pyranoquinones of formula (26) can then be coupled with appropriately functionalized homophthalic anhydrides (23) in an aprotic solvent with basic catalysis, preferentially lithium diisopropylamide or sodium hydride. Tetracyclic derivative (27) can be separated from (24). The free phenol can then be protected to give compounds of the general formula (25). Bromination and solvolysis as described can give the aglycones of formula (12).

Preferred processes for the preparation of the compounds of formula (12) are illustrated in reaction Scheme IV. In route a of Scheme IV, the lithio salt, obtained after treatment of 2,5-dimethoxybenzaldehyde dioxane acetal (15) with an alkyl lithium, is reacted with an epoxide of general formula (31) optionally in the presence of a Lewis acid such as boron trifluoride etherate to give the adduct of formula (32).

Route b represents an alternative approach for the preparation of adduct (32). Consequently, the addition of an aldehyde of general formula (28) to the lithio salt of 2,5-dimethoxybenzaldehydedioxane acetal (15) can give an adduct of formula (29). In aldehyde (28), $R'_1$ is a protecting group, which includes, but is not limited to, methoxymethyl, methoxyethyl, methyl, benzyl, trityl, t-butyldimethylsilyl, t-butyldiphenylsilyl or other groups conveniently used for the protection of alcohols in the art of organic synthesis. The hydroxyl in formula (29) can be transformed to a variety of functionalities by using general methods obvious to those familiar with organic synthesis. Therefore, compounds of formula (30) can be obtained which upon deprotection of the secondary protected alcohol, by using known methods, yield the desired substituted benzaldehydedioxane acetal adduct (32).

The adduct of formula (32) is then cyclized in the presence of a mild aqueous acid to give 1-hydroxyisochroman of the formula (33).

The tetracyclic aglycones (39) and (40) can be prepared according to route c. Pyranoquinones of formula (34) are prepared by oxidizing isochromans of formula (33) with an agent such as silver oxide or ceric ammonium nitrate. Quinones of formula (35), in which the hydroxyl has been protected with a group $R'_2$, selected but not limited to, methyl, ethyl, methoxymethyl, methoxyethyl, trimethylsilyl, t-butyldimethylsilyl, t-butyldiphenylsilyl, benzyl, p-nitrobenzyl and trityl, can then be added to an homophthalic anhydride of formula (23) in the presence of strong base, or to a benzomonoketene of formula (23') under U.V. irradiation (Krohn K., et al, Liebigs Ann. Chem. 943–948 [1988]), to yield, after deprotection, the tetracyclic aglycones of general structures (39) and (40).

The tetracyclic aglycones (39) and (40) can also be prepared according to route d from isochroman (33) which after bis chlorination with a reagent such as t-butyl hypochlorite gives isochromans of formula (36). Subsequent oxidation with an agent such as ceric ammonium nitrate yields bischloropyranoquinones of formula (37). Addition of these quinones to o-quinodimethanes, generated thermolytically from benzosulfones such as (38), can give tetracyclic aglycones of formula (39) and (40). Compounds of the formula (12) are then accessible from these aglycones through functional group interconversion of the phenol group.

Reaction Scheme IV
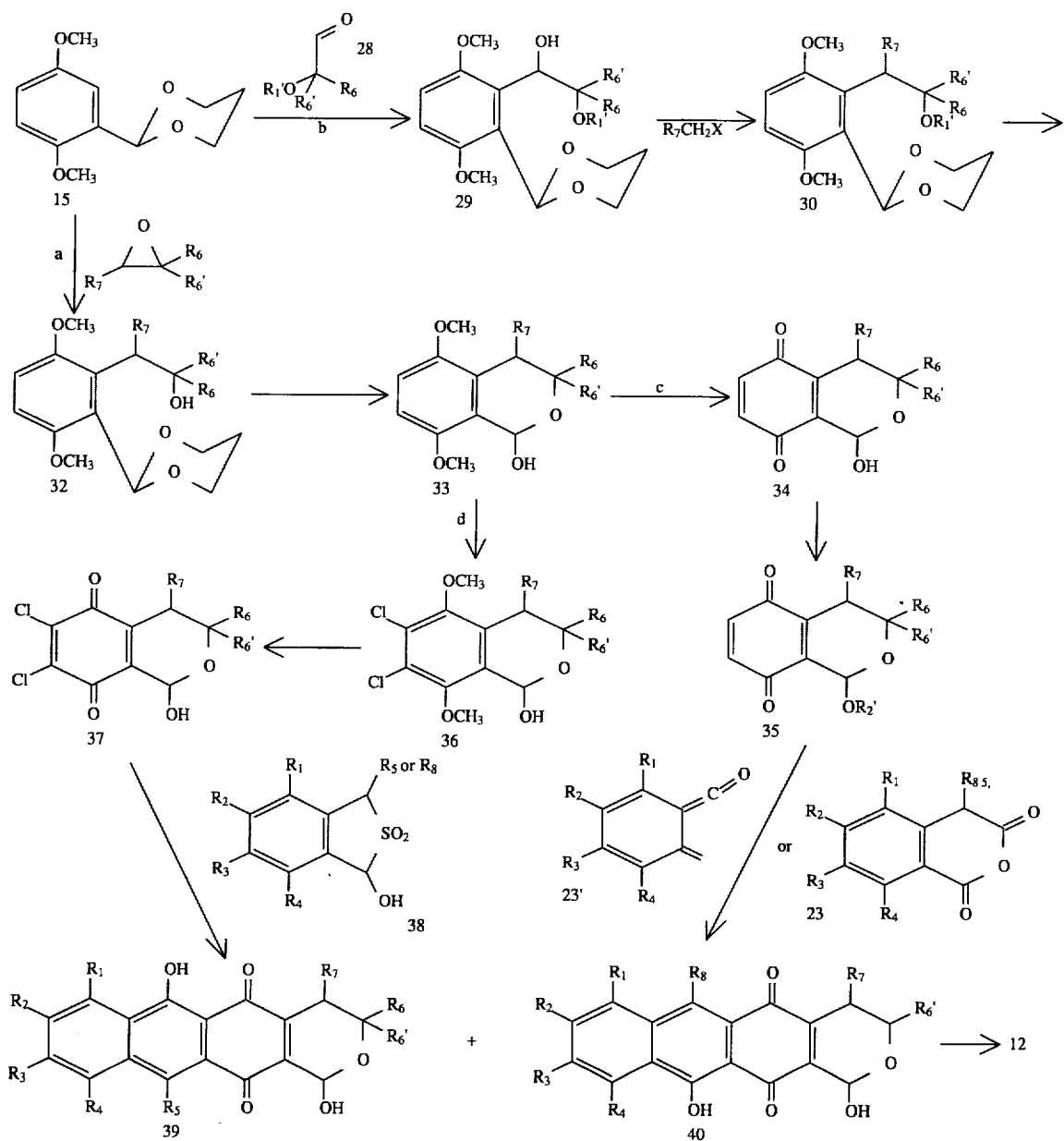
A method of preparing compounds of formula (12) wherein $R_8=R_5=H$, is illustrated in Reaction Scheme V.
Reaction Scheme V
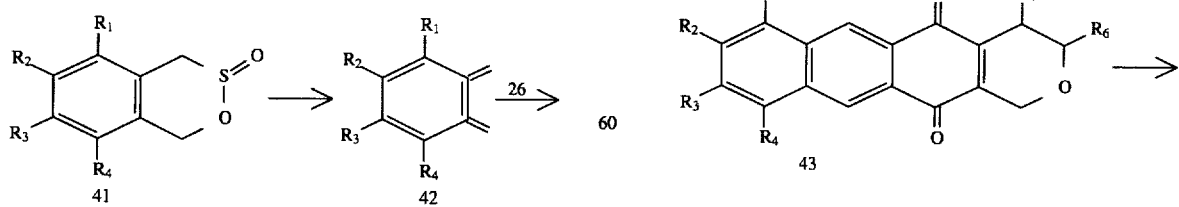
-continued
Reaction Scheme V

-continued
Reaction Scheme V

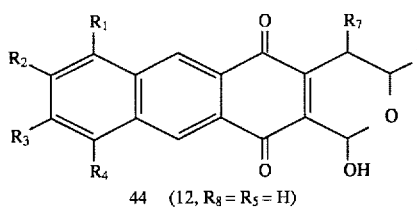

44 (12, R$_8$ = R$_5$ = H)

With reference to Reaction Scheme V, the cycloaddition reaction between an o-quinodimethane reactive intermediate (42), which can be generated by heating a precursor such as d-sultine (41) (prepared by the method described for compound (18) in Reaction Scheme II), and a pyranoquinone such as (26) can yield pyranoquinone structures such as (43), after consecutive treatment with silica gel. Bromination and solvolysis as described for intermediate (23) can give pyranoquinone aglycones with no substituents on ring C such as (44).

The process for the preparation of compounds of formula (10) in which $R_5=R_8=OH$, which tautomerizes into compounds of formula (11), is illustrated in Reaction Scheme VI.

Reaction scheme VI

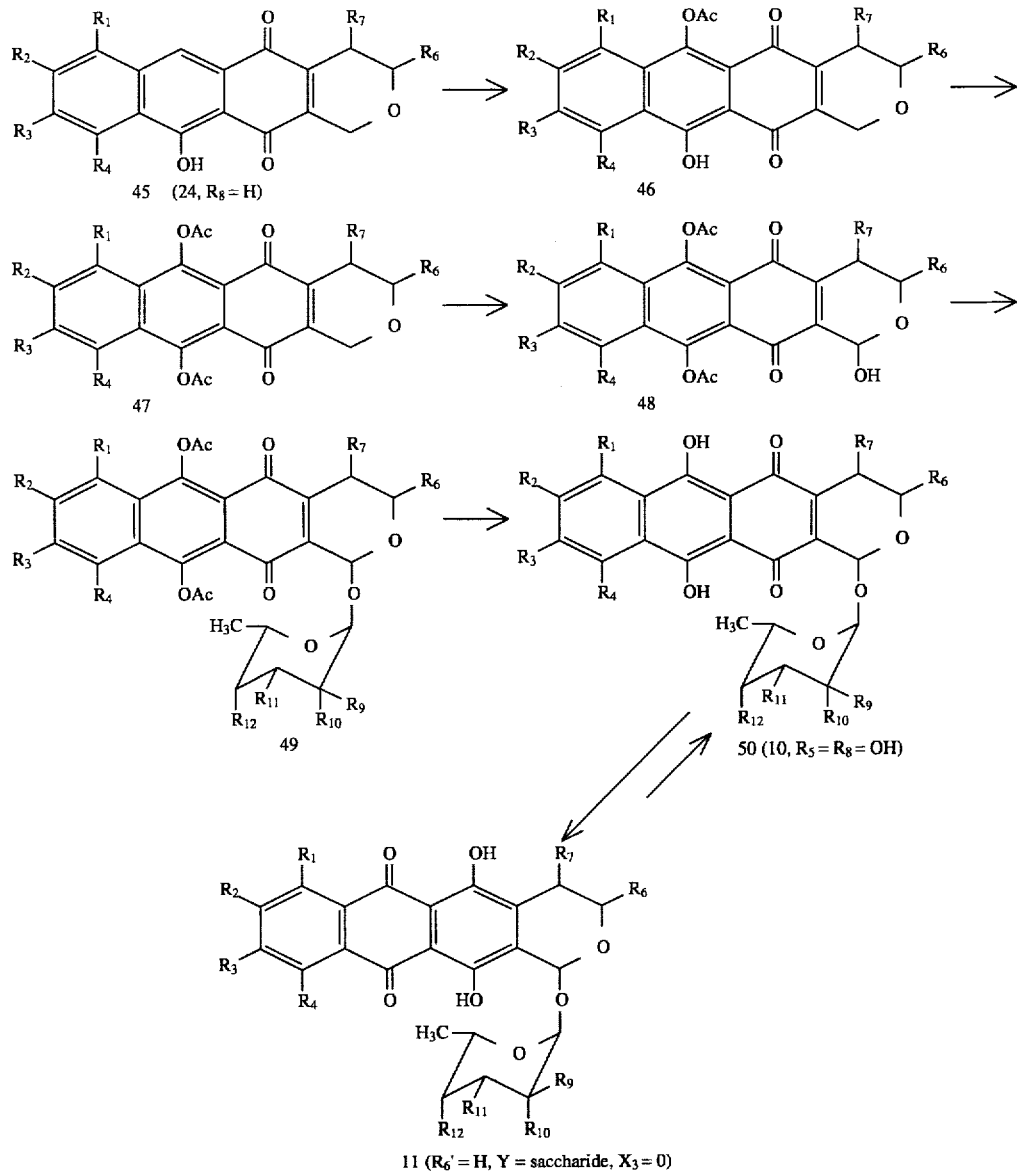

With reference to Reaction Scheme VI, the treatment of pyranoquinone derivatives such as (45), prepared by the method described for the compound (24), with lead tetraacetate in glacial acetic acid can give the acetoxylated pyranoquinones with structures such as (46). These can then be acetylated by treatment with acetic anhydride or acetyl chloride in the presence of a base such as pyridine. The resulting tetracyclic intermediates of formula (47) can be brominated and solvolyzed to give the diacetoxy pyranoquinone aglycone structures (48). Glycosidation can then give the bisacetoxypyranoquinone glycosides of formula (49). These, upon alkaline removal of the acetyl groups, yield glycosides (50) which would exist preferentially in the tautomeric form illustrated as structure (11).

Preferred processes for the preparation of compounds of formula (11) and (44) are illustrated in Reaction Scheme VII. In Reaction Scheme VII pyranoquinones such as (34) can be added to o-quinodimethanes, obtained from the thermolysis of d-sultine (41), as described in reaction scheme V, to give directly pyranoanthraquinone aglycones of general formula (44). The cycloaddition reaction between a bisbenzoketene derivative such as (52), conveniently generated from benzocyclobutanediones of formula (51) using a method as described by Krohn, [Liebig's Ann. Chem. 943–948 (1988)], can give, in the presence of formula (34) and under ultraviolet irradiation, tetracyclic derivatives such as (53), which will tautomerize to the more favorable structure (54). Glycosidation of aglycones of formula (54) as described in reaction Scheme I can give the glycosides of formula (11).

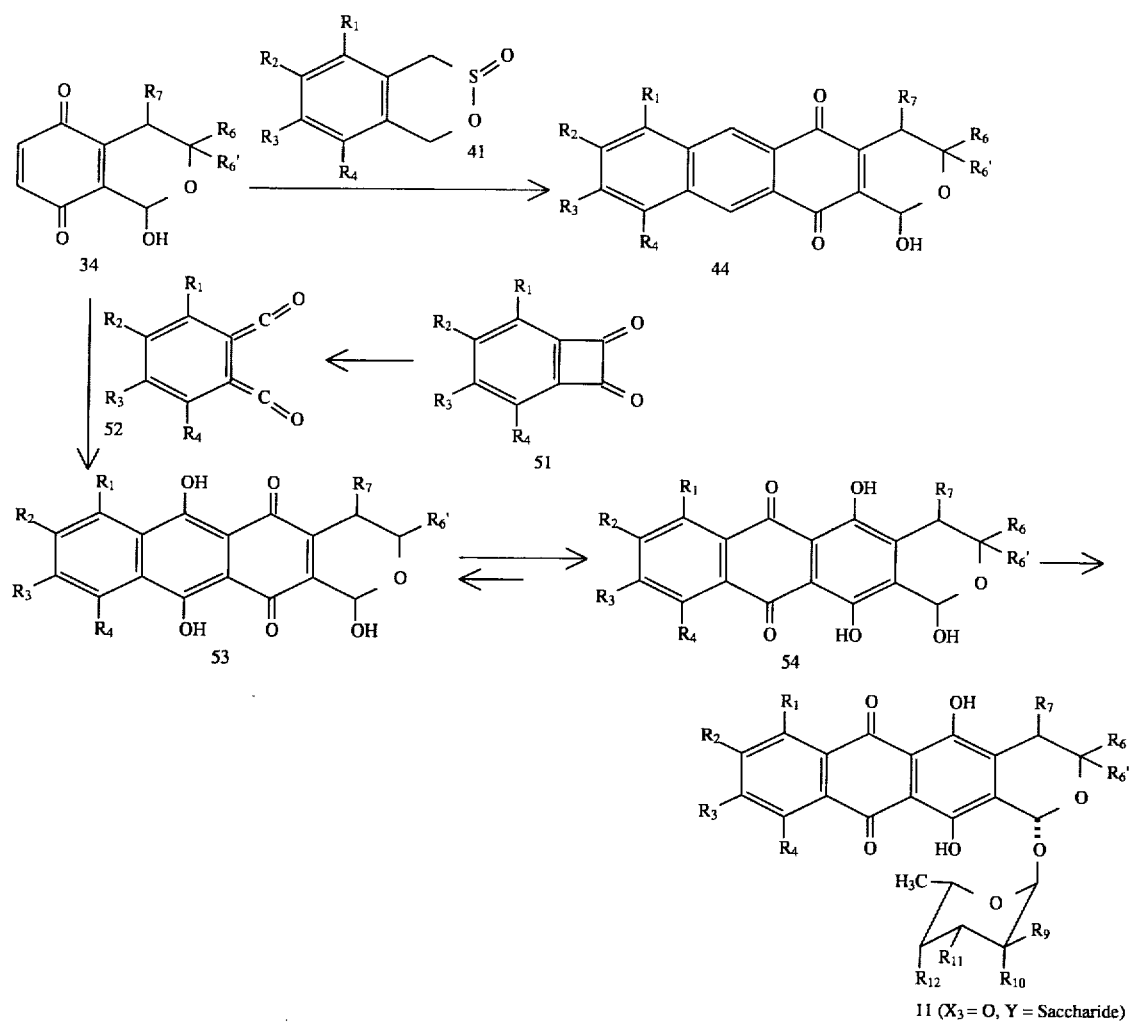

Reaction Scheme VII 11 (X₃ = O, Y = Saccharide)

An alternative approach for the preparation of compounds of general formula (12) is shown in scheme VIII. With reference to scheme VIII, 2,5-dimethoxybenzoic acid is transformed to the benzamide of formula (55a) by first converting the acid, into an acid chloride, with oxalyl chloride in the presence of a base such as pyridine in a solvent such as dichloromethane, and then treating with diethyl amine in ether. The lithio salt of (55a) is then generated with a strong base such as sec-Butyllithium in a convenient solvent such as tetrahydrofuran in the presence of TMEDA and reacted with an electrophile, L—CH2R₇, wherein R₇ is as defined herein and L is a displaceable atom or group such as an halogen. The resulting benzo derivative of formula (55b) is then treated with a strong base such as lithium diisopropyl amide or n-Butyllithium in a solvent such as tetrahydrofuran and added to a carbonyl electrophile of formula (56) to give an adduct of formula (57). The latter can then be cyclised to an isochromanone derivative of formula (58) by treating compound (57) with an acid.

Reduction of (58) with a hydride such as DIBAL in a compatible solvent such as dichloromethane can give the 1-hydroxylated isochroman of formula (33). Oxidative demethylation of (33) in a solvent system such as acetonitrile-water with, for example, ceric ammonium nitrate can give an isochromandione such as (34) which can then be transformed to a tetracyclic derivative such as (12) as explained in scheme IV. Functional group interconversion of the hydroxyl group of compound (12) into Y can be accomplished readily by employing methodology common to one familiar with the art of organic synthesis.

For example, glycosidation as described herein in scheme I of tetracyclic derivative (12) can give structures of formula (10) in which Y is a saccharide; acetylation or benzoylation of compound (12) can give structures of formula (10) in which Y is O—COR and R is an alkyl or aryl; alkylation of the hydroxyl in derivatives of formula (12) can be accomplished with various known electrophiles, for example alkyl halides, orthoformates, or others, with or without catalysis, to give compounds of formula (10) in which Y is an alkoxyl; the hydroxyl group in formula (10) can be converted into a displaceable atom or group L in which L is selected among

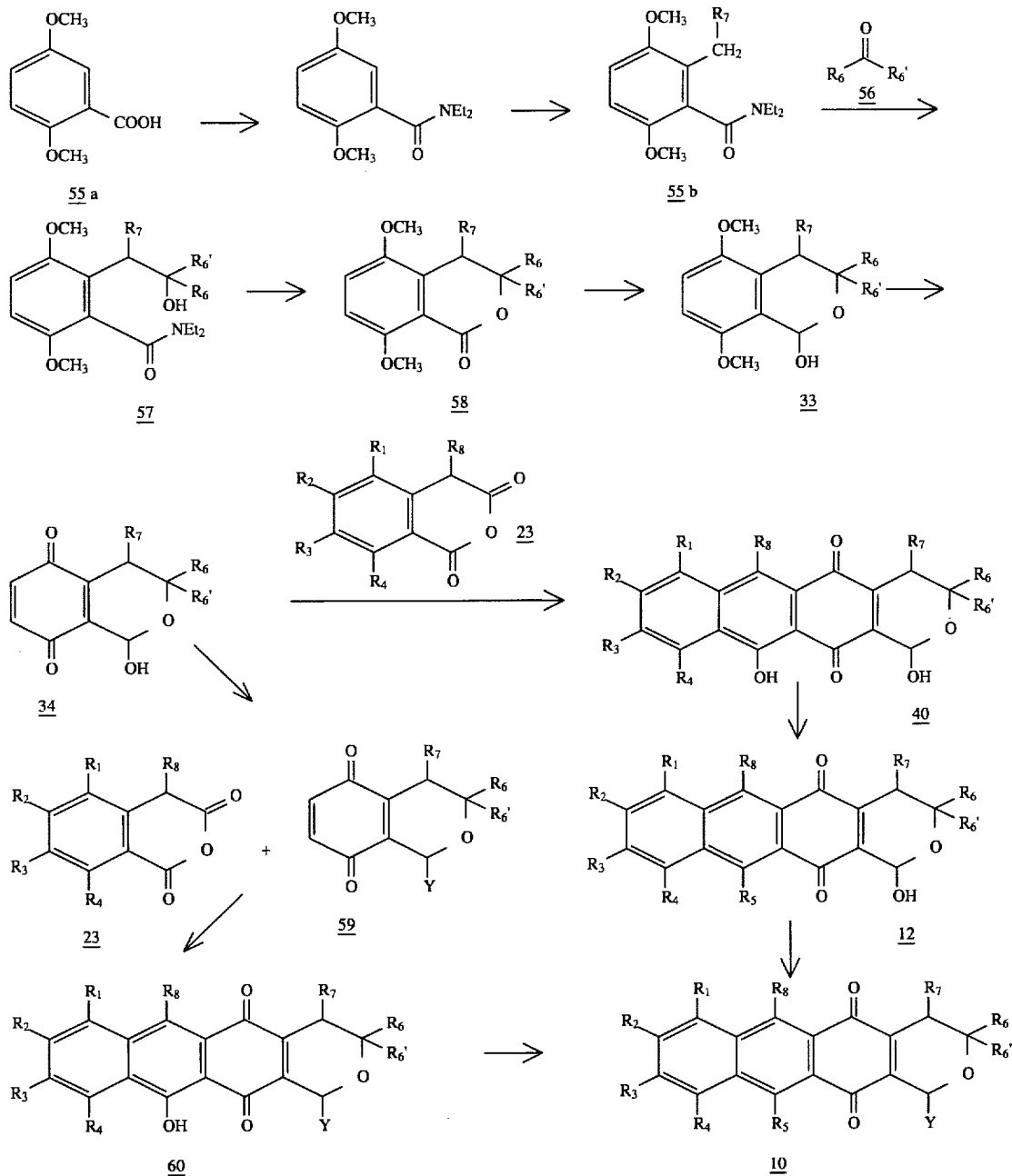

known leaving groups such as a halide, obtained for example by treating the alcohol with triphenylphosphine in the presence of carbon tetrachloride, carbon tetrabromide or iodine, or a sulfonate such as a mesylate, a tosylate or a triflate, obtained for example by treating the alcohol with mesyl chloride, tosylchloride, triflic anhydride, or the like, in the presence of a base such as pyridine or triethylamine and in an adequate solvent for example benzene or dichlorometane, or L is any other appropriate leaving groups. Displacement of L with various nucleophiles would give compounds of formula (10) with different functional groups Y. For example, Y=CN can be obtained by displacement of L with a cyanide; Y=alkyl, alkenyl, or alkyne, can be obtained by displacement with a carbanion. The above examples are not intended to limit this invention in any way.

In the event that such methodology is not compatible with the other substituents at the $R_1$–$R_8$ positions around the tetracyclic structure (12), then quinone (34) can be transformed into the isochromandione of formula (59), with the desired Y group as defined herein, by applying readily available techniques in organic chemistry. Reaction of an homophtalic anhydride of formula (23) with an isochroman such as (59) in the presence of a strong base such as lithium diisopropylamide or sodium hydride in a solvent such as tetrahydrofuran can then give the tetracyclic intermediate of formula (60). The phenol of this latter compound can then be transformed into various functional groups by using techniques available to the organic chemists, thus giving the tetracycle of formula (10).

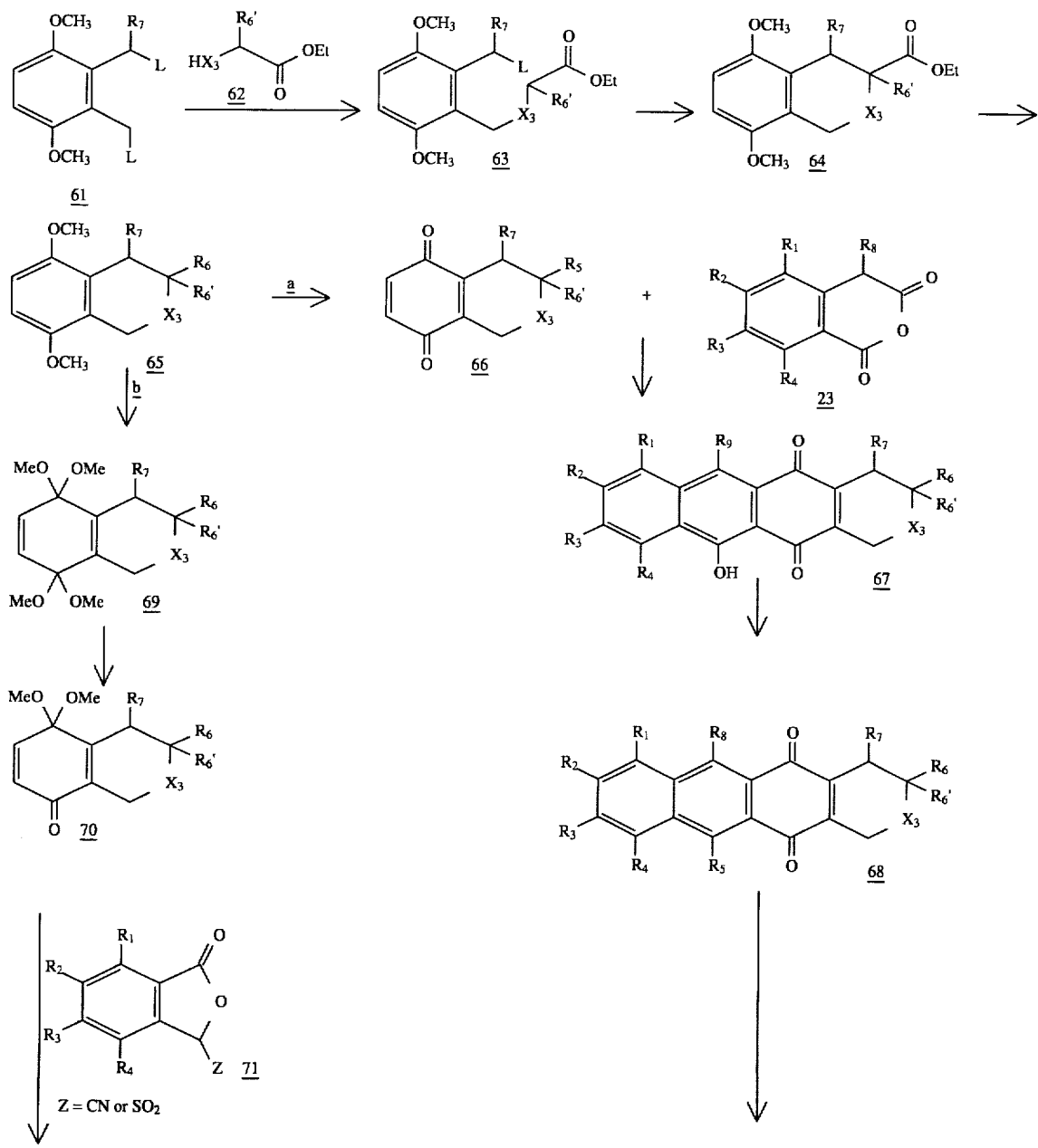

Reaction Scheme IX

-continued
Reaction Scheme IX

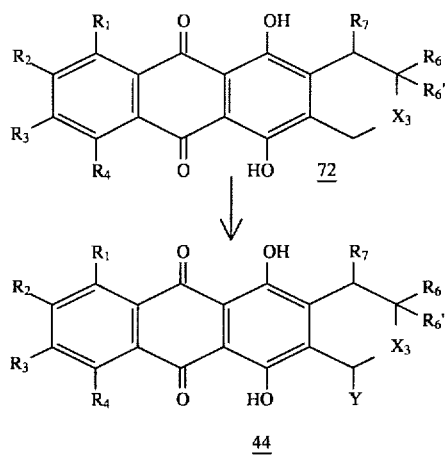

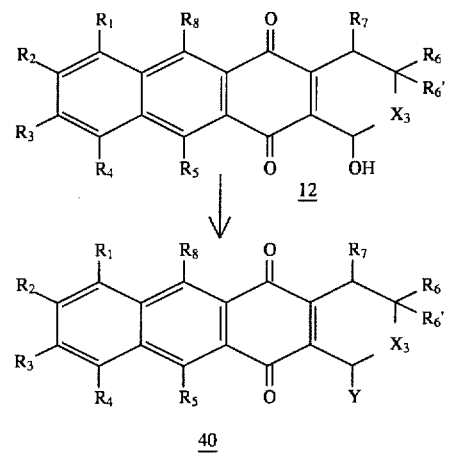

A more general approach for the preparation of compounds of general formula (10) is shown in scheme IX. With reference to scheme IX known compounds of formula (61), in which L is a displaceable atom or group such as an halogen or a mesylate, tosylate, or triflate, can be reacted with an intermediate of formula (62) in the presence of base to give an adduct of formula (63). The required acyclic compounds of formula (62) are either known or easily obtainable. Cyclization of (63) to give (64) can be accomplished in an aprotic solvent such as tetrahydrofuran or ether and in the presence of a non nucleophilic base such as sodium hydride or lithium diisopropylamide. The ester group of (64) can then be transformed into various groups, as defined herein for $R_6$, by using known methodology. Intermediates of general formula (65) can then be used to prepare the desired tetracycle (10) by following route a. Thus oxidative demethylation of (65) with an oxidant such as ceric ammonium nitrate would give quinones of formula (66), which can then be coupled with various homophtalic anhydrides of formula (23) to give tetracyclic heteronaptacenediones of formula (68). Oxidation of (68), for example via free radical bromination with n-bromosuccinamide or bromine in carbon tetrachloride or other compatible solvents, followed by treatment of the bromide with water can lead to aglycones of formula (12). Depending on $X_3$, alternative oxidation procedures may be required. For example, when $X_3$=S it is desirable to oxidise the sulfur heteroatom to the sulfoxide ($X_3$=SO), and then to carry out a Pummeror rearrangement with subsequent hydroxide treatment. Such approaches are common and well described in the literature. The conversion of compound (12) into (10) can be accomplished as described herein in other schemes.

Intermediate (65) can also be used in the direct preparation of the tautomeric form of (10), in the case when $R_5$=$R_8$=OH, by following route b. With reference to route b, electrochemical reduction of intermediate (65) in methanol in the presence of sodium methoxide can give the bisketal intermediate of formula (69). Mono deprotection in the presence of a weak acid in aqueous media can give the quinone monoketal of formula (70). This latter intermediate can then be coupled under strongly basic conditions achieved for example with NaH in aprotic media, with known benzofuranones of formula (71) in which Z is an electron withdrawing group such as cyano or phenylsulfone. The resulting heteronaphtacenediones of formula (72) can then be converted to the desired tautomer (11) by using the same methodology as described herein for compounds (25) or (68).

Reaction Scheme X

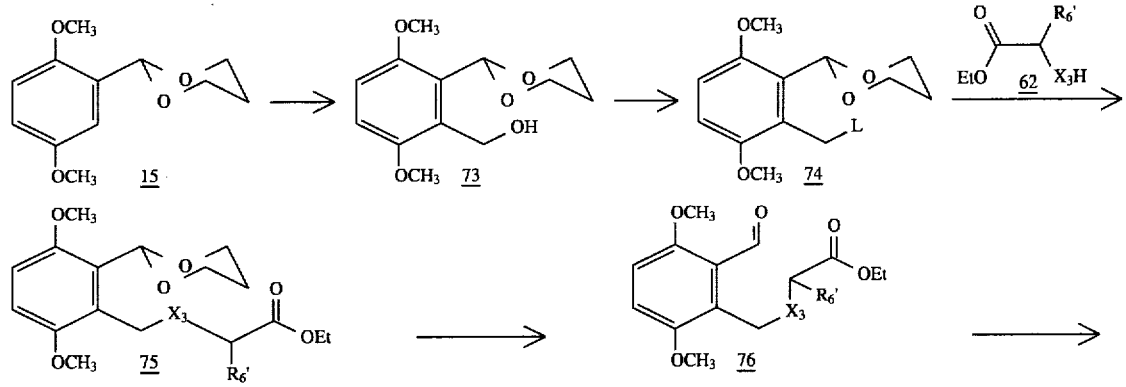

-continued
Reaction Scheme X

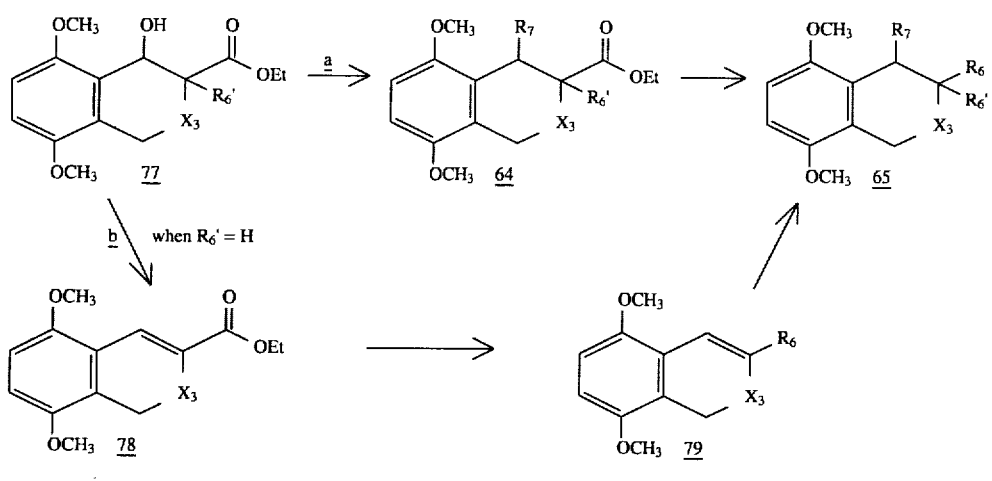

An alternate method for preparing key bicyclic intermediates of formula (65) is depicted in Scheme X. With reference to Scheme X, 2,5-dimethoxybenzaldehyde dioxane acetal is treated with a strong base such as n-butyllithium in an aprotic solvent such as diethyl ether, and the resulting lithio salt is alkylated with formaldehyde which can be conveniently generated from p-formaldehyde. The resulting hydroxyl in intermediate (73) can then be converted into a leaving group, for example such as a mesylate, by mesylating with mesyl chloride in the presence of a base such as pyridine in aprotic media. The leaving group of compound (74) can then be displaced with a nucleophile such as (62), as discussed in scheme IX herein, to give key intermediates of formula (75). These latter compounds can then be deprotected in acidic aqueous media to give benzaldehydes of formula (76). Cyclization of these intermediates can be accomplished with bases such as methoxide, carbonates, sodium hydride or lithium diisopropylamides in compatible solvents. Intermediates of formula (77) can then be further transformed to the desired key compounds of formula (65) by following either routes a or b.

In route a, the hydroxyl group of benzoderivative (77) can be transformed into functional groups $R_7$ to give (64) and subsequently (65), by using simple derivatizing techniques commonly used by the one familiar with organic synthesis. Route b can be employed when $R_6'$ is a hydrogen. In this case, dehydration of (77) to give (78) can be carried out under basic or acidic media. Transformation of the ester functionality of structure (78) into $R_6$, as defined herein, is possible by using known methods. The resulting derivatives of formula (79) can then be oxidized to give compounds of general formula (65) by using known oxidation techniques.

Reaction Scheme XI

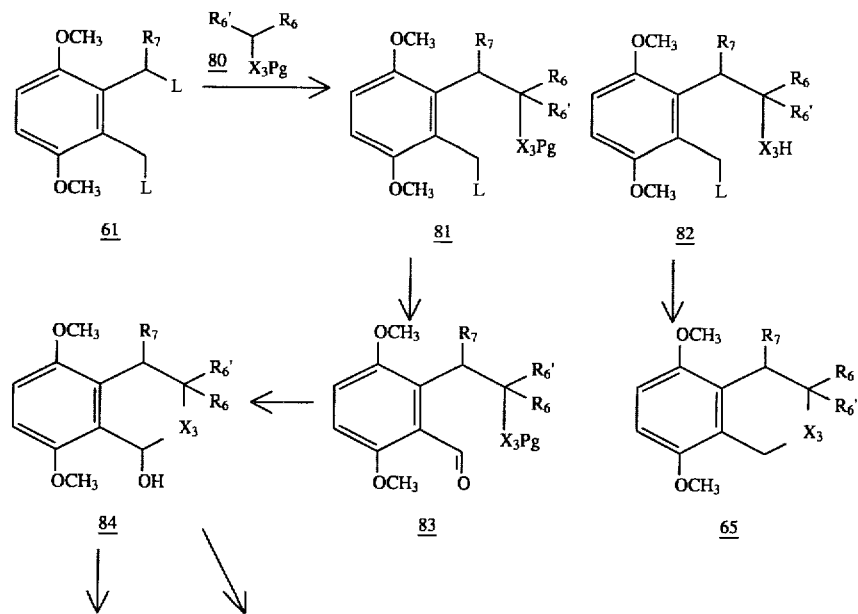

-continued
Reaction Scheme XI

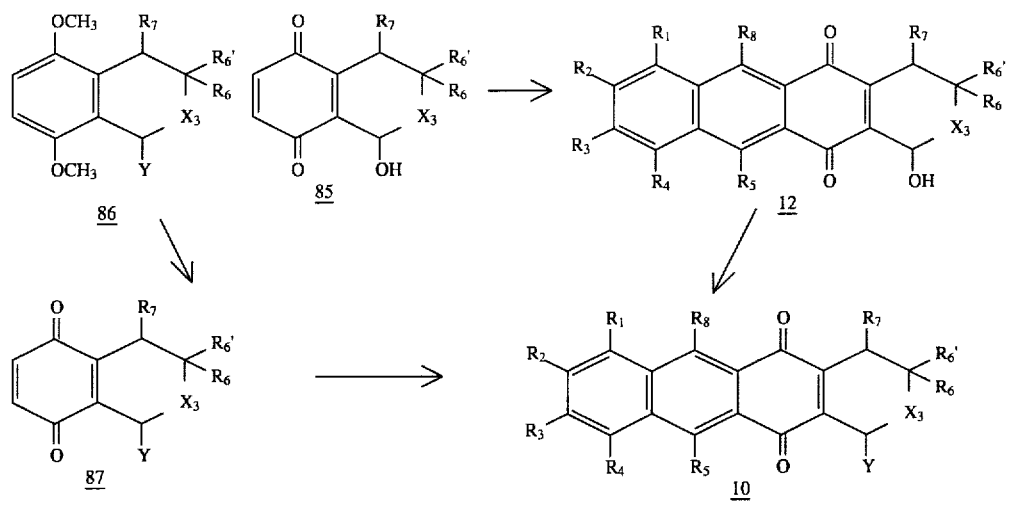

A preferred mode for the preparation of compounds with general structure (10) is shown in Scheme XI. With reference to Scheme XI, compounds of formula (61) are coupled, under basic conditions in a suitable solvent such as benzene or tetrahydrofuran, with intermediates of formula (80) to give adducts such as (81). Compounds of formula (80), in which Pg is a protecting group such as benzoyl, and $R_6'$ or $R_6$ are preferably electron withdrawing groups, are accessible by derivatising known compounds. Deprotection of (81) with sodium hydroxide in protic solvent can give intermediates of formula (82) which can thereafter be cyclized under basic media in aprotic solvent to give the bicyclic intermediates of formula (65).

Although key intermediates such as (65) are readily preparable as described herein, it is best to use compounds of formula (81) for the preparation of quinone derivatives such as (85) or (87). Thus, compounds of formula (81) can be oxidized to give (83) by using known methods. For example, benzylic bromides can be oxidised with sodium bicarbonate in dimethylsulfoxide or with other known reagents to give aromatic aldehydes. Deprotection of (83), for example benzoate hydrolysis with sodium hydroxide, can directly give hydroxylated heterocyclic compounds of formula (84). These latter derivatives are easily oxidatively demethylated with an agent such as ceric ammonium nitrate to give quinones of formula (85). Compounds of formula (10) are readily prepared from (85) by using methodology described herein in other schemes.

Alternatively, functional group interconversion of the hydroxy into Y can be accomplished from quinone (85) as described herein in other schemes, or from benzo derivatives (84) to give (86) by employing known techniques. Compounds of formula (10) can then be obtained from (86) by following the same procedure as described for (84).

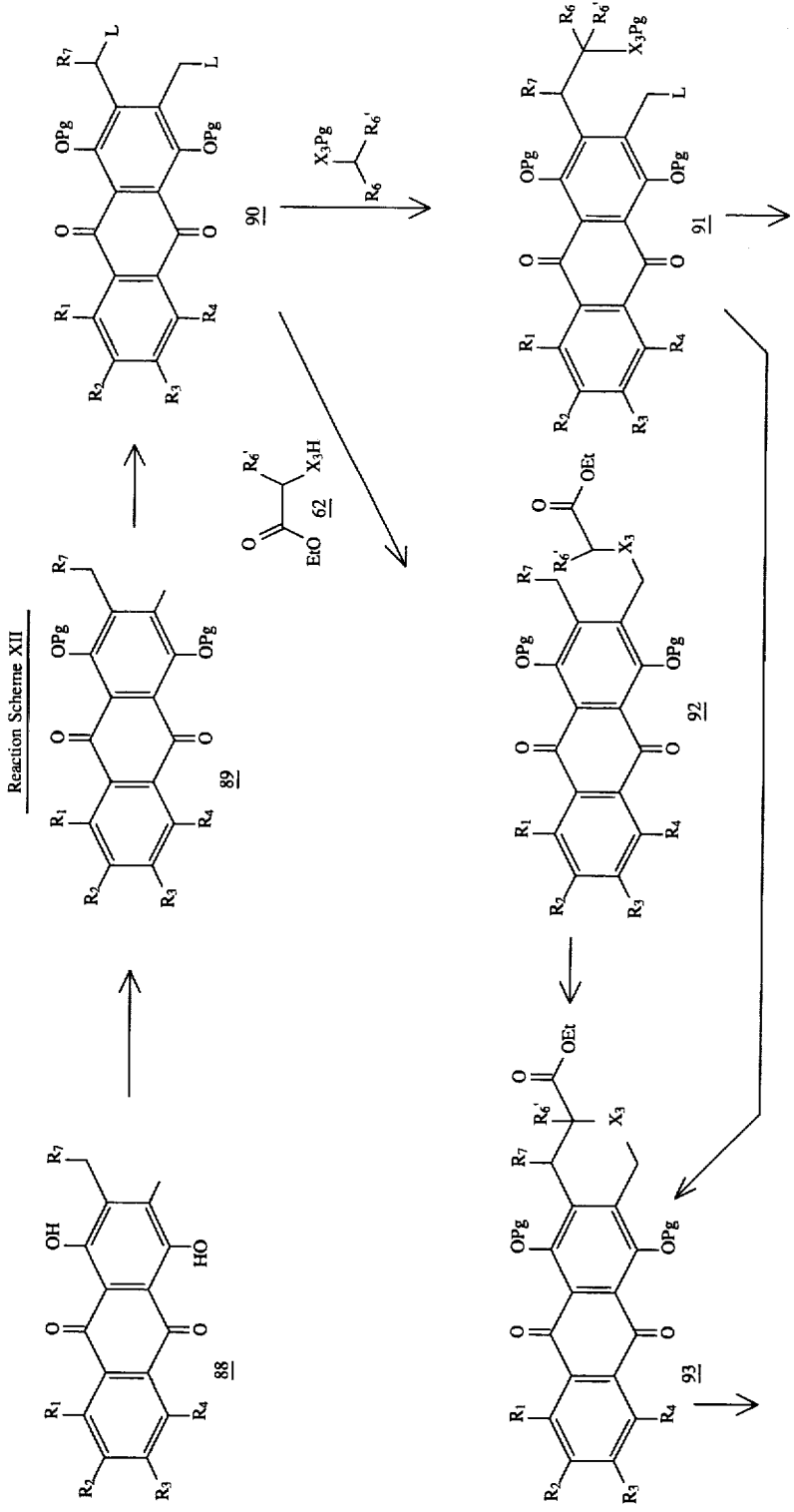

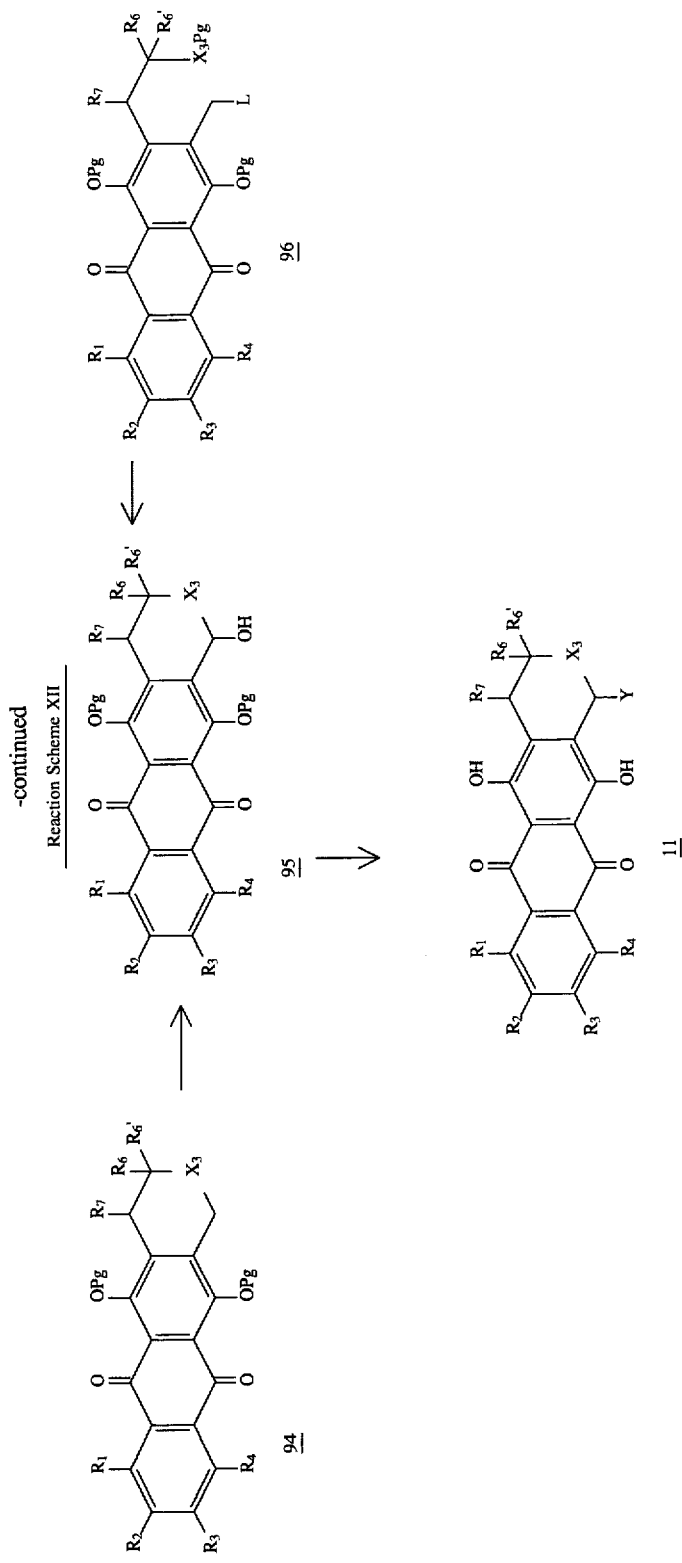

A shorter and more direct approach for the preparation of compounds of general formula (11), which is the tautomer of (10) when $R_5=R_8=OH$, is shown in scheme XII. With reference to scheme XII a known quinizarin derivative of formula (88) is converted to anthraquinone (90), in which OPg is a protected phenol and L is a displaceable atom or group, by protecting the hydroquinone in (88) as an alkoxyl, an acyl, a silyl or an ether by using known protecting methodology, and then treating for example the resulting protected quinizarin of formula (89) with n-bromosuccinamide or bromine, in a solvent such as carbon tetrachloride under free radical catalysis. The conversion of compound (90) into (11) can be achieved by using methodology already described herein in other schemes. For examples, compound (90) can be converted into (11), via (91), (96) and (95), by using the method as described for the conversion of (61) into (86) in scheme XI; compound (90) can be converted into (93), via (91), by using the method as described for the conversion of (61) into (65) in scheme XI; compound (94) can be obtained from (90), via (92) and (93), by following the sequence as described for converting (61) into (65) in scheme IX. The same methods for transforming (67) into (10) can be used for converting (94) into (11).

It will be appreciated that the anthracyclines of formulae (10) and (11) can further be transformed to a variety of structures by using synthetic methodologies well understood in the art of anthracycline chemistry.

It will be further appreciated that compounds of formula (10) in which $X_3=SO$ or $SO_2$ can be obtained by oxidizing any of the intermediates in which $X_3=S$, as convenienced by the synthesis. Convenient reagents for this oxidation are m-chloroperbenzoic acid, hydrogen peroxide or any other known reagents. Compounds in which $X_3=NO$ can be obtained from those where $X_3=NH$ via oxidation.

It will also be appreciated that the following reactions may require the use of, or conveniently may be applied to, starting materials having protected functional groups, and deprotection might thus be required as an intermediate or final step to yield the desired compound. Protection and deprotection of functional groups may be effected using conventional means. Thus, for example, amino groups may be protected by a group selected from aralkyl (e.g. benzyl), acyl or aryl (e.g. 2,4-dinitrophenyl), subsequent removal of the protecting group being effected when desired by hydrolysis or hydrogenolysis as appropriate using standard conditions. Hydroxyl groups may be protected using any conventional hydroxyl protecting group, for example, as described in "Protective Groups in Organic Chemistry", Ed. J. F. W. McOmie (Plenum Press, 1973) or "Protective Groups in Organic Synthesis" by Theodora W. Greene (John Wiley and Sons, 1981). Examples of suitable hydroxyl protecting groups include groups selected from alkyl (e.g. methyl, t-butyl or methoxymethyl), aralkyl (e.g. benzyl, diphenylmethyl or triphenylmethyl), heterocyclic groups such as tetrahydropyranyl, acyl, (e.g. acetyl or benzoyl) and silyl groups such as trialkylsilyl (e.g. t-butyldimethylsilyl). The hydroxyl protecting groups may be removed by conventional techniques. Thus, for example, alkyl, silyl, acyl and heterocyclic groups may be removed by solvolysis, e.g. by hydrolysis under acidic or basic conditions. Aralkyl groups such as triphenylmethyl may be similarly removed by solvolysis, e.g. by hydrolysis under acidic conditions. Aralkyl groups such as benzyl may be cleaved, for example, by treatment with $BF_3$/etherate and acetic anhydride followed by removal of acetate groups.

In the above processes, the compounds of formula (10) and (11) are generally obtained as a mixture of diastereoisomers. These isomers may be separated by conventional chromatography or fractional crystallization techniques.

Where the compound of formula (10) or (11) is desired as a single isomer, it may be obtained either by resolution of the final product or by stereospecific synthesis from isomerically pure starting material or any convenient intermediate.

Resolution of the final product, or an intermediate or starting material therefor, may be effected by any suitable method known in the art: see for example, "Stereochemistry of Carbon Compounds", by E. L. Eliel (McGraw Hill, 1962) and "Tables of Resolving Agents", by S. H. Wilen.

The compounds of the formula (10) and (11) possess anti-cancer and anti-tumor activity. The compounds are also believed to possess antibacterial, antifungal and antiviral activity. While it is possible to administer one or more of the compounds of the invention as a raw chemical, it is preferred to administer the active ingredient(s) as a pharmaceutical composition.

In another aspect, the invention therefore provides pharmaceutical compositions primarily suitable for use as antitumor and anticancer agents, comprising an effective amount of at least one compound of the invention or a pharmaceutically acceptable derivative thereof in association with one or more pharmaceutically acceptable carriers and optionally other therapeutic and/or prophylactic ingredients. All the pharmaceutically acceptable salts for example the HCl and tartaric acid salts of the compounds useful as antitumor agents in mammals, including humans, are included in this invention.

It will be appreciated by those familiar with the art of clinical oncology that the compound(s) of this invention can be used in combination with other therapeutic agents, including chemotherapeutic agents (Cancer: Principles and Practices of Oncology, 3rd Edition, V. T. DeVito Jr., S. Hellman and S. A. Rosenberg; Antineoplastic Agents edited by W. A. Remers, John Wiley and Sons, New York, 1984). Thus, it will be understood that the compounds or pharmaceutical compositions of the invention may be formulated with the therapeutic agent to form a composition and administered to the patient or the compounds or compositions and the therapeutic agent may be administered separately, as appropriate for the medical condition being treated.

Therefore, for therapeutic purposes, a compound or composition of this invention can be used in association with one or more of the therapeutic agents belonging to any of the following groups:

1) Alkylating agents such as:
   2-haloalkylamines (e.g. melphalan and chlorambucil);
   2-haloalkylsulfides;
   N-alkyl-N-nitrosoureas (e.g. carmustine, lomustine or semustine);
   aryltriazines (e.g. decarbazine);
   mitomycins (e.g. mitomycin C);
   methylhydrazines (e.g. procarbazine);
   bifunctional alkylating agents (e.g. mechlorethamine);
   carbinolamines (e.g. sibiromycin);
   streptozotocins and chlorozotocins;
   phosphoramide mustards (e.g. cyclophosphamide);
   urethane and hydantoin mustards
2) Antimetabolites such as:
   mercaptopurines (e.g. 6-thioguanine and 6-[methylthio]purine);
   azapyrimidines and pyrimidines;
   hydroxyureas;
   5-fluorouracil;
   folic acid antagonists (e.g. amethopterin);

cytarabines;
prednisones;
diglycoaldehydes
3) Intercalators such as:
bleomycins and related glycoproteins;
anthracylines (e.g. doxorubicin, daunorubicin, epirubicin, esorubicin, idarubicin, aclacinomycin A);
acridines (e.g. m-AMSA);
hycanthones;
ellipticines (e.g. 9-hydroxyellipticine);
actinomycins (e.g. actinocin);
anthraquinones (e.g. 1,4-bis[(aminoalkyl)-amino]-9, 10-anthracenediones);
anthracene derivatives (e.g. pseudourea and bisanthrene);
phleomycins;
aureolic acids (e.g. mithramycin and olivomycin);
4) Mitotic inhibitors such as:
dimeric catharanthus alkaloids (e.g. vincristine, vinblastine and vindesine);
colchicine derivatives (e.g. trimethylcolchicinic acid)
epipodophyllotoxins and podophylotoxins (e.g. etoposide and teniposide);
maytansinoids (e.g. maytansine and colubrinol);
terpenes (e.g. helenalin, tripdiolide and taxol);
steroids (e.g. 4b-hyroxywithanolide E);
quassiniods (e.g. bruceantin);
pipobroman; methylglyoxals (e.g. methylglyoxalbis(thiosemicarbazone);
5) Hormones (e.g. estrogens, androgens, tamoxifen, nafoxidine, progesterone, glucocorticoids, mitotane, prolactin);
6) Immunostimulants (e.g. human interferons, levamisole, and tilorane);
7) Monoclonal and polyclonal antibodies;
8) Radiosensitizing and radioprotecting compounds (e.g. metronidazole and misonidazole);
9) Other miscellaneous cytotoxic agents such as:
camptothecins;
quinolinequinones (e.g. streptonigrin and isopropylidene, azastreptonigrin);
cisplatin and related platinum complexes;
tricothecanes (e.g. trichodermol or vermicarin A);
cephalotoxines (e.g. harringtonine);
10) Cardioprotecting compounds, such as (±)-1,2-bis(3, 5-dioxopiperazin-1-yl) propane, commonly known as ICRF-187, and ICRF-198;
11) Drug-resistance reversal compounds such as P-glycoprotein inhibitors, for example Verapamil;
12) Cytotoxic cells such as lymphokine activated killer-cells or T-cells,
13) Immunostimulants such as interleukin factors or antigens.
14) Polynucleotides of sence or antisencing nature.
15) Polynucleotides capable of forming triple helices with DNA or RNA.
16) Polyethers
17) Distamycin and analogs.

The above list of possible therapeutic agents is not intended to limit this invention in any way.

The pharmaceutical compositions of the invention can be in forms suitable for oral, rectal, nasal, topical (including buccal and sublingual), vaginal or parenteral (including intraarterial intraperitoneal, intramuscular, subcutaneous and intravenous administration) by inhalation or by insufflation. Where appropriate, the formulations may be conveniently presented in discrete dosage units and may be prepared by any method well known in the art of pharmacy. All methods include the step of bringing into association the active compound with liquid carriers or finely divided solid carriers or both and then, if necessary, shaping the product into the desired formulation.

For injectable use, the pharmaceutical composition forms include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, chremophor-el, twin 80, glycerol, dimethyl sulfoxide (DMSO), propylene glycol, and liquid polyethylene glycol, and the like suitable mixtures thereof, and vegetable oils. The proper fluidity can be maintained for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredient or ingredients in the required amount in the appropriate solvent with various of the other ingredients enumerated above, as required followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

Pharmaceutical formulations suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils) or preservatives.

As used herein, the expression "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except isofar as any conventional media or agent is incompatible with the active ingredient, its use in the present compositions is contemplated. Supplementary active ingredients can be incorporated into the inventive compositions.

It is especially advantageous to formulate compositions in dosage unit form for ease of administration and uniformity of dosage. Dosage unit form as used in the specification and claims herein refers to physically discrete units suited as unitary dosages for the animal subjects to be treated, each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved and (b) the limitations inherent in the art of compounding such an active material for the treatment of disease in living subjects having a diseased condition in which bodily health is impaired as disclosed in detail in this specification.

The dosage of the principal active ingredient for the treatment of the indicated conditions depends upon the age, weight and condition of the subject being treated; the particular condition and its severity; the particular form of the active ingredient, the potency of the active ingredient, and the route of administration. A daily dose of from about 0.001 to about 100 mg/kg of body weight given singly or in divided doses of up to 5 times a day or by continuous infusion embraces the effective range for the treatment of most conditions for which the novel compounds are effective and substantially non-toxic. For a 75 kg subject, this translates into between about 0.075 and about 7500 mg/day. If the dosage is divided for example, into three individual dosages, these will range from about 0.25 to about 2500 mg. of the active ingredient. The preferred range is from about 0.1 to about 50 mg/kg of body weight/day with about 0.2 to about 30 mg/kg of body weight/day being more preferred.

The principal active ingredient is compounded for convenient and effective administration in effective amounts with a suitable pharmaceutically acceptable carrier in dosage unit form as hereinbefore disclosed. A unit dosage form can, for example, contain the principal active ingredient in amounts ranging from about 0.1 to about 1000 mg., with from about 1.0 to about 500 mg. being preferred. Expressed in proportions, the active ingredient is generally present in from about 0.1 to about 500 mg/ml of carrier. In the case of compositions containing supplementary active ingredients, the dosages are determined by reference to the usual dose and manner of administration of the said ingredients.

Antitumor treatment comprises the administration of any of the compounds of this invention in an acceptable pharmaceutical formulation at the effective therapeutic dosage. It is understood that chemotherapy can require the use of any of the compounds of this invention bound to an agent which facilitates targeting the compound to the tumor cells. The agent may be chosen from, for example, monoclonal or polyclonal antibodies, proteins and liposomes. The compounds of this invention could also be administered as monomeric, dimeric or oligomeric metal chelate complexes with, for example iron, magnesium or calcium.

The compounds of the invention exhibit antitumor or anticancer activity, most notably, antitumor or anticancer activity with human breast cancer, leukemia, colon cancer, lung cancer, renal cancer, ovarian cancer, CNS cancer and melanoma. This list of conditions is however not exclusive, and it is believed that the compounds of the invention will exhibit activity against other tumors and cancers, such as for example pancreatic cancer and bladder cancer.

The compounds of the invention may also be used for ex vivo treatment of patients before bone marrow transplant or other sorts of treatments to get rid of cancerous cells outside of the body.

Certain of the above described intermediates employed in the synthesis of compounds of the invention are also of interest from a pharmacological standpoint. Compounds believed to possess antibacterial, antifungal, antiviral, antitumor and anticancer activity include the following compounds as outlined in the different reaction schemes: (10), (11), as well as the compounds (12), (17), (18), (20), (21), (22), (24), (25), (26), (27), (29), (30), (32) through (41), (43) through (50), (53) and (54), (58), (59), (60), (64) to (70), (72), (77) to (79), (83) to (87), (91) to (96).

As with the compounds (10) and (11), the intermediates are preferably administered as a pharmaceutical composition for the treatment of the conditions listed above, and may be administered in the dosages noted above for the compounds (10) and (11). Moreover, the intermediates may be administered as pharmaceutically acceptable salts or as metal chelate complexes where appropriate, and may be administered as a mixture with other of the intermediates compounds, and/or with compounds of the formula (10) or (11), and/or with one or more of the therapeutic agents or agents targeting cancer or tumor cells.

Penultimate glycoside intermediates of the present invention comprise:

(1S',1R,3S)-methyl(6-hydroxy-1-(2',3',6'-trideoxy-3'-trifluoroacetamido-L-4'-O-p-nitrobenzoyl-L-lyxohexopyranose)-6-hydroxy-5,12-dioxo-3,4,5,12-tetrahydroanthraceno[2,3-C]pyran-3-yl)ketone;

(1'S, 1S, 3R)-methyl(6-hydroxy-1-(2',3',6'-trideoxy-3'-trifluoroacetamido-L-4'-O-p-nitrobenzoyl-L-lyxohexopyranose)-6-hydroxy-5,12-dioxo-3,4,5,12-tetrahydroanthraceno[2,3-C]pyran-3-yl)ketone;

(1'S,1R,3S)-methyl(1-(2',3',6'-trideoxy-3'-trifluoroacetamido-4'-O-p-nitrobenzoyl-L-lyxohexopyranose)-6,11dioxo-5-hydroxy-12acetoxy-3,4,6,11-tetrahydroanthraceno[2,3-C]pyran-3-yl)ketone;

(1'S,1S,3R)-methyl(1-(2',3',6'-trideoxy-3'-trifluoroacetamido-4'-O-p-nitrobenzoyl-L-lyxohexopyranose)-6,11dioxo-5-hydroxy-12acetoxy-3,4,6,11-tetrahydroanthraceno[2,3-C]pyran-3-yl)ketone;

(1'S,1R,3R)-5,12-dioxo-3-ethyl-6-hydroxy-1-(2',3',6'-trideoxy-3'-trifluoroacetamido-4'-O-p-nitrobenzoyl-L-lyxohexopyranose)-3,4,5,12-tetrahydroanthraceno[2,3-C]pyran;

(1'S,1S,3S)-5,12-dioxo-3-ethyl-6-hydroxy-1-(2',3',6'-trideoxy-3'-trifluoroacetamido-4'-O-p-nitrobenzoyl-L-lyxohexopyranose)-3,4,5,12-tetrahydroanthraceno[2,3-C]pyran;

(1'S,1R,3S)-1,2,3,4,5,12-hexahydro-6-hydroxy-3-trimethylacetoxyaceto-1-(N-trifluoroacetyl-4'-O-p-nitrobenzoyl-L-daunosamine)-(2-oxo)-naphthacene-6,11-dione;

(1'S,1S,3R)-1,2,3,4,5,12-hexahydro-6-hydroxy-3-trimethylacetoxyaceto-1-(N-trifluoroacetyl-4'-O-p-nitrobenzoyl-L-daunosamine)-(2-oxo)-naphthacene-6,11-dione;

(1'S,1R,3S)-3-bromoaceto-1-O-(3,4-di-O-acetyl-2',6'-dideoxy-2-lyxohexopyronosyl)-1,2,3,4,5,12-hexahydro-6-hydroxy(2-OXO)naphthacene-5,12-dione;

(1'S,1S,3R)-3-bromoaceto-1-O-(3,4-di-O-acetyl-2',6'-dideoxy-2-1yxohexopyronosyl)-1,2,3,4,5,12-hexahydro-6-hydroxy-(2-OXO)naphthacene-5,12-dione;

(1'S,1R,3S)-3-aceto-1-O-(3',4'-di-O-acetyl-2',6'-dideoxy-a-lyxohexopyranosyl)-1,2,3,4,5,12-hexahydro-6-hydroxy[2-oxo]naphthacene-5,12-dione;

(1'S,1S,3R)-3-aceto-1-O-(3',4'-di-O-acetyl-2',6'-dideoxy-a-lyxohexopyranosyl)-1,2,3,4,5,12-hexahydro-6-hydroxy[2-oxo]naphthacene-5,12-dione;

(1'S,1R,3S)-6-hydroxy-1-(2',3',6'-trideoxy-4'-p-nitrobenzoyl-3'-trifluoroacetamido-L-lyxohexopyranose)-3-(2-aza-3-acetamidothienyl)-5,-12-dioxo-3,4,5,12-tetrahydroanthraceno-[2,3-C]-pyran;

(1'S,1R,3S)-6-hydroxy-1-(2',3',6'-trideoxy-4'-p-nitrobenzoyl-3'-trifluoroacetamido-L-lyxohexopyranose)-3-(2-aza-3-acetamidothienyl)-5,-12-dioxo-3,4,5,12-tetrahydroanthraceno-[2,3-C]-pyran;

(1R,3R) or (1S,3S)cis-p-nitrobenzyl(5,12-dioxo-1-methyl-3,4,5,12-tetrahydroanthraceno[2,3-c]pyran-3-yl) formate; and (1'S,1S,3R) or (1'S,1R,3S)Methyl[11-acetoxy-6-hydroxy-1-(2',3',6'-trideoxy-3'-trifluoroacetamido-4'-O-p-nitrobenzoyl-L-lyxohexopyranose)-5,12-dioxo-3,4,5,12-tetrahydroanthraceno[2,3-c]pyran-3-yl]ketone;

(1S,3R) or (1R,3S)trans-p-nitrobenzyl(5,12-dioxo-1-methyl-3,4,5,12-tetrahydroanthraceno[2,3-c]pyran-3-yl) formate;

(1R,3R) or (1S,3S)cis-p-nitrobenzyl(5,12-dioxo-7,10-dimethoxy-1-methyl-3,4,5,12-tetrahydroanthraceno[2,3-c]pyran-3-yl)formate;

(1S,3R) or (1R,3S)trans-p-nitrobenzyl(5,12-dioxo-7,10-dimethoxy-1-methyl-3,4,5,12-tetrahydroanthraceno[2,3-c]pyran-yl)formate;

(1'S,1R,3S) or (1'S,1S,3R)Ethyl[11-acetoxy-1-(2',3',6'-trideoxy-3'-trifluoroacetamido-4'-O-p-nitrobenzoyl-L-lyxohexopyranose)- 5,12-dioxo-3,4,5,12-tetrahydroanthranceno[2,3-c]pyran-3-yl]formate;

(1'S,1R,3S) or (1'S,1S,3R)Methyl[6-acetoxy-1-(2',3',6'-trideoxy-3'-trifluoroacetamido-4'-O-p-nitrobenzoyl-L-lyxohexopyranose)-5,12-dioxo-3,4,5,12-tetrahydroanthraceno[2,3-c]pyran-3-yl]formate;

(1'S,1R,3S) or (1'S,1S,3R)Ethyl[6-acetoxy-1-(2',3',6'-trideoxy-3'-trifluoroacetamido-4'-O-p-nitrobenzoyl-L-lyxohexopyranose)-5,12-dioxo-3,4,5,12-tetrahydroanthraceno[2,3-c]pyran-3-yl]formate;

(1'S,1S,3R) or (1'S,1R,3S)ethyl[11-acetoxy-6-hydroxy-1-(2',3',6'-trideoxy-3'-trifluoroacetamido-4'-O-p-nitrobenzoyl-L-lyxohexopyranose)-5,12-dioxo-3,4,5,12-tetrahydroanthraceno[2,3-c]pyran-3-yl]formate;

(1'S,1R,3S) or (1'S,1S,3R)P-nitrobenzyl[-1-(2',3',6'-trideoxy-3'-trifluoroacetamido-4'-O-p-nitrobenzoyl-L-lyxohexopyranose)-5,12-dioxo-3,4,5,12-tetrahydroanthraceno[2,3-c]pyran-3-yl]formate.

Other aglycone intermerdiates of the invention comprise:

3-Ethyl-1,2,3,4-tetrahydro-1,5,12-trihydroxy(2-oxygen) naphthacene-6,11-dione;

1,6-Dihydroxy-3-ethyl-1,2,3,4-tetrahydro-(2-oxygen) naphthacene-5,12-dione;

Trans-3-aceto-1,6-hydroxy-1,2,3,4,5,12-hexahydro-2-(sulfur)naphthacene-5,12-dione;

cis-3-aceto-1,6-hydroxy-1,2,3,4,5,12-hexahydro-2-(sulfur)naphthacene-5,12-dione;

(1S,3S) or (1R,3R)Ethyl[11-acetoxy-1-hydroxy-5,12-dioxo-3,4,5,12-tetrahydroanthraceno[2,3-c]pyran-3-yl] formate;

(1S,3S) or (1R,3R)Methyl[6-acetoxy-1-hydroxy-5,12-dioxo-3,4,5,12-tetrahydroanthraceno[2,3-c]pyran-3-yl] formate;

(1S,3S) or (1R,3R)Ethyl[6-acetoxy-1-hydroxy-5,12-dioxo-3,4,5,12-tetrahydroanthraceno[2,3-c]pyran-3-yl] formate;

(1S,3S) or (1R,3R)Ethyl[11-acetoxy-1,6-dihydroxy-5,12-dioxo-3,4,5,12-tetrahydroanthraceno [2,3-c]pyran-3-yl]formate;

(1S,3S) or (1R, 3R)P-nitrobenzyl[11-hydroxy-5,12-dioxo-3,4,5,12-tetrahydroanthraceno[2,3-c]pyran-3-yl] formate;

(1S,3S) or (1R, 3R)Methyl[11-acetoxy-1,6-dihydroxy-5, 12-dioxo-3,4,5,12-tetrahydroanthraceno[2,3-c]pyran-3-yl]ketone;

(1R,3R) or (1S, 3S)-3-(2-acetoxy-1-propeneketal)aceto-6-acetoxy-1-hydroxy-1,2,3,4-tetrahydro-(2e-oxygen)-naphthacene-5,12-dione;

(1R,3R) or (1S,3S)-3-(2-acetoxy-1-propeneketal)aceto-11-acetoxy-1-hydroxy-1,2,3,4-tetrahydro-(2-oxygen) naphthacene-5,12-dione;

(1R,3R) or (1S,3S)-3-(2-hydroxy)aceto-6-acetoxy-1-hydroxy-1,2,3,4-tetrahydro-(2-oxygen)naphthacene-5,12-dione;

(1R,3R) or (1S,3S)-3-(2-hydroxy)aceto-11-acetoxy-1-hydroxy-1,2,3,4-tetrahydro-(2-oxygen)naphthacene-5,12-dione;

(1S,3S) or (1R,3R)-Methyl(1-methoxy-6-hydroxy-5,12-dioxo-3,4,5,12-tetrahydroanthraceno[2,3-c]pyran-3-yl)ketone;

(1S,3S) or (1R,3R)-Methyl(1-methoxy-11-hydroxy-5,12-dioxo-3,4,5,12-tetrahydroanthraceno[2,3-c]pyran-3-yl) ketone;

(1S,3S) or(1R,3R)-Methyl(1,6-dihydroxy-5,12-dioxo-3,4,5,12-tetrahydroanthraceno[2,3-c]pyran-3-yl) ketone;

(1S,3S) or (1R,3R)-Methyl(1,11-dihydroxy-5,12-dioxo-3,4,5,12-tetrahydroanthraceno[2,3-c]pyran-3-yl) ketone;

(1S,3S) or (1R,3R)-6-hydroxy-1-methoxy-1,2,3,4-tetrahydro-3-vinyl-(2-oxygen)naphthacene-5,12-dione;

(1S,3S) or (1R,3R)-6-acetoxy-1-methoxy-1,2,3,4-tetrahydro-3-vinyl-(2-oxygen)naphthacene-5,12-dione;

(1S,3S) or (1R,3R)-6-acetoxy-1-hydroxy-1,2,3,4-tetrahydro-3-vinyl-(2-oxygen)naphthacene-5,12-dione;

(1S,3S) or(1R,3R)-Methyl[1,11-dihydroxy-5,12-dioxo-3,4,5,12-tetrahydroanthraceno[2,3-c]pyran-3-yl]formate; and (1S,3S) or (1R,3R)-Methyl[1,6-dihydroxy-5,12-dioxo-3,4,5,12-tetrahydroanthraceno[2,3-c]pyran-3-yl]formate.

Further deoxy-aglycone intermediates of the present invention comprise:

Ethyl[11-acetoxy-5,12-dioxo-3,4,5,12-tetrahydroanthraceno[2,3-c]pyran-3-yl]formate;

methyl[6-hydroxy-5,12-dioxo-3,4,5,12-tetrahydroanthraceno[2,3-c]pyran-3-yl]formate;

Methyl[11-hydroxy-5,12-dioxo-3,4,5,12-tetrahydroanthraceno[2,3-c]pyran-3-yl]formate;

Methyl[6-acetoxy-5,12-dioxo-3,4,5,12-tetrahydroanthraceno[2,3-c]pyran-3-yl]formate;

Methyl[11-acetoxy-5,12-dioxo-3,4,5,12-tetrahydroanthraceno[2,3-c]pyran-3-yl]formate;

Ethyl[11-hydroxy-5,12-dioxo-3,4,5,12-tetrahydroanthraceno[2,3-c]pyran-3-yl]formate;

Ethyl[6-acetoxy-5,12-dioxo-3,4,5,12-tetrahydroanthraceno[2,3-c]pyran-3-yl]formate;

P-nitrobenzyl[5,12-dioxo-3,4,5,12-tetrahydroanthraceno[2,3-c]pyran-3-yl]formate;

Methyl(11-hydroxy-5,12-dioxo-3,4,5,12-tetrahydroanthraceno[2,3-c]pyran-3-yl)ketone;

Methyl(6-hydroxy-5,12-dioxo-3,4,5,12-tetrahydroanthraceno[2,3-c]pyran-3-yl)ketone;

(2-methoxymethoxy)aceto-6-hydroxy-1,2,3,4-tetrahydro-(2-oxygen)naphthacene-5,12-dione;

(2-methoxymethoxy)aceto-11-hydroxy-1,2,3,4-tetrahydro-(2-oxygen)naphthacene-5,12-dione;

(2-methoxymethoxy)aceto-6-acetoxy-1,2,3,4-tetrahydro-(2-oxygen)naphthacene-5,12-dione;

(2-methoxymethoxy)aceto-11-acetoxy-1,2,3,4-tetrahydro-(2-oxygen)naphthacene-5,12-dione;

(2-hydroxy-1-propeneketal)aceto-6-acetoxy-1,2,3,4-tetrahydro-(2-oxygen)naphthacene-5,12-dione;

(2-hydroxy-1-propeneketal)aceto-11-acetoxy-1,2,3,4-tetrahydro-(2-oxygen)naphthacene-5,12-dione;

(2-acetoxy-1-propeneketal)aceto-6-acetoxy-1,2,3,4-tetrahydro-(2-oxygen)naphthacene-5,12-dione;

(2-acetoxy-1-propeneketal)aceto-11-acetoxy-1,2,3,4-tetrahydro-(2-oxygen)naphthacene-5,12-dione;

(2-hydroxy)aceto-6-hydroxy-1,2,3,4-tetrahydro-(2-oxygen)naphthacene-5,12-dione;

(2-hydroxy)aceto-11-hydroxy-1,2,3,4-tetrahydro-(2-oxygen)naphthacene-5,12-dione;

3-carbomethoxy-6-hydroxy-1,2,3,4-tetrahydro-(2-sulfur)naphthacene-5,12-dione;

3-carbomethoxy-11-hydroxy-1,2,3,4-tetrahydro-(2-sulfur)naphthacene-5,12-dione;

3-carbomethoxy-6-acetoxy-1,2,3,4-tetrahydro-(2-sulfur)naphthacene-5,12-dione; and 3-carbomethoxy-11-acetoxy-1,2,3,4-tetrahydro-(2-sulfur)naphthacene-5,12-dione;

Ethyl(5,12-dihydroxy-6,11-dioxo-3,4,6,11-tetrahydroanthraceno[2,3-C]pyran-3-yl)formate;

Ethyl[6-acetoxy-11-hydroxy-5,12-dioxo-3,4,5,12-tetrahydroanthraceno[2,3-c]pyran-3-yl]formate;

Ethyl[6-hydroxy-11-acetoxy-5,12-dioxo-3,4,5,12-tetrahydroanthraceno[2,3-c]pyran-3-yl]formate;

Ethyl[6,11-diacetoxy-5,12-dioxo-3,4,5,12-tetrahydroanthraceno[2,3-c]pyran-3-yl]formate;

6,11-diacetoxy-3-(2-methoxymethoxy)aceto-1,2,3,4-tetrahydro-(2-oxygen)naphthacene-5,12-dione;

Methyl[6,11-diacetoxy-5,12-dioxo-3,4,5,12-tetrahydroanthraceno[2,3-c]pyran-3-yl]ketone;

Methyl(6-hydroxy-11-acetoxy-5,12-dioxo-3,4,5,12-tetrahydroanthraceno-[2,3-c]pyran-3-yl)ketone;

Methyl(11-hydroxy-6-acetoxy-5,12-dioxo-3,4,5,12-tetrahydroanthraceno-[2,3-c]pyran-3-yl)ketone;

5,12-dimethoxy-3-carbomethoxy-1,2,3,4-tetrahydro-(2-sulfur)-naphthacene-6,11-dione; and 5,12-dihydroxy-3-carbomethoxy-1,2,3,4-tetrahydro-(2-sulfur)-naphthacene-6,11-dione.

Compounds of formula (10) of the invention comprise:

(1'S,1R,3S) or (1'S,1S,3R)-Methyl(6-hydroxy-1-(3'-trifluoroacyl-daunosamine)-5,12-dioxo-3,4,5,12-tetrahydroanthraceno[2,3-C]pyran-3-yl)ketone, and mixture thereof;

(1S',1R,3S)Methyl(6-hydroxy-1-daunosamine)-5,12-dioxo-3,4,5,12-tetrahydroanthraceno[2,3-C]pyran-3-yl)ketone (1S',1S,3R)Methyl(6-hydroxy-1-daunosamine)-5,12-dioxo-3,4,5,12-tetrahydroanthraceno[2,3-C]pyran-3-yl)ketone;

(1'S,1R,3S)-methyl(1-(2',3',6'-trideoxy-3'-trifluoroacetamido-L-lyxohexopyranose)-6,11-dioxo-5,12-dihydroxy-3,4,6,11-tetrahydroanthraceno[2,3-C]pyran-3-yl)ketone;

(1'S,1S,3R)-methyl(1-(2',3',6'-trideoxy-3'-trifluoroacetamido-L-lyxohexopyranose)-6,11-dioxo-5,12-dihydroxy-3,4,6,11-tetrahydroanthraceno[2,3-C]pyran-3-yl)ketone;

(1'S,1R,3S)-methyl(1-(2',3',6'-trideoxy-3'amino-L-lyxohexopyranose)-6,11-dioxo-5,12-dihydroxy-3,4,6,11-tetrahydroanthraceno[2,3-C]pyran-3-yl)ketonehydrochloride;

(1'S,1S,3R)-methyl(1-(2',3',6'-trideoxy-3'amino-L-lyxohexopyranose)-6,11-dioxo-5,12-dihydroxy-3,4,6,11-tetrahydroanthraceno-[2,3-C]pyran-3-yl)ketonehydrochloride;

(1'S,1R,3S)-methyl(1-(2',3',6'-trideoxy-3'-morpholino-L-lyxohexopyranose)-6,11-dioxo-5,12-dihydroxy-3,4,6,11-tetrahydroanathraceno[2,3-C]pyran-3-yl)ketonehydrochloride;

(1'S,1S,3R)-methyl(1-(2',3',6'-trideoxy-3'-morpholino-L-lyxohexopyranose)-6,11-dioxo-5,12-dihydroxy-3,4,6,11-tetrahydroanathraceno[2,3-C]pyran-3-yl)ketonehydrochloride;

(1'S,1R,3S)-methyl(1-(2',3',6', -trideoxy-3'-(1"-cyanomorpholino)-L-lyxohexopyranose)-6,11-dioxo-5,12-dihydroxy-3,4,6,11-tetrahydroanthraceno[2,3-C]pyran-3-yl)ketone;

(1'S,1S,3R)-methyl(1-(2',3',6', -trideoxy-3'-(1"-cyanomorpholino)-L-lyxohexopyranose)-6,11-dioxo-5,12-dihydroxy-3,4,6,11-tetrahydroanthraceno[2,3-C]pyran-3-yl) ketone;

(1'S,1R,3R)-5,12-dioxo-3-ethyl-6-hydroxy-1-(2',3',6'-trideoxy-3'-trifluoroacetamido-4'-hydroxy-L-lyxohexopyranose)-3,4,5,12-tetrahydroanthraceno[2,3-c]pyran;

(1'S,1R,3R)-5,12-dioxo-3-ethyl-6-hydroxy-1-(2',3',6'-trideoxy-3'-amino-4'-hydroxy-L-lyxohexopyranose)-3,4,5,12-tetrahydroanthraceno[2,3-c]pyranhydrochloride;

(1'S,1S,3S)-5,12-dioxo-3-ethyl-6-hydroxy-1-(2',3',6'-trideoxy-3'-trifluoroacetamido-4'-hydroxy-L-lyxohexopyranose)-3,4,5,12-tetrahydroanthraceno[2,3-c]pyran;

(1S,1S,3S)-5,12-dioxo-3-ethyl-6-hydroxy-1-(2',3',6'-trideoxy-3'-amino-4'-hydroxy-L-lyxohexopyranose)-3,4,5,12-tetrahydroanthraceno[2,3-c]pyranhydrochloride;

(1'S,1R,3S)-1,2,3,4,5,12-hexahydro-6-hydroxy-3-trimethylacetoxyaceto-1-N-trifluoroacetyl-L-daunosamine-(2-oxo)naphthacene-5,12-dione;

(1', S,1R,3S)-1,2,3,4,5,12-hexahydro-6-hydroxy-3-hydroxy-aceto-1-N-trifluoroacetyl-L-daunosamine-(2-oxo)napthhacene-5,12-dione;

(1'S,1S,3R)-1,2,3,4,5,12-hexahydro-6-hydroxy-3-trimethylacetoxyaceto-1-N-trifluoroacetyl-L-daunosamine-(2-oxo)naphthacene-5,12-dione;

(1'S,1S,3R)-1,2,3,4,5,12-hexahydro-6-hydroxy-3-hydroxyaceto-1-N-trifluoroacetyl-L-daunosamine-(2-oxo)naphthacene-5,12-dione;

(1'S,1S,3R) or (1'S,1R,3S)-Methyl-(6-hydroxy-1-(2',6'-dideoxy-L-lyxohexopyranose)-5,12-dioxo-3,4,5,12-tetrahydroanthraceno(2,3-c)pyran-3-yl) ketone, and mixture thereof;

(1'S,1R,3S)-6-hydroxy-1-(2',3',6'-trideoxy-3'-trifluoroacetamido-L-lyxohexopyranose)-3-(2-aza-3-acetamidothienyl)-5,12-dioxo-3,4,5,12tetrahydroanthraceno[2,3-C]-pyran;

(1'S,1S,3R)-6-hydroxy-1-(2',3',6'-trideoxy-3'-trifluoroacetamido-L-lyxohexopyranose)-3-(2-aza-3-acetamidothienyl)-5,12-dioxo-3,4,5,12-tetrahydroanthraceno[2,3-C]pyran;

(1'S,1R,3S) or (1'S,1S,3R)methyl[11-hydroxy-1-(2',3',6'-trideoxy-3'-trifluoroacetamido-L-lyxohexopyranose)-5,12-dioxo-3,4,5,12-tetrahydroanthraceno[2,3-c]pyran-3-yl]formate, and mixture thereof;

(1'S,1R,3S) or (1'S,1S,3R)Ethyl[11-hydroxy-1-(2',3',6'-trideoxy-3-trifluoroacetamido-L-lyxohexopyranose)-5,12-dioxo-3,4,5,12-tetrahydroanthraceno[2,3-c]pyran-3-yl]formate, and mixture thereof;

(1'S,1R,3S) or (1'S,1S,3R) Ethyl[6-Methoxy, 11-hydroxy-1-(2',3',6'-trideoxy-3'-trifluoroacetamido-L-lyxohexopyranose)-5,12-dioxo-3,4,5,12-tetrahydroanthraceno[2,3-c]pyran-3-yl]formate, and mixture thereof;

(1'S,1R,3S) or (1'S,1S,3R)Ethyl[11-Methoxy, 6-hydroxy-1-(2',3',6'-trideoxy-3'-trifluoroacetamido-L-lyxohexopyranose)-5,12-dioxo-3,4,5,12-tetrahydroanthraceno[2,3-c]pyran-3-yl]formate, and mixture thereof;

(1'S,1R,3S) or (1'S, 1S,3R) Ethyl[6-hydroxy-1-(2',3',6'-trideoxy-3'-trifluoroacetamido-L-lyxohexopyranose)-5,12-dioxo-3,4,5,12-tetrahydroanthraceno[2,3-c]pyran-3-yl]formate, and mixture thereof;

(1'S,1R,3S) or (1'S,1S,3R) Methyl[6-hydroxy, 1-( 2',3',6'-trideoxy-3,4,5,12-trifluoroacetamido-L-lyxohexopyranose)-5,12-dioxo-3,4,5,12-tetrahydroanthraceno[2,3-c]pyran-3-yl]formate, and mixture thereof;

(1'S,1R,3S) or (1'S,1S,3R)methyl[1-(2',3',6'-trideoxy-3'-trifluoroacetamido-L-lyxohexopyranose)-5,12-dioxo-3,4,5,12-tetrahydroanthraceno[2,3-c]pyran-3-yl]formate, and mixture thereof;

(1'S,1S,3S) or (1'S,1R,3R)methyl[1-(2',3',6'-trideoxy-3'-trifluoroacetamido-L-lyxohexopyranose)-5,12-dioxo-3,4,5,12-tetrahydroanthraceno[2,3-c]pyran-3-yl]formate, and mixture thereof;

(1'S,1S,3S) or (1'S,1R,3S)Methyl[11-acetoxy-6-hydroxy-1-(2',3',6'-trideoxy-3'-L-trifluoroacetamido-L-lyxohexopyranose)-5,12-dioxo-3,4,5,12-tetrahydroanthraceno[2,3-c]pyran-3-yl]ketone, and mixture thereof;

(1'S,1R,3S)-methyl(6-hydroxy-1-(2',3',6'-trideoxy-3'-amino-L-lyxohexopyranose)-5,12-dioxo-3,4,5,12-tetrahydroanthraceno[2,3-C]pyran-3-yl)ketone;

(1'S,1S,3R)-methyl(6-hydroxy-1-(2',3',6'-trideoxy-3'-amino-L-lyxohexopyranose)-5,12-dioxo-3,4,5,12-tetrahydroanthraceno[2,3-C]pyran-3-yl)ketone;

(1'S,1R,3S)-methyl(5,12-dihydroxy-1-(2',3',6'-trideoxy-3'-amino-L-lyxohexopyranose)-6,11-dioxo-3,4,6,11-tetrahydroanthraceno[2,3-C]pyran-3-yl)ketone;

(1'S,1S,3R)-methyl(5,12-dihydroxy-1-(2',3',6,-trideoxy-3-amino-L-lyxohexopyranose)-6,11-dioxo-3,4,6,11-tetrahydroanthraceno[2,3-C]pyran-3-yl)ketone;

(1'S,1R,3S)-3-aceto-1-(2'-iododaunosamine)-6-hydroxy-5,12-dioxo-3,4,5,12-tetrahydroanthraceno[2,3-C]pyran;

(1'S,1S,3R)-3-aceto-1-(2'-iododaunosamine)-6-hydroxy-5,12-dioxo-3,4,5,12-tetrahydroanthraceno[2,3-C]pyran;

(1'S,1R,3S)-3-aceto-1-(2'-iododaunosamine)-5,12-dihydroxy-6,11-dioxo-3,4,6,11-tetrahydroanthraceno[2,3-C]pyran;

(1'S,1S,3R)-3-aceto-1-(2'-iododaunosamine)-5,12-dihydroxy-6,11-dioxo-3,4,6,11-tetrahydroanthraceno[2,3-C]pyran;

(1'S,1R,3S)-3-aceto-1-(2'-deoxy-2'-iodofucose)-6-hydroxy-5,12-dioxo-3,4,5,12-tetrahydroanthraceno[2,3-C]pyran;

(1'S,1S,3R)-3-aceto-1-(2'-deoxy-2'-iodofucose)-6-hydroxy-5,12-dioxo-3,4,5,12-tetrahydroanthraceno[2,3-C]pyran;

(1'S,1R,3S)-3-aceto-1-(2'-deoxy-2'-iodofucose)-5,12-dihydroxy-6,11-dioxo-3,4,6,11-tetrahydroanthraceno[2,3-C]pyran; and (1'S,1S,3R)-3-aceto-1-(2'-deoxy-2'-iodofucose)-5,12-dihydroxy-6,11-dioxo-3,4,6,11-tetrahydroanthraceno[2,3-C]pyran.

Preferred compounds of the invention may also be selected from those that show an average activity below 10 μM:

BCH-657: Ethyl[1-hydroxy-11-acetoxy-5,12-dioxo-3,4-5,12-tetrahydroanthraceno(2,3-C)pyran-3-yl]formate;

BCH-659: Ethyl[6-acetoxy-5,12-dioxo-3,4-5,12-tetrahydroanthraceno(2,3-C)pyran-3-yl]-formate;

BCH-660: Ethyl[1-hydroxy-6-acetoxy-5,12-dioxo-3,4-5,12-tetrahydroanthraceno(2,3-C) pyranyl]formate;

BCH-671: (1'S,1R,3S) Methyl(1-[2',3',6'-trideoxyacetamido-4'-hydroxy-L-lyxohexopyranose)-5,12-dioxo-3,4,5,12-tetra-hydroanthraceno(2,3-c)pyran-3-yl)formate;

BCH-674 and BCH-675: (1'S,1S,3R) and 1'S',1R,3S) Methyl(11-hydroxy-6-methoxy-1-[2',3',6'-trideoxy-3-trifluoroacetamido-4'-hydroxy-L-lyxohexopyranose]-5,12-dioxo-3,4,5,12-tetrahydroanthra-ceno[2,3-c]pyran-3-yl)formate;

BCH-681: (1'S,1R,3S)Ethyl[6-hydroxy-5,12-dioxo-1-(3'-trifuloroacetamido-1-daunosaminyl)-3,4,5,12-tetrahydroanthraceno(2,3-C)pyran-3-yl]formate;

BCH-684: (1'S,1S,3R)Ethyl[6-hydroxy-5,12-dioxo-1-(3'-trifluoroacetamido-1-daunosaminyl)-3,4,5,12-tetrahydroanthraceno(2,3-C)pyran-3-yl]formate;

BCH-689: (1'S',1R,3S) and (1'S,1S,3R)Ethyl[6-hydroxy-11-methoxy-5,12-dioxo-1-(3'-trifuloroacetamido-1-daunosaminyl)-3,4,5,12-tetrahydroanthraceno(2,3-C)pyran-3-yl]formate;

BCH-691: (1'S,1R,3S)-Methyl-{11-hydroxy-1-(2',3',6'-trideoxy-3'-trifluoroacetamido-4'-hydroxy-L-lyxoheoxpyranose)-5,12-dioxo-3,4,5,12-tetrahydroanthraceno[2,3-c]pyran-3-yl}formate;

BCH-710: 3-[2-Acetoxy-1-trimethylene-ketal]-aceto-6-acetoxy-1-hydroxy-1,2,3,4-tetrahydro-(2-oxygen)-naphthacene-5,12-dione; and 3-[2-Acetoxy-1-trimethylene-ketal]-aceto-11-acetoxy-1-hydroxy-1,2,3,4-tetrahydro-(2-oxygen)-naphthacene-5,12-dione;

BCH-724: (1'S,1S,3R)-Methyl-[11-hydroxy-1-(2',3',6'-trideoxy-3'-trifluoroacetamido-4'-hydroxy-L-lyxohexopyranose)-5,12-dioxo-2,3,5,12-tetrahydroanthraceno(2,3-C)pyran-3-yl]ketone;

BCH-725: (1S,3S) and (1R,3R)-6-hydroxy-3-hydroxymethyl-1-methoxy-1,2,3,4-tetrahydro-(2-sulfur)-naphthacene-5,12-dione;

BCH-730: (1'S,1R,3S)Methyl(6-hydroxy-1-(2',3',6'-trideoxy-3'-trifluoroacetamido-4-hydroxy-L-lyxohexopyranose-5,12-dioxo-3,4,5,12-tetrahydroanthraceno(2,3-C) pyran-3-yl]ketone;

BCH-731: (1'S,1R,3S) and (1'S,1S,3R)-3-(2-acetoxy-1-trimethyleneketal)aceto-6-acetoxy-1,2,3,4,5,12-hexahydro-1-N-trifluoroacetyl-L-daunosamine(2-oxygen)naphthacene-5,12-dione; and (1'S,1R,3S) and (1'S,1S,3R)-3-(2-acetoxy-1-trimethyleneketal) aceto-11-acetoxy-1,2,3,4,5,12-hexahydro-1-N-trifluoroacetyl-L-daunosamine(2-oxygen)naphthacene-5,12-dione;

BCH-733: 3-(2-Acetoxy-1-propeneketal-aceto-11-acetoxy-1-hydroxy-1,2,3,4,-tetrahydro-(2-oxygen)naphtacene-5,12-dione;

BCH-734: 3-(2-Acetoxy-1-propeneketal)aceto-6-acetoxy-1-hydroxy-1,2,3,4-tetrahydro-(2-oxygen)naphthacene-5,12-dione; and BCH-736: (1'S,3R) or (1R,3S)-6-Acetoxy-3-acetoxyaceto-1,2,3,4,5,12-hexahydro-1-hydroxy(2-oxygen)-naphthacene-5,12-dione; and (1S,3R) or (1R,3S)-11-Acetoxy-3-acetoxyaceto-1,2,3,4,5,12-hexahydro-1-hydroxy(2-oxygen)naphthacene-5,12-dione;

BCH-746: (1'S,1S,3S) and (1'S,1R,3S)-3-(2-acetoxy-1-trimethyleneketal)aceto-1,2,3,4,5,12-hexahydro-6-hydroxy-1-N-trifluoroacetyl-L-daunosamine(2-oxygen)-naphthacene-5,12-dione; and (1'S,1S,3R) and (1'S,1R,3S)-3-(2-acetoxy-1-trimethyleneketal) aceto-1,2,3,4,5,12-hexahydro-11-hydroxy-1-N-trifluoroacetyl-L-daunosamine(2-oxygen) naphthacene-5,12-dione;

BCH-1112: 3-ethyleneketalaceto-1,2,3,4,5,12-hexahydro-11-hydroxy-(2-oxygen)naphthacene-5,12-dione;

BCH-1123: (1'S,1S,3R)-Methyl-[6-hydroxy-1-(2',3',6'-trideoxy-3',4'-dihydroxy-L-lyxohexopyranose)-5,12-dioxo-3,4,5,12-tetrahydroanthraceno(2,3-C)pyran-3-yl]ketone;

BCH-1124: (1'S,1R,3S)-Methyl-[6-hydroxy-1-(2',3',6'-trideoxy-3',4'-dihydroxy-L-lyxohexopyranose)-5,12-dioxo-2,3,5,12-tetrahydroxyanthraceno(2,3-C)pyran-3-yl]ketone;

BCH-1127: (1'S,1S,3R)-Methyl-[6-hydroxy-1-(2',3',6'-trideoxy-3'-amino-4'-hydroxy-L-lyxohexopyranose)-5,12-dioxo-3,4,5,12-tetrahydroanthraceno-(2,3-C)pyran-3-yl]ketone hydrochloride;

BCH-1128: (1'S,1R,3S)-Methyl-[6-hydroxy-1-(2',3',6'-trideoxy-3'-amino-4'-hydroxy-L-lyxohexopyranose-5,12-dioxo-3,4,5,12-tetrahydroanthraceno-(2,3-C)pyran-3-yl]ketone hydrochloride;

BCH-1130: (1'S',1S,3R) and (1'S,1R,3S)-Methyl-[5,12-dihydroxy-1-(2',3',6'-trideoxy-3'-amino-4'-hydroxy-L-lyxohexopyranose)-6,11-dioxo-3,4,6,11-tetrahydroanthraceno-(2,3-C)pyran-3-yl]ketone hydrochloride;

BCH-1131: (1'S,1S,3R) and (1'S,1R,3S)-Methyl-[5,12-dihydroxy-1-(2',3',6'-trideoxy-3'-trifluoroacetamido-4'-hydroxy-L-lyxohexopyranose)-6,11-dioxo-3,4,6,11,tetrahydroanthraceno-(2,3-C)pyran-3-yl]ketone;

BCH-1153: (1'S,1S,3R) or (1'S,1R,3S)-3-(2-hydroxy-1-trimethyleneketal)aceto-1,2,3,4,5,12-hexahydro-6-hydroxy-1-L-daunosamine(2-oxo)naphthacene-5,12-dione-hydrochloride;

BCH-1179: (1'S,1S,3R) or (1'S,1R,3S)-3-(2-acetoxy-1-trimehtyleneketal)aceto-1,2,3,4,5,12-hexahydro-11-acetoxy-1-(N-trifluoroacetyl-L-daunosamine)(2-oxo) naphthacene-5,12-dione;

BCH-1187: (1'S,1S,3S)-5,12-Dioxo-3-ethyl-6-hydroxy-1-(2',3',6'-trideoxy-3'-trifluoroacetamido-4'-hydroxy-L-lyxohexopyranose)-3,4,5,12-tetrahydroanthraceno(2,3-C)pyran;

BCH-1191: (1'S,1R,3S) and (1'S,1S,3R)-Methyl(1-(2',3',6'-trideoxy-3'-morpholino-L-lyxohexopyranose)-6,11-dioxo-5,12-dihydroxy-3,4,6,11-tetrahydroanthraceno[2,3-c]pyran-3-yl)ketone;

BCH-1193: (1'S',1R,3S) and (1'S,1S,3R)-Methyl(1-(2',3',6'-trideoxy-3'-morpholino-L-lyxohexopyranose)-6,11-dioxo-5,12-dihydroxy-3,4,6,11-tetrahydroanthraceno[2,3-c]pyran-3-yl)ketone hydrochloride;

BCH-1194: (1'S,1R,3S)-Methyl-[5,12-dihydroxy-1-(2',3',6'-trideoxy-3'-amino-4'-hydroxy-L-lyxohexopyranose)-6,11-dioxo-3,4,6,11-tetrahydroanthraceno-(2,3-C)pyran-3-yl]ketone hydrochloride;

BCH-1195: (1'S,1S,3R)-Methyl-[5,12-dihydroxy-1-(2',3',6'-trideoxy-3'-amino-4'-hydroxy-L-lyxohexopyranose)-6,11-dioxo-3,4,6,11-tetrahydroanthraceno-(2,3-C)pyran-3-yl]ketone hydrochloride;

BCH-1606: (1'S,1R,3R)-5,12-Dioxo-3-ethyl-6-hydroxy-1-[2',3',6'-trideoxy-3'-trifluoroacetamido-4'-hydroxy-L-lyxohexopyranose]-3,4,5,12-tetrahydroanthraceno(2,3-C)pyran;

BCH-1610: (1'S,1S,3s)-5,12-Dioxo-3-ethyl-6-hydroxy-1-[2',3',6'-trideoxy-3'-amino-4'-hydroxy-L-lyxohexopyranose]-3,4,5,12-tetrahydroanthraceno (2,3-C)pyran hydrochloride;

BCH-1611: (1'S,1R,3S) or (1'S,1S,3R)-1,2,3,4,5,12-hexahydro-6-hydroxy-1-L-daunosamine -3-vinyl(2-oxo)naphthacene-5,12-dione;

BCH-1614: (1'S,1R,3R)-5,12-Dioxo-3-ethyl-6-hydroxy-1-[2',3',6'-trideoxy-3'-amino-4'-hydroxy-L-lyxohexopyranose]-3,4,5,12-tetrahydroanthraceno (2,3-C)pyran hydrochloride;

BCH-1617: (1'S,1R,3S)-Methyl-(6-hydroxy-1-(2',3',4',6'-tetradeoxy-3'-trifluoroacetamido-4,-iodo-L-lyxohexopyranose)-5,12-dioxo-3,4,5,12-tetrahydroanthraceno[2,3-c]pyran-3-yl)ketone;

BCH-1618: (1'S,1S,3R)-Methyl-(6-hydroxy-1-(2',3',4',6'-tetradeoxy-3'-trifluoroacetamido-4'-iodo-L-lyxohexopyranose)-5,12-dioxo-3,4,5,12-tetrahydroanthraceno[2,3-c]pyran-3-yl)ketone;

BCH-1619: (1'S,1S,3R)-6-Hydroxy-1-[2',3',6'-trideoxy-3'-trifluoroacetamido-L-lyxohexopyranose]-3-(2-aza-3-acetamidothienyl)-5,12-dioxo-3,4,5,12-tetrahydroanthraceno(2,3-C)pyran;

BCH-1626: (1'S,1R,3S) and (1'S,1S,3R)-1-O-(3',4'-di-O-acetyl-2',6'-dideoxy-α-lyxohexopyranosyl)-1,2,3,4,5,12-hexahydro-6-hydroxy-3-hydroxyaceto-(2-oxo)naphthacene-5,12-dione;

BCH-1628: 3-Aceto-1-O-(ethanoamino)-1,2,3,4,5,12-hexahydro-6-hydroxy-(2-sulfur)naphthacene-5,12-dione hydrochloride;

BCH-1633: (1'S,1S,3S)-3-Ethyl-5,12-dihydroxy-1-(2',3',6'-trideoxy-3'-amino-4'-hydroxy-L-lyxohexopyranose)-1,2,3,4-tetrahydro-(2-oxygen)naphthacene-6,11-dione-hydrochloride;

BCH-1635: (1'S,1R,3S) and (1'S', 1S,3R)-3-aceto-1,2,3,4,5,12-hexahydro-6-hydroxy-1-N-trifluoroacetyl-L-daunosamine-(2-sulfur)naphthacene-5,12-dione;

BCH-1636: (4'R,1R,3S) and (4'R,1S,3R)-3-aceto-1-(2',2'-dimethyl-1',3'-dioxanyl-4'-methoxyl)-6-hydroxyl-1,2,3,4,5,12-hexahydro-(2-sulfur)naphthacene-5,12-dione;

BCH-1641: (1'S,1S,3R)-3-Aceto-1,2,3,4,5,12,hexahydro-6-hydroxy-1-N-trifluoroacetyl-L-daunosamine-(2-sulfur)naphthacene-5,12-dione;

BCH-1645: (2'R,1R,3S) and (2'R,1S,3R)-3-aceto-1-(2',3'-dihydroxy)-N-propoxy-6-hydroxy-1,2,3,4,5,12-hexahydro-(2-sulfur)naphthacene-5,12-dione;

BCH-1646: (1'S,1R)-1-[(2',3',6'-trideoxy-3'-acetamido-L-lyxohexopyranosyl)oxy]-6-hydroxy-3,4,5,12-tetrahydro-5,12-dioxo-1H-anthra(2,3-C)pyran;

BCH-1647: (1'S,1S)-1-[(2',3',6'-tetradeoxy-3'-acetamido-L-lyxohexopyranosyl)oxy]-6-hydroxy-3,4,5,12-tetrahydro-5,12-dioxo-1H-anthra(2,3-C)pyran;

BCH-1650: 3-Dimethylphosphonoacetyl-6-hydroxy-1-methoxy-5,12-dioxo-3,4,5,12-tetrahydroanthraceno-(2,3-C)pyran;

BCH-1652: 3-Phenylsulfonyl-6-hydroxy-1,2,3,4-tetrahydro-(2-oxygen)naphthacene-5,12-dione; and 3-phenylsulfonyl-11-hydroxy-1,2,3,4-tetrahydro-(2-oxygen)naphthacene-5,12-dione;

BCH-1653: (1'S,1R,3S)-6-Hydroxy-1-(2',3',6'-trideoxy-3'-trifluoroacetamido-L-lyxohexopyranose)-3-diethylaminocarbonyl-5,12-dioxo-3,4,5,12-tetrahydroanthraceno-(2,3-C)pyran;

BCH-1656: (1'S,1R,3S)-6-hydroxy-1-(2',3',6',-trideoxy-3'-trifluoroacetamido-L-lyxohexopyranose)-3-diethylaminocarbonyl-5,12-dioxo-3,4,5,12-tetrahydroanthraceno-(2,3-C)-pyran;

BCH-1657: (1S,2'S,3R) and (1R,2'S,3S)-Methyl-(6-hydroxy-1-[O-serine methyl ester]-5,12-dioxo-3,4,5,12-tetrahydroanthraceno-[2,3-C]pyran-3-yl)ketone hydrochloride;

BCH-1660: (4'S,1R,3S) and (4'S,1S,3R)-3-Aceto-1-(2',2'-dimethyl-1',3'-dioxanyl-4'-methoxy)-6-hydroxy-1,2,3,4,5,12-hexahydro-(2-sulfur)naphthacene-5,12-dione;

BCH-1661: (4'R,1R,3S) and (4'R,1S,3R)-3-Aceto-1-(2',2'-dimethyl-1',3'-dioxanyl-4'-methoxy)-6-hydroxy-1,2,3,4,5,12-hexahydro-(2-oxo)naphthacene-5,12-dione;

BCH-1668: (1R,1'S)-3,3-Bis-carbomethoxy-1-(1'-carbomethoxyethoxy)- 5,12-dioxo-6-hydroxy-3,4,5,12-tetrahydroanthraceno[2,3-C]pyran;

BCH-1669: (2'R,1R,3S) and (2'R,1S,3R)-3-Acetyl-1-(2',3'-dihydroxy)-n-propoxy-6-hydroxy-1,2,3,4,5,12-hexahydro-(2-oxo)naphthacene-5,12-dione;

BCH-1670: (2'S,1R,3S) and (2'S,1S,3R)-3-acetyl-1-(2',3'-dihydroxy)-n-propoxy-6-hydroxy-1,2,3,4,5,12-hexahydro-(2-sulfur)naphthacene-5,12-dione;

BCH-1671: (1'S,1S,3R)-3-acetyl-1-O-(3',4'-di-O-acetyl-2',6'-dideoxy-α-lyxohexopyranosyl)-1,2,3,4,5,12-hexahydro-6-hydroxy(2-sulfur)naphthacene-5,12-dione;

BCH-1672: (1'S,1R,3S)-Methyl-[5,12-dihydroxy-1-(2',6'-dideoxy-3',4'-dihydroxy-2'-iodo-L-lyxohexopyranose)-6,11-dioxo-3,4,6,11-tetrahydroanthraceno-(2,-C)pyran-3-yl]ketone;

BCH-1675: (1'S,1S,3R)-Methyl-(5,12-dihydroxy-1-(2',6'-dideoxy-3',4'-dihydroxy-2'-iodo-L-lyxohexopyranose)-6,11-dioxo-3,4,6,11-tetrahydroanthraceno(2,3-C)pyran-3-yl]ketone;

BCH-1676 & 1677:(1'S,1R,3S) and (1'S,1S,3R)-5,12-dioxo-3-(1,1-difluoroethyl)-6-hydroxy-1-(2',3',6'-trideoxy-3'-trifluoroacetamido-L-lyxohexopyranose)-3,4,5,12-tetrahydroanthraceno-[2,3-c]-pyran;

BCH-1678: (1'S,1R,3S)-6-hydroxy-1-(2',3',6'-trideoxy-3'-trifluroacetamido-L-lyxohexopyranose)-3-dimethylphosphonoacetyl-5,12-dioxo-3,4,5,12-tetrahydroanthraceno[2,3-C]-pyran;

BCH-1679: (1'S,1S,3R)-6-hydroxy-1-(2',3',6'-trideoxy-3'-trifluroacetamido-L-lyxohexopyranose)-3-dimethylphosphonoacetyl-5,12-dioxo-3,4,5,12-tetrahydroanthraceno-[2,3-C]-pyran;

BCH-1680: (1'S,1S,3R) and (1'S,1R,3S)-Methyl-(6-hydroxy- 1-(2',3',4',6'-tetradeoxy-4'-trifluoroacetamido-L-lyxohexopyranose)-5,12-dioxo-3,4,5,12-tetrahydroanthraceno-[2,3-C]pyran-3-yl)ketone;

BCH-1681: (1'S,1S,3R)-Methyl-(1-[2',6'-dideoxy-3',4'-diacetyl-2'-iodo-L-lyxohexopyranose]-6-hydroxy-3,4,5,10-tetrahydroanthracenо[2,3-c]pyran-3-yl)ketone;

BCH-1683: (1'S,1S,3R) and (1'S,1R,3S)-3-(2-aminoethyl)-5,12-dihydroxy-1-(2',3',6'-trideoxy-3',4'-dihydroxy-L-lyxohexopyranose)-6,11-dioxo-3,4,6,11-tetrahydro-1H-anthra[2,3-C]pyran hydrochloride;

BCH-1686: (1'S,1S,3S)-3-(6-hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl)propene;

BCH-1687: (1'S,1R,3R)-3-(6hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3'-C]pyran-3-yl)porpene;

BCH-1694: (1'S,1R,3S)-5,12-dioxo-6-hydroxy-3-methoxymethyl-1-(2',3',6'-trideoxy-3'-trifluoroacetamido-L-lyxohexopyranose)-3,4,5,12-tetrahydroanthraceno-[2,3-C]pyran;

BCH-1696: (1'S,1S,3R)-5,12-dioxo-6-hydroxy-3-methoxymethyl-1-(2',3',6'-trideoxy-3'-trifluoroacetamido-L-lyxohexopyranose)-3,4,5,12-tetrahydroanthraceno-[2,3-C]pyran;

BCH-1698: (1'S,1S)-5,12-dioxo-6-hydroxy-3,3-bis-methoxymethyl-1-(2',3',6'-trideoxy-3'-trifluoroacetamido-L-lyxohexopyranose)-3,4,5,12-tetrahydroanthraceno-[2,3-C]pyran;

BCH-1990: (1'S,1R,3S)-methyl-(1[2',6'-dideoxy-3',4'-dihydroxy-2'-iodo-L-lyxohexopyranose]-5,12-dioxo-3,4,5,12-tetrahydroanthraceno[2,3-C]pyran-3-yl)ketone;

BCH-1991: (1'S,1S)-5,12-dioxo-6-hydroxy-3,3-bis-methoxymethyl-1-(2',3',6'-trideoxy-3'-amino-L-lyxohexopyranose)-3,4,5,12-tetrahydroanthraceno-[2,3-c]-pyran hydrochloride;

BCH-1992: (1'S,1S,3R) and (1'S,1R,3S)-5,12-dihydroxy-3-methoxymethyl-1-(2',3',6'-trideoxy-3'-amino-L-lyxohexopyranose)-1,2,3,4-tetrahydro-(2-oxygen)-naphthacene-6,11-dione hydrochloride;

BCH-1993: (4'S,1R,3S)-3-aceto-1-(2',2'-dimethyl-1',3'-dioxanyl-4'-methoxy)-6-hydroxy-1,2,3,4,5,12-hexahydro-(2-sulfur)naphthacene-5,12-dione;

BCH-1994: (4'S,1S,3R)-3-aceto-1-(2',2'-dimethyl-1',3'-dioxanyl-4'-methoxy)-6-hydroxy-1,2,3,4,5,12-hexahydro-(2-sulfur)naphthacene-5,12-dione;

BCH-1997: (1'S,1S,3R,13R)-3-dihydroxyethyl-6-hydroxy-1-(N-trifluoroacetyl-L-daunosamine-(2-oxo)naphthacene-5,12-dione;

BCH-2001: (1'S,1R,3S)-3-{6-hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl}(phenyl)sulfone;

BCH-2002: (1'S,1S)-6-hydroxy-1-(2',3',6'-trideoxy-3'-trifluoroacetamido-4'-hydroxy-L-lyxohexopyranose)-5,12-dioxo-5,12-dihydroanthraceno-[2,3-C]pyran;

BCH-2005: (1'S,1R,3R)-3-{6-Hydroxy-1-(2',3',6-trideoxy-3'amino-4'-hydroxy-L-lyxohexopyranose)-5,12-dioxo-3,4,5,12-tetrahydroanthraceno-[2,3-C]pyran-3'yl}propene hydrochloride;

BCH-2006: (1'S,1S,3S)-3-{6-Hydroxy-1-(2',3',6'-trideoxy-3'-amino-4'-hydroxy-L-lyxohexopyranose)-5,12-dioxo-3,4,5,12-tetrahydroanthraceno-[2,3-C]pyran-3-yl}propene hydrochloride;

BCH-2007: (1'S,1R,3S)-3-{6-Hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]-pyran-3-yl}nitrile;

BCH-2008: (1'S,1S,3R)-3-{6-Hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl}nitrile;

BCH-2012: (1'S,1R,3S)-3-{6-Hydroxy-1-(2',3',6'-trideoxy-3'-amino-4'-hydroxy-L-lyxohexopyranose)-5,12-dioxo-3,4,5,12-tetrahydroanthraceno-[2,3-C]pyran-3-yl}benzene hydrochloride;

BCH-2016: (1'S,1R,3R)-3-Ethyl-5,12-dihydroxy-1-(2',3',6'-trideoxy-3'-amino-L-lyxohexopyranose)-1,2,3,4-tetrahydro-(2-oxygen)-naphtacene-6,11-dione hydrochloride;

BCH-2025: (1'S,1S,3R)-3-{6-hydroxy-1-(2',3',6'-trideoxy-3'-trifluoroacetamido-4'-hydroxy-L-lyxohexopyranose)-5,12-dione-3,4,5,12-tetrahydroanthraceno-[2,3-c]pyran-3-yl}(phenyl) sulfone;

BCH-2034: (2'S,1R,3S) and (2'S,1S,3R)-3-acetyl (-2',3'-dihydroxy)-N-propoxy-6-hydroxy-1,2,3,4,5,12-hexahydro-(2-oxo)naphthacene-5,12-dione;

BCH-2036: Trans 3-acetyl-6-hydroxy-1-[3'-N-(vinyl carboxy)amino propoxy]-1,2,3,4,5,12-hexahydro (2-oxo)naphthacene-5,12-dione;

BCH-2048: (1'S,1R,3S)-5,12-dioxo-6-hydroxy-3-phenyloxy-1-(2',3',6'-trideoxy-3'-trifluoroacetamido-L-lyxohexopyranose)-3,4,5,12-tetrahydroanthraceno-[2,3-c]pyran;

BCH-2049: (1'S,1S,3R)-5,12-trihydroxy-3-isopropyl-1-(2',3',6'-trideoxy-3'-amino-L-lyxohexopyranose)-1,2,3,4-tetrahydro-(2-oxygen)-naphtacene-6,11-dione-hydrochloride;

BCH-2050: (1'S,1R,3S)-5,12-Dixydroxy-3-isopropy-1-(2',3',6'-trideoxy-3'-amino'L-lyxohexopyranose)-1,2,3,4-tetrahydro-(2-oxygen)-naphtacene-6,11-dione-hydrochloride;

BCH-2055: Diastereomeric mixture of (1'-S,1-R,3-S) and (1'-S,1-S,3-R)(5,12-dihydroxy-1-(2',3',6'-trideoxy-3'-trifluoroacetamido-4'hydroxy-L-lyxohexopyranose)-6,11-dioxo-3,4,5,12-tetrahydroanthraceno-[2,3-c]pyran-3-yl)nitrile;

BCH-2056: Diastereomeric mixture of (1'-S,1-R,3-S) and (1'-S,3-R)(5,12-dihydroxy-1-(2',3',6'-trideoxy-3'-amino-4'-hydroxy-L-lyxohexopyranose)-6,11-dioxo-3,4,5,12-tetrahydroanthraceno-[2,3-c]pyran-3-yl)nitrile;

BCH-2057: (1'S,1S,3R)-5,12-dioxo-6-hydroxy-3-phenyloxymethyl-1-(2',3',6'-trideoxy-3'-trifluoroacetamido-L-lyxohexopyranose)-3,4,5,12-tetrahydroanthraceno-[2,3-c]pyran;

BCH-2058 & 2059:(1'S,1R,3S) and (1'S,1S,3R)-5,12-Dihydroxy-3-phenyloxymethyl-1-(2',3',6'-trideoxy-3'-amino-L-lyxohexopyranose)-1,2,3,4-tetrahydro-(2-oxygen)naphtacene-6,11-dione-hydrochloride;

BCH-2063: (1'S,1R,3S)-Methyl-(5,12-dihydroxy-1-(2',3',6'-trideoxy-3'-trifluoroacetamido-2'-iodo-4'-hydroxy-L-lyxohexopyranose)-6,11-dioxo-3,4,6,11-tetrahydroanthraceno-[2,3C]-pyran-3-yl)-ketone;

BCH-2064: (1'S,1S,3R)-Methyl-(1-[2',3',6'-trideoxy-3'-trifluoroacetamido-4'-hydroxy-2'-iodo-L-lyxohexopyranose]-5,12-dioxo-3,4,5,12-tetrahydroanthraceno[2,3-C]pyran-3-yl)ketone;

BCH-2066: (1'S,1R,3S)-Methyl-(5,12-dihydroxy-1-[2',3',6'-trideoxy- 3'-amino-4'hydroxy-2'-iodo-L-lyxohexopyranose]-6,11-dioxo-3,4,6,11-tetrahydroanthraceno-[2,3C]-pyran-3-yl) ketone hydrochloride;

BCH-2073: (1,R,1R,3S)-3-Aceto-6-hydroxy-1-(2-deoxy-2-chloroethylnitrosoureido-D-glucopyranose)-5,12-dioxo-3,4,5,12-tetrahydro-1H-anthra[2,3-c]pyran;

BCH-2074: (1'S,1S,3R)-3-(2-oximoethyl)-5,12-dihydroxy-1-(2,3,6'-trideoxy-3-amino-L-lyxohexopyranose)-6,11-dioxo-3,4,5,12-tetrahydro-1H-anthra[2,3-C]pyran hydrochloride;

BCH-2080 & 2084:(1'S,1S,4S) and (1'S,1R,4R)-5,12-Dioxo-4-ethyl-6-hydroxy-1-(2',3',6'-trideoxy-3'-trifluoroacetamido-L-lyxohexopyranose)-3,4,5,12-tetrahydroanthraceno-[2,3-c]-pyran;

BCH-2085 & 2086:(1'S,1S,4S) and (1'S,1R,4R)-5,12-Dihydroxy-4-ethyl-1-(2',3',6'-trideoxy-3'-amino-L-lyxohexopyranose)-1,2,3,4-tetrahydro-(2-oxygen)naphthacene-6,11-dione-hydrochloride;

BCH-2088: (1'S,1S,3S)-5,12-mihydroxy-3-pentyl-1-(2',3',6'-trideoxy-3'-amino-L-lyxohexopyranose)-1,2,3,4-tetrahydro-(2-oxygen)-naphtacene-6,11-dione-hydrochloride;

BCH-2089: (1'S,1R,3R)-5,12-Dihydroxy-3-pentyl-1-(2',3',6'-trideoxy-3'-amino-L-lyxohexopyranose)-1,2,3,4-tetrahydro-(2-oxygen)-naphtacene-6,11-dione-hydrochloride along with its (1'S,1S,3S) diastereomer (4:1);

BCH-2094: A 4.5:1 diastereomeric mixture of (1'-S,1-S,3-R) and (1'-S,1-R,3-S)-methyl-(6-hydroxy-1-(2',3',4',6'-tetradeoxy-3'-trifluoroacetamido-4'-O-methanesulfonyl-L-lyxohexopyranose)-5,12-dioxo-3,4,5,12-tetrahydroanthraceno[2,3-C]pyran-3-yl)ketone;

BCH-2097: (1'-S,1-R,3-S) and (1'-S,1-S,3-R)(6-Hydroxy-1-(2',3',6'-trideoxy, 3'-trifluoroacetamido-4'-hydroxy-L-lyxohexopyranose)-5,12-dioxo-3,4,5,12-tetrahydroanthraceno[2,3-c]pyran-3-yl)propanone;

BH-2110: (1'-S,1-S,3-S)3-(5,12-Dihydroxy-1-(2',3',6'-trideoxy-3'-(2-chloroethylureido),4'-hydroxy-L-lyxohexopyranose)-6,11-dioxo-3,4,5,12-tetrahydroanthraceno-[2,3-c]pyran-3-yl)propene;

BCH-2111: (1'-S,1-R,3-S) and (1'-S,1-S,3-R)-3-(6-hydroxy-1-(2',3',6'-trideoxy-3'amino-4'-hydroxy-L-lyxohexopyranose)-5-12-dioxo-3,4,5,12-tetrahydroanthraceno[2,3-c]pyran-3yl)propanone hydrochloride;

BCH-2120: (1'S,1R,3S) and (1'S,1R,3S)-Isopropyl-[5,12-dihydroxy-6,11-dioxo-1-(2',3',6'-trideoxy-3'-amino-L-lyxohexopyranose)-3,4,6,11-tetrahydroanthraceno-[2,3-c]-pyran-3-yl]-ketone hydrochloride;

BCH-2133: (1'S,1S,3R) and (1'S,1R,3S)-cyclopropyl-(6-hydroxy-1-((2',3',6'-trideoxy-3'-trifluoroacetamido-4'-hydroxy-L-arabino-hexopyranose)-5,10-dioxo-3,4,5,12-tetrahydronaphto-[2,3-c]pyran-3-yl)methylene);

BCH-2156: 1S,3R-Methyl(1-[2',3',6'-trideoxy-3'-trifluoroacetamido-4'-hydroxy-1,5-dihydro-L-lyxohexopyranose-2-yl)-6,11-dioxo-3,4,5,12-tetrahydroanthraceno [2,3-c]pyran-3-yl)ketone;

BCH-2188: (1'S,1S,3R)-5,12-dihydroxy-6,11-dioxo-3-isopropenyl-1-(2',3',6'-trideoxy-3'-amino-L-lyxohexopyranose)-3,4,5,12-tetrahydroanthraceno-[2,3-c]-pyran hydrochloride;

BCH-2189: (1'S,1R,3S)-5,12-dihydroxy-6,11-dioxo-3-isopropenyl-1-(2',3',6'-trideoxy-3'-amino-L-lyxohexopyranose)- 3,4,5,12-tetrahydroanthraceno-[2,3-c]-pyran hydrochloride;

BCH-2190: (1'S,1S,3R)-5,12-dihydroxy-6,11-dioxo-3-isopropyl-1-(2',3',6-trideoxy-3'-(4-morpholinyl)-L-lyxohexopyranose)-3,4,5,12-tetrahydroanthraceno-[2,3-c]-pyran;

BCH-2192: (1'S,1S,3R)-5,12-dihydroxy-6,11-dioxo-3-isopropyl-1-(2',3',6'-trideoxy-3'(4-morpholinyl)-L-lyxohexopyranose)-3,4,5,12-tetrahydroanthraceno-[2,3-c]-pyran hydrochloride;

BCH-2195: (1'S,1S,3R)-5,12-dihydroxy-6,11-dioxo-3-isopropyl-1-(2',3',6'-trideoxy-3'(3-cyano-4-morpholinyl)-L-lyxohexopyranose)-3,4,5,12-tetrahydroanthraceno-[2,3-c]-pyran;

BCH-2197 & 2198: (1'S',1S,3S) and (1'S,1R,3R)-aert-butyl-(6-hydroxy-1-(2',3',6'-trideoxy-3'-trifluoroacetamido-4-hydroxy-L-lyxohexopyranose)-5,12-dioxo-3,4,5,12-tetrahydroanthraceno-[2,3-c]pyran-3-yl)ketone.

BCH-2817: (1'S,2'R,3'S,5'R,1S,3R) and (1'S,2'R,3'S,5'R,1R,3S)-1-(3-amino-2-hydroxy-1-methyl tetrahydropyran-5-yl)methyl-3-ethyl-5,12-dihydroxy-6,11-dioxo-3,4,6,11-tetrahydroanthraceno-[2,3-c]pyran hydrochloride: and BCH-2850: (1'R,1S,3R)-6-Hydroxy-1-(3'-trifluoroacetamido-2',3',6'-trideoxy-L-lyxohexopyranose)-3-t-butoxycarbonyl-5,12-dioxo-3,4,5,12-tetrahydro-1H-anthroceno-[2,3-c]-pyran.

Preferably, compounds of the invention are selected from those that show an average activity lower than 5 µM:

BCH-671: (1'S',1R,3S) Methyl(1-[2',3',6'-trideoxyacetamido-4'-hydroxy-L-lyxohexopyranose]-5,12-dioxo-3,4,5,12-tetra-hydroanthraceno(2,3-c)pyran-3-yl)formate;

BCH-689: (1'S,1R,3S) and (1'S,1S,3R)Ethyl[6-hydroxy-11-methoxy-5,12-dioxo-1-(3'-trifuloroacetamido-1-daunosaminyl)-3,4,5,12-tetrahydroanthraceno(2,3-C)pyran-3-yl]formate;

BCH-691: (1'S,1R,3S)-Methyl-{11-hydroxy-1-(2',3',6'-trideoxy-3'-trifluoroacetamido-4'-hydroxy-L-lyxoheoxpyranose)-5,12-dioxo-3,4,5,12-tetrahydroanthraceno[2,3-c]pyran-3-yl}formate;

BCH-710: 3-[2-Acetoxy-1-trimethylene-ketal]-aceto-6-acetoxy-1-hydroxy-1,2,3,4-tetrahydro-(2-oxygen)naphthacene-5,12-dione; and
3-[2-Acetoxy-1-trimethylene-ketal]-aceto-11-acetoxy-1-hydroxy-1,2,3,4-tetrahydro-(2-oxygen)-naphthacene-5,12-dione;

BCH-724: (1'S,1S,3R)-Methyl-[11-hydroxy-1-(2',3',6'-trideoxy-3'-trifluoroacetamido-4'-hydroxy-L-lyxohexopyranose)-5,12-dioxo-2,3,5,12-tetrahydroanthraceno (2,3-C ) pyran-3-yl]ketone;

BCH-725: (1S,3S) and (1R,3R)-6-hydroxy-3-hydroxymethyl-1-methoxy-1,2,3,4-tetrahydro-(2-sulfur)-naphthacene-5,12-dione;

BCH-730: (1'S,1R,3S)Methyl(6-hydroxy-1-(2',3',6'-trideoxy-3'-trifluoroacetamido-4-hydroxy-L-lyxohexopyranose-5,12-dioxo-3,4,5,12-tetrahydroanthraceno(2,3-C) pyran-3-yl]ketone;

BCH-731: (1'S,1R,3S) and (1'S,1S,3R)-3-(2-acetoxy-1-trimethyleneketal)aceto-6-acetoxy-1,2,3,4,5,12-hexahydro-1-N-trifluoroacetyl-L-daunosamine(2-oxygen)naphthacene-5,12-dione; and
(1'S,1R,3S) and (1'S,1S,3R)-3-(2-acetoxy-1-trimethyleneketal) aceto-11-acetoxy-1,2,3,4,5,12-hexahydro-1-N-trifluoroacetyl-L-daunosamine(2-oxygen)naphthacene-5,12-dione;

BCH-733:3-(2-Acetoxy-1-propeneketal-aceto-11-acetoxy-1-hydroxy-1,2,3,4,-tetrahydro-(2-oxygen)naphtacene-5,12-dione;

BCH-736: (1'S,3R) or (1R,3S)-6-Acetoxy-3-acetoxyaceto-1,2,3,4,5,12-hexahydro-1-hydroxy(2-oxygen)naphthacene-5,12-dione; and
(1S,3R) or (1R,3S)-11-Acetoxy-3-acetoxyaceto-1,2,3,4,5,12-hexahydro-1-hydroxy(2-oxygen)naphthacene-5,12-dione;

BCH-746: (1'S,1S,3S) and (1'S,1R,3S)-3-(2-acetoxy-1-trimethyleneketal)aceto-1,2,3,4,5,12-hexahydro-6-hydroxy-1-N-trifluoroacetyl-L-daunosamine(2-oxygen)naphthacene-5,12-dione; and
(1'S,1S,3R) and (1'S,1R,3S)-3-(2-acetoxy-1-trimethyleneketal)aceto-1,2,3,4,5,12-hexahydro-11-hydroxy-1-N-trifluoroacetyl-L-daunosamine(2-oxygen)napthacene-5,12-dione;

BCH-1123: (1'S,1S,3R)-Methyl-[6-hydroxy-1-(2',3',6'-trideoxy-3',4'-dihydroxy-L-lyxohexopyranose)-5,12-dioxo-3,4,5,12-tetrahydroanthraceno(2,3-C)pyran-3-yl]ketone;

BCH-1124: (1'S,1R,3S)-Methyl-[6-hydroxy-1-(2',3',6'-trideoxy-3',4'-dihydroxy-L-lyxohexopyranose)-5,12-dioxo-2,3,5,12-tetrahydroxyanthraceno(2,3-C)pyran-3-yl]ketone;

BCH-1127: (1'S,1S,3R)-Methyl-[6-hydroxy-1-(2',3',6'-trideoxy-3'-amino-4'-hydroxy-L-lyxohexopyranose)-5,12-dioxo-3,4,5,12-tetrahydroanthraceno-(2,3-C)pyran-3-yl]ketone hydrochloride;

BCH-1128: (1'S,1R,3S)-Methyl-[6-hydroxy-1-(2',3',6'-trideoxy-3'-amino-4'-hydroxy-L-lyxohexopyranose-5,12-dioxo-3,4,5,12-tetrahydroanthraceno-(2,3-C)pyran-3-yl]ketone hydrochloride;

BCH-1130: (1'S,1S,3R) and (1'S,1R,3S)-Methyl-[5,12-dihydroxy-1-(2',3',6'-trideoxy-3'-amino-4'-hydroxy-L-lyxohexopyranose)-6,11-dioxo-3,4,6,11-tetrahydroanthraceno-(2,3-C)pyran-3-yl]ketone hydrochloride;

BCH-1187: (1'S,1S,3S)-5,12-Dioxo-3-ethyl-6-hydroxy-1-(2',3',6'-trideoxy-3'-trifluoroacetamido-4'-hydroxy-L-lyxohexopyranose)-3,4,5,12-tetrahydroanthraceno(2,3-C)pyran;

BCH-1191: (1'S,1R,3S) and (1'S,1'S,3R)-Methyl(1-(2',3',6'-trideoxy-3'-morpholino -L-lyxohexopyranose)-6,11-dioxo-5,12-dihydroxy-3,4,611-tetrahydroanthraceno [2,3-c]pyran-3-yl)ketone;

BCH-1193: (1'S,1R,3S) and (1'S,1S,3R)-Methyl(1-(2',3', 6'-trideoxy-3'-morpholino -L-lyxohexopyranose)-6,11-dioxo-5,12-dihydroxy-3,4,6,11-tetrahydroanthraceno [2,3-c]pyran-3-yl)ketone hydrochloride;

BCH-1194: (1'S,1R,3S)-Methyl-[5,12-dihydroxy-1-(2',3', 6'-trideoxy-3'-amino-4'-hydroxy-L-lyxohexopyranose)-6,11-dioxo-3,4,6,11-tetrahydroanthraceno-(2,3-C)pyran-3-yl]ketone hydrochloride;

BCH-1195: (1'S,1S,3R)-Methyl-[5,12-dihydroxy-1-(2',3', 6'-trideoxy-3'-amino-4'-hydroxy-L-lyxohexopyranose)-6,11,dioxo-3,4,6,11-tetrahydroanthraceno-(2,3-C)pyran-3-yl]ketone hydrochloride;

BCH-1606: (1'S,1R,3R)-5,12-Dioxo-3-ethyl-6-hydroxy-1-[2',3',6'-trideoxy-3'-trifluoroacetamido-4'-hydroxy-L-lyxohexopyranose)-3,4,5,12-tetrahydroanthraceno(2,3-C)pyran;

BCH-1610: (1'S,1S,3s)-5,12-Dioxo-3-ethyl-6-hydroxy-1-[2',3',6'-trideoxy-3'-amino-4'-hydroxy-L-lyxohexopyranose)-3,4,5,12-tetrahydroanthraceno(2,3-C)pyran hydrochloride;

BCH-1611: (1'S,1R,3S) or (1'S,1S,3R)-1,2,3,4,5,12-hexahydro-6-hydroxy-1-L-daunosamine-3-vinyl(2-oxo)naphthacene-5,12-dione;

BCH-1614: (1'S,1R,3R)-5,12-Dioxo-3-ethyl-6-hydroxy-1-[2',3',6'-trideoxy-3'-amino-4'-hydroxy-L-lyxohexopyranose]-3,4,5,12-tetrahydroanthraceno(2,3-C)pyran hydrochloride;

BCH-1617: (1'S,1R,3S)-Methyl-(6-hydroxy-1-(2',3',4',6'-tetradeoxy-3'-trifluoroacetamido-4'-iodo-L-lyxohexopyranose)-5,12-dioxo-3,4,5,12-tetrahydroanthraceno[2,3-c]pyran-3-yl)ketone;

BCH-1618: (1'S,1S,3R)-Methyl-(6-hydroxy-1-(2',3',4',6'-tetradeoxy-3'-trifluoroacetamido-4'-iodo-L-lyxohexopyranose)-5,12-dioxo-3,4,5,12-tetrahydroanthraceno[2,3-c]pyran-3-yl)ketone;

BCH-1619: (1'S,1S,3R)-6-Hydroxy-1-[2',3',6'-trideoxy-3'-trifluoroacetamido-L-lyxohexopyranose]-3-(2-aza-3-acetamidothienyl)-5,12-dioxo-3,4,5,12-tetrahydroanthraceno(2,3-C)pyran;

BCH-1626: (1'S,1R,3S) and (1'S,1S,3R)-1-O-(3',4'-di-O-acetyl-2',6'-dideoxy-α-lyxohexopyranosyl)-1,2,3,4,5,12-hexahydro-6-hydroxy-3-hydroxyaceto-(2-oxo)naphthacene-5,12-dione;

BCH-1628: 3-Aceto-1-O-(ethanoamino)-1,2,3,4,5,12-hexahydro-6-hydroxy-(2-sulfur)naphthacene-5,12-dione hydrochloride;

BCH-1633: (1'S,1S,3S)-3-Ethyl-5,12-dihydroxy-1-(2',3',6'-trideoxy-3'-amino-4'-hydroxy-L-lyxohexopyranose)-1,2,3,4-tetrahydro-(2-oxygen)naphthacene-6,11-dione-hydrochloride;

BCH-1635: (1'S,1R,3S) and (1'S,1S,3R)-3-aceto-1,2,3,4,5,12-hexahydro-6-hydroxy-1-N-trifluoroacetyl-L-daunosamine-(2-sulfur)naphthacene-5,12-dione;

BCH-1636: (4'R,1R,3S) and (4'R,1S,3R)-3-aceto-1-(2',2'-dimethyl-1',3'-dioxanyl-4'-methoxyl)-6-hydroxyl-1,2,3,4,5,12-hexahydro-(2-sulfur)naphthacene-5,12-dione;

BCH-1637: (1'S,1S,3R)-and (1'S,1R,3S)-Methyl-(6-hydroxy-1-(2',3',6'-trideoxy-3'-trifluoroacetamido-4-hydroxy-L-arabino-hexopyranose)-5,12-dioxo-3,4,5,12-tetrahydroanthraceno-[2,3-c]pyran-3-yl)ketone;

BCH-1641: (1'S,1S,3R)-3-Aceto-1,2,3,4,5,12'hexahydro-6-hydroxy-1-N-trifluoroacetyl-L-daunosamine-(2-sulfur)naphthacene-5,12-dione;

BCH-1645: (2'R,1R,3S) and (2'R,1S,3R)-3-aceto-1-(2',3'-dihydroxy)-N-propoxy-6-hydroxy-1,2,3,4,5,12-hexahydro-(2-sulfur)naphthacene-5,12-dione;

BCH-1646: (1'S,1R)-1-[(2',3',6'-trideoxy-3'-acetamido-L-lyxohexopyranosyl)oxy]-6-hydroxy-3,4,5,12-tetrahydro-5,12-dioxo-1H-anthra(2,3-C)pyran;

BCH-1647: (1'S,1S)-1-[(2',3',6'-tetradeoxy-3'-acetamido-L-lyxohexopyranosyl)oxy]-6-hydroxy-3,4,5,12-tetrahydro-5,12-dioxo-1H-anthra(2,3-C)pyran;

BCH-1650: 3-Dimethylphosphonoacetyl-6-hydroxy-1-methoxy-5,12-dioxo-3,4,5,12-tetrahydroanthraceno-(2,3-C)pyran;

BCH-1652: 3-Phenylsulfonyl-6-hydroxy-1,2,3,4-tetrahydro-(2-oxygen)naphthacene-5,12-dione; and 3-Phenylsulfonyl-11-hydroxy-1,2,3,4-tetrahydro-(2-oxygen)naphthacene-5,12-dione;

BCH-1653: (1'S,1R,3S)-6-Hydroxy-1-(2',3',6'-trideoxy-3'-trifluoroacetamido-L-lyxohexopyranose)-3-diethylaminocarbonyl-5,12-dioxo-3,4,5,12-tetrahydroanthraceno-(2,3-C)pyran;

BCH-1656: (1'S,1R,3S)-6-hydroxy-1-(2',3',6',-trideoxy-3'-trifluoroacetamido-L-lyxohexopyranose)- 3-diethylaminocarbonyl-5,12-dioxo-3,4,5,12-tetrahydroanthraceno-(2,3-C)-pyran;

BCH-1657: (1S,2'S,3R) and (1R,2'S,3S)-Methyl-(6-hydroxy-1-[O-serine methyl ester]-5,12-dioxo-3,4,5,12-tetrahydroanthraceno-[2,3-C]pyran-3-yl)ketone hydrochloride;

BCH-1660: (4'S,1R,3S) and (4'S,1S,3R)-3-Aceto-1-(2',2'-dimethyl-1',3'-dioxanyl-4'-methoxy)-6-hydroxy-1,2,3,4,5,12-hexahydro-(2-sulfur)naphthacene-5,12-dione;

BCH-1661: (4'R,1R,3S) and (4'R,1S,3R)-3-Aceto-1-(2',2'-dimethyl-1',3'-dioxanyl-4'-methoxy)-6-hydroxy-1,2,3,4,5,12-hexahydro-(2-oxo)naphthacene-5,12-dione;

BCH-1669: (2'R,1R,3S) and (2'R,1S,3R)-3-Acetyl-1-(2',3'-dihydroxy)-n-propoxy-6-hydroxy-1,2,3,4,5,12-hexahydro-(2-oxo)naphthacene-5,12-dione;

BCH-1670: (2'S,1R,3S) and (2'S,1S,3R)-3-acetyl-1-(2',3'-dihydroxy)-n-propoxy-6-hydroxy-1,2,3,4,5,12-hexahydro-(2-sulfur)naphthacene-5,12-dione;

BCH-1671: (1'S,1S,3R)-3-acetyl-1-O-(3',4'-di-O-acetyl-2',6'-dideoxy-α-lyxohexopyranosyl)-1,2,3,4,5,12-hexahydro-6-hydroxy(2-sulfur)naphthacene-5,12-dione;

BCH-1672: (1'S,1R,3S)-Methyl-[5,12-dihydroxy-1-(2',6'-dideoxy-3',4'-dihydroxy-2'-iodo-L-lyxohexopyranose)-6,11-dioxo-3,4,6,11-tetrahydroanthraceno-(2'-C)pyran-3-yl]ketone;

BCH-1675: (1'S,1S,3R)-Methyl-(5,12-dihydroxy-1-(2',6'-dideoxy-3',4'-dihydroxy-2'-iodo-L-lyxohexopyranose)-6,11-dioxo-3,4,6,11-tetrahydroanthraceno(2,3-C)pyran-3-yl]ketone;

BCH-1676:(1'S,1R,3S)-5,12-dioxo-3-(1,1-difluoroethyl)-6-hydroxy-1-(2',3',6'-trideoxy-3'-trifluoroacetamido-L-lyxohexopyranose)-3,4,5,12-tetrahydroanthraceno-[2,3-c]-pyran;

BCH-1679: (1'S,1S,3R)-6-hydroxy-1-(2',3',6'-trideoxy-3'-trifluroacetamido-L-lyxohexopyranose)-3-dimethylphosphonoacetyl-5,12-dioxo-3,4,5,12-tetrahydroanthraceno-[2,3-C]-pyran;

BCH-1680: (1'S,1S,3R) and (1'S,1R,3S)-Methyl-(6-hydroxy-1-(2',3',4',6'-tetradeoxy-4'-trifluoroacetamido-L-lyxohexopyranose)-5,12-dioxo-3,4,5,12-tetrahydroanthraceno-[2,3-C]pyran-3-yl)ketone;

BCH-1681: (1'S,1S,3R)-Methyl-(1-[2',6'-dideoxy-3',4'-diacetyl-2'-iodo-L-lyxohexopyranose]-6-hydroxy-3,4,5,10-tetrahydroanthraceno[2,3-c]pyran-3-yl) ketone;

BCH-1683: (1'S, 1S,3R) and (1'S,1R,3S)-3-(2-aminoethyl)-5,12-dihydroxy-1-(2',3',6'-trideoxy-3',4'-dihydroxy-L-lyxohexopyranose)-6,11-dioxo-3,4,6,11-tetrahydro-1H-anthra[2,3-C]pyran hydrochloride;

BCH-1686: (1'S,1S,3S)-3-(6-hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl)propene;

BCH-1687: (1'S,1R,3R)-3-(6hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl)porpene;

BCH-1694: (1'S,1R,3S)-5,12-dioxo-6-hydroxy-3-methoxymethyl-1-(2',3',6'-trideoxy-3'-trifluoroacetamido-L-lyxohexopyranose)-3,4,5,12-tetrahydroanthraceno-[2,3-C]pyran;

BCH-1696: (1'S,1S,3R)-5,12-dioxo-6-hydroxy-3-methoxymethyl-1-(2',3',6'-trideoxy-3'-trifluoroacetamido-L-lyxohexopyranose)-3,4,5,12-tetrahydroanthraceno-[2,3-C]pyran;

BCH-1698: (1'S,1S)-5,12-dioxo-6-hydroxy-3,3-bis-methoxymethyl-1-(2',3',6'-trideoxy-3'-trifluoroacetamido-L-lyxohexopyranose)-3,4,5,12-tetrahydroanthraceno-[2,3-C]pyran;

BCH-1990: (1'S,1R,3S)-methyl-(l[2',6'-dideoxy-3',4'-dihydroxy-2'-iodo-L-lyxohexopyranose]-5,12-dioxo-3,4,5,12-tetrahydroanthraceno[2,3-C]pyran-3-yl)ketone;

BCH-1991:(1'S,1S)-5,12-dioxo-6-hydroxy-3,3-bis-methoxymethyl-1-(2',3',6'-trideoxy-3'-amino-L-lyxohexopyranose)-3,4,5,12-tetrahydroanthraceno-[2,3-c]-pyran-hydrochloride;

BCH-1992: (1'S,1S,3R) and (1'S,1R,3S)-5,12-dihydroxy-3-methoxymethyl-1-(2',3',6'-trideoxy-3'-amino-L-lyxohexopyranose)-1,2,3,4-tetrahydro-(2-oxygen)-naphthacene-6,11-dione hydrochloride;

BCH-1994: (4'S,1S,3R)-3-aceto-1-(2',2'-dimethyl-1',3'-dioxanyl-4'-methoxy)-6-hydroxy-1,2,3,4,5,12-hexahydro-(2-sulfur)naphthacene-5,12-dione (tent. ass);

BCH-1997: (1'S,1S,3R,13R)-3-dihydroxyethyl-6-hydroxy-1-(N-trifluoroacetyl-L-daunosamine-(2-oxo)naphthacene-5,12-dione (tent ass);

BCH-2001: (1'S,1R,3S)-3-{6-hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl}(phenyl)sulfone;

BCH-2002: (1'S,1S)-6-hydroxy-1-(2',3',6'-trideoxy-3'-trifluoroacetamido-4'-hydroxy-L-lyxohexopyranose)-5,12-dioxo-5,12-dihydroanthraceno-[2,3-C]pyran;

BCH-2005: (1'S,1R,3R)-3-{6-Hydroxy-1-(2',3',6-trideoxy-3'amino-4'-hydroxy-L-lyxohexopyranose)-5,12-dioxo-3,4,5,12-tetrahydroanthraceno-[2,3-C]pyran-3-yl}propene hydrochloride;

BCH-2006: (1'S,1S,3S)-3-{6-Hydroxy-1-(2',3',6'-trideoxy-3'-amino-4'-hydroxy-L-lyxohexopyranose)-5,12-dioxo-3,4,5,12-tetrahydroanthraceno-[2,3-C]pyran-3-yl}propene hydrochloride;

BCH-2007: (1'S,1R,3S)-3-{6-Hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]-pyran-3-yl}nitrile;

BCH-2008: (1'S,1S,3R)-3-{6-Hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl}nitrile;

BCH-2012: (1'S,1R,3S)-3-{6-Hydroxy-1-(2',3',6'-trideoxy-3'-amino-4'-hydroxy-L-lyxohexopyranose)-5,12-dioxo-3,4,5,12-tetrahydroanthraceno-[2,3-C]pyran-3-yl}benzene hydrochloride;

BCH-2016: (1'S,1R,3R)-3-Ethyl-5,12-dihydroxy-1-(2',3',6'-trideoxy-3'-amino-L-lyxohexopyranose)-1,2,3,4-tetrahydro-(2-oxygen)-naphtacene-6,11-dione hydrochloride;

BCH-2025: (1'S,1S,3R)-3-{6-hydroxy-1-(2',3',6'-trideoxy-3'-trifluoroacetamido-4'-hydroxy-L-lyxohexopyranose)-5,12-dione-3,4,5,12-tetrahydroanthraceno-[2,3-c]pyran-3-yl }(phenyl)sulfone;

BCH-2034: (2'S,1R,3S) and (2'S,1S,3R)-3-acetyl (-2',3'-dihydroxy)-N-propoxy-6-hydroxy-1,2,3,4,5,12-hexahydro-(2-oxo)naphthacene-5,12-dione;

BCH-2049: (1'S,1S,3R)-5,12-rihydroxy-3-isopropyl-1-(2',3',6'-trideoxy-3'-amino-L-lyxohexopyranose)-1,2,3,4-tetrahydro-(2-oxygen)-naphtacene-6,11-dione-hydrochloride;

BCH-2050: (1'S,1R,3S)-5,12-Dixydroxy-3-isopropy-1-(2',3',6'-trideoxy-3'-amino'L-lyxohexopyranose)-1,2,3,4-tetrahydro-(2-oxygen)-naphtacene-6,11-dione-hydrochloride;

BCH-2055: Diastereomeric mixture of (1'-S,1-R,3-S) and (1'-S,1-S,3-R)(5,12-dihydroxy-1-(2',3',6'-trideoxy-3'-trifluoroacetamido-4'hydroxy-L-lyxohexopyranose)-6,11-dioxo-3,4,5,12-tetrahydroanthraceno-[2,3-c]pyran-3-yl)nitrile;

BCH-2056: Diastereomeric mixture of (1'-S,1-R,3-S) and (1'-S,3-R)(5,12-dihydroxy-1-(2',3',6'-trideoxy-3'-amino-4'-hydroxy-L-lyxohexopyranose)-6,11-dioxo-3,4,5,12-tetrahydroanthraceno-[2,3-c]pyran-3-yl)nitrile;

BCH-2057: (1'S,1S,3R)-5,12-dioxo-6-hydroxy-3-phenyloxymethyl-1-(2',3',6'-trideoxy-3'-trifluoroacetamido-L-lyxohexopyranose)-3,4,5,12-tetrahydroanthraceno [2,3-c]pyran;

BCH-2058 & 2059: (1'S,1R,3S) and (1'S,1S,3R)-5,12-Dihydroxy-3-phenyloxymethyl-1-(2',3',6'-trideoxy-3'-amino-L-lyxohexopyranose)-1,2,3,4-tetrahydro-(2-oxygen)-naphthacene-6,11-dione-hydrochloride;

BCH-2063: (1'S,1R,3S)-Methyl-(5,12-dihydroxy-1-(2',3',6'-trideoxy-3'-trifluoroacetamido-2'-iodo-4'-hydroxy-L-lyxohexopyranose)-6,11-dioxo-3,4,6,11-tetrahydroanthraceno-[2,3C]-pyran-3-yl)-ketone;

BCH-2064: (1'S,1S,3R)-Methyl-(1-[2',3',6'-trideoxy-3'-trifluoroacetamido-4'-hydroxy-2'-iodo-L-lyxohexopyranose]-5,12-dioxo-3,4,5,12-tetrahydroanthraceno[2,3-C]pyran-3-yl)ketone;

BCH-2066: (1'S,1R,3S)-Methyl-(5,12-dihydroxy-1-[2',3',6'-trideoxy- 3'-amino-4'hydroxy-2'-iodo-L-lyxohexopyranose]-6,11-dioxo-3,4,6,11-tetrahydroanthraceno-[2,3C]-pyran-3-yl)ketone hydrochloride;

BCH-2074: (1'S,1S,3R)-3-(2-oximoethyl)-5,12-dihydroxy-1-(2,3,6,-trideoxy-3-amino-L-lyxohexopyranose)-6,11-dioxo-3,4,5,12-tetrahydro-1H-anthra[2,3-C]pyran hydrochloride;

BCH-2080: (1'S,1S,4S)-5,12-Dioxo-4-ethyl-6-hydroxy-1-(2',3',6'-trideoxy-3'-trifluoroacetamido-L-lyxohexopyranose)-3,4,5,12-tetrahydroanthraceno-[2,3- c]-pyran BCH-2085 & 2086: (1'S,1S,4S) and (1'S,1R,4R)-5,12-Dihydroxy-4-ethyl-1-(2',3',6'-trideoxy-3'-amino-L-lyxohexopyranose)-1,2,3,4-tetrahydro-(2-oxygen) naphthacene-6,11-dione-hydrochloride;

BCH-2088: (1'S,1S,3S)-5,12-mihydroxy-3-pentyl-1-(2',3',6'-trideoxy-3'-amino-L-lyxohexopyranose)-1,2,3,4-tetrahydro-(2-oxygen)-naphtacene-6,11-dione-hydrochloride;

BCH-2089: (1'S,1R,3R)-5,12-Dihydroxy-3-pentyl-1-(2',3',6'-trideoxy-3'-amino-L-lyxohexopyranose)-1,2,3,4-tetrahydro-(2-oxygen)-naphtacene-6,11-dione-hydrochloride along with its (1'S,1S,3S) diastereomer (4:1);

BCH-2097: (1'-S,1-R,3-S) and (1'-S,1-S,3-R)(6-Hydroxy-1-(2',3',6'-trideoxy, 3'-trifluoroacetamido-4'-hydroxy-L-lyxohexopyranose)-5,12-dioxo-3,4,5,12-tetrahydroanthraceno[2,3-c]pyran-3-yl)propanone;

BH-2110: (1'-S,1-S,3-S)3-(5,12-Dihydroxy-1-(2',3',6'-trideoxy-3'-(2-chloroethylureido),4'-hydroxy-L-lyxohexopyranose)-6,11-dioxo-3,4,5,12-tetrahydroanthraceno-[2,3-c]pyran-3-yl)propene;

BCH-2111: (1'-S,1-R,3-S) and (1'-S,1-S,3-R)-3-(6-hydroxy-1-(2',3',6'-trideoxy-3'-amino-4'-hydroxy-L-lyxohexopyranose)-5-12-dioxo-3,4,5,12-tetrahydroanthraceno[2,3-c]pyran-3yl)propanone hydrochloride;

BCH-2120: (1'S',1R,3S) and (1'S,1R,3S)-Isopropyl-[5,12-dihydroxy-6,11-dioxo-1-(2',3',6'-trideoxy-3'-amino- L-lyxohexopyranose)-3,4,6,11-tetrahydroanthraceno-[2,3-c]-pyran-3-yl]-ketone hydrochloride;

BCH-2133: (1'S',1S,3R) and (1'S,1R,3S)-cyclopropyl-(6-hydroxy-1-((2',3',6'-trideoxy-3'-trifluoroacetamido-4'-hydroxy-L-arabino-hexopyranose)-5,10-dioxo-3,4,5,12-tetrahydronaphto-[2,3-c]pyran-3-yl)methylene);

BCH-2156: 1S,3R-Methyl(1-[2',3',6'-trideoxy-3'-trifluoroacetamido-4'-hydroxy-1,5-dihydro-L-lyxohexopyranose-2-yl)-6,11-dioxo-3,4,5,12-tetrahydroanthraceno[2,3-c]pyran-3-yl)ketone;

BCH-2188: (1'S,1S,3R)-5,12-dihydroxy-6,11-dioxo-3-isopropenyl-1-(2',3',6'-trideoxy-3'-amino-L-lyxohexopyranose)-3,4,5,12-tetrahydroanthraceno-[2,3-c]-pyran hydrochloride;

BCH-2189: (1'S,1R,3S)-5,12-dihydroxy-6,11-dioxo-3-isopropenyl-1-(2',3',6'-trideoxy-3'-amino-L-lyxohexopyranose)-3,4,5,12-tetrahydroanthraceno-[2,3-c]-pyran hydrochloride;

BCH-2190: (1'S,1S,3R)-5,12-dihydroxy-6,11-dioxo-3-isopropyl-1-(2',3',6'-trideoxy-3'-(4-morpholinyl)-L-lyxohexopyranose)-3,4,5,12-tetrahydroanthraceno-[2,3-c]-pyran;

BCH-2192: (1'S,1S,3R)-5,12-dihydroxy-6,11-dioxo-3-isopropyl-1-(2',3',6'-trideoxy-3'(4-morpholinyl)-L-lyxohexopyranose)-3,4,5,12-tetrahydrothraceno-[2,3-c]-pyran hydrochloride;

BCH-2197 & 2198: (1'S,1S,3S) and (1'S,1R,3R)-aert-butyl-(6-hydroxy-1-(2',3',6'-trideoxy-3'-trifluoroacetamido-4-hydroxy-L-lyxohexopyranose)-5,12-dioxo-3,4,5,12-tetrahydroanthraceno-[2,3-c]pyran-3-yl)ketone; and BCH-2850: (1'R,1S,3R)-6-Hydroxy-1-(3'-trifluoroacetamido-2',3',6'-trideoxy-L-lyxohexopyranose)-3-t-butoxycarbonyl-5,12-dioxo-3,4,5,12-tetrahydro-1H-anthroceno-[2,3-c]-pyran.

More preferably, compounds of the invention are selected from those that show an average activity lower than 2 μM:

BCH-691: (1'S,1R,3S)-Methyl-{11-hydroxy-1-(2',3',6'-trideoxy-3'-trifluoroacetamido-4'-hydroxy-L-lyxoheoxpyranose)-5,12-dioxo-3,4,5,12-tetrahydroanthraceno[2,3-c]pyran-3-yl}formate;

BCH-724: (1'S,1S,3R)-Methyl-[11-hydroxy-1-(2',3',6'-trideoxy-3'-trifluoroacetamido-4'-hydroxy-L-lyxohexopyranose)-5,12-dioxo-2,3,5,12-tetrahydroanthraceno(2,3-C)pyran-3-yl]ketone;

BCH-731: (1'S,1R,3S) and (1'S,1S,3R)-3-(2-acetoxy-1-trimethyleneketal)aceto-6-acetoxy-1,2,3,4,5,12-hexahydro-1-N-trifluoroacetyl-L-daunosamine(2-oxygen)naphthacene-5,12-dione; and
(1'S,1R,3S) and (1'S,1S,3R)-3-(2-acetoxy-1-trimethyleneketal) aceto-11-acetoxy-1,2,3,4,5,12-hexahydro-1-N-trifluoroacetyl-L-daunosamine(2-oxygen)naphthacene-5,12-dione;

BCH-736: (1'S,3R) or (1R,3S)-6-Acetoxy-3-acetoxyaceto-1,2,3,4,5,12-hexahydro-1-hydroxy(2-oxygen)naphthacene-5,12-dione; and
(1S,3R) or (1R,3S)-11-Acetoxy-3-acetoxyaceto-1,2,3,4,5,12-hexahydro-1-hydroxy(2-oxygen)naphthacene-5,12-dione;

BCH-1123: (1'S,1S,3R)-Methyl-[6-hydroxy-1-(2',3',6'-trideoxy-3',4'-dihydroxy-L-lyxohexopyranose)-5,12-dioxo-3,4,5,12-tetrahydroanthraceno(2,3-C)pyran-3-yl]ketone;

BCH-1127: (1'S,1S,3R)-Methyl-[6-hydroxy-1-(2',3',6'-trideoxy-3'-amino-4'-hydroxy-L-lyxohexopyranose)-5,12-dioxo-3,4,5,12-tetrahydroanthraceno-(2,3-C)pyran-3-yl]ketone hydrochloride;

BCH-1128: (1'S,1R,3S)-Methyl-[6-hydroxy-1-(2',3',6'-trideoxy-3'-amino-4'-hydroxy-L-lyxohexopyranose-5,12-dioxo-3,4,5,12-tetrahydroanthraceno-(2,3-C)pyran-3-yl]ketone hydrochloride;

BCH-1130: (1'S,1S,3R) and (1'S,1R,3S)-Methyl-[5,12-dihydroxy-1-(2',3',6'-trideoxy-3'-amino-4'-hydroxy-L-lyxohexopyranose)-6,11-dioxo-3,4,6,11-tetrahydroanthraceno-(2,3-C)pyran-3-yl]ketone hydrochloride;

BCH-1187: (1'S,1S,3S)-5,12-Dioxo-3-ethyl-6-hydroxy-1-(2',3',6'-trideoxy-3'-trifluoroacetamido-4'-hydroxy-L-lyxohexopyranose)-3,4,5,12-tetrahydroanthraceno(2,3-C)pyran;

BCH-1191: (1'S',1R,3S) and (1'S,1S,3R)-Methyl(1-(2',3',6'-trideoxy-3'-morpholino-L-lyxohexopyranose)-6,11-dioxo-5,12-dihydroxy-3,4,611-tetrahydroanthraceno[2,3-c]pyran-3-yl)ketone;

BCH-1194: (1'S,1R,3S)-Methyl-[5,12-dihydroxy-1-(2',3',6'-trideoxy-3'-amino-4'-hydroxy-L-lyxohexopyranose)-6,11-dioxo-3,4,6,11-tetrahydroanthraceno-(2,3-C)pyran-3-yl]ketone hydrochloride;

BCH-1195: (1'S,1S,3R)-Methyl-[5,12-dihydroxy-1-(2',3',6'-trideoxy-3'-amino-4'-hydroxy-L-lyxohexopyranose)-6,11,dioxo-3,4,6,11-tetrahydroanthraceno-(2,3-C)pyran-3-yl]ketone hydrochloride;

BCH-1606: (1'S,1R,3R)-5,12-Dioxo-3-ethyl-6-hydroxy-1-[2',3',6'-trideoxy-3'-trifluoroacetamido-4'-hydroxy-L-lyxohexopyranose]-3,4,5,12-tetrahydroanthraceno(2,3-C)pyran;

BCH-1610: (1'S,1S,3s)-5,12-Dioxo-3-ethyl-6-hydroxy-1-[2',3',6'-trideoxy-3'-amino-4'-hydroxy-L-lyxohexopyranose]-3,4,5,12-tetrahydroanthraceno(2,3-C)pyran hydrochloride;

BCH-1614: (1'S,1R,3R)-5,12-Dioxo-3-ethyl-6-hydroxy-1-[2',3',6'-trideoxy-3'-amino-4'-hydroxy-L-lyxohexopyranose]-3,4,5,12-tetrahydroanthraceno(2,3-C)pyran hydrochloride;

BCH-1617: (1'S,1R,3S)-Methyl-(6-hydroxy-1-(2',3',4',6'-tetradeoxy-3'-trifluoroacetamido-4'-iodo-L-lyxohexopyranose)-5,12-dioxo-3,4,5,12-tetrahydroanthraceno[2,3-c]pyran-3-yl)ketone;

BCH-1633: (1'S,1S,3S)-3-Ethyl-5,12-dihydroxy-1-(2',3', 6'-trideoxy-3'-amino-4'-hydroxy-L-lyxohexopyranose)-1,2,3,4-tetrahydro-(2-oxygen)naphthacene-6,11-dione-hydrochloride;

BCH-1641: (1'S,1S,3R)-3-Aceto-1,2,3,4,5,12'hexahydro-6-hydroxy-1-N-trifluoroacetyl-L-daunosamine-(2-sulfur)naphthacene-5,12-dione;

BCH-1645: (2'R,1R,3S) and (2'R,1S,3R)-3-aceto-1-(2',3'-dihydroxy)-N-propoxy-6-hydroxy-1,2,3,4,5,12-hexahydro-(2-sulfur)naphthacene-5,12-dione;

BCH-1650: 3-Dimethylphosphonoacetyl-6-hydroxy-1-methoxy-5,12-dioxo-3,4,5,12-tetrahydroanthraceno-(2,3-C)pyran;

BCH-1669: (2'R,1R,3S) and (2'R,1S,3R)-3-Acetyl-1-(2', 3'-dihydroxy)-n-propoxy-6-hydroxy-1,2,3,4,5,12-hexahydro-(2-oxo)naphthacene-5,12-dione;

BCH-1670: (2'S,1R,3S) and (2'S,1S,3R)-3-acetyl-1-(2',3'-dihydroxy)-n-propoxy-6-hydroxy-1,2,3,4,5,12-hexahydro-(2-sulfur)naphthacene-5,12-dione;

BCH-1672: (1'S,1R,3S)-Methyl-[5,12-dihydroxy-1-(2', 6'-dideoxy-3',4'-dihydroxy-2'-iodo-L-lyxohexopyranose)-6,11-dioxo-3,4,6,11-tetrahydroanthraceno-(2'-C)pyran-3-yl]ketone;

BCH-1679: (1'S,1S,3R)-6-hydroxy-1-(2',3',6'-trideoxy-3'-trifluroacetamido-L-lyxohexopyranose)-3-dimethylphosphonoacetyl-5,12-dioxo-3,4,5,12-tetrahydroanthraceno-[2,3-C]-pyran;

BCH-1681: (1'S,1S,3R)-Methyl-(1-[2',6'-dideoxy-3',4'-diacetyl-2'-iodo-L-lyxohexopyranose]-6-hydroxy-3,4,5,10-tetrahydroanthraceno[2,3-c]pyran-3-yl)ketone;

BCH-1686: (1'S,1S,3S)-3-(6-hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl)propene;

BCH-1687: (1'S,1R,3R)-3-(6hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl)porpene;

BCH-1696: (1'S,1S,3R)-5,12-dioxo-6-hydroxy-3-methoxymethyl-1-(2',3',6'-trideoxy-3'-trifluoroacetamido-L-lyxohexopyranose)-3,4,5,12-tetrahydroanthraceno-[2,3-C]pyran;

BCH-1698: (1'S,1S)-5,12-dioxo-6-hydroxy-3,3-bismethoxymethyl-1-(2',3',6'-trideoxy-3'-trifluoroacetamido-L-lyxohexopyranose)-3,4,5,12-tetrahydroanthraceno-[2,3-C]pyran;

BCH-1991: (1'S,1S)-5,12-dioxo-6-hydroxy-3,3-bismethoxymethyl-1-(2',3',6'-trideoxy-3'-amino-L-lyxohexopyranose)-3,4,5,12-tetrahydroanthraceno-[2,3-c]-pyran-hydrochloride;

BCH-1992: (1'S,1S,3R) and (1'S,1R,3S)-5,12-dihydroxy-3-methoxymethyl-1-(2',3',6'-trideoxy-3'-amino-L-lyxohexopyranose)-1,2,3,4-tetrahydro-(2-oxygen) naphtacene-6,11-dione hydrochloride;

BCH-2002: (1'S,1S)-6-hydroxy-1-(2',3',6'-trideoxy-3'-trifluoroacetamido-4'-hydroxy-L-lyxohexopyranose)-5,12-dioxo-5,12-dihydroanthraceno-[2,3-C]pyran;

BCH-2006: (1'S,1S,3S)-3-{6-Hydroxy-1-(2',3',6'-trideoxy-3'-amino-4'-hydroxy-L-lyxohexopyranose)-5,12-dioxo-3,4,5,12-tetrahydroanthraceno-[2,3-C]pyran-3-yl}propene hydrochloride;

BCH-2007: (1'S,1R,3S)-3-{6-Hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]-pyran-3-yl}nitrile;

BCH-2008: (1'S,1S,3R)-3-{6-Hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl}nitrile;

BCH-2012: (1'S,1R,3S)-3-{6-Hydroxy-1-(2',3',6'-trideoxy-3'-amino-4'-hydroxy-L-lyxohexopyranose)-5,12-dioxo-3,4,5,12-tetrahydroanthraceno-[2,3-C]pyran-3-yl}benzene hydrochloride;

BCH-2016: (1'S,1R,3R)-3-Ethyl-5,12-dihydroxy-1-(2',3',6'-trideoxy-3'-amino-L-lyxohexopyranose)-1,2,3,4-tetrahydro-(2-oxygen)-naphtacene-6,11-dione hydrochloride;

BCH-2034: (2'S,1R,3S) and (2'S,1S,3R)-3-acetyl(-2',3'-dihydroxy)-N-propoxy-6-hydroxy-1,2,3,4,5,12-hexahydro-(2-oxo)naphthacene-5,12-dione;

BCH-2049: (1'S,1S,3R)-5,12-rihydroxy-3-isopropyl-1-(2',3',6'-trideoxy-3'-amino-L-lyxohexopyranose)-1,2,3,4-tetrahydro-(2-oxygen)-naphtacene-6,11-dione-hydrochloride;

BCH-2050: (1'S,1R,3S)-5,12-Dixydroxy-3-isopropy-1-(2',3',6'-trideoxy-3'-amino'L-lyxohexopyranose)-1,2,3,4-tetrahydro-(2-oxygen)-naphtacene-6,11-dione-hydrochloride;

BCH-2055: Diastereomeric mixture of (1'-S,1-R,3-S) and (1'-S,1-S,3-R)(5,12-dihydroxy-1-(2',3',6'-trideoxy-3'-trifluoroacetamido-4'hydroxy-L-lyxohexopyranose)-6,11-dioxo-3,4,5,12-tetrahydroanthraceno-[2,3-c]pyran-3-yl)nitrile;

BCH-2056: Diastereomeric mixture of (1'-S,1-R,3-S) and (1'-S,3-R)(5,12-dihydroxy-1-(2',3',6'-trideoxy-3'-amino-4'-hydroxy-L-lyxohexopyranose)-6,11-dioxo-3,4,5,12-tetrahydroanthraceno-[2,3-c]pyran-3-yl)nitrile;

BCH-2057: (1'S,1S,3R)-5,12-dioxo-6-hydroxy-3-phenyloxymethyl-1-(2',3',6'-trideoxy-3'-trifluoroacetamido-L-lyxohexopyranose)-3,4,5,12-tetrahydroanthraceno-[2,3-c]pyran;

BCH-2058 & 2059:(1'S,1R,3S) and (1'S,1S,3R)-5,12-Dihydroxy-3-phenyloxymethyl-1-(2',3',6'-trideoxy-3'-amino-L-lyxohexopyranose)-1,2,3,4-tetrahydro-(2-oxygen)-naphtacene-6,11-dione-hydrochloride;

BCH-2063: (1'S,1R,3S)-Methyl-(5,12-dihydroxy-1-(2',3',6'-trideoxy-3'-trifluoroacetamido-2'-iodo-4'-hydroxy-L-lyxohexopyranose)-6,11-dioxo-3,4,6,11-tetrahydroanthraceno-[2,3C]-pyran-3-yl)-ketone;

BCH-2066: (1'S,1R,3S)-Methyl-(5,12-dihydroxy-1-[2',3',6'-trideoxy-3'-amino-4'hydroxy-2'-iodo-L-lyxohexopyranose]-6,11-dioxo-3,4,6,11-tetrahydroanthraceno-[2,3C]-pyran-3-yl) ketone hydrochloride;

BCH-2085 & 2086:(1'S,1S,4S) and (1'S,1R,4R)-5,12-Dihydroxy-4-ethyl- 1-(2',3',6'-trideoxy-3'-amino-L-lyxohexopyranose)-1,2,3,4-tetrahydro-(2-oxygen)-naphthacene-6,11-dione-hydrochloride;

BCH-2088: (1'S,1S,3S)-5,12-mihydroxy-3-pentyl-1-(2',3',6'-trideoxy-3'-amino-L-lyxohexopyranose)-1,2,3,4-tetrahydro-(2-oxygen)-naphtacene-6,11-dione-hydrochloride;

BCH-2089: (1'S,1R,3R)-5,12-Dihydroxy-3-pentyl-1-(2',3',6'-trideoxy-3'-amino-L-lyxohexopyranose)-1,2,3,4-tetrahydro-(2-oxygen)-naphtacene-6,11-dione-hydrochloride along with its (1'S,1S,3S) diastereomer (4:1);

BH-2110: (1,-S,1-S,3-S)3-(5,12-Dihydroxy-1-(2',3',6'-trideoxy-3'-(2-chloroethylureido),4'-hydroxy-L-lyxohexopyranose)-6,11-dioxo-3,4,5,12-tetrahydroanthraceno-[2,3-c]pyran-3-yl)propene;

BCH-2120: (1'S,1R,3S) and (1'S,1R,3S)-Isopropyl-[5,12-dihydroxy-6,11-dioxo-1-(2',3',6'-trideoxy-3'-amino-L-lyxohexopyranose)-3,4,6,11-tetrahydroanthraceno-[2,3-c]-pyran-3-yl]-ketone hydrochloride;

BCH-2188: (1'S,1S,3R)-5,12-dihydroxy-6,11-dioxo-3-isopropenyl-1-(2',3',6'-trideoxy-3'-amino-L-lyxohexopyranose)-3,4,5,12-tetrahydroanthraceno-[2,3-c]-pyran hydrochloride; and BCH-2189: (1'S,1R,3S)-5,12-dihydroxy-6,11-dioxo-3-isopropenyl-1-(2',3',6'-trideoxy-3'-amino-L-lyxohexopyranose)-3,4,5,12-tetrahydroanthraceno-[2,3-c]-pyran hydrochloride.

Most preferred compounds of the invention are selected from those that show an average activity lower than IBM:

BCH-1128: (1'S,1R,3S)-Methyl-[6-hydroxy-1-(2',3',6'-trideoxy-3'-amino-4'-hydroxy-L-lyxohexopyranose-5,12-dioxo-3,4,5,12-tetrahydroanthraceno-(2,3-C)pyran-3-yl]ketone hydrochloride BCH-1130: (1'S,1S,3R) and (1'S,1R,3S)-Methyl-[5,12-dihydroxy-1-(2',3',6'-trideoxy-3'-amino-4'-hydroxy-L-lyxohexopyranose)-6,11-dioxo-3,4,6,11-tetrahydroanthraceno-(2,3-C)pyran-3-yl]ketone hydrochloride;

BCH-1194: (1'S,1R,3S)-Methyl-[5,12-dihydroxy-1-(2',3', 6'-trideoxy-3'-amino-4'-hydroxy-L-lyxohexopyranose)-6,11-dioxo-3,4,6,11-tetrahydroanthraceno-(2,3-C)pyran-3-yl]ketone hydrochloride;

BCH-1633: (1'S,1S,3S)-3-Ethyl-5,12-dihydroxy-1-(2',3',6'-trideoxy-3'-amino-4'-hydroxy-L-lyxohexopyranose)-1,2,3,4-tetrahydro-(2-oxygen)naphthacene-6,11-dione-hydrochloride;

BCH-1669: (2'R,1R,3S) and (2'R,1S,3R)-3-Acetyl-1-(2',3'-dihydroxy)-n-propoxy-6-hydroxy-1,2,3,4,5,12-hexahydro-(2-oxo)naphthacene-5,12-dione;

BCH-1670: (2'S,1R,3S) and (2'S,1S,3R)-3-acetyl-1-(2',3'-dihydroxy)-n-propoxy-6-hydroxy-1,2,3,4,5,12-hexahydro-(2-sulfur)naphthacene-5,12-dione;

BCH-1672: (1'S,1R,3S)-Methyl-[5,12-dihydroxy-1-(2',6'-dideoxy-3',4'-dihydroxy-2'-iodo-L-lyxohexopyranose)-6,11-dioxo-3,4,6,11-tetrahydroanthraceno-(2'-C)pyran-3-yl]ketone;

BCH-1681: (1'S,1S,3R)-Methyl-(1-[2',6'-dideoxy-3',4'-diacetyl-2'-iodo-L-lyxohexopyranose]-6-hydroxy-3,4,5,10-tetrahydroanthraceno[2,3-c]pyran-3-yl) ketone;

BCH-1992: (1'S,1S,3R) and (1'S,1R,3S)-5,12-dihydroxy-3-methoxymethyl-1-(2',3',6'-trideoxy-3'-amino-L-lyxohexopyranose)-1,2,3,4-tetrahydro-(2-oxygen)naphthacene-6,11-dione hydrochloride;

BCH-2007: (1'S,1R,3S)-3-{6-Hydroxy-1-(2',3',6'-trideoxy-3'-trifluoroacetamido- 4'-hydroxy-L-lyxohexopyranose)-5,12-dioxo-3,4,5,12-tetrahydroanthraceno[2,3-C]-pyran-3-yl}nitrile;

BCH-2008: (1'S,1S,3R)-3-(6-Hydroxy-1-(2',3',6'-trideoxy-3'-trifluoroacetamido-4'-hydroxy-L-lyxohexopyranose)-5,12-dioxo-3,4,5,12-tetrahydroanthraceno[2,3-C]pyran-3-yl)nitrile;

BCH-2016: (1'S,1R,3R)-3-Ethyl-5,12-dihydroxy-1-(2',3',6'-trideoxy-3'-amino-L-lyxohexopyranose)-1,2,3,4-tetrahydro-(2-oxygen)-naphtacene-6,11-dione hydrochloride;

BCH-2034: (2'S,1R,3S) and (2'S,1S,3R)-3-acetyl(-2',3'-dihydroxy)-N-propoxy-6-hydroxy-1,2,3,4,5,12-hexahydro-(2-oxo)naphthacene-5,12-dione;

BCH-2049: (1'S,1S,3R)-5,12-rihydroxy-3-isopropyl-1-(2',3',6'-trideoxy-3'-amino-L-lyxohexopyranose)-1,2,3,4-tetrahydro-(2-oxygen)-naphtacene-6,11-dione-hydrochloride;

BCH-2050: (1'S,1R,3S)-5,12-Dixydroxy-3-isopropy-1-(2',3',6'-trideoxy-3'-amino'L-lyxohexopyranose)-1,2,3,4-tetrahydro-(2-oxygen)-naphtacene-6,11-dione-hydrochloride;

BCH-2056: Diastereomeric mixture of (1'-S,1-R,3-S) and (1'-S,3-R)(5,12-dihydroxy-1-(2',3',6'-trideoxy-3'-amino-4'-hydroxy-L-lyxohexopyranose)-6,11-dioxo-3,4,5,12-tetrahydroanthraceno-[2,3-c]pyran-3-yl)nitrile;

BCH-2058 & 2059:(1'S,1R,3S) and (1'S,1S,3R)-5,12-Dihydroxy-3-phenyloxymethyl-1-(2',3',6'-trideoxy-3'-amino-L-lyxohexopyranose)-1,2,3,4-tetrahydro-(2-oxygen)-naphthacene-6,11-dione-hydrochloride;

BCH-2066: (1'S,1R,3S)-Methyl-(5,12-dihydroxy-1-[2',3',6'-trideoxy-3'-amino-4'hydroxy-2'-iodo-L-lyxohexopyranose]- 6,11-dioxo-3,4,6,11-tetrahydroanthraceno-[2,3C]-pyran-3-yl) ketone hydrochloride;

BCH-2086: (1'S,1R,4R)-5,12-Dihydroxy-4-ethyl-1-(2',3',6'-trideoxy-3'-amino-L-lyxohexopyranose)-1,2,3,4-tetrahydro-(2-oxygen)-naphthacene-6,11-dione-hydrochloride;

BCH-2088: (1'S,1S,3S)-5,12-mihydroxy-3-pentyl-1-(2',3',6'-trideoxy-3'-amino-L-lyxohexopyranose)-1,2,3,4-tetrahydro-(2-oxygen)-naphtacene-6,11-dione-hydrochloride;

BCH-2089: (1'S,1R,3R)-5,12-Dihydroxy-3-pentyl-1-(2',3',6'-trideoxy-3'-amino-L-lyxohexopyranose)-1,2,3,4-tetrahydro-(2-oxygen)-naphtacene-6,11-dione-hydrochloride along with its (1'S,1S,3S) diastereomer (4:1);

BCH-2120: (1'S',1R,3S) and (1'S,1R,3S)-Isopropyl-[5,12-dihydroxy-6,11-dioxo-1-(2',3',6'-trideoxy-3'-amino-L-lyxohexopyranose)-3,4,6,11-tetrahydroanthraceno-[2,3-c]-pyran-3-yl]-ketone hydrochloride;

BCH-2188: (1'S,1S,3R)-5,12-dihydroxy-6,11-dioxo-3-isopropenyl-1-(2',3',6'-trideoxy-3'-amino-L-lyxohexopyranose)-3,4,5,12-tetrahydroanthraceno-[2,3-c]-pyran hydrochloride; and BCH-2189: (1'S,1R,3S)-5,12-dihydroxy-6,11-dioxo-3-isopropenyl-1-(2',3',6'-trideoxy-3'-amino-L-lyxohexopyranose)-3,4,5,12-tetrahydroanthraceno-2,3-c]-pyran hydrochloride.

Finally, further preferred compounds of the invention may be synthesized, such as:

(1'S,1R,3S) methyl (11-hydroxy-1-(2',3',6'-trideoxy-3'-trifluoroacetamido-4'-hydroxy-L-lyxohexopyranose)-5,12-dioxo-3,4,5,12-tetrahydroanthraceno[2,3-C]pyran-3-yl) ketone;

(1'S, 1S,3R) methyl (11-hydroxy-1-(2',3',6'-trideoxy-3'-trifluoroacetamido-4'-hydroxy-L-lyxohexopyranose)-5,12-dioxo-3,4,5,12-tetrahydroanthraceno[2,3-C]pyran-3-yl) ketone;

(1'S,1R,3S) methyl (11-hydroxy-1-(2',3',6'-trideoxy-3'-amino-4'-hydroxy-L-lyxohexopyranose)-5,12-dioxo-3,4,5,12-tetrahydroanthraceno[2,3-C]pyran-3-yl) ketone;

(1'S,1S,3R) methyl (11-hydroxy-1-(2',3',6'-trideoxy-3'-amino-4'-hydroxy-L-lyxohexopyranose)-5,12-dioxo-3,4,5,12-tetrahydroanthraceno[2,3-C]pyran-3-yl) ketone;

(1'S,1R,3S) methyl (6-hydroxy-10-methoxy-1-(2',3',6'-trideoxy-3'-trifluoroacetamido-4'-hydroxy-L-lyxohexopyranose)-5,12-dioxo-3,4,5,12-tetrahydroanthraceno [2,3-C]pyran-3-yl) ketone;

(1'S,1S,3R) methyl (6-hydroxy-10-methoxy-1-(2',3',6'-trifluoroacetamido-4'-hydroxy-L-lyxohexopyranose)-5,12-dioxo-3,4,5,12-tetrahydroanthraceno[2,3-C]pyran-3-yl) ketone;

(1'S,1R,3S) methyl (6-hydroxy-10-methoxy-1-(2',3',6'-trideoxy-3'-amino-4'-hydroxy-L-lyxohexopyranose)-5,12-dioxo-3,4,5,12-tetrahydroanthraceno[2,3-C]pyran-3-yl) ketone;

(1'S, 1S,3R) methyl (6-hydroxy-10-methoxy-1-(2',3',6'-trideoxy-3'-amino-4'-hydroxy-L-lyxohexopyranose)-5,12-dioxo-3,4,5,12-tetrahydroanthraceno[2,3-C]pyran-3-yl) ketone;

(1'S,1R,3S) methyl (5,12-dihydroxy-10-methoxy-1-(2',3',6'-trideoxy-3'-amino-4'-hydroxy-L-lyxohexopyranose)-6,11-dioxo-3,4,6,11-tetrahydroanthraceno[2,3-C]pyran-3-yl) ketone;

(1'S',1S,3R) methyl (5,12-dihydroxy-10-methoxy-1-(2',3',6'-trideoxy-3'-amino-4'-hydroxy-L-lyxohexopyranose)-6,11-dioxo-3,4,6,11-tetrahydroanthraceno[2,3-C]pyran-3-yl) ketone;

(1'S,1R,3 S)-3-aceto-1,2,3,4,5,12-hexahydro-6-hydroxy-1-daunosamine-(2-sulfur)naphthacene-5,12-dione;

(1'S,1S,3R)-3-aceto-1,2,3,4,5,12-hexahydro-6-hydroxy-1-daunosamine-(2-sulfur)naphthacene-5,12-dione;

(1'S,1R,3S)-3-aceto-1,2,3,4,5,12-hexahydro-6-hydroxy-10-methoxy-1-daunosamine-(2-sulfur)naphthacene-5,12-dione;

(1'S,1S,3R)-3-aceto-1,2,3,4,5,12-hexahydro-6-hydroxy-10-methoxy-1-daunosamine-(2-sulfur)naphthacene-5,12-dione;

(1'S,1R,3S)-3-aceto-1,2,3,4,5,12-hexahydro-6-hydroxy-10-methoxy-1-(N-trifluoroacetyl-L-daunosamine)-(2-sulfur)naphthacene-5,12-dione;

(1'S,1S,3R)-3-aceto-1,2,3,4,5,12-hexahydro-6-hydroxy-10-methoxy-1-(N-trifluoroacetyl-L-daunosamine)-(2-sulfur)naphthacene-5,12-dione;

(1'S,1R,3S)-3-aceto-1,2,3,4,6,11-hexahydro-5,12-dihydroxy-1-(N-trifluoroacetyl-L-daunosamine)-(2-sulfur)naphthacene-6,11-dione;

(1'S,1S,3R)-3-aceto-1,2,3,4,6,11-hexahydro-5,12-dihydroxy-1-(N-trifluoroacetyl-L-daunosamine)-(2-sulfur)naphthacene-6,11-dione;

(1'S,1R,3 S)-3-aceto-1,2,3,4,6,11-hexahydro-5,12-dihydroxy-1-L-daunosamine)-(2-sulfur)naphthacene-6,11-dione;

(1'S,1S,3R)-3-aceto-1,2,3,4,6,11-hexahydro-5,12-dihydroxy-1-L-daunosamine)-(2-sulfur)naphthacene-6,11-dione;

(1'S,1R,3S)-3-aceto-1,2,3,4,6,11-hexahydro-5,12-dihydroxy-10-methoxy-1-L-daunosamine)-(2-sulfur)naphthacene-6,11-dione;

(1'S,1S,3R)-3-aceto-1,2,3,4,6,11-hexahydro-5,12-dihydroxy-10-methoxy-1-L-daunosamine)-(2-sulfur)naphthacene-6,11-dione;

(1'S,1R,3S)-3-ethyl-1,2,3,4,6,11-hexahydro-5,12-dihydroxy-10-methoxy-1-L-daunosamine)-(2-sulfur)naphthacene-6,11-dione;

(1'S,1S,3R)-3-ethyl-1,2,3,4,6,11-hexahydro-5,12-dihydroxy-10-methoxy-1-L-daunosamine)-(2-sulfur)naphthacene-6,11-dione;

(1'S,1R,3S)-3-ethyl-1,2,3,4,6,11-hexahydro-5,12-dihydroxy-1-L-daunosamine)-(2-sulfur)naphthacene-6,11-dione;

(1'S,1S,3R)-3-ethyl-1,2,3,4,6,11-hexahydro-5,12-dihydroxy-1-L-daunosamine)-(2-sulfur)naphthacene-6,11-dione;

(1'S,1R,3S)-3-difluoroethyl-1,2,3,4,6,11-hexahydro-5,12-dihydroxy-1-L-daunosamine)-naphthacene-6,11-dione;

(1'S,1S,3R)-3-difluoroethyl-1,2,3,4,6,11-hexahydro-5,12-dihydroxy-1-L-daunosamine)-naphthacene-6,11-dione;

(1'S,1R,3S)-3-difluoroethyl-1,2,3,4,5,12-hexahydro-6-hydroxy-1-L-daunosamine)-naphthacene-5,12-dione;

(1'S,1S,3R)-3-difluoroethyl-1,2,3,4,5,12-hexahydro-6-hydroxy-1-L-daunosamine)-naphthacene-5,12-dione;

(1'S,1R,3S)-3-ethyl-1,2,3,4,6,11-hexahydro-5,12-dihydroxy-1-(2'-deoxyfucose)-naphthacene-5,12-dione;

(1'S,1S,3R)-3-ethyl-1,2,3,4,6,11-hexahydro-5,12-dihydroxy-1-(2'-deoxyfucose)-naphthacene-5,12-dione;

(1'S,1R,3S)-3-ethyl-1,2,3,4,5,12-hexahydro 6-hydroxy-1-(2'deoxyfucose)-naphthacene-5,12-dione;

(1'S,1S,3R)-3-ethyl-1,2,3,4,5,12-hexahydro 6-hydroxy-1-(2'deoxyfucose)-naphthacene-5,12-dione;

(1'S,1R,3S)-1-(2',3',6'-trideoxy-3'-amino -L-lyxohexopyranose)-3-oxazole-5,12-dihydroxy-6,11-dioxo-3,4,6,11-tetrahydroanthraceno[2,3-C]pyran;

(1'S,1S,3R)-1-(2',3',6'-trideoxy-3'-amino-L-lyxohexopyranose)-3-oxazole-5,12-dihydroxy-6,11-dioxo-3,4,6,11-tetrahydroanthraceno[2,3-C]pyran;

(1'S,1R,3S)-1-(2',3',6'-trideoxy-3'-amino-L-lyxohexopyranose)-3-oxazole-6-hydroxy-5,12-dioxo-3,4,5,12-tetrahydroanthraceno[2,3-C]pyran;

(1'S,1S,3R)-1-(2',3',6'-trideoxy-3'-amino-L-lyxohexopyranose)-3'-oxazole-6-hydroxy-5,12-dioxo-3,4,5,12-tetrahydroanthraceno[2,3-C]pyran;

(1'S,1R,3S)-3-aceto-1,2,3,4,5,12-hexahydro-6-hydroxy-1-(2',3',4'6'-tetradeoxy-4'-amino-L-lyxohexopyranose)-naphthacene-5,12-dione;

(1'S,1S,3R)-3-aceto-1,2,3,4,5,12-hexahydro-6-hydroxy-1-(2',3',4',6'-tetradeoxy-4'-amino-L-lyxohexopyranose)-naphthacene-5,12-dione;

(1'S,1R,3S)-3-aceto-1,2,3,4,6,11-hexahydro-5,12-dihydroxy-1-(2',3',4',6'-tetradeoxy-4'-amino-L-lyxohexopyranose)naphthacene-6,11-dione;

(1'S,1S,3R)-3-aceto-1,2,3,4,6,11-hexahydro-5,12-dihydroxy-1-(2',3',4',6'-tetradeoxy-4'-amino-L-lyxohexopyranose)naphthacene-6,11-dione;

(1'S,1R,3S)-3-aceto-1,2,3,4,5,12-hexahydro-6-hydroxy-1-(2',3',4',6'-tetradeoxy-4'-amino-L-arabinohexopyranose)naphthacene-5,12-dione;

(1'S,1S,3R)-3-aceto-1,2,3,4,5,12-hexahydro-6-hydroxy-1-(2',3',4',6'-tetradeoxy-4'-amino-L-arabinohexopyranose)naphthacene-5,12-dione;

(1'S,1R,3S)-3-aceto-1,2,3,4,6,11-hexahydro-5,12-dihydroxy-1-(2',3',4',6'-tetradeoxy-4'-amino-L-arabinohexopyranose)naphthacene-6,11-dione;

(1'S,1S,3R)-3-aceto-1,2,3,4,6,11-hexahydro-5,12-dihydroxy-1-(2',3',4',6'-tetradeoxy-4'-amino-L-arabinohexopyranose)naphthacene-6,11-dione;

(1'S,1R,3S)-6-hydroxy-1-(2',3',6'-trideoxy-3'-amino-4'hydroxy-L-lyxohexopyranose)-5,12-dioxo-3,4,5,12-tetrahydroanthraceno[2,3-C]pyran-3-acetic acid;

(1'S,1S,3R)-6-hydroxy-1-(2',3',6'-trideoxy-3'-amino-4'hydroxy-L-lyxohexopyranose)-5,12-dioxo-3,4,5,12-tetrahydroanthraceno[2,3-C]pyran-3-acetic acid;

(1'S,1R,3S)-5,12-dihydroxy-1-(2',3',6'-trideoxy-3'-amino-4'hydroxy-L-lyxohexopyranose)-6,11-dioxo-3,4,6,11-tetrahydroanthraceno[2,3-C]pyran-3-acetic acid;

(1'S,1S,3R)-5,12-dihydroxy-1-(2',3',6'-trideoxy-3'-amino-4'hydroxy-L-lyxohexopyranose)-6,11-dioxo-3,4,6,11-tetrahydroanthraceno[2,3-C]pyran-3-acetic acid;

(1'S,1R)-6-hydroxy-1-(2',3',6'-trideoxy-3'-trifluoroacetamido-4'-hydroxy-L-lyxohexopyranose)-5,12-dioxo-3,4,5,12-tetrahydroanthraceno[2,3-C]pyran;

(1'S,1S)-6-hydroxy-1-(2',3',6',-trideoxy-3'-trifluoroacetamido-4'-hydroxy-L-lyxohexopyranose)-5,12-dioxo-3,4,5,12-tetrahydroanthraceno[2,3-C]pyran;

(1'S,1R)-6-hydroxy-1-(2',3',6',-trideoxy-3'-amino-4'-hydroxy-L-lyxohexopyranose)-6,11-dioxo-3,4,6,11-tetrahydroanthraceno[2,3-C]pyran;

(1'S,1S)-6-hydroxy-1-(2',3',6',-trideoxy-3'-amino-4'-hydroxy-L-lyxohexopyranose)-6,11-dioxo-3,4,6,11-tetrahydroanthraceno[2,3-C]pyran;

(1'S,1R)-5,12-dihydroxy-1-(2',3',6',-trideoxy-3'-amino-4'-hydroxy-L-lyxohexopyranose)-6,11-dioxo-3,4,6,11-tetrahydroanthraceno[2,3-C]pyran;

(1'S,1S)-5,12-dihydroxy-1-(2',3',6',-trideoxy-3'-amino-4'-hydroxy-L-lyxohexopyranose)-6,11-dioxo-3,4,6,11tetrahydroanthraceno[2,3-C]pyran;

(1'S,1R)-5,12-dihydroxy-1-(2',3',6',-trideoxy-3'-trifluoroacetamido-4'-hydroxy-L-lyxohexopyranose)-6,11-dioxo-3,4,6,11-tetrahydroanthraceno[2,3-C]pyran; and (1'S,1S)-5,12-dihydroxy-1-(2',3',6',-trideoxy-3'-trifluoro-acetamido-4'-hydroxy-L-lyxohexopyranose)-6,11-dioxo-3,4,6,11-tetrahydroanthraceno[2,3-C]pyran.

EXAMPLES

The invention will now be further described with reference to the following examples.

Standard chemical abbreviations used in this application are:

t-Bu = —C(CH$_3$)$_3$

Ac = —COCH$_3$

Me = —CH$_3$

Et = —CH$_2$CH$_3$

TFA = —COCF$_3$

OMOM = —OCH$_3$OCH$_3$

PNBz = 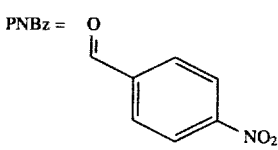

Bz = 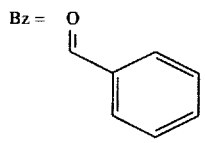

Mz = 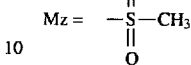

OPv = 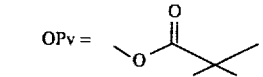

MMTr = —C(C$_5$H$_5$)$_2$ 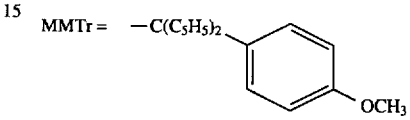

Example 1

Preparation of BCH-242: (1'S,1R,3S) and (1'S,1S,3R)-Methyl[11-hydroxy-1-2',3',6'-trideoxy-3-trifluroacetamido-L-lyxohexopyranose)-5,12-dioxo-3,4,5,12-tetrahydroanthraceno[2,3-c]pyran-3-yl]formate

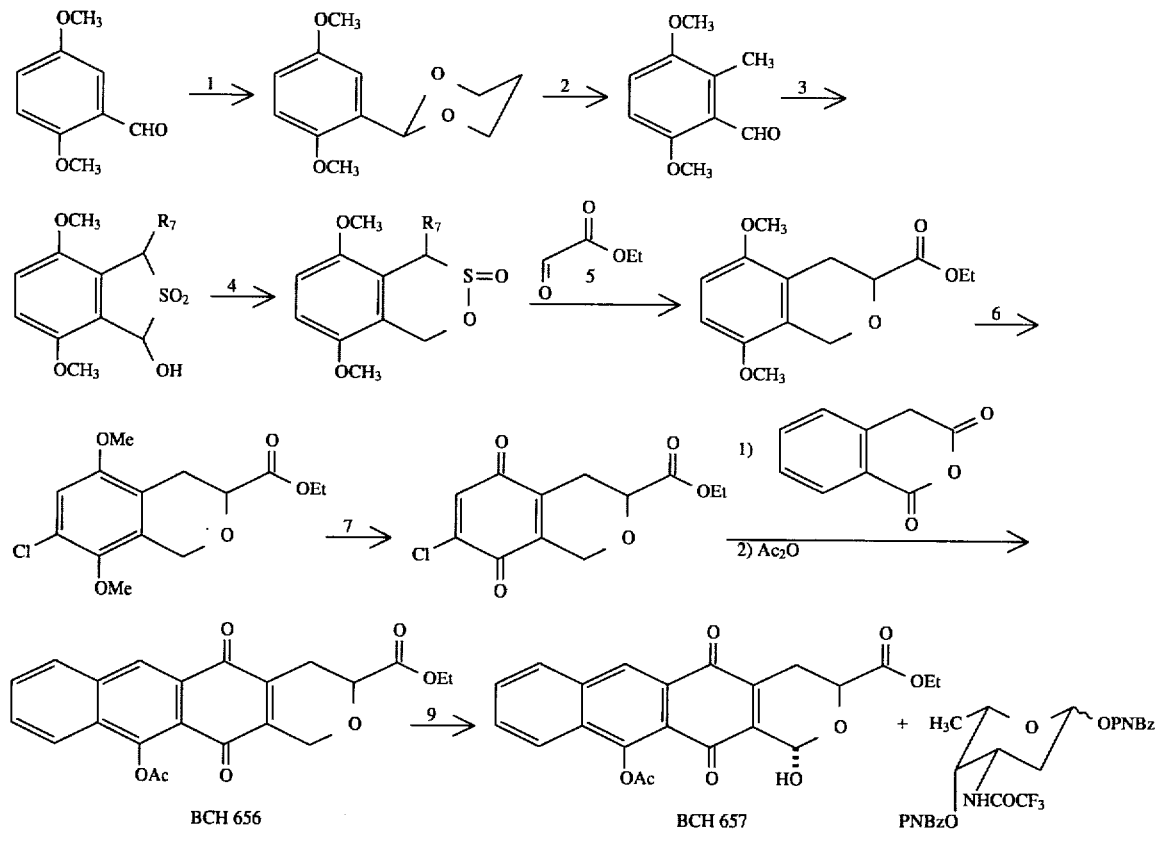

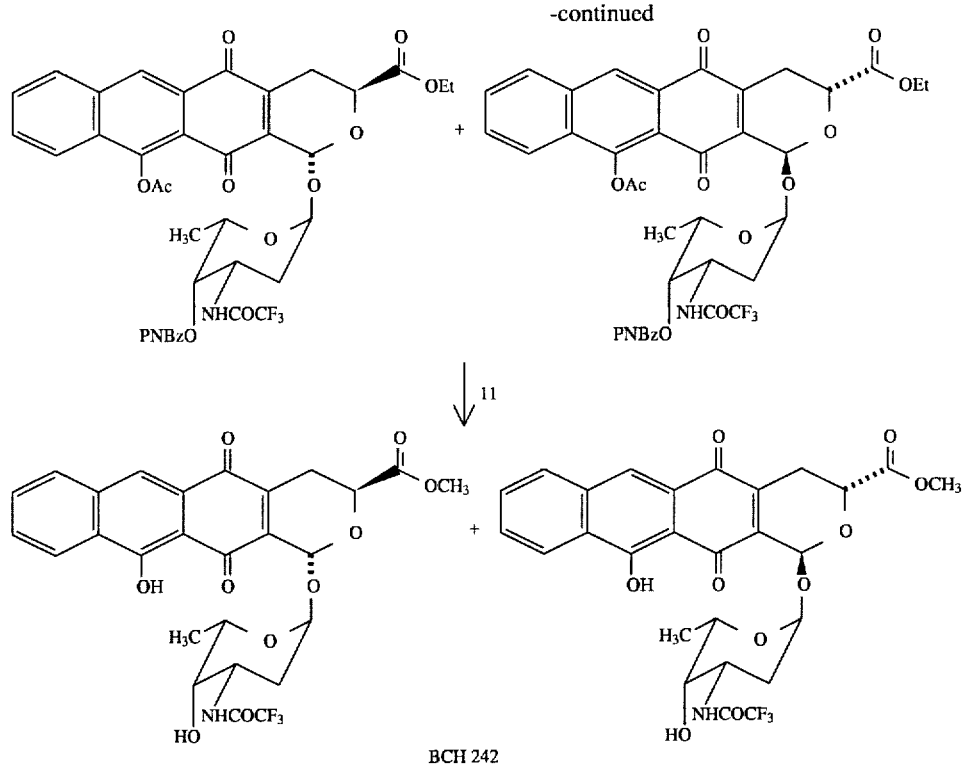

BCH 242

Example 1

Step 1: 2,5-Dimethoxybenzaldehydedioxane acetal

A solution containing 200 g (1.2 mmol) of 2,5-dimethoxybenzaldehyde, 150 g (2.0 mmol) of 1,3-propanediol, and 1.0 g of p-toluene-sulfonic acid in 1.0 L of benzene was refluxed until no more water could be isolated in the Dean-Stark water separator (6 hours). The reaction mixture was then cooled and washed with 400 ml of saturated aqueous sodium bicarbonate, 200 ml of water and 200 ml of saturated aqueous sodium chloride. The organic layer was then dried over MgSO$_4$ and the solvent was removed in vacuo. Distillation of the residue under reduced pressure (B.P. 167° C. at 1 mmHg) gave 263.7 g (98% yield) of a slightly yellow oil characterised as 2,5-dimethoxybenzaldehydedioxane acetal. $^1$H NMR (200 MHz, CDCl$_3$) δ: 1.40 (d m, 1H, HCHa), 2.24 (m, 1H, HCHe), 3.77 (s, 3H, OCH$_3$), 3.78 (s, 3H, OCH$_3$), 4.00 (dt, 2H, O—HCHa), 4.24 (dd, 2H, O—HCHe), 5.84 (s, 1H, O—CH—O), 6.82 (dd, 2H, ArH), 7.19 (d, 1H, ArH).

Step 2: 2,5-Dimethoxy-6-methylbenzaldehyde

To a cooled (–40° C.) solution containing 84.0 g (0.37 mmol) of 2,5-dimethoxybenzaldehydedioxane acetal in 2.0 L of dry diethyl-ether was added with stirring and under argon 240 ml of a 2.5M n-butyl lithium solution in hexanes. The mixture was stirred for four hours at –25° C. and then 24 hours at –10° C. Then to the cooled (–25° C.) stirred reaction mixture under argon was added 90.0 g of methyl iodide and stirred overnight at room temperature. The solution was then washed twice with 300 ml of water, once with 300 ml of saturated sodium chloride and dried over MgSO$_4$. The organic solvent was evaporated and the residue was dissolved in 500 ml of ether and stirred for 1½ hours with 500 ml of 1N aqueous HCl. The organic layer was separated and washed twice with 200 ml water, once with 200 ml of brine and dried over MgSO$_4$. Evaporation of the solvent gave a yellow oil which was flash chromatographed with 2.5% ethyl acetate in toluene. A 67% yield (45 g) of 2,5-dimethoxy-6-methylbenzaldehyde was obtained (MP: 61°–61.5° C.). $^1$H NMR (200 MHz, CDCl$_3$) δ: 2.46 (s, 3H, CH3), 3.78 (s, 3H, OCH$_3$), 3.83 (s, 3H, OCH$_3$), 6.90 (dd, 2H, ArH), 10.58 (s, 1H, CHO).

Step 3: 5,8-dimethoxy-1-hydroxy-1,3-dihydrobenzo[c]thiophen-2,2-dioxide

Procedure 1: Under an argon atmosphere, a deoxygenated solution containing 1.60 g (8.9 mmol) of 2,5-dimethoxy-6-methyl-benzaldehyde, 11.0 g of SO$_2$ in 100 ml of thiophene free benzene was irradiated at 350 nm for 36 hours. The precipitated crystals (2.01 g, 93% yield) were filtered and found sufficiently pure for further use.

Procedure 2: For larger scale, under argon, a deoxygenated solution containing 10.0 g (55.5 mmol) of 2,5-dimethoxy-6-methylbenzaldehyde, 50 g of SO$_2$ in 600 ml of thiophene free benzene was irradiated with a medium pressure mercury immersion lamp with pyrex filtration for four days. The resulting sludge was extracted three times with 400 ml of 1N NaOH and the combined aqueous layer was washed twice with 200 ml of methylene chloride. The aqueous layer was then neutralised with concentrated aqueous HCl and the resulting mixture was then extracted three times with 500 ml of methylene chloride. The combined organic layer was then washed once with 200 ml water, 200 ml of saturated aqueous sodium bicarbonate, 200 ml of water, 200 ml of brine, and then dried over MgSO$_4$. Following evaporation of solvent, 11.2 g (83%) of pure 5,8-dimethoxy-1-hydroxy-1,3-dihydrobenzo[c]thiophene-2,2-dioxide was obtained (MP: 140° C. decomposes) $^1$H NMR (200 MHz, CDCl$_3$) d:3.57 (s, 3H, OCH$_3$), 3.60 (s, 3H, OCH$_3$), 4.44 (ddd, 2H, CH2), 5.65 (s, 1H, CH), 6.85 (dd, 2H, ArH).

Step 4: 4,7-dimethoxy-3'S-dihydrobenzo[b]-1,2-oxathiin-2-oxide.

Following a slightly modified procedure (Charlton J. L., and Durst T., Tet. Lett', 25(46), 5290–1984), to a stirred and cooled (0° C.) solution of 7.30 g (30 mmol) of the 1-hydroxysulfone, prepared in step 3, in 275 ml of methanol was added in portions over fifteen minutes 5.65 g of sodium borohydride. The mixture was stirred for one hour and then warmed at 50° C. for five minutes. The reaction mixture was then evaporated to dryness and to the residue was added 200 ml of concentrated aqueous HCl. After warming at 50° C. for five minutes, 300 ml of water was added and the aqueous mixture was extracted three times with 300 ml of $CH_2Cl_2$. The combined organic layer was washed twice with 200 ml of water, once with 200 ml of brine and dried over $MgSO_4$ After evaporation of the solvent, the residue was found to be sufficiently pure to be used in the next step (MP: 90.0°–91.0° C.). $^1$H NMR (200 MHz, DMSO-$d_6$) δ: 3.63 (d, 1H, J=16 Hz, $CH_2SO$), 3.80 (s, 3H, $OCH_3$), 3.81 (s, 3H, $OCH_3$), 4.13 (d, 1H, J=16 Hz, $CH_2SO$), 5.14 (dd, 2H, $CH_2O$—), 6.78 (s, 2H, aryl-H).

Step 5: Ethyl(5,8-dimethoxyisochroman-3-yl)formate

In a 250 ml triple necked round bottom flask, equipped with a Dean-Stark, was refluxed a solution containing 30.6 g (0.3 mmol) of ethylglyoxalate (Kelly et al, Synthesis, 544, 1972) in 100 ml of benzene until no more water could be separated. A solution containing 4.39 g (19.2 mmol) of the sultine from step 4 in 75 ml of benzene was then added dropwise over 3 hours. During the addition argon was bubbled in the reaction mixture. Reflux was continued overnight and after cooling, the excess glyoxalate was extracted from the mixture with four portions of 200 ml water. The benzene layer was dried and evaporated to give a residue from which was separated 3.13 g (61%) of dimethoxyisochroman after flash chromatography from ethyl acetate/toluene. (MP: 59.8° C.). $^1$H NMR (200 MHz, $CDCl_3$) δ: 1.34 (s, 3H, J=7.1 Hz, $CH_3$), 2.78 (broad dd, 1H, J=17.0, 10.8, 1.3 Hz, HCHaCHC=O), 3.10 (ddd, 1H, J=16.9, 3.9, 1.44 Hz, HCHe, CHC=O), 3.77 (s, 3H, $OCH_3$), 3.80 (s, 3H, $OCH_3$), 4.26 (dd, 1H, J=10.8, 3.9 Hz, OCHC=O), 4.30 (q, 2H, J=7.1 Hz, —$OCH_2$), 4.68 (broad dt, 1H, J=16.0, 1.4, 1.3, ArHCHaO—) 5.07 (broad d, J=16.0 Hz, ArHCHeO—), 6.66 (dd, J=8.9 H, ArH).

Step 6: Ethyl(7-chloro-5,8-dimethoxyisochroman-3-yl)formate

Under argon and at room temperature, was added dropwise 0.820 g (7.6 mmol) of t-butylhypochlorite to a stirred solution containing 1.973 g (7.4 mmol) of the isochroman from step 5 in 75 ml of anhydrous $CH_2Cl_2$. The reaction mixture was stirred for 3 hours and then washed successively with 25 ml portions of saturated aqueous sodium thiosulfate, water and brine. After drying over $Na_2SO_4$, the organic layer was evaporated and the residue was flash chromatographed with 2.5% ethyl acetate in toluene as the eluting solvent mixture. The title compound was obtained in 46% yield (1.02 g). (MP: 95.0° C.) $^1$H NMR (200 MHz, $CDCl_3$) δ: 1.35 (t, 3H, J=7.1 Hz, $CH_3$), 2.93 (broad dd, J=16.8, 10.3 Hz, HCHaCHC=O), 3.16 (broad dd, J=16.9, 3.2 Hz, HCHeCHC=O), 3.78 (s, 3H, $OCH_3$), 3.81 (s, 3H, $OCH_3$), 4.27 (dd, J=10.2, 3.3 Hz, —CH), 4.31 (q, 2H, J=7.1Hz, $OCH_2$), 4.63 (broad d, 1H, J=16.2 Hz, HCHa0), 5.01 (d, 1H, J=16.2 Hz, HCHeO), 6.73 (s, 1H, ArH).

Step 7: Ethyl(7-chloro-5,8-dioxo-5,8-dihydro-isochroman-3-yl)formate

To a stirred solution of 1.0 g (3.7 mmol) of the chloroisochroman from step 6 in 20 ml of acetonitrile was added dropwise a solution containing 6.25 g (11.4 mmol) of ceric ammonium nitrate in 20 ml of water. The mixture was stirred overnight and then diluted with 50 ml of $CH_2Cl_2$. The organic layer was separated and the aqueous phase was extracted twice with 25 ml $CH_2Cl_2$. The combined organic layer was washed once with 50 ml $H_2O$, 50 ml brine and then dried over $Na_2SO_4$. After evaporation of solvents, flash chromatography of the residue with a solvent gradient of 5 to 20% ethyl acetate in toluene yielded 495 mg (55%) of the titled compound. (MP: 83.5° C.) $^1$H NMR (200 MHz, $CDCl_3$) δ: 1.27 (t, 3H, J=7.1 Hz, $CH_3$), 2.58 (ddt, 1H, J=19.0, 8.8, 3.2 Hz, HCHaCHC=O), 2.83 (d multiplets, 1H, HCHeCHC=O), 4.17 (dd, 1H, J=8.7, 3.3 Hz, OCHC=O), 4.20 (q, 2H, J=7.0 Hz, $OCH_2$), 4.44 (dt, 1H, J=18.8, 3.4 Hz, HCHaO), 4.78 (d multipier, 1H, J=18.8, 2.6, 1.7 Hz, HC HeO), 6.95 (s, 1H, C=CH).

Step 8: Ethyl[11-acetoxy-5,12-dioxo-3,4,5,12-tetrahydroanthraceno[2,3-c]pyran-3-yl]formate (BCH-656)

To a cooled (0° C.) and stirred solution of 203 mg of dry diisopropylamine in 7 ml of dry tetrahydrofuran under argon was added 0.74 ml of a 2.5M solution of n-butyl lithium in hexanes. The mixture was cooled to −78° C. and stirring was continued for ½ hour. A solution containing 325 mg (2.0 mmol) of homophthalic anhydride in 7 ml THF was slowly added over five minutes. Next was added in one portion a solution containing 500 mg (1.85 mmol) of the chloroquinone from step 9, in 9 ml THF. The reaction mixture was then stirred for 20 min at −78° C., allowed to warm up to room temperature and stirred for one hour. The reaction was then quenched with 10 ml of saturated ammonium chloride, and partitioned between 10 ml of 5% aqueous HCl and 100 ml $CH_2Cl_2$. The organic layer was then separated and washed with 25 ml of water, 25 ml of brine and dried over $Na_2SO_4$. Evaporation of solvents yielded the crude pyranoanthracyclinone which was immediately acetylated in 90 ml of $CH_2Cl_2$ at room temperature for 10 hours with acetic anhydride (1.25 ml) in the presence of 100 mg of dimethylaminopyridine and 1.5 ml of pyridine. To this reaction mixture was then added 50 g of ice, and the isolated organic layer was washed consecutively with 25 ml portions of 5% aqueous HCl, water and brine. The organic solution was then dried over $Na_2SO_4$ and evaporated. The residue was then subjected to flash chromatography (5% ethyl-acetate in toluene) and gave 351 mg (34% yield) of the desired titled compound. (MP: 171°–173° C.) $^1$H NMR (300 MHz, $CDCl_3$) δ: 1.32 (t, 3H, J=7.1 Hz, $CH_3$), 2.64 (s, 3H, $COCH_3$), 2.80 (ddt, 1H, J=19.1, 9.0, 3.0 Hz, HC HaCHC=O), 3.07 (d M, 1H, J=18.9 Hz, HC HeCHC=O), 4.29 (dd, 1H, J=9.0, 4.8 Hz, OCHC=O), 4.28 (q,1 H, J=7.1 Hz, $OCH_2$), 4.59 (dt, 1H, J=18.9, 3.2 Hz, HC HaO), 4.97 (broad d, 1H, J=18.9 Hz, HCHeO), 7.72 (m, 2H, ArH), 8.20 (m, 2H, ArH), 8.58 (s, 1H, ArH). CMR (75.44 MHz, $CDCl_3$) δ: 13.9, $CH_3$, 20.9, $CH_3$, 24.6, $CH_2$, 61.6, $OCH_2$; 71.1, OCH; 123.9, 127.4, 130.3, 130.5, 130.6, aryl CH; 117.9, 128.6, 130.4, 135.6, 140.9, 144.4, 148.2, aryl C; 166.7, 170.4, ester C=O; 181.7, 182.5, quinone C=O. IR (FT, $CDCl_3$) $^v$max: 1774 acetate C=O, 1750, ester C=O; 1667, 1643, quinone C=O. HRMS calculated for $C_{22}H_{18}O_7$: (M+) 394.1053 found 394.1067.

Step 9: (1S,3S) and (1R,3R)-Ethyl[11-acetoxy-1-hydroxy-5,12-dioxo-3,4,5,12-tetrahydroanthraceno[2,3-c]pyran-3-yl] formate (BCH-657)

A mixture containing 257 mg (0.65 mmol) of the pyranotetra-cycle obtained in step 8, 121 mg of n-bromosuccinimide, and 15 mg of AIBN in 25 ml of carbon tetrachloride was refluxed for 2 hours. After cooling, the solvent was removed in vacuo and the residue was treated with 40 ml of a 1:1 THF/water solvent mixture for one hour. Most of the THF was then removed in a rotaevaporator and the residual aqueous mixture was extracted three times with 30 ml $CH_2Cl_2$. The combined organic layer was then washed with 25 ml aliquots of water and brine. After drying over $Na_2SO_4$, the solvent was removed and the residue was flash chromatographed to give 178 mg (67%) of the titled aglycone. (MP: 190°–192° C.). $^1$H NMR (300 MHz, $CDCl_3$) m235: 1.25 (t, 3H, J=7.1 Hz, $CH_3$), 2.54 (s, 3H, $OCOCH_3$), 2.59 (dd, 1H, J=11.5, 19.1 Hz, HCHa), 2.89 (dd, 1H, J=4.0, 19.1 Hz, HCHe), 4.21 (q, 2H, J=7.1 Hz, $OCH_2$), 4.73 (dd, 1H, J=4.1, 11.6 Hz, OCH), 5.89 (bs, 1H, OCH—OH), 7.34 (bs, 1H, exchangeable OH), 7.84 (m, 2H, ArH), 8.25 (m, 1H, ArH), 8.34 (m, 1H, ArH), 8.63 (s, 1H, ArH). CMR (75.44 MHz, DMSO-$d_6$) δ: 14.0, $CH_3$; 20.9, $CH_2$; 61.0, $OCH_2$;

64.4, OCH; 85.9, O—CH—OH; 120.0, 126.8, 130.8, 130.9, 135.1, aryl CH; 118.0, 128.5, 130.0, 142.1, 142.7, 147.7, aryl C; 169.3, 170.5, ester C=O; 180.8, 183.2, quinone C=O.

IR (FT, CDCl$_3$) $^v$max: 3575, bs, OH; 1774, 1750, ester C=O; 1670, quinone C=O. HRMS calculated for C$_{22}$H$_{18}$O$_8$: [M+] 410.1002 found 410.1010.

Step 10: (1'S,1R,3S) and (1'S,1S,3R)-Ethyl[11-acetoxy-1-(2',3',6'-trideoxy-3'-trifluoroacetamido-4'-O-p-nitrobenzoyl-L-lyxohexopyranose)-5,12-dioxo-3,4,5,12-tetrahydroanthraceno-(2,3-c)pyran-3-yl]formate To a stirred and cooled (−40° C.) solution of 222 mg (0.41 mmol) of 2,3,6-trideoxy-3-trifluoroacetamido-1,4-di-O-p-nitrobenzoyl-a (or b)-L-lyxohexopyranose in 20 ml of a 3:1 CH$_2$Cl$_2$—Et$_2$O solvent system was added 0.15 ml of trimethylsilyltrifluoromethane sulfonate under argon atmosphere and in the presence of 4A molecular sieves. The mixture was stirred one hour at −5° C. and then cooled to −15° C. A solution containing 121 mg (0.30 mmol) of the pyranoaglycone from step 9 above in 10 ml CH$_2$Cl$_2$ was added next and the mixture was stirred for 20 hours at −15° C. The reaction mixture was then poured in 50 ml of a 1:1 ethyl acetate saturated sodium bicarbonate solvent system, filtered and the separated organic layer was washed with 10 ml of water, 10 ml of brine and dried over Na$_2$SO$_4$. After removal of solvents, the residue was flash chromatographed with 10% ethyl acetate in toluene. The desired titled pyranoanthracycline glycosides were obtained as a 1:1 diastereomeric mixture in 65% yield (239 mg). (MP: 160–162° C. decomposes). $^1$H NMR (200 MHz, CDCl$_3$) of the (1'S, 1S,3R) diastereomer, δ: 1.24 (d, 3H, J=6.5 Hz, H$_3$C-6'), 1.37 (t, 3H, J=7.1 Hz, CH$_3$), 2.06 (m, 2H, H$_2$C-2'), 2.58 (s, 3H, acetyl, CH$_3$) 2.74 (dd, 1H, J=17.5, 12 Hz, HCHaCHC=O), 3.17 (dd, 1H, J=19.4, 3.8 Hz, HCHeCHC=O), 4.32 (q, 2H, J=7.0 Hz, OCH$_2$CH$_3$), 4.42 (broad q, 1H, J=7.1 Hz, HC-5'), 4.66 (m, 1H, HC-3'), 4.74 (dd, 1H, J=11.9, 3.8 Hz, OCHC=O), 5.47 (broad s, 1H, HC-4'), 5.75 (broad s, 1H, HC-1'), 6.05 (s, 1H, O—CH—O), 6.31 (d, 1H, J=6.6 Hz, NH), 7.76 (m, 2H, ArH), 8.14 (dm, 2H, ArH), 8.31 (dd, 4H, p-nitroben-zoyl-H), 8.60 (s, 1H, ArH). $^1$H NMR (200 MHz, CDCl$_3$) of the (1'S, 1R,3S) diastereomer, δ: 1.26 (d, 3H, J=6.5 Hz, H$_3$C-6'), 1.35 (t, 3H, J=7.1 Hz, OCH2CH$_3$), 2.06 (m, 2H, H$_2$C-2'), 2.59 (s, 3H, acetyl- CH$_3$), 2.76 (dd, 1H, J=18.8, 12 Hz, HC HaCHC=O), 3.15 (dd, 1H, J=19.4, 4.1 Hz, HC HeCHC=O), 4.31 (q, 2H, J=7.1 Hz, OCH$_2$CH$_3$), 4.66 (m, 2H, overlaped HC-3' and HC-5'), 4.76 (dd, 1H, J=11.9, 4.0 Hz, OCHC=O), 5.44 (broad s, 1H, HC-4'), 5.65 (broad s, 1H, HC-1'), 6.42 (d, 1H, J=7.4 Hz, NH), 7.76 (m, 2H, ArH), 8.14 (dm, 2H, ArH), 8.32 (dd, 4H, p-nitrobenzoyl- H), 8.60 (s, 1H, ArH). CMR of the mixture (75.44 MHz, CDCl$_3$) γ:13.9 and 14.0, CO$_2$CH$_2$CH$_3$; 16.6, 16.8, 6'-CH$_3$; 20.9, acyl CH$_3$; 24.1, 24.6, 2'-CH$_2$; 29.4, 29.8, 4-CH$_2$; 45.4, 45.5, CHNH; 61.7, 61.8, ester OCH$_2$; 65.6, 66.3, 5'-OCH; 66.5, 4'-OCH; 71.8, 72.4, 3-OCH; 87.9, 92.7, 1-O—CH—O; 92.7, 98.0, 1'-O—CH-O; 115.6, quartet, J=289.2 Hz, CF$_3$; 124.0, 127.57, 127.64, 130.5, 130.6, 130.7, 131.18, 131.22, 135.6, aryl CH; 118.0, 128.4, 134.6, 134.7, 141.0, 141.5, 142.2, 143.1, 148.3, 151.10, 151.14, aryl C; 157.1, quartet, J=37.7, COCF$_3$; 164.8, 165.2, 169.2, 169.8, 170.2, ester C=O; 181.2, 183.2, quinone C=O. IR (FT, CDCl$_3$)$^v$max: 1775 1737, bs, ester C=O; 1670, quinone C=O.

Step 11: (2R,1R,3S) and (1'S,1S,3R)-Methyl[11-hydroxy-1-(2',3',6'-trideoxy-3'trifluoroetamido-L-lyxohexoyranose)-5,12-dioxo-3,4,5,12-tetrahydroanthraceno (2,3-C) pyran-3-yl] formate) (BCH-242)

Under argon, at room temperature a solution containing 115 mg (0.13 mmol) of the glycosides from step 10 above in 10 ml of dry methanol was treated with 0.16 ml of a 1.0M NaOCH$_3$ methanolic solution for two hours. The reaction mixture was then quenched with three drops of saturated aqueous NH$_4$Cl and the solvent was evaporated to dryness. The residue was stirred with pentane for five hours and then filtered. The pentane insoluble portion was then taken up in ether and filtered. The ether was evaporated and the residue was flash chromatographed with a solvent gradient ranging from 50% ethyl acetate in toluene to 20% methanol in ethyl acetate. The titled heteroanthracycline glycosides were obtained in 74% yield (56 mg) as a 1:1 mixture (MP: 147°–150° C.). $^1$H NMR (300 MHz, CDCl$_3$) of the (1'S,1R, 3S) diastereomer, δ: 1.30 (d, 3H, J=6.9 Hz, H$_3$C-6'), 1.88 (m, 1H, Hac-2'), 2.04 (m, 1H, HeC-2'), 2.72 (dd, 1H, J=19.0, 12.0 Hz, HCHaCHC=O), 3.18 (dd, 1H, J=19.0, 3.9 Hz, HC HeCHC=O), 3.66 (broad s, 1H, HC-3'), 3.86 (s, 3H, OCH$_3$) 4.33 (m, 2H, HC-4' and HC-5'), 4.73 (dd, 1H, J=11.8, 3.9 Hz, O—CHC=O), 5.50 (broad s, 1H, HC-1'), 5.88 (singlet, 1H, O—CH—O), 6.74 (broad d, 1H, NH), 7.74 (m, 2H, ArH), 7.98 (m, 1H, ArH), 8.18 (s, 1H, ArH), 8.50 (m, 1H, ArH).

$^1$H NMR (300 MHz, CDCl$_3$) of the (1'S,1S,3R) diastereomer, δ:1.34 (d, 3H, J=7.0 Hz, H$_3$C-6'), 1.88 (m, 1H, HaC-2'), 2.04 (m, 1H, HeC-2'), 2.72 (dd, 1H, J=19.0, 12.0 Hz, HCHaCHC=O), 3.18 (dd, 1H, J=19.0, 3.9 Hz, HC HeCHC=O), 3.66 (broad s, 1H, HC-3'), 3.87 (s, 3H, OCH$_3$), 4.33 (m, 1H, HC-4'), 4.59 (broad q, 1H, J=7.1 Hz, HC-5'), 4.73 (dd, 1H, J=11.8, 3.9 Hz, O—CHC—O), 5.60 (broad s, 1H, HC-1'), 6.04 (s, 1H, O—CH—O), 6.74 (broad d, 1H, NH), 7.74 (m, 2H, ArH), 7.98 (m, 1H, ArH), 8.18 (s, 1H, ArH), 8.50 (m, 1H, ArH). HRMS calculated for C$_{28}$H$_{26}$F$_3$NO$_{10}$: [M+]579.1353, found 579.1358.

Example 2

Preparation of (1'S,1R,3S) and (1'S, 1S,3R)-Methyl[6-acetoxy-1-(2',3',6'-trideoxy-3'-trifluoroacetamido-4'-O-p-nitrobenzoyl-L-lyxohexopyranose)-5,12-dioxo-3,4,5,12-tetrahydroanthraceno-[2,3-c]pyran-3-yl]formate

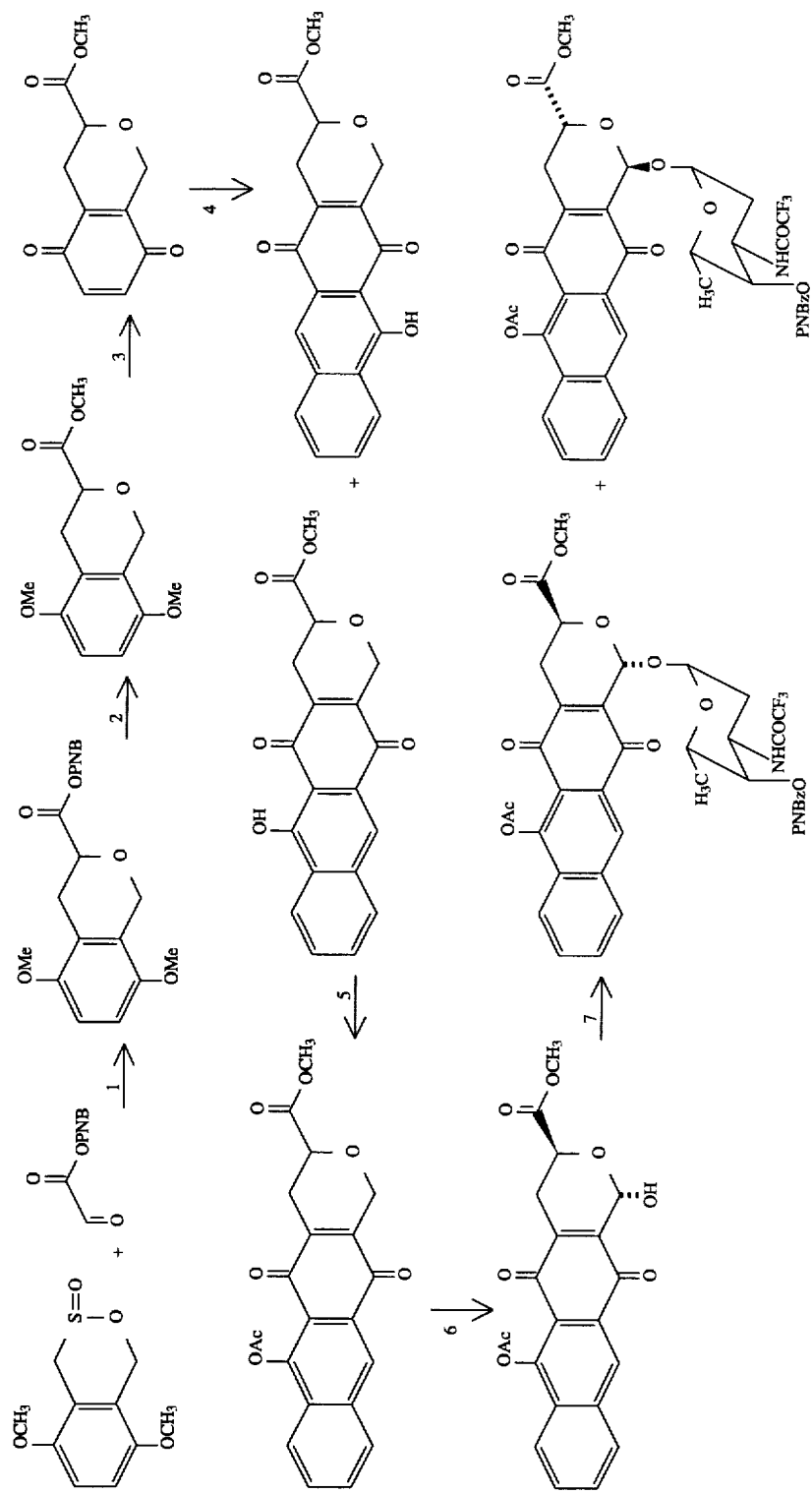

EXAMPLE 2

Step 1: p-Nitrobenzyl(5,8-dimethoxyisochroman-3-yl)formate

The same methodology as used in Example 1 step 5 was used but with 40 g (0.18 mmol) of p-nitrobenzylglyoxalate hydrate. A 58% (4.1 g) of the titled compound was obtained after flash chromatography (MP: 140°–141° C.). $^1$H NMR (200 MHz, CDCl$_3$) δ: 2.84 (dd, 1H, J=16.3, 10.3 Hz, HC H$_a$CHC=O), 3.09 (dd, 1H, J=16.2, 4.0 Hz, HC H$_e$CHC=O), 3.77 (s, 3H, OCH$_3$), 3.80 (s, 3H, OCH$_3$), 4.39 (dd, 1H, J=10.3, 4.0 Hz, OCHC=O), 4.70 (d, 1H, J=16.0H$_3$, HCH$_a$O), 5.07 (d, 1H, J=15.9 Hz, HCH$_e$O), 5.36 (broad s, 2H, CH$_2$), 6.67 (broad s, 2H, ArH), 7.54 (d, 2H, ArH), 8.24 (d, 2H, ArH).

Step 2: Methyl(5,8-dimethoxyisochroman-3-yl)formate

To a cooled (0° C.) solution containing 500 mg (1.34 mmol) of the p-nitrobenzylate from step 1 in 10 ml THF was added under inert atmosphere 15 ml of a 0.1M sodium methoxide solution in methanol. After stirring ten minutes, a few drops of saturated aqueous ammonium chloride were added and the solvent was removed. Flash chromatography of the residue gave 282 mg (84%) of the desired isochroman. (MP: 89°–90° C.). $^1$H NMR (200 MHz, CDCl$_3$) δ: 2.80 (broad dd, 1H, J=16.9, 10.8 Hz, HCH$_a$CHC=O), 3.12 (ddd, 1H, J=17.0 3.9, 1.4 Hz, HCH$_e$CHC=O, 3.78(s, 3H, OCH$_3$, 3.81(s, 3H, OCH$_3$), 3.84 (s, 3H, COOCH$_3$), 4.30 (dd, 1H, J=10.8, 3.9 Hz, OCHC=O), 4.70 (dt, 1H, J=16.2, 1.5 Hz, HCH$_a$O), 5.08 (d, 1H, J=16.2 Hz, HCH$_e$O), 6.67 (dd, 2H, ArH).

Step 3: Methyl(5,8-dioxo-5,8-dihydroisochroman-3-yl)formate

To a solution containing 265 mg (1.0 mmol) of the isochroman from step 2 in 5 ml of acetonitrile was added dropwise a solution of 1.726 g of ceric ammonium nitrate in 5 ml of water at room temperature. After stirring for ten minutes, the mixture was diluted with 50 ml of methylene chloride. The organic phase was separated and the aqueous layer was extracted twice with 25 ml of CH$_2$Cl$_2$. The combined organic extract were washed once with water, once with brine and then dried over MgSO$_4$. Evaporation of solvents gave 228 mg (98%) of residue which was found to be above 95% pure pyranoquinone. (MP: 55°–58° C.) $^1$H NMR (200 MHz, CDCl$_3$) δ: 2.68 (dddd, 1H, J=19.0, 9.0, 3.7, 2.8 Hz, HCH$_a$CHC=O), 2.93 (d septet, 1H, J=19.0 Hz, HC H$_e$CHC=O), 3.84 (s, 3H, OCH$_3$), 4.31 (dd, 1H, J=9.0, 4.4 Hz, CH), 4.52 (dr, 1H, J=18.7, 3.3 Hz, HCH$_a$O), 4.86 (ddd, 1H, J=18.9, 2.8, 1.6 Hz, HCH$_e$O), 6.78 (dd, 2H, HC=CH).

Step 4: Methyl[6-and 11-hydroxy-5,12-dioxo-3,4,5,12-tetrahydroanthraceno[2,3-c]pyran-3-yl]formate A solution of 2.5M n-butyl lithium (0.20 mmol) is added under argon at 0° C. to a stirred solution of 0.07 ml of dry diisopropy-lamine in 2 ml of THF and then stirred for 0.5 hour at −78° C. To the LDA was added dropwise over several minutes a solution of 73 mg (0.45 mmol) of homophthalic anhydride in 2 ml of THF and then 100 mg (0.45 mmol) of the pyranoquinone from step 3 dissolved in 3 ml of THF. The resulting mixture was stirred 20 minutes at −78° C., warmed to room temperature, and stirred for one hour. After quenching with 5 ml of saturated aqueous ammonium chloride the mixture was partitioned between 5 ml of 5% HCl and 50 ml CH$_2$Cl$_2$. The organic layer was separated, washed with 10 ml of brine and dried over Na$_2$SO$_4$. Flash chromatography of the residue obtained after evaporation of solvents gave the pyranotetracycles in 54% yield. The less polar regioisomer had (MP: 202°–204° C.). $^1$H NMR (300 MHz, CDCl$_3$) δ: 2.80 (dd t, 1H, J=19.1, 9.1, 3.1 Hz, HC H$_a$CHC=O), 3.11 (dm, 1H, J=19.1 Hz, HCH$_e$CHC=O), 3.84 (s, 3H, OCH$_3$), 4.35 (dd, J=9.1, 4.3 Hz, OCHC=O), 4.68 (dt, 1H, J=19.0, 3.3 Hz, HCH—O), 5.06 (broad d, 1H, J=18.9 Hz, HCH$_e$—O), 7.71 (m, 2H, ArH), 7.95 (m, 1H, ArH), 8.13 (s, 1H, ArH), 8.46 (m, 1H, ArH), 13.70 (s, 1H, exchangeable OH). CMR (75.44 MHz, CDCl$_3$), δ: 25.7, CH$_2$; 53.1, CH$_3$O; 63.3 CH$_2$O, 72.2 CHO; 122.7, 125.4, 129.8, 131.1 and 131.9, aryl CH; 127.6, 128.2, 136.4, 143.0 and 143.4 aryl C; 163.1 and 171.0, aryl COH and ester CO; 182.4, 187.1 quinone CO. HRMS calculated for C$_{19}$H$_{15}$O$_6$ 339.0869 found 339.0853. The more polar regioisomer had (MP: 225°–235° C. dec.) $^1$H NMR (300 MHz, CDCl$_3$) d 2.85 (ddt, 1H, J=19.0, 9.2 Hz, HCH$_a$CHC=O), 3.13 (dm, 1H, J=19.0 Hz, HCH$_e$CHC=O), 3.86 (s, 1H, OCH$_3$), 4.37 (dd, J=9.1 et 4.3 Hz, OCHC=O), 4.68 (dt, 1H, J=19.0, 3.4 Hz, HCH$_a$—O), 5.04 (broad d, 1H, J=21.1 Hz, HC H$_e$—O), 7.73 (m, 2H, ArH), 7.97 (m, 1H, ArH), 8.12 (s, 1H, ArH), 8.50 (m, 1H, ArH), 13.85 (s, 1H, exchangeable OH).

Step 5: Methyl[6-acetoxy-5,12-dioxo-3,4,5,12-tetrahydroanthraceno[2,3-c]pyran-3-yl]formate A mixture containing 60 mg (0.18 mmol) of pyranotetracycle from step 4, 0.25 ml acetic anhydride, 0.3 ml pyridine and 6 mg of dimethylaminopyridine in 20 ml of CH$_2$Cl$_2$ was stirred overnight at room temperature under argon atmosphere. The mixture was then diluted with 25 ml CH$_2$Cl$_2$ and washed consecutively twice with 15 ml of water, twice with 10 ml of 1N HCl, once with 15 ml of water and dried over NaSO$_4$. Flash chromatography of the residue obtained after flash chromatography yielded 55 mg (81%) of the titled acetylated pyranotetracycle. (MP: 196°–198° C.) $^1$H NMR (200 MHz, CDCl$_3$) δ: 2.60 (s, 3H, COCH$_3$), 2.81 (ddt, 1H, J=18.7, 9.1, 3.3 Hz, HCH$_a$CHC=O), 3.10 (dm, 1H, J=19.0 Hz, HCH$_e$CHC=O), 3.85 (s, 3H, OCH$_3$), 4.31 (dd, 1H, J=9.3, 4.2 Hz, CH), 4.64 (dr, 1H, J=19.0, 3.2 Hz, HCH$_a$—O), 5.02 (broad d, 1H, J=19.0 Hz, HCH$_e$—O, 7.73 (m, 2H, ArH), 8.05 (m, 1H, ArH), 8.13 (m, 1H, ArH), 8.58 (s, 1H, ArH).

Step 6: (1S,3S) and (1R,3R)-Methyl[6-acetoxy-1-hydroxy-5,12-dioxo-3,4,5,12-tetrahydro-anthraceno[2,3-c]pyran-3-yl]formate A mixture containing 47 mg (0.12 mmol) of the acetylated pyranotetracycle from step 5, 0.23 mg of N-bromosuccinimide, and 0.1 mg of AIBN in 5 ml of CCl$_4$ was refluxed for two hours. The solvent was then removed in vacuo and to the residue was added 10 ml of a 3:1 THF-H$_2$O solvent mixture. After stirring for one hour at room temperature, the mixture was extracted with three 10 ml portions of CH$_2$Cl$_2$. The combined organic extracts were washed once with 10 ml of water and dried over Na$_2$SO$_4$. Flash chromatography of the residue obtained after removal of solvents gave 35 mg (71%) of the titled pyranotetracyclic aglycone. (MP: 190° C. decomposes) $^1$H NMR (200 MHz, DMSO-d$_6$) δ: 2.60 (dd, 1H, J=19.6, 11.8 Hz, HCH$_a$CHC=O), 3.15 (dd, 1H, J=19.6, 4.3 Hz, HCH$_e$CHC=O), 3.74 (s, 3H, OCH$_3$), 4.86 (dd, 1H, J=11.5, 4.5 Hz, OCHC=O), 6.21 (d, 1H, J=6.2 Hz, C HOH), 7.34 (d, 1H, J=6.3 Hz, exchangeable OH), 7.75 (m, 2H, ArH), 8.1 (m, 2H, ArH), 8.61 (s, 1H, ArH).

Step 7: (1'S,1R,3S) and (1'S,1S,3R)-Methyl[6-acetoxy-1-(2', 3',6'-trideoxy-3'-trifluoro-acetamido-4'-O-p-nitrobenzoyl-L-lyxohexopyranose)-5,12-dioxo-3,4,5,12-tetrahydroanthraceno[2,3-c]pyran-3-yl]formate Glycosidation of the pyranoanthraquinone from step 6 could be carried out by the procedure as described for example 1 step 10. The titled pyranoanthraquinone glycoside could be obtained in an overall yield of 77% (MP: 158°–160° C of 1'S,1S,3R and 225°–227° C. of 1R,3S). $^1$H NMR (200 MHz, CDCl$_3$) of the 1'S,1S,3R) diastereomers, δ: 1.25 (d, 3H, J=6.8 Hz, H3C-6'), 2.06 (m, 2H, H$_2$C-2'), 2.62 (s, 3H, acetyl CH₃), 2.77 (dd, 1H, J=19.5, 11.3 Hz, HC HaCHC=O), 3.19 (dd, 1H, J=19.3, 3.7 Hz, HC HcCHC=O), 3.89 (s, 3H, OCH₃), 4.42 (broad q, 1H, J=6.9 Hz, HC-5'), 4.65 (m, 1H, HC-3'), 4.78 (dd, 1H, J=11.4, 3.7 Hz, OCHC=O), 5.48 (broad s, 1H, HC-4'), 5.76 (broad s, 1H, HC-1'), 6.05 (s, 1H, O—CH—O), 6.35 (d, 1H, 1 Hz, NH), 7.76 (m, 2H, ArH) 8.12 (m, 2H, ArH), 8.31 (dd, 4H, p-nitrobenzoyl-H), 8.65 (s, 1H, ArH).

¹H NMR (200 MHz, CDCl₃) of the (1'S,1R,3S) diastereomer, δ: 1.40 (d, 3H, J=6.6 Hz, H3C-6'), 2.06 (m, 2H, H2C-2'), 2.61 (s, 3H, acetyl CH₃), 2.81 (dd, 1H, J=19.0, 11.7, HCHaCHC=O), 3.19 (dd, 1H, J=19.4, 3.9 Hz, HC HeCHC=O 3.89 (s, 3H, OCH₃), 4.72 (broad m, 3H, overlaped HC-5', HC-3', OCHC=O), 5.46 (broad s, 1H, HC-4'), 5.67 (broad s, 1H, HC-1'), 6.26 (s, 1H, O—CH—O), 6.41 (d, 1H, J=8.0 Hz, NH), 7.72 (m, 2H, ArH), 8.18 (dm, 2H, ArH), 8.35 (dd, 4H, p-nitrobenzoyl-H), 8.67 (s, 1H, ArH).

Example 3

Preparation of various pyrano modified heteroanthracyclinones and heteroanthracyclines

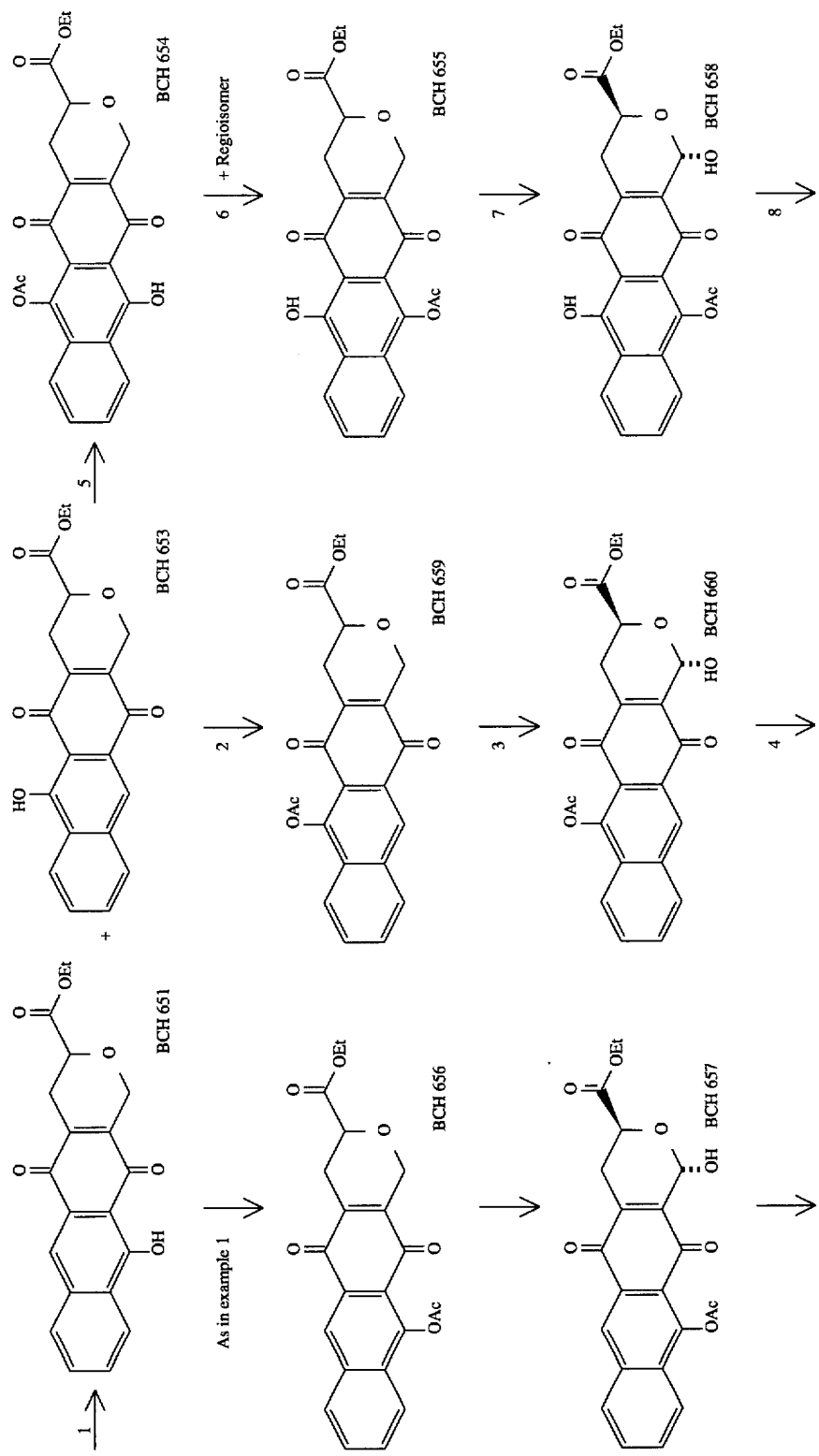

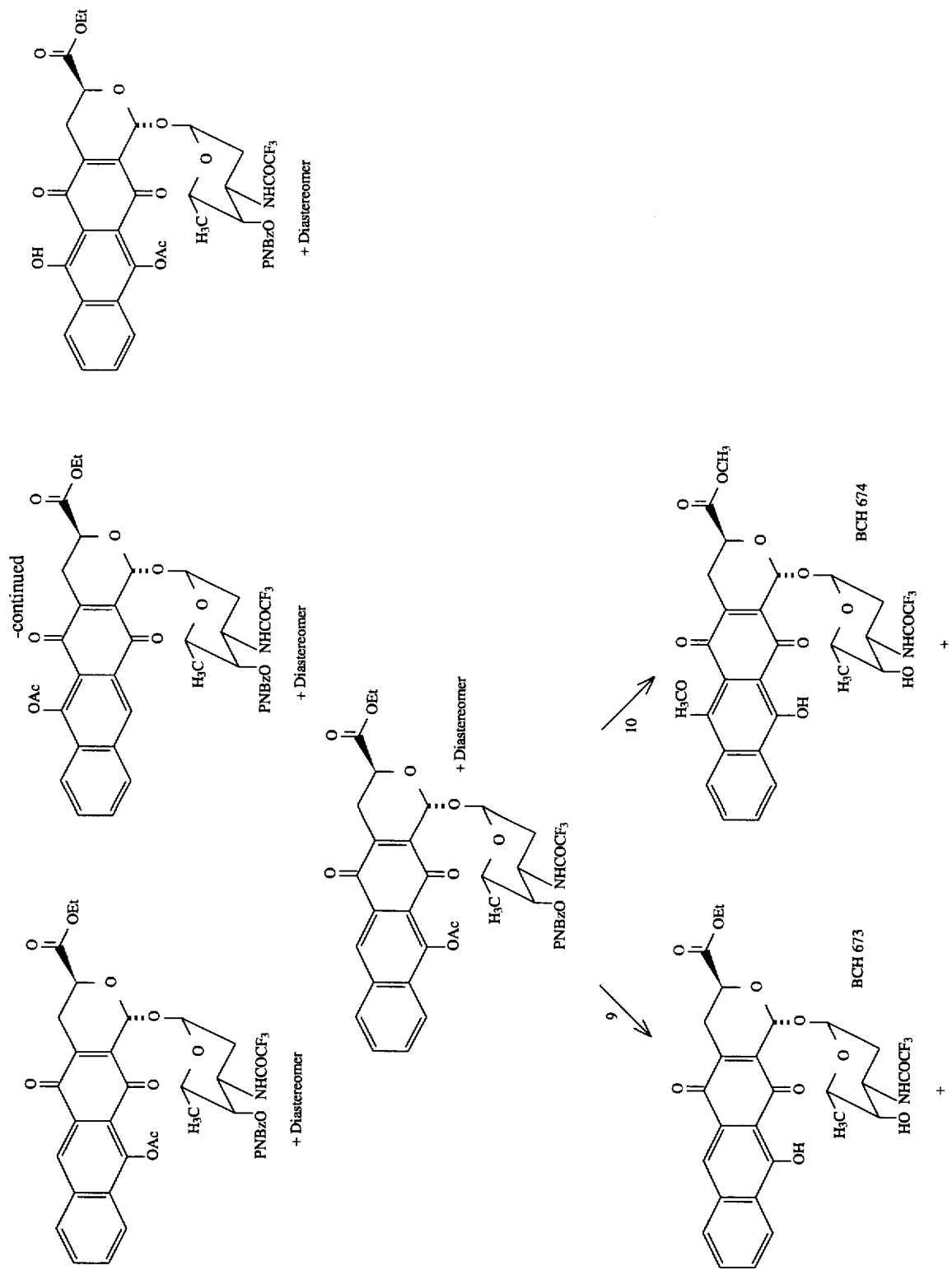

-continued
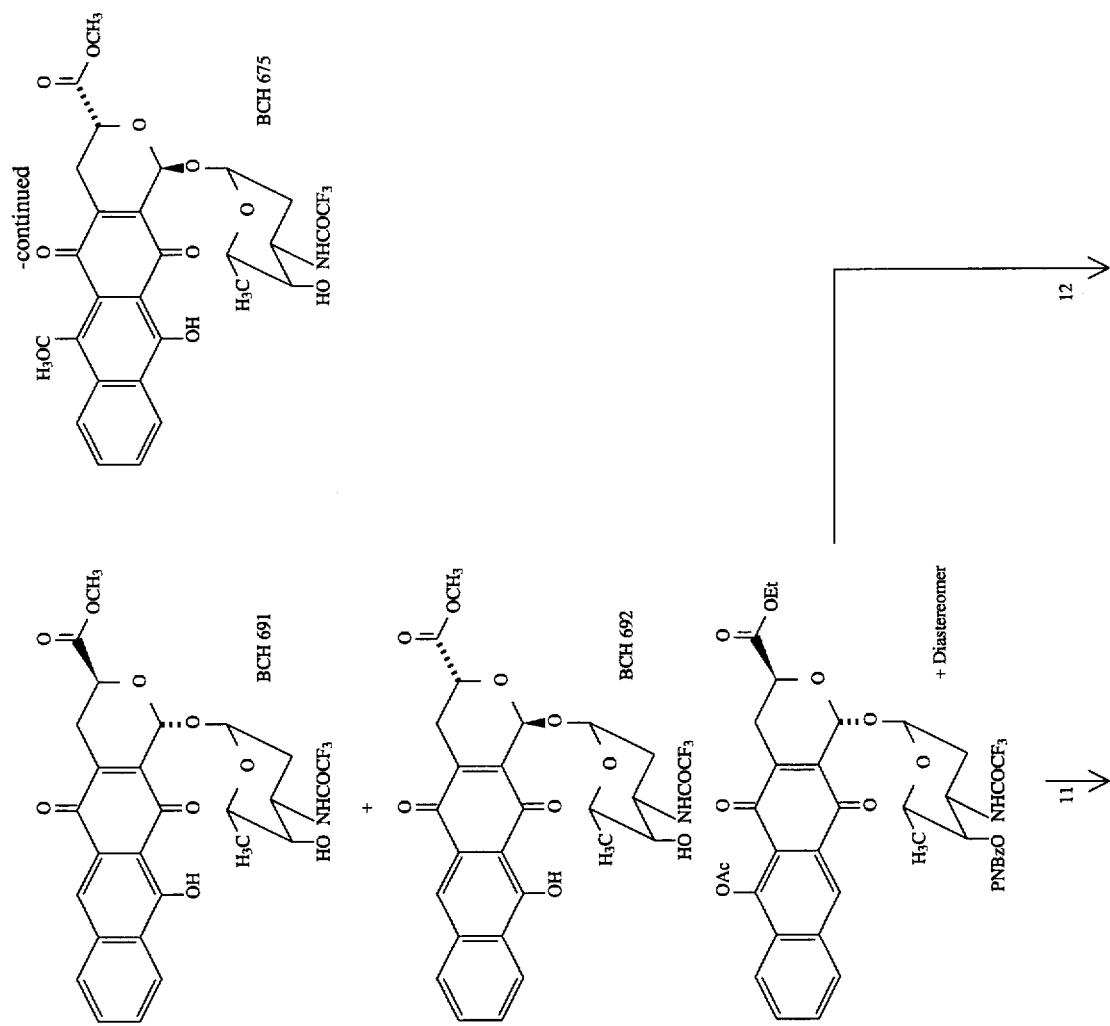

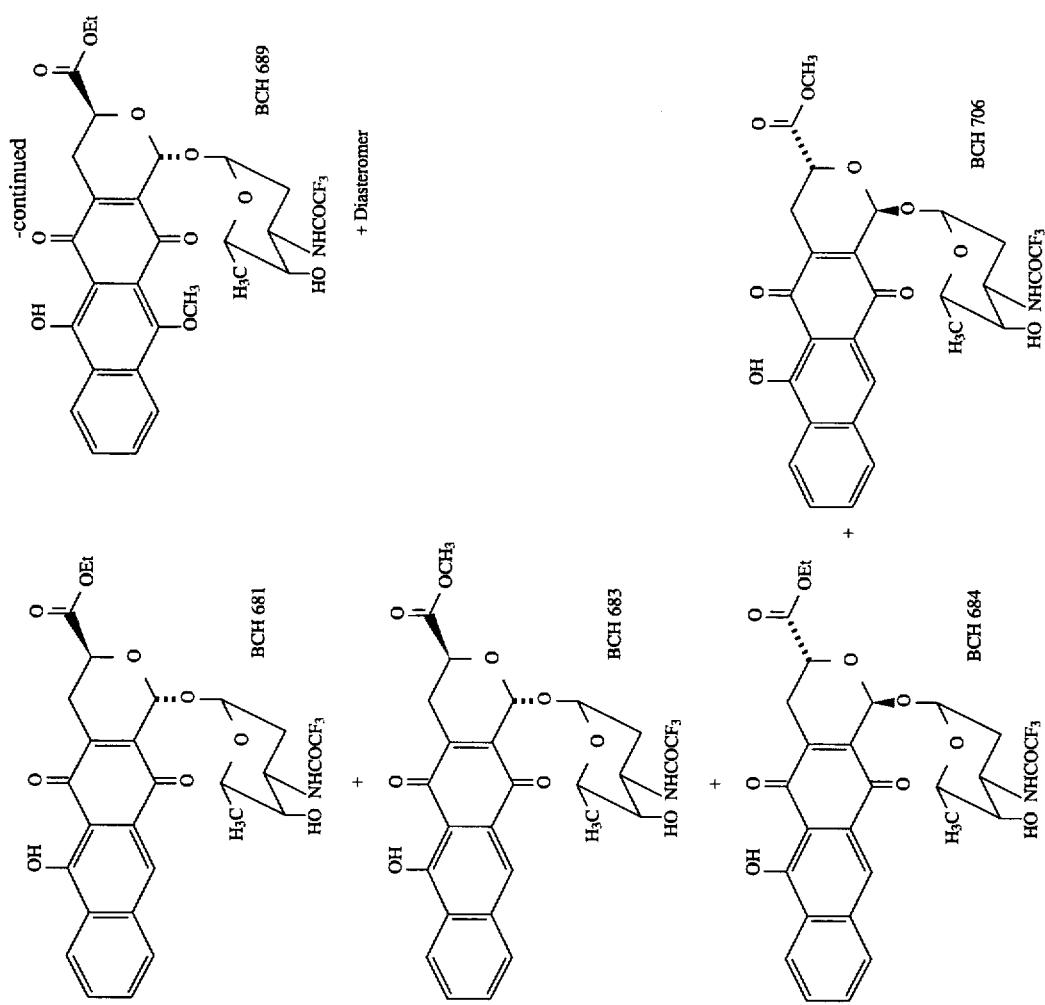

Example 3

Step 1: Ethyl(6 and 11 hydroxy-5,12-dioxo-3,4,5,12-tetrahydro-anthraceno[2,3-c]pyran-3-yl)]formate (BCH-651 & 653)

A solution of 2.5M n-butyl lithium (0.20 mmol) was added under argon at 0° C. to a stirred solution of 0.07 ml of dry diisopropylamine in 2 ml of THF and stirred for 0.5 hour at −78° C. To the LDA was added dropwise over several minutes a solution of 73 mg (0.45 mmol) of homophtalic anhydride in 2 ml of THF and then 100 mg (0.45 mmol) of the pyranoquinone, from the previous step, dissolved in 3 ml of THF. The resulting mixture was stirred 20 minutes at −78° C., warmed to room temperature, and stirred for one hour. After quenching with 5 ml of saturated aqueous ammonium chloride the mixture was partitioned between 5 ml of 5% HCl and 50 ml $CH_2Cl_2$. The organic layer was separated, washed with 10 ml of brine and dried over $Na_2SO_4$. Flash chromatography of the residue (10% EtOAc in toluene) obtained after evaporation of solvents, gave a polar component which was tentatively assigned as the 6-hydroxytetracycle, in 15% yield. (MP: 150°–152° C.). $^1$H NMR (200 MHz, $CDCl_3$) δ: 1.36 (t, 3H, J=7.1 Hz, $CH_3$), 2.84 (ddt, 1H, J=19.1, 9.1, 3.2 Hz, HCHaCHC=O), 3.13 (d m, 1H, J=19.1 Hz, HCHeCHC=O), 4.32 (q, 2H, J=7.1 Hz, $OCH_2$), 4.34 (dd, J=9.1, 4.3 Hz, OCHC=O), 4.67 (dt, 1H, J=19.0, 3.3 Hz, HCHa—O), 5.06 (broad d, 1H, J=19.0 Hz, HCHe—O), 7.71 (multiplet, 2H, ArH), 7.94 (multiplet, 1H, ArH), 8.11 (s, 1H, ArH), 8.47 (multiplet, 1H, ArH), 13.7 (s, 1H, exchangeable OH). CMR (75.44 MHz, $CDCl_3$) δ: 14.0, $CH_3$; 24.4, $CH_2$; 61.6, 63.2, $OCH_2$; 71.7, OCH; 121.9, 125.0, 129.4, 130.7, 131.5, aryl CH; 127.2, 127.6, 131.0, 136.0, 141.7, 144.2, 162.7, aryl C; 170.4, ester C=O; 183.5, 187.5, quinone C=O. IR (FT, $CDCl_3$) $^v$max: 3405, bs, OH; 1748, ester C=O; 1660, 1644, quinone C=O, 1609, C=C. HRMS calculated for $C_{20}H_{16}O_6$: [M+]=352.0947 found 352.0997.

The less polar component, tentatively assigned as ethyl [11-hydroxy-5,12-dioxo-3,4,5,12-tetrahydroanthraceno (2,3-C) pyran-3-yl]formate, was obtained in 32% yield. (MP: 149°–150° C.). $^1$H NMR (300 MHz, $CDCl_3$) δ: 1.35 (t, 3H, J=7.1 Hz, $CH_3$), 2.78 (ddt, 1H, J=3.4, 9.1, 19.0 Hz, HCHa), 3.07 (d m, 1H, J=19.0 Hz, HCHe), 4.31 (overlaped of with dd, 3H, $OCH_2$ and OCH), 4.65 (dr, 1H, J=3.3, 18.8 Hz, HCHa) 5.04 (bd, 1H, J=18.8 Hz, HCHe), 7.71 (m, 2H, ArH), 7.93 (dd, 1H, J=1.3, 7.3 Hz, ArH), 8.07 (s, 1H, ArH), 8.43 (dd, 1H, J=1.2, 7.2 Hz, ArH). CMR (75.44 MHz, $CDCl_3$) δ: 13.9, $CH_3$; 24.8, $CH_2$; 61.6, 62.6, $OCH_2$; 71.6, OCH; 122.1, 124.8, 129.3, 130.6, 131.4, aryl CH; 106.1, 127.0, 127.6, 135.7, 142.6, 143.0, 162.6, CH; 170.3, ester C=O; 182.0, 186.0, quinone C=O. IR (FT, $CDCl_3$) $^v$max: 3590, broad, OH; 1748, ester C=O; 1662, 1645, quinone C=O, 1607, C=C. HRMS calculated for $C_{20}H_{16}O_6$: [M+]=352.0947 found 352.0946.

In addition, ethyl(5,12-dihydroxy-6,11-dioxo-3,4,6,11-tetrahydroanthraceno[2,3-c]pyran-3-yl)formate BCH-650, could be isolated in 10% yield. (MP: 153°–154° C.). $^1$H NMR (300 MHz, $CDCl_3$) δ: 1.36 (t, 3H, J=6.0 Hz, $CH_3$), 2.96 (ddt, 1H, J=2.0, 10.1, 18.2 Hz, HCHa), 3.26 (ddd, 1H, J=1.8, 4.0, 18.3 Hz, HCHe), 4.33 (q, 2H, J=6.2 Hz, $OCH_2$), 4.37 (dd, 1H, J=4.0, 10.0 Hz, OCH), 4.82 (dr, 1H, J=2.0, 17.6 Hz, O—HCHa), 5.23 (d, 1H, J=17.5 Hz, O—HCHe), 7.85 (m, 2H, ArH), 8.35 (m, 2H, ArH), 13.17 (s, 1H, ArOH), 13.34 (s, 1H, ArOH).

Step 2: Ethyl[6-acetoxy-5,12-dioxo-3,4,5,12-tetrahydroanthraceno (2,3-c) pyran-3-yl]formate (BCH-659)

A mixture containing 60 mg (0.18 mmol) of the more polar pyranotetracycle, from the previous step, 0.25 ml acetic anhydride, 0.3 ml pyridine and 6 mg of dimethylaminopyridine in 20 ml of $CH_2Cl_2$ was stirred overnight at room temperature under argon atmosphere. The mixture was then diluted with 25 ml $CH_2Cl_2$ and washed consecutively twice with 15 ml of water, twice with 10 ml of 1N HCl, once with 15 ml of water and dried over $NaSO_4$. Flash chromatography of the residue obtained after flash chromatography yielded 55 mg (81%) of the titled acetylated pyranotetracycle. (MP: 196°–198° C.). $^1$H NMR (300 MHz, $CDCl_3$), δ: 1.34 (t, 3H, J=7.2 Hz, $CH_3$), 2.63 (s, 3H, $COCH_3$), 2.78 (ddt, 1H, J=3.3, 9.1, 18.7 Hz, HCHa), 3.10 (dm, 1H, J=19.0 Hz, HCHe), 4.29 (q, 2H, J=7.2 Hz, $OCH_2$), 4.31 (dd, 1H, J=4.2, 9.3 Hz, OCH), 4.61 (dr, 1H, J=3.2, 19.0 Hz, HCHa—O), 5.02 (bd, 1H, J=19.0 Hz, HCHe—O), 7.73 (m, 2H, ArH), 8.05 (m, 1H, ArH), 8.13 (m, 1H, ArH), 8.58 (s, 1H, ArH). IR (FT, $CDCl_3$) $^v$max: 1773, 1751, ester C=O; 1667, 1644, quinone C=O; 1618, C=C. HRMS calculated for $C_{22}H_{18}O_7$: [M+]394.1053 found 394.1020.

Step 3: (1S,3S) and (1R,3R)-Ethyl-[6-acetoxy-1-hydroxy-5,12-dioxo-3,4,5,12-tetrahydroanthraceno (2,3-c) pyran-3-yl] formate (BCH-660)

A mixture containing 47 mg (0.12 mmol) of the acetylated pyranotetracycle 0.23 mg of N-bromosuccinimide, and 0.1 mg of AIBN in 5 ml of $CC_{14}$ was refluxed for two hours. The solvent was then removed in vacuo and to the residue was added 10 ml of a 3:1 THF-$H_2O$ solvent mixture. After stirring for one hour at room temperature, the mixture was extracted with three 10 ml portions of $CH_2Cl_2$. The combined organic extracts were washed once with 10 ml of water and dried over $Na_2SO_4$. Flash chromatography of the residue obtained after removal of solvents gave 35 mg (71%) of pyranotetracyclic aglycone (MP: 215°–220° C. decomposes). $^1$H NMR (300 MHz, $CDCl_3$) δ: 1.35 (t, 3H, J=7.1 Hz, $CH_3$), 2.61 (s, 3H, $OCOCH_3$) 2.71 (dd, 1H, J=19.6, 11.8 Hz, HCHaCHC=O), 3.15 (dd, 1H, J=19.6, 4.3 Hz, HCHeCHC=O), 4.32 (q, 2H, J=7.1 Hz, $OCH_2$), 4.86 (dd, 1H, J=11.5, 4.5 Hz, OCHC=O), 6.22 (s, 1H, C HOH), 7.74 (m, 2H, ArH), 8.12 (m, 2H, ArH), 8.61 (s, 1H, ArH). CMR (75.44 MHz, DMSO-$d_6$) δ: 13.9, $CH_3$; 20.9, $CH_3$; 24.7, $CH_2$; 60.9, $OCH_2$; 64.6, OCH; 85.9, O—CH—O; 124.1, 126.7, 130.8, 130.9, 131.0, aryl CH; 118.1, 126.6, 129.7, 135.3, 141.1, 143.9, 147.6, aryl C; 169.3, 170.5, ester C=O; 181.3, 182.6, quinone C=O. IR (FT, $CDCl_3$) $^v$max: 3365, bs, OH; 1774, 1748, ester C=O; 1668, quinone C=O. HRMS calculated for $C_{22}H_{18}O_8$: [M+]410.1002 found 410.1009.

Step 4: (1'S,1R,3S) and (1'S,1S,3R)-Ethyl[6-acetoxy-1-(2',3',6'-trideoxy-3'-trifluoroacetamido-4'-O-p-nitrobenzoyl-L-lyxohexopyranose)-5,12-dioxo-3,4,5,12-tetrahydroan-thraceno (2,3-c) pyran-3-yl]formate Glycosidation of the pyranoanthraquinone from step 3 above, could be carried out by following the procedure as described in example 1, step 10. The titled pyranoanthraquinone glycoside could be obtained in an overall yield of 77% (MP: 158°–160° C. of 1'S,1S,3R and 225°–227° C. of 1'S,1R,3S). $^1$H NMR (300 MHz, $CDCl_3$) of the (1'S,1S, 3R) diastereomers, δ: 1.25 (d, 3H, J=6.8 Hz, $H_3$C-6'), 1.36 (t, 3H, J=7.0 Hz, $CH_3$), 2.06 (m, 2H, $H_2$C-2'), 2.62 (s, 3H, acetyl, $CH_3$), 2.77 (dd, 1H, J=19.5, 11.3 Hz, HC HaCHC=O), 3.19 (dd, 1H, J=19.3, 3.7 Hz, HC HeCHC=O), 4.31 (q, 2H, J-7.0 Hz, $OCH_2$), 4.42 (broad q, 1H, J=6.9 Hz, HC-5'), 4.65 (m, 1H, HC-3'), 4.78 (dd, 1H, J=11.4, 3.7 Hz, OCHC=O), 5.48 (broad s, 1H, HC-4'), 5.76 (broad s, 1H, HC-1'), 6.05 (s, 1H, O—CH—O), 6.35 (d, 1H, J=6.4 Hz, NH), 7.76 (m, 2H, ArH) 8.12 (m, 2H, ArH), 8.31 (dd, 4H, p-nitrobenzoyl-H), 8.65 (s, 1H, ArH). $^1$H NMR (300 MHz, $CDCl_3$) of the (1'S,1R,3S) diastereomer, δ: 1.40

(d, 3H, J=6.6 Hz, H₃C-6'), 1.37 (t, 3H, J=7.0 Hz, CH₃), 2.06 (m, 2H, H₂C-2'), 2.61 (s, 3H, acetyl, CH₃), 2.81 (dd, 1H, J=19.0, 11.7, HcHaCHC=O), 3.19 (dd, 1H, J=19.4, 3.9 Hz, HCHeCHC=O), 4.31 (q, 2H, J=7.0 Hz, OCH₂), 4.72 (broad m, 3H, overlaped HC-5', HC-3', OCHC=O), 5.46 (broad s, 1H, HC-4'), 5.67 (broad s, 1H, HC-1'), 6.26 (s, 1H, O—CH—O), 6.41 (d, 1H, J=8.0 Hz, NH), 7.72 (m, 2H, ArH), 8.18 (dm, 2H, ArH), 8.35 (dd, 4H, p-nitrobenzoyl-H), 8.67 (s, 1H, ArH). CMR of the diastereomeric mixture (75.44 MHz, CDCl₃) δ: 14.3 and 14.5, CO₂CH₂CH₃; 17.0 and 17.2, 6'-CH₃; 21.4, acyl CH₃; 24.9 and 25.4, 2'-CH₂; 29.9 and 30.0, 4-CH₂; 45.9 and 46.0, CHNH; 62.1 and 62.2, ester OCH₂; 66.2 and 66.8, 5'-OCH; 66.9 and 67.1, 4'-OCH; 72.2 and 72.8, 3-OCH; 88.0 and 92.7, 1-O—CH—O; 92.8 and 98.7, 1'-O—CH—O; 113.1, quartet, J=287.1 Hz, CF₃; aromatic CH: 124.5, 127.8, 128.1, 131.0, 131.2, 131.6, 131.7, 135.0, aromatic quaternary C: 118.5, 128.9, 130.9, 131.0, 131.2, 134.97, 138.16, 138.23, 139.5, 140.0, 144.9, 145.8, 148.85, 148.94, 151.7, 157.5, quartet J=37.3 Hz, COCF₃; 165.4, 165.7, 169.6, 169.7, 170.1, 170.5, ester C=O; 182.0, 182.3, 182.7, quinone C=O. IR (FT, CDCl₃) $^v$max: 1774, 1737, broad, ester C=O; 1669, quinone C=O, 1532, amide.

Step 5: Ethyl[6-11-hydroxy-5,12-tetrahydroanthraceno(2,3-c) pyran-3-yl]formate and Ethyl[11-acetoxy-6-hydroxy-5, 12-dioxo-3,4,5,12-tetrahydroanthraceno(2,3-c)pyran-3-yl] formate (BCH-654)

A mixture containing 387 mg (1.1 mmol) of the unacetylated pyranotetracycle obtained in step 1 above, 2.5 g lead tetraacetate, 60 ml of acetic acid, and 30 ml of CH₂Cl₂ was stirred for 48 hours under argon at room temperature. The mixture was then diluted with 100 ml of CH₂Cl₂, extracted twice with 50 ml of water and dried over Na₂SO₄. After removal of solvents, the residue was found to contain the titled compounds. CMR (75.44 MHz, CDCl₃) δ: 13.94, 20.66, 20.80, 24.98, 25.68, 61.57, 61.70, 63.60, 63.67, 71.97, 72.07, 126.76, 126.82, 127.48, 127.53, 134.19, 135.04, 135.07, 157.10, 159.03, 170.46, 170.52, 181.37, 188.78, 188.82, FT (IR, CDCl₃), $^v$max: 1759.8, 1754.5, ester C=O; 1671.7, 1634.7, quinone C=O.

Step 6: Ethyl[6,11-diacetoxy-B,12-dioxo-3,4,5,12-tetrahydroanthraceno (2,3-c) pyran-3-yl]formate (BCH-655)

The residue from step 5 above was added to a solution containing 5 ml of acetic anhydride, 6 ml of pyridine and 60 mg of dimethylaminopyridine in 50 ml of CH₂Cl₂. The mixture was stirred at room temperature overnight under argon and then added to 50 g of ice. The aqueous layer was separated and extracted twice with 50 ml of CH₂Cl₂. The combined organic extracts were then consecutively washed once with 25 ml of water, twice with 25 ml of 1N HCl, 25 ml of water, 25 ml of brine and then dried over Na₂SO₄. After evaporation of solvents, flash chromatography of the residue yielded 175 mg (35%) of the titled bisacetylated pyranoanthraquinone. (MP: 203°–205° C.). ¹H NMR (200 MHz, CDCl₃) δ: 1.36 (t, 3H, J=7.1 Hz, CH₃), 2.50 (s, 3H, COCH₃), 2.54 (s, 3H, COCH₃), 3.05 (broad m, 2H,CH₂CHC=O, 4.35 (masked dd, 1H, OCHC=O), 4.32 (q, 2H, J=7.1 Hz, OCH₂CH₃), 4.75 (broad d, 1H, J=16.7 Hz, HCHa—O), 5.11 (broad d, 1H, J=16.5 Hz, HCHe—O), 7.75 (m, 2H, ArH), 8.16 (m, 2H, ArH). IR (FT, CDCl₃) $^v$max: 1771, broad s, ester CO; 1677, quinone C=O, 1591, C=C. HRMS calculated for C₂₄H₁₉O₁₉: 451.1029 found 451.1061.

Step 7: (1S,3S) and (1R,3R) Ethyl[11-acetoxy-1,6-dihydroxy-5,12-dioxo-3,4,5,12-tetrahydroanthraceno (2,3-c) pyran-3-yl]formate.(BCH-658)

A mixture containing 75 mg (0.17 mmol) of the pyranotetracycle from step 6 above, 32 mg (0.17 mmol) of n-bromosuccinimide, 1 mg AIBN in 15 ml of CCl₄ was refluxed under argon for 2.5 hours. After removal of solvent, 25 ml of a 4:1 THF-H₂O solvent mixture was added to the residue and stirred for 0.5 hour. The mixture was then extracted three times with 25 ml of CH₂Cl₂ and the combined extracts were washed with 25 ml of water, 25 ml of brine and dried over Na₂SO₄. After evaporation of solvent, flash chromatography of the residue gave 61 mg (77%) of the desired bis acetylated tetracyclic aglycone. (MP: 220°–250° C. decomposes).

¹H NMR (300 MHz, DMSO-d₆) δ: 1.25 (t, 3H, J=7.1 Hz, CH₃), 2.42 (s, 3H, COCH₃), 2.35 (bm, 1H, HCHa), 2.47 (bm, 1H, HCHe), 4.21 (q, 2H, J=7.1 Hz, OCH₂), 4.42 (m, 1H, OCH), 6.11 (d, 1H, J=5.8 Hz, O—CH—OH), 7.42 (d, 1H, J=5.8 Hz, exchangeable, OH), 7.95 (m, 2H, ArH), 8.12 (m, 1H, ArH), 8.22 (m, 1H, ArH), 13.3 (s, 1H, exchangeable, ArOH). IR (FT, CDCl₃)$_v$max: 3690, OH; 3500, 3700, bs, OH; 1764, 1730, ester C=O; 1668, 1636, quinone C=O; 1601, C=C. HRMS calculated for C₂₂H₁₈O₉: [M+]425.0951 found Step 8: (1'S, 1R,3S) and (1'S, 1S,3R) Ethyl[11-hydroxy-6-acetoxy-1-(2',3',6'-trideoxy-3'-trifluoroacetamido-4'-O-p-nitrobenzoyl-L-lyxohexopyranose) 5,12-dioxo-3,4,5,12-tetrahydroanthraceno (2,3-C) pyran-3-yl]formate These compounds were obtained in 61% yield by following the same procedure as described in example 1, step 10 and using the aglycone from step 7 above. (MP: 155°–158° C. of 1'S,1S,3R and 182°–184° C. of 1'S,1R,3S). ¹H NMR (200 MHz, CDCl₃) of the less polar (1'S,1S,3R) diastereomer, δ: 1.26 (d, 3H, J=6.5 Hz, H₃C-6'), 1.39 (t, 3H, J=7.1 Hz, CH₃), 2.21 (m, 2H, H₂C-2'), 2.54 (s, 3H, O=C—CH₃), 2.88 (m, 1H, HCHaCHC=O), 3.13 (m, 1H, HC HeCHC=O), 4.37 (q, 2H, J=7.1 Hz, OCH₂), 4.49 (broad q, 1H, J=6.5 Hz, HC-5'), 4.67 (m, 1H, HC-3'), 4.83 (dd, 1H, J=11.6, 4.45 Hz, OCHC=O), 5.49 (broad s, 1H, HC-4'), 5.77 (broad s, 1H, Wh<6 Hz, HC-1'), 6.21 (s, 1H ,O—CH-O), 6.24 (d, 1H, J=9.1 Hz, NH), 7.84 (m, 2H, ArH), 8.60 (m, 2H, ArH), 8.33 (dd, 4H, p-nitroaryl- H), 13.54 (s, 1H, exchangeable, OH). ¹H NMR (200 MHz, CDCl₃) of the (1'S, 1R,3S) diastereomer δ: 1.29 (d, 3H, J=6.5 Hz, H3C-6'), 1.37 (t, 3H, J=7.1 Hz, CH₃), 2.08 (m, 2H, H₂C-2'), 2.88 (broad m, 1H, HCHaCHC—O), 3.11 (broad m, 1H, HC HeCHC=O), 4.25 (q, 2H, J=7.0 Hz, OCH₂), 4.67 (m, 1H, HC-3'), 4.81 (m, 1H, HC-5'), 4.85 (m, 1H, OCHC=O), 5.45 (broad s, 1H, HC-4'), 5.71 (broad s, 1H, H—C-1'), 6.37 (broad d, 1H, J=9 Hz, NH), 6.39 (s, 1H, O—CH—O), 7.85 (m, 2H, ArH), 8.30 (m, 2H, ArH), 8.33 (dd, 4H, p-nitroaryl-H), 13.66 (s, 1H, exchangeable, OH). IR (FT, CDCl₃) $^v$max: 3431, OH; 1737, bs ester C=O; 1674, quinone, C=O; 1595, C=C.

Step 9: (1'S,1S,3R) and (1'S,1R,3S) Methyl[11-hydroxy-1-(2',3',6'-trideoxy-3'-trifluoroacetamido-4'-hydroxy-L-lyxohexopyranose)-5,12-dioxo-3,4,5,12-tetrahydro-anthraceno [2,3-c]pyran-3-yl]formate, BCH-692 and BCH-691 respectively.

Deprotection as described in example 1, step 11 (done at room temperature) gave the titled compounds in 65% yield. The less polar component was assigned to BCH-692. ¹H NMR (300 MHz, CDCl₃) δ: 1.31 (d, H, J=6.6 Hz, CH₃), 1.87 (dr, 1H, J=3.8, 13.5 Hz, 2'-HCHa), 2.04 (dd, 1H), J=5.2, 13.4 Hz, 2'-HCHe), 2.76 (dd, 1H, J=11.8, 19.5 Hz, HCHa), 3.18 (dd, 1H, J=3.9, 19.5 Hz, HCHe), 3.64 (bs, 1H, 4'—CH), 3.87 (s, 3H, OCH₃), 4.23 (bq, 1H, J=6.6 Hz, 5'-CH), 4.39 (m, 1H, 3'-CH), 4.75 (dd, 1H, J=3.9, 11.8 5.59 (bd, 1H, J=3.5 Hz, 1'-CH), 6.02 (s, 1H, O—CH—O), 6.71 (bd, 1H, J=9.1 Hz, NH), 7.72 (m, 2H, ARH), 7.96 (M, 1H, ArH), 8.15 (s, 1H, ArH), 8.48 (m, 1H, ArH), 13.75 (s, 1H, ArOH).

The more polar component was assigned to BCH-691. $^1$H NMR (300 MHz, CDCl$_3$) δ: 1.40 (d, 3H, J=6.6 Hz, CH$_3$), 1.88 (m, 2H, 2'-CH$_2$), 2.75 (dd, 1H, J=11.7, 19.7 Hz, HCHa), 3.17 (dd, 1H, J=4.1, 19.7 Hz, HCHe), 3.64 (bs, 1H, 4'-CH), 3.85 (s, 3H, OCH$_3$), 4.31 (m, 1H, 3'-CH), 4.58 (bq, 1H, J=6.7 Hz, 5'-CH), 4.71 (dd, 1H, J=4.1, 11.6 Hz, O—CH), 5.49 (bs, 1H, 1'-CH), 6.19 (s, 1H, O—CH—O), 6.72 (bd, 1H, J=7.9 Hz, NH), 7.70 (m, 2H, ArH), 7.97 (bd, 1H, J=7.4 Hz, ArH), 8.17 (s, 1H, ArH), 8.47 (bd, 1H, J=7.4 Hz, ArH), 13.8 (s, 1H, ArOH). Small amounts of BCH-673 (5–10%) could also be obtained. The spectral data was similar as the one obtained with BCH-691 except for the presence of the ethyl ester group.

Step 10: (1'S,1S,3R) and 1'S,1R,3S) Methyl(11-hydroxy-6-methoxy-1-[2',3',6'-trideoxy-3-trifluoroacetamido-4'-hydroxy-L- lyxohexopyranose]-5,12-dioxo-3,4,5,12-tetrahydroanthra- ceno[2,3-c]pyran-3-yl) formate, BCH-674 and BCH-675 respectively.

Deprotection was done as described in step 9 above but at −15° C. BCH-674 is assigned to the compound giving the following data: $^1$H NMR (300 MHz, CDCl$_3$) δ1.33 (d, 3H, J=6.6 Hz, CH$_3$), 1.89 (m, 2H, 2'-CH$_2$), 2.89 (dd, 1H, J=12.2, 18.6 Hz, HCHa), 3.31 (dd, 1H, J=4.2, 18.6 Hz, HCHe), 3.62 (bs, 1H, 4'-CH), 3.85 (s, 3H, OCH$_3$), 3.92 (s, 3H, OCH$_3$), 4.35 (m, 1H, 3'-CH), 4.53 (bq, 1H, J=6.6 Hz, 5'-CH), 5.49 (bs, 1H, 1'-CH), 6.25 (s, 1H, O—CH—O), 6.76 (bd, 1H, NH), 7.82 (m, 2H, ArH), 8.24 (m, 2H, ArH), 12.54 (s, 1H, ArOH).

BCH-675 was assigned to the compound which gave the following data: $^1$H NMR (300 MHz, CDCl$_3$) δ: 1.28 (d, 3H, J=6.6 Hz, CH$_3$), 1.87 (m, 1H, 2'-HCHa), 2.04 (m, 1H, 2'-HC He), 2.86 (dd, 1H, J=12.1, 18.4 Hz, HCHa), 3.32 (dd, 1H, J=3.9, 18.3 Hz, HCHe), 3.63 (bs, 1H, 4'-CH), 3.86 (s, 3H, OCH$_3$), 3H, OCH$_3$), 4.20 (bq, 1H, J=6.6 Hz, 5'-CH), 4.33 (m, 1H, 3'-CH), 4.83 (dd, 1H, J=3.9, 12.1 Hz, O—CH), 5.51 (bs, 1H, 1'-CH), 6.13 (s, 1H, O—CH—O), 6.75 (bd, 1H, J=8 Hz, NH), 7.27 (m, 2H, ArH), 8.27 (m, 2H, ArH), 13.6 (s, 1H, ArOH).

Step: 11 (1'S,1R,3S) and (1'S,1S,3R)-(6-hydroxy-5,12-dioxo-1-(3'-trifluoroacetamido-1-daunosaminyl)-3,4,5,12-tetrahydro-anthraceno[2,3-C]pyran-3-yl)formate (BCH-681, 683, 684 & 706)

Under argon, a (28° C.) solution containing 196 mg (0.25 mmol) of glycoside from step 4 above in 50 ml of dry methanol was treated with a total of 5 equivalent (0.25 ml) of a 4.37 M, NaOCH$_3$ methanolic solution which were added according to the progress of the reaction. The reaction mixture was then quenched with 10 ml of saturated aqueous NH$_4$Cl and extracted with dichloromethane (2×50 ml). The combined organic layers were washed with water (2×75 ml) and dried (Na$_2$SO$_4$). Purification by HPLC gave 7.8 mg (5% yield) of the 1'S,1R,3S diastereomer, BCH-681, (MP: 200° C. dec.). $^1$H NMR (300 MHz, CDCl$_3$) δ: 1.35 (t, 3H, J=7.1 Hz, CH$_2$ CH$_3$), 1.42 (d, 3H, J=6.6 Hz, H$_3$C-6'), 1.89 (2H, HaC-2'and HeC-2'), 2.76 (dd, 1H, J=19.6, 11.4 Hz, HC HaCHC=O), 3.19 (dd, 1H, J=19.6, 4.1 Hz, HC HeCHC=O), 3.64 (broad s, 1H, HC-4'), 4.31 (q, 2H, J=7.2 Hz, OCH$_2$CH$_3$), 4.32 (m, 1H, HC-3'), 4.61 (bq, 1H, J=6.5 Hz, HC-5'), 4.69 (dd, 1H, J=11.8 and 4.2 Hz, O—CH), 5.48 (broad s, 1H, HC-1'), 6.17 (s, 1H, O—CH—O), 6.73 (broad d, 1H, NH), 7.74 (m, 2H, ArH), 7.96 (m, 1H, ArH), 8.13 (s, 1H, ArH), 8.51 (m, 1H, ArH), 13.83 (s, 1H, Ar—OH).

The 1'S, 1S,3R diastereomer, BCH-684, was also obtained with 2% yield (2.9 mg). (MP: 175° C. melt and dec.). $^1$H NMR (300 MHz, CDCl$_3$) δ: 1.32 (d, 3H, J=6.6 Hz, H$_3$C-6'), 1.38 (t, 3H, J=7.2 Hz, OCH$_2$CH$_3$), 1.85 (m 1H, HaC-2'), 2.02 (m, 1H, HeC-2'), 2.62 (dd, 1H, J=19.5, 11.8 Hz, HCHaCHC=O), 3.21 (dd, 1H, J=19.5, 4.0 Hz, HC HeCHC=O), 3.65 (broad s, 1H, HC-4'), 4.25 (bq, 1H, HC-5'), 4.35 (m, 3H, OCH$_2$CH$_3$ and HC-4'), 4.75 (dd, 1H, J=12.0, 3.8 Hz, OCHC=O), 5.61 (broad s, 1H, HC-1'), 6.02 (s, H, O—CH—O), 6.72 (broad d, 1H, NH), 7.75 (m, 2H, ArH), 7.98 (m, 1H, ArH), 8.12 (s, 1H, ArH), 8.52 (m, 1H, ArH), 13.86 (s, 1H, Ar—OH).

BCH-706 could be isolated by HPLC in 2% yield. Its NMR spectrum is similar to the one obtained from BCH-684 except for the presence of a proton signal for the methoxy ester group at 3.87 ppm instead of signals for the ethyl ester.

BCH-683 was also obtained in 17% yield and was assigned to the compound giving the following data. (MP: 190°–215° C. dec.) $^1$H NMR (300 MHz, CDCl$_3$) δ: 1.41 (d, 3H, J=6.6 Hz, CH$_3$), 1.89 (m, 2H, 2'-CH$_2$), 2.78 (dd, 1H, J=11.8, 19.2 Hz, HCHa), 3.20 (dd, 1H, J=4.0, 19.6 Hz, HC He), 3.66 (bs, 1H, 4'-CH), 3.87 (s, 3H, OCH$_3$), 4.34 (m, 1H, 3'-C 4.63 (bq, 1H, J=6.6, 5'-CH), 4.73 (dd, 1H, J=4.0, 11.8 Hz, O—CH), 5.49 (bs, 1H, 1'-CH), 6.18 (s, 1H, O—CH—O), 6.77 (bd, 1H, J=7.1 Hz, NH), 7.74 (m, 2H, ArH), 7.98 (dd, 1H, J=2.4, 7.1 Hz, ArH), 8.14 (s, 1H, ArH), 8.52 (dd, 1H, J=2.4, 7.1 Hz, ArH), 13.8 (s, 1H, ArOH).

Step 12: (1'S,1R,3S) and (1'S,1S,3R) Ethyl (6-hydroxy-11-methoxy-5,12-dioxo-1-(3,-trifluoroacetamido-1-daunosaminyl)-3,4,5,12-tetrahydroanthraceno[2,3-c]pyran-3-yl)formate (BCH-689)

The reaction from step 11 above, carried out at −15° C., yielded (20% yield) a mixture of 1'S,1R,3S and 1'S,1S,3R ethyl(6-hydroxy-11-methoxy-5,12-dioxo-1-(3'-trifluoroaceta-mido-1-daunosaminyl)-3,4,5,12-tetrahydroanthraceno [2,3-c]pyran-3-yl) formate. (MP: 176°–180° C.). $^1$H NMR (300 MHz, CDCl$_3$) of the (1'S,1R,3S) diastereomer δ: 1.34 (d, 3H, J=6.6 Hz, H$_3$C-6'), 1.38 (t, 3H, J=7.1 Hz, OCH$_2$C H$_3$), 1.90 (m, 1H, HaC-2'), 2.04 (m, 1H, HeC-2'), 2.94 (dd, 1H, J=18.7, 12.2 Hz, HCHaCHC=O), 3.33 (dd, 1H, J=18.4, 3.3 Hz, HCHe CHC=O), 3.65 (broad S,1H, HC-4'), 3.95 (s, 3H, ArOCH$_3$), 4.35 (q, 2H, J=7.1 Hz, OCH$_2$CH$_3$), 4.42 (m, 1H, HC-3'), 4.68 (bq, 1H, HC-5'), 4.78 (dd, 1H, J=11.9, 4.2 Hz, O—CH), 5.53 (broad s, 1H, HC-1'), 6.34 (s, 1H, O—CH—O), 6.76 (broad d, 1H, NH), 7.83 (m, 2H, ArH), 8.31 (m, 2H, ArH), 13.70 (s, 1H, ArOH). $^1$H NMR (300 MHz, CDCl$_3$) of the 1'S,1S,3R diastereomer δ: 1.31 (d, 3H, J=6.6 Hz, H$_3$C-6'), 1.38 (t, 3J=7.1 Hz, OCH$_2$CH$_3$), 1.90 (m, 1H, HaC-2'), 2.04 (m, 1H, HeC-2'), 2.91 (dd, 1H, J=18.2, 12.0 Hz, HCHaCHC=O), 3.34 (dd, 1H, J=18.3, 3.7 Hz, HC HeCHC=O), 3.65 (broad s, 1H, HC-4'), 3.94 (s, 3H, ArOCH$_3$), 4.28 (bq, 1H, HC-5'), 4.35 (q, 2H, J=7.1 Hz, OC H$_2$CH$_3$), 4.42 (m, 1H, HC-3'), 4.81 (dd, 1H, J=12.4, 4.0 Hz, O—CH), 5.59 (broad s, 1H, HC-1'), 6.14 (s, 1H, O—CH—O), 6.74 (broad d, 1H, NH), 7.83 (m, 2H, ArH), 8.31 (m, 2H, ArH), 13.59 (s, 1H, ArOH).

Example 4

Preparation of (1'S,1S,3R) and (1'S,1R,3S)methyl[1-(2',3', 6'-trideoxy-trifluoroacetamido-4'-hydroxy-L-lyxohexopyranose)-3,12-dioxo-3,4,5,12-tetrahydroanthraceno[2,3-c] pyran-3-yl]formate

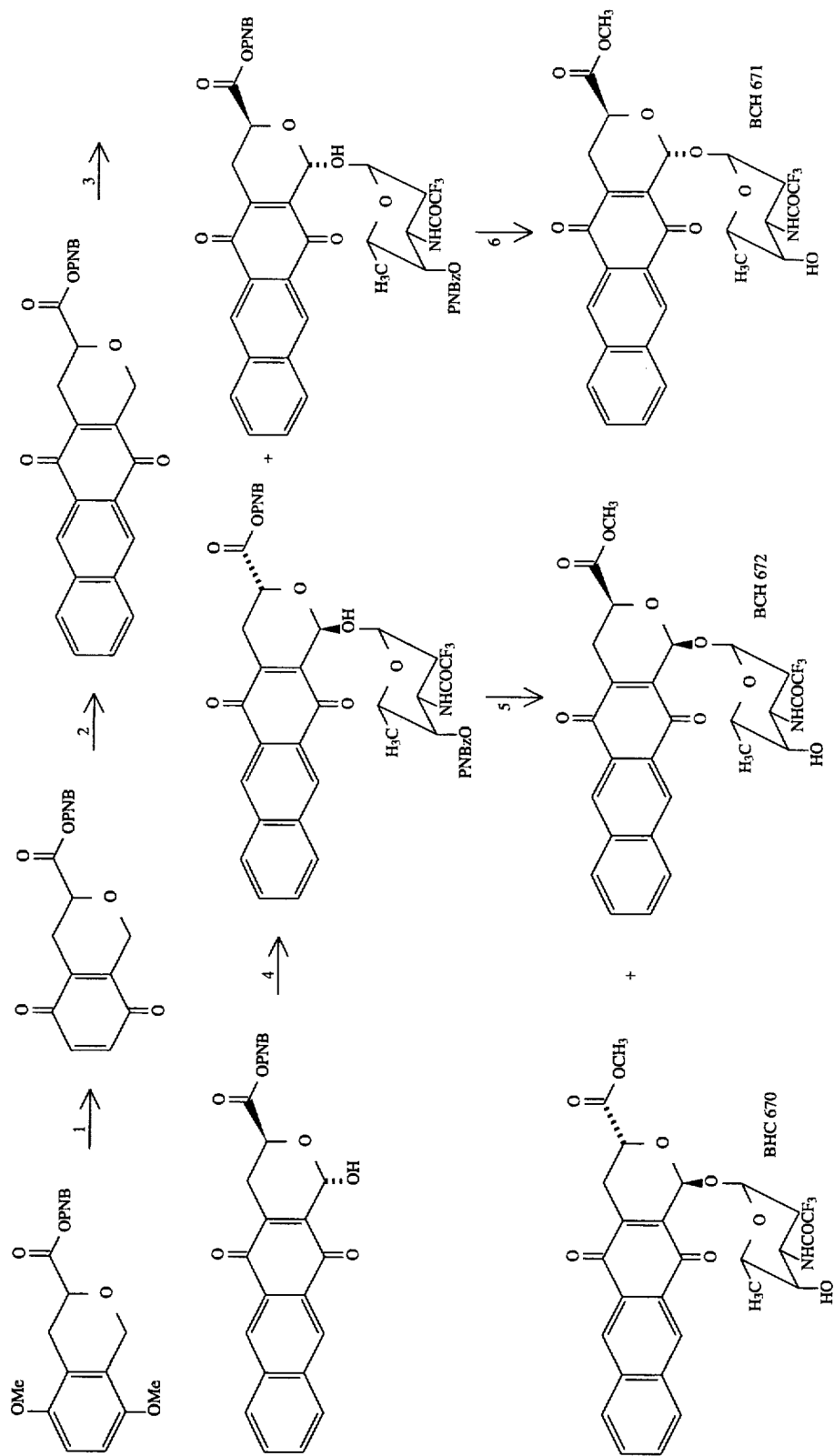

Example 4

Step 1: p-nitrobenzyl(5,8-dioxo-5,8-dihydroisochroman-3-yl) formate p-Nitrobenzyl 5,8-dimethoxy-isochroman-3-yl formate was oxidized as described in example 2, step 3. The titled compound was obtained in 92% yield. (MP:133° C. decomposes) $^1$H NMR (200 MHz CDCL$_3$) δ: 2.70 (ddt, 1H, J=18.7, 9.0, 3.0 Hz, HCHaCHC=O), 2.95 (d multiplet, 1H, J=19.0 Hz, HCHcCHC=O), 4.38 (dd, 1H, J=8.9, 4.3 Hz, OCHC=O), 4.56 (dr, 1H, J=17.1, 3.0 Hz, HCHa—O), 4.88 (ddd, 1H, J=17.3, 2.8, 1.7 Hz, HCHe—O), 5.36 (broad s, 2H, CH$_2$ ArH), 6.79 (dd, 2H, ArH), 7.57 (d, 2H, ArH), 8.29 (d, 2H, ArH).

Step 2: p-nitrobenzyl[5,12-dioxo-3,4,5,12-tetrahydroanthraceno[2,3-c]pyran-3-yl]formate

A solution containing 669 mg (1.9 mmol) of pyranoquinone from step 1, 485 mg (2.9 mmol) of 3,6-dihydrobenzo[b]-1,2-oxathiin-2-oxide (Charlton U. L. and Durst T., Tet. Lett., 25, 5287, 1984) in 50 ml of xylenes was refluxed overnight. The solvent was then removed in vacuo. The residue was flash chromatographed with ethyl acetate in toluene and gave 536 mg (62%) of the titled pyranoanthraquinone. (MP: 214°–215° C. decomposes) $^1$H NMR (200 MHz, CDCl$_3$) δ: 2.84 (ddt, 1H, J=18.9, 9.0, 2.7 Hz, HC HaCHC=O), 3.12 (broad d, 1H, J=19.0 Hz, HC HcCHC=O), 4.40 (dd, 1H, J=9.1, 4.4 Hz, OCHC=O), 4.67 (dt, 1H, J=19.0, 3.0 Hz, HCHa—O), 5.04 (broad d, 1H, J=18.9Hz, HCHc—O), 5.33 (broad s, 2H, ARCH2), 7.53 (d, 2H, ArH), 7.67 (m, 2H, ArH), 8.04 (m, 2H, ArH) 8.21 (d, 2H, ArH), 8.58 (s, 1H, ArH, 8.62 (s, 1H, ArH).

Step 3: (1S,3S) and (1R,3R) p-nitrobenzyl[1-hydroxy- 5,12-dioxo-3,4,5,12-tetrahydroanthraceno[2,3-c]pyran-3-yl]formate

A mixture containing 164 mg (0.37 mmol) of the pyranoanthracyclinone from step 2, 65 mg (0.37 mmol) of N-bromosuccinimide and 10 mg of AIBN in 25 ml of CCl$_4$ was refluxed for 2 hours. The solvent was then removed and the residue was stirred with 35 ml of a 7:3 solution of THF in water for ten hours. The mixture was then extracted three times with 25 ml aliquots of CH$_2$Cl$_2$. The combined organic layer was washed once with 10 ml of water, 10 ml of brine, and then dried over NaSO$_4$. After evaporation of solvents, flash chromatography of the residue gave 118 mg (69%) of the desired pyranoanthraquinone aglycone. (MP: 275° C. decomposes) $^1$H NMR (200 MHz, DMSO-d$_6$) δ: 2.68 (dd, 1H, J=19.1, 11.5 Hz, HCHaCHC=O), 3.00 (dd, 1H, J=19.4, 4.4 Hz, HCHcCHC=O), 4.89 (dd, 1H, J=11.4, 4.1 Hz, OCHC=O), 5.39 (broad s, 2H, ARCH$_2$), 5.98 (d, 1H, J=6.3 Hz, CHOH), 7.40 (d, 1H, J=6.1, exchangeable OH), 7.7 (d, 2H, ArH), 7.8 (m, 2H, ArH), 8.27 (d, 2H, ArH), 8.29 (m, 2H, ArH), 8.66 (s, 1H, ArH), 8.67 (s, 1H, ArH).

Step 4: (1'S,1R,3S) and (1'S,1S,3R)-p-nitrobenzyl[1-(2',3',6'-trideoxyacetamido-4'-O-p-nitrobenzoyl-L-lyxohexopyranose)-5,12-dioxo-3,4,5,12-tetrahydroanthraceno[2,3-c]pyran-3-yl]formate

These glycosides were obtained by the same procedure as described in step 10 of example 1 and by using the aglycone from step 3 of this example. (MP: 192°–195° C. for 1'S,1S, 3R and 173°–174° C. for 1'S,1R,3S). $^1$H NMR (200 MHz, CDCl$_3$) of the (1'S,1S,3R) diastereomer, δ: 1.12 (d, 3H, J=6.3 Hz, H$_3$C-6'), 2.09 (m, 2H, H$_2$C-2'), 2.83 (dd, 1H, J=19.4, 11.7 Hz, HCHaCHC=O), 3.26 (dd, 1H, J=19.1, 3.7 Hz, HCHcCHC=O), 4.4 (broad q, 1H, J=6.1 Hz, HC-5'), 4.65 (m, 1H, HC-3'), 4.89 (dd, 1H, J=11.8, 3.6 Hz, OCHC=O), 5.42 (broad s, 3H, HC-4'and aralCH$_2$), 5.82 (broad s, 1H, W$_h$<6 Hz, HC-1'), 6.13 (s, 1H, W$_h$<0.7 Hz, OCH—O), 6.40 (d, 1H, J=7.3 Hz, NH), 7.28 (d, 2H, p-nitrobenzyl-H), 7.73 (m, 2H, ArH), 8.09 (m, 2H, ArH), 8.29 (d, 2H, p-nitrobenzyl-H), 8.31 (dd, 4H, benzoyl H), 8.64 (s, 1H, ArH), 8.69 (s, 1H, ArH). $^1$H NMR (200 MHz, CDCl$_3$) of the (1'S,1R,3S) diastereomer, δ: 1.42 (d, 3H, J=6.4 Hz, H$_3$C-6'), 2.09 (m, 2H, H$_2$C-2'), 2.85 (dd, 1H, J=19.4, 11.3 Hz, HCHaCHC=O) 3.25 (dd, 1H, J=19.4, 4.3 Hz, HCHcCHC=O), 4.63 (m, 1H, HC-3'), 4.84 (overlaped, m, 2H, HC-5' and OCHC=O), 5.41 (broad s, 2H, aralCH2), 5.47 (s, 1H, W$_h$=5 Hz, HC-4'), 5.69 (s, 1H, W$_h$<0.7Hz, O—CH—O), 6.57 (d, 1H, J=7.2 Hz, NH) 7.73 (d, 2H, p-nitrobenzyl 7.75 (m, 2H, ArH), 8.11 (m, 2H, ArH), 8.33 (d, 2H, p-nitrobenzyl-H), 8.37 (dd, 4H, p-nitrobenzoyl-H), 8.69 (s, 1H, ArH).

Step 5: (1'S,1S,3S) Methyl(1-[2',3',6'-trideoxyacetamido-4'-hydroxy-L-lyxohexopyranose]-5,12-dioxo-3,4,5,12-tetrahydroantraceno[2,3-c]pyran-3-yl)formate BCH-672

Deprotection of the less polar glycoside, from step 4 above, by using the method described in example 1, step 11, gave the titled compound in 20% yield. $^1$H NMR (300 MHz, CDCl$_3$) δ: 1.29 (d, 3H, J=3.3 Hz, CH$_3$), 1.85 (dt, 1H, J=3.8, 13.3 Hz, 2'-HCHa), 2.00 (dd, 1H, J=5.4, 13.4 Hz, 2'-HC He), 2.76 (ddd, 1H, J=1.0, 11.8, 19.5 Hz, HCHa), 3.18 (dd, 1H, J=3.8, 19.5 Hz, HCHe), 3.63 (bs, 1H, 4'-CH), 3.86 (s, 3H, OCH$_3$), 4.23 (bq, 1H, J=6.6 Hz, 5'-CH), 4.35 (m, 1H, 3'-CH), 4.75 (dd, 1H, J=3.9, 11.8 5.61 (bd, 1H, J=3.4 Hz, 1'-CH), 6.04 (s, 1H, O—CHO), 6.71 (bd, 1H, J=9.0 Hz, NH), 7.70 (m, 2H, ArH), 8.06 (m, 2H, ArH), 8.60 (s, 1H, ArH), 8.67 (s, 1H, ArH).

A second less polar component, tentatively assigned as (1'S, 1S,3R) methyl (1-[2',3',6'-trideoxyacetamido-4'-hydroxy-L-lyxo-hexopyranose]-5,12-dioxo-3,4,5,12-tetrahydroanthraceno[2,3-C]pyran-3-yl)formate, BCH-670, was obtained in 60% yield.

$^1$H NMR (300 MHz, CDCl$_3$) δ: 1.25 (d, 3H, J=6.6 Hz, CH$_3$), 1.86 (dt, 1H, J=3.84, 13.2, 2'-HCHa), 2.09 (dd, 1H, J=5.2, 13.4 Hz, 2'-HCHe), 2.51 (dd, 1H, J=11.9, 15.2 Hz, HCHa), 2.88 (dd, 1H, J=2.9, 15.2 Hz, HCHe), 3.61 (bd, 1H, J=4.2 Hz, 4'-CH), 3.82 (s, 3H, OCH$_3$), 4.21 (bq, 1H, J=6.8 Hz, 5'-CH), 4.44 (m, 1H, 3'-CH), 4.57 (dd, 1H, J=2.74, 11.87 Hz, O—CH), 5.53 (bd, 1H, J=3.6 Hz, 1'-CH), 6.19 (s, 1H, O—CH—O), 7.67 (bd, 1H, J=8.6 Hz, NH), 7.71 (m, 2H, ArH), 8.06 (m, 2H, ArH), 8.57 (s, 1H, ArH), 8.58 (s, 1H, ArH).

Step 6: (1'S,1R,3S) Methyl(1-[2',3',6'-trideoxyacetamido-4'-hydroxy-L-lyxohexopyranose]-5,12-dioxo-3,4,5,12-tetrahydroanthraceno(2,3-c)pyran-3-yl)formate, BCH-671.

Deprotection of the more polar glycoside, from step 4 above by using the method described in example 1, step 11, gave BCH-671 in 70% yield. $^1$H NMR (300 MHz, CDCl$_3$) δ: 1.41 (d, 3H, J=6.6 Hz, CH$_3$), 1.93 (m, 2H, 2'-CH$_2$), 2.51 (dd, 1H, J=12.0, 15.1 Hz, HCHa), 2.85 (dd, 1H, J=3.0, 15.1 Hz, HCHe), 3.65 (bs, 1H, 4'-CH), 3.80 (s, 3H, OCH$_3$), 4.46 (overlapped m, 3H, 3',5'-CH and O—CH), 5.42 (bd, 1H, J=3.2 Hz, 1'-CH), 6.32 (s, 1H, O—CH—O), 6.69 (bd, 1H, J=8.3 Hz, NH), 7.70 (m, 2H, ArH), 8.05 (m, 2H, ArH), 8.57 (s, 1H, ArH) 8.58 (s, 1H, ArH).

Example 5:

Preparation of 1-methylated tetrahydroanthraceno[2,3-c]pyran-3-yl derivatives

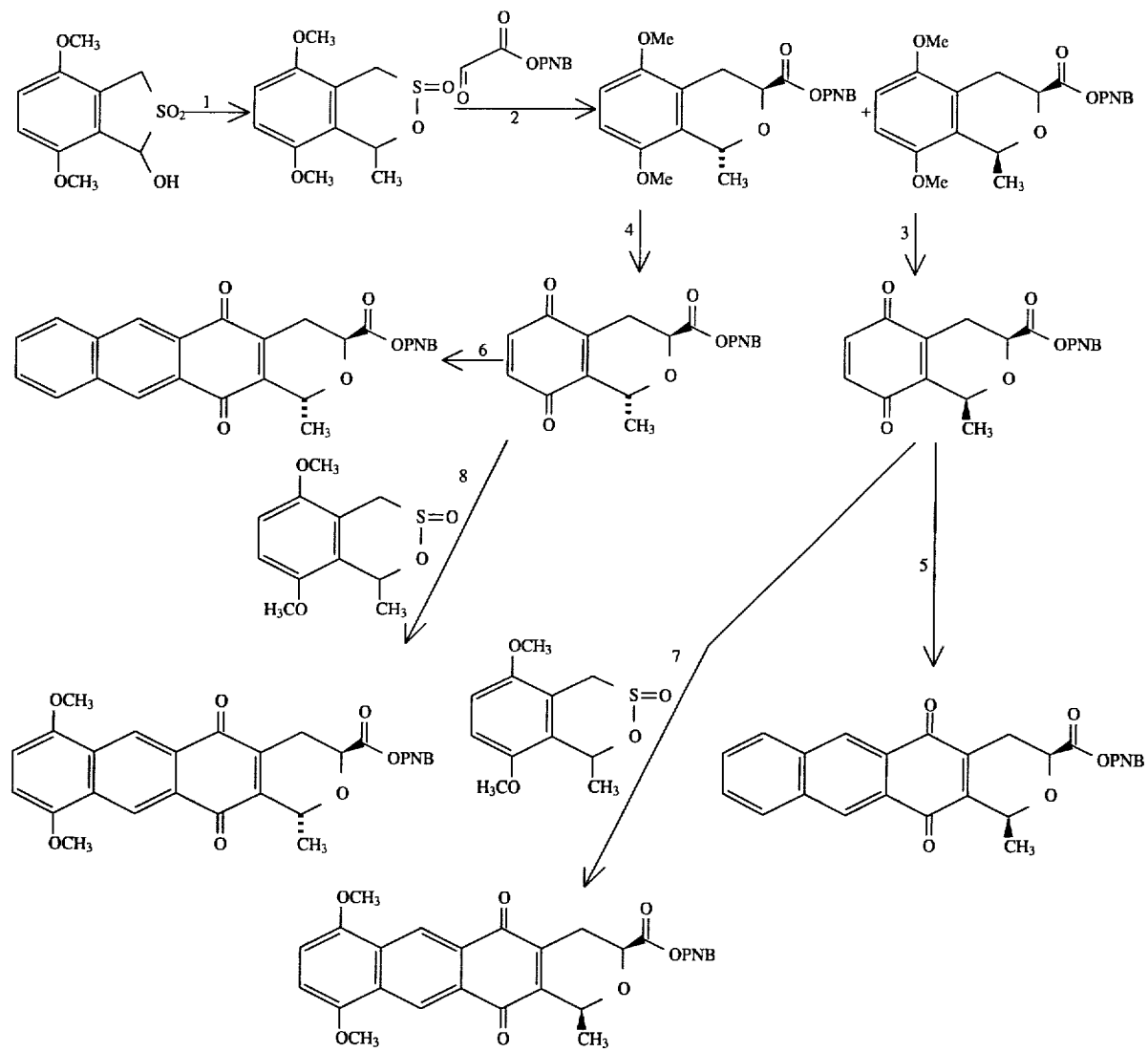

Example 5

Step 1: 5,8-dimethoxy-1-methylbenzo[C]1,2-oxathiin-2-oxide

Following a slight modification of Durst and Charlton procedure (Tel. Lett', 25 (46), 5290, 1984), 800 ml of a 2.5M solution of methyl lithium in hexanes was added, at room temperature and under argon, to a solution containing 14.38 g (59 mmol) of hydroxysulfone from "example 1—step 3" in 2.5 l of anhydrous THF. After stirring for 16 hours, 400 ml of methanol was added to the mixture. Solvents were removed under vaccuo and the residue was treated with 500 ml of 12M HCl at 50° C. for 3 min. The solution was then diluted in 1 l of water and extracted three times with 300 ml of dichloromethane. The combined organic layer was washed twice with water, once with brine and dried over MgSO$_4$. After removal of solvents, flash chromatography of the residue gave the titled sultine as a yellow solid in 47% yield. (MP: 152°–153° C.). $^1$H NMR (200 MHz, CDCl$_3$) d:1.58 (d, 3H, J=6.2 Hz, CH$_3$), 3.49 (d, 1H, J=14.8 Hz, CH), 3.79 (s, 3H, OCH$_3$), 3.80 (s, 3H, OCH$_3$), 4.29 (d, 1H, J=14.8 Hz, CH), 5.63 (q, 1H, J=6.2 Hz, CH$_3$CH), 6.82 (s, 2H, ArH). CMR (75.44 MHz, CDCl$_3$) d:15.3, CH$_3$; 52.2, CH$_2$; 55.7, OCH$_{3, 59.9}$, CH; 110.1, 110.6, aryl CH; 123.6, 123.8, 149.8, 149.9, aryl C. MS (CI, NH$_3$, 137° C.). m/e: 246 (100, M'NH$_4$).

Step 2: Cis and trans p-nitrobenzyl(5,8-dimethoxy-1-methylisochroman-3-yl) formate These 1-methylated isochromans were obtained by following the same procedure as described for the isochroman of "example 1, step 5". Thus, the reaction between 4 g (16.5 mmol) of the 1-methylated sultine from step 1 above and 18.76 g (83 mmol) of p-nitrobenzyl-glyoxalate hydrate resulted in a black residue which after flash chromatography (10% ethyl acetate-25% toluene-65% cyclohexane) gave the two titled diastereomeric isochromans in a 3:1 ratio. The trans isomer (2.8 g, 44% yield) haδ: (MP:110°–111° C.). $^1$H NMR (200 MHz, CDCl$_3$) d:1.53 (d, 3H, J=6.8 Hz, CH$_3$), 2.85 (dd, 1H, J=9.8, 16.8 Hz, Hcha), 3.07 (dd, 1H, J=4.4, 16.7 Hz, HCHe), 3.78 (s, 3H, OCH$_3$), 3.79 (s, 3H, OCH$_3$), 4.69 (dd, 1H, J=4.7, 9.9 Hz, OCH), 5.29 (q, 1H, J=6.7 Hz, OCHCH$_3$), 5.33 (bs, 2H, OCH$_2$), 6.68 (s, 2H, H—C=C—H), 7.49 (d, 2H, J=8.9 Hz, ArH), 8.22 (d, 2H, J=8.9 Hz, ArH). CMR (75.44 MHz, CDCl$_3$) d:19.6, CH$_3$; 25.5, CH$_2$; 55.3, 55.4, OCH$_3$; 65.0, OCH$_2$; 67.2, 68.6, OCH; 107.8, 123.6, 128.2, aryl CH; 121.0, 128.0, 142.8, 147.6, 149.2, 150.6, aryl C; 171.4, ester C=O.

IR (FT, CDCl$_3$) $^v$max: 1756, ester C=O, 1216, C—O. MS (CI, NH$_3$, 191° C.) m/e: 405 (52, M+NH$_4$), 270 (100, M+NH$_4$—C$_7$H$_5$NO$_2$). The cis isomer (247) (0.9 g, 14% yield, oil) haδ: $^1$H NMR (200 MHz, CDCl$_3$) d:1.62 (d, 3H, J=6.4 Hz, CH$_3$, 2.73 (ddd, 1H, J=2.1, 11.4, 16.0 Hz, HC H̱a), 3.17 (dddd, 1H, J=1.2, 2.4, 16.0 Hz, HCHe), 3.79 (s, 3H, OCH$_3$), 3.80 (s, 3H, OCH$_3$), 4.23 (dd, 1H, J=2.4, 11.4, OCH), 5.09 (bq, 1H, J=6.5 Hz, CH̱CH$_3$), 5.36 (bs, 2H, OCH$_2$), 6.71 (bs, 2H, ArH), 7.80 (d, 2H, J=8.9 Hz, ArH), 8.25 (d, 2H, J=8.9 Hz, ArH). CMR (75.44 MHz, CDCl$_3$) d:21.5, CH$_3$; 26.7, CH$_2$; 55.2, 55.6, OCH$_3$; 65.0, OCH$_2$, 71.5, 72.1, OCH; 108.4, 123.7, 128.3, aryl CH$_2$; 107.9, 122.9, 142.8 148.1, 149.9, 150.4, aryl C; 170.8, ester C=O. IR (FT, CDCl$_3$) $^v$max: 1755, ester C=O, 1219, C=O. HRMS calculated for C$_{20}$H$_{21}$NO$_7$ 387.1318 found 387.1299.

Step 3: Cis-p-nitrobenzyl(5,8-dioxo-1-methyl-3,4,5,8-tetrahy-drobenzo[2,3-c]pyran-3-yl) formate 1 mg (1.0 mmol) of the cis isochroman from step 2 above in 10 ml of acetonitrile was added, dropwise over 5 min and with stirring, a solution containing 1.96 g (3.6 mmol) of ceric ammonium nitrate in 10 ml of water. After five minutes the mixture was diluted with 25 ml of water and then extracted three times with 50 ml of methylene chloride. The combined organic layer was washed once with 50 ml of water, once with 25 ml of brine, and then dried over MgSO$_4$. Following evaporation of solvent, the oily yellow residue was found to be pure (95% yield) isochromandione. Flash chormatography, with 20% ethyl acetate in toluene, reduced the yield (65%) considerably without significantly increasing the purity. $^1$H NMR (200 MHz, CDCl$_3$) d:1.57 (d, 3H, J=6.7 Hz, CH$_3$), 2.57 (ddd, 1H, J=4.3, 10.8, 18.4 Hz, HCH̱a), 2.98 (bdt, 1H, J=2.8, 18.4 Hz, HCH̱e), 4.19 (dd, 1H, J=2.75, 10.8 Hz, O—CH), 4.81 (m, 1H, OCHCH$_3$), 5.36 (bs, 2H, OCH$_2$), 6.76 (dd, 2H, J=10.1 Hz, ArH), 7.57 (d, 2H, J=9.0 Hz, ArH), 8.24 (d, 2H, J=9.0 Hz, ArH). CMR (75.44 MHz, CDCl$_3$) d:20.2, CH$_3$; 25.2, CH$_2$; 65.3, OCH$_2$; 70.2, 71.1, OCH; 123.6, 128.4, aryl CH; 135.7, 136.8, CH; 138.4, 142.2, 143.4, 147.6, quaternary C; 169.2, ester C=O; 185.2, 185.4, quinone C=O.

Step 4: Trans-p-nitrobenzyl(5,8-dioxo-1-methyl-5,8-dihydroisochroman-3-yl) formate Oxydative demethylation of 160 mg (0.4 mmol) of trans-p-nitrobenzyl(5,8-dimethoxy-1-methylisochroman-3-yl) formate with 780 mg (1.4 mmol) of ceric ammonium nitrate, as described in step 3 above, give 137 mg of the titled isochromandione as a yellow oil. $^1$H NMR (200 MHz, CDCl$_3$) d: 1.5 (d, 3H, J=6.8 Hz, CH$_3$), 2.67 (ddd, 1H, J=2.2, 8.9, 19.0 Hz, HCH̱a), 2.89 (ddd, 1H, J=1.3, 4.6, 19.0 Hz, HC H̱e), 4.59 (dd, 1H, J=4.7, 8.9 Hz, OCH), 5.04 (bq, 1H, J=6.8 Hz, OCH̱CH$_3$), 5.33 (bs, 2H, OCH$_2$), 6.75 (dd, 2H, J=10.1 Hz, H—C=C—H), 7.54 (d, 2H, J=8.9 Hz, ArH), 8.24 (d, 2H, J=8.9 Hz, ArH). CMR (75.44 MHz,CDCl$_3$) δ: 19.4, CH$_3$; 24.4, CH$_2$; 65.5, OCH$_2$; 66.7, 67.1, OCH; 123.8, 128.6, 136.0, 136.5, aryl CH; 137.3, 142.2, 143.5, 146.7, aryl C; 185.0, 185.3, quinone C=O.

Step 5: (1R,3R) and (1S,3S) Cis-p-nitrobenzyl(5,12-dioxo-1-methyl-3,4,5,12-tetrahydroanthraceno(2,3-c)pyran-3-yl)formate This compound was obtained by following the same procedure as described in "example 4, step 2". Thus, reaction of 250 mg (1.5 mmol) of 3,6-dihydrobenzo-(b)-1,2-oxathin-2-oxide with 268 mg (0.7 mmol) of the cis isochromandione from step 3 above gave 157 mg (49% yield) of the titled tetracycle. (MP: 118°–120° C.). $^1$H NMR (200 MHz, CDCl$_3$ d:1.69 (d, 3H, J=6.5 Hz, CH$_3$), 2.74 (ddd, 1H, J=3.7, 10.8, 18.5 Hz, HcH̱a), 3.24 (dt, 1H, J=2.8, 18.5 Hz, HCH̱e), 4.26 (dd, 1H, J=2.9, 10.9 Hz, OCH), 5.04 (m, 1H, CH̱CH$_3$), 5.38 (bs, 2H, OCH$_2$), 7.59 (d, 2H, J=9.2 Hz, ArH), 7.7 (m, ArH), 8.05 (m, 2H, ArH), 8.26 (d, 2H, J=8.9 Hz, ArH), 8.60 (s, 1H, ArH), 8.61 (s, 1H, ArH), CMR (75.44 MHz, CDCl$_3$) d:20.6, CH$_3$; 26.2, CH$_2$; 65.5, OCH$_2$; 71.0, 71.4, OCH; 123.9, 128.6, 129.9, 129.7, 130.2, aryl CH; 127.8, 127.9, 128.2, 134.7, 141.1, 142.2, 146.7, 147.2, aryl C; 169.7, ester C=O; 182.2, 182.5, quinone C=O.

Step 6: (1S,3R) and (1R,3S) Trans-p-nitrobenzyl(5,12-dioxo-1-methyl-3,4,5,12-tetrahydroanthraceno[2,3-c]pyran-3-yl)formate Following the procedure as described in "example 4, step 2", the reaction between 175 mg (1.1 mmol) of 3,6-dihydrobenzo-(b)-1,2-oxathiin-2-oxide with 187 mg (0.5 mmol) of the quinone from step 4 above gave 119 mg (52% yield) of the titled compound. (MP: 131°–132° C.). $^1$H NMR (200 MHz, CDCl$_3$) d:1.62 (d, 3H, J=6.8 Hz, CH$_3$), 2.89 (ddd, 1H, J=2.0, 8.9, 19.0 Hz, HCH̱a), 3.11 (ddd, 1H, J=1.0, 4.6, 19.1 Hz, HCH̱e, 4.69 (dd, 1H, J=4.7, 8.8 Hz, OCH), 5.30 (bq, 1H, J=6.8 Hz, CH̱CH$_3$), 5.35 (bs, 2H, OCH$_2$), 7.55 (d, 2H, J=8.7 Hz, ArH), 7.7 (m, 2H, ArH), 8.05 (m, 2H, ArH), 8.20 (d, 2H, J=8.7 Hz, ArH), 8.58 (bs, 2H, ArH). CMR (75.44 MHz, CDCl$_3$) δ: 19.6, CH$_3$; 25.3, CH$_2$; 65.5, OCH$_2$; 67.0, OCH; 123.9, 128.7, 128.8, 129.6, 130.2, aryl CH; 127.9, 128.0, 128.2, 134.8, 141.1, 142.3,146.7, 147.6, aryl C; 170.3, ester C=O; 182.8, 182.9, quinone C=O.

Step 7: (1R,3R) and (1S,3S) Cis-p-nitrobenzyl(5,12-dioxo-7,10-dimethoxy-1-methyl-3,4,5,12-tetrahydroanthraceno[2,3-c]pyran-3-yl)formate Following the procedure as described in "example 4, step 2", the reaction between 95 mg (0.4 mmol) of the sultine from example 1, step 4, with 71 mg (0.2 mmol) of the quinone from step 3 above gave 42 mg (41% yield) of the titled tetracycle. (MP: 154°–156° C.). $^1$H NMR (200 MHz, CDCl$_3$) d:1.68 (d, 3H, J=7.6 Hz, CH$_3$), 2.75 (ddd, 1H, J=3.6, 10.7, 18.6 Hz, CHH̱a), 3.27 (bdt, 1H, J=2.8, 18.6 Hz, HC H̱e), 4.00 (s, 3H, OCH$_3$), 4.01 (s, 3H, OCH$_3$), 4.28 (dd, 1H, J=2.8, 10.7 Hz, OCH), 5.06 (m, 1H, OCH̱CH$_3$), 5.38 (bs, 2H, OCH2), 6.90 (s, 2H, ArH), 7.59 (d, 2H, J=8.9 Hz, ArH), 8.26 (d, 2H, J=8.9 Hz, ArH), 8.95 (s, 1H, ArH), 8.98 (s, 1H, ArH). IR (FT, CDCl$_3$) $^v$max: 1757, este C=O; 1664, quinone C=O. MS (DCI, 240, NH$_3$) m/e: 517 (100, M+), 382 (68, M+-C$_7$H5NO$_2$).

Step 8: (1R,3R) and (1R,3S) Trans-p-nitrobenzyl(5,12-dioxo-7,10-dimethoxy-1-methyl-3,4,5,12-tetrahydroanthraceno[2,3-c]pyran-3-yl)formate Following the same procedure as described in "example 4, step 2" the reaction between 70 mg (0.3 mmol) of the sultine from "example 1, step 4", and 53 mg (0.15 mmol) of quinone from step 4 above gave 30 mg (44% yield) of the titled tetracycle. (MP: 180°–182° C.). H NMR (200 MHz, CDCl$_3$) δ: 1.57 (d, 3H, J=6.8 Hz, CH$_3$), 2.84 (ddd, 1H, J=2.1, 9.1, 19.0 Hz, HCH̱a), 3.06 (ddd, 1H, J=1.2, 4.6, 18.9 Hz, HCH̱e), 3.95 (s, 3H, OCH$_3$), 3.96 (s, 3H, OCH$_3$), 4.63 (dd, 1H, J=4.69, 8.9 Hz, OCH), 5.29 (m, 1H, OCH̱CH$_3$), 5.30 (bs, 2H, OCH2), 6.86 (s, 2H, ArH), 7.50 (d, 2H, J=8.8 Hz, ArH), 8.16 (d, 1H, J=8.8 Hz, ArH), 8.91 (s, 1H, ArH), 8.92 (s, 1H, ArH). CMR (75.44 MHz, CDCl$_3$) δ: 19.7, CH$_3$; 25.4, CH$_2$; 55.9, 2×OCH$_3$; 65.5, OCH$_2$; 67.1, 67.8, OCH; 107.6, 123.4, 123.9, 128.7, aryl CH; 127.4, 127.5, 128.6, 140.9, 142.3, 146.8, 150.9, aryl C; 170.4, ester C=O; 182.8, 182.9, quinone C=O. IR (FT, CDCl$_3$) $^v$max: 1757, ester C=O; 1664, quinone C=O.

Example 6

Preparation of tetrahydroanthraceno[2,3-c]pyran-3-yl derivatives with a methyl ketone substituent

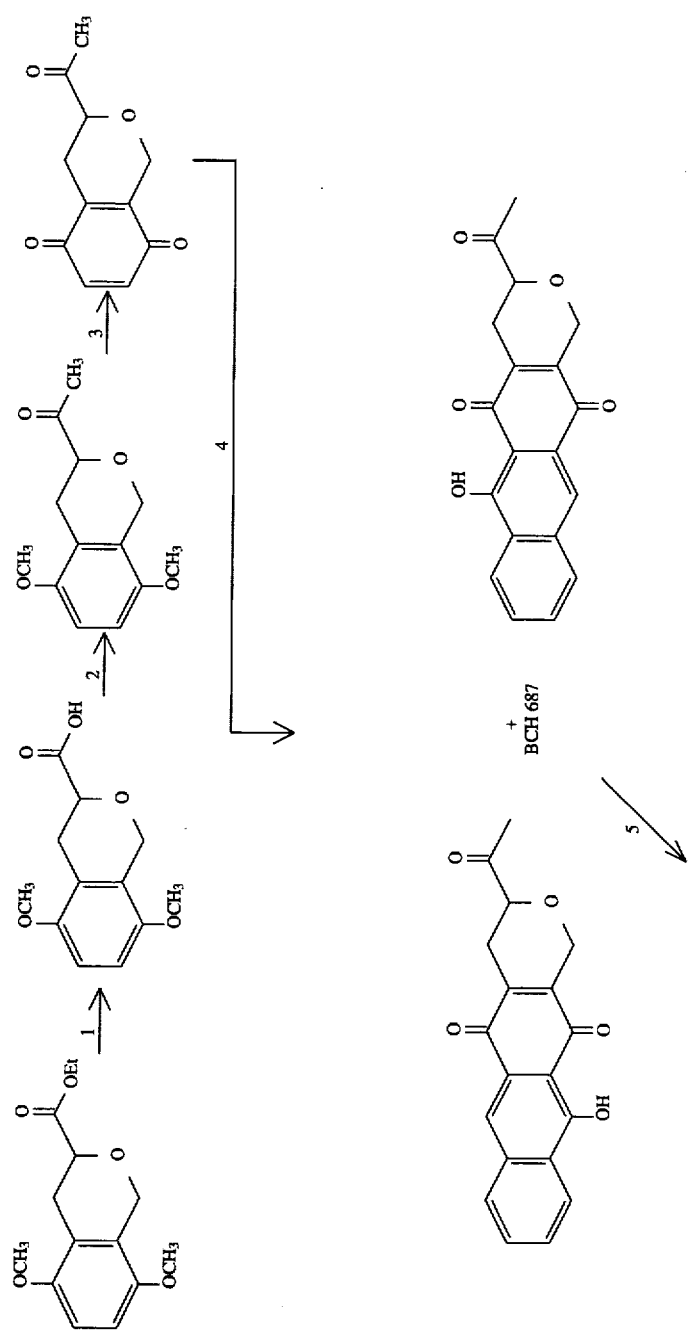

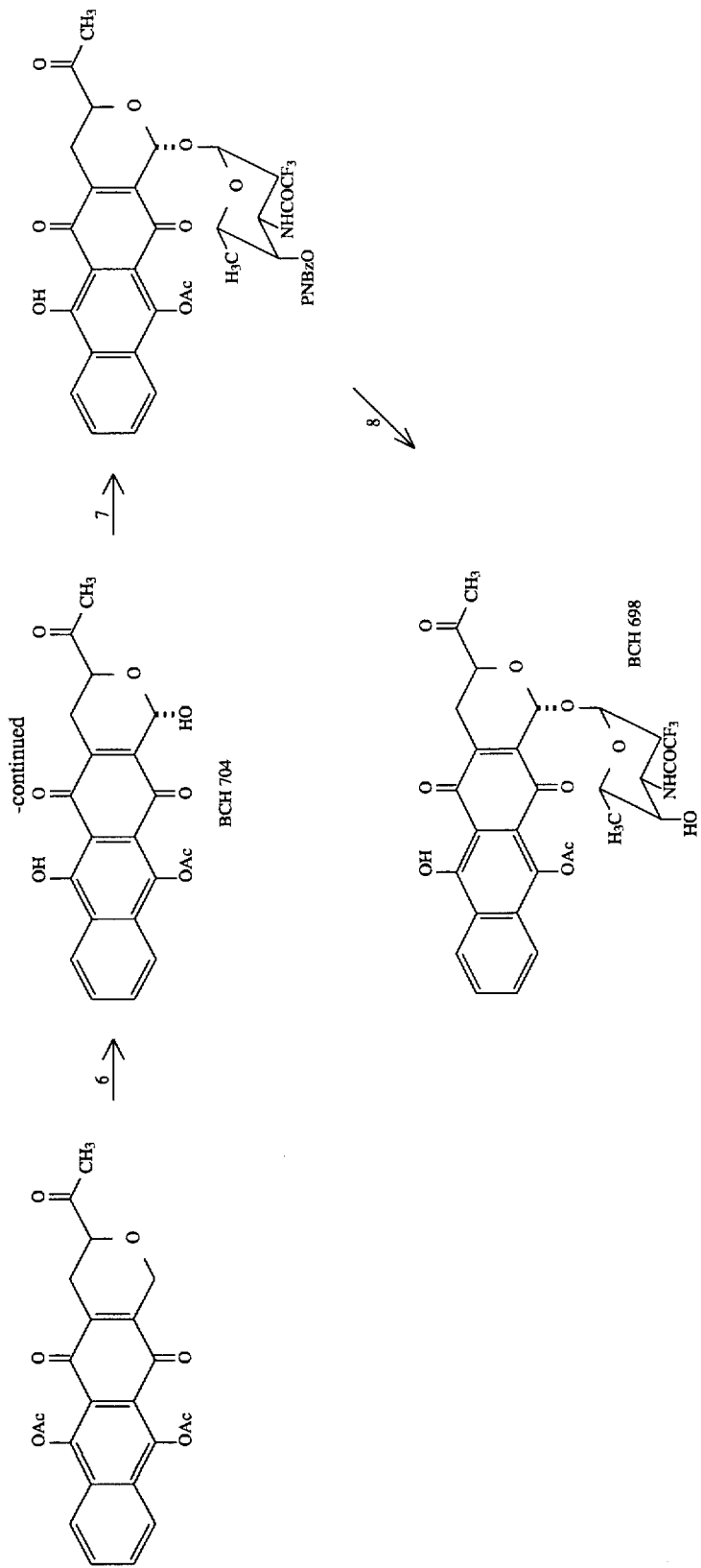

EXAMPLE 6

Step 1: 5,8-dimethoxyisochroman-3-yl carboxylic acid

A solution containing 133 mg (0.5 mmol) of the ethylbenzyl-isochroman formate from "example 1, step 5", in 10 ml of THF was added 10 ml of a 1M aqueous sodium hydroxide solution. After stirring at room temperature for 0.5 hour, the mixture was evaporated down to 5 ml and then diluted with 25 ml of water. The aqueous layer was extracted three times with 20 ml aliquots of $CH_2Cl_2$, then acidified with concentrated aqueous HCl and reextracted four times with 50 ml of ethyl acetate. Only the combined ethyl acetate layers were kept, and after washing twice with water, evaporation of solvent gave 125 mg (99% yield) of the titled isochromanyl acid. (MP: 217°–218° C.). $^1$H NMR (200 MHz, DMSO-$d_6$) δ:2.88 (broad ddt, 1H, J=9.9, 17 Hz, HC HaCH), 3.15 (ddd, 1H, J=1.4, 4.6, 17 Hz, HCHeCH), 3.91 (s, 3H, OCH$_3$), 3.93 (s, 3H, OCH$_3$), 4.46 (dd, 1H, J=4.5, 9.9, OCHC=O), 4.75 (broad dt, 1H, J=16.4 Hz, ArH, CHaO), 5.05 (broad dd, 1H, J=16.5 Hz, ArHCHeO), 6.92 (dd, 2H, J=11.2 Hz, ArH). CMR (75.44 MHz, CDCl$_3$) d:26.7, CH$_2$; 49.9, OCH$_2$; 55.9, 56.1, ArOCH$_3$; 65.3, OCH; 108.7, 109.1, aryl CH; 123.1, 124.5, 150.6, 152.3, aryl CH; 210.2, CO$_2$H.

Step 2: Methyl(5,8-dimethoxyisochroman-3-yl)ketone

To a solution containing 150 mg (6.3 mmol) of isochromanyl acid (261) in 15 ml of anhydrous THF was added dropwise, over 5 minutes at −78° C. and under argon, 0.94 ml of a 1.4M methyl lithium in ether solution. The solution was stirred for 10 minutes at −78° C. then warmed to room temperature and stirred for two more hours. Methanol (1 ml) was then added, followed with 25 ml of water, and the mixture was extracted three times with 50 ml of dichloromethane. The combined organic layer was washed with 25 ml water, 25 ml of saturated aqueous NaCl, and dried over MgSO$_4$. After evaporation of solvent, flash chromatography of the residue (10% ethylacetate in toluene) gave 110 mg (74%) of the titled isochroman ketone. (MP: 84°–85° C.). $^1$H NMR (200 MHz, CHCl$_3$) d:2.32 (s, 3H, COCH$_3$), 2.59 (bdd, 1H, J=11.3, 17.0 OHz, HCHa), 3.04 (ddd, 1H, J=1.5, 3.8, 17.1, HCHe), 3.78 (s, 3H, OCH$_3$), 3.79 (s, 3H, OCH$_3$), 4.08 (dd, 1H, J=3.8, 11.4 Hz, O—CH), 4.66 (bd, 1H, J=15.9 Hz, HcHa—O), 5.04 (bd, 1H, J=15.9 Hz, HCHe—O), 6.66 (dd, 2H, J=9.0 Hz, ArH). CMR (75.44 MHz, CDCl$_3$) d:24.7, CH$_2$; 25.9, CH$_3$; 55.4, 55.6, ArOCH$_3$; 64.7, OCH$_2$; 79.1, OCH; 107.2, 107.7, aryl CH; 122.2, 123.9, 149.2, 151.0, aryl C; 208.4, C=O. IR (CDCl$_3$) $^v$max: 1717, C=O.

Step 3: Methyl(5,8-dioxo-5,8-dihydroisochroman-3-yl)ketone

To a stirred solution containing 700 mg (3 mmol) of the isochroman from step 2 above in 20 ml of acetonitrile was added dropwise over 5 minutes, at room temperature, a solution containing 2.0 g (3.6 mmol) of ceric ammonium nitrate in 20 ml of water. Stirring was continued for five minutes and then 100 ml of dichloromethane was added to the mixture. Successive washings of the organic layer were done with 50 ml of water and 50 ml of brine. After drying over MgSO$_4$, evaporation of solvent gave 560 mg (92% yield) of the yellow isochromandione, as a dark yellow oil.

$^1$H NMR (300 MHz, CDCl$_3$) d:2.34 (s, 3H, COCH$_3$), 2.48 (dddd, 1H, J=2.8, 4.0, 10.1, 19.2 Hz, HCHa), 2.87 (dm, 1H, J=19.2 Hz, HCHe), 4.06 (dd, 1H, J=4.0, 10.1 Hz, OCH), 4.52 (dt, 1H, J=3.3, 18.6 Hz, HCHa—O), 4.83 (ddd, 1H, J=1.0, 2.7, 18.6 Hz, HCHe—O), 6.80 (dd, 2H, J=10.2 Hz, HC=CH). CMR (75.44 MHz, CDCl$_3$) δ:23.1, CH$_2$; 25.8, CH$_3$; 62.7, OCH$_2$; 77.7, OCH; 136.0, 136.4, CH; 183.3, 139.6, quaternary C; 185.17, 185.24, quinone C=O, 206.4, COCH$_3$. IR (CDCl$_3$) $^v$max: 1722, COCH$_3$; 1659, quinone C=O.

Step 4: Methyl(11-hydroxy-5,12-dioxo-3,4,5,12-tetrahydroanthraceno[2,3-c]pyran-3-yl)ketone and Methyl(5-hydroxy-5,12-dioxo-3,4,5,12-tetrahydroanthraceno[2,3-c]pyran-3-yl)ketone, BCH-687

These compounds were obtained by following the same procedure as described in step 1 of example 3 and using the methyl 5,8-dimethoxyisochroman-3-yl ketone in this example. Flash chromatography of the residue gave a mixture of both regioisomers (64%) which were not necessarily separated for the next step. The two regioisomers could however, be separated by preparative HPLC. The less polar regioisomer had $^1$H NMR (300 MHz, CDCl$_3$) δ: (s, 3H, CH$_3$), 2.62 (m, 1H, HCH$_2$CHC=O), 3.08 (m, 1H, HCHaCHC=O), 4.10 (dd, 1H, J=10.0, 3.7 Hz, HCHa—O), 5.02 (broad d, 1H, HCHe—O), 7.73 (m, 2H, ArH), 7.97 (m, 1H, ArH), 8.12 (s, 1H, ArH), 8.50 (m, 1H, ArH), 13.86 (s, 1H, ArOH). The more polar regioisomer had $^1$H NMR (300 MHz, CDCl$_3$) δ:2.35 (s, 3H, CH$_3$), 2.59 (m, 1H, HCHeCHCO), 3.05 (broad dr, J=19.0, 2.8 Hz, HC HaCHCO), 4.08 (dd, 1H, J=10.0, 3.9 Hz, CH), 4.44 (dr, 1H, J=22.5, 6.7, 3.3 Hz, HCHa—O), 5.03 (broad d, 1H, J=18.7 Hz, HCHe—O), 7.71 (m, 2H, ArH), 7.95 (m, 1H, ArH), 8.13 (s, 1H, ArH), 8.46 (m, 1H, ArH), 13.70 (s, 1H, ArOH).

The autoxidized product, methyl (5,12-dihydroxy-6,11-dioxo-3,4,6,11-tetrahydroanthraceno[2,3-c]pyran-3-yl)ketone BCH-688, was also obtained in 8% yield. (MP. 210° C. decomposes). $^1$H NMR (300 MHz, CDCl$_3$, CDCl$_3$) δ:2.40 (s, 3H, COCH$_3$), 2.81 (m, 1H, HCHa), 3.22 (ddd, 1H, J=2.0, 4.0, 18.1 Hz, HCHe), 4.15 (dd, 1H, J=3.9, 10.6 Hz, OCH), 4.79 (dt, 1H, J=2.2, 17.4 Hz, OHCHa), 5.20 (dd, 1H, J=1.1, 17.4 Hz, HCHe), 7.84 (m, 2H, ArH), 8.36 (m, 2H, ArH), 13.18 (s, 1H, ArOH), 13.31 (s, 1H, ArOH).

Step 5: Methyl(6,11-diacetoxy-5,12-dioxo-3,4,5,12-tetrahydroanthraceno[2,3-c]pyran-3-yl)ketone The titled compound was obtained in 45% yield by following the same procedure as described in example 3 by sequentially carrying out step 7 and 8. $^1$H NMR (300 MHz, CDCl$_3$) δ:2.35 (s, 3H, COCH$_3$), 2.51 (s, 3H, OCOCH$_3$), 2.54 (s, 3H, OCOCH$_3$), 2.72 (m, 1H, HCHa), 3.05 (m, 1H, HC He), 4.08 (m, 1H, OCHC=O), 4.73 (bd, 1H, OHCHa), 5.08 (bd, 1H, OHCHe), 7.65 (m, 2H, ArH), 8.15 (m, 2H, ArH).

The mixture of monoacetoxylated compounds BCH-721 methyl (6-hydroxy-11-acetoxy and 6-acetoxy-11-hydroxy-5,12-dioxo-3,4,5,12-tetrahydroanthraceno[2,3-c]pyran-3-yl)ketone, could be recovered in 10%.

Step 6: Methyl(11-acetoxy-1,6-dihydroxy-5,12-dioxo-3,4,5,12-tetrahydroanthraceno[2,3-c]pyran-3-yl)ketone.(BCH-704)

The titled compound was obtained in 24% yield by following the same procedure as described in example 3, step 9. $^1$H NMR (300 MHz, CDCl$_3$) δ: 2.38 (s, 3H, COCH$_3$), 2.52 (s, 3H, OCOCH$_3$), 3.04 (m, 2H, CH$_2$), 4.55 (m, 1H, OCHC=O), 6.36 (bs, 1H, OCHOH), 7.82 (m, 2H, ArH), 8.23 (m, 2H, ArH).

Step 7: (1'S,1R,3S) and (1'S,1S,3R) Methyl (1-[2',3',6'-trideoxy-3'-trifluoroacetamido-L-4'-O-p-nitrobenzoyl-L-lyxohexopyranose)-6-hydroxy-11-acetoxy-5,12-dioxo-3,4,5,12-tetrahydroanthraceno(2,3-c)pyran-3-yl)ketone Following the regular glycosylation procedure (step 10, example 1) the desired titled pyranoanthracycline gycoside 2 were obtained in 37% yield. $^1$H NMR (300 MHz, CDCl$_3$) δ:1.21 (overlapped d, 3H, 6'-CH$_3$), 2.11 (m, 2H, 2'-CH$_2$), 2.38 (s, 3H, —COCH$_3$), 2.53 (s, 3H, -OCOCH$_3$), 2.68 (m, 1H, HCHa), 3.21 (m, 1H, HCHe), 4.39 (m, 1H, 5'-CH), 4.63 (m, 2H, 3' and 4' CH), 5.16 (dd, 1H, J=4.1, 12.6 Hz, O—CH), 5.48 and 5.78 (bs, 1H, 1'-CH), 6.21 (s, 1H, O—CH—O), 7.81 (m, 2H, ArH), 8.25 (overlapped m, 6H, ArH), 13.69 (s, 1H, ArOH).

Step 8: (1'S')Methyl[1-(N-trifluoroacyldaunosamine)-6-hydroxy-11-acetoxy-5,12-dioxo-3,4,5,12-tetrahydroanthraceno(2,3-C)pyran-3-yl]ketone (BCH-698)

A cooled (−5° C.) solution containing 48.4 mg (0.06 mmol) of the glycoside from step (before) in 5 ml of dichloromethane was treated with 5 ml of a 0.2M NaOH methanolic solution for 15 minutes. The reaction mixture was then quenched by acidification with 0.1N HCl to pH 6, extracted with $CH_2Cl_2$ (2×15 ml) and the combined organic phases were washed with water (2×30 ml) and dried ($Na_2SO_4$). Purification by HPLC (spherex CN5U; hexane; ethylacetate; 80% −20%) gave 5.3 mg (14% yield) of the desired compound. (MP. 235°–236° C.). $^1$H NMR (300 MHz, $CDCl_3$) δ:1.30 (d, 3H, J=6.7 Hz, $CH_3$), 1.87 (m, 1H, 2'- HCHa), 2.12 (m, 1H, 2'-HCHe), 2.37 (s, 3H, —$COCH_3$), 2.53 (s, 3H, $OCOCH_3$), 2.62 (m, 1H, HCHa), 3.14 (m, 1H, HCHe), 3.63 (bs, 1H, 4'-CH), 4.17 (bq, 1H, J=6.7 Hz, 5'-CH), 4.39 (m, 1H, 3'-CH), 4.60 (dd, 1H, J-3.6, 11.4, O—CH), 5.57 (bs, 1H, 1'-CH), 6.13 (s, 1H, O—CH—O), 6.67 (bd, 1H, J-8.4 Hz, NH), 7.79 (m, 2H, ArH), 8.21 (m, 1H, ArH), 8.29 (m, 1H ArH), 13.49 (s, 1H, ArOH).

Example 7

Preparation of tetrahydroanthraceno[2,3-c]pyran-3-yl derivatives with a hydroxymethyl ketone substituent

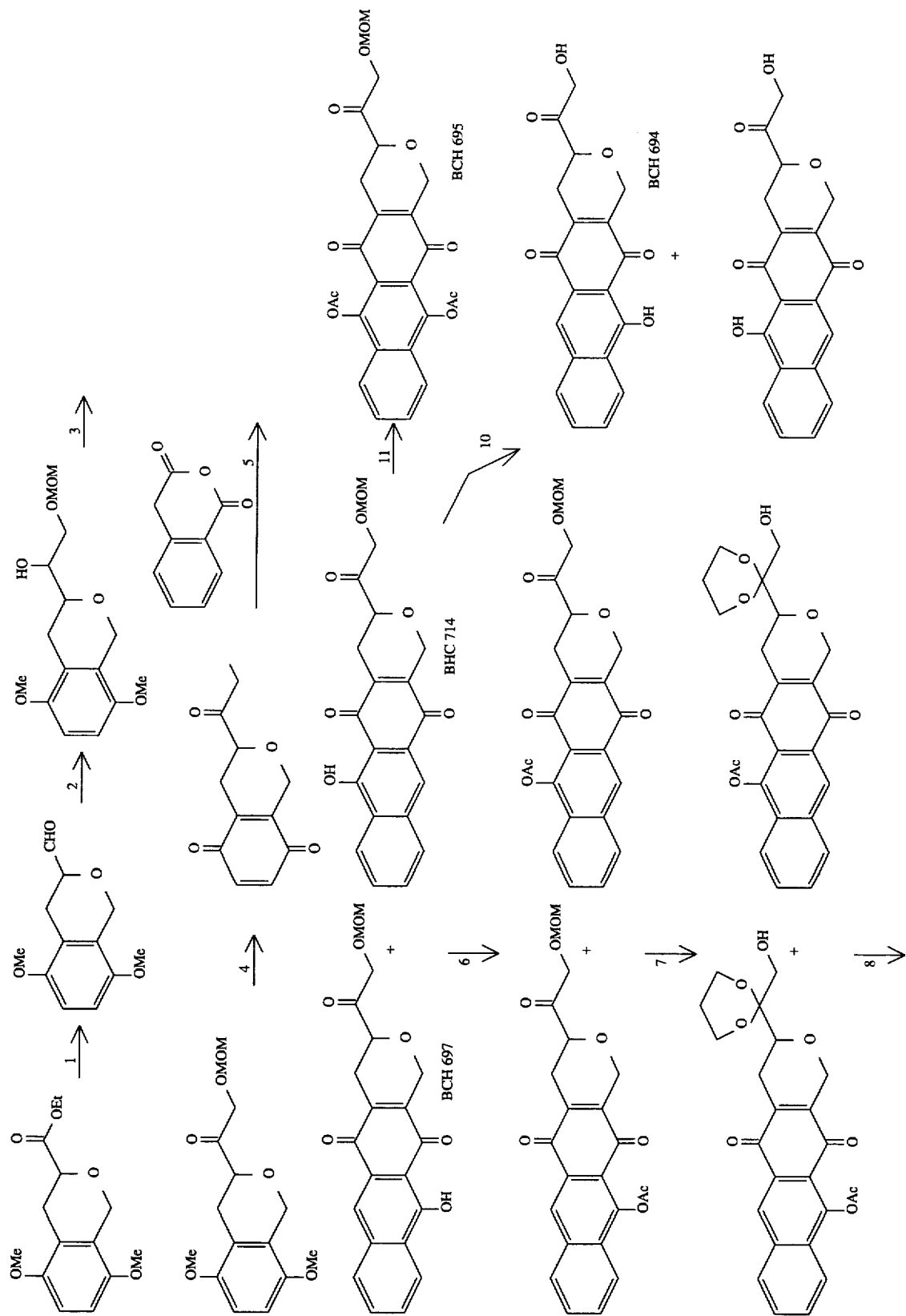

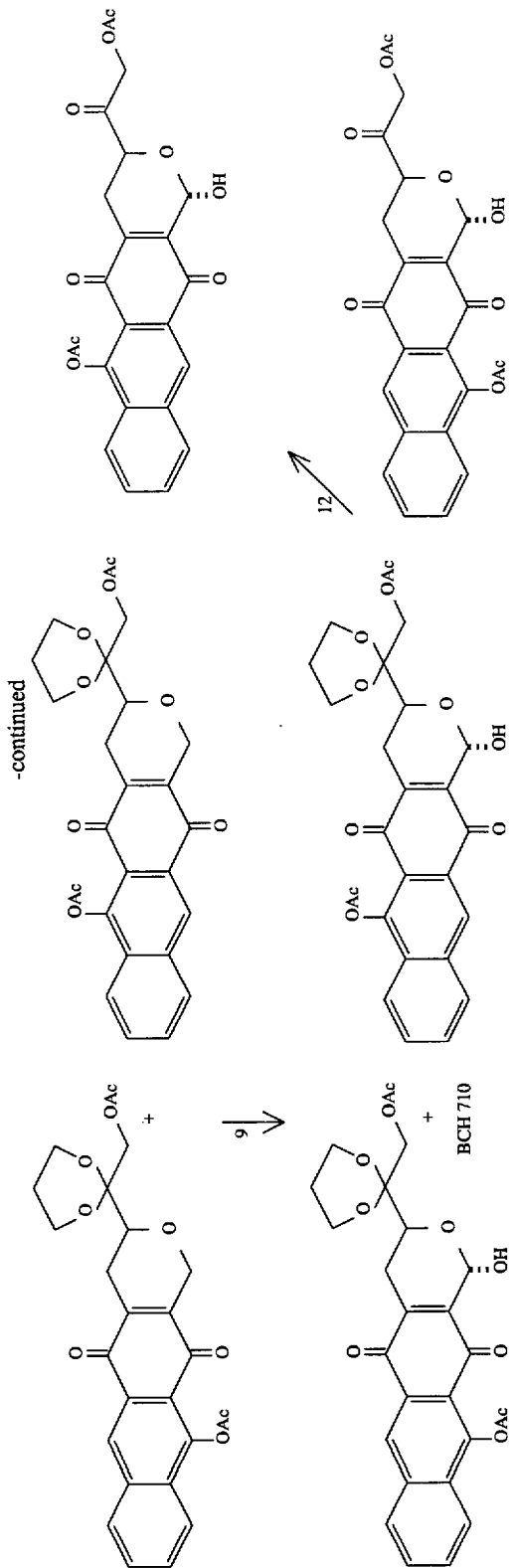

Example 7

Step 1: 3-formyl-5,8-dimethoxyisochroman

Ethyl-(5,8-dimethoxyisochroman-3-yl)formate (697 mg, 2.62 mmol) was dissolved in toluene (20 ml) and cooled to −78° C. DIBAL (2.97 ml, 1.5M, 4.45 mmol) was cooled to −78° C. and added slowly to the reaction mixture over a period of 15–20 minutes. A TLC taken right away after the addition revealed that the reaction was over. Cold MeOH (4 ml) was added slowly ($H_2$ evolution!) and the mixture was extracted with ethyl acetate (3×50 ml). The organic phases were combined, washed with brine and dried over $MgSO_4$. Flash chromatography of the crude residue gave the title products (483 mg, 83%). $^1H$ NMR (300 MHz, $CDCl_3$) d:2.63 (dd, 1H, J=16.8, 11.3 Hz, HCHaCHC=O), 2.99 (dd, 1H, J=17.0, 3.8 Hz, HCHeCHC=O), 3.76 (s, 3H, $OCH_3$), 3.77 (s, 3H, $OCH_3$), 4.09 (dd, 1H, J=10.7, 4.4 Hz, He=O), 4.87 (dd, 2H, J=103.8, 15.9 Hz, HCHa,e—O), 6.66 (m, 2H, ArH).

Step 2: 3-(1-hydroxy-2-methoxymethoxy)ethyl-5,8-dimethoxyiso-chroman

A solution of $nBu_3SnCH_2OMOM$ (1,066 g, 2.92 mmol) in 12 ml of THF was cooled to −78° C. under argon. The solution was stirred while n-BuLi (1,1 ml, 2.5M, 2.75 mmol) was added. After 30 minutes, 3-formyl-5,8-dimethoxyisochroman (483 mg, 2.18 mmol) was added. After 45 minutes, the cold reaction mixture was partitioned between water and ether. The organic phase was dried over $MgSO_4$, filtered, and concentrated. Flash chromatography of the crude residue (hexane/ethyl acetate; 1:1) gave the title compound in 66% yield (431 mg). The following spectral data were obtained from the mixture of two diastereoisomers. $^1H$ NMR (300 MHz, $CDCl_3$, ppm) δ:From 2.49 to 3.10 (m, 3H, HC Ha,e—CH—C—O and OH), 3.35 (s, 3H, $CH_2OCH_3$), from 3.55 to 3.92 (m, 6H, $CH_2$-OMOM, CHaeCH=O and CH—OH), 3.69 (s, 3H, $OCH_3$), 3.71 (s, 3H, $OCH_3$), 4.55 (m, 1H, HCHa—O), 4.64 (s, 2H, $OCH_2$—$OCH_3$), 4.90 (m, 1H, HCHe—O), 6.57 (m, 2H, ArH). IR: (neat), 3464 (OH), 2940, 2830, 1480, $cm^{-1}$.

Step 3: 5,8-dimethoxy-3-(methoxymethoxy)acetoisochroman

To a stirred solution of oxalyl chloride (3.37 ml, 38.67 mmol) in 80 ml of $CH_2Cl_2$ was added dropwise a solution of DMSO (2.99 ml, 38.67 mmol) in 10 ml of $CH_2Cl_2$ at −78° C. under argon over a period of 5–10 minutes. The stirring was continued for 15 minutes before adding a solution of 3-(1-hydroxy-2-methoxy-methoxy) ethyl-5,8-dimethoxy-isochroman (3,842 g, 12.89 mmol) in 20 ml of $CH_2Cl_2$ over a period of 5 minutes. After the mixture was stirred for 45 minutes at −78° C., triethylamine (19.6 ml) was introduced. The reaction mixture was warmed to room temperature over 1 hour, quenched with 100 ml of water. The aqueous layer was extracted with $CH_2Cl_2$ (3×100 ml) and the combined organic phases were washed with water and brine, dried over $MgSO_4$, filtered, and concentrated to a yellow residue that was purified by flash chromatography (hexane/ethyl acetate; 7:3) to give the titled compounds (3.295 g, 86%). $^1H$ NMR (300 MHz, $CDCl_3$) d:2.63 (dd, 1H, J=13.9, 5.7 Hz, HC HaCHC=O), 3.07 (dm, 1H, HCHeCHCO), 3.39 (s, 3H, $CH_2OCH_3$), 3.75 (s, 3H, $OCH_3$), 3.76 (s, 3H, $OCH_3$), 4.19 (dd, 1H, J=11.4, 3.8 Hz, CH—O), 4.60 (s, 2H, C $H_2OCH_3$), 4.79 (dd, 2H, J=111.0, 15.9 Hz), 6.63 (m, 2H, ArH). $^{13}C$ NMR (75.44 MHz, $CDCl_3$) δ:25.37, 56.01, 56.18, 65.31, 70.21, 97.06, 107.84, 108.37, 122.59, 124.33, 149.81, 151.62, 206.78. IR.(neat) 2960, 2910, 1735 CO, 1620, 1580, 1540, 1480 $cm^{-1}$.

Step 4: 3-(methoxymethoxy)aceto-5,8-dioxoisochroman

5,8-dimethoxy-3-(methoxymethoxy)-acetoisochroman (3.155 g, 10.59 mmol) was dissolved in acetonitrile (35 ml) and cooled to 0° C. A solution of ceric ammonium nitrate (CAN) (17.53 g in 35 ml of $H_2O$) was added dropwise with stirring. The ice bath was then removed and stirred for an extra 15 minutes. Water (30 ml) was added and the mixture was extracted with $CH_2Cl_2$. The organic phases were washed with water, dried over $MgSO_4$, filtered and concentrated in vacuo to give a reddish oil which was found to be pure title compound without flash chromatography. (2.38 g, 85% yield). $^1H$ NMR (300 MHz, $CDCl_3$, ppm) δ:2.52 (m, 1H, HCHa—CHC=O), 2.90 (m, 1H, HCHeCHC=O), 3.39 (s, 3H, $OCH_2OCH_3$), 4.19 (dd, 1H, J=10.3, 3.8 Hz, HC—O), 4.44 (td, 1H, J=18.7, 3.7 Hz, HCHa—O), 4.54 (s, 2H, OC $H_2$—$OCH_3$), 4.70 (s, 3H, $COCH_2$—OMOM), 4.77 (dd, 1H, J=18.6, 2.5 Hz, HCHe—O), 6.75 (m, 2H, ArH).

Step 5: 3-(2-methoxymethoxy)aceto-6-hydroxy-1,2,3,4-tetrahydro-(2-oxygen)napthacene-5,12-dione(BCH-697) and 3-(2-methoxymethoxy)aceto-11-hydroxy-1,2,3,4-tetrahydro-(2-oxygen)-napthacene-5,12-dione (BCH-714)

To a solution of LDA (9.42 mmol) in 30 ml of THF was added dropwise a solution of homophthalic anhydride (1.53 g, 9.43 mmol) in 30 ml of THF at −78° C. under argon. After 5 minutes, a solution of 3-( 2-methoxymethoxy)aceto-5,8-dioxoisochroman (2.3589, 8.14 mmol) in 35 ml of THF was introduced. The stirring was continued at −78° C. for 20 minutes and then at room temperature for 30 minutes. After the mixture was kept in the fridge overnight, it was quenched with sat. $NH_4Cl$ solution (40 ml) and then carefully partitioned between 1N HCl (15 ml) and $CH_2Cl_2$ (150 ml). The organic layer was washed with brine, dried over $Na_2SO_4$, and then concentrated to a crude residue which was purified by flash chromatography to give a mixture of the two regioisomers (46%). The following spectral data were obtained from the mixture of two regioisomers. $^1H$ NMR (300 MHz, $CDCl_3$), d:2.58 (m, 2H, HCHaCHC=O), 3.04 (dd, 2H, J=19.2, 3.26 Hz, HCHe—CHCO), 3.40 (s, 6H, $OCH_3$), 4.22 (m, 2H, CH—O), 4.57 (s, 4H, $OCH_2OCH_3$), 457 (m, 2H, HCHa—O), 4.58 (s, 4H, $COCH_2$—OMOM), 4.87 (m, 2H, HCHe—O, 7.67 (m, 4H, ArH), 7.69 (m, 2H, ArH), 7.86 (m, 2H, ArH), 8.38 (m, 2H, ArH). IR: (neat) 2925, 2843, 1740 (CO), 1654, 1639, 1608, 1568 $cm^{-1}$.

Step 6: 6 and 11-acetoxy-3-(2-methoxymethoxy)aceto-1,2,3,4-tetrahydro-(2-oxygen)naphtacene-5,12-dione

The regioisomeric mixture from step 5 above (1,962 g, 5.13 mmol) was dissolved in $CH_2Cl_2$ (130 ml). Acetic anhydride (26.7 ml), pyridine (26.7 ml) and DMAP (0,518 g) were successively added and stirred at room temperature for 30 minutes. The reaction mixture was then poured onto ice water, and extracted with $CH_2Cl_2$. The organic layers were combined, washed with HCl (4%), water, dried over sodium sulfate, and concentrated to give a crude residue which was flash chromatographed using hexane/EtOAc (1:1) to give a mixture of the desired titled compounds in greater than 80% yield. The following spectral data were obtained from the two regioisomeric mixtures. $^1H$ NMR (300 MHz, $CDCl_3$), d:2.54 (m, 2H, HCHaCHC=O), 3.10 (m, 2H, HCHeCHC=O), 3.40 (s, 3H, $CH_2OCH_3$), 3.41 (s, 3H, $CH_2OCH_3$), 4.23 (dd, 2H, J=10.48, 3.84 Hz, OCHC=O), 4.58 (s, 2H, CO—$CH_2$OMOM), 4.58 (s, 2H, $COCH_2$OMOM), 4.58 (m, 2H, HCHa—O), 4.72 (s, 4H, $COCH_2OCH_3$), 4.95 (m, 2H, HCHe—O), 7.72 (m, 4H, ArH), 8.19 (m, 4H, ArH), 8.54 (s, 1H, ArH), 8.58 (s, 1H, ArH).

Step 7: 3-(2-hydroxy-1-propeneketal)aceto-6-acetoxy-1,2,3,4-tetrahydro-(2-oxygen)naphtacene-5,12-dione and 3-(2-hydroxy-1-propeneketal)-aceto-11-acetoxy-1,2,3,4-tetrahydro-(2-oxygen)naphtacene-5,12-dione

The mixture of tetracycles from step 6 above (70 mg, 0.16 mmol) was dissolved in toluene (30 ml) followed by the addition of 1,3-propanediol (1 ml) and PPTS (2 mg). The reaction mixture was refluxed overnight using a Dean Stark trap to remove the water formed during the process. The reaction mixture was extracted with CH$_2$Cl$_2$, the organic phases were combined, washed with H$_2$O, dried over sodium sulfate, and concentrated in vacuo. The crude residue obtained was flash chromatographed using EtOAc/CH$_2$Cl$_2$ (1:1) to give the desired title products (66 mg) in 94% yield. The following spectral data were recorded on the two regioisomeric mixtures. $^1$H NMR (300 MHz, CDCl$_3$) d:1.55 (m, 2H, O—CH$_2$CH—H—CH$_2$—O), 1.85 (m, 2H, O—CH$_2$—CH—H—CH$_2$O), 2.05 (m, 2H, OH), 2.25 (m, 2H, HCHaCHC<), 2.58 (s, 3H, OCOCH$_3$), 2.61 (s, 3H, OCOCH$_3$), 2.80 (m, 2H, HCHeCHC<), from 3.55 to 4.15 (m, 14H, O—CH$_2$—CH$_2$—O, CH$_2$OH and HC—O), 4.52 (m, 2H, HCHa—O), 4.94 (m, 2H, HCHe—O), 7.69 (m, 4H, ArH), 8.07 (m, 4H, ArH), 8.52 (s, 1H, ArH), 8.57 (s, 1H, ArH). IR: (neat) 3454.6, 2929.2, 2878.6, 1766.4 (CO), 1658.0, 1612.4 cm$^{-1}$.

Step 8: 3-(2-acetoxy-1-propeneketal)aceto-6-acetoxy-1,2,3,4-tetrahydro-(2-oxygen)naphtacene-5,12-dione and 3-(2-acetoxy-1-propeneketal)aceto-11-acetoxy-1,2,3,4-tetrahydro-(2-oxygen)naphtacene-5,12-dione A mixture of tetracyclic compounds of step 7 above (367 mg, 0.84 mmol) was dissolved in CH$_2$Cl$_2$ (20 ml) followed by the successive addition of acetic anhydride (1,0 ml), pyridine (1,0 ml) and DMAP (60.9 mg). Within half hour, the reaction was complete. It was extracted with CH$_2$Cl$_2$. The organic phases combined, washed with H$_2$O, dried over MgSO$_4$, and concentrated in vacuo. The crude residue obtained was flash chromatographed using hexane/EtOAc (7:3) to give the desired products as a mixture (278 mg, 0.6 mmol, 69%). The following spectral data were recorded on the two regioisomeric mixtures. $^1$H NMR (300 MHz, CDCl$_3$, ppm) d:1.85 (m, 4H, OCH$_2$CH$_2$—CH$_2$O), 2.11 (s, 6H, CH$_2$OCOCH$_3$), 2.60 (s, 3H, OCOCH$_3$), 2.63 (s, 3H, OCOCH$_3$), 2.86 (m, 4H, HCHa,eCHC<) 3.98 (m, 10H, OC H$_2$—CH$_2$—O and OCHC<), 4.29 (d, 2H, J=11.87, C H$_2$—OCOCH$_3$), 4,5 (m, 2H, HCHa—O), 4.94 (dd, 2H, HC HeO), 5.05 (d, 2H, CH$_2$OCOCH$_3$), 7.70 (m, 4H, ArH), 8.10 (m, 4H, ArH), 8.56 (s, 1H, ArH), 8.61 (s, 1H, ArH), IR: (neat) 2922.3, 1774.8, 1745.6 (C=O), 1669.9, 1617.5 (C=O quinone), 1431.1 cm$^{-1}$.

Step 9: 3-(2-acetoxy-1-propeneketal)aceto-6-acetoxy-1-hydroxy-1,2,3,4-tetrahydro-(2-oxygen)naphtacene-5,12-dione and 3-(2-acetoxy-1-propeneketal)-aceto-11-acetoxy-1-hydroxy-1,2,3,4-tetrahydro-(2-oxygen)naphtacene-5,12-dione (BCH-710)

A mixture of tetracyclic compounds of step 8 above (34 mg, 0.09 mmol) was dissolved in CCl$_4$ (13 ml) followed by addition of NBS (32 mg, 0.18 mmol) and benzoyl peroxide (2 mg). The reaction mixture was refluxed and irradiated by sun-lamp under argon for about one hour. It was then concentrated in vacuo and treated with stirred in THF/H$_2$O (6 ml, 1:1) before it was extracted with CH$_2$Cl$_2$. The organic phases were combined, washed with H$_2$O, dried over sodium sulfate and concentrated in vacuo. The crude residue obtained was flash chromatographed using EtOAc/CH$_2$Cl$_2$ (1:1) to give the desired products as a mixture (26.5 mg, 0.05 mmol, 59%). The following spectral data were recorded on the two regioisomeric mixtures. $^1$H NMR (300 MHz, CDCl$_3$, ppm) δ:1.85 (m, 4H, OCH$_2$—CH$_2$—CH$_2$—O), 2.12 (s, 6H, CH$_2$OCOCH$_3$), 2.60 (s, 3H, OCOCH$_3$), 2.62 (s, 3H, OCOCH$_3$), 2.86 (m, 4H, HCHa,eCHC<), 4.08 (m, 8H, OC H$_2$—CH$_2$—O), 4.38 (d, 2H, CH$_2$—OCOCH$_3$), 4.46 (dd, 2H, OCHC<, 4.89 (broad d, 2H, J=12.03, CH$_2$—OCOCH$_3$), 6.14 (broad d, 2H, J=12.64, CHOH 7.71 (m, 4H, ArH), 8.05 (m, 4H, ArH), 8.56 (s, 1H, ArH), 8.59 (s, 1H, ArH). IR: (neat) 3402.0 (OH), 2925.3, 1772.2; 1735.0, 1666.8, 1617.3, 1443.7 cm$^{-1}$.

Step 10: 3-(2-hydroxy)aceto-6-hydroxy-1,2,3,4-tetrahydro-(2-oxygen)naphthacene-5,12-dione and 3-(2-hydroxy)aceto-11-hydroxy-1,2,3,4-tetrahydro-(2-oxygen)naphthacene-5,12-dione (BCH-694)

A reaction mixture containing both tetracyclic regioisomers from step 5 above (500 mg, 30%, 0.39 mmol) was dissolved in 20 ml of CH$_3$OH followed by addition of 10 ml of 2.5 HCl solution. The mixture was stirred at room temperature for 0.5 h before it was extracted with CH$_2$Cl$_2$ (150 ml). The organic layer was washed with H$_2$O, dried over MgSO$_4$, filtered and then concentrated to a residue that was purified by flash to give an inseparable mixture of the titled compounds. (20 mg, 15%). The following spectra were recorded on the two regioisomeric mixtures. $^1$H NMR (300 MHz, CDCl$_3$) d:2.80 (m, 1H, HCHaCHC=O), 3.1 (m, 1H, HCHeCHC=O), 3.67 (s, 2H, CH$_2$OH), 3.84 (s, 3H, OCH$_3$), 4.33 (m, 1H, CH—O), 4.68 (m, 1H HCHaO), 5.03 (m, 1H, HCHe—O), 7.71 (m, 2H, ArH), 7.94 (m, 1H, ArH), 8.11 (m, 1H, ArH), 8.48 (m, 1H, ArH), 13.70 (s, 1H, exchangeable OH), 13.83 (s, 1H, exchangeable OH).

Step 11: 6,11-diacetoxy-3-(2-methoxymethoxy)aceto-1,2,3,4-tetrahydro-(2-oxygen)naphthacene-5,12-dione (BCH-695)

A mixture of tetracyclic compounds from step 5 above (273 mg, 0.71 mmol) was treated with pb(OAc)$_4$ (370 mg, 3.1 mmol) in dark in the presence of 10 ml CH$_2$Cl$_2$ and 30 ml AcOH at room temperature for 2 days. The mixture was concentrated in vacuo. The residue was partioned between H$_2$O and CHCl$_3$. The organic layer was washed with brine, dried over MgSO$_4$ and concentrated to a residue which was then treated with Ac$_2$O (4 ml), pyridine (4 ml) and DMAP (68 mg) for 2 hours. 20 ml of H$_2$O and 50 ml of CH$_2$Cl$_2$ were added. The organic layer was separated, washed with NaCl solution and dried over MgSO$_4$. Flash chromatography of the residue gave the titled compound (47 mg, 17%). The following spectral data were recorded on the two regiosomeric mixtures. $^1$H NMR (300 MHz, CDCl$_3$) δ: 2.50 (s, 3H, OCOCH$_3$), 2.51 (s, 3H, OCOCH$_3$), 2.25 (m, 1H, HC HaCH—C=O), 3.10 (m, 1H, HCHeCHC=O), 3.40 (s, 3H, CH$_2$OCH$_3$), 4.27 (m, 1H, CHO), 4.61 (s, 2H, CH$_2$OCH$_3$), 4.72 (s, 2H, COCHH$_2$OMOM), 4.70 (m, 1H, HCHe—O), 5.05 (m, 1H, HCHe—O), 7.73 (m, 2H, ArH), 8.16 (m, 2H, ArH). IR: (neat) 2934, 1775, 1742 (CO), 1683, 1598, cm$^{-1}$.

Step 12: 3-(2-acetoxy)aceto-6-acetoxy-1-hydroxy-1,2,3,4-tetrahydro-(2-oxygen)naphtacene-5,12-dione and 3-(2-acetoxy)aceto-11-acetoxy-1-hydroxy-1,2,3,4-tetrahydro-(2-oxygen)naphtacene-5,12-dione BCH-736

A mixture of tetracyclic compounds from step 9 above (30 mg, 0.06 mmol) was dissolved in acetone and H$_2$O (12 ml, 1:1, 58.42) followed by the dropwise addition of HCl conc. (~4 ml). The mixture was stirred at room temperature for several hours until the starting material was consumed. NaHCO$_3$ solution (sat.) was then added until a pH of 8 was obtained. The mixture was then extracted with CH$_2$Cl$_2$, dried over sodium sulfate and concentrated in vacuo. The crude residue obtained was flash chromatographied using ethyl acetate:CH$_2$Cl$_2$ (1:1) to give the title compounds as a mixture (9.3 mg, 0.02 mmol, 39%). The following spectral data were obtained from the regioisomeric mixtures. $^1$H NMR (300 MHz, CDCl$_3$) d:2.62 (s, 6H, OCOCH$_3$), 3.15 (m, 2H, HCHaCHC=O), 3.62 (m, 2H, HCHeCHC=O), 4.62 (m, 4H, CH$_2$OH), 4.88 (m, 2H, CH=O), 6.16 (d, 2H, J=13.95 Hz, CHOH), 7.74 (m, 4H, ArH), 8.11 (m, 4H, ArH), 8.62 (m, 2H, ArH). IR: (neat) 3367.6 (broad, OH), 2932.2, 2855.7, 1771.7, 1738.8 (C=O), 1664.9, 1617.9 (CO, quinone) cm$^{-1}$.

Example 8

Preparation of tetrahydroanthraceno[2,3-c]thiopyran-3-yl derivatives

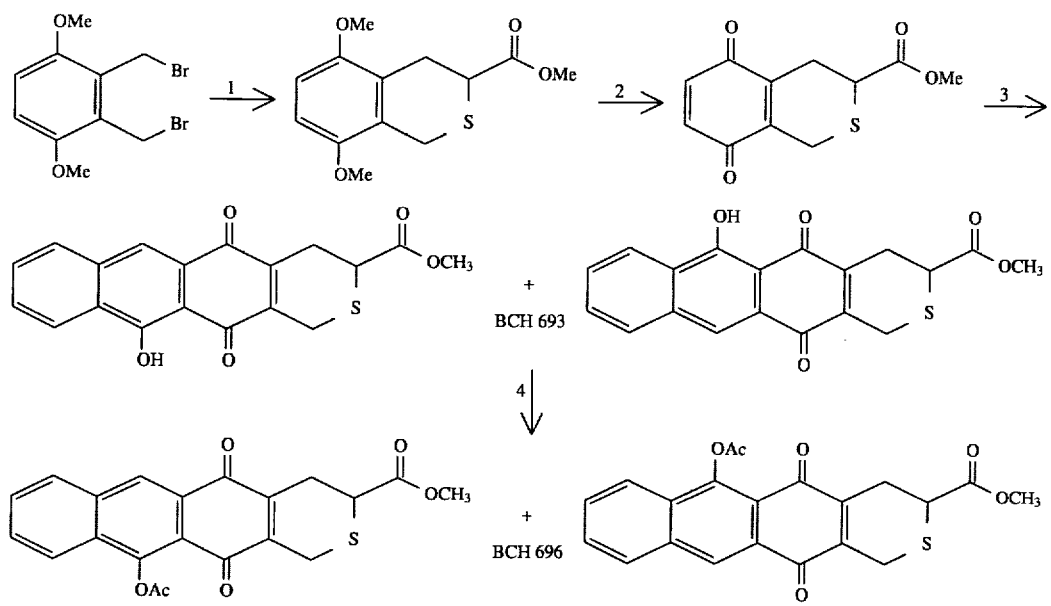

Example 8

Step 1: 3-carbomethoxy-5,8-dimethoxyisothiochroman 1,4-dimethoxy-2,3-dibromomethylbenzene (10.0 g, 30.88 mmol) was dissolved in CH$_2$Cl$_2$ and MeOH (750 ml, 6:4) followed by addition of ethyl 2-mercaptoacetate (4.02 ml, 37.06 mmol) with stirring under argon. The mixture was then cooled to 0° C. followed by dropwise addition of sodium methoxide (4.37M, 8.5 ml, 37.06 mmol) over a period of 2 h using an automatic syringe pump. After 5 minutes the solvent was evaporated and the crude was redissolved in THF (400 ml) and cooled to 0° C. again. NaOEt (2.10 g, 30.88 mmol) was then added. The ice bath was removed and the reaction was stirred for 2 more hours. The reaction mixture was then quenched with NH$_4$Cl (sat.) and extracted with ether. The organic phases were combined, dried over MgSO$_4$, filtered and concentrated. The crude residue was then treated with NaOME in MeOH and THF at 0° C. for 2 hours. The reaction mixture was extracted with ether (100 ml×2). The combined organic phases were washed with H$_2$O, dried over MgSO$_4$, filtered and concentrated to a residue that was purified by flash chromatography to give title compound in 45% yield. $^1$H NMR (300 MHz, CDCl$_3$, ppm) d:2.97 (dd, 1H, J=16.51, 8.79 Hz, HCHaCHC=O), 3.36 (dd, 1H, J=16.7, 5.1 Hz, HC HeCHC=O), 3.73 (m, 2H, HCHa,e—O), 3.75 (s, 3H, OCH$_3$), 3.78 (s, 6H, 2×OCH$_3$), 3.85 (m, 1H, HC—S), 6.69 (m, 2H, ArH).

Step 2: 3-carbomethoxy-5,8-dioxoisothiochroman

To a stirred solution of isothiochroman from step 1 above (253 mg, 0.94 mmol) in 3 ml of CH$_3$CN was added dropwise a solution of ceric ammonium nitrate (1.550 g, 283 mmol) in 3 ml of H$_2$O. The reaction mixture was stirred at 0° C. for 10 minutes and then at room temperature for 10 minutes, followed by extraction with CH$_2$Cl$_2$ (10 ml×3). The combined organic layers were washed with brine and water, dried over MgSO$_4$, and then concentrated to a yellow residue (213 mg, 0.89 mmol) in 95% yield, which was found to be pure by H$^1$NMR. $^1$H NMR (300 MHz, CDCl$_3$) d:2.90 (m, 2H, HCHa,eCHC=O), 3.56 (m, 2H, HCHae—S), 3.73 (s, 3H, OCH$_3$), 3.74 (s, 3H, OCH$_3$), 3.75 (m, 1H, HC—S), 6.75 (m, 2H, ArH). $^{13}$C NMR (75.44 MHz, CDCl$_3$) δ:22.2, 26.0, 37.4, 52.8, 136.2, 137.0, 140.0, 140.5, 172.0 (CO ester), 185.8, 187.0 (CO quinones). IR: (neat) 2956, 1736, 1658, 1607, 1442, 1409 cm$^{-1}$.

Step 3: 3-carbomethoxy-6-hydroxy-1,2,3,4-tetrahydro-(2-sulfur)naphthacene-5,12-dione and 3-carbomethoxy-11-hydroxy-1,2,3,4-tetrahydro(2-sulfur)naphthacene-5,12-dione (BCH-693)

To a stirred solution of LDA (0.98 mmol in 4 ml of THF) was added dropwise a solution of homophthalic anhydride (160.2 mg, 0.99 mmol) in 4 ml of dry THF at −78° C. under argon. After stirring for 10 minutes a solution of quinone from step 3 above (213.0 mg, 0.89 mmol) in 4 ml of THF was introduced. The stirring was continued at −78° C. for 20 minutes and then at room temperature for 1 h. The mixture was quenched with sat. NH$_4$Cl solution (10 ml) and then partioned between 0.5N HCl (10 ml) and CH$_2$Cl$_2$ (50 ml). The organic layer was washed with brine, dried over Na$_2$SO$_4$ and concentrated in vacuo. The residue was purified by flash chromatography with hexane and ethyl acetate (7:3) to give a mixture of titled compounds (125 mg, 40%). The following spectral data were obtained from the two regioisomeric mixtures. $^1$H NMR (300 MHz, CDCl$_3$, d:3.09 (dm, 1H, HCHaCHC=O), 3.21 (dm, 1H, HCHeCHC=O), 3.73 (m, 1H, CHS), 3.76 (s, 3H, OCH$_3$), 3.77 (s, 3H, OCH$_3$), 3.82 (m, 2H, HCHa,e—O), 7.69 (m, 2H, ArH), 7.71 (m, 1H, ArH), 8.09 (s, 1H, ArH), 8.44 (m, 1H, ArH), 13.80 (s, 1H, exchangeable OH), 13.89 (s, 1H, exchangeable OH).

Step 4: 6-acetoxy-3-carbomethoxy-1,2,3,4-tetrahydro-(2-sulfur) napthacene-5,12-dione and 11-acetoxy-3-carbomethoxy-1,2,3,4-tetrahydro-(2-sulfur) napthacene-5,12-dione (BCH-696)

A mixture of tetracycles from step 3 above (95 mg, 0.268 mmol) was treated with Ac$_2$O (2 ml), pyridine (2 ml) and catalytic amount of DMAP (34 mg) in 10 ml of CH$_2$Cl$_2$ at room temperature. After stirring for 0.5 h, the mixture was poured into 25 ml of ice water and then diluted with 25 ml of CH$_2$Cl$_2$. The organic layer was washed twice with 0.5 N HCl solution (2×20 ml) and then dried over Na$_2$SO$_4$. Filtration followed by concentration in vacuo provided a yellow residue that was purified by flash chromatography to give the titled products (56 mg, 53%). The following spectral data were obtained from the two isomeric mixtures. $^1$H NMR (300 MHz, CDCl$_3$, ppm) d:2.60 (s, 3H, OCOCH$_3$), 3.10 (m, 2H', HC<u>Ha,e</u>CHCO), 3.7 (m, 1H, CH—S), 3.74 (s, 3H, OCH$_3$), 3.75 (s, 3H, OCH$_3$), 3.81 (m, 2H, HC<u>Ha,e</u>—S), 7.73 (m, 2H, ArH), 8.06 (m, 2H, ArH), 8.59 (s, H, ArH). IR: (neat) 2960, 2922, 1770, 1738 (CO), 1662, 1634, 1623 (CO, quinone) cm$^{-1}$.

Example 9

Short synthesis of anthraceno[2,3-c]pyran-3-yl aglycones with a methyl ketone side chain

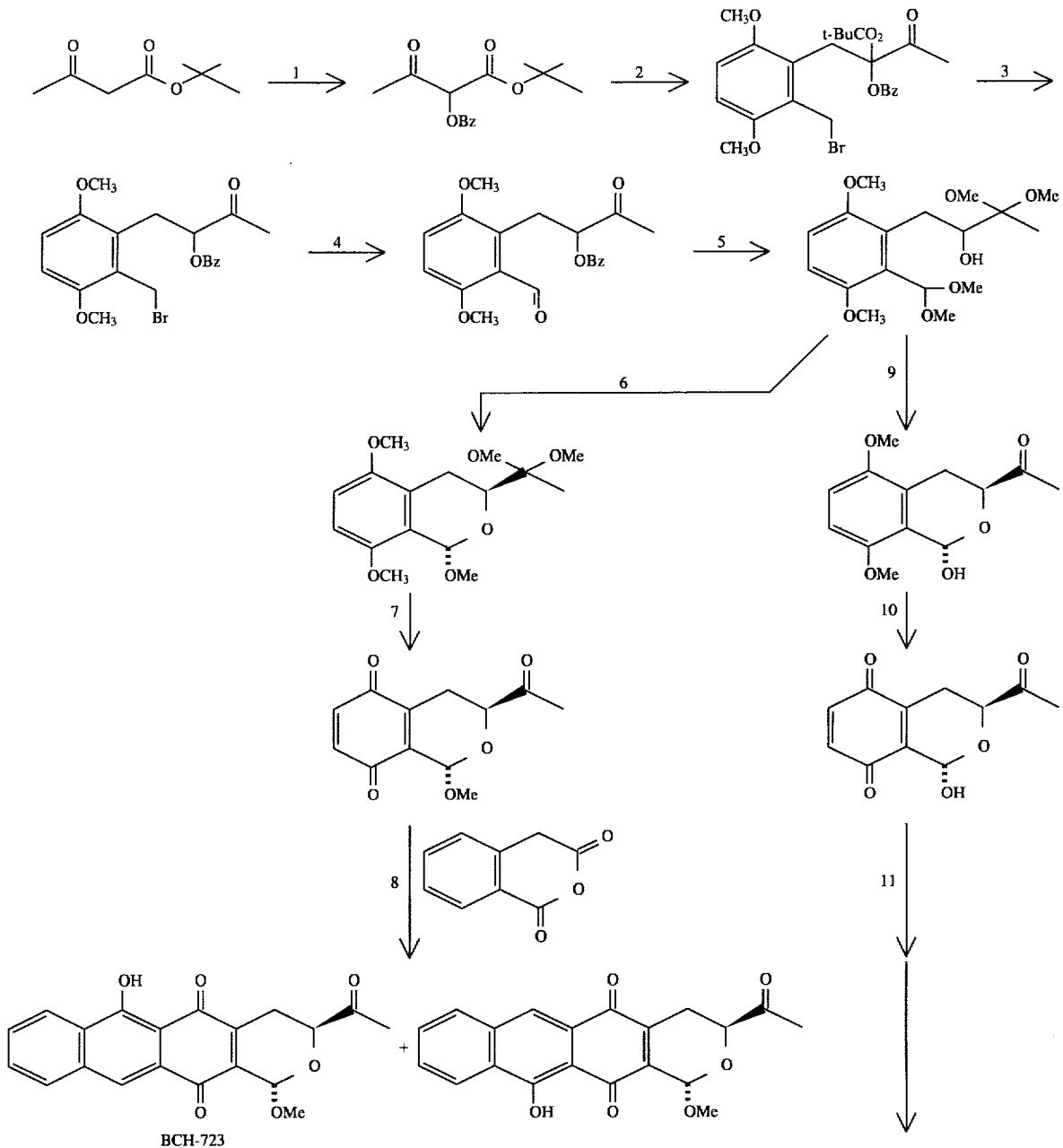

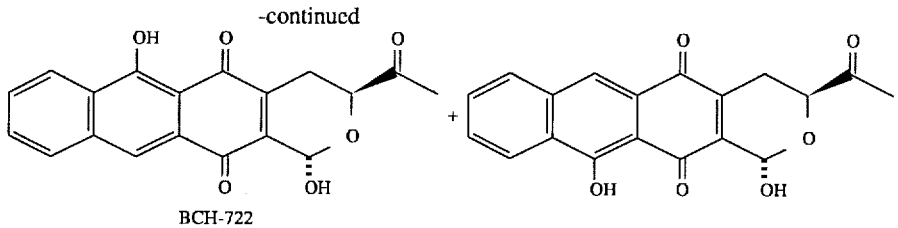

BCH-722

Example 9

Step 1: t-Butyl acetoacetate 2-benzoate

To a stirred solution of t-butyl acetoacetate (10 ml, 60 mmol) in benzene (120 ml) and THF (60 ml) was added NaH (1.5 g, 61 mmol) in portions after 15 minutes, benzoyl peroxide (2.91 g, 12 mmol) dissolved in benzene (30 ml) was added. After 1 hour at room temperature, the reaction mixture was washed with 50 ml of saturated aqueous ammonium chloride, 2×50 ml of saturated aqueous sodium bicarbonate, and 50 ml of saturated aqueous sodium chloride. The organic layer was then dried over $MgSO_4$ and the solvent was removed in vacuo. The excess of t-butyl acetoacetate was removed by distillation under reduced pressure. The residue (2.4 g, 72%) is obtained as a slightly yellow oil characterized as t-butyl acetoacetate 2-benzoate. $^1$H NMR (300 MHz, $CDCl_3$) d:1.52 (s, 9H, —$C(CH_3)_3$), 2.42 (s, 3H, —$CH_3$), 5.63 (s, 1H, —CH—O), 7.47 (dt, J=0.7 and 7.4 Hz, 2H, ArH), 7.61 (dt, J=0.7 and 7.4 Hz, 1H, ArH), 8.13 (dd, J=1.4 and 7.1 Hz, 2H, ArH).

Step 2: 3,6-dimethoxy-2-bromomethylene-1-(3-t-Butyl-carboxylate, 3-benzoate, 2-butanone 4-yl)benzene To a stirred solution containing 500 mg, (1.55 mmol) of 3,6-dimethoxy, 1,2-dibromomethylene benzene and 684 mg (2.46 mmol) of t-Butyl acetoacetate-2-benzoate in 11 ml of acetonitrile and 6.5 ml of THF was added 1 g of cesium carbonate. After 45 minutes, the reaction mixture was filtered over silica gel. The solvent was removed in vacuo, 948 mg of crude 3,6-dimethoxy,2-bromome-thylene 1-(3-t-Butyl carboxylate, 3-benzoate, 2-butanone 4-yl)benzene was obtained. $^1$H NMR (300 MHz, $CDCl_3$) d:1.45 (s, 9H, —$C(CH_3)_3$), 2.41 (s, 3H, —$COCH_3$), 3.53 (s, 3H, —$OCH_3$), 3.82 (s, 3H, —$OCH_3$), 3.83 (2xd, J=14.8 Hz, 2H, Ar$HCH_2$—), 4.79 (s, 2H, —$CH_2$—Br), 6.72 (2xd, J=9.0 Hz, 2H, ArH), 7.38 (m, 2H, ArHCO—), 7.54 (m, 1H, ArHCO—), 7.81 (m, 2H, ArHCO—).

Step 3: 3,6-dimethoxy, 2-bromomethylene,1-(3-benzoate, 2-butanone,4-yl)-benzene

To a stirred solution containing 948 mg of crude β-Ketoester in 12 ml of acetone was slowly added 6 ml of HBr 48%. The reaction mixture was heated to 50° C. for 105 minutes, then poured in 50 ml of water and 50 ml of ether, 100 ml of a saturated aqueous sodium bicarbonate was slowly added. The aqueous layer was extracted with 50 ml of ether. The organic layers were washed with 50 ml of a saturated aqueous sodium chloride, then dried over $MgSO_4$. Evaporation of the solvent gave 828 mg of a slightly yellow oil characterized as 3,6-dimethoxy 2-bromome-thylene, 1-(3-benzoate, 2-butanone, 4-yl)benzene. $^1$H NMR (300 MHz, $CDCl_3$) d:2.29 (s, 3H, —$COCH_3$), 3.24 (dd, J=9.0 and 14.3 Hz, 1H, —$CH_2$—CH—O—), 3.45 (dd, J=4.6 and 14.3 Hz, 1H, —$CH_2$—CH—O—), 3.81 (s, 3H, —$OCH_3$), 3.83 (s, 3H, —$OCH_3$), 4.80 (2xd, J=9.7 Hz, 2H, —$CH_2$—Br), 5.51 (dd, J=4.6 and 9.0 Hz, 1H, —CH—O—), 6.77 (2xd, J=9.0 Hz, 2H, ArH), 7.43 (m, 2H, ArHCO—), 7.55 (m, 1H, ArHCO—), 7.95 (m, 2H, ArHCO—).

Step 4: 3,6-dimethoxy 2-(3-benzoate, 2-butanone, 4-yl) benzaldehyde

To a stirred solution containing 828 mg of the crude benzylic bromide in 10 ml of dimethylsulfoxide was added 390 mg (4.65 mmol) of sodium bicarbonate. The reaction mixture was heated to 90° C. for 25 minutes, then poured in 150 ml of water and extracted with 3×50 ml of ethyl ether. The organic layers were washed with 50 ml of a saturated aqueous sodium chloride, dried over $MgSO_4$ and the solvent was evaporated. The residue was flash chromatographed with hexanes-ethyl acetate 3-1 as the eluting solvent mixture. The titled compound was obtained in 60% yield (319 mg) for 3 steps. $^1$H NMR (300 MHz, $CDCl_3$) d:2.34 (s, 3H, —$COCH_3$), 3.65 (m, 2H, ArH—$CH_2$—), 3.81 (s, 3H, —$OCH_3$), 3.84 (s, 3H, —$OCH_3$), 5.42 (dd, J=5.1 and 9.1 Hz, 1H, —CH—O—), 6.85 (d, J=9.2 Hz, 1H, ArH), 7.04 (d, J=9.2 Hz, 1H, ArH), 7.41 (m, 2H, Ar$HCO_2$—), 7.54 (m, 1H, Ar$HCO_2$—), 8.00 (m, 2H, ArHCO—), 10.62 (s, 1H, —CHO).

Step 5: 3,6-dimethoxy 2-(3-hydroxy,2-butanone, 4-yl)benzaldehyde dimethyl acetal To a stirred solution containing 319 mg (0.93 mmol) of keto-aldehyde in 10 ml of methanol and 2 ml of methyl orthoformate was added 30 mg of p-toluenesulfonic acid. After 3.5 hours, 600 mg of potassium hydroxide and 3 ml of water were added and the reaction mixture was heated to reflux for 4 hours. The solution was then cooled and the methanol evaporated, 25 ml of water and 25 ml of ethyl ether were added. The aqueous layer was extracted with 2×25 ml of ethyl ether. The organic layers were washed with 25 ml of a saturated aqueous sodium chloride and dried over $MgSO_4$. Evaporation of the solvent gave 280 mg as an oil of crude 3.6-dimethoxy 2-(3-hydroxy, 2-butanone, 4-yl) benzaldehyde dimethyl acetal. $^1$H NMR (300 MHz, $CDCl_3$) d:1.33 (s, 1H, —$CH_3$), 3.03 (dd, J=2.9 and 13.9 Hz, 1H, —$CH_2$—CH—O—), 3.26 (s, 3H, —$OCH_3$), 3.27 (m, 1H,—$CH_2$—CH—O), 3.30 (s, 3H, —$OCH_3$), 3.31 (s, 3H, —$OCH_3$), 3.53 (s, 3H, —$OCH_3$), 3.75 (s, 3H, —$OCH_3$), 3.76 (s, 3H, —$OCH_3$), 4.07 (m, 1H, —CH—O—), 4.17 (d, J=6.6 Hz, 1H,—OH), 5.86 (s, 1H, ArHC$\underline{H}$—O), 6.75 (2xd, J=9.0 Hz, ArH).

Step 6: Methyl 1,5,8-trimethoxyisochroman-3-yl-ketone dimethyl acetal

To a stirred solution containing 280 mg of the crude product from step 5 in 4 ml of methanol was added 30 mg of pyridinium p-toluenesulfonate. After 30 minutes, 100 ml of triethylamine was added and methanol was evaporated. The residue was dissolved in methylene chloride and filtered over silica gel. The solvent was evaporated and the residue was purified (not necessary, the crude is clean by NMR) by flash chromatography with henanes-ethyl acetate 2:1 as the eluting solvent mixture. The isochroman analog was obtained in greater then 80% yield (225 mg) for 2 steps. $^1$H NMR (300 MHz, $CDCl_3$) δ:1.40 (s, 3H, —$CH_3$), 2.47 (dd, J=11.8 and 17.6 Hz, 1H, —C$\underline{H}$a—CH—), 2.79 (dd, J=3.8 and 17.6 Hz, 1H, —C$\underline{H}$e—CH—), 3.29 (s, 3H, —$OCH_3$), 3.32 (s, 3H, —$OCH_3$), 3.62 (s, 3H,—$OCH_3$), 3.78 (s, 3H, —OCH₃), 3.81 (s, 3H, —OCH₃), 4.35 (dd, J=3.8 and 11.8 Hz, 1H, —CH₂—CH—O), 5.63 (s, 1H, ArH—CH—O), 6.73 (2xd, J=8.9 Hz, 2H, ArH).

Step 7: Methyl(methoxy-1,5,8-dioxo-5,8-dihydroisochroman-3-yl)ketone

To a stirred solution of I (7 mg, 0.023 mmol) in acetonitrile (0.5 ml) at 0° C. was slowly added Ceric ammonium nitrate (CAN) (44 mg, 0.069 mmol) in water (0.5 ml). After 30 minutes, water (10 ml) was added and the mixture was extracted with CH₂Cl₂. The organic phases were washed with brine and dried over MgSO₄, filtered and concentrated in vacuo to give a yellow oil (II) which did not need any purification. ¹H NMR (300 MHz, CDCl₃) δ:2.34 (s, 3H, —CO—CH₃), 2.39 (dd, J=11.3 and 19.8 Hz, 1H, —CHa—CH), 2.85 (dd, J=4.1 and 19.8 Hz, 1H, —CHe—CH), 3.61 (s, 3H, —OMe), 4.48 (dd, J=4.1 and 11.3 Hz, 1H, CH₂—CH—O), 5.52 (s, 1H, ArH—CH—O), 6.78 (2xd, J=10.2 Hz, 2H, ArH).

Step 8: Methyl(1-methoxy-6 and 11-hydroxy-5,12-dioxo-3,4,5,12-tetrahydroanthraceno(2,3-c)pyran-3-yl)ketone (BCH-723)

To a stirred mixture of NaH (8.7 mg, 0.36 mmol) in THF (2 ml) at 0° C. was added homophtalic anhydride (57 mg, 0.35 mmol). After 10 minutes, I (79 mg, 0.35 mmol) in THF (2 ml) was added and the reaction mixture was warmed up to room temperature. After 1 hour HCl 1N (10 ml) was added and the mixture was extracted with CH₂Cl₂. The organic phases were washed with brine, dried over MgSO₄, filtered and concentrated in vacuo. The residue was purified by flash chromatography using toluene-acetone 95:5 gave 13 mg (10% yield) of II. ¹H NMR (300 MHz, CDCl₃) δ: 2.36 (s, 3H, —CO—CH₃), 2.55 (dd, J=11.8 and 19.7 Hz, 1H, —CHa—CH—O), 3.07 (dd, J=4.1 and 19.7 Hz, 1H, —CHe—CH—O), 3.68 (s, 3H, —OCH₃), 4.56 (dd, J=4.1 and 11.8 Hz, 1H, —CH—CO), 5.71 (s, 1H, —O—CH—O), 7.7 (m, 2H, ArH), 7.95 (dd, J=1.6 and 7.1 Hz, 1H, ArH), 8.09 (s, 1H, ArH), 8.46 (dd, J=1.6 and 8.7 Hz, 1H, ArH).

Step 9: Methyl 5,8-dimethoxy-1-hydroxyisochroman-3-yl ketone

To a stirred solution of crude product from step 5 (1.89 g; 5.49 mmol) in a mixture of acetone (80 ml) and water (25 ml) was added p-toluene sulfonic acid monohydrate (70 mg; 0.37 mmol). After stirring at room temperature for 3 hours, triethylamine (2 ml; 1.43 mmol) was added and stirred for 5 minutes. The mixture was evaporated until volume went down to 10 ml. A mixture of acetone (80 ml) and water (15 ml) was added followed by addition of p-toluene sulfonic acid monohydrate (70 mg; 0.37 mmol). After 3.5 hours, triethylamine (3 ml; 2.15 mmol) was added, evaporated to a small volume, extracted with ether (3×100 ml). The extract was washed with brine (50 ml), dried over MgSO₄ and evaporated yielding quite pure 1-hydroxyisochroman (1.3 g; 94%), (MP. 136°–138° C.). NMR (CDCl₃; 300 MHz) δ:2.32 (3H, s, CH₃O), 2.51 (1H, dd, J=12.4, 17.5 Hz, H-4), 2.97 (1H, d, J=3.5 Hz; —OH), 3.06 (1H, dd, J=4.1, 17.5 Hz, H-4), 3.77, 3.82 (3H, s each, ArOCH₃), 4.70 (1H, dd, J=4.1, 12.4 Hz, H-3), 6.22 (1H, d, J=3.4 Hz, 1H), 6.71, 6.76, (1H, d each, J=9.0 Hz, ArH).

Step 10: Methyl(hydroxy-1,5,8-dioxo-5,8-dihydroisochroman-3-yl)ketone

To a stirred solution of I (123 mg, 0.488 mmol) in acetonitrile (10 ml) at 0° C. was slowly added Ceric ammonium nitrate (CAN) (802 mg, 1.46 mmol) in water (6 ml). After 30 minutes, water (40 ml) was added and the mixture was extracted with CH₂Cl₂. The organic phases were washed with brine and dried over MgSO₄, filtered and concentrated in vacuo to give a yellow oil (II) which did not need any purification (106 mg, 98%). ¹H NMR (300 MHz, CDCl₃) δ:2.31 (s, 3H, —CO—CH₃), 2.39 (dd, J=11.5 and 19.6 Hz, 1H, —CHa—CH), 2.88 (dd, J=4.2 and 19.6 Hz, 1H, —CH—CH), 3.90 (broad s, 1H, —OH), 4.65 (dd, J=4.2 and 11.5 Hz, 1H, CH₂—CH—O), 6.04 (s, 1H, ArH—CH—O), 6.80 (2d, J=10.2 Hz, 2H, ArH).

Step 11: Methyl(1-hydroxy-6 and 11-hydroxy-5,12-dioxo-3,4-5,12-tetrahydroanthraceno(2,3-c)pyran-3-yl)ketone BCH-722

To a stirred solution of homophtalic anhydride (87 mg, 0.536 mmol) in THF (6 ml) at 0° C. was added a solution of sodium bis (trimethylsilyl) amide (0.536 mmol, 536 ml) 1M in THF. After 5 minutes the reaction mixture was cooled down to −78° C. and a solution of I (obtained from hydroxy-quinone (119 mg, 0.536 mmol), methoxypropene (300 ml) and catalytic amount of pyridinium p-toluenesulfonate) in CH₂Cl₂ (2 ml). After 1 hour at −78° C. the reaction mixture was warmed up to room temperature for 2.5 hours then HCl 1N (5 ml) was added and after 5 minutes the mixture was extracted with CH₂Cl₂. The organic phases were washed with brine, dried over MgSO₄, filtered and concentrated in vacuo. The residue was purified by flash chromatography using toluene-acetone 90:10 gave 12 mg (7% yield) of II. ¹H NMR (300 MHz, DMSO) δ:2.26 (s, 3H, —CO—CH₃), 2.49 (dd, J=11.5 and 19.4 Hz, 1H, —CHa—CH—O), 2.85 (dd, J=4.2 and 19.4 Hz, 1H, —CHe—CH—O), 4.64 (dd, J=4.2 and 11.5 Hz, 1H, —CH—CO), 5.95 (d, J=6.2 Hz, 1H, —O—CH—O), 6.26 (d, J=6.2 Hz, 1H, —OH), 7.81 (m, 2H, ArH), 8.13 (s, 1H, ArH), 8.22 (d, J=7.7 Hz, 1H, ArH), 8.36 (d, J=8.0 Hz, 1H, ArH), 13.71 (s, 1H, ArOH).

Example 10

Preparation of tetrahydroanthraceno[2,3-c]pyran-3-yl derivetive with a vinyl side chain

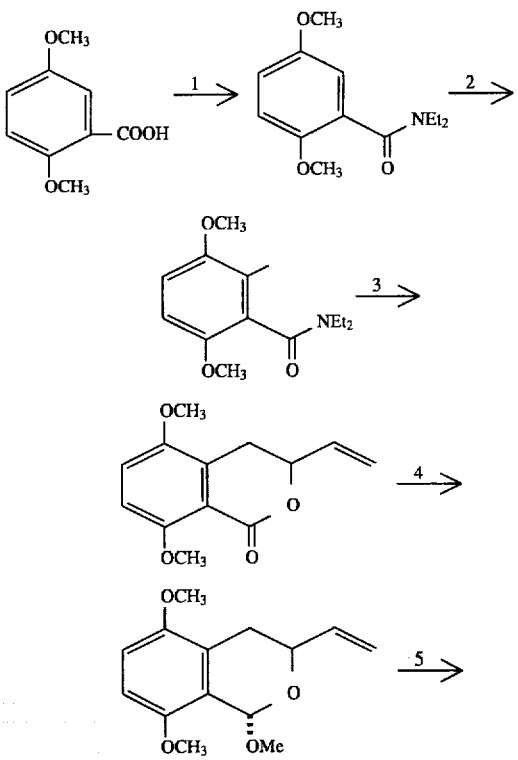

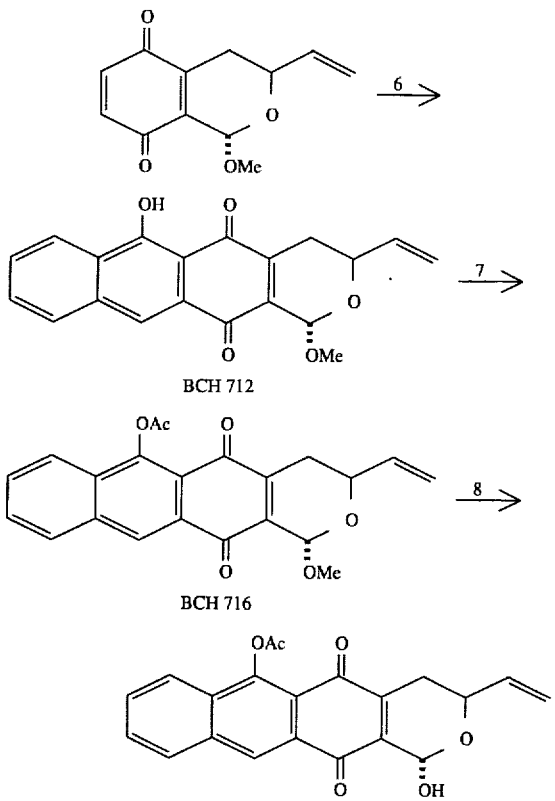

BCH 712

BCH 716

Example 10

Step 1: N,N-diethyl(2,5-dimethoxy)benzamide

To a stirred solution of 2,5-dimethoxybenzoic acid (6.61 g, 36.3 mmol) in 50 ml of $CH_2Cl_2$ was added a solution of $(COCl)_2$ in $CH_2Cl_2$ (2.0M, 20 ml, 40.0 mmol) at 0° C. under argon. After addition of catalytic amount of pyridine (0.2 ml) an evolution of gas was observed. The reaction was warmed up to room temperature and stirred for 3 hours. The volatile were removed and the residue was dissolved in 300 ml of diethyl ether. Diethylamine (5.26 ml, 50.8 mmol) was introduced dropwise at 0° C. under argon. The resulting mixture was stirred at room temperature for another 3 hours, and then quenched with saturated $K_2CO_3$ solution. The organic layer was washed with 2N NaOH and water, dried over $MgSO_4$, filtered and then evaporated. Flash chromatography of the residue with $CH_2Cl_2$ and $CH_3CO_2Et$ (1:1) provided pure title compound (8.34 g, 35.1 mmol) in 97% yield as white solid. $^1H$ NMR ($CDCl_3$) δ:1.05 (3H, t, J=7.1 Hz), 1.24 (3H, t, J=7.1 Hz), 3.16 (2H, q, J=7.1 Hz), 3.56 (2H, m), 3.77 (3H, s), 3.78 (3H, s), 6.77 (1H, m), 6.84 (2H, m).

Step 2: N,N-diethyl(2,5-dimethoxy-6-methyl)benzamide

To a stirred solution of TMEDA (2.23 ml, 14.8 mmol) in 25 ml of THF was added s-BuLi (1.3M, 11.35 ml, 14.8 mmol) at −78° C. under argon. After 20 minutes, a solution of N,N-diethyl(2,5-dimethoxy)benzamide (1.4 g, 5.9 mmol) in 5 ml of THF was introduced dropwise at −78° C. The stirring was continued at −78° C. for 1 hour before MeI (1.40 ml, 22.5 mmol) was added. The resulting mixture was stirred at −78° C. for 1 hour, followed by addition of 20 ml saturated $NH_4Cl$ solution. The reaction mixture was extracted with $Et_2O$. The combined organic layers were dried over $MgSO_4$, filtered and concentrated. Flash chromatography of the residue with $CH_2Cl_2$ and ethyl acetate (1:1) gave pure title compound (1.42 g, 5.66 mmol) in 96% yield. $^1H$ NMR ($CDCl_3$) δ:1.02 (3H, t, J=7.2 Hz), 1.26 (3H, t, J=7.2 Hz), 2.11 (3H, s), 3.12 (2H, q, J=7.2 Hz), 3.45 (2H, m), 3.75 (3H, s), 3.79 (3H, s), 6.68 (1H, d, J=8.9 Hz), 6.76 (1H, d, J=8.9 Hz).

Step 3: 3,4-dihydro-5,8-dimethoxy-3-vinylisocoumarin

To a stirred solution of the benzamide from step 2 above (3.51 g, 14.0 mmol) in 140 ml of THF at −78° C. under argon was added n-butyllithium (2.5M, 9.0 ml, 22.5 mmol) dropwise, generating a red solution. After stirred for 30 minutes, acrolein (2.25 ml, 33.6 mmol) was added. The stirring was continued at −78° C. for 1 hour before it was quenched with 100 ml of saturated $NH_4Cl$ solution. The mixture was extracted with $CH_2Cl_2$, and the combined organic layers were washed with $H_2O$, dried over $MgSO_4$, filtered and concentrated to a residue. Without further purification, the residue was dissolved in 180 ml of benzene and then heated to reflux in the presence of camphorsulfonic acid (2.93 g, 12.6 mmol) for 5 days. After cooled to room temperature, 200 ml of $NaHCO_3$ (5%) and 200 ml of $CH_2Cl_2$ were added. The organic layer was washed with $H_2O$, dried over $MgSO_4$, filtered and then concentrated. Flash chromatography of the residue with $CH_2Cl_2$, hexane, and ethyl acetate (2:4:1) provided the title isocoumarin (1.28 g, 5.47 mmol) in 39% overall yield. $^1H$ NMR ($CDCl_3$) d:2.76 (1H, dd, J=16.9, 10.9 Hz), 3.22 (1H, dd, J=16.9, 3.3 Hz), 3.83 (3H, s), 3.91 (3H, s), 4.85 (1H, m), 5.29 (1H, dd, J=10.6, 1.1 Hz), 5.44 (1H, dd, J=17.3, 1.1 Hz), 6.0 (1H, m), 6.88 (1H, d, J=9.1 Hz), 7.06 (1H, d, J=9.1 Hz).

Step 4: 3,4-dihydro-1,5,8-trimethoxy-3-vinylisocoumarin

To a stirred solution of the isocaumarin from step 3 above (9.4 mg, 0.4 mmol) in 8 ml of toluene was added dropwise a solution of DIBAL-H (1M, 0.50 ml, 0.50 mmol) at −78° C. under argon. The resulting mixture was stirred at −78° C. for 1.5 hour before $Na_2SO_4$ 10 $H_2O$ (100 mg, 0.31 mmol). After the reaction was warmed to room temperature, it was filtered to remove the solids, and washed with acetone. The filtrate was evaporated to give an oily residue which contained the corresponding lactol. Without further purification, the residue was treated with 5 ml of $CH_3OH$, 1 ml of $CH(OMe)_3$, and PTSA (30 mg, 0.16 mmol) at room temperature for 10 minutes. The solvents were removed by rotavapor and the residue was purified by flash chromatography with hexane and ethyl acetate (7:3) to give pure title isocoumarin (65 mg, 0.26 mmol) in 65% overall yield. $^1H$ NMR ($CDCl_3$) δ:2.47 (1H, dd, J=17.2, 12.0 Hz), 2.85 (1H, dd, J=17.2, 3.6 Hz), 3.56 (3H, s), 3.78 (3H, s), 3.82 (3H, s), 4.63 (1H, m), 5.24 (1H, dt, J=10.6, 1.4 Hz), 5.43 (1H, dt, J=17.3, 1.4 Hz), 5.63 (1H, s), 6.05 (1H, m), 6.70 (1H, d, J=8.9 Hz), 6.76 (1H, d, J=8.9 Hz).

Step 5: 1-methoxy-3-vinylisochroman-5,8-dione

To a stirred solution of the isocoumarin from step 4 above (30 mg, 0.12 mmol) in 2 ml of $CH_3CN$ was added dropwise a solution of $(NH_4)_2Ce(NO_3)_6$ in 1 ml of $H_2O$ at 0° C. After 5 minutes, the reaction was warmed to room temperature and stirred for another 30 minutes. The reaction mixture was diluted with 10 ml of $CH_2Cl_2$ and 10 ml of $H_2O$. The organic layer was washed with $H_2O$, dried over $MgSO_4$, filtered and then concentrated to a residue that was purified by flash chromatography (hexane/ethyl acetate; 7:3) to provide pure product (15 mg, 0.07 mmol) in 57% yield along with a by-product (10 mg, 0.05 mmol, 40%). The by-product could be converted to desired product in 92% yield by treating it with $CH(OMe)_3$ in MeOH with PTSA at room temperature. $^1H$ NMR ($CDCL_3$) δ: 2.29 (1H, dd, J=19.4, 11.4 Hz), 2.65 (1H, dd, J=19.4, 3.6 Hz), 3.55 (3H, s), 4.52 (1H, m), 5.27

(1H, dd, J=10.5, 1.4 Hz), 5.41 (1H, dd, J=17.3, 1.4 Hz), 5.43 (1H, s), 5.98 (1H, m), 6.74 (1H, d, J=10.2 Hz), 6.78 (1H, d, J=10.2 Hz).

Step 6: 6-hydroxy-1-methoxy-1,2,3,4-tetrahydro-3-vinyl-(2-oxygen) naphthacene-5,12-dione BCH-712

To a stirred solution of i-Pr$_2$NH (0.254 ml, 1.8 mmol) in 6 ml of THF was added a solution of n-BuLi (2.5M, 0.725 ml, 1.8 mmol) at 0° C. under argon. After stirring for 20 minutes, the newly made LDA solution was cooled to −78° C. and stirred for additional 5 minutes. A solution of homophthalic anhydride (294 mg, 1.8 ml) in 4 ml of THF was added dropwise, causing the color change from yellow, green and then to yellowish. Upon stirring for 5 minutes after completion of the addition, a solution of the quinone from step 5 above (332 mg, 1.5 mmol) in 4 ml of. THF was quickly injected. The resulting mixture was stirred at −78° C. for 20 minutes at room temperature for 2 hours and then placed in the fridge overnight. The mixture was quenched with 10 ml saturated NH$_4$Cl solution and partitioned between 1N HCl and CH$_2$Cl$_2$. The organic layer was washed with H$_2$O, dried over MgSO$_4$, filtered and then concentrated to a residue that was purified by flash chromatography with hexane, CH$_2$Cl$_2$, ethyl acetate (2:2:1) to give title compound (276 mg, 0.82 mmol) in 55% yield as a single regioisomer. MP: 150° C. (decomposes). $^1$H NMR (CDCl$_3$) d:2.46 (1H, dd, J=19.2, 11.4 Hz), 2.89 (1H, dd, J=19.4, 3.7 Hz), 3.61 (3H, s), 4.60 (1H, m), 5.30 (1H, dd, J=10.6, 1.3 Hz), 5.45 (1H, dd, J=17.3, 1.4 Hz), 5.63 (1H, s), 6.04 (1H, m), 7.70 (2H, m), 7.95 (1H, d, J=7.4 Hz), 8.11 (1H, s), 8.48 (1H, d, J=7.3 Hz), 13.83 (1H, s); $^{13}$C NMR (CDCl$_3$) δ: 27.80, 56.85, 66.90, 94.11, 117.31, 122.41, 125.43. 128.64, 129.68, 130.42, 131.11, 131.87, 136.63, 137.49, 142.12, 144.99, 163.21, 181.95, 188.66.

Step 7: 6-acetoxy-1-methoxy-1,2,3,4-tetrahydro-3-vinyl-(2-oxygen)naphthacene-5,12-dione BCH-716

To a stirred solution of the tetracyclic quinone from step 6 above (230 mg, 0.68 mmol) in 35 ml of CH$_2$Cl$_2$ were added 7 ml of pyridine, 7 ml of Ac$_2$O, and 123 mg of DMAP (1.00 mmol) at room temperature. The mixture was then stirred for 2 hours before it was poured into a mixture of ice water (20 ml) and CH$_2$Cl$_2$ (20 ml). The organic layer was washed with H$_2$O, 0.1N HCl, dried over MgSO$_4$, filtered and then concentrated to a crude residue that was purified by flash chromatography to give the title compound (178 mg, 0.47 mmol) in 69% yield as yellow solid. MP 228°–229° C., IR (neat) 1208, 1611, 1643, 1667, 1763, 2912 CM$^{-1}$, $^1$H NMR (CDCl$_3$) δ:2.41 (1H, dd, J=19.0, 11.0 Hz), 2.61 (s, 3H), 2.82 (1H, dd, J=19.0, 3.5 Hz), 3.61 (3H, s), 4.58 (1H, m), 5.29 (1H, dd, J=11.0, 1.5 Hz), 5.44 (1H, dd, J=17.0, 1.5 Hz), 5.64 (1H, s), 6.01 (1H, m), 7.72 (2H, m), 8.06 (1H, m), 8.14 (1H, m), 8.59 (1H, s), $^{13}$C NMR (CDCl$_3$) d:21.14, 27.78, 56.22, 93.43, 116.62, 123.77, 127.00, 128.61, 130.01, 130.16, 130.24, 130.31, 135.52, 136.93, 139.80, 145.38, 168.90, 181.70, 182.50.

Step 8: 6-acetoxy-1-hydroxy-1,2,3,4-tetrahydro-3-vinyl-(2-oxygen)naphthacene-5,12-dione BCH-727

To a stirred solution of the tetracycle form step 7 above (16 mg, 42 mmol) in 3 ml of CH$_2$Cl$_2$ was added a solution of B-bromo-9-BBN in CH$_2$Cl$_2$ (1M, 0.105 ml, 105 mmol) at 0° C. under argon. After stirred at 0° C. for 1 h, 3 ml of ice water was added. The reaction mixture was extracted with CH$_2$Cl$_2$, washed with water, dried over MgSO$_4$, filtered, and then concentrated to a crude residue that was purified by flash chromatography (hexane, CH$_2$Cl$_2$, ethyl acetate, 2:2:1) to give title compound (4 mg, 11 mmol) in 26% yield. IR (neat) 1191, 1610, 1640, 1770, 2919, 3440 CM$^{-1}$, $^1$H NMR (CDCl$_3$) δ:2.43 (1H, dd, J=19.0, 11.0 Hz), 2.60 (3H, s), 2.86 (1H, dd, J=19.0, 3.5 Hz), 4.61 (1H, M), 5.28 (1H, dd, J=11.0, 1.5 Hz), 5.42 (1H, dd, J=17.0, 1.5 Hz), 5.62 (1H, br, s), 5.81 (1H, s), 6.00 (1H, m), 7.73 (2H, m), 8.67 (1H, m), 8.14 (1H, m), 8.63 (1H, s).

Example 11

Short synthesis of anthraceno[2,3-c]pyran-3-yl derivatives with an ester side chain

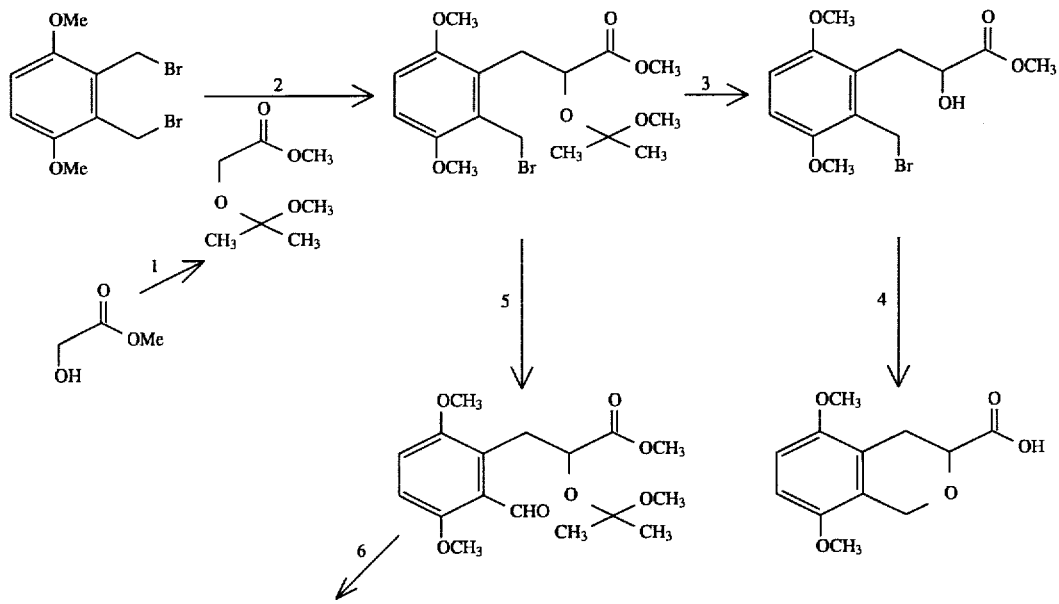

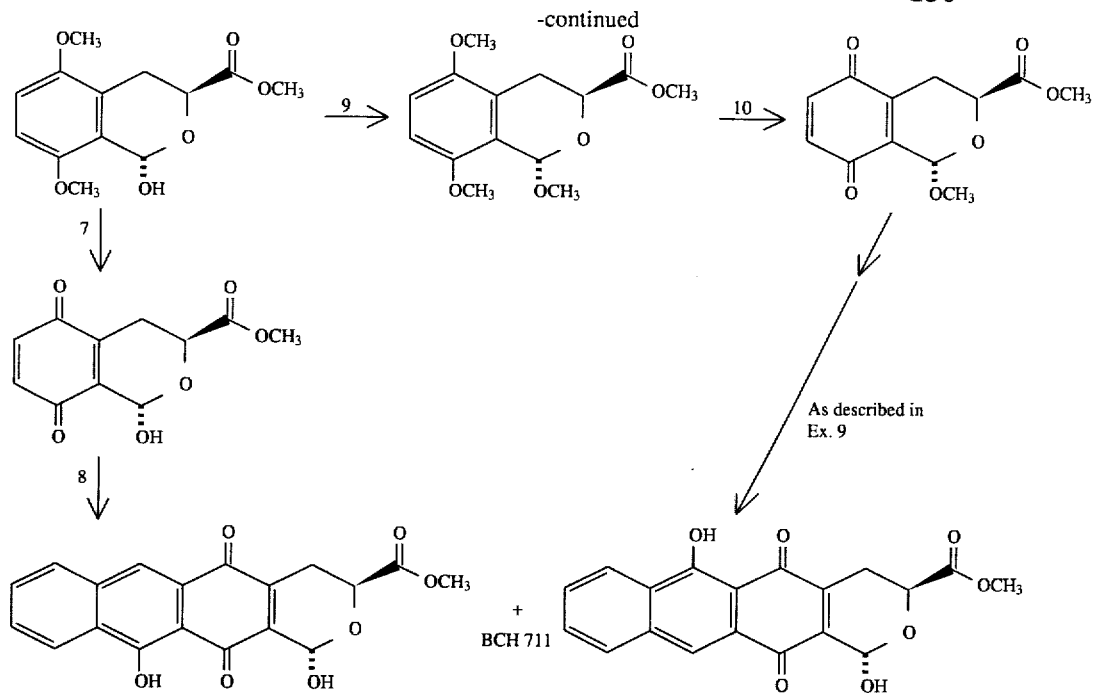

Example 11

Step 1: Methyl 2-methoxyisopropyloxy-acetate

To a stirred solution of methyl glycolate (5 ml, 64.8 mmol) and 2-methoxypropene (12.5 ml, 130.5 mmol) in dry dichloromethane (15 ml) at 0° C. was added catalytic amount of pyridinium p-toluene-sulfonate (100 mg). The mixture was stirred at 0° C. for 2 hours. Saturated sodium bicarbonate solution was added and methylene chloride layer was separated, dried over anhydrous magnesium sulfate. Solvent was evaporated and the product was distilled over anhydrous potassium carbonate under reduced pressure (20 mmHg) at 62°–64° C. (yield=9.9 g, 94%), $^1$H NMR (300 MHz, D$_6$-acetone) d:1.28 (6H, s), 3.15 (3H, s), 3.67 (3H, s), 4.01 (2H, s).

Step 2: Methyl 3-(2'bromomethyl-3'-6'-dimethoxy)phenyl-2-methoxyisopropyloxy propionate To a solution of cyclohexylisopropylamine (1.6 ml, 9.8 mmol) in dry. THF (30 ml) at 0° C. was added 2.5M BuLi in hexanes (3.95 ml, 9.8 mmol). After stirring at 0° C. for 10 minutes, the mixture was cooled to −78° C. The protected methyl glycolate from step 1 (1.59 g, 9.7 mmol) in THF (6 ml) was added. After stirring for 15 minutes at −78° C., 1,2-dibromomethyl-3,6-dimethoxybenzene (1.5 g, 5.1 mmol) in dry THF (16 ml) was added followed by addition of HMPA (2 ml) in 10 minutes. The mixture was stirred at −78° C. for 1 hour. Temperature was then raised to −40° C. slowly during the next 50 minutes. Saturated NH$_4$Cl solution (20 ml) was added, THF was removed at 25° C. and the residue was extracted with ether. Ether extract was washed with sat. NaHCO$_3$, dried over MgSO$_4$, evaporated and the residue was chromatographed over silica gel washed with 5% triethylamine (eluent: hexanes/EtOAc=4:1), yielding 1.37 g (66%) of the title compound. $^1$H NMR (300 MHz, d6-acetone) d:1.05 (3H, s, CH$_3$), 1.15 (3H, s, CH$_3$), 2.78 (3H, s, OMe), 3.01 (1H, dd, J=8.9, 13.5 Hz, H-3), 3.66 (3H, s, CO$_2$Me), 3.83 (6H, s, ArOCH$_3$), 4.43 (1H, dd, J=5.0, 8.8 Hz, H-2), 4.81 (2H, s, ArCH$_2$Br), 3.21 (1H, dd, J=5.1, 13.5 Hz, H-3), 6.88, 6.95 (1H, d, each, J=9 Hz, ArH).

Step 3: Methyl 3-(2'-bromomethyl-3'-6'-dimethoxy)phenyl-2-hydroxy propionate

To a solution of methyl 3-(2'-bromomethyl-3'-6'-dimethoxy)-phenyl- 2-methoxy-isopropyloxy propionate (29 g, 71 mmol) in diethyl ether (40 ml) was added 1N HCl (20 ml). After stirring at ambient temperature for three hours, ether layer was separated, washed with brine, dried over MgSO$_4$ and evaporated to give the title product as an oil in quantitative yield. $^1$H NMR (300 MHz, CDCl$_3$) d:3.10 (1H, dd, J=8.7, 13.9 Hz, H-3), 3.29 (1H, dd, J=13.8, 4.3 Hz, H-3) 3.77 (3H, s, CO$_2$Me), 3.79, 3.83 (3H, s, each, ArOMe), 4.47 (1H, dd, J=8.7, 4.5 Hz, H-2), 4.72 (2H, s, ArCH$_2$), 6.74, 6.80 (1H, d, each, J=9.0 Hz, ArH).

Step 4: 5,8-dimethoxy-isochroman-3-yl-formic acid

To a solution of methyl-3(2'-bromomethyl-3'-6'-dimethoxy)phenyl-2-hydroxy propionate (30 mg, 0.09 mmol) in dry THF (3 ml) was added sodium hydride (60% dispersion in oil, 25 mg, 0.6 mmol). The mixture was stirred at 50° C. for 2.5 hours. Small amount of ice was carefully added, extracted with dichloromethane. Aqueous portion was acidified with dil. HCl, extracted with EtOAc, washed with brine, dried and evaporated (yield ~85%). $^1$H NMR (300 MHz, CDCl$_3$) δ:2.74 (1H, dd, J=11.2, 17.1, H-2, H-4), 3.19 (1H, ddd, J=1.3, 3.8, 17.1 Hz, H-4), 3.74, 3.77 (3H, s, each, OMe), 4.26 (1H, dd, J=3.9, 11.2, H-3) 4.7 (1H, d, J=15.9, H-1), 5.06 (1H, d, J=15.9, H-1), 6.63 and 6.67 (1H, d, each, J=12.2, aromatic protons).

Step 5: Methyl 3-(2'-formyl-3',6'-dimethoxy)phenyl-2-methoxyisopropyloxypropionate Methyl 3-(2'-bromomethyl-3',6'-dimethoxy)phenyl-2-methoxyisopropyloxy propionate (1.2 g, 2.9 mmol) was dissolved in dry DMSO (25 ml) and sodium bicarbonate (622 mg, 7.4 mmol) was added. The mixture was stirred at 95° C. for 45 minutes. It was cooled, quenched with water (125 ml), extracted with ether (3×200 ml). Extracts were washed with brine (25 ml) dried over MgSO$_4$. Solvent was evaporated, yielding 9 g of the title compound (90%). $^1$H NMR data (300 MHz, d$_6$-acetone) d:1.16 (3H, s, CH$_3$), 1.18 (3H, s, CH$_3$), 2.99 (3H, s, OCH$_3$), 3.53 (3H, s, CO$_2$Me), 3.82 (3H, s, ArOH), 3.88 (3H, s, ArOMe), 7.04 (1H, d, J=10.0 Hz, ArH), 7.21 (1H, d, J=10.0 Hz, ArH), 10.50 (1H, s, CHO).

Step 6: Methyl-5,8-dimethoxy-1-hydroxyisochroman-3-yl-formate

To a solution of methyl-3-(2'-formyl-3'-6'-dimethoxy)phenyl-2-methoxyisopropyloxy-propionate (4.2 g, 12.4 mmol) in THF (75 ml) containing water (4 ml) was added pyridinium p-toluenesulfonate (230 mg). After stirring at room temperature for 1.75 hours, triethylamine (3 ml) and saturated NH$_4$Cl solution (60 ml) were added. THF was removed at 25° C. and the mixture was extracted with ether (3×150 ml). Ether extract was washed with brine, dried and evaporated yielding 3.9 g of 1-hydroxyisochroman (95%) (quite pure from NMR spectrum). (MP. 127°–129° C.)

$^1$H NMR (300 MHz, CDCl$_3$) δ:2.69 (1H, dd, J=12.3, 17.6 Hz, H-4), 3.07 (1H, broad peak, OH), 3.13 (1H, dd, J=17.5, 3.8 Hz, H-4), 3.78 (3H, s, CO$_2$Me), 3.82, 3.83 (3H, s, each, ArOMe), 4.91 (1H, dd, J=12.3, 3.8 Hz, H-3), 6.24 (1H, br, s, H-1), 6.71 and 6.77 (1H, d, each, J=8.9 Hz, ArH).

Step 7: 1-Hydroxy-3-carbomethoxy-5,8-dioxoisochroman

To a stirred solution of the isochroman from step 6 above (232 mg, 0.865 mmol) in 10 ml of CH$_3$CN was added a solution of cerium ammonium nitrate (1.422 g, 2.59 mmol) in 7 ml of H$_2$O at 0° C. The reaction mixture was slowly warmed to room temperature and stirred for 15 minutes. After it was quenched with H$_2$O (20 ml), the mixture was extracted with CH$_2$Cl$_2$ (2×50 ml). The combined organic layers were dried over MgSO$_4$, filtered, concentrated to a residue that was found to be pure title compound and used for next reaction without further purification (201 mg, 0.844 mmol, 98%). $^1$H NMR (CDCl$_3$) δ:2.55 (1H, m), 2.95 (1H, dd, J=19.5, 4.0 Hz), 3.15 (1H, br s), 3.84 (3H, s), 4.86 (1H, m), 6.04 (1H, s), 6.79 (2H, m).

Step 8: 3-Carbomethoxy-1,11-dihydroxy-1,2,3,4-tetrahydro-(2-oxygen)naphthacene-5,12-dione 3-Carbomethoxy-1,6-dihydroxy-1,2,3,4-tetrahydro-(2-oxygen)naphthacene-5,12-dione BCH-711

To a freshly made LDA solution (1.7 mmol, 5 ml of THF) at –78° C. was added dropwise a solution of homophathalic anhydride I (189.7 mg, 1.17 mmol) in 4 ml of THF under argon over 15 minutes. After stirring at –78° C. for 5 minutes, a solution of quinone II (1.15 mmol) in 4 ml of THF was injected. Stirring was continued at –78° C. for 1 hour and then at room temperature for 2 hours. After kept in fridge for overnight, the whole mixture was poured into 25 ml of 1N HCl solution. The reaction mixture was extracted with CH$_2$Cl$_2$ (20 ml×3). The combined organic phases were washed with water, dried over MgSO$_4$, filtered and then concentrated to a crude residue that was purified by flash chromatographied to give a mixture of III and IV (1:1, 130.0 mg, 32%). The following spectral data were obtained from the two regioisomeric mixtures. I.R. (neat) 146 g, 1501, 1612, 1658, 1742, 2952, 3428 cm$^{-1}$. $^1$H NMR (CDCl$_3$) δ:2.71 (2H, m), 3.18 (2H, m), 3.18 (2H, m), 3.87 (3H, s), 3.88 (3H, s), 4.92 (2H, m), 6.23 (1H, s), 6.27 (1H, s), 7.71 (4H, m), 7.95 (2H, d, J=7.7 Hz), 8.10 (1H, s), 8.12 (1H, s), 8.46 (2H, d, J=7.6 Hz), 13.75 (1H, s), 13.77 (1H, s).

Step 9: Methyl(1,5,8-trimethoxyisochroman-3-yl)formate

The compound from step 6 above was treated at room temperature with excess trimethyl orthoformate in methanol for twelve hours. A quantitative yield of the titled compound was obtained. $^1$H NMR (300 MHz, CDCl$_3$) δ:2.71 (dd, 1H, J=12.4, 17.3 Hz, HCH<u>a</u>), 3.10 (dd, 1H, J=4.0, 17.3 Hz, HC H<u>e</u>), 3.59 (s, 3H, CO$_2$CH$_3$), 3.79 (s, 3H, OCH$_3$), 3.81 (s, 3H, OCH$_3$), 3.85 (s, 3H, OCH$_3$), 4.80 (dd, 1H, J=4.0, 12.4 Hz, O—CH), 5.71 (s, 1H, O—CH—O), 6.74 (2d, 2H, HC=H).

Step 10: Methyl(1-methoxy-5,8-dioxo-5,8-dihydioisochroman-3-yl)formate

This compound was obtained in 90% yield by using the procedure in step 7, example 9. $^1$H NMR (300 MHz, CDCl$_3$) δ:2.54 (ddd, 1H, J=1.2, 11.7, 19.5 Hz, HCH<u>a</u>), 2.88 (dd, 1H, J=4.1, 19.5 Hz, HCH<u>e</u>), 3.53 (s, 3H, CO$_2$CH$_3$), 3.57 (s, 3H, OCH$_3$), 4.10 (dd, 1H, J=4.1, 11.7 Hz, OCHO), 5.49 (s, 1H, O—CH—O), 6.75 (2d, 2H, HC=CH).

Example 12

Alternative approaches to isochroman and isothiochroman derivatives

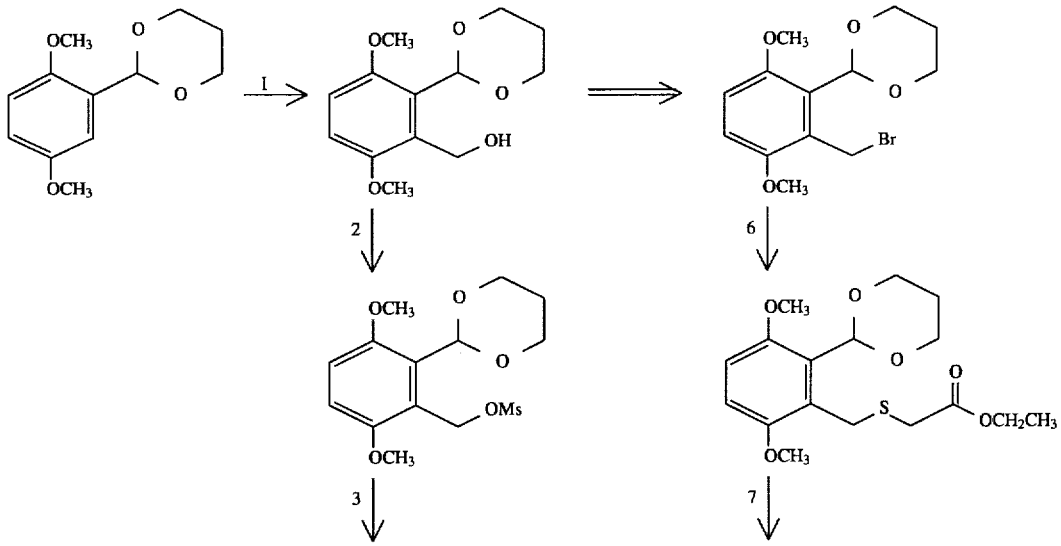

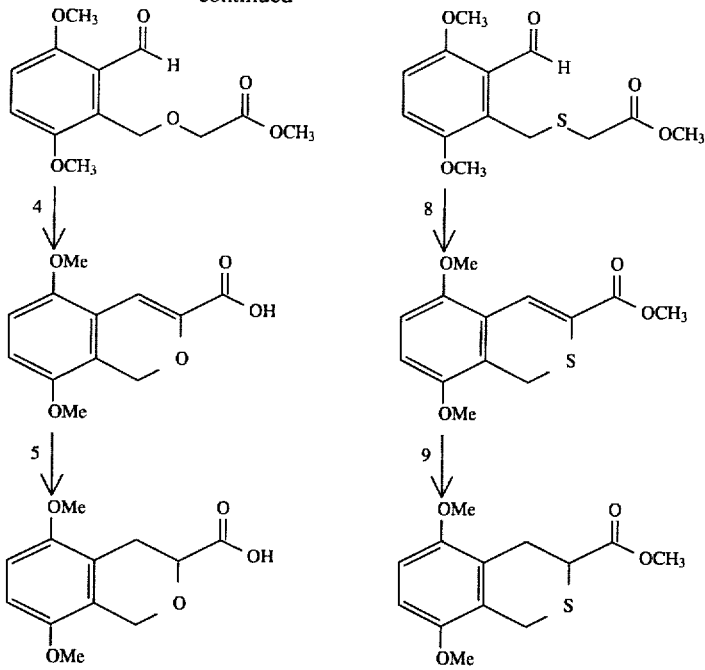

Example 12

Step 1: 2,5-dimethoxy-6-hydroxymethyl benzaldehyde dioxane acetal

To a solution of 2,5-dimethoxybenzaldehyde dioxane acetal (10.5 g, 46.9 mmol) in dry ether (200 ml) at −10° C. was added 2.5M BuLi (30 ml, 75 mmol). The mixture was stirred at −7° C. for 5.5 hours. Dry paraformaldehyde (2.6 g) was quickly added and the mixture was stirred at 0° C. for 2 hours. It was stirred at room temperature overnight, poured into saturated NH$_4$Cl solution and diluted with ether. Ether-layer was separated, washed with brine (50 ml), dried over MgSO$_4$ and evaporated. The crude product was chromatographed over silica gel with CH$_2$Cl$_2$ and EtOAc as eluent (7:1) yielding pure product (5.5 g, 46%) as an oil. $^1$H NMR (300 MHz, CDCl$_3$) d:2.30 (2H, m, CH$_2$ of dioxane acetal), 3.23 (1H, t, J=6.8 Hz, CH$_2$OH), 3.78, 3.80 (3H, s, each, —OMe), 3.98 (2H, m, CH$_2$ of dioxane acetal), 4.26 (2H, dd, J=4.6, 11.3 Hz, CH$_2$ of dioxane acetal), 5.03 (2H, d, J=6.8 Hz, CH$_2$OH), 6.21 (1H, s, methine proton of dioxane acetal), 6.77, 6.86 (1H, d each, J=10 Hz, ArH).

Step 2: 2,5-dimethoxy-6-mesyloxymethylbenzaldehyde dioxane acetal

To a solution of 2,5-dimethoxy-6-hydroxymethylbenzaldehyde dioxane acetal (19.8 g, 78 mmol) in dry CH$_2$Cl$_2$ (225 ml) at 0° C. was added triethylamine (22 ml, 156 mmol) and methanesulfonyl chloride (9 ml). The mixture was stirred at 0° C. for 2 hours. Saturated NH$_4$Cl solution (50 ml) was slowly added. CH$_2$Cl$_2$ layer was separated, washed with water (25 ml) and brine (25 ml) dried over MgSO$_4$, evaporated (25 g, 96%). MP: 87°–90° C., $^1$H NMR (300 MHz, CDCl$_3$) d:3.22 (3H, S, —OSO$_2$Me), 3.77, 3.80 (3H, s, each, OMe), 3.95 (2H, m, CH$_2$ of dioxane acetal), 4.24 (2H, dd, J=4.6, 11.3 Hz, CH$_2$ of dioxane acetal), 5.77 (2H, s, C H$_2$-OMS), 6.18 (1H, s, Methine proton of dioxane acetal), 6.88 (2H, tightly bored, aromatic), 2.35 (2H, m, CH$_2$ of dioxane acetal).

Step 3: Methyl-2-(2'formyl-3',6'-dimethoxy benzyloxy)acetate

A mixture of methyl glycolate (3.2 ml, 41 mmol) and sodium methoxide in methanol (4.37M solution, 7.3 ml, 32 mmol) was held at 50° C. for 4.5 hours under nitrogen. Methanol was removed, and dry DMSO (5 ml) was added. The mixture was cooled to 10° C. The mesylate (4.9 g, 14.9 mmol) from step 2 in DMSO (50 ml) was added slowly, and the mixture was stirred at room temperature overnight. Ice (~50 g) was added and the mixture was extracted with ether (200 ml×3), washed with water (30 ml), dried and evaporated. The residue was dissolved in ether (100 ml) and 50 ml 1N HCl was added. The mixture was stirred at room temperature for 1.5 hour. Ether layer was separated, washed with brine (20 ml), dried and evaporated. Crude product was chromatographed over silica gel (hexanes/ethyl acetate: 2:1 as eluent), yielding 1.89 of pure product (45%). (MP: 177°–179° C.). 1H NMR data (300 MHz, CDCl$_3$) d3.73, 3.81, 3.84 (3H, s, each, OMe), 4.16 (2H, s, C H$_2$—CO$_2$CH$_3$), 4.97 (2H, s, benzylic CH$_2$), 6.94, 7.08 (1H, d, each, J=9.2 Hz, aromatic protons), 10.58 (1H, s, —CHO).

Step 4: 3,4-dihydro-5,8-dimethoxy-isochroman-3-yl-formic acid

A mixture of sodium (280 mg, 12.2 mmol) and dry toluene (15 ml) was heated to reflux under nitrogen. Methyl 2-(2'-formyl-3',6'-dimethoxy benzyloxy) acetate (1.26 g, 4.7 mmol) in toluene (15 ml) was added dropwise. The mixture was held under reflux for 5 hours, cooled, and then transferred slowly into methanol (10 ml). Methanol was removed. THF (25 ml) and 2N NaOH (25 ml) were added, the mixture was stirred for 1.5 h at room temperature. THF was removed, extracted with CH$_2$Cl$_2$ (50 ml). Aqueous portion was acidified with dil. HCl, extracted with ethyl acetate (2×150 ml) washed with brine (25 ml) dried and evaporated. Crude product in CH$_2$Cl$_2$ (25 ml) was treated with p-toluenesulfonyl chloride (500 mg) pyridine (1 ml) overnight at 5° C. Product obtained after usual work-up was heated with pyridine (5 ml) at 120° C. for 3 hours. The mixture was cooled diluted with water, neutralised with 3N HCl, extracted with ethyl acetate (3×50 ml). Solvent was removed and the product was dissolved in CH$_2$Cl$_2$ (50 ml). It was extracted with 10% NaHCO$_3$ (2×25 ml). The aqueous extract was acidified with dil. HCl, extracted with EtOAc (2×75 ml) washed with brine, dried and evaporated yielding fairly pure solid product (300 mg, 27%). NMR (300 MHz, CDCl$_3$) δ:3.77, 3.79 (3H, s, each, OMe), 5.26 (2H, s, benzylic CH$_2$), 6.71, 6.77 (1H, d, each, J=9.1 Hz, aromatic proton), 7.32 (1H, s, olefinic proton).

Step 5: 5,8-dimethoxy-isochroman-3-yl-formic acid

To a solution of isochroman (5 mg, 0.02 mmol) in dry methanol (5 ml) magnesium turnings (10 small pieces) were added gradually (one at a time) over 4 hours. The mixture was stirred overnight, acidified with dil. HCl. Methanol was removed and extracted with ether. Ether extract was washed with brine, dried and evaporated. The residue (1 mg) showed identical NMR spectrum as that of 5,8-dimethoxy-isochroman-3-yl-formic acid. (MP: 164°–166° C.).

Step 6: Ethyl(1-formyl-trimethyleneacetal-3,6-dimethoxy) benzylthioacetate

To a stirred solution of 2-bromomethyl-3,6-dimethoxyben-zaldehyde trimethylene acetal (650 mg, 2.05 mmol) were added a solution of 2-mercaptoacetate (0.25 ml, 2.28 mmol) in 2 ml of CH$_3$OH and a solution of NaOMe (4.37M in CH$_3$OH, 0.47 ml, 2.05 mmol) at 0° C. under argon. The resulting mixture was slowly warmed to room temperature and stirred for 6 hours. 20 ml of H$_2$O and 100 ml of Et$_2$O were added. The aqueous layer was extracted with ether (3×20 ml). The combined organic layers were washed with H$_2$O, dried over MgSO$_4$, filtered and then concentrated to a residue which was found to be almost pure title product and used for next reaction without further purification.

Step 7: Methyl(1-formyl-3,6-dimethoxy)benzylthioacetate

The reaction residue from step 6 above was dissolved in 20 ml of ether and 15 ml of 1N HCl solution. After stirred at room temperature for 2 hours, the organic layer was separated, washed with 5% NaHCO$_3$ solution, dried, filtered and then concentrated. Flash chromatography of the residue with hexane and ethyl acetate (7:3) provided title product (474 mg, 1.67 mmol) in 81% overall yield for two steps. $^1$H NMR (CDCl$_3$) δ:3.32 (s, 2H), 3.72 (s, 3H), 3.82 (s, 3H), 3.87 (s, 3H), 4.29 (s, 2H), 6.89 (1H, d, J=9.0 Hz), 7.08 (1H, d, J=9.0 Hz), 10.60 (1H, s); $^{13}$C NMR (CDCl$_3$) δ:26.45, 34.47, 52.57, 56.54, 56.70, 111.46, 117.70, 123.71, 130.34, 152.11, 157.96, 171.74, 193.12.

Step 8: 3,4-dihydro-3-carbmethoxy-5,8-dimethoxyisothiochroman

To a stirred solution of the aldehyde from step 7 above (400 mg, 1.4 mmol) in 30 ml of benzene was added NaOMe powder (152 mg, 2.8 mmol). The resulting mixture was heated to reflux for 3 hours. The solid was removed by filtration, washed with benzene. The filtrate was evaporated to a residue that was purified by flash chromatography to give the title compound (166.1 mg, 0.63 mmol) in 45% yield along with recovered starting material (83 mg, 20%). $^1$H NMR (CDCl$_3$) δ:3.82 (s, 3H), 3.83 (s, 3H), 3.87 (s, 3H), 3.94 (s, 2H), 6.73 (1H, d, J=9.0 Hz), 6.91 (1H, d, J=9.0 Hz), 8.14 (1H, s); $^{13}$C NMR (CDCl$_3$) δ:23.81, 52.74, 56.30, 56.47, 109.96, 114.13, 119.38, 123.36, 128.30, 128.97, 149.68, 151.45, 166.17.

Step 9: 3-carbomethoxy-5,8-dimethoxyisothiochroman

To a stirred solution of the isothiochroman from step 8 above (129 mg, 0.48 mmol) in 20 ml of MeOH was added about 50 mg of magnesium chips. The reaction mixture started bubbling after 20 minutes induction period at room temperature in water bath. Magnesium chips were added until all the starting material consumed. 10 ml of Nat. NH$_4$Cl solution, 10 ml of H$_2$O, and 50 ml of ether were added. The organic layer was separated, washed with H$_2$O, dried over MgSO$_4$, filtered and concentrated to a crude residue that was purified by flash chromatography to give the title compound (105 mg, 0.39 mmol) in 82% yield. The spectral data of title compound were found to be identical with the compound obtained in step 1, Example 8.

Example 13

Preparation of other key isochromandiones useful in the synthesis of various heteroanthracyclinones

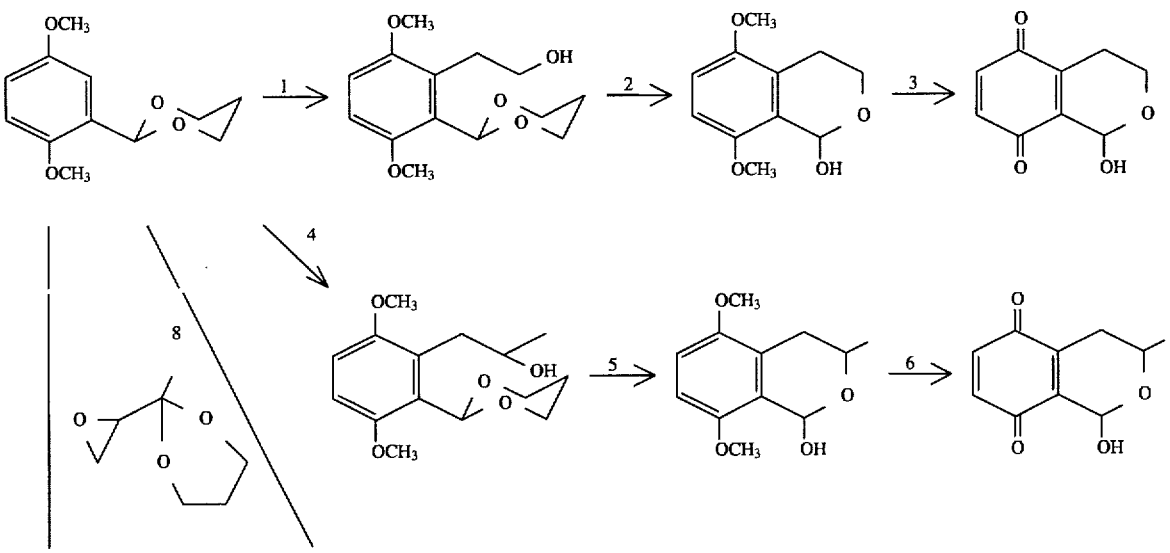

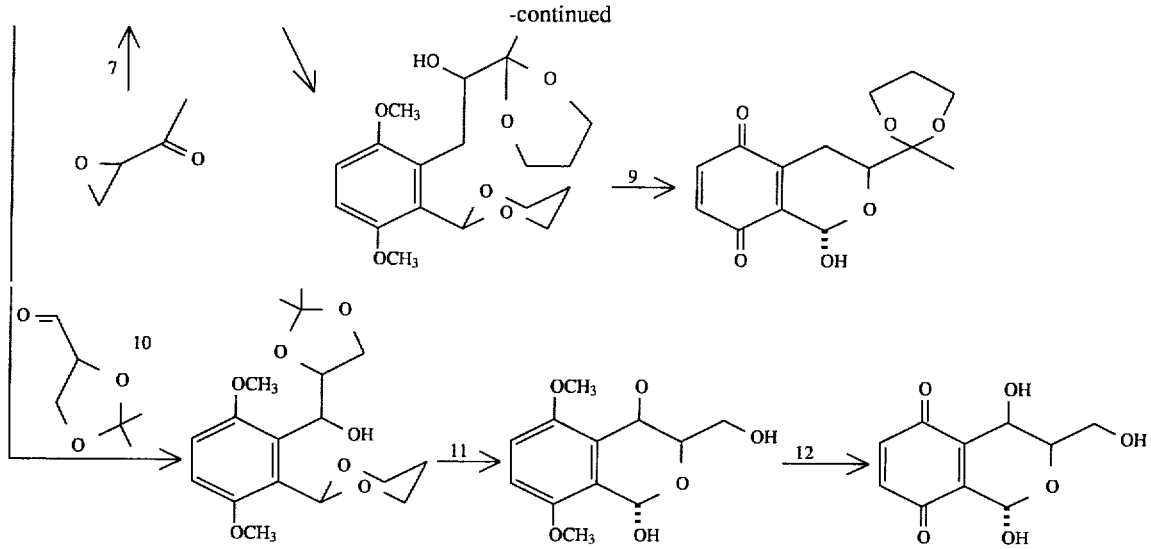

Example 13

Step 1: 2,5-dimethoxy-6-hydroxyethylbenzaldehydedioxane acetal

To a cooled (–40° C.) solution containing 1.68 g (7.4 mmol) of 2,5-dimethoxybenzaldehydedioxane acetal in 50 ml of anhydrous diethylether was added, with stirring and under argon, 4.8 ml of a 2.5M n-butyl lithium in hexanes solution. The mixture was stirred for five hours at –5° C., 537 mg (6.0 mmol) of CuCN was then added, and stirring was continued for one more hour. To the mixture was then added 1.0 g of ethylene oxide and stirred overnight at 4° C. The mixture was then washed with 20 ml of water, 20 ml of saturated aqueous sodium chloride and dried over MgSO$_4$. Flash chromatography of the residue obtained after removal of solvent gave 547 mg (27% yield) of 2,5-dimethoxy-6-hydroxyethylbenzaldehyde dioxane acetal as a white solid. MP: 135°–136° C. $^1$H NMR (200 MHz, CDCl$_3$) d:1.48 (bd, 1H, J=13.6 Hz, HCHe), 2.32 (m, 1H, HCHa), 3.48 (dr, 2H, J=4.76, 12.0 Hz, ArCH$_2$), 3.79 (s, 6H, 2XOCH$_3$), 3.86–4.08 (overlapped m, 4H, 2XOHCHe and CH$_2$OH), 4.29 (m, 2H, 2XOHCHa), 6.28 (s, 1H, O—CH—O), 6.79 (dd, 2H, J=9.0 Hz, ArH). CMR (75.44 MHz, CDCl$_3$) δ:25.9, 29.5, CH$_2$; 55.7, 56.3, OCH$_3$; 62.3, CH$_2$OH; 67.9, 2XOCH$_2$; 97.6, O—CH—O; 109.5, 111.8, aryl CH; 126.3, 129.2, 150.8, 152.8, aryl C. IR (FT, CDCl$_3$) ʋMax: 3350, 3550, bs, OH; 1257, 1089, C—O. HRMS calculated for C$_{14}$H$_{20}$O$_5$: [M$^+$] 268.1311 found 268.1316.

Step 2: 5,8-Dimethoxy-1-hydroxyisochroman

A solution containing 150 mg (0.56mmol) of 2,5-dimethoxy-6-hydroxyethylbenzaldehydedioxane acetal in 5 ml of THF was stirred for one hour at room temperature with 5 ml of 0.2M aqueous HCl. The mixture was then diluted with 25 ml of dichloromethane, washed successively with 25 ml aliquots of aqueous sodium bicarbonate, water, brine and then dried over MgSO$_4$. Flash chromatography of the residue obtained after removal of solvent gave 97 mg (82% yield) of the titled 1-hydroxyisochroman. (MP: 217°–219° C.). $^1$H NMR (200 MHz, CDCl$_3$) δ:2.73 (m, 2H, CH$_2$), 3.09 (bs, 1H, exchangeable, OH), 3.84 (s, 3H, OCH$_3$), 3.88 (s, 3H, OCH$_3$), 4.03 (m, 1H, OHCH), 4.27 (m, 1H, OHCH), 6.12 (bs, 1H, OCH), 6.77 (dd, 2H, J=7.2 Hz, ArH). CMR (75.44 MHz, CDCl$_3$) δ:22.2, CH$_3$; 55.5, 55.7, OCH$_3$; 56.8, OCH$_2$; 87.4, OCH; 107.9, 109.4, aryl CH; 124.2, 124.8, 150.4, 150.6, aryl C. IR (FT, CDCl$_3$) ʋMax: 3650, bs, OH; 1260, C—O. HRMS calculated for C$_{11}$H$_{14}$O$_4$: [M$^+$] 210.0892 found 210.0871.

Step 3: 1-Hydroxy-5,8-dioxo-5,8-dihydroisochroman

To a stirred solution containing 75 mg (0.36 mmol) of 5,8-dimethoxy-1-hydroxyisochroman from step 2 above in 2 ml of THF was added dropwise over four minutes, a solution containing 546 mg (1.0 mmol) of ceric ammonium nitrate in 2 ml of water. The mixture was stirred for five minutes and then diluted with 10 ml of dichlorome-thane. The separated organic phase was washed with 5 ml of water, 5 ml of brine and dried over MgSO$_4$. Following evaporation of solvent, the yellow oil (62 mg, 96% yield) was found to be pure isochromandione. 1H NMR (200 MHz, CDCl$_3$), δ:2.54 (m, 2H, CH$_2$), 3.51 (d, 1H, J=4.4 Hz, exchangeable, OH), 4.09 (m, 2H, OCH$_2$), 5.88 (d, 1H, J=4.4 Hz, O—CH—O), 6.79 (dd, 2H, J=10.1 Hz, H—C=C—H). CMR (75.44 Mhz, CDCl$_3$) δ:21.5, CH$_2$; 56.4, OCH$_2$; 85.3, OCH; 136.3, 136.4, aryl CH; 138.4, 141.3, CH; 185.3, 186.4, quinone C=O.

Step 4: 2,5-Dimethoxy-6-(2-hydroxypropyl)benzaldehydedioxane acetal

Application of the procedure described in step 1 of this example gave 238 mg (32% yield) of the desired benzaldehydedioxane acetal from 739 mg (3.3 mmol) of 2,5-dimethoxybenzaldehydedioxane acetal and excess propylene oxide, after flash chromatography from 5% ethyl acetate in toluene. (MP: 160°–161° C.). $^1$H NMR (300 MHz, CDCl$_3$) δ:1.33 (d, 3H, J=6.1 Hz, CH$_3$), 1.49 (bd, 1H, J=13.7 Hz, HCHe), 2.30 (m, 1H, HCHa), 3.10 (dd, 1H, J=2.4, 14.1 Hz, HCH), 3.47 (dd, 1H, J=9.5, 13.9 Hz, HCH), 3.78 (s, 6H, OCH$_3$), 4.02 (overlapped m, 3H, HO—CH and 2XHC He—O), 4.30 (m, 2H, 2XCH$_2$—O), 6.27 (s, 1H, O—CH—O), 6.78 (dd, 2H, J=9.0 Hz, ArH). CMR (75.44 MHz, CDCl$_3$) δ:25.1, CH$_3$; 25.8, 35.7, CH$_2$; 55.6, 56.3, OCH$_3$; 67.5, CHOH; 67.6, 67.7, OCH$_2$; 97.4, O—CH—O; 109.4, 111.7, aryl CH; 125.9, 129.3, 150.7, 152.7, aryl C. HRMS calculated for C$_{15}$H$_{22}$O$_5$: [M$^+$]282.1467 found 282.1449. IR (FT, CDCl$_3$) ʋMax: 3300–3550, bs, OH; 1257, 1094, C—O.

Step 5: 5,8-Dimethoxy-1-hydroxy-3-methylisochroman

Application of the procedure described in step 2 of this example gave 215 mg (86% yield) of the 3-methyl substituted isochroman from 250 mg of 2,5-dimethoxy-6-(2-hydroxypropyl)benzaldehydedioxane acetal after flash chromatography with 20% ethyl acetate in hexanes. (MP: 240°–241° C.). $^1$H NMR (200 MHz, CDCl$_3$) δ:1.41 (d, 3H, J=6.2 Hz, CH$_3$), 2.34 (dd, 1H, J=11.4, 17.4 Hz, HC<u>Ha</u>), 2.81 (dd, 1H, J=3.25, 17.3 Hz, HC<u>Hc</u>), 3.02 (d, 1H, exchangeable, J=3.4 Hz, OH), 3.81 (s, 3H, OCH$_3$), 3.85 (s, 3H, OCH$_3$), 4.37 (m, 1H, OCH), 6.12 (d, 1H, J=3.3 Hz, O—CH—O), 6.74 (dd, 2H, J=8.9 Hz, ArH). CMR (75.44 MHz, CDCl$_3$): 21.3, CH$_3$; 29.8, CH$_2$; 55.7, 55.8, OCH$_3$; 62.6, O—CH; 88.6, O—CH—O; 107.9, 109.5, aryl CH; 124.6, 150.47, 150.53, aryl C. IR (FT, CDCl$_3$) ʋMax: 3630, bs, OH; 1260, C—O. HRMS calculated for C$_{12}$H$_{16}$O$_4$: [M$^+$]224.1049 found 224.1036.

Step 6: 1-Hydroxy-5,8-dioxo-3-methyl-5,8-dihydroisochroman

Oxidative demethyllation of 336 mg (1.5 mmol) of 5,8-dimethoxy-1-hydroxy-3-methylisochroman with 2.94 g (5 mmol) of ceric ammonium nitrate as described in step 3 of this example gave 262 mg (90% yield) of isochromandione as a yellow oil. $^1$H NMR (200 MHz, CDCl$_3$) δ:1.38 (d, 3H, J=6.3 Hz, CH$_3$), 2.15 (ddd, 1H, J=1.2, 11.0, 19.5 Hz, HC <u>Ha</u>), 2.62 (dd, 1H, J=3.3, 19.5 Hz, HC<u>He</u>), 3.16 (d, 1H, J=4.3 Hz, exchangeable, OH), 4.31 (m, 1H, O—C<u>H</u>CH$_3$), 5.91 (d, 1H, J=4.3 Hz, O—CH—O), 6.78 (dd, 2H, J=10.2 Hz, ArH).

Step 7: 1,2-oxiranebutane-3-one dioxane ketal

In a three neck, round bottom flask (29.776 g, 0.35 mmol) 1,2-oxiranebutane-3-one, which had been previously obtained following House's procedure (Organic synthesis Vol. III, p. 552), was mixed with 1,3-propanediol (118 ml, 1.59 mmol) and benzene (350 ml). To this mixture pyridinium tosylate was added (8.49 g, 0.033 mmol). The mixture was refluxed, with water separation by a Dean-Stark trap, until the starting ketone has been completely used. The solution was washed twice with saturated sodium hydrogen carbonate solution, once with saturated sodium chloride solution, the organic phase was dried over sodium sulfate, and the bulk of the solvent was evaporated. The remaining mixture was distilled under reduced pressure to give the pure protected epoxy ketone in 22% yield. (BP: 20 mmHg, 75° C.). $^1$H NMR (300 MHz, CDCl$_3$) ppm: 1.28 (s, 3H, CH$_3$), 1.60 (multiplet, 2H, dioxane ring), 2.61 (dd, 1H, HCH—O—CH), 2.66 (dd, 1H, HCH—O—CH), 3.00 (t, 1H, HCH—O—C<u>H</u>), 3.91 (multiplet, 4H, dioxane ring). $^{13}$C NMR (75.44 MHz, CDCl$_3$) ppm: 19.80 (CH$_3$, R$_3$C—CH$_3$), 25.42 (CH$_2$, —O—CH$_2$—<u>C</u>H$_2$—CH$_2$—O—), 43.27 (CH$_2$, <u>C</u>H$_2$—O—CH—), 56.46 (CH$_2$—O—CH), 60.84 (CH$_2$,—O—<u>C</u>H$_2$—CH$_2$—CH$_2$—O—), 61.15 (CH$_2$, —O—CH$_2$—<u>C</u>H$_2$—<u>C</u>H$_2$—O—), 96.65 (quaternary C, CH$_3$C(O(CH$_2$)$_3$O). IR (FT, CDCl$_3$) cm$^{-1}$: 1494 (multiple bands, CH$_2$—O, oxirane ring. HRMS Clcd for C$_7$H$_{12}$O$_3$: [M$^+$]=144.0786 found 144.0746.

Step 8: 1,4-dihydroxy-3-(ethane-1-one-dioxaneketal)-5,8-dimethoxy isochroman

A solution of 2.5M n-butyllithium (4.01 mmol) is added under argon at −15° C., to a stirred solution of 0.5 g of 2,5-dimethoxy benzaldehyde dioxane acetal (2.23 mmol) in 20 ml of anhydrous ether and stirred for 5 hours at −7° C. At this point, 1.48 ml of BF$_3$ etherate (12.04 mmol) are added to 0.868 g of 1,2-oxiranebu-tane-3-one dioxane ketal (6.02 mmol) at −78° C., with stirring. To this new mixture is added the lithio salt just formed. The reaction is left stirring at −78° C. overnight. Then the mixture is quenched with 20 ml of HH$_4$Cl sat. Ether is added and the phases are separated. The organic layer is washed twice with 75 ml of water. Once with NaCl sat. and dried over MgSO$_4$. Flash chromatography of the residue obtained gave the desired isochroman (13% yield). $^1$H NMR (300 MHz, CDCl$_3$) ppm: 1.54 (s, 3H, CH$_3$), 1.58 (multiplet, 1H, —O—CH$_2$—Ha <u>C</u>H—CH$_2$—O—), 1.88 (multipict, 1H, —O—CH$_2$—H C<u>H</u>e—CH$_2$—O—), 2.71 (dd, 1H, H<u>C</u>H—CH(OH)), 2.78 (dd, 1H, <u>H</u>CH—CH—O), 3.76 (broad s, 6H, 2X O$_3$CH$_3$), 3.95 (multiplet, 4H, —O—<u>C</u>H$_2$—CH$_2$—<u>C</u>H$_2$—O—), 5.75 (s, 1H, dioxane ring), 6.70 (dd, 2H, ArH). $^{13}$C NMR (75.44 MHz, CDCl$_3$) ppm: 21.53 (—C—<u>C</u>H$_3$) ppm: 21.53 (—C—<u>C</u>H$_3$), 25.33 (O—CH$_2$—<u>C</u>H$_2$—CH$_2$—O—), 55.66, 56.10 (O—CH$_2$—CH$_2$—<u>C</u>H$_2$—O—), 59.99 (CH$_2$—CH—O), 63.43, 68.21 (O—<u>C</u>H$_3$), 76.56 (CH$_2$—<u>C</u>H—O), 94.16 (CH—OH), 99.11 (C-quaternary, dioxane ring), 108.60, 109.86 (CH, aromatic). IR: (FT, CDCl$_3$) cm$^{-1}$: 3670 (OH).

Step 9: 1-hydroxy-3-(ethane-1-one dioxane ketal)-5,8-dioxo-5,8-dihydroisochroman A solution of 63.59 g ceric ammonium nitrate (1.16×10$^{-4}$ mmol) in 1 ml of H$_2$O is added dropwise to a stirred solution of 12 mg of 1-hydroxy-3-(ethane-1-one dioxane ketal)-5,8-dimethoxy isochroman (3.87×10$^{-5}$ mmol) in 1 ml of acetonitrile, at room temperature. After 8 minutes, the mixture is diluted with 10 ml of CH$_2$Cl$_2$. The layers are separated. The aqueous layer is extracted twice with CH$_2$Cl$_2$ and the organic layers are washed twice with water, once with NaCl sat., and dried over MgSO$_4$. The residue obtained after evaporation of solvent gave a mixture of compounds including the desired quinone. IR: (FT CDCl$_3$) cm$^{-1}$: 3600–3700 (broad OH), 1664.1 (C=O, stong band, quinone).

Step 10: 2,5-dimethoxy-6-(1-hydroxy-2,3-isopropylidenepropane) benzaldehyde dioxane acetal A solution of 2.5M n-butyllithium (4.014 mmol) is added under argon at −15° C., to a stirred solution of 0.5 g of 2,5-dimethoxy benzaldehyde dioxane acetal (2.23 mmol) in 20 ml of anhydrous ether and stirred for 5 hours at −7° C. To this mixture is added 0.78 g of isopropylidene-D-glyceraldehyde (6.02 mmol) at −78° C. Isopropyli-dene was previously prepared using David Y. Jackson's procedure (Synthetic Communications, 18(4), 337, 1988). The new mixture is warmed up to room temperature and left reacting overnight. Ether is added and the solution is washed twice with H$_2$O, once with NaCl sat., and dried over MgSO$_4$. Flash chromatography of the residue obtained after evaporation of the solvent gave the desired product. $^1$H NMR (300 MHz, CDCl$_3$) ppm: 1.35 (multiplet, 1H, —O—CH$_2$—Ha <u>C</u>H—CH$_2$—O—), 1.42 (broad s, 3H, CH$_3$), 1.50 (broad s, 3H, CH$_3$), 2.25 (multiplet, 1H, —O—CH$_2$—H C<u>H</u>e—CH$_2$—O—), 3.76, 3.79 (2 s, 6H, O—CH$_3$), 3.90 (multiplet, 4H, —O—<u>C</u>H$_2$—CH$_2$—<u>C</u>H$_2$—O—), 4.24 (2 dd, 2H, CH$_2$ group on isopropylidene), 4.85 (q, 1H, CH group on isopropylidene), 5.76 (t, 1H, —CH(OH)), 6.21 (s, 1H, dioxane ring) 6.81 (dd, 2H, aromatic). IR: (FT, neat) cm$^{-1}$: 3400 (OH, broad band). HRMS Clcd for C$_{18}$H$_{26}$O$_7$: [m$^+$] =354.1678 found 354,1670.

Step 11: 1,4-dihydroxy-3-hydroxymethyl-5,8-dimethoxy-isochroman

Treatment of 2,5-dimethoxy-6-(1-hydroxy-2,3-isopropylidene-propane) benzaldehyde dioxaneacetal with silica gel gave the desired isochroman (23% yield). $^1$H NMR (300 MHz, CDCl$_3$) ppm: 3.48 (dd, 1H, CH(OH)—CH—HC—OH), 3.81, 3.86 (2 s, 6H, O—CH$_3$), 4.03 (t, 1H, —CH(OH)—CH—HCH—OH), 4.51 (broad d, 1H, —CH—(OH)—CH—CH$_2$OH), 4.89 (dd, 1H, (OH)CH—<u>C</u>H—CH$_2$OH), 6.50 (s, 1H, —<u>C</u>H—O—CH—CH$_2$OH), 6.81 (dd, 2H, aromatic). $^{13}$C NMR (75.44 MHz, CDCl$_3$) ppm: 56.11 (—CH$_2$OH), 56.39 (OH)CH(O)—CH—CH$_2$OH) , 63.64, 66.07 (2×O —CH$_3$), 76.92 ((OH)CH—CH—CH$_2$OH), 95.13 ((OH)<u>C</u>H—O—CH—CH$_2$OH), 111.40, 11.75 (CH, aromatic), 122.02, 125.36 (C, aromatic; attached to pyranyl ring), 149.80, 152.36 (C, aromatic; bearing a methoxy group). IR: (FT, neat) cm$^{-1}$: 3520 (OH, not too intensed due to hydrogen bonding.) HRMS Clcd for C$_{12}$H$_{14}$O$_5$: (M$^+$-H$_2$O)=238.0841 found 238.0871.

147

Step 12: 1,4-dihydroxy-3-hydroxymethyl-5,8-dioxo-3,4,5,8-tetrahydrobenzo(2,3c)pyran

A solution of ceric ammonium nitrate ($1.40 \times 10^{-4}$ mmol) in 1 ml of $H_2O$ is added dropwise to a stirred solution of 12 mg of 1,3-dihydroxy-3-hydroxymethyl-5,8-dimethoxy isochroman in 2 ml of acetonitrile, at room temperature. The reaction is followed by TLC; the product migrates at same height as the starting material, but is much more U.V. active than the starting material and therefore can be differentiated. After about 10 minutes of stirring, the reaction is over. $CH_2Cl_2$ (10 ml) is added, and the layers are separated. The aqueous layer is extracted twice with $H_2O$, once with NaCl sat., and dried over $MgSO_4$. The residue obtained after evaporation of the solvents gave the desired isochroman (628 yield) (MP: 138°–140° C.). $^1H$ NMR (300 MHz, $CDCl_3$) ppm: 3.44 (dd, 1H, J=8.43, 2.08 Hz, CH(OH)—

148

CH—CH(OH)), 4.04 (dd, 1H, J=8.38, 6.70 Hz, CH(OHO—O—CH—HCH(OH)), 4.32 (broad s, 1H, —CH(OH)—CH—CH$_2$(OH)), 4.87 (ddd, 1H, J=6.55, 2.16, 1.21 Hz, (OH) CH—CH—CH$_2$ (OH)), 6.20 (broad s, 1H, (OH)CH—O—CH—CH$_2$(OH)), 6.80 (dd, 2H, aromatic). IR: (FT, CDCl$_3$) cm$^{-1}$: 3600–3650 (OH, medium band), 1670.7 (C—O, quinone).

Example 14

Preparation of pyrano and thiopyrano modified anthracyclinones from 2,3-dimethyl quinizarine

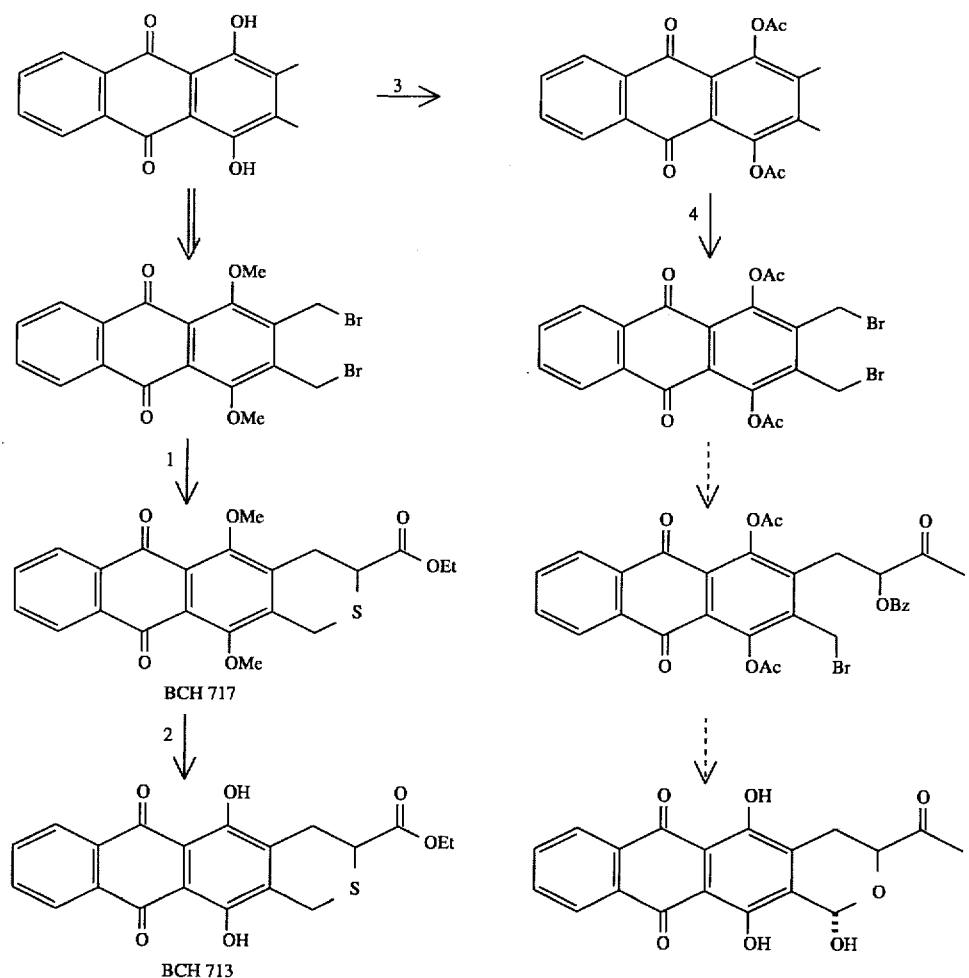

Example 14

Step 1: 5,12-dimethoxy-3-carbomethoxy-1,2,3,4-tetrahydro-(2-sulfur)naphtacene-6,11-dione BCH-717

1,4-Dimethoxy-2,3-dibromomethyl-anthraquinone (3.5 g, 7.76 mmol) was dissolved in $CH_2Cl_2/MeOH$ (300 ml, 6:4) followed by the addition of ethyl 2-mercaptoacetate (1,02 ml, 9.31 mmol) with stirring under argon. The mixture was then cooled to 0° C. followed by dropwise addition of sodium methoxide (4.37M, 2.13 ml, 9.31 mmol). The reaction mixture was stirred for an additional 1 h, and then concentrated in vacuo. The crude residue was redissolved in THF and cooled to 0° C., followed by the addition of NaOEt (0.63 g, 9.31 mmol). The ice bath was then removed and the reaction was stirred until it had warmed to room temperature. The reaction mixture was quenched with $NH_4Cl$ and extracted with $CH_2Cl_2$. The organic layers were combined, washed with $H_2O$, dried over $MgSO_4$ and concentrated in vacuo to give a residue which was flash chromatographed using hexane, EtOAc, and $CH_2Cl_2$ (5:1:6) giving the desired products (679 mg) in 22% yield. $^1H$ NMR (300 MHz, $CDCl_3$) δ:1.28 (t, 3H, J=7.0 Hz), 3.17 (dd, 1H, J=16.62, 7.83, HCHa-C=O), 3.44 (dd, 1H, J=16.7, 5.5 Hz, HCHcCHC=O), 3.76, 3.77 (m, 2H, OCHC=O or HC Ha—S), 3.78 (s, 6H, $OCH_3$), 3.99 (m, 1H, HCHc—S), 4.20 (q, 2H, J=7.0 Hz), 7.74 (m, 2H, ArH). 8.17 (m, 2H, ArH).

Step 2: 3-carbethoxy-5,12-dihydroxy-1,2,3,4-tetrahydro-(2-sulfur)naphthacene-6,11-dione BCH-713

To a stirred solution of I (20 mg, 0.05 mmol) in 5 ml of $CH_2Cl_2$ at −78° C. was added dropwise $BBr_3$ (2.04 ml) under argon. The reaction mixture was stirred at −78° C. for 1.5 hour before it was quenched with 5 ml of $H_2O$ and 10 ml of $CH_2Cl_2$. The organic layer was separated, washed with $H_2O$, dried over $MgSO_4$, filtered and concentrated to residue which was found to be pure II (19 mg, 0.05 mmol, 100%). $^1H$ NMR ($CDCl_3$) δ:1.29 (3H, t, J=7.0 Hz), 3.28 (2H, m), 3.90 (3H, m), 4.22 (2H, q, J=7.1 Hz), 7.80 (2H, m), 8.31 (2H, m), 13.49 (1H, s), 13.50 (1H, s), $^1H$ NMR ($C_6D_6$) d:0.90 (3H, t, J=7.1 Hz), 3.08 (1H, m), 3.33 (1H, m), 3.42 (1H, m), 3.88 (4H, m), 7.85 (2H, m), 8.14 (2H, m), 13.78 (1H, s), 13.86 (1H, s), $^{13}C$ NMR ($CDCl_3$) δ:14.13, 22.74, 26.11, 39.32, 61.74, 126.93, 133.48, 134.36, 155.10, 156.30, 168.01, 186.64.

Step 3: 1,4-diacetyl-2,3-dimethylanthraquinone

To a stirred suspension of 2,3-dimethylquinizarin (5.00 g, 18.637 mmol) in dry $CH_2Cl_2$ (250 ml) was added acetic anhydride (40 ml) pyridine (40 ml) and dimethylaminopyridine (DMAP, 1.7 g) at room temperature under argon. After two hours, the reaction mixture was poured into a mixture of ethyl acetate and ice (1:1, 800 ml), extracted with $CH_2Cl_2$, and the combined organic layers were dryed over $MgSO_4$. Flash chromatography with toluene and ethylacetate; (95.5%) gave 2.517 g of pure compound (38% yield). (MP: 222°–224° C.). $^1H$ NMR ($CDCl_3$) δ:2.27 (s, 6H, $CH_3$, 2.53 (s, 6H, $COCH_3$), 7.72 (m, 2H, ArH), 8.15 (m, 2H, ArH).

Step 4: 1,4-diacetyl-2,3-bis-(bromomethyl)-anthraquinone

A mixture of diacetylated quinizarin from step 1 above, (2.221 g, 8.801 mmol), NBS (3.956 g, 22.002 mmol) and benzoyl peroxide (178 mg) in $CCl_4$ (350 ml) was refluxed and irradiated under argon with a 100 W lamp for 5 hours. Additional NBS (0.5 mmol) and benzoyl peroxide (0.2 mmol) were added. Reflux was continued for 3 hours and the solution was then cooled. Evaporation of the solvent in vacuo followed by flash chromatography with toluene and ethylacetate (97.5%: 2.5%) gave 3.095 g of the titled compound (88% yield). (MP: 225°–227° C.). $^1H$ NMR ($CDCl_3$) δ:2.56 (s, 6H, $OCOCH_3$), 4.59 (br.s, 4H, $CH_2Br$), 7.75 (m, 2H, ArH), 8.14 (m, 2H, ArH).

Example 15

Antitumor Activity

BCH-242 was subjected to an in vitro cytotoxicity evaluation against 57 tumor cell lines to assess its potential as an anticancer drug. These assays were carried out at the Developmental Therapeutics Program, Division of Cancer Treatment, National Cancer Institute (Bethesda, Md., U.S.A.). The method consists of incubating varying concentrations of the drug with an inoculum of cells for two days. At the end of the assay, the number of viable cells is estimated with a dye, sulforhodamine B. The protocol is described in M. R. Boyd, "Status of the NCI Preclinical Antitumor Drug Discovery Screen", Principles and Practices of Oncology, 3, pp. 1–12, 1989. The 57 cell lines included two mouse leukemia lines (P388 parental and adriamycin resistant) and 56 human cell lines.

There are three parameters calculated $GI_{50}$, the log molar conc. of drug required to inhibit cell growth by 50%; TGI, the log molar conc. of drug required to completely block cell growth; $LC_{50}$, the log molar concentration of drug required to reduce the original cell number by 50%. It should be noted that the first two parameters ($GI_{50}$ and TGI) relate to antiproliferation effects while the third one ($LC_{50}$) indicates true cytotoxicity. A value of −4 or greater is considered to denote resistance (inactivity). The results are presented in Table 0.

A number of interesting observations can be made regarding the activity profile of BCH-242. This analog is able to inhibit cell growth of both mouse leukemia cell lines (P388 parental and adriamycin resistant) to an equal extent (−5.78 vs −5.63). Likewise, BCH-242 shows a similar cytotoxic effect against MCF-7 parental and adriamycin resistant lines (−5.27 vs −5.15). The ability of BCH-242 to show activity against cell lines having known drug resistance suggests that the compound may be acting by an advantageous mechanism and that the compound may be clinically useful.

In addition, the various human and mouse leukemia lines, although sensitive to the antiproliferative effect of BCH-242, display some resistance to the cytotoxic effect of the drug. However, most of the cell lines of solid tumors ultimately show cytotoxicity to the drug. Since the potency of drugs against experimental leukemia usually predicts clinical bone marrow toxicity, it suggests that BCH-242 might be active clinically against certain solid tumors while exhibiting a minimal myelotoxic effect.

Example 16

In Vitro Clonogenic Assays of Heteroanthracyclines

A series of heteroanthracycline analogs were evaluated by the NCI at Bethesda, Md., USA. The same protocol as described in example 15 for BCH-242 was used. Tables 1 and 2 summarise the $GI_{50}$ and $LC_{50}$ average values obtained from a group of cell lines, per type of cancer. The original NCI data for the various derivatives, is provided herein in Tables 3 to 12.

With reference to Table 1, the heteroanthracycline derivatives show a weaker antiproliferative activity than daunomycin (DNM) or adriamycin (ADR) in the different type of cancers. However, the ability of the heteroanthracycline agents to kill the solid tumor cells is clearly denoted in Table 2. Cytotoxycity ranges from a mean potency of −4.09 in BCH-674 to as high as −5.32 in BCH-242 in solid tumors. Most notably is the fact that average cytotoxicity in leukemia is generally much lower than with DNM or ADR. This is a desirable feature and may indicate a lower bone marrow toxicity than with the clinical agents, DNM and ADR. Since myelotoxicity limits the single dosage that can be administered to a patient, these results suggest that higher and more therapeutically useful single dosages would be permissible with the heteroanthracyclines of this invention in the chemotherapy against solid tumors.

Example 17

In Vitro Clonogenic Assays of Heteroanthracyclinones.

Tables 13 and 14 summarize the $GI_{50}$ and $LC_{50}$ average values obtained from a group of cell lines, per type of cancer, for various heteroanthracyclinones. The original results obtained from the NCI, Bethesda, Md., for these compounds are shown in Tables 15 to 22. The same protocol as used for BCH-242 in example 15 was employed in this example.

It is most interesting to note that some of the heteroanthrocyclinones (BCH-651, BCH-657, BCH-660) listed in Tables 13 and 14 show strong antiproliferative ($GI_{50}$) and potent cytotoxic ($LC_{50}$) activities. In the case of BCH-657 and BCH-660 the mean $LC_{50}$ potency in solid tumors is similar to the one observed for DNM and ADR. The same trend observed with the heteroanthracyclines of example 16, where antileukemic activity is depressed, recurs with the heteroanthracyclinones of this example. This aspect may be beneficial to the clinical use of heteroanthracyclinones in the chemotherapy of solid tumors.

BCH-687, a compound in which there are no benzylic substituents, has significant antiproliferative ($GI_{50}$) and cytotoxic ($LC_{50}$) activities in solid tumors. This is unprecedented because known anthracyclinones which lack benzylic substituents are normally devoid of anticancer activity.

Example 18

In Vitro Activity of Heteroanthrocyclinones in Cell Lines Displaying Multi Drug Resistance (MDR)

The anticancer activity of heteroanthracyclinones and heteroanthracyclines from this invention was confirmed from a second independent assay. This biological study was carried out at the Oncology department of the faculty of medicine at McGill University, in Montreal, Canada. It involved the use of adriamycin sensitive cells lines as well as multidrug resistant ones. The following describes the methodology used for anticancer testing. Biological results follow the protocol.

SCREENING TEST

For the IN VITRO test, we chose a tumor clonogenic assay which measures the ability of tumoral cells to form colonies (multicellular growth units) as a result of cell division in semisolid agar support (2,3). A more elaborate version of this fundamental assay, the soft agar colony formation disk diffusion assay was used. This assay defines the relative activity of one particular drug versus a tumoral cell line type. The effect of the test drug against tumoral cells could be measured by its inhibitory capacity against colony formation after the delivery of the compound, in different concentrations on an filter disk(4).

COLONY FORMATION DISK DIFFUSION ASSAY

A modified technique of this assay was used in order to investigate the antiproliferative activity of candidate compounds. Tumoral cells from solid tumors and ascitic lines were plated separately in a two layer agar matrix. Cell lines to be tested were suspended in an upper layer of 0.4% Noble agar (Difco#00142-01) in RPMI-1066 (Gibco#3201875) at a yield varying between $10^4$ to $2 \times 10^5$ cells per 60 mm Petri dish. Plating efficiency was determined for each line in order to achieve an optimal number of colonies per dish. Plates were examined before drug administration to confirm a uniform dispersion of single cells. The bottom layer consisted of 0.8% Noble agar, 0.8% Tryptic Soy Broth (difco#0037001) in CMRL-1066/Fischer's. The bottom layers were used within 2 and 9 days of preparation. Plated dishes (bottom layer of agar, upper layer of cells and administered drug were incubated in humidified atmosphere at 37° C., 5% $CO_2$ for 10–20 days depending upon the time necessary to observe adequate colonies (defined as a cell aggregate of more than 50 cells) both control and drug inhibited. Drugs were administered on a paper filter disk (Whatman No. 1) of 6.5 mm diameter placed on the upper layer at ⅓ distance from the edge of the dish. The anticlonogenic activity of the compounds was measured as the zone of inhibition from the disk edge to the most proximal colonies. This zone of inhibition was checked on an inverted microscope (40×) and was measured with a micrometer mounted in the eyepiece. The ocular micrometer was calibrated with a stage micrometer set for a particular combination of ocular and objective lenses.

Our calibration values were converted to those already used in other laboratories in order to have comparable values. 200 units of activity are equivalent to 6.5 mm distance from the disk edge to the first colonies (5). Each concentration was run in triplicate and dispersion of the values was surprisingly small for the type of biological tests. We made a modification of the initial technique by not plating a solid tumor and a leukemia simultaneously in the same Petri dish. Anti-clonogenic tests performed on leukemia cell line have helped in the discovery of the majority of current clinically used cytostatic drugs. Our tests on solid tumor lines (animal or human) may help define active compounds with solid tumor specificity. This specific activity would be indicated by a higher level of cloning inhibition in solid tumors versus leukemias (6).

Materials and methods:

CELL LINES: 5 murine tumor lines and 2 rat tumor lines and 5 human tumor lines were used (Table 1).

ANIMAL TUMORS: 2 transplantable solid tumors, one reticulum cell sarcoma and one leukemia with and ADR resistant form were passaged IN VIVO. P388 and P388/ADR (7) routinely passaged in DBA/2, M5076 (8), B16 melanoma (9), Lewis lung carcinoma (9) routinely passaged in C57B1/6, were supplied by NCI, DCT Tumor Repository, NCI-FCRF, Frederick, Md. Rat breast carcinoma MATB WT (18) and MATB/ADR (18) obtained from the Oncology Dept. of the Montreal General Hospital were passaged IN VITRO. Murine tumors were maintained IN VIVO in order to diminish the selection of subpopulations of cells normally present in the heterogenous IN VIVO tumor. The actual drug sensitivity assay was done IN VITRO. For these experiments cells from freshly excised tumors or from ascitic fluids were maintained in RPMI-1066.

MICE: Inbred C57B1/6 females and DBA/2 females (20±2 g) were obtained from Charles River Laboratory, Que. and used as tumor recipient.

CELL PREPARATION. The protocol described by Corbett et al (6) was used. Tumors were excised aseptically from the host and cut in 200–300 mg fragments in HBSS (Gibco# 3104020). The fragmented tumor was forced through a 60 mesh sieve and the sieve rinsed twice with cold HBSS. The cell suspension was gently centrifuged (100–150) g/5 min), resuspended in HBSS and once again centrifuged. The cell pellet was finally suspended in an adequate volume of medium. Difficult to disrupt tumors were digested with 0.25% Trypsin EDTA (Gibco#6105305). The viability was over 90% for all cell lines prior starting experiments except for the LL line and P399/ADR which showed a varying degree of viability between 40 and 60%.

HUMAN TUMORS. MCF7 (10) and MCF7/ADR(11) HT29(12) were obtained from NCI, DCT Tumor Repository, NCI-FCRF, Frederick, MD. LS180 (13) and BE1(14) were obtained from the Oncology Dept. of the Montreal General Hospital. Cell lines were initially maintained in RPMI-1640 supplemented with 10% fetal bovine serum and 100 units of Penicillin-Streptomycin (Gibco#6005140). Cell lines were routinely passaged twice a week by trypsinization and maintained in 25, or 75-sq. cm Falcon Plastic flasks at 37° C., 5% $CO_2$ in humidified atmosphere.

DRUGS: Doxorubicin hydrochloride available from a commercial source was used as an internal control. For some line the DOX control was run simultaneously for both new synthesised agents. Our values for DOX as an internal control were consistently in accord with references(15,16).

Both compounds were dissolved in DMSO (1 mg/100 ul) and brought to final volume (250 ul) with Millipore deionized sterile water. Further dilutions were made with Milliwater. A volume of 25 ul of freshly prepared solution was placed on the filter disk and allowed to dry. A second control with vehicle (DMSO/Milliwater) was run simultaneously. Control disks with vehicle were found to produce no zone of inhibition. For the determination of drug action the compounds were tested in serial ten-fold dilutions. The results were expressed as units of inhibition of colony formation (Zone Units) produced at the same mass concentrations as DOX. Dilutions of the compounds as well as of DOX were stored in sterile Cryovials (Gibco#366656) at −20° C. for no longer than 3 days.

BIOLOGICAL RESULTS

The results obtained with the tumor clonogenic assay, in which a semisolid agar support was used, confirm the antitumor activity of the heteroanthracyclinones and heteroanthracyclines described herein (Tables 23 and 24). In the human breast cancer lines, MCF7 and MCF7/ADR, a similar level of activity occurred for BCH's:687, 692, 699, 700, 701 and 706 between both cell lines, indicating a lack of cross resistance with adriamycin (Table 23). Most notably is the fact that BCH-684 and 712 were more active in the adriamycin resistant cell line, MCF7/ADR, than in the sensitive one. Similar results were obtained with the rat breast tumor cell lines MATB.WT and MATB/ADR. In this case BCH's: 677, 681, 684, 700, 705 and 712 displayed no cross resistance with adriamycin in MATB; BCH's: 704, 710 and 711 displayed a greater cytotoxicity in the resistant breast tumor cell line, MATB/ADR, than in the sensitive line. The results obtained with the breast tumor lines indicate that the heteroanthracyclinones and heteroanthracyclines of the present invention operate via an advantageous cytotoxic mechanism. A range of activity was observed from the compounds described herein in this example. The most active were BCH's: 684, 687, 691, 692, 700, 704, 706 and 710. BCH 710 shows specificity for the MATB/ADR rat breast ADR resistant adenocarcinoma and mouse ovarian reticulum cell sarcoma. Specificity for breast cancer was demonstrated by BCH's 700 and 704. Good broad spectrum activity was observed from BCH's: 684, 691, and 692, except in the leukemic cell lines P388 and P388/ADR, confirming the specificity of these compounds for solid tumors. Human colon adenocarcinoma HT-29, LS180 and BE1 responded well with BCH-687, an analog in which no benzylic substituents are present. This is noteworthy because analogous compounds in the field of anthracyclines are normally not significantly cytotoxic towards tumor cells.

The data presented in this example supports the results presented in examples 15, 16 and 17. Heteroanthracyclinones and heteroanthracyclines, with an heteroatom in ring A as described herein, display a range of antineoplastic activity with specificity towards solid tumors. Cross resistance with doxorubicin or dannorubicin in some cases is not observed. The fact that cytotoxicity in hematologic malignancies is low in comparison with solid tumors suggest that myeclotoxicity should be decreased. This recurrent feature suggests that the therapeutic index of the compounds of the present invention has been increased. Therefore compounds of the present invention should be clinically useful because of reduced bone marrow toxicity and because of their demonstrated activity towards some resistant tumor cell lines.

TABLE O

EXAMPLE 15
ANTIPROLIFERATIVE AND CYTOTOXIC EFFECTS
OF BCH-242 IN TUMOR CELLS LINES

| Panel/Cell Line | $Log_{10}GI50$ | $Log_{10}TGI$ | $Log_{10}LC50$ |
| --- | --- | --- | --- |
| Leukemia | | | |
| CCRF-CEM | −5.83 | −5.35 | >−4.00 |
| HL-60 (TB) | −5.70 | −5.30 | >−4.00 |
| K-562 | −5.72 | −5.35 | >−4.00 |
| MOLT-4 | −5.89 | −5.49 | −5.09 |
| RPMI-8226 | −5.77 | −5.35 | −4.47 |
| Non-Small Cell Lung Cancer | | | |
| A-549 | −5.51 | −5.00 | −4.42 |
| EKVX | −5.75 | −5.47 | −5.20 |
| HOP-18 | −5.72 | −5.31 | −4.78 |
| HOP-62 | −5.25 | −4.75 | −4.37 |
| HOP-92 | −5.70 | −5.43 | −5.17 |
| NCI-H226 | −5.56 | −5.18 | −4.59 |
| NCI-H23 | −5.74 | −5.49 | −5.23 |
| NCI-H322 | −4.90 | −4.53 | −4.16 |
| NCI-H460 | −5.71 | −5.40 | −5.09 |
| NCI-H522 | −6.04 | −5.68 | −5.34 |
| Small Cell Lung Cancer | | | |
| DMS 114 | −5.80 | −5.52 | −5.24 |
| DMS 273 | −5.68 | −5.35 | −5.01 |
| Colon Cancer | | | |
| COLO-205 | −5.95 | −5.63 | −5.31 |
| DLD-1 | −5.80 | −5.49 | −5.17 |
| HCC-2998 | −5.63 | −5.24 | −4.72 |
| HCT-15 | −5.78 | −5.45 | −5.12 |
| HT-29 | −5.81 | −5.45 | −5.09 |
| KM-12 | −5.49 | −4.97 | −4.49 |
| KM-20L2 | −5.66 | −5.27 | −4.75 |
| SW-620 | −5.88 | −5.54 | −5.19 |
| CNS Cancer | | | |
| SF-268 | −5.31 | −4.59 | −4.40 |
| SF-295 | −5.62 | −5.15 | −4.59 |
| SF-539 | −5.69 | −5.36 | −5.03 |
| SNB-19 | −5.42 | −4.88 | −4.44 |
| SNB-75 | −5.53 | −5.06 | −4.52 |
| SNB-78 | −4.82 | >−4.00 | >−4.00 |
| U-251 | −5.60 | −5.14 | −4.59 |
| XF-498 L | −5.79 | −5.50 | −5.22 |
| Melanomia | | | |
| LOX-IMVI | −5.73 | −5.49 | −5.24 |
| MALMB-3M | −5.75 | −5.49 | −5.24 |
| M19-MEL | −5.81 | −5.51 | −5.21 |
| SK-MEL-2 | −5.77 | −5.51 | −5.24 |
| SK-MEL-28 | −5.62 | −5.37 | −5.11 |
| SK-MEL-5 | −5.83 | −5.55 | −5.26 |
| UACC-257 | −5.70 | −5.44 | −5.18 |
| UACC-62 | −5.76 | −5.50 | −5.25 |
| Ovarian Cancer | | | |
| IGROV-1 | −5.75 | −5.42 | −5.10 |

TABLE O-continued

EXAMPLE 15
ANTIPROLIFERATIVE AND CYTOTOXIC EFFECTS
OF BCH-242 IN TUMOR CELLS LINES

| Panel/Cell Line | $Log_{10}GI50$ | $Log_{10}TGI$ | $Log_{10}LC50$ |
|---|---|---|---|
| OVCAR-3 | −5.82 | −5.52 | −5.23 |
| OVCAR-4 | −5.74 | −5.48 | −5.22 |
| OVCAR-5 | −5.70 | −5.46 | −5.23 |
| OVCAR-8 | −5.49 | −5.49 | −5.19 |
| SK-OV-3 | −5.27 | −4.77 | −4.38 |
| Renal Cancer | | | |
| A-498 | −4.86 | −4.57 | −4.28 |
| CAK1-1 | −5.52 | −5.12 | −4.59 |
| RXF-393L | −5.89 | −5.58 | −5.27 |
| SN-12C | −5.79 | −5.52 | −5.26 |
| SN12K1 | −5.48 | −5.12 | −4.60 |
| UO-31 | −5.62 | −5.25 | −4.77 |
| Miscellaneous | | | |
| MCF-7 | −5.81 | −5.54 | −5.27 |
| MCF-7/ADR | −5.76 | −5.46 | −5.15 |
| P388 | −5.76 | — | >−4.00 |
| P388/ADR | −5.63 | −4.99 | −4.16 |
| Mean | −5.65 | −5.28 | −4.84 |

TABLE 1

| | Average $LOG_{10}GI_{50}$ Multiple cell lines | | | | |
|---|---|---|---|---|---|
| | Leukemia | NSC Lung | SC Lung | Colon | CNS |
| DNM | −7.25 ± 0.10 | −7.04 ± 0.23 | −7.14 ± 0.01 | −6.82 ± 0.31 | −7.04 ± 0.15 |
| ADR | −7.51 ± 0.52 | −7.33 ± 0.76 | −7.27 ± 0.12 | −6.61 ± 0.35 | −7.07 ± 0.26 |
| BCH-242 | −6.50 ± 0.14 | −6.01 ± 0.34 | −6.45 ± 0.26 | −6.50 ± 0.32 | −5.81 ± 0.23 |
| BCH-670 | −5.78 ± 0.10 | −5.51 ± 0.32 | −5.48 ± 0.23 | −5.69 ± 0.17 | −5.44 ± 0.30 |
| BCH-671 | −5.74 ± 0.05 | −5.34 ± 0.38 | −5.60 ± 0.06 | −5.72 ± 0.05 | −5.37 ± 0.19 |
| BCH-672 | −5.89 ± 0.09 | −5.45 ± 0.29 | −5.69 ± 0.14 | −5.78 ± 0.18 | −5.33 ± 0.25 |
| BCH-673 | −5.97 ± 0.06 | −5.76 ± 0.36 | −5.74 ± 0.00 | −6.10 ± 0.32 | −5.65 ± 0.06 |
| BCH-674 | −5.06 ± 0.14 | −5.03 ± 0.38 (1R) | −4.88 ± 0.14 | −4.87 ± 0.29 | −4.86 ± 0.07 |
| BCH-675 | −5.53 ± 0.11 | −5.03 ± 0.33 | −5.14 ± 0.22 | −5.06 ± 0.24 | −4.97 ± 0.19 |
| BCH-681 | −5.69 ± 0.05 | −5.54 ± 0.28 | −5.77 ± 0.04 | −5.85 ± 0.21 | −5.54 ± 0.15 |
| BCH-683 | −5.74 ± 0.03 | −5.52 ± 0.23 | −5.73 ± 0.01 | −5.89 ± 0.24 | −5.47 ± 0.17 |
| BCH-689 | −4.81 ± 0.04 | −4.87 ± 0.13 | −4.94 ± 0.02 | −4.95 ± 0.05 | −4.89 ± 0.10 |

| | Melanoma | Ovarian | Renal | Mean Potency in solid tumors |
|---|---|---|---|---|
| DNM | −6.95 ± 0.21 | −6.86 ± 0.18 | −6.79 ± 0.47 | −6.95 ± 0.22 |
| ADR | −6.92 ± 0.26 | −6.55 ± 0.19 | −6.74 ± 0.41 | −6.93 ± 0.29 |
| BCH-242 | −6.36 ± 0.41 | −6.13 ± 0.41 | −6.02 ± 0.22 | −6.18 ± 0.24 |
| BCH-670 | −5.75 ± 0.12 | −5.42 ± 0.40 | −5.36 ± 0.35 | −5.52 ± 0.13 |
| BCH-671 | −5.68 ± 0.09 | −5.44 ± 0.35 | −5.55 ± 0.14 | −5.53 ± 0.14 |
| BCH-672 | −5.81 ± 0.14 | −5.50 ± 0.35 | −5.38 ± 0.26 | −5.56 ± 0.18 |
| BCH-673 | −5.83 ± 0.05 | −5.81 ± 0.26 | −5.80 ± 0.09 | −5.81 ± 0.13 |
| BCH-674 | −4.88 ± 0.12 | −4.80 ± 0.09 | −5.05 ± 0.27 | −4.91 ± 0.09 |
| BCH-675 | −5.23 ± 0.23 | −5.07 ± 0.28 | −5.04 ± 0.30 | −5.08 ± 0.08 |
| BCH-681 | −5.95 ± 0.29 | −5.57 ± 0.12 | −5.52 ± 0.27 | −5.68 ± 0.16 |
| BCH-683 | −5.95 ± 0.25 | −5.68 ± 0.12 | −5.50 ± 0.29 | −5.68 ± 0.18 |
| BCH-689 | −4.90 ± 0.05 | −4.94 ± 0.05 | −4.95 ± 0.04 | −4.92 ± 0.03 |

*Represents the number of cell lines which are considered to be refractory towards the compound's cytotoxicity ($Log_{10}GI_{50} < -4.00$)

TABLE 2

| | \multicolumn{5}{c}{Average $LOG_{10}LC_{50}$ Multiple cell lines} | | | | |
| | Leukemia | NSC Lung | SC Lung | Colon | CNS |
|---|---|---|---|---|---|
| DNM | −4.30 ± 0.36 | −5.07 ± 0.37 | −5.58 ± 0.09 | −4.83 ± 0.37 | −5.08 ± 0.42 |
| ADR | −4.76 ± 0.10 | −5.01 ± 0.26 | −5.39 ± 0.18 | −4.86 ± 0.27 | −5.03 ± 0.35 |
| BCH-242 | > −4.00 | −5.21 ± 0.38 | −5.58 ± 0.27 | −5.59 ± 0.36 | −4.86 ± 0.24 |
| BCH-670 | > −4.00 | −4.62 ± 0.27 | −4.41(1R) | −4.60 ± 0.29 | −4.58 ± 0.15 |
| BCH-671 | > −4.00 | −4.52 ± 0.41 | −4.26 ± 0.20 | −4.80 ± 0.50 | −4.37 ± 0.24 |
| BCH-672 | −4.37 ± 0.15 | −4.56 ± 0.08 | −4.40 ± 0.20 | −4.55 ± 0.18 | −4.50 ± 0.16 |
| BCH-673 | > −4.00 | −4.66 ± 0.43 | −4.44 ± 0.04 | −4.46 ± 0.45 | −4.57 ± 0.22 |
| BCH-674 | > −4.00 | −4.16 ± 0.10 | −3.92 ± 0.14 | −4.01 ± 0.27 | −4.20 ± 0.06 |
| BCH-675 | > −4.00 | −4.25 ± 0.23 | −4.21 ± 0.04 | −4.07 ± 0.22 | −4.21 ± 0.11 |
| BCH-681 | < −4.00 | −4.64 ± 0.41 | −5.18 | −5.14 ± 0.27 | −4.65(1) ± 0.24 |
| BCH-683 | < −4.00 | −4.55 ± 0.42 | −5.08 | −4.98(1) ± 0.38 | −4.50(1) ± 0.21 |
| BCH-689 | < −4.00 | −4.38(± 0.06)3R | −4.37(± 0.05) | −4.41(± 0.03) | −4.39(± 0.05)2R |

| | Melanoma | Ovarian | Renal | Mean Potency in solid tumors |
|---|---|---|---|---|
| DNM | −5.64 ± 0.17 | −4.78 ± 0.20 | −4.78 ± 0.46 | −5.11 ± 0.34 |
| ADR | −5.56 ± 0.29 | −4.74 ± 0.05 | −4.87 ± 0.38 | −5.07 ± 0.28 |
| BCH-242 | −5.41 ± 0.07 | −5.35 ± 0.19 | −5.22 ± 0.21 | −5.32 ± 0.20 |
| BCH-670 | −4.69 ± 0.29 | −4.40 ± 0.13 | −4.53 ± 0.16 | −4.57 ± 0.09 |
| BCH-671 | −4.67 ± 0.57 | −4.47 ± 0.35 | −4.63 ± 0.24 | −4.53 ± 0.17 |
| BCH-672 | −4.67 ± 0.18 | −4.59 ± 0.13 | −4.62 ± 0.08 | −4.56 ± 0.08 |
| BCH-673 | −4.87 ± 0.50 | −4.66 ± 0.50 | −4.96 ± 0.32 | −4.66 ± 0.18 |
| BCH-674 | −4.05 ± 0.17 | −4.08 ± 0.17 | −4.24 ± 0.14 | −4.09 ± 0.11 |
| BCH-675 | −4.10 ± 0.23 | −4.20 ± 0.16 | −4.25 ± 0.10 | −4.18 ± 0.07 |
| BCH-681 | −5.30 ± 0.12 | −4.78 ± 0.18 | −4.66(1) ± 0.40 | −4.91 ± 0.27 |
| BCH-683 | −5.15 ± 0.22 | −4.80 ± 0.33 | −4.58 ± 0.36 | −4.81 ± 0.25 |
| BCH-689 | −4.38(± 0.04) | −4.37(± 0.07) | −4.43(± 0.01)2R | −4.39(± 0.02) |

*Represents the number of cell lines which are considered to be refractory towards the compound's cytotoxicity ($Log_{10}GI_{50}$ < −4.00)

TABLE 3

| \multicolumn{7}{c}{BCH-242} | | | | | | |
| National Cancer Institute Developmental Therapeutics Program Mean Graphs | | NSC: D-627446-p/1  Units: Molar Report Date: July 16, 1990 | | SSPL: Y71X  Exp. ID: 8910NS76 Test Date: November 7, 1989 | | |
|---|---|---|---|---|---|---|
| Panel/Cell Line | $Log_{10}GI50$ | GI50 | $Log_{10}TGI$ | TGI | $Log_{10}LC50$ | LC50 |
| Leukemia | | | | | | |
| CCRF-CEM | −6.55 | | > −4.00 | | > −4.00 | |
| HL-60 TB | −6.46 | | > −4.00 | | > −4.00 | |
| K-562 | −6.26 | | — | | > −4.00 | |
| MOLT-4 | −6.69 | | — | | −4.20 | |
| RPMI-8226 | −6.52 | | −5.03 | | > −4.00 | |
| Non-Small Cell Lung Cancer | | | | | | |
| A-549 | −6.09 | | −5.56 | | −5.08 | |
| EKVX | −5.83 | | 5.55 | | −5.27 | |
| HOP-18 | −5.94 | | −5.45 | | −4.92 | |
| HOP-62 | −5.69 | | −5.27 | | −4.73 | |
| HOP-92 | −6.21 | | −5.76 | | −5.36 | |
| NCI-H226 | −5.71 | | −5.44 | | −5.17 | |
| NCI-H23 | −5.99 | | −5.65 | | −5.31 | |
| NCI-H322 | −5.67 | | −5.27 | | −4.76 | |
| NCI-H460 | −6.16 | | −5.70 | | −5.33 | |
| NCI-H522 | −6.87 | | −6.50 | | −6.13 | |
| Small Cell Lung Cancer | | | | | | |
| DMS 114 | −6.71 | | −6.32 | | −5.84 | |
| DMS 273 | −6.19 | | −5.70 | | −5.31 | |
| Colon Cancer | | | | | | |
| COLO-205 | −6.79 | | −6.50 | | −6.22 | |
| DLD-1 | −6.77 | | −6.40 | | −6.03 | |
| HCC-2998 | −5.92 | | −5.61 | | −5.30 | |
| HCT-116 | −6.88 | | −6.45 | | −6.03 | |
| HCT-15 | −6.56 | | −5.96 | | −5.38 | |
| HT-29 | −6.57 | | −5.94 | | −5.42 | |

TABLE 3-continued

BCH-242

| National Cancer Institute Developmental Therapeutics Program Mean Graphs | | | NSC: D-627446-p/1 Units: Molar Report Date: July 16, 1990 | | SSPL: Y71X Exp. ID: 8910NS76 Test Date: November 7, 1989 | |
|---|---|---|---|---|---|---|
| Panel/Cell Line | Log$_{10}$GI50 | GI50 | Log$_{10}$TGI | TGI | Log$_{10}$LC50 | LC50 |
| KM-12 | −6.07 | | −5.68 | | −5.33 | |
| KM-20L2 | −6.51 | | −6.02 | | −5.44 | |
| SW-620 | > −4.00 | | > −4.00 | | > −4.00 | |
| CNS Cancer | | | | | | |
| SF-268 | −5.72 | | −5.36 | | −5.01 | |
| SF-295 | −5.70 | | −5.41 | | −5.12 | |
| SF-539 | −5.90 | | −5.60 | | −5.30 | |
| SNB-19 | −5.64 | | −5.21 | | −4.65 | |
| SNB-75 | −5.63 | | −5.25 | | −4.73 | |
| SNB-78 | −5.76 | | −5.32 | | > −4.00 | |
| U-251 | −6.33 | | −5.73 | | −5.22 | |
| Malanomia | | | | | | |
| LOX-IMVI | −6.48 | | −5.90 | | −5.43 | |
| MALMB-3M | −6.02 | | −5.67 | | −5.33 | |
| M19-MEL | −6.60 | | −6.13 | | −5.55 | |
| SK-MEL-2 | −6.40 | | −5.85 | | −5.39 | |
| SK-MEL-28 | −6.33 | | −5.75 | | −5.37 | |
| SK-MEL-5 | −6.22 | | −5.73 | | −5.36 | |
| UACC-257 | −6.51 | | −6.03 | | −5.47 | |
| UACC-62 | −6.29 | | −5.77 | | −5.37 | |
| Ovarian Cancer | | | | | | |
| IGROV-1 | > −4.00 | | > −4.00 | | > −4.00 | |
| OVCAR-3 | −6.60 | | −6.18 | | −5.63 | |
| OVCAR-4 | −5.94 | | −5.63 | | −5.31 | |
| OVCAR-5 | −5.73 | | −5.49 | | −5.24 | |
| OVCAR-8 | −6.65 | | −6.13 | | −5.57 | |
| SK-OV-3 | −5.75 | | −5.49 | | −5.23 | |
| Renal Cancer | | | | | | |
| A498 | −5.78 | | −5.51 | | −5.25 | |
| CAK1-1 | −5.91 | | −5.59 | | −5.26 | |
| RXF-393 L | −6.05 | | −5.67 | | −5.32 | |
| SN-12C | −5.94 | | −5.62 | | −5.31 | |
| SN-12K1 | −6.42 | | −5.85 | | −5.42 | |
| UO-31 | > −4.00 | | > −4.00 | | > −4.00 | |
| Miscellaneous | | | | | | |
| MCF-7 | −6.49 | | −5.86 | | −5.38 | |
| MCF-7/ADR | −6.50 | | −5.98 | | −5.40 | |
| P388 | −6.51 | | > −4.00 | | > −4.00 | |
| P388/ADR | −6.49 | | > −4.00 | | > −4.00 | |
| MG_MID | −6.10 | | −5.52 | | −5.09 | |
| Delta | 0.77 | | 0.98 | | 1.12 | |
| Range | 2.83 | | 2.50 | | 2.22 | |

TABLE 4

BCH-670

| National Cancer Institute Developmental Therapeutics Program Mean Graphs | | | NSC: 636525-J/1 Units: Molar Report Date: November 26, 1990 | | SSPL: Exp. ID: 9010SC22 Test Date: October 22, 1990 | |
|---|---|---|---|---|---|---|
| Panel/Cell Line | Log$_{10}$GI50 | GI50 | Log$_{10}$TGI | TGI | Log$_{10}$LC50 | LC50 |
| Leukemia | | | | | | |
| CCRF-CEM | −5.85 | | −5.33 | | > −4.15 | |
| HL-60 (TB) | −5.81 | | −5.35 | | > −4.15 | |
| K-562 | −5.61 | | > −4.15 | | > −4.15 | |
| MOLT-4 | −5.75 | | −5.28 | | > −4.15 | |
| RPMI-8226 | −5.89 | | −5.31 | | > −4.15 | |
| SK-WJU | — | | — | | — | |
| Non-Small Cell Lung Cancer | | | | | | |
| A-549/ATCC | −5.17 | | −4.76 | | −4.36 | |
| EKVX | −5.64 | | −5.08 | | −4.60 | |

TABLE 4-continued

BCH-670

| National Cancer Institute Developmental Therapeutics Program Mean Graphs | | | NSC: 636525-J/1  Units: Molar Report Date: November 26, 1990 | | SSPL:  Exp. ID: 9010SC22 Test Date: October 22, 1990 | |
|---|---|---|---|---|---|---|
| Panel/Cell Line | Log$_{10}$GI50 | GI50 | Log$_{10}$TGI | TGI | Log$_{10}$LC50 | LC50 |
| HOP-18 | −4.99 | | −4.70 | | −4.41 | |
| HOP-62 | — | | — | | — | |
| HOP-92 | — | | — | | — | |
| NCI-H226 | −5.65 | | −5.16 | | −4.61 | |
| NCI-H23 | −5.56 | | > −5.15 | | > −5.15 | |
| NCI-H322M | −5.67 | | −5.18 | | −4.66 | |
| NCI-H460 | −5.14 | | −4.78 | | −4.42 | |
| NCI-H522 | −6.08 | | −5.67 | | −5.27 | |
| LXFL-529L | −5.68 | | −5.08 | | −4.59 | |
| Small Cell Lung Cancer | | | | | | |
| DMS 114 | −5.71 | | −5.19 | | > −4.15 | |
| DMS 273 | −5.25 | | −4.80 | | −4.41 | |
| Colon Cancer | | | | | | |
| COLO-205 | −5.76 | | −5.04 | | > −4.15 | |
| DLD-1 | −5.72 | | −5.16 | | −4.60 | |
| HCC-2998 | — | | — | | — | |
| HCT-116 | −5.92 | | −5.54 | | −5.17 | |
| HCT-15 | −5.72 | | −5.12 | | −4.26 | |
| HT-29 | −5.68 | | −5.09 | | −4.33 | |
| KM-12 | −5.29 | | −4.55 | | > −4.15 | |
| KM-20L2 | −5.67 | | −5.11 | | −4.59 | |
| SW-620 | −5.79 | | −5.41 | | −4.67 | |
| CNS Cancer | | | | | | |
| SF-268 | −5.69 | | −5.15 | | > −5.15 | |
| SF-295 | −5.26 | | −4.85 | | −4.50 | |
| SF-539 | −5.50 | | −5.00 | | −4.57 | |
| SNB-19 | −5.05 | | −4.75 | | −4.44 | |
| SNB-75 | −5.44 | | −4.93 | | −4.53 | |
| SNB-78 | −5.85 | | −5.47 | | −4.84 | |
| U-251 | −4.99 | | −4.70 | | −4.42 | |
| XF-498 | −5.72 | | −5.33 | | −4.79 | |
| Melanomia | | | | | | |
| LOX-IMVI | −5.67 | | −5.15 | | −4.26 | |
| MALMB-3M | −5.85 | | −5.46 | | −4.94 | |
| M-14 | −5.82 | | −5.42 | | −4.89 | |
| M19-MEL | −5.74 | | −5.38 | | −4.71 | |
| SK-MEL-2 | −5.88 | | −5.29 | | −4.68 | |
| SK-MEL-28 | −5.50 | | −4.94 | | −4.52 | |
| SK-MEL-5 | −5.88 | | −5.53 | | −5.18 | |
| UACC-257 | −5.69 | | −5.17 | | −4.33 | |
| UACC-62 | −5.69 | | −5.24 | | >4.15 | |
| Ovarian Cancer | | | | | | |
| IGROV-1 | −5.60 | | −5.09 | | −4.21 | |
| OVCAR-3 | −5.62 | | −5.03 | | −4.47 | |
| OVCAR-4 | −5.73 | | −5.15 | | −4.63 | |
| OVCAR-5 | −4.92 | | −4.66 | | −4.41 | |
| OVCAR-8 | −5.81 | | −5.35 | | −4.35 | |
| SK-OV-3 | −4.81 | | −4.58 | | −4.35 | |
| Renal Cancer | | | | | | |
| 786-0 | −5.76 | | −5.21 | | −4.57 | |
| ACHN | −5.28 | | −4.86 | | −4.50 | |
| CAKI-1 | −4.99 | | −4.71 | | −4.43 | |
| RXF-393 | −5.75 | | −5.29 | | −4.74 | |
| RXF-631 | −5.36 | | −4.84 | | −4.44 | |
| SN-12C | −5.80 | | −5.38 | | −4.82 | |
| TK-10 | −4.81 | | −4.55 | | −4.29 | |
| UO-31 | −5.13 | | −4.80 | | −4.48 | |
| MG_MID | −5.56 | | −5.08 | | −4.53 | |
| Delta | 0.52 | | 0.60 | | 0.74 | |
| Range | 1.27 | | 1.52 | | 1.12 | |

TABLE 5

| | BCH-671 | | | | | | |
|---|---|---|---|---|---|---|---|
| National Cancer Institute Developmental Therapeutics Program Mean Graphs | | | NSC: 636526-K/1 Units: Molar Report Date: November 26, 1990 | | SSPL: Exp. ID: Test Date: October 22, 1990 | | |
| Panel/Cell Line | $Log_{10}GI50$ | GI50 | $Log_{10}TGI$ | TGI | $Log_{10}LC50$ | LC50 | |
| Leukemia | | | | | | | |
| CCRF-CEM | −5.79 | | −5.29 | | > −4.00 | | |
| HL-60 (TB) | — | | — | | — | | |
| K-562 | −5.67 | | −5.17 | | > −4.00 | | |
| MOLT-4 | −5.70 | | −5.31 | | > −4.00 | | |
| RPMI-8226 | −5.79 | | −5.34 | | > −4.00 | | |
| SK-WJU | — | | — | | — | | |
| Non-Small Cell Lung Cancer | | | | | | | |
| A-549/ATCC | −4.94 | | −4.56 | | −4.18 | | |
| EKVX | −5.65 | | −5.25 | | −4.64 | | |
| HOP-18 | −4.84 | | −4.56 | | −4.28 | | |
| HOP-62 | — | | — | | — | | |
| HOP-92 | — | | — | | — | | |
| NCI-H226 | −4.86 | | −4.54 | | −4.22 | | |
| NCI-H23 | −5.39 | | −4.74 | | −4.09 | | |
| NCI-H460 | −5.48 | | −4.92 | | −4.40 | | |
| NCI-H522 | −5.78 | | −5.43 | | −5.09 | | |
| LXFL-529L | −5.79 | | −5.51 | | −5.24 | | |
| Small Cell Lung Cancer | | | | | | | |
| DMS 114 | −5.67 | | −5.13 | | −4.05 | | |
| DMS 273 | −5.54 | | −5.10 | | −4.46 | | |
| Colon Cancer | | | | | | | |
| COLO-205 | −5.70 | | −5.31 | | > −4.00 | | |
| DLD-1 | −5.79 | | −5.43 | | −5.06 | | |
| HCC-2998 | — | | — | | — | | |
| HCT-116 | −5.80 | | −5.52 | | −5.25 | | |
| HCT-15 | −5.69 | | −5.19 | | > −4.00 | | |
| HT-29 | −5.69 | | −5.36 | | −5.03 | | |
| KM-12 | −5.74 | | −5.37 | | −5.00 | | |
| KM-20L2 | −5.63 | | −5.12 | | −4.52 | | |
| SW-620 | −5.69 | | −5.38 | | −5.07 | | |
| CNS Cancer | | | | | | | |
| SF-268 | −5.49 | | −4.87 | | −4.19 | | |
| SF-295 | −5.14 | | −4.63 | | −4.18 | | |
| SF-539 | −5.59 | | −5.14 | | −4.60 | | |
| SNB-19 | −5.19 | | −4.67 | | −4.26 | | |
| SNB-75 | −5.37 | | −4.89 | | −4.42 | | |
| SNB-78 | −5.49 | | −5.00 | | −4.09 | | |
| U-251 | −5.09 | | −4.68 | | −4.34 | | |
| XF-498 | −5.60 | | −5.27 | | −4.86 | | |
| Melanomia | | | | | | | |
| LOX-IMVI | −5.49 | | −4.90 | | > −4.00 | | |
| MALMB-3M | −5.76 | | −5.47 | | −5.19 | | |
| M-14 | −5.79 | | −5.49 | | −5.19 | | |
| M19-MEL | −5.76 | | −5.43 | | −5.11 | | |
| SK-MEL-2 | −5.66 | | −5.29 | | −4.77 | | |
| SK-MEL-28 | −5.68 | | −5.27 | | −4.71 | | |
| SK-MEL-5 | −5.57 | | −5.18 | | −4.61 | | |
| UACC-257 | −5.72 | | −5.37 | | −5.02 | | |
| UACC-62 | −5.68 | | −5.18 | | −4.01 | | |
| Ovarian Cancer | | | | | | | |
| IGROV-1 | −5.55 | | −5.04 | | −4.09 | | |
| OVCAR-3 | −5.75 | | −5.02 | | −4.51 | | |
| OVCAR-4 | −5.71 | | −5.46 | | −5.20 | | |
| OVCAR-5 | −5.14 | | −4.70 | | −4.34 | | |
| OVCAR-8 | −5.68 | | −5.22 | | −4.43 | | |
| SK-OV-3 | −4.81 | | −4.53 | | −4.24 | | |
| Renal Cancer | | | | | | | |
| 786-0 | −5.66 | | −5.27 | | −4.74 | | |
| ACHN | −5.69 | | −5.29 | | −4.79 | | |
| CAK1-1 | −5.41 | | −4.86 | | −4.42 | | |
| RXF-393 | −5.71 | | −5.37 | | −5.03 | | |

TABLE 5-continued

BCH-671

| National Cancer Institute Developmental Therapeutics Program Mean Graphs | | | NSC: 636526-K/1  Units: Molar Report Date: November 26, 1990 | | SSPL:  Exp. ID: Test Date: October 22, 1990 | |
|---|---|---|---|---|---|---|
| Panel/Cell Line | $Log_{10}GI50$ | GI50 | $Log_{10}TGI$ | TGI | $Log_{10}LC50$ | LC50 |
| RXF-631 | −5.34 | | −4.75 | | −4.24 | |
| SN-12C | −5.67 | | −5.30 | | −4.80 | |
| TK-10 | −5.42 | | −5.06 | | −4.54 | |
| UO-31 | −5.49 | | −4.88 | | −4.44 | |
| MG_MID | −5.54 | | −5.11 | | −4.53 | |
| Delta | 0.25 | | 0.41 | | 0.72 | |
| Range | 0.99 | | 1.00 | | 1.25 | |

TABLE 6

BCH-673

| National Cancer Institute Developmental Therapeutics Program Mean Graphs | | | NSC:  Units: Molar Report Date: December 6, 1990 | | SSPL:  Exp. ID: Test Date: October  , 1990 | |
|---|---|---|---|---|---|---|
| Panel/Cell Line | $Log_{10}GI50$ | GI50 | $Log_{10}TGI$ | TGI | $Log_{10}LC50$ | LC50 |
| Leukemia | | | | | | |
| CCRF-CEM | −6.05 | | −5.36 | | > −4.12 | |
| HL-60 (TB) | — | | — | | — | |
| K-562 | −5.89 | | −5.24 | | > −4.12 | |
| MOLT-4 | −5.96 | | −5.56 | | −5.16 | |
| RPMI-8226 | −5.97 | | −5.48 | | > −4.12 | |
| SK-WJU | — | | — | | — | |
| Non-Small Cell Lung Cancer | | | | | | |
| A-549/ATCC | −5.59 | | −5.11 | | −4.29 | |
| EKVX | −5.70 | | −5.41 | | −5.11 | |
| HOP-18 | −5.36 | | −4.85 | | −4.48 | |
| HOP-62 | — | | — | | — | |
| HOP-92 | −5.81 | | −5.48 | | −5.15 | |
| NCI-H226 | −5.74 | | −5.24 | | −4.46 | |
| NCI-H23 | −5.45 | | −4.78 | | > −4.12 | |
| NCI-H460 | −5.63 | | −5.15 | | −4.36 | |
| NCI-H522 | −6.67 | | −6.11 | | — | |
| LXFL-529L | −5.91 | | −5.60 | | −5.30 | |
| Small Cell Lung Cancer | | | | | | |
| DMS 114 | −5.74 | | −5.18 | | −4.40 | |
| DMS 273 | −5.74 | | −5.36 | | −4.48 | |
| Colon Cancer | | | | | | |
| COLO-205 | −5.87 | | −5.47 | | > −4.12 | |
| DLD-1 | −5.82 | | −5.36 | | −4.56 | |
| HCC-2998 | — | | — | | — | |
| HCT-116 | −6.53 | | −5.91 | | −5.30 | |
| HCT-15 | −6.33 | | −5.28 | | > −4.12 | |
| HT-29 | −6.42 | | −5.40 | | −4.53 | |
| KM-12 | −5.68 | | −5.06 | | > −4.12 | |
| KM-20L2 | −5.79 | | −5.33 | | > −4.12 | |
| SW-620 | −6.36 | | −5.69 | | −4.84 | |
| CNS Cancer | | | | | | |
| SF-268 | −5.60 | | −5.00 | | −4.31 | |
| SF-295 | −5.64 | | −5.07 | | −4.49 | |
| SF-539 | −5.68 | | −5.16 | | −4.64 | |
| SNB-19 | −5.57 | | −4.99 | | −4.54 | |
| SNB-75 | −5.62 | | −5.07 | | −4.51 | |
| SNB-78 | −5.70 | | −5.19 | | −4.38 | |
| U-251 | −5.65 | | −5.12 | | −4.59 | |
| XF-498 | −5.77 | | −5.44 | | −5.08 | |
| Melanomia | | | | | | |
| LOX-IMVI | −5.73 | | −5.27 | | > −4.12 | |
| MALMB-3M | −5.82 | | −5.54 | | −5.26 | |
| M-14 | −5.90 | | −5.61 | | −5.33 | |
| M19-MEL | −5.88 | | −5.40 | | > −4.12 | |

TABLE 6-continued

BCH-673

| National Cancer Institute Developmental Therapeutics Program Mean Graphs | | | NSC: Units: Molar Report Date: December 6, 1990 | | SSPL: Exp. ID: Test Date: October , 1990 | |
|---|---|---|---|---|---|---|
| Panel/Cell Line | Log$_{10}$GI50 | GI50 | Log$_{10}$TGI | TGI | Log$_{10}$LC50 | LC50 |
| SK-MEL-2 | −5.82 | | −5.50 | | −5.18 | |
| SK-MEL-28 | −5.86 | | −5.46 | | −4.94 | |
| SK-MEL-5 | −5.84 | | −5.55 | | −5.27 | |
| UACC-257 | −5.83 | | −5.49 | | −5.16 | |
| UACC-62 | −5.78 | | −5.38 | | −4.67 | |
| Ovarian Cancer | | | | | | |
| IGROV-1 | −5.85 | | −5.46 | | −4.41 | |
| OVCAR-3 | −6.16 | | −5.14 | | −4.61 | |
| OVCAR-4 | −5.90 | | −5.62 | | −5.34 | |
| OVCAR-5 | −5.80 | | −5.52 | | −5.24 | |
| OVCAR-8 | −5.82 | | −5.28 | | > −4.12 | |
| SK-OV-3 | −5.30 | | −4.82 | | −4.46 | |
| Renal Cancer | | | | | | |
| 786-0 | −5.84 | | −5.52 | | −5.21 | |
| ACHN | −5.88 | | −5.56 | | −5.24 | |
| CAK1-1 | −5.68 | | −5.35 | | −4.87 | |
| RXF-393 | −5.93 | | −5.64 | | −5.36 | |
| RXF-631 | −5.68 | | −5.10 | | −4.36 | |
| SN-12C | −5.75 | | −5.35 | | −4.75 | |
| TK-10 | −5.74 | | −5.31 | | −4.72 | |
| UO-31 | −5.88 | | −5.54 | | −5.20 | |
| MG_MID | −5.83 | | −5.35 | | −4.68 | |
| Delta | 0.84 | | 0.76 | | 0.68 | |
| Range | 1.37 | | 1.33 | | 1.23 | |

TABLE 7

BCH-674

| National Cancer Institute Developmental Therapeutics Program Mean Graphs | | | NSC: 636529-N/1 Units: Molar Report Date: November 26, 1990 | | SSPL: Exp. ID: 9010SC22 Test Date: October 22, 1990 | |
|---|---|---|---|---|---|---|
| Panel/Cell Line | Log$_{10}$GI50 | GI50 | Log$_{10}$TGI | TGI | Log$_{10}$LC50 | LC50 |
| Leukemia | | | | | | |
| CCRF-CEM | −4.97 | | −4.44 | | > −4.00 | |
| HL-60 (TB) | — | | — | | — | |
| K-562 | −4.89 | | −4.34 | | > −4.00 | |
| MOLT-4 | −5.18 | | −4.55 | | > −4.00 | |
| RPMI-8226 | −5.21 | | −4.57 | | −4.00 | |
| SK-WJU | — | | — | | — | |
| Non-Small Cell Lung Cancer | | | | | | |
| A-549/ATCC | −4.84 | | −4.49 | | −4.15 | |
| EKVX | −4.74 | | −4.42 | | −4.10 | |
| HOP-18 | −4.77 | | −4.50 | | −4.22 | |
| HOP-62 | — | | — | | — | |
| HOP-92 | −5.55 | | −4.80 | | −4.29 | |
| NCI-H226 | −4.85 | | −4.51 | | −4.17 | |
| NCI-H23 | −4.76 | | −4.38 | | > −4.00 | |
| NCI-H460 | −4.81 | | −4.48 | | −4.15 | |
| NCI-H522 | > −5.00 | | > −5.00 | | > −5.00 | |
| LXFL-529L | −4.93 | | −4.59 | | −4.24 | |
| Small Cell Lung Cancer | | | | | | |
| DMS 114 | −5.02 | | −4.40 | | > −4.00 | |
| DMS 273 | −4.74 | | −4.40 | | −4.05 | |
| Colon Cancer | | | | | | |
| COLO-205 | −4.64 | | −4.18 | | > −4.00 | |
| DLD-1 | −4.89 | | −4.54 | | −4.20 | |
| HCC-2998 | — | | — | | — | |
| HCT-116 | −4.80 | | −4.42 | | −4.03 | |
| HCT-15 | −4.85 | | −4.39 | | > −4.00 | |
| HT-29 | −5.59 | | −5.12 | | −4.43 | |

TABLE 7-continued

BCH-674

| National Cancer Institute Developmental Therapeutics Program Mean Graphs | | | NSC: 636529-N/1 Units: Molar Report Date: November 26, 1990 | | SSPL: Exp. ID: 9010SC22 Test Date: October 22, 1990 | |
|---|---|---|---|---|---|---|
| Panel/Cell Line | Log$_{10}$GI50 | GI50 | Log$_{10}$TGI | TGI | Log$_{10}$LC50 | LC50 |
| KM-12 | −4.60 | | −4.08 | | > −4.00 | |
| KM-20L2 | −4.77 | | −4.44 | | −4.12 | |
| SW-620 | −4.78 | | −4.47 | | −4.16 | |
| CNS Cancer | | | | | | |
| SF-268 | −4.89 | | −4.50 | | −4.11 | |
| SF-295 | −4.80 | | −4.47 | | −4.15 | |
| SF-539 | −4.75 | | −4.49 | | −4.23 | |
| SNB-19 | > −5.00 | | > −5.00 | | > −5.00 | |
| SNB-75 | −4.98 | | −4.63 | | −4.28 | |
| SNB-78 | −4.85 | | −4.50 | | −4.15 | |
| U-251 | −4.92 | | −4.61 | | −4.29 | |
| XF-498 | −4.82 | | −4.52 | | −4.22 | |
| Melanomia | | | | | | |
| LOX-IMVI | −5.03 | | −4.54 | | −4.07 | |
| MALMB-3M | −4.76 | | −4.47 | | −4.19 | |
| M-14 | −4.84 | | −4.47 | | −4.09 | |
| M19-MEL | −4.76 | | −4.31 | | > −4.00 | |
| SK-MEL-2 | −4.84 | | −4.50 | | −4.17 | |
| SK-MEL-28 | −4.82 | | −4.47 | | −4.12 | |
| SK-MEL-5 | −4.85 | | −4.51 | | −4.17 | |
| UACC-257 | −5.10 | | −4.58 | | −4.12 | |
| UACC-62 | −4.69 | | −4.19 | | > −4.00 | |
| Ovarian Cancer | | | | | | |
| IGROV-1 | −4.76 | | −4.29 | | > −4.00 | |
| OVCAR-3 | −4.73 | | −4.37 | | −4.02 | |
| OVCAR-4 | −4.99 | | −4.64 | | −4.30 | |
| OVCAR-5 | −4.80 | | −4.53 | | −4.25 | |
| OVCAR-8 | −4.78 | | −4.39 | | −4.00 | |
| SK-OV-3 | −4.71 | | −4.41 | | −4.10 | |
| Renal Cancer | | | | | | |
| 786-0 | −4.82 | | −4.55 | | −4.27 | |
| ACHN | −4.86 | | −4.57 | | −4.29 | |
| CAK1-1 | −5.27 | | −4.72 | | −4.29 | |
| RXF-393 | −5.43 | | −4.76 | | −4.33 | |
| RXF-631 | −4.86 | | −4.41 | | > −4.00 | |
| SN-12C | −4.81 | | −4.49 | | −4.18 | |
| TK-10 | −4.87 | | −4.57 | | −4.27 | |
| UO-31 | −5.45 | | −4.81 | | −4.35 | |
| MG_MID | −4.91 | | −4.52 | | −4.17 | |
| Delta | 0.68 | | 0.61 | | 0.26 | |
| Range | 0.99 | | 1.04 | | 0.43 | |

TABLE 8

BCH-675

| National Cancer Institute Developmental Therapeutics Program Mean Graphs | | | NSC: 636530-O/1 Units: Molar Report Date: November 26, 1990 | | SSPL: Exp. ID: 9010SC22 Test Date: October 22, 1990 | |
|---|---|---|---|---|---|---|
| Panel/Cell Line | Log$_{10}$GI50 | GI50 | Log$_{10}$TGI | TGI | Log$_{10}$LC50 | LC50 |
| Leukemia | | | | | | |
| CCRF-CEM | −5.45 | | −4.82 | | > −4.00 | |
| HL-60 (TB) | — | | — | | — | |
| K-562 | −5.41 | | −4.62 | | > −4.00 | |
| MOLT-4 | −5.56 | | −5.08 | | −4.10 | |
| RPMI-8226 | −5.69 | | −5.26 | | > −5.00 | |
| SK-WJU | — | | — | | — | |
| Non-Small Cell Lung Cancer | −4.81 | | −4.48 | | −4.15 | |
| A-549/ATCC | −4.79 | | −4.46 | | −4.13 | |
| EKVX | −4.79 | | −4.53 | | −4.26 | |
| HOP-18 | — | | — | | — | |
| HOP-62 | −5.52 | | −5.11 | | > −5.00 | |

TABLE 8-continued

| | BCH-675 | | | | | |
|---|---|---|---|---|---|---|
| National Cancer Institute Developmental Therapeutics Program Mean Graphs | | | NSC: 636530-O/1 Units: Molar Report Date: November 26, 1990 | | SSPL: Exp. ID: 9010SC22 Test Date: October 22, 1990 | |
| Panel/Cell Line | Log$_{10}$GI50 | GI50 | Log$_{10}$TGI | TGI | Log$_{10}$LC50 | LC50 |
| HOP-92 | −4.73 | | −4.43 | | −4.13 | |
| NCI-H226 | −4.78 | | −4.39 | | > −4.00 | |
| NCI-H23 | −4.89 | | −4.59 | | −4.30 | |
| NCI-H460 | −4.99 | | −4.62 | | −4.25 | |
| NCI-H522 | −5.67 | | −5.32 | | −4.79 | |
| LXFL-529L | −5.34 | | −4.78 | | −4.37 | |
| Small Cell Lung Cancer | | | | | | |
| DMS 114 | −5.35 | | −4.73 | | −4.17 | |
| DMS 273 | −4.92 | | −4.58 | | −4.24 | |
| Colon Cancer | | | | | | |
| COLO-205 | −4.95 | | −4.51 | | −4.07 | |
| DLD-1 | −5.21 | | −4.63 | | −4.10 | |
| HCC-2998 | — | | — | | — | |
| HCT-116 | −5.59 | | −5.18 | | −4.44 | |
| HCT-15 | −5.20 | | −4.58 | | −4.02 | |
| HT-29 | −4.82 | | −4.37 | | > −4.00 | |
| KM-12 | −4.92 | | −4.29 | | > −4.00 | |
| KM-20L2 | −4.88 | | −4.55 | | −4.21 | |
| SW-620 | −4.94 | | −4.54 | | −4.14 | |
| CNS Cancer | | | | | | |
| SF-268 | −4.99 | | −4.52 | | −4.05 | |
| SF-295 | −4.84 | | −4.52 | | −4.20 | |
| SF-539 | −4.85 | | −4.57 | | −4.28 | |
| SNB-19 | > −5.00 | | > −5.00 | | > −5.00 | |
| SNB-75 | −5.42 | | −4.83 | | −4.38 | |
| SNB-78 | −4.91 | | −4.49 | | −4.06 | |
| U-251 | −4.87 | | −4.58 | | −4.29 | |
| XF-498 | −4.93 | | −4.59 | | −4.24 | |
| Melanomia | | | | | | |
| LOX-IMVI | −5.41 | | −4.76 | | > −4.00 | |
| MALMB-3M | −5.15 | | −4.68 | | −4.28 | |
| M-14 | −5.00 | | −4.64 | | −4.28 | |
| M19-MEL | −5.48 | | −4.86 | | −4.06 | |
| SK-MEL-2 | −5.32 | | −4.76 | | −4.24 | |
| SK-MEL-28 | −5.16 | | −4.67 | | −4.27 | |
| SK-MEL-5 | — | | — | | — | |
| UACC-257 | −4.81 | | −4.47 | | −4.14 | |
| UACC-62 | −5.54 | | −4.93 | | > −4.00 | |
| Ovarian Cancer | | | | | | |
| IGROV-1 | −5.10 | | −4.54 | | −4.04 | |
| OVCAR-3 | −5.49 | | −4.82 | | −4.32 | |
| OVCAR-4 | −5.40 | | −4.84 | | −4.40 | |
| OVCAR-5 | −4.78 | | −4.52 | | −4.26 | |
| OVCAR-8 | −4.85 | | −4.40 | | > −4.00 | |
| SK-OV-3 | −4.82 | | −4.51 | | −4.20 | |
| Renal Cancer | | | | | | |
| 786-0 | −4.84 | | −4.52 | | −4.21 | |
| ACHN | −4.91 | | −4.61 | | −4.30 | |
| CAK1-1 | −4.84 | | −4.55 | | −4.27 | |
| RXF-393 | −5.65 | | −5.04 | | −4.42 | |
| RXF-631 | −4.98 | | −4.53 | | −4.08 | |
| SN-12C | −4.89 | | −4.53 | | −4.17 | |
| TK-10 | −4.78 | | −4.49 | | −4.21 | |
| UO-31 | −5.42 | | −4.76 | | −4.37 | |
| MG_MID | −5.10 | | −4.67 | | −4.24 | |
| Delta | 0.58 | | 0.65 | | 0.55 | |
| Range | 0.96 | | 1.03 | | 0.79 | |

TABLE 9

BCH-681

| National Cancer Institute Developmental Therapeutics Program Mean Graphs | | | NSC: D-638334-Y/1 Units: Molar Report Date: March 1, 1991 | | SSPL: Exp. ID: 9012NS84 Test Date: December 18, 1990 | |
|---|---|---|---|---|---|---|
| Panel/Cell Line | $Log_{10}GI50$ | GI50 | $Log_{10}TGI$ | TGI | $Log_{10}LC50$ | LC50 |
| Leukemia | | | | | | |
| CCRF-CEM | −5.66 | | −5.13 | | > −4.00 | |
| HL-60 (TB) | −5.77 | | −5.39 | | −4.95 | |
| K-562 | −5.63 | | −5.26 | | > −4.00 | |
| MOLT-4 | −5.69 | | −5.13 | | > −4.00 | |
| RPMI-8226 | −5.70 | | −5.15 | | > −4.00 | |
| SR | — | | — | | — | |
| Non-Small Cell Lung Cancer | | | | | | |
| A-549/ATCC | −5.74 | | −5.46 | | — | |
| EKVX | −5.48 | | −4.92 | | −4.46 | |
| HOP-62 | −4.88 | | −4.58 | | −4.28 | |
| HOP-92 | −5.61 | | −5.21 | | −4.65 | |
| NCI-H226 | −5.32 | | −4.80 | | −4.32 | |
| NCI-H23 | — | | — | | — | |
| NCI-H322M | −5.70 | | −5.34 | | −4.94 | |
| NCI-H460 | −5.54 | | −4.87 | | −4.06 | |
| NCI-H522 | −5.79 | | −5.48 | | −5.18 | |
| LXFL-529L | −5.78 | | −5.52 | | −5.26 | |
| Small Cell Lung Cancer | | | | | | |
| DMS 114 | −5.73 | | −5.45 | | −5.18 | |
| DMS 273 | −5.81 | | −5.49 | | −5.18 | |
| Colon Cancer | | | | | | |
| COLO-205 | −6.32 | | −5.75 | | −5.37 | |
| DLD-1 | −5.80 | | −5.51 | | −5.23 | |
| HCC-2998 | — | | — | | — | |
| HCT-116 | −5.82 | | −5.47 | | −5.11 | |
| HCT-15 | −5.85 | | −5.56 | | −5.26 | |
| HT-29 | −5.89 | | −5.57 | | −5.26 | |
| KM-12 | −5.53 | | −5.02 | | −4.46 | |
| KM-20L2 | −5.76 | | −5.47 | | −5.18 | |
| SW-620 | −5.84 | | −5.56 | | −5.28 | |
| CNS Cancer | | | | | | |
| SF-268 | −5.51 | | −4.96 | | −4.45 | |
| SF-295 | −5.52 | | −4.93 | | −4.46 | |
| SF-539 | −5.73 | | −5.37 | | −5.02 | |
| SNB-19 | −5.25 | | −4.74 | | −4.37 | |
| SNB-75 | −5.60 | | −5.29 | | −4.94 | |
| SNB-78 | −5.44 | | −4.75 | | > −4.00 | |
| U-251 | −5.53 | | −5.07 | | −4.54 | |
| XF-498 | −5.74 | | −5.29 | | −4.74 | |
| Melanomia | | | | | | |
| LOX-IMVI | −5.87 | | −5.57 | | −5.27 | |
| MALMB-3M | −5.65 | | −5.43 | | −5.21 | |
| M-14 | −5.84 | | −5.56 | | −5.28 | |
| M19-MEL | −6.60 | | −6.13 | | −5.58 | |
| SK-MEL-28 | −5.74 | | −5.45 | | −5.16 | |
| SK-MEL-5 | −5.84 | | −5.56 | | −5.28 | |
| UACC-257 | −5.80 | | −5.52 | | −5.25 | |
| UACC-62 | −6.22 | | −5.72 | | −5.34 | |
| Ovarian Cancer | | | | | | |
| IGROV-1 | −5.67 | | −5.35 | | −5.02 | |
| OVCAR-3 | −5.72 | | −5.31 | | −4.78 | |
| OVCAR-4 | −5.59 | | −5.26 | | −4.81 | |
| OVCAR-5 | −5.40 | | −5.17 | | −4.81 | |
| OVCAR-8 | −5.49 | | −4.95 | | −4.47 | |
| Renal Cancer | | | | | | |
| 786-0 | −5.53 | | −4.95 | | −4.47 | |
| A498 | −4.89 | | −4.56 | | −4.23 | |
| ACHN | −5.76 | | −5.49 | | −5.23 | |
| CAK1-1 | −5.29 | | −4.69 | | −4.12 | |
| RXF-393 | −5.75 | | −5.36 | | −4.89 | |
| RXF-631 | −5.65 | | −5.04 | | > −4.00 | |

TABLE 9-continued

BCH-681

| National Cancer Institute Developmental Therapeutics Program Mean Graphs | | | NSC: D-638334-Y/1   Units: Molar Report Date: March 1, 1991 | | SSPL:   Exp. ID: 9012NS84 Test Date: December 18, 1990 | |
|---|---|---|---|---|---|---|
| Panel/Cell Line | $Log_{10}GI50$ | GI50 | $Log_{10}TGI$ | TGI | $Log_{10}LC50$ | LC50 |
| SN-12C | −5.81 | | −5.53 | | −5.26 | |
| TK-10 | −5.44 | | −5.03 | | −4.50 | |
| UO-31 | −5.57 | | −5.11 | | −4.57 | |
| MG_MID | −5.67 | | −5.26 | | −4.79 | |
| Delta | −0.94 | | 0.87 | | 0.80 | |
| Range | −1.73 | | 1.58 | | 1.58 | |

TABLE 10

BCH-683

| National Cancer Institute Developmental Therapeutics Program Mean Graphs | | | NSC: D-638335-Z/1   Units: Molar Report Date: March 1, 1991 | | SSPL: Y71X   Exp. ID: 9012NS84 Test Date: December 18, 1990 | |
|---|---|---|---|---|---|---|
| Panel/Cell Line | $Log_{10}GI50$ | GI50 | $Log_{10}TGI$ | TGI | $Log_{10}LC50$ | LC50 |
| Leukemia | | | | | | |
| CCRF-CEM | −5.71 | | −5.26 | | > −4.00 | |
| HL-60 (TB) | −5.74 | | −5.33 | | > −4.00 | |
| K-562 | −5.79 | | −5.29 | | > −4.00 | |
| MOLT-4 | −5.79 | | −5.43 | | −5.06 | |
| RPMI-8226 | −5.74 | | −5.28 | | −4.04 | |
| SR | — | | — | | — | |
| Non-Small Cell Lung Cancer | | | | | | |
| A-549/ATCC | −5.75 | | −5.45 | | — | |
| EKVX | −5.39 | | −4.85 | | −4.41 | |
| HOP-62 | −5.10 | | −4.67 | | −4.29 | |
| HOP-92 | −5.67 | | −5.35 | | −5.03 | |
| NCI-H226 | −5.23 | | −4.69 | | −4.24 | |
| NCI-H23 | −5.50 | | −4.90 | | −4.01 | |
| NCI-H322M | −5.57 | | −5.12 | | −4.48 | |
| NCI-H460 | −5.38 | | −4.70 | | −4.18 | |
| NCI-H522 | −5.83 | | −5.50 | | −5.16 | |
| LXFL-529L | −5.74 | | −5.46 | | −5.18 | |
| Small Cell Lung Cancer | | | | | | |
| DMS 114 | −5.72 | | −5.40 | | — | |
| DMS 273 | −5.73 | | −5.40 | | −5.08 | |
| Colon Cancer | | | | | | |
| COLO-205 | −6.42 | | −5.89 | | −5.37 | |
| DLD-1 | −5.80 | | −5.52 | | −5.24 | |
| HCC-2998 | — | | — | | — | |
| HCT-116 | −5.77 | | −5.43 | | −5.09 | |
| HCT-15 | −5.91 | | −5.57 | | −5.23 | |
| HT-29 | −5.95 | | −5.42 | | > −4.00 | |
| KM-12 | −5.55 | | −5.01 | | −4.26 | |
| KM-20L2 | −5.74 | | −5.26 | | −4.55 | |
| SW-620 | −5.95 | | −5.55 | | −5.15 | |
| CNS Cancer | | | | | | |
| SF-268 | −5.54 | | −4.94 | | −4.38 | |
| SF-295 | −5.35 | | −4.81 | | −4.36 | |
| SF-539 | −5.66 | | −5.24 | | −4.67 | |
| SNB-19 | −5.13 | | −4.70 | | −4.35 | |
| SNB-75 | −5.35 | | −4.82 | | −4.39 | |
| SNB-78 | −5.58 | | −4.93 | | > −4.00 | |
| U-251 | −5.60 | | −5.07 | | −4.41 | |
| XF-498 | −5.55 | | −5.27 | | −4.95 | |
| Melanomia | | | | | | |
| LOX-IMVI | −5.96 | | −5.63 | | −5.29 | |
| MALMB-3M | −5.82 | | −5.53 | | — | |
| M-14 | −5.77 | | −5.49 | | −5.21 | |
| M19-MEL | −6.47 | | −6.03 | | −5.24 | |
| SK-MEL-28 | −5.63 | | −5.23 | | −4.62 | |

TABLE 10-continued

BCH-683

| National Cancer Institute Developmental Therapeutics Program Mean Graphs | | NSC: D-638335-Z/1 Units: Molar Report Date: March 1, 1991 | | SSPL: Y71X Exp. ID: 9012NS84 Test Date: December 18, 1990 | |
|---|---|---|---|---|---|
| Panel/Cell Line | $\text{Log}_{10}\text{GI50}$ GI50 | $\text{Log}_{10}\text{TGI}$ | TGI | $\text{Log}_{10}\text{LC50}$ | LC50 |
| SK-MEL-5 | −5.97 | −5.65 | | −5.32 | |
| UACC-257 | −5.84 | −5.49 | | −5.15 | |
| UACC-62 | −6.16 | −5.66 | | −5.24 | |
| Ovarian Cancer | | | | | |
| IGROV-1 | −5.67 | −5.30 | | −4.67 | |
| OVCAR-3 | −5.84 | −5.29 | | −4.67 | |
| OVCAR-4 | −5.77 | −5.51 | | −5.25 | |
| OVCAR-5 | −5.49 | −5.29 | | −5.10 | |
| OVCAR-8 | −5.63 | −5.00 | | −4.34 | |
| Renal Cancer | | | | | |
| 786-0 | −5.51 | −4.95 | | −4.44 | |
| A498 | −4.85 | −4.55 | | −4.25 | |
| ACHN | −5.38 | −4.86 | | −4.35 | |
| CAK1-1 | −5.38 | −4.81 | | −4.22 | |
| RXF-393 | −5.86 | −5.47 | | −5.07 | |
| RXF-631 | −5.72 | −5.19 | | > −4.00 | |
| SN-12C | −5.84 | −5.54 | | −5.24 | |
| TK-10 | −5.36 | −4.84 | | −4.41 | |
| UO-31 | −5.62 | −5.22 | | −4.69 | |
| MG_MID | −5.67 | −5.24 | | −4.66 | |
| Delta | −0.80 | 0.79 | | 0.71 | |
| Range | 1.62 | 1.48 | | 1.37 | |

TABLE 11

BCH-689

| National Cancer Institute Developmental Therapeutics Program Mean Graphs | | NSC: D-638340-H/1 Units: Molar Report Date: March 1, 1991 | | SSPL: Y71X Exp. ID: 9012NS84 Test Date: December 18, 1990 | |
|---|---|---|---|---|---|
| Panel/Cell Line | $\text{Log}_{10}\text{GI50}$ GI50 | $\text{Log}_{10}\text{TGI}$ | TGI | $\text{Log}_{10}\text{LC50}$ | LC50 |
| Leukemia | | | | | |
| CCRF-CEM | −4.77 | −4.24 | | > −4.18 | |
| HL-60 (TB) | −4.84 | −4.49 | | > −4.18 | |
| K-562 | −4.80 | −4.30 | | > −4.18 | |
| MOLT-4 | −4.78 | > −4.18 | | > −4.18 | |
| RPMI-8226 | −4.86 | −4.24 | | > −4.18 | |
| SR | — | — | | — | |
| Non-Small Cell Lung Cancer | | | | | |
| A-549/ATCC | −4.82 | −4.45 | | > −4.18 | |
| EKVX | −4.73 | −4.21 | | > −4.18 | |
| HOP-62 | −4.99 | −4.68 | | −4.38 | |
| HOP-92 | −4.81 | −4.60 | | −4.39 | |
| NCI-H226 | −4.93 | −4.65 | | −4.37 | |
| NCI-H23 | — | — | | — | |
| NCI-H322M | −4.63 | > −4.18 | | > −4.18 | |
| NCI-H460 | −4.91 | −4.58 | | −4.26 | |
| NCI-H522 | −5.03 | −4.74 | | −4.45 | |
| LXFL-529L | −4.98 | −4.71 | | −4.44 | |
| Small Cell Lung Cancer | | | | | |
| DMS 114 | −4.92 | −4.62 | | −4.32 | |
| DMS 273 | −4.96 | −4.69 | | −4.42 | |
| Colon Cancer | | | | | |
| COLO-205 | −5.03 | −4.74 | | −4.46 | |
| DLD-1 | −4.95 | −4.66 | | −4.38 | |
| HCC-2998 | — | — | | — | |
| HCT-116 | −4.94 | −4.67 | | −4.40 | |
| HCT-15 | −5.00 | −4.72 | | −4.44 | |
| HT-29 | −4.87 | −4.62 | | −4.36 | |
| KM-12 | −4.89 | −4.65 | | −4.41 | |
| KM-20L2 | — | — | | — | |

TABLE 11-continued

BCH-689

| National Cancer Institute Developmental Therapeutics Program Mean Graphs | | NSC: D-638340-H/1 Units: Molar Report Date: March 1, 1991 | | SSPL: Y71X Exp. ID: 9012NS84 Test Date: December 18, 1990 | |
|---|---|---|---|---|---|
| Panel/Cell Line | Log₁₀GI50 GI50 | Log₁₀TGI | TGI | Log₁₀LC50 | LC50 |
| SW-620 | −4.96 | −4.69 | | −4.42 | |
| CNS Cancer | | | | | |
| SF-268 | — | — | | — | |
| SF-295 | −4.94 | −4.66 | | −4.37 | |
| SF-539 | −5.02 | −4.74 | | −4.45 | |
| SNB-19 | −4.74 | > −4.18 | | > −4.18 | |
| SNB-75 | −4.87 | −4.59 | | −4.31 | |
| SNB-78 | −4.73 | −4.31 | | > −4.18 | |
| U-251 | −4.95 | −4.67 | | −4.39 | |
| XF-498 | −4.96 | −4.69 | | −4.43 | |
| Melanomia | | | | | |
| LOX-IMVI | −4.95 | −4.65 | | −4.35 | |
| MALMB-3M | −4.82 | −4.58 | | −4.34 | |
| M-14 | −4.94 | −4.68 | | −4.42 | |
| M19-MEL | −4.87 | −4.62 | | −4.38 | |
| SK-MEL-28 | −4.84 | −4.59 | | −4.34 | |
| SK-MEL-5 | −4.98 | −4.72 | | −4.45 | |
| UACC-257 | −4.90 | −4.64 | | −4.38 | |
| UACC-62 | −4.88 | −4.63 | | −4.38 | |
| Ovarian Cancer | | | | | |
| IGROV-1 | −4.85 | −4.56 | | −4.27 | |
| OVCAR-3 | −4.95 | −4.64 | | −4.33 | |
| OVCAR-4 | −4.94 | −4.67 | | −4.41 | |
| OVCAR-5 | — | — | | — | |
| OVCAR-8 | −5.00 | −4.73 | | −4.45 | |
| Renal Cancer | | | | | |
| 786-0 | −4.95 | −4.69 | | −4.44 | |
| A498 | −4.97 | −4.57 | | > −4.18 | |
| ACHN | −4.97 | −4.71 | | −4.44 | |
| CAK1-1 | −4.97 | −4.71 | | −4.44 | |
| RXF-393 | −4.98 | −4.71 | | −4.43 | |
| RXF-631 | −4.88 | −4.39 | | > −4.18 | |
| SN-12C | −4.97 | −4.70 | | −4.43 | |
| TK-10 | −4.89 | −4.65 | | −4.41 | |
| UO-31 | −5.01 | −4.73 | | −4.45 | |
| MG_MID | −4.90 | −4.58 | | −4.34 | |
| Delta | 0.13 | 0.16 | | 0.12 | |
| Range | 0.40 | 0.56 | | 0.28 | |

TABLE 12

BCH-672

| National Cancer Institute Developmental Therapeutics Program Mean Graphs | | NSC: Units: Molar Report Date: December 6, 1990 | | SSPL: Exp. ID: Test Date: October , 1990 | |
|---|---|---|---|---|---|
| Panel/Cell Line | Log₁₀GI50 GI50 | Log₁₀TGI | TGI | Log₁₀LC50 | LC50 |
| Leukemia | | | | | |
| CCRF-CEM | −5.93 | −5.45 | | > −4.31 | |
| HL-60 (TB) | — | — | | — | |
| K-562 | −5.73 | −5.11 | | > −4.31 | |
| MOLT-4 | −5.95 | −5.53 | | −4.61 | |
| RPMI-8226 | −5.94 | −5.22 | | −4.36 | |
| SR-WJU | — | — | | — | |
| Non-Small Cell Lung Cancer | | | | | |
| A-549/ATCC | −5.26 | −4.88 | | −4.49 | |
| EKVX | −5.60 | −5.07 | | −4.65 | |
| HOP-18 | −5.13 | −4.85 | | −4.58 | |
| HOP-62 | — | — | | — | |
| HOP-92 | — | — | | — | |
| NCI-H226 | −5.09 | −4.75 | | −4.42 | |
| NCI-H23 | −5.44 | −4.92 | | −4.47 | |

TABLE 12-continued

BCH-672

| National Cancer Institute Developmental Therapeutics Program Mean Graphs | | | NSC:      Units: Molar Report Date: December 6, 1990 | | SSPL:      Exp. ID: Test Date: October , 1990 | |
|---|---|---|---|---|---|---|
| Panel/Cell Line | $Log_{10}GI50$ | GI50 | $Log_{10}TGI$ | TGI | $Log_{10}LC50$ | LC50 |
| NCI-H460 | −5.55 | | −5.01 | | −4.58 | |
| NCI-H522 | −6.04 | | −5.61 | | −4.60 | |
| LXFL-529L | −5.52 | | −5.03 | | −4.66 | |
| Small Cell Lung Cancer | | | | | | |
| DMS 114 | −5.83 | | −5.19 | | > −4.31 | |
| DMS 273 | −5.55 | | −5.02 | | −4.60 | |
| Colon Cancer | | | | | | |
| COLO-205 | −5.84 | | −5.22 | | > −4.31 | |
| DLD-1 | −5.83 | | −5.23 | | −4.74 | |
| HCC-2998 | — | | — | | — | |
| HCT-116 | −5.86 | | −5.31 | | −4.74 | |
| HCT-15 | −5.86 | | −5.25 | | −4.38 | |
| HT-29 | −5.86 | | −5.30 | | −4.44 | |
| KM-12 | −5.31 | | −4.96 | | −4.61 | |
| KM-20L2 | −5.82 | | −5.27 | | −4.72 | |
| SW-620 | −5.82 | | −5.31 | | −4.57 | |
| CNS Cancer | | | | | | |
| SF-268 | −5.77 | | −5.09 | | > −4.31 | |
| SF-295 | −5.16 | | −4.82 | | −4.49 | |
| SF-539 | −5.22 | | −4.91 | | −4.61 | |
| SNB-19 | −5.20 | | −4.89 | | −4.59 | |
| SNB-75 | −5.06 | | −4.79 | | −4.52 | |
| SNB-78 | −5.60 | | −4.99 | | −4.44 | |
| U-251 | −5.11 | | −4.84 | | −4.57 | |
| XF-498 | −5.55 | | −5.05 | | −4.67 | |
| Melanomia | | | | | | |
| LOX-IMVI | −5.73 | | −5.06 | | −4.31 | |
| MALMB-3M | −5.96 | | −5.48 | | −4.86 | |
| M-14 | −5.85 | | −5.29 | | −4.75 | |
| M19-MEL | −5.95 | | −5.54 | | −4.90 | |
| SK-MEL-2 | −5.63 | | −5.02 | | −4.64 | |
| SK-MEL-28 | −5.53 | | −5.02 | | −4.61 | |
| SK-MEL-5 | −5.87 | | −5.38 | | −4.75 | |
| UACC-257 | −5.91 | | −5.36 | | −4.71 | |
| UACC-62 | −5.86 | | −5.24 | | −4.47 | |
| Ovarian Cancer | | | | | | |
| IGROV-1 | −5.74 | | −5.08 | | −4.37 | |
| OVCAR-3 | −5.78 | | −5.26 | | −4.78 | |
| OVCAR-4 | −5.44 | | −5.01 | | −4.65 | |
| OVCAR-5 | −5.05 | | −4.80 | | −4.56 | |
| OVCAR-8 | −5.94 | | −5.46 | | −4.64 | |
| SK-OV-3 | −5.05 | | −4.79 | | −4.53 | |
| Renal Cancer | | | | | | |
| 786-0 | −5.39 | | −4.98 | | −4.62 | |
| ACHN | −5.39 | | −4.99 | | −4.64 | |
| CAK1-1 | −5.12 | | −4.84 | | −4.55 | |
| RXF-393 | −5.69 | | −5.11 | | −4.70 | |
| RXF-631 | −5.39 | | −4.95 | | −4.56 | |
| SN-12C | −5.86 | | −5.31 | | −4.77 | |
| TK-10 | −5.02 | | −4.77 | | −4.52 | |
| UO-31 | −5.20 | | −4.91 | | −4.61 | |
| MG_MID | −5.58 | | −5.10 | | −4.57 | |
| Delta | 0.45 | | 0.51 | | 0.33 | |
| Range | 1.02 | | 0.86 | | 0.59 | |

TABLE 13

Average $LOG_{10}GI_{50}$ Multiple cell lines

|  | Leukemia | NSC Lung | SC Lung | Colon | CNS |
|---|---|---|---|---|---|
| DNM | −7.25 ± 0.10 | −7.04 ± 0.23 | −7.14 ± 0.01 | −6.82 ± 0.31 | −7.04 ± 0.15 |
| ADR | −7.51 ± 0.52 | −7.33 ± 0.76 | −7.27 ± 0.12 | −6.61 ± 0.35 | −7.07 ± 0.26 |
| BCH-650 | −4.21 ± 0.16(3R) | > −4.00 | > −4.00 | > −4.00 | −4.34 ± 0.15(1R)* |
| BCH-651 | −5.48 ± 0.06 | −5.11 ± 0.33 | −5.56 ± 0.09 | −5.47 ± 0.12 | −5.00 ± 0.25 |
| BCH-653 | −4.80 ± 0.40 | −4.35 ± 0.20(3R) | −4.54 ± 0.06 | −4.45 ± 0.12(1R) | −4.30 ± 0.17(1R) |
| BCH-657 | −6.36 ± 0.06 | −5.95 ± 0.36 | −5.90 ± 0.26 | −6.10 ± 0.30 | −5.73 ± 0.14 |
| BCH-658 | > −4.00 | > −4.00 | > −4.00 | −4.21 ± 0.10(4R) | −4.33 ± 0.16 |
| BCH-660 | −6.50 ± 0.08 | −6.01 ± 0.55(1R) | −6.00 ± 0.28 | −6.21 ± 0.25 | −6.02 ± 0.24 |
| BCH-687 | −4.91 ± 0.12 | −4.81 ± 0.35 | −5.09 ± 0.25 | −4.95 ± 0.28 | −4.59 ± 0.16 |
| BCH-688 | −4.44 ± 0.21 | > −4.00 | > −4.00 | > −4.00 | −4.27 ± 0.14(3R) |

|  | Melanoma | Ovarian | Renal | Mean Potency in solid tumors |
|---|---|---|---|---|
| DNM | −6.95 ± 0.21 | −6.86 ± 0.18 | −6.79 ± 0.47 | −6.95 ± 0.22 |
| ADR | −6.92 ± 0.26 | −6.55 ± 0.19 | −6.74 ± 0.41 | −6.93 ± 0.29 |
| BCH-650 | > −4.00 | > −4.00 | −4.28 ± 0.20(4R) | −4.28 ± 0.05 |
| BCH-651 | −5.56 ± 0.13 | −5.23 ± 0.12 | −5.00 ± 0.27 | −5.28 ± 0.23 |
| BCH-653 | −4.48 ± 0.16 | −4.42 ± 0.23 | −4.24 ± 0.22(3R) | −4.40 ± 0.10 |
| BCH-657 | −5.87 ± 0.22 | −5.77 ± 0.22 | −5.88 ± 0.25 | −5.89 ± 0.11 |
| BCH-658 | > −4.00 | > −4.00 | −4.33 ± 0.17(4R) | −4.29 ± 0.06 |
| BCH-660 | −6.02 ± 0.28 | −6.02 ± 0.24 | −6.04 ± 0.34 | −6.05 ± 0.07 |
| BCH-687 | −5.05 ± 0.27 | −4.94 ± 0.37 | −4.69 ± 0.23 | −4.87 ± 0.17 |
| BCH-688 | > −4.00 | −4.12 ± 0.01(2R) | > −4.00 | −4.28 ± 0.13 |

*Represents the number of cell lines which are considered to be refractory towards the compound's cytotoxicity ($Log_{10}GI_{50} \leq -4.00$)

TABLE 14

Average $LOG_{10}LC_{50}$ Multiple cell lines

|  | Leukemia | NSC Lung | SC Lung | Colon | CNS |
|---|---|---|---|---|---|
| DNM | −4.30 ± 0.36 | −5.07 ± 0.37 | −5.58 ± 0.09 | −4.83 ± 0.37 | −5.08 ± 0.42 |
| ADR | −4.76 ± 0.10 | −5.01 ± 0.26 | −5.39 ± 0.18 | −4.86 ± 0.27 | −5.03 ± 0.35 |
| BCH-650 | > −4.00 | > −4.00 | > −4.00 | > −4.00 | > −4.00 |
| BCH-651 | > −4.00 | −4.30 ± 0.36(3R)* | −4.21 ± 0.01 | −4.38 ± 0.11(2R) | −4.19 ± 0.10 |
| BCH-653 | > −4.00 | > −4.00 | > −4.00 | > −4.00 | > −4.00 |
| BCH-657 | > −4.00 | −4.94 ± 0.31(4R) | > −4.00 | −4.87 ± 0.43(6R) | −4.88 ± 0.36(2R) |
| BCH-658 | > −4.00 | > −4.00 | > −4.00 | > −4.00 | > −4.00 |
| BCH-660 | > −4.00 | −4.71 ± 0.43(2R) | > −4.00 | > −4.00 | −4.80 ± 0.45 |
| BCH-687 | > −4.00 | > −4.23(± 0.07) | > −4.18 | −4.25(± 0.09)3R | > −4.15 |
| BCH-688 | > −4.00 | > −4.00 | > −4.00 | > −4.00 | > −4.00 |

|  | Melanoma | Ovarian | Renal | Mean Potency in solid tumors |
|---|---|---|---|---|
| DNM | −5.64 ± 0.17 | −4.78 ± 0.20 | −4.78 ± 0.46 | −5.11 ± 0.34 |
| ADR | −5.56 ± 0.29 | −4.74 ± 0.05 | −4.87 ± 0.38 | −5.07 ± 0.28 |
| BCH-650 | > −4.00 | > −4.00 | > −4.00 | > −4.00 |
| BCH-651 | −4.46 ± 0.23 | −4.33 ± 0.04(1R) | −4.26 ± 0.10 | −4.30 ± 0.09 |
| BCH-653 | > −4.00 | > −4.00 | > −4.00 | > −4.00 |
| BCH-657 | −4.88 ± 0.29(4R) | −4.76 ± 0.39(1R) | −4.92 ± 0.49 | −4.88 ± 0.06 |
| BCH-658 | > −4.00 | > −4.00 | > −4.00 | > −4.00 |
| BCH-660 | −4.98 ± 0.42(3R) | −5.18 ± 0.08(1R) | −5.10 ± 0.40 | −4.95 ± 0.18 |
| BCH-687 | −4.28(± 0.09)1R | −4.15(± 0.11)2R | > −4.21 | −4.21(± 0.05) |
| BCH-688 | > −4.00 | > −4.00 | > −4.00 | > −4.00 |

*Represents the number of cell lines which are considered to be refractory towards the compound's cytotoxicity ($Log_{10}GI_{50} < -4.00$)

TABLE 15

BCH-650

| National Cancer Institute Developmental Therapeutics Program Mean Graphs | | NSC: D-638327-R/1 Units: Molar Report Date: March 1, 1991 | | SSPL: Y71X Exp. ID: 9012NS84 Test Date: December 18, 1990 | |
|---|---|---|---|---|---|
| Panel/Cell Line | $Log_{10}GI50$   GI50 | $Log_{10}TGI$ | TGI | $Log_{10}LC50$ | LC50 |
| Leukemia | | | | | |
| CCRF-CEM | > −4.00 | > −4.00 | | > −4.00 | |
| HL-60 (TB) | −4.13 | > −4.00 | | > −4.00 | |
| K-562 | > −4.00 | > −4.00 | | > −4.00 | |
| MOLT-4 | −4.07 | > −4.00 | | > −4.00 | |
| RPMI-8226 | −4.44 | > −4.00 | | > −4.00 | |
| SR | > −4.00 | > −4.00 | | > −4.00 | |
| Non-Small Cell Lung Cancer | | | | | |
| A-549/ATCC | > −4.00 | > −4.00 | | > −4.00 | |
| EKVX | > −4.00 | > −4.00 | | > −4.00 | |
| HOP-62 | −4.35 | > −4.00 | | > −4.00 | |
| HOP-92 | −4.28 | > −4.00 | | > −4.00 | |
| NCI-H226 | > −4.00 | > −4.00 | | > −4.00 | |
| NCI-H23 | — | — | | — | |
| NCI-H322M | > −4.00 | > −4.00 | | > −4.00 | |
| NCI-H460 | > −4.00 | > −4.00 | | > −4.00 | |
| NCI-H522 | −4.04 | > −4.00 | | > −4.00 | |
| LXFL-529L | > −4.00 | > −4.00 | | > −4.00 | |
| Small Cell Lung Caner | | | | | |
| DMS 114 | > −4.00 | > −4.00 | | > −4.00 | |
| DMS 273 | > −4.00 | > −4.00 | | > −4.00 | |
| Colon Cancer | | | | | |
| COLO-205 | > −4.00 | > −4.00 | | > −4.00 | |
| DLD-1 | > −4.00 | > −4.00 | | > −4.00 | |
| HCC-2998 | — | — | | — | |
| HCT-116 | > −4.00 | > −4.00 | | > −4.00 | |
| HCT-15 | > −4.00 | > −4.00 | | > −4.00 | |
| HT-29 | > −4.00 | > −4.00 | | > −4.00 | |
| KM-12 | > −4.00 | > −4.00 | | > −4.00 | |
| KM-20L2 | — | — | | — | |
| SW-620 | > −4.00 | > −4.00 | | > −4.00 | |
| CNS Cancer | | | | | |
| SF-268 | — | — | | — | |
| SF-295 | > −4.00 | > −4.00 | | > −4.00 | |
| SF-539 | −4.03 | > −4.00 | | > −4.00 | |
| SNB-19 | −4.31 | > −4.00 | | > −4.00 | |
| SNB-75 | −4.48 | −4.07 | | > −4.00 | |
| SNB-78 | −4.39 | > −4.00 | | > −4.00 | |
| U-261 | −4.47 | > −4.00 | | > −4.00 | |
| XF-498 | −4.36 | > −4.00 | | > −4.00 | |
| Melanomia | | | | | |
| LOX-IMVI | −4.06 | > −4.00 | | > −4.00 | |
| MALMB-3M | > −4.00 | > −4.00 | | > −4.00 | |
| M-14 | > −4.00 | > −4.00 | | > −4.00 | |
| M19-MEL | > −4.00 | > −4.00 | | > −4.00 | |
| SK-MEL-28 | > −4.00 | > −4.00 | | > −4.00 | |
| SK-MEL-5 | > −4.00 | > −4.00 | | > −4.00 | |
| UACC-257 | > −4.00 | > −4.00 | | > −4.00 | |
| UACC-62 | > −4.00 | > −4.00 | | > −4.00 | |
| Ovarian Cancer | | | | | |
| IGROV-1 | > −4.00 | > −4.00 | | > −4.00 | |
| OVCAR-3 | > −4.00 | > −4.00 | | > −4.00 | |
| OVCAR-4 | −4.52 | > −4.00 | | > −4.00 | |
| OVCAR-5 | > −4.00 | > −4.00 | | > −4.00 | |
| OVCAR-8 | > −4.00 | > −4.00 | | > −4.00 | |
| Renal Cancer | | | | | |
| 786-0 | −4.03 | > −4.00 | | > −4.00 | |
| A498 | > −4.00 | > −4.00 | | > −4.00 | |
| ACHN | −4.29 | > −4.00 | | > −4.00 | |
| CAK1-1 | > −4.00 | > −4.00 | | > −4.00 | |
| RXF-393 | −4.55 | −4.07 | | > −4.00 | |
| RXF-631 | −4.09 | > −4.00 | | > −4.00 | |

TABLE 15-continued

BCH-650

| National Cancer Institute Developmental Therapeutics Program Mean Graphs | | | NSC: D-638327-R/1 Units: Molar Report Date: March 1, 1991 | | SSPL: Y71X Exp. ID: 9012NS84 Test Date: December 18, 1990 | |
|---|---|---|---|---|---|---|
| Panel/Cell Line | Log$_{10}$GI50 | GI50 | Log$_{10}$TGI | TGI | Log$_{10}$LC50 | LC50 |
| SN-12C | > −4.00 | | > −4.00 | | > −4.00 | |
| TK-10 | −4.46 | | > −4.00 | | > −4.00 | |
| UO-31 | > −4.00 | | > −4.00 | | > −4.00 | |
| MG_MID | −4.10 | | −4.00 | | −4.00 | |
| Delta | 0.45 | | 0.07 | | 0.00 | |
| Range | 0.55 | | 0.07 | | 0.00 | |

TABLE 16

BCH-651

| National Cancer Institute Developmental Therapeutics Program Mean Graphs | | | NSC: D-638328-S/1 Units: Molar Report Date: March 1, 1991 | | SSPL: Y71X Exp. ID: 9012NS84 Test Date: December 18, 1990 | |
|---|---|---|---|---|---|---|
| Panel/Cell Line | Log$_{10}$GI50 | GI50 | Log$_{10}$TGI | TGI | Log$_{10}$LC50 | LC50 |
| Leukemia | | | | | | |
| CCRF-CEM | −5.41 | | > −4.00 | | > −4.00 | |
| HL-60 (TB) | −5.49 | | > −4.00 | | > −4.00 | |
| K-562 | −5.46 | | > −4.00 | | > −4.00 | |
| MOLT-4 | −5.49 | | > −4.00 | | > −4.00 | |
| RPMI-8226 | −5.60 | | > −4.00 | | > −4.00 | |
| SR | −5.45 | | > −4.00 | | > −4.00 | |
| Non-Small Cell Lung Cancer | | | | | | |
| A-549/ATCC | −5.11 | | −4.54 | | −4.02 | |
| EKVX | −5.32 | | −4.76 | | −4.33 | |
| HOP-62 | −4.83 | | −4.40 | | > −4.00 | |
| HOP-92 | −5.24 | | −4.64 | | > −4.00 | |
| NCI-H226 | −4.73 | | −4.37 | | −4.01 | |
| NCI-H23 | — | | — | | — | |
| NCI-H322M | −4.80 | | −4.33 | | > −4.00 | |
| NCI-H460 | −4.80 | | −4.45 | | −4.09 | |
| NCI-H522 | −5.73 | | −5.38 | | −5.04 | |
| LXFL-529L | −5.47 | | −4.88 | | −4.40 | |
| Small Cell Lung Cancer | | | | | | |
| DMS 114 | −5.65 | | −5.28 | | −4.20 | |
| DMS 273 | −5.48 | | −4.86 | | −4.22 | |
| Colon Cancer | | | | | | |
| COLO-205 | −5.36 | | −4.80 | | −4.36 | |
| DLD-1 | −5.47 | | −4.93 | | > −4.00 | |
| HCC-2998 | — | | — | | — | |
| HCT-116 | −5.73 | | −5.28 | | −4.55 | |
| HCT-15 | −5.55 | | −4.95 | | −4.41 | |
| HT-29 | −5.39 | | −4.73 | | > −4.00 | |
| KM112 | −5.43 | | −4.88 | | −4.37 | |
| KM-20L2 | — | | — | | — | |
| SW-620 | −5.37 | | −4.84 | | −4.21 | |
| CNS Cancer | | | | | | |
| SF-268 | — | | — | | — | |
| SF-295 | −4.84 | | −4.55 | | −4.25 | |
| SF-539 | −5.02 | | −4.63 | | −4.26 | |
| SNB-19 | −4.93 | | −4.51 | | −4.09 | |
| SNB-75 | −4.74 | | −4.38 | | −4.02 | |
| SNB-78 | −5.06 | | > −4.00 | | > −4.00 | |
| U-251 | −5.57 | | −5.15 | | −4.23 | |
| XF-498 | −4.84 | | −4.56 | | −4.27 | |
| Melanomia | | | | | | |
| LOX-IMVI | −5.59 | | −4.92 | | −4.41 | |
| MALMB-3M | −5.69 | | −5.20 | | −4.58 | |
| M-14 | −5.61 | | −5.14 | | −4.56 | |
| M19-MEL | −5.52 | | −5.05 | | −4.28 | |
| SK-MEL-28 | −5.24 | | −4.60 | | −4.04 | |

TABLE 16-continued

BCH-651

| National Cancer Institute Developmental Therapeutics Program Mean Graphs | | | NSC: D-638328-S/1 Units: Molar Report Date: March 1, 1991 | | SSPL: Y71X Exp. ID: 9012NS84 Test Date: December 18, 1990 | |
|---|---|---|---|---|---|---|
| Panel/Cell Line | Log₁₀GI50 | GI50 | Log₁₀TGI | TGI | Log₁₀LC50 | LC50 |
| SK-MEL-5 | −5.67 | | −5.31 | | −4.88 | |
| UACC-257 | −5.60 | | −5.16 | | −4.53 | |
| UACC-62 | −5.52 | | −5.07 | | −4.38 | |
| Ovarian Cancer | | | | | | |
| IGROV-1 | −4.95 | | −4.39 | | > −4.00 | |
| OVCAR-3 | −5.63 | | −5.24 | | −4.37 | |
| OVCAR-4 | −5.28 | | −4.74 | | −4.35 | |
| OVCAR-5 | −4.79 | | −4.53 | | −4.26 | |
| OVCAR-8 | −5.51 | | −4.96 | | −4.33 | |
| Renal Cancer | | | | | | |
| 786-0 | −5.08 | | −4.61 | | −4.18 | |
| A498 | −4.73 | | −4.46 | | −4.20 | |
| ACHN | −5.13 | | −4.69 | | −4.31 | |
| CAK1-1 | −4.84 | | −4.49 | | −4.13 | |
| RXF-393 | −5.56 | | −5.04 | | −4.47 | |
| RXF-631 | −4.91 | | −4.11 | | > −4.00 | |
| SN-12C | −5.19 | | −4.69 | | −4.29 | |
| TK-10 | −4.60 | | −4.40 | | −4.19 | |
| UO-31 | −4.93 | | −4.61 | | −4.30 | |
| MG_MID | −5.26 | | −4.67 | | −4.23 | |
| Delta | 0.47 | | 0.71 | | 0.80 | |
| Range | 1.13 | | 1.38 | | 1.04 | |

TABLE 17

BCH-653

| National Cancer Institute Developmental Therapeutics Program Mean Graphs | | | NSC: D-638329-T/1 Units: Molar Report Date: March 1, 1991 | | SSPL: Y71X Exp. ID: 9012NS84 Test Date: December 18, 1990 | |
|---|---|---|---|---|---|---|
| Panel/Cell Line | Log₁₀GI50 | GI50 | Log₁₀TGI | TGI | Log₁₀LC50 | LC50 |
| Leukemia | | | | | | |
| CCRF-CEM | −4.93 | | −4.37 | | > −4.00 | |
| HL-60 (TB) | −4.93 | | −4.40 | | > −4.00 | |
| K-562 | −4.81 | | −4.36 | | > −4.00 | |
| MOLT-4 | −4.68 | | −4.23 | | > −4.00 | |
| RPMI-8226 | −4.77 | | −4.28 | | > −4.00 | |
| SR | −4.66 | | −4.20 | | > −4.00 | |
| Non-Small Cell Lung Cancer | | | | | | |
| A-549/ATCC | −4.06 | | > −4.00 | | > −4.00 | |
| EKVX | −4.27 | | > −4.00 | | > −4.00 | |
| HOP-62 | > −4.00 | | > −4.00 | | > −4.00 | |
| HOP-92 | −4.24 | | > −4.00 | | > −4.00 | |
| NCI-H226 | > −4.00 | | > −4.00 | | > −4.00 | |
| NCI-H23 | — | | — | | — | |
| NCI-H322M | −4.40 | | > −4.00 | | > −4.00 | |
| NCI-H460 | > −4.00 | | > −4.00 | | > −4.00 | |
| NCI-H522 | −4.73 | | −4.20 | | > −4.00 | |
| LXFL-529L | −4.39 | | > −4.00 | | > −4.00 | |
| Small Cell Lung Cancer | | | | | | |
| DMS 114 | −4.60 | | −4.25 | | > −4.00 | |
| DMS 273 | −4.48 | | > −4.00 | | > −4.00 | |
| Colon Cancer | | | | | | |
| COLO-205 | −4.39 | | > −4.00 | | > −4.00 | |
| DLD-1 | −4.58 | | −4.09 | | > −4.00 | |
| HCC-2998 | — | | — | | — | |
| HCT-116 | −4.57 | | > −4.00 | | > −4.00 | |
| HCT-15 | −4.56 | | > −4.00 | | > −4.00 | |
| HT-29 | −4.27 | | > −4.00 | | > −4.00 | |
| KM-20L2 | > −4.00 | | > −4.00 | | > −4.00 | |
| SW-620 | −4.35 | | > −4.00 | | > −4.00 | |

TABLE 17-continued

| | BCH-653 | | | | | |
|---|---|---|---|---|---|---|
| National Cancer Institute Developmental Therapeutics Program Mean Graphs | NSC: D-638329-T/1 Units: Molar Report Date: March 1, 1991 | | | SSPL: Y71X Exp. ID: 9012NS84 Test Date: December 18, 1990 | | |
| Panel/Cell Line | Log₁₀GI50 | GI50 | Log₁₀TGI | TGI | Log₁₀LC50 | LC50 |
| CNS Cancer | | | | | | |
| SF-268 | — | | — | | — | |
| SF-295 | −4.09 | | > −4.00 | | > −4.00 | |
| SF-539 | −4.41 | | > −4.00 | | > −4.00 | |
| SNB-19 | −4.28 | | > −4.00 | | > −4.00 | |
| SNB-75 | −4.08 | | > −4.00 | | > −4.00 | |
| SNB-78 | −4.45 | | > −4.00 | | > −4.00 | |
| U-251 | −4.51 | | > −4.00 | | > −4.00 | |
| XF-498 | > −4.00 | | > −4.00 | | > −4.00 | |
| Melanomia | | | | | | |
| LOX-IMVI | −4.60 | | > −4.00 | | > −4.00 | |
| MALMB-3M | −4.30 | | > −4.00 | | > −4.00 | |
| M-14 | −4.29 | | > −4.00 | | > −4.00 | |
| M19-MEL | −4.52 | | > −4.00 | | > −4.00 | |
| SK-MEL-28 | −4.33 | | > −4.00 | | > −4.00 | |
| SK-MEL-5 | −4.39 | | > −4.00 | | > −4.00 | |
| UACC-257 | −4.65 | | −4.21 | | > −4.00 | |
| UACC-62 | −4.74 | | −4.29 | | > −4.00 | |
| Ovarian Cancer | | | | | | |
| IGROV-1 | −4.04 | | > −4.00 | | > −4.00 | |
| OVCAR-3 | −4.64 | | −4.23 | | > −4.00 | |
| OVCAR 4 | −4.49 | | > −4.00 | | > −4.00 | |
| OVCAR-8 | −4.51 | | > −4.00 | | > −4.00 | |
| Renal Cancer | | | | | | |
| 786-0 | −4.03 | | > −4.00 | | > −4.00 | |
| A498 | > −4.00 | | > −4.00 | | > −4.00 | |
| ACHN | −4.49 | | > −4.00 | | > −4.00 | |
| CAK1-1 | > −4.00 | | > −4.00 | | > −4.00 | |
| RXF-393 | −4.50 | | −4.05 | | > −4.00 | |
| RXF-631 | −4.37 | | > −4.00 | | > −4.00 | |
| SN-12C | > −4.00 | | > −4.00 | | > −4.00 | |
| TK-10 | −4.01 | | > −4.00 | | > −4.00 | |
| UO-31 | −4.03 | | > −4.00 | | > −4.00 | |
| MG_MID | −4.37 | | −4.00 | | −4.00 | |
| Delta | 0.56 | | 0.34 | | 0.00 | |
| Range | 0.93 | | 0.40 | | 0.00 | |

TABLE 18

| | BCH-657 | | | | | |
|---|---|---|---|---|---|---|
| National Cancer Institute Developmental Therapeutics Program Mean Graphs | NSC: Units: Molar Report Date: November 26, 1990 | | | SSPL: Exp. ID: Test Date: October 22, 1990 | | |
| Panel/Cell Line | Log₁₀GI50 | GI50 | Log₁₀TGI | TGI | Log₁₀LC50 | LC50 |
| Leukemia | | | | | | |
| CCRF-CEM | −6.38 | | −5.56 | | > −4.00 | |
| HL-60 (TB) | — | | — | | — | |
| K-562 | −6.27 | | −5.40 | | > −4.00 | |
| MOLT-4 | −6.35 | | −5.53 | | −4.29 | |
| RPMI-8226 | −6.45 | | −5.67 | | > −4.00 | |
| SR | — | | — | | — | |
| Non-Small Cell Lung Cancer | | | | | | |
| A-549/ATCC | −5.59 | | −5.09 | | −4.41 | |
| EKVX | −5.62 | | −5.26 | | > −4.00 | |
| HOP-18 | −5.81 | | −5.50 | | −5.19 | |
| HOP-62 | — | | — | | — | |
| HOP-92 | −6.55 | | > −6.00 | | > −6.00 | |
| NCI-H226 | −5.69 | | −5.32 | | −4.85 | |
| NCI-H23 | −5.89 | | −5.45 | | > −4.00 | |
| NCI-H322M | −5.85 | | −5.41 | | −4.93 | |
| NCI-H460 | −5.68 | | −5.34 | | > −4.00 | |

TABLE 18-continued

| BCH-657 | | | | | | |
|---|---|---|---|---|---|---|
| National Cancer Institute Developmental Therapeutics Program Mean Graphs | | | NSC: Units: Molar Report Date: November 26, 1990 | | SSPL: Exp. ID: Test Date: October 22, 1990 | |
| Panel/Cell Line | Log$_{10}$GI50 | GI50 | Log$_{10}$TGI | TGI | Log$_{10}$LC50 | LC50 |
| NCl-H522 | −6.62 | | −6.12 | | — | |
| LXFL-529L | −6.23 | | −5.71 | | −5.30 | |
| Small Cell Lung Cancer | | | | | | |
| DMS 114 | −6.15 | | −5.49 | | > −4.00 | |
| DMS 273 | −5.64 | | −5.27 | | > −5.00 | |
| Colon Cancer | | | | | | |
| COLO-205 | −6.10 | | −5.35 | | > −4.00 | |
| DLD-1 | −6.10 | | −5.44 | | −4.44 | |
| HCC-2998 | — | | — | | — | |
| HCT-116 | −6.49 | | −5.92 | | −5.30 | |
| HCT-15 | −6.43 | | −5.48 | | > −4.00 | |
| HT-29 | −5.79 | | −5.05 | | > −4.00 | |
| KM112 | −5.55 | | −4.78 | | > −4.00 | |
| KM-20L2 | −6.32 | | −5.63 | | > −4.00 | |
| SW-620 | −6.02 | | −5.17 | | > −4.00 | |
| CNS Cancer | | | | | | |
| SF-268 | −5.87 | | −5.39 | | > −5.00 | |
| SF-295 | −5.44 | | −4.98 | | −4.28 | |
| SF-539 | −5.78 | | −5.50 | | −5.22 | |
| SNB-19 | −5.83 | | −5.28 | | −4.54 | |
| SNB-75 | −5.82 | | −5.52 | | −5.22 | |
| SNB-78 | −5.61 | | −5.14 | | > −4.00 | |
| U-251 | −5.86 | | −5.49 | | −5.13 | |
| XF-498 | −5.62 | | −5.29 | | −4.88 | |
| Melanomia | | | | | | |
| LOX-IMVI | −5.79 | | −5.30 | | −4.37 | |
| MALMB-3M | −5.69 | | −5.35 | | −5.01 | |
| M-14 | −5.92 | | −5.49 | | −5.05 | |
| M19-MEL | −6.30 | | −5.53 | | > −4.00 | |
| SK-MEL-2 | −5.76 | | −5.42 | | −5.08 | |
| SK-MEL-28 | −6.12 | | −4.96 | | > −4.00 | |
| SK-MEL-5 | — | | — | | — | |
| UACC-257 | −5.63 | | −5.19 | | > −4.00 | |
| UACC-62 | −5.73 | | −5.15 | | > −4.00 | |
| Ovarian Cancer | | | | | | |
| IGROV-1 | −5.92 | | −5.39 | | −4.29 | |
| OVCAR-3 | −5.85 | | −5.37 | | −4.72 | |
| OVCAR-4 | −5.79 | | −5.52 | | −5.25 | |
| OVCAR-5 | −5.74 | | −5.45 | | −5.15 | |
| OVCAR-8 | −6.01 | | −5.36 | | > −4.00 | |
| SK-OV-3 | −5.31 | | −4.77 | | −4.37 | |
| Renal Cancer | | | | | | |
| 786-0 | −5.75 | | −5.39 | | −5.03 | |
| ACHN | −5.92 | | −5.60 | | −5.28 | |
| CAK1-1 | −5.50 | | −4.97 | | −4.29 | |
| RXF-393 | −6.41 | | −5.87 | | −5.43 | |
| RXF-631 | −5.84 | | −5.16 | | > −4.00 | |
| SN-12C | −5.92 | | −5.49 | | −5.06 | |
| TK-10 | −5.67 | | −5.34 | | −5.01 | |
| UO-31 | −6.00 | | −5.65 | | −5.31 | |
| MG_MID | −5.93 | | −5.39 | | −4.58 | |
| Delta | 0.70 | | 0.73 | | 0.85 | |
| Range | 1.32 | | 1.35 | | 1.43 | |

TABLE 19

BCH-658

| National Cancer Institute Developmental Therapeutics Program Mean Graphs | | NSC: D-636532-Q/1 Units: Molar Report Date: November 26, 1990 | | SSPL: Exp. ID: 9010SC22 Test Date: October 22, 1990 | |
|---|---|---|---|---|---|
| Panel/Cell Line | $Log_{10}GI50$ GI50 | $Log_{10}TGI$ | TGI | $Log_{10}LC50$ | LC50 |
| Leukemia | | | | | |
| CCRF-CEM | > −4.00 | > −4.00 | | > −4.00 | |
| HL-60 (TB) | — | — | | — | |
| K-562 | > −4.00 | > −4.00 | | > −4.00 | |
| MOLT-4 | > −4.00 | > −4.00 | | > −4.00 | |
| RPMI-8226 | > −4.00 | > −4.00 | | > −4.00 | |
| SR | — | — | | — | |
| Non-Small Cell Lung Cancer | | | | | |
| A-549/ATCC | > −4.00 | > −4.00 | | > −4.00 | |
| EKVX | > −4.00 | > −4.00 | | > −4.00 | |
| HOP-18 | > −4.00 | > −4.00 | | > −4.00 | |
| HOP-62 | — | — | | — | |
| HOP-92 | −4.70 | −4.16 | | > −4.00 | |
| NCI-H226 | > −4.00 | > −4.00 | | > −4.00 | |
| NCI-H23 | > −4.00 | > −4.00 | | > −4.00 | |
| NCI-H460 | > −4.00 | > −4.00 | | > −4.00 | |
| NCI-H522 | −4.52 | > −4.00 | | > −4.00 | |
| LXFL-529L | > −4.00 | > −4.00 | | > −4.00 | |
| Small Cell Lung Cancer | | | | | |
| DMS 114 | −4.53 | > −4.00 | | > −4.00 | |
| DMS 273 | > −4.00 | > −4.00 | | > −4.00 | |
| Colon Cancer | | | | | |
| COLO-205 | > −4.00 | > −4.00 | | > −4.00 | |
| DLD-1 | > −4.00 | > −4.00 | | > −4.00 | |
| HCC-2998 | — | — | | — | |
| HCT-116 | −4.15 | > −4.00 | | > −4.00 | |
| HCT-15 | −4.07 | > −4.00 | | > −4.00 | |
| HT-29 | −4.32 | > −4.00 | | > −4.00 | |
| KM12 | > −4.00 | > −4.00 | | > −4.00 | |
| KM-20L2 | −4.30 | > −4.00 | | > −4.00 | |
| SW-620 | > −4.00 | > −4.00 | | > −4.00 | |
| CNS Cancer | | | | | |
| SF-268 | −4.23 | > −4.00 | | > −4.00 | |
| SF-295 | −4.33 | > −4.00 | | > −4.00 | |
| SF-539 | −4.41 | > −4.00 | | > −4.00 | |
| SNB-19 | −4.31 | > −4.00 | | > −4.00 | |
| SNB-75 | −4.68 | −4.34 | | −4.00 | |
| SNB-78 | −4.11 | > −4.00 | | > −4.00 | |
| U-251 | −4.32 | > −4.00 | | > −4.00 | |
| XF-498 | −4.24 | > −4.00 | | > −4.00 | |
| Melanomia | | | | | |
| LOX-IMVI | > −4.00 | > −4.00 | | > −4.00 | |
| MALMB-3M | −4.28 | > −4.00 | | > −4.00 | |
| M-14 | > −4.00 | > −4.00 | | > −4.00 | |
| M19-MEL | −4.51 | −4.00 | | > −4.00 | |
| SK-MEL-2 | −4.06 | > −4.00 | | > −4.00 | |
| SK-MEL-28 | > −4.00 | > −4.00 | | > −4.00 | |
| SK-MEL-5 | — | — | | — | |
| UACC-257 | > −4.00 | > −4.00 | | > −4.00 | |
| UACC-62 | > −4.00 | > −4.00 | | > −4.00 | |
| Ovarian Cancer | | | | | |
| IGROV-1 | > −4.00 | > −4.00 | | > −4.00 | |
| OVCAR-3 | −4.67 | > −4.00 | | > −4.00 | |
| OVCAR-4 | > −4.00 | > −4.00 | | > −4.00 | |
| OVCAR-5 | > −4.00 | > −4.00 | | > −4.00 | |
| OVCAR-8 | −4.08 | > −4.00 | | > −4.00 | |
| SK-OV-3 | > −4.00 | > −4.00 | | > −4.00 | |
| Renal Cancer | | | | | |
| 786-0 | −4.42 | > −4.00 | | > −4.00 | |
| ACHN | > −4.00 | > −4.00 | | > −4.00 | |
| CAK1-1 | > −4.00 | > −4.00 | | > −4.00 | |
| RXF-393 | −4.54 | −4.02 | | > −4.00 | |

TABLE 19-continued

BCH-658

| National Cancer Institute Developmental Therapeutics Program Mean Graphs | | | NSC: D-636532-Q/1 Units: Molar Report Date: November 26, 1990 | | SSPL: Exp. ID: 9010SC22 Test Date: October 22, 1990 | |
|---|---|---|---|---|---|---|
| Panel/Cell Line | $Log_{10}GI50$ | GI50 | $Log_{10}TGI$ | TGI | $Log_{10}LC50$ | LC50 |
| RXF-631 | −4.24 | | > −4.00 | | > −4.00 | |
| SN-12C | > −4.00 | | > −4.00 | | > −4.00 | |
| TK-10 | −4.10 | | > −4.00 | | > −4.00 | |
| UO-31 | > −4.00 | | > −4.00 | | > −4.00 | |
| MG_MID | −4.15 | | −4.01 | | −4.00 | |
| Delta | 0.54 | | 0.33 | | 0.00 | |
| Range | 0.70 | | 0.34 | | 0.00 | |

TABLE 20

BCH-660

| National Cancer Institute Developmental Therapeutics Program Mean Graphs | | | NSC: D-636533-R/1 Units: Molar Report Date: November 26, 1990 | | SSPL: Exp. ID: 9010SC22 Test Date: October 22, 1990 | |
|---|---|---|---|---|---|---|
| Panel/Cell Line | $Log_{10}GI50$ | GI50 | $Log_{10}TGI$ | TGI | $Log_{10}LC50$ | LC50 |
| Leukemia | | | | | | |
| CCRF-CEM | −6.51 | | −5.91 | | > −4.00 | |
| HL-60 (TB) | — | | — | | — | |
| K-562 | −6.40 | | −5.70 | | > −4.00 | |
| MOLT-4 | −6.47 | | −5.92 | | −5.10 | |
| RPMI-8226 | −6.63 | | −6.20 | | > −4.00 | |
| SR | — | | — | | — | |
| Non-Small Cell Lung Cancer | | | | | | |
| A-549/ATCC | −5.69 | | −5.24 | | −4.55 | |
| EKVX | −5.71 | | −5.34 | | −4.67 | |
| HOP-18 | −4.99 | | −4.61 | | −4.22 | |
| HOP-62 | — | | — | | — | |
| HOP-92 | −6.58 | | −6.02 | | −5.39 | |
| NCI-H226 | > −6.00 | | > −6.00 | | > −6.00 | |
| NCI-H23 | −6.29 | | −5.67 | | — | |
| NCI-H460 | −5.65 | | −5.25 | | > −4.00 | |
| NCI-H522 | −6.68 | | −6.23 | | — | |
| LXFL-529L | −6.48 | | −5.91 | | −5.43 | |
| Small Cell Lung Cancer | | | | | | |
| DMS 114 | −6.27 | | −5.58 | | > −4.00 | |
| DMS 273 | −5.72 | | −5.37 | | — | |
| Colon Cancer | | | | | | |
| COLO-205 | −6.20 | | −5.37 | | > −4.00 | |
| DLD-1 | −6.37 | | −5.65 | | > −4.00 | |
| HCC-2998 | — | | — | | — | |
| HCT-116 | −6.49 | | −5.98 | | −5.46 | |
| HCT-15 | −6.47 | | −5.82 | | > −4.00 | |
| HT-29 | −5.65 | | > −4.00 | | > −4.00 | |
| KM112 | −6.12 | | −5.40 | | > −4.00 | |
| KM-20L2 | −6.13 | | −5.32 | | > −4.00 | |
| SW-620 | −6.27 | | −5.61 | | > −4.00 | |
| CNS Cancer | | | | | | |
| SF-268 | −6.26 | | −5.38 | | −4.38 | |
| SF-295 | −5.65 | | −5.03 | | −4.09 | |
| SF-539 | −6.00 | | −5.67 | | −5.33 | |
| SNB-19 | −6.05 | | −5.30 | | −4.56 | |
| SNB-75 | −6.38 | | −5.83 | | −5.33 | |
| SNB-78 | −6.22 | | −5.51 | | > −4.00 | |
| U-251 | −5.86 | | −5.37 | | −4.80 | |
| XF-498 | −5.76 | | −5.44 | | −5.13 | |
| Melanomia | | | | | | |
| LOX-IMVI | −6.07 | | −5.49 | | > −4.00 | |
| MALMB-3M | −5.71 | | −5.39 | | — | |
| M-14 | −6.15 | | −5.66 | | −5.25 | |
| M19-MEL | −6.42 | | −5.83 | | — | |

TABLE 20-continued

BCH-660

| National Cancer Institute Developmental Therapeutics Program Mean Graphs | | | NSC: D-636533-R/1 Units: Molar Report Date: November 26, 1990 | | SSPL: Exp. ID: 9010SC22 Test Date: October 22, 1990 | |
|---|---|---|---|---|---|---|
| Panel/Cell Line | $\text{Log}_{10}\text{GI50}$ | GI50 | $\text{Log}_{10}\text{TGI}$ | TGI | $\text{Log}_{10}\text{LC50}$ | LC50 |
| SK-MEL-2 | −5.67 | | −5.30 | | −4.39 | |
| SK-MEL-28 | −6.31 | | −5.75 | | −5.30 | |
| SK-MEL-5 | — | | — | | — | |
| UACC-257 | −5.68 | | −5.27 | | > −4.00 | |
| UACC-62 | −6.19 | | −5.46 | | > −4.00 | |
| Ovarian Cancer | | | | | | |
| IGROV-1 | −6.07 | | −5.54 | | −5.04 | |
| OVCAR-3 | −6.26 | | −5.67 | | −5.18 | |
| OVCAR-4 | −5.92 | | −5.61 | | −5.29 | |
| OVCAR-6 | −5.76 | | −5.49 | | −5.22 | |
| OVCAR-8 | −6.36 | | −5.61 | | > −4.00 | |
| SK-OV-3 | −5.74 | | −5.45 | | −5.15 | |
| Renal Cancer | | | | | | |
| 786-0 | −5.98 | | −5.65 | | −5.31 | |
| ACHN | −6.23 | | −5.61 | | −5.06 | |
| CAK1-1 | −5.47 | | −5.04 | | −4.25 | |
| RXF-393 | −6.55 | | −6.08 | | −5.55 | |
| RXF-631 | −5.92 | | −5.55 | | −5.18 | |
| SN-12C | −6.15 | | −5.69 | | −5.31 | |
| TK-10 | −5.66 | | −5.25 | | −4.70 | |
| UO-31 | −6.39 | | −5.86 | | −5.40 | |
| MG_MID | −6.09 | | −5.55 | | −4.67 | |
| Delta | 0.59 | | 0.68 | | 0.88 | |
| Range | 1.69 | | 2.23 | | 1.55 | |

TABLE 21

BCH-687

| National Cancer Institute Developmental Therapeutics Program Mean Graphs | | | NSC: D-638338-F/1 Units: Molar Report Date: March 1, 1991 | | SSPL: Y71X Exp. ID: 9012NS84 Test Date: December 18, 1990 | |
|---|---|---|---|---|---|---|
| Panel/Cell Line | $\text{Log}_{10}\text{GI50}$ | GI50 | $\text{Log}_{10}\text{TGI}$ | TGI | $\text{Log}_{10}\text{LC50}$ | LC50 |
| Leukemia | | | | | | |
| CCRF-CEM | −4.74 | | > −4.00 | | > −4.00 | |
| HL-60 (TB) | −5.10 | | −4.17 | | > −4.00 | |
| K-562 | −4.87 | | −4.34 | | > −4.00 | |
| MOLT-4 | −4.89 | | −4.36 | | > −4.00 | |
| RPMI-8226 | −4.93 | | −4.44 | | > −4.00 | |
| SR | — | | — | | — | |
| Non-Small Cell Lung Cancer | | | | | | |
| A-549/ATCC | −5.17 | | > −4.00 | | > −4.00 | |
| EKVX | −4.78 | | −4.51 | | −4.24 | |
| HOP-18 | −4.52 | | −4.10 | | > −4.00 | |
| HOP-62 | −4.84 | | −4.49 | | −4.13 | |
| HOP-92 | −4.19 | | > −4.00 | | > −4.00 | |
| NCI-H226 | — | | — | | — | |
| NCI-H23 | −4.66 | | > −4.00 | | > −4.00 | |
| NCI-H460 | −4.72 | | −4.04 | | > −4.00 | |
| NCI-H522 | −5.50 | | −4.78 | | > −4.00 | |
| LXFL-529L | −4.95 | | −4.63 | | −4.31 | |
| Small Cell Lung Cancer | | | | | | |
| DMS 114 | −5.33 | | −4.66 | | > −4.00 | |
| DMS 273 | −4.84 | | −4.51 | | −4.18 | |
| Colon Cancer | | | | | | |
| COLO-205 | −5.25 | | −4.72 | | −4.32 | |
| DLD-1 | −4.89 | | −4.52 | | −4.14 | |
| HCC-2998 | — | | — | | — | |
| HCT-116 | −5.12 | | −4.59 | | −4.13 | |
| HCT-15 | −5.23 | | −4.70 | | −4.30 | |
| HT-29 | −4.66 | | −4.18 | | > −4.00 | |

TABLE 21-continued

BCH-687

| National Cancer Institute Developmental Therapeutics Program Mean Graphs | | NSC: D-638338-F/1   Units: Molar Report Date: March 1, 1991 | | SSPL: Y71X   Exp. ID: 9012NS84 Test Date: December 18, 1990 | |
|---|---|---|---|---|---|
| Panel/Cell Line | $Log_{10}GI50$   GI50 | $Log_{10}TGI$ | TGI | $Log_{10}LC50$ | LC50 |
| KM112 | −4.71 | −4.30 | | > −4.00 | |
| KM-20L2 | −4.51 | −4.05 | | > −4.00 | |
| SW-620 | −5.21 | −4.72 | | −4.34 | |
| CNS Cancer | | | | | |
| SF-268 | −4.52 | > −4.00 | | > −4.00 | |
| SF-295 | −4.56 | > −4.00 | | > −4.00 | |
| SF-539 | −4.91 | −4.53 | | −4.15 | |
| SNB-19 | −4.55 | > −4.00 | | > −4.00 | |
| SNB-75 | −4.47 | −4.12 | | > −4.00 | |
| SNB-78 | −4.41 | > −4.00 | | > −4.00 | |
| U-251 | −4.74 | −4.18 | | > −4.00 | |
| XF-498 | — | — | | — | |
| Melanomia | | | | | |
| LOX-IMVI | −4.94 | −4.61 | | −4.27 | |
| MALMB-3M | −4.89 | −4.59 | | −4.28 | |
| M-14 | −4.84 | −4.53 | | −4.21 | |
| M19-MEL | −5.47 | −5.00 | | −4.36 | |
| SK-MEL-28 | −4.72 | −4.18 | | > −4.00 | |
| SK-MEL-5 | −5.36 | −4.77 | | −4.37 | |
| UACC-257 | −5.32 | −4.75 | | −4.35 | |
| UACC-62 | −4.87 | −4.49 | | −4.11 | |
| Ovarian Cancer | | | | | |
| IGROV-1 | −4.70 | −4.35 | | > −4.00 | |
| OVCAR-3 | −5.55 | −5.11 | | > −4.00 | |
| OVCAR-4 | −4.86 | −4.58 | | −4.29 | |
| OVCAR-5 | −4.48 | −4.32 | | −4.16 | |
| OVCAR-8 | −5.11 | −4.53 | | −4.01 | |
| Renal Cancer | | | | | |
| 786-0 | −4.61 | > −4.00 | | > −4.00 | |
| A498 | −4.71 | −4.33 | | > −4.00 | |
| ACHN | −5.21 | −4.72 | | −4.34 | |
| CAK1-1 | −4.51 | −4.03 | | > −4.00 | |
| RXF-393 | −4.73 | −4.38 | | −4.03 | |
| RXF-631 | −4.69 | > −4.00 | | > −4.00 | |
| SN-12C | −4.84 | −4.55 | | −4.27 | |
| TK-10 | −4.37 | −4.02 | | > −4.00 | |
| UO-31 | −4.52 | > −4.00 | | > −4.00 | |
| MG_MID | −4.85 | −4.37 | | −4.10 | |
| Delta | 0.70 | 0.74 | | 0.27 | |
| Range | 1.36 | 1.11 | | 0.37 | |

TABLE 22

BCH-688

| National Cancer Institute Developmental Therapeutics Program Mean Graphs | | NSC: D-638339-G/1   Units: Molar Report Date: March 1, 1991 | | SSPL: Y71X   Exp. ID: 9012NS84 Test Date: December 18, 1990 | |
|---|---|---|---|---|---|
| Panel/Cell Line | $Log_{10}GI50$   GI50 | $Log_{10}TGI$ | TGI | $Log_{10}LC50$ | LC50 |
| Leukemia | | | | | |
| CCRF-CEM | −4.78 | −4.28 | | > −4.00 | |
| HL-60 (TB) | −4.60 | > −4.00 | | > −4.00 | |
| K-562 | −4.32 | > −4.00 | | > −4.00 | |
| MOLT-4 | −4.25 | > −4.00 | | > −4.00 | |
| RPMI-8226 | −4.26 | > −4.00 | | > −4.00 | |
| SR | — | — | | — | |
| Non-Small Cell Lung Cancer | | | | | |
| A-549/ATCC | > −4.00 | > −4.00 | | > −4.00 | |
| EKVX | −4.42 | > −4.00 | | > −4.00 | |
| HOP-18 | > −4.00 | > −4.00 | | > −4.00 | |
| HOP-62 | > −4.00 | > −4.00 | | > −4.00 | |
| HOP-92 | > −4.00 | > −4.00 | | > −4.00 | |

TABLE 22-continued

BCH-688

| National Cancer Institute Developmental Therapeutics Program Mean Graphs | | NSC: D-638339-G/1 Units: Molar Report Date: March 1, 1991 | | SSPL: Y71X Exp. ID: 9012NS84 Test Date: December 18, 1990 | |
|---|---|---|---|---|---|
| Panel/Cell Line | Log$_{10}$GI50 | GI50 | Log$_{10}$TGI | TGI | Log$_{10}$LC50 | LC50 |
| NCI-H226 | — | | — | | — | |
| NCI-H23 | > −4.00 | | > −4.00 | | > −4.00 | |
| NCI-H460 | > −4.00 | | > −4.00 | | > −4.00 | |
| NCI-H522 | −4.56 | | > −4.00 | | > −4.00 | |
| LXFL-529L | −4.08 | | > −4.00 | | > −4.00 | |
| Small Cell Lung Cancer | | | | | | |
| DMS 114 | −4.07 | | > −4.00 | | > −4.00 | |
| DMS 273 | > −4.00 | | > −4.00 | | > −4.00 | |
| Colon Cancer | | | | | | |
| COLO-205 | > −4.00 | | > −4.00 | | > −4.00 | |
| DLD-1 | > −4.00 | | > −4.00 | | > −4.00 | |
| HCC-2998 | — | | — | | — | |
| HCT-116 | −4.11 | | > −4.00 | | > −4.00 | |
| HCT-15 | −4.17 | | > −4.00 | | > −4.00 | |
| HT-29 | > −4.00 | | > −4.00 | | > −4.00 | |
| KM112 | > −4.00 | | > −4.00 | | > −4.00 | |
| KM-20L2 | — | | — | | — | |
| SW-620 | > −4.00 | | > −4.00 | | > −4.00 | |
| CNS Cancer | | | | | | |
| SF-268 | — | | — | | — | |
| SF-295 | −4.03 | | > −4.00 | | > −4.00 | |
| SF-539 | −4.37 | | > −4.00 | | > −4.00 | |
| SNB-19 | > −4.00 | | > −4.00 | | > −4.00 | |
| SNB-75 | > −4.00 | | > −4.00 | | > −4.00 | |
| SNB-78 | −4.37 | | > −4.00 | | > −4.00 | |
| U-251 | −4.31 | | > −4.00 | | > −4.00 | |
| XF-498 | > −4.00 | | > −4.00 | | > −4.00 | |
| Melanomia | | | | | | |
| LOX-IMVI | −4.25 | | > −4.00 | | > −4.00 | |
| MALMB-3M | > −4.00 | | > −4.00 | | > −4.00 | |
| M-14 | > −4.00 | | > −4.00 | | > −4.00 | |
| M19-MEL | −4.30 | | > −4.00 | | > −4.00 | |
| SK-MEL-28 | > −4.00 | | > −4.00 | | > −4.00 | |
| SK-MEL-5 | −4.07 | | > −4.00 | | > −4.00 | |
| UACC-257 | > −4.00 | | > −4.00 | | > −4.00 | |
| UACC-62 | > −4.00 | | > −4.00 | | > −4.00 | |
| | | | > −4.00 | | > −4.00 | |
| Ovarian Cancer | | | | | | |
| IGROV-1 | > −4.00 | | > −4.00 | | > −4.00 | |
| OVCAR-3 | −4.11 | | > −4.00 | | > −4.00 | |
| OVCAR-4 | > −4.00 | | > −4.00 | | > −4.00 | |
| OVCAR-5 | — | | — | | — | |
| OVCAR-8 | −4.12 | | > −4.00 | | > −4.00 | |
| Renal Cancer | | | | | | |
| 786-0 | −4.23 | | > −4.00 | | > −4.00 | |
| A498 | > −4.00 | | > −4.00 | | > −4.00 | |
| ACHN | > −4.00 | | > −4.00 | | > −4.00 | |
| CAK1-1 | > −4.00 | | > −4.00 | | > −4.00 | |
| RXF-393 | −4.14 | | > −4.00 | | > −4.00 | |
| RXF-631 | −4.21 | | > −4.00 | | > −4.00 | |
| SN-12C | > −4.00 | | > −4.00 | | > −4.00 | |
| TK-10 | > −4.00 | | > −4.00 | | > −4.00 | |
| UO-31 | −4.02 | | > −4.00 | | > −4.00 | |
| MG_MID | −4.12 | | −4.01 | | −4.00 | |
| Delta | 0.66 | | 0.28 | | 0.00 | |
| Range | 0.78 | | 0.28 | | 0.00 | |

TABLE 23

| | \multicolumn{6}{c}{CONCENTRATION: 10 µg/DISK} |
|---|---|---|---|---|---|---|
| | MCF7 | MCF7/ADR | HT29 | LS180 | BE-1 | MATB.WT |
| BCH-651 | 0a) | 10.0 ± 5.0 | 0 | 0 | 0 | 0 |
| BCH-654 | 0 | 0 | 0 | 24.4 ± 8.6 | 24.4 ± 8.6 | 0 |
| BCH-658 | 0 | 0 | 0 | 48.8 ± 34.5 | 0 | 0 |
| BCH-660 | 27.4 ± 4.3 | 9.1 ± 4.3 | 27.4 ± 4.3 | 15.0 ± 4.2 | 45.7 ± 21.5 | 137.2 ± 21.5 |
| BCH-674 | 0 | 0 | 122.2 ± 80.6 | 0 | — | 30.5 ± 13.0 |
| BCH-675 | 0 | 0 | 0 | 0 | 0 | 0 |
| BCH-681 | —b) | 82.7 ± 30.1 | 106.7 ± 21.5 | — | — | 51.8 ± 4.3 |
| BCH-684 | 115.9 ± 8.6 | 161.6 ± 30.1 | 137.2 ± 21.5 | — | — | 131.3 ± 12.9 |
| BCH-687 | 71.1 ± 9.3 | 61.0 ± 6.1 | 61.0 ± 12.2 | 152.5 ± 30.5 | 85.0 ± 44.2 | 42.7 ± 6.1 |
| BCH-691 | 186.5 ± 4.9 | 115.5 ± 9.1 | 137.0 ± 21.2 | 148.5 ± 4.9 | 55.0 ± 10.0 | 120.0 ± 50.5 |
| BCH-692 | 131.0 ± 12.7 | 122.0 ± 10.0 | 105.0 ± 5.0 | 130.0 ± 12.5 | 0 | 150.0 ± 18.5 |
| BCH-693 | 0 | 24.4 ± 17.2 | 0 | 0 | 0 | 0 |
| BCH-694 | 61.0 ± 0.0 | 0 | 30.5 ± 8.6 | 48.8 ± 17.2 | 54.9 ± 8.6 | 76.2 ± 2.5 |
| BCH-704 | 183.0 ± 10.8 | 122.0 ± 25.8 | 39.6 ± 12.9 | 38.3 ± 2.4 | — | 198.5 ± 21.9 |
| BCH-706 | 103.7 ± 25.5 | 91.5 ± 8.6 | — | — | — | — |
| BCH-710 | 0 | 0 | 30.0 ± 8.4 | 48.5 ± 26.1 | — | 44.0 |
| BCH-711 | 0 | 24.4 ± 8.5 | 27.0 ± 4.2 | 18.0 ± 16.9 | — | 27.0 ± 4.2 |
| BCH-712 | 0 | 24.0 ± 8.4 | 0 | 9.0 ± 4.2 | — | 21.0 ± 4.3 |
| BCH-713 | 0 | 24.0 ± 8.6 | 0 | 0 | — | 0 |
| BCH-714 | 0 | 0 | 0 | 9.0 ± 4.2 | — | 0 |
| BCH-717 | 0 | 0 | 0 | 0 | — | 0 |
| BCH-721 | 55.0 ± 8.4 | 91.0 ± 86.2 | 55.5 ± 8.0 | 18.9 | — | 33.0 ± 4.2 |

| | MATB/ADR | P388 | P388/ADR | M5076 | B16 | LL |
|---|---|---|---|---|---|---|
| BCH-651 | 0 | 45.7 ± 12.9 | 10.0 ± 0.0 | 15.2 ± 4.3 | 0 | — |
| BCH-654 | 0 | 0 | 0 | 0 | 0 | — |
| BCH-658 | 0 | 42.7 ± 17.2 | 18.3 ± 8.6 | 26.6 ± 13.6 | 0 | — |
| BCH-660 | 24.4 ± 8.6 | 18.3 ± 8.6 | 6.1 ± 8.6 | 24.4 ± 8.6 | 6.1 ± 8.6 | — |
| BCH-674 | 24.4 ± 8.6 | 30.5 ± 25.8 | 0 | — | 91.5 ± 60.3 | 54.9 ± 8.6 |
| BCH-675 | 22.3 ± 3.5 | 0 | 10.1 ± 9.3 | 0 | 0 | 75.2 ± 40.5 |
| BCH-681 | 54.9 ± 8.6 | — | — | — | — | — |
| BCH-684 | 122.0 ± 17.0 | — | — | — | — | — |
| BCH-687 | 69.1 ± 7.0 | 81.3 ± 30.0 | 0 | 0 | 34.6 ± 3.6 | 62.8 ± 30.7 |
| BCH-691 | 0 | 100.5 ± 50.0 | 50.0 ± 10.0 | 120.0 ± 28.8 | 114.0 ± 30.2 | 50.6 ± 25.5 |
| BCH-692 | 0 | 50.5 ± 10.9 | 25.0 ± 10.0 | 50.0 ± 25.5 | 0 | 80.5 ± 20.5 |
| BCH-693 | 0 | 120.0 ± 0.0 | 20.0 ± 0.0 | 27.4 ± 4.3 | 0 | — |
| BCH-694 | 27.4 ± 4.3 | 67.1 ± 8.6 | 6.1 ± 8.6 | 27.4 ± 4.3 | 0 | — |
| BCH-704 | 320.2 ± 64.7 | — | — | — | — | — |
| BCH-706 | — | — | — | — | — | — |
| BCH-710 | 288.0 ± 21.9 | 13.0 ± 0.0 | 0 | 209.5 ± 21.9 | 21.0 ± 2.1 | — |
| BCH-711 | 45.5 ± 21.9 | 45.5 ± 21.9 | 40.0 ± 20.0 | 55.0 ± 8.4 | 27.0 ± 4.2 | — |
| BCH-712 | 0 | 6.1 ± 0.0 | 0 | 0 | 0 | — |
| BCH-713 | 0 | 0 | 0 | 0 | 0 | — |
| BCH-714 | 0 | 0 | 0 | 15.5 ± 5.0 | 0 | — |
| BCH-717 | 0 | 0 | 0 | 18.3 | 0 | — |
| BCH-721 | 45.5 ± 21.9 | 45.5 ± 21.9 | 21.0 ± 21.2 | 78.0 ± 18.3 | 76.0 ± 21.2 | — | a) Zone Units, 200 units of activity represents 6.5 mm of a clear zone from the disk edge.
b) Compounds were not tested in cell lines with a slash indicated above.

TABLE 24

| | \multicolumn{6}{c}{CONCENTRATION: 100 µg/DISK} |
|---|---|---|---|---|---|---|
| | MCF7 | MCF7/ADR | HT29 | LS180 | BE-1 | MATB.WT |
| BCH-651 | 115.9 ± 8.6 | 131.1 ± 30.1 | 61.0 ± 1.0 | 76.2 ± 21.5 | 106.7 ± 21.5 | 36.6 ± 8.6 |
| BCH-653 | 106.1 ± 21.5 | 91.5 ± 43.1 | 42.7 ± 8.6 | 35.5 ± 0.7 | 76.2 ± 21.5 | 0 |
| BCH-654 | 115.9 ± 8.6 | 155.6 ± 12.7 | 106.5 ± 21.9 | 158.5 ± 9.1 | 153.0 ± 1.4 | 152.5 ± 25.8 |
| BCH-658 | 0a) | 0 | 0 | 164.7 ± 25.8 | 0 | 0 |
| BCH-660 | 82.3 ± 12.9 | 109.8 ± 10.0 | 103.7 ± 2.1 | 76.0 ± 4.2 | 125.0 ± 12.7 | 137.2 ± 21.5 |
| BCH-674 | 76.2 ± 21.6 | 339.6 ± 4.3 | 36.6 ± 17.2 | 67.1 ± 8.6 | — | 198.2 ± 21.5 |
| BCH-675 | 30.5 ± 10.5 | 26.3 ± 14.0 | 0 | 148.4 ± 31.3 | 46.7 ± 5.3 | 32.5 ± 9.3 |
| BCH-681 | — | 326.3 ± 56.0 | 213.5 ± 43.1 | — | — | 176.9 ± 8.6 |
| BCH-684 | 225.7 ± 25.8 | 437.1 ± 30.1 | 170.8 ± 86.2 | — | — | 366.0 ± 172.5 |
| BCH-687 | 152.5 ± 50.0 | 140.0 ± 32.3 | 150.4 ± 25.3 | 233.8 ± 17.6 | 162.6 ± 70.4 | 97.6 ± 20.0 |
| BCH-691 | 417.5 ± 99.7 | 213.5 ± 43.1 | 198.0 ± 21.2 | 287.0 ± 80.3 | 155.5 ± 50.3 | 380.0 ± 120.0 |
| BCH-692 | 289.5 ± 22.0 | 237.9 ± 8.6 | 181.5 ± 2.1 | 250.0 ± 8.4 | 100.0 ± 50.0 | 400.5 ± 100.0 |
| BCH-693 | 67.1 ± 34.5 | 67.1 ± 25.8 | 39.6 ± 4.3 | 39.6 ± 4.3 | 76.2 ± 21.5 | 42.7 ± 8.8 |
| BCH-694 | 149.4 ± 12.9 | 161.5 ± 13.4 | 143.3 ± 30.1 | 153.2 ± 1.0 | 189.0 ± 8.4 | 207.0 ± 33.9 |
| BCH-704 | 320.5 ± 21.5 | 323.0 ± 16.8 | 152.5 ± 43.1 | 131.1 ± 31.1 | — | 414.8 ± 25.8 |
| BCH-705 | 79.3 ± 8.6 | 35.5 ± 7.3 | — | — | — | 259.2 ± 21.5 |
| BCH-706 | 213.5 ± 43.1 | 183.0 | — | — | — | — |

TABLE 24-continued

| | CONCENTRATION: 100 μg/DISK | | | | | |
|---|---|---|---|---|---|---|
| BCH-710 | 24.0 ± 8.4 | 106.0 ± 21.9 | 69.0 ± 30.0 | 110.0 ± 50.2 | — | 366.0 ± 0.0 |
| BCH-711 | 244.0 ± 17.2 | 222.4 ± 159.2 | 91.5 ± 43.1 | 182.5 ± 43.1 | — | 137.0 ± 21.2 |
| BCH-712 | 54.5 ± 9.1 | 79.0 ± 8.4 | 55.0 ± 8.4 | 158.0 ± 34.6 | — | 76.0 ± 21.2 |
| BCH-713 | 0 | 94.5 ± 64.7 | 0 | 45.7 ± 21.5 | — | 27.4 ± 4.3 |
| BCH-714 | 0 | 0 | 0 | 42.0 ± 26.0 | — | 0 |
| BCH-717 | 0 | 0 | 0 | 61.0 ± 0.0 | — | 0 |
| BCH-721 | 167.0 ± 21.9 | 183.0 ± 86.2 | 121.5 ± 43.1 | 122.0 ± 0.0 | — | 143.0 ± 12.7 |

| | MATB/ADR | P388 | P388/ADR | M5076 | B16 | LL |
|---|---|---|---|---|---|---|
| BCH-651 | 100.0 | 294.5 ± 101.1 | 30.5 ± 8.6 | 51.3 ± 43.3 | 27.5 ± 13.4 | 27.4 ± 4.3 |
| BCH-653 | 0 | 64.0 ± 4.2 | 66.8 ± 8.2 | 85.4 ± 25.8 | 0 | 18.3 ± 0.0 |
| BCH-654 | 134.3 ± 17.3 | 0 | 0 | 0 | 137.4 ± 21.8 | 0 |
| BCH-658 | 0 | 61.0 ± 0.0 | 51.3 ± 20.7 | 76.2 ± 21.5 | 0 | 51.9 ± 21.5 |
| BCH-660 | 161.5 ± 30.4 | 54.9 ± 0.0 | 54.9 ± 8.6 | 61.0 ± 0.0 | 85.4 ± 8.6 | 55.0 ± 8.4 |
| BCH-674 | 213.5 ± 25.8 | 137.2 ± 38.8 | 150.0 ± 8.0 | — | 122.0 ± 86.2 | 115.9 ± 8.0 |
| BCH-675 | 59.4 ± 8.6 | 152.5 ± 30.5 | 146.3 ± 32.3 | 142.0 ± 35.2 | 0 | 264.0 ± 38.0 |
| BCH-681 | 244.0 ± 43.1 | — | — | — | — | — |
| BCH-684 | 320.2 ± 107.8 | — | — | — | — | — |
| BCH-687 | 101.6 ± 35.2 | 183.0 ± 81.0 | 153.6 ± 30.6 | 410.8 ± 46.5 | 70.1 ± 13.0 | 182.6 ± 35.2 |
| BCH-691 | 200.0 ± 95.0 | 200.2 ± 50.0 | 98.0 ± 15.0 | 220.0 ± 50.8 | 250.0 ± 58.0 | 180.0 ± 120.0 |
| BCH-692 | 180.0 ± 50.5 | 180.0 ± 50.6 | 150.5 ± 50.0 | 200.0 ± 100.0 | 200.0 ± 55.0 | 140.3 ± 40.5 |
| BCH-693 | 67.1 ± 8.6 | 400.0 | 76.5 ± 21.9 | 51.8 ± 12.9 | 27.4 ± 4.3 | 45.7 ± 21.5 |
| BCH-694 | 213.5 ± 43.1 | 115.9 ± 94.8 | 39.6 ± 12.9 | 137.2 ± 99.2 | 128.0 ± 26.0 | 30.5 ± 8.6 |
| BCH-704 | 527.4 ± 72.9 | — | — | — | — | — |
| BCH-705 | 155.5 ± 4.3 | — | — | — | — | — |
| BCH-706 | — | — | — | — | — | — |
| BCH-710 | 350.0 ± 64.3 | 326.5 ± 43.1 | 110.0 ± 0.0 | 533.0 ± 20.0 | 21.0 ± 2.1 | — |
| BCH-711 | 107.0 ± 21.9 | 183.0 ± 0.0 | 150.0 ± 30.0 | 198.0 ± 21.2 | 137.0 ± 21.2 | — |
| BCH-712 | 64.0 ± 4.2 | 70.0 ± 21.2 | 42.5 ± 9.1 | 158.0 ± 34.6 | 27.0 ± 4.2 | — |
| BCH-713 | 0 | 45.7 ± 21.5 | 61.0 ± 0.0 | 42.7 ± 8.6 | 24.4 ± 8.6 | — |
| BCH-714 | 0 | 27.0 ± 4.2 | 0 | 55.0 ± 8.4 | 0 | — |
| BCH-717 | 0 | 122.0 ± 0.0 | 0 | 39.5 ± 30.4 | 106.0 ± 64.3 | — |
| BCH-721 | 137.0 ± 21.2 | 137.0 ± 21.2 | 183.0 ± 86.2 | 259.0 ± 21.2 | 198.0 ± 21.2 | — | a) Zone Units, 200 units of activity represents 6.5 mm of a clear zone from the disk edge.
b) Compounds were not tested in cell lines with a slash indicated above.

Example 19

Preparation of (1'S,1R,3S) and (1'S,1R,3R)-methyl[6-hydroxy-1-daunosamine-5,12-dioxo-3,4,5,12-tetrahydroanthraceno[2,3-C]pyran-3-yl]-ketone BCH-1127 & BCH-1128

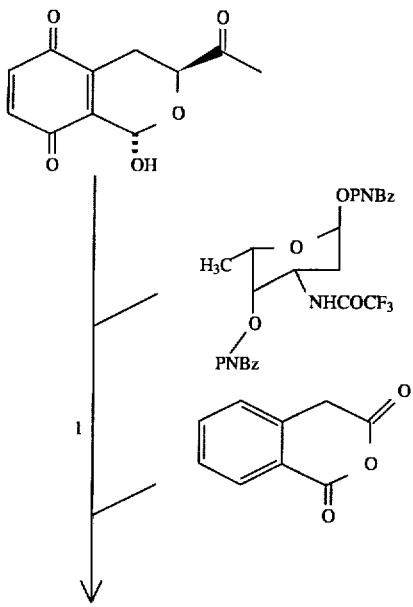

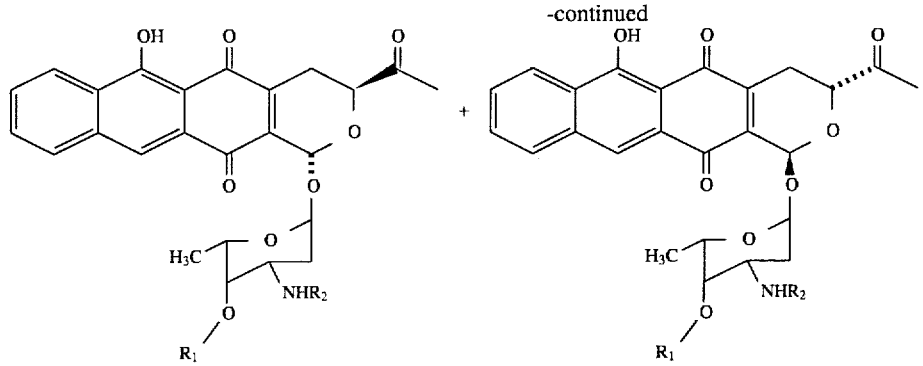

BCH-1122

2 ┌── R₁ = PNBz, R₂ = COCF₃
  ├──> R₁ = H, R₂ = COCF₃, BCH-730
4 └──> R₁ = H, R₂ = H₂Cl, BCH-1128

3 ┌── R₁ = PNBz, R₂ = COCF₃
  ├──> R₁ = H, R₂ = COCF₃, BCH-724
5 └──> R₁ = H, R₂ = H₂Cl, BCH-1127

Example 19

Step 1. (1S',1R,3S) and (1'S,1S,3R)-methyl (6-hydroxy-1-(2',3',6'-trideoxy-3'-trifluoroacetamido-4'-O-p-nitrobenzoyl-L-lyxohexopyranose)-6-hydroxy-5,12-dioxo-3,4,5,12-tetrahydroanthraceno[2,3-C]pyran-3-yl) ketone BCH-1122

To a stirred suspension of molecular sieves 3A (1.79 g) and di-O-p-nitrobenzoyl-3-trifluoroacetamido-2,3,6-trideoxy-α,β-L-lyxo-hexopyranose (2,70 g, 4.98 mmol) in dry methylene chloride (191 ml) and ether (68 ml), at −25° C., was added trimethylsilyltrifluoro-methane sulfonate (1.92 ml, 9.96 mmol). The reaction mixture was stirred at 0° C. for 1 hour, then cooled to −15° C. Methyl[1-hydroxy, 5,8-dioxo-5,8-dihydroisochroman-3yl]ketone (1.05 g, 4.75 mmol) in methylene chloride (30 ml) over molecular sieves (520 mg) was then added via canula. After 3 hours, the reaction mixture was poured in 5% NaHCO₃ (200 ml) and methylene chloride (200 ml). The aqueous layer was extracted twice with methylene chloride (100 ml). The combined organic layer was washed with brine and then dried over MgSO₄. Evaporation of solvents gave a yellow solid which was dissolved in ether (65 ml) and THF (11 ml). This solution was slowly added (over 15 min) to a stirred solution of the lithium enolate of homophtalic anhydride, obtained from the treatment of a solution of homophtalic anhydride (770 mg, 4.75 mmol) in THF (111 ml) with a solution of LDA (4.75 mmol) in THF (22 ml) at −78° C. After stirring for 20 minutes at −78° C., the mixture was warmed to room temperature for 1 hour then poured in an aqueous solution of ammonium chloride and methylene chloride. The aqueous layer was extracted twice with methylene chloride. The combined organic layer was washed with brine and then dried over MgSO₄. Evaporation of the solvents yielded a red residue which, after flash chromatography with acetone/toluene (5:95) as eluent, gave 471 mg (14%) of the (1'S,1R,3S) titled diastereomer (MP:183°–185° C.), 358 mg (11%) of mixed fractions, and 481 mg (14%) of the (1'S,1S,3R) titled diastereomer (MP:242°–246° C.). The (1'S,1S,3R) diastereomer had ¹H NMR (300 MHz,CDCl₃) δ:1.19 (d,J=6.9 Hz,3H,—CH₃), 2.12 (m,2H,H-2'), 2.35 (s,3H,—CO—CH₃), 2.50 (dd,J=12.1 Hz and 19.6 Hz, 1H, H$_{ax}$-4), 3.09 (dd,J=3.9 Hz and 19.6 Hz,1H,H$_{eq}$-4), 4.35 (q,J=6.9 Hz,1H,H-5'), 4.55 (dd,J=3.9 Hz and 12.1 Hz,1H, H-3), 4.65 (m,1H,H-3') 5.46 (d,J=2.0 Hz, 1H,H-4'), 5.77 (s,1H,H-1'), 6.01 (s,1H,H-1), 6.49 (d,J=7.5 Hz,1H,—NH), 7.70 (m,2H,ArH), 7.91 (m,1H,ArH), 8.03 (s,1H,ArH), 8,27 (q, J=2.7 Hz,4H, p-Nitrobenzoate), 8.44 (m,1H,ArH), 13.74 (s,1H,—OH phenol)

The (1'S,1S,3R) diastereomer had:
¹H NMR (300 MHz, CDCl₃) d:1.38 (d,J=6.5 Hz,3H,—CH₃), 2.20 (m,2H,H-2'), 2.34 (s,3H,—COCH₃), 2.58 (dd, J=11.4 Hz and 19.6 Hz,1H,H$_{ax}$-4), 3.11 (dd, J=4 Hz and 19.6 Hz, 1H,H$_{eq}$-4), 4.52 (dd,J=4 Hz and 11.4 Hz,1H,H-3) 4.62 (m,1H,H-3'), 4.87 (q,J=6.5 Hz,1H,H-5'), 5.47 (s,1H,H-1'), 5.62 (d, J=2.8 Hz,1H,H-4'), 6.21 (s,1H,H-1), 6.51 (d,J=7.2 Hz,1H,—NH), 7.71 (m,2H,ArH), 7.94 (m,1H,ArH), 8.11 (s,1H,ArH), 8.29 (q,J=2.3 Hz,4H, p-Nitrobenzoate), 8.44 (m,1H,ArH), 13.76 (s, 1H, OH phenol).

Step 2. (1S',1R,3S)-Methyl-(6-hydroxy-1-(3'-trifluoroacyldaunosamine)-5,12-dioxo-3,4,5,12-tetrahydroanthraceno [2,3-C]pyran-3-yl) ketone BCH-730

To a stirred solution of the (1'S,1R,3S) diastereomer (380 mg, 0.533 mmol) from step 1 in THE (14 ml) and MeOH (40 ml) at 0° was added a solution of sodium methoxide in methanol (0.6M, 1 ml). After 20 minutes, the mixture was poured in aqueous ammonium chloride (50 ml) and CH₂Cl₂ (200 ml). The aqueous layer was extracted twice with methylene chloride. The combined organic layer was washed with brine and then dried over MgSO₄. Evaporation of solvents yielded a red residue which was flash chromatographed on a short column with acetone/toluene (5:95) as the first eluent to remove the methyl p-nitrobenzoate, and then with acetone/toluene (50:50). The titled compound was obtained in 96% yield (290 mg). MP:207°–210° C.

¹H NMR (300 MHz, CDCl₃) δ:1.27 (d,J=6.5 Hz,3H,—CH₃), 2.10 (m,3H,H-2-OH), 2.33 (s,3H,—COCH₃), 2.50 (dd, J=11.6 Hz and 19.5 Hz,1H,H$_{ax}$-4), 3.09 (dd,J=3.8 Hz and 19.5 Hz,1H,H$_{eq}$-4), 3.63 (broad s,1H,H-4'), 4.14 (q, J=6.5 Hz,1H,H-5'), 4.33 (m,1H,H-3') 4.53 (dd,J=3.8 Hz and 11.6 Hz,1H, H-3'), 5.58 (d,J=2.5 Hz,1H,H-1'), 5.94 (s,1H, H-1), 6.78 (d,J=8.1 Hz, 1H,—NH), 7.65 (m,2H,ArH), 7.85 (m,1H,ArH), 7.98 (s,1H,ArH), 8.40 (m,1H,ArH), 13.71 (s,1H,OH).

Step 3. (1S',1S,3R)-Methyl-(6-hydroxy-1-(3'-trifluoroacyldaunosamine)-5,12-dioxo-3,4,5,12-tetrahydroanthraceno [2,3-C]pyran-3-yl) ketone BCH-724

Application of the same procedure as used in Step 2 above on the (1'S,1S,3R) protected diastereomer (350 mg) from Step 1, gave the titled compound in 96% yield (266 mg). MP: 240°–242° C.

¹H NMR (300 MHz, CDCl₃) δ:1.43 (d,J=6.4 Hz,3H,—CH₃), 1.62 (broad s, 1H,—OH), 1.89 (m,2H,H-2'), 2.32 (s,3H,—COCH₃), 2.60 (dd,J=11.6 Hz and 19.7 Hz,1H,H$_{ax}$-4'), 3.13 (dd,J=4.2 Hz and 19.7 Hz,1H,H$_{eq}$-4), 3.66 (d,J=2.2 Hz,1H,—H-4') 4.32 (m,1H,H-3'), 4.51 (dd,J=4.2 Hz and 11.6 Hz,1H,H-3), 4.65 (q,J=6.4 Hz,1H,H-5'), 5.45 (d,J=2.3 Hz,1H,H-1'), 6.17 (s,1H,H-1), 6.70 (d,J=9.0 Hz,1H,—NH), 7.70 (m,2H,ArH), 7.04 (m, 1H,ArH), 8.10 (s,1H,ArH), 8.47 (m,1H,ArH), 13.81 (s,1H,—OH).

Step 4: (1S',1R,3S)-Methyl-(6-hydroxy-1-daunosamine)-5,12-dioxo-3,4,5,12-tetrahydroanthraceno[2,3-C]pyran-3-yl)ketone BCH-1128

To a stirred solution of the product from Step 2 above, (35 mg, 0.062 mmol) in CH₃CN (8 ml) at 0° was added potionwise over 10 minutes, an aqueous solution of sodium hydroxide (0.1N 6 ml) and then washed twice with methylene chloride. The aqueous layer was treated with a saturated solution of sodium bicarbonate and then extracted three times with methylene chloride. The combined organic layer was washed with brine and dried over MgSO₄. Evaporation of solvents yielded the free amino compound. The hydrochloric salt of the latter was easily obtained from the treatment with HCl (0.1N) in methanol followed with precipitation by adding ether to yield a red-brown solid which was washed with ether. The titled compound was obtained in 32% yield (10 mg). MP: 180° C. (decompose).

¹H NMR (250 MHz, CD₃OD) δ:1.13 (d,J=6.5 Hz,3H,—CH₃), 1.60–2.00 (m, 2H,H-2'), 2.28 (s,3H,—COCH₃), 2.52 (dd,J=12.2 Hz and 19.7 Hz, 1H,H$_{ax}$-4'), 2.95 (dd,J=4.3 Hz and 19.7 Hz,1H,H$_{eq}$-4), 3.25 (m,1H,H-3'), 3.56 (broad s,1H, H-4'), 4.00 (q,J=6.5 Hz,1H,H-5'), 4.62 (dd,J=4.3 Hz and 12.2 Hz,1H,H-3), 5.49 (d,J=1.9 Hz,1H,H-1'), 5.94 (s,1H, ArH), 8.23 (m,1H,ArH), 8.39 (m,1H,ArH), 13.81 (s,>1H,—OH).

Step 5: (1S',1S,3R)-Methyl-(6-hydroxy-1-daunosamine)-5,12-dioxo-3,4,5,12-tetrahydroanthraceno[2,3-C]pyran-3-yl)ketone BCH-1127

Following the same procedure as described in Step 4 above alkaline hydrolysis of the (1'S,1S,3R) trifluoroacyl-derivative from Step 3 (22 mg) gave the titled compound (7 mg) (35%) MP:166° C. (decompose).

¹H NMR (250 MHz, CD₃OD) δ:1.40 (d,J=6.6 Hz,3H,—CH₃), 1.88 (m,1H,H-2'), 2.14 (m,1H,H-2'), 2.35 (s,3H,—CO—CH₃), 2.55 (dd,J=11.6 Hz and 19.5 Hz,1H,H$_{ax}$-4), 3.02 (dd,J=3.9 Hz and 19.5 Hz,1H,H$_{eq}$-4), 3.55 (m,1H, H-3'), 3.70 (broad s,1H,H-4'), 4.57 (dd,J=3.9 Hz and 11.6 Hz,1H, H-3), 5.52 (broad s,1H,H-1'), 6.09 (s,1H,H-1), 7.75 (m,2H, ArH), 8.00 (m, 2H,ArH), 8.40 (m,1H,ArH).

Example 20

Preparation of (1'S,1R,3S) and (1'S,1S,3R)-Methyl-(1-(2',3',6'-trideoxy-3'-morpholino-L-lyxohexopyranose)-6,11-deoxy-5,12-dihydroxy-3,4,6,11-tetrahydroanthraceno-[2,3-c]-pyran-3-yl)ketone hydrochloride BCH-1191 and (1"S,1S,1R,3S) and (1"R,1'S,1S,3R)-Methyl-(1-(2',3',6'-trideoxy-3-(1"-cyanomorpholino)-L-lyxohexopyranose)-6,11-deoxy-5,12-dihydroxy-3,4,6,11-tetrahydroanthraceno-[2,3-c]-pyran-3-yl)-ketone

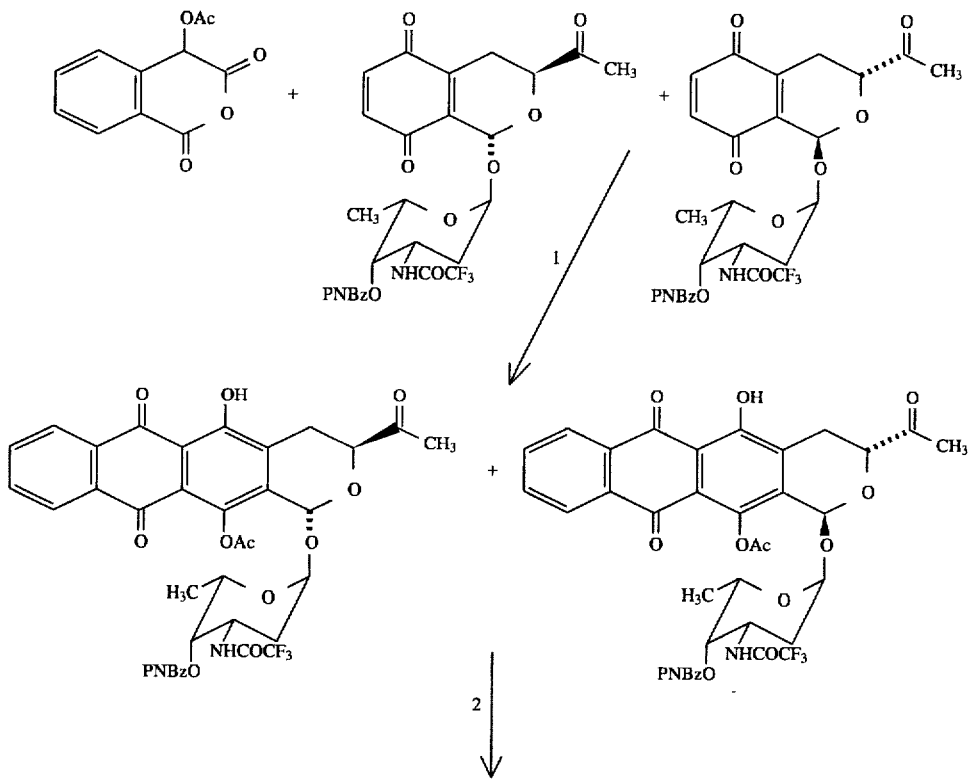

213

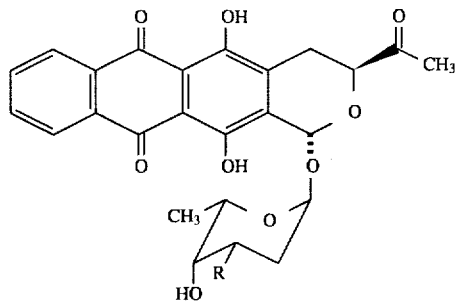

R = NH₃Cl, BCH-1194

214 -continued

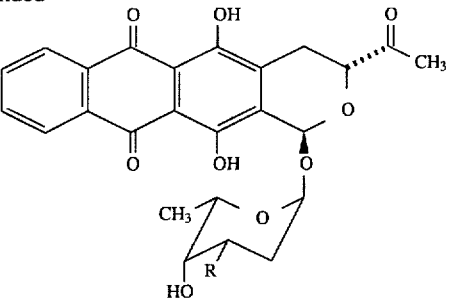

R = NH₃Cl, BCH-1195
R = NHCOCF₃, BCH-1163

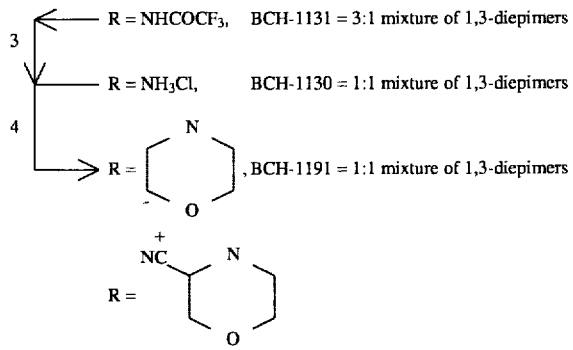

EXAMPLE 20

Step 1: (1'S,1R,3S) and (1'S,1S,3R)-Methyl-(5,8-dioxo-1-(2',3',6'-trideoxy-3'-trifluoroacetamido-4'-O-p-nitrobenzoyl-L-lyxohexopyranose)-3,4,5,8-tetrahydrobenzo-[2,3-C]-pyran-3-yl)ketone.

To a stirred solution of 1,4-di-O-p-nitrobenzoyl-N-trifluoro-acyl daunosamine (1.584 g, 2.93 mmol) in 160 ml of dry dichlorome-thane and 40 ml of anhydrous ether, maintained at −35° C. under argon atmosphere, was added dropwise 1.132 ml (5.85 mmol) of TMSOTf. After stirring for 1.5 hours at 0° C., the temperature was lowered to −15° C. and a cooled (0° C.) solution of methyl (1-hydroxy-5,8-dioxo-3,4,5,8-tetrahydrobenzo[2,3-C]pyran-3-yl)ketone in dry dichlorome-thane (40 ml) was added. After 5 hours of stirring, the reaction mixture was thrown in 150 ml of ethyl acetate and 50 ml of a saturated NaHCO₃ solution. The organic layer was washed with water and dried (Na₂SO₄). Flash chromatography of the residue gave 917 mg (69% yield) of the mixture of titled stereoisomers. A second flash chromatography separated the individual diastereomers.

The 1S,1S,3R titled diastereomer had ¹H NMR (250 MHz, acetone-d₆) δ:1.28 (d,3H,J=6.4 Hz,CH₃), 2.05 (hidden m,1H,2'-CH₂), 2.30 (s, 1H,COCH₃), 2.42–2.49 (m,2H,2'-CH₂ overlapped with HCHa), 2.84 (dd, 1H,HCHe), 4.53–4.65 (broad m,1H,3'-CH), 4.635(dd,2H,J=4.2,11.6 Hz, O—CH—COCH₃), 4.76 (broad q,1H,5'-CH), 5.50 (broad s,1H,4'-CH), 5.69 (broad s,1H,1'-CH), 6.02 (s,1H,O—CH—O), 6.90 (dd,2H,2X C═CH), 8.37 (m,4H,ArH), 8.68 (broad d,1H,NH).

The 1'S,1R,3S titled diastereomer had ¹H NMR (250 MHz, acetone-d₆) δ:1.19 (d,3H,J=6.6 Hz,CH₃), 1.89 (dd, 1H,J=4.6,13.1 Hz,2'—CH₂), 2.32 (s,3H,COCH₃), 2.29–2.47 (m,2H,2'-CH₂ overlapped with HCHa), 2.89 (dd,1H,J=4.1 Hz,HCHe), 4.60 (m,2H,3'-CH overlapped with 5'-CH), 4.71 (dd,1H,J=4.1,11.5 Hz,O—CH—COCH₃), 5.48 (broad s,1H, 4'-CH), 5.64 (broad s,1H,1'-CH), 5.89 (s,1H,O—CH—O), 6.87 (dd,2H,2XC═CH), 8.37 (dd,4H,ArH), 8.69 (broad d,1H,NH).

Step 2: (1'S,1R,3S) and (1'S,1S,3R)-Methyl-1-(2',3',6'-trideoxy-3-trifluoroacetamido-4'-O-p-nitrobenzoyl-L-lyxohexopyranose)-6,11'dioxo-5'-hydroxy-12-acetoxy-3,4,6,11-tetrahydroanthra-ceno-[2,3-C]-pyran-3-yl) ketone BCH-1194, BCH-1195, BCH-1163, & BCH-1131

To a stirred solution of acetyl homophtalic anhydride (551 mg, 2.25 mmole) in anhydrous THF (60 ml) at 0° C. and under argon atmosphere was added 90 mg of NaH 60% (2.25 mmol). After stirring for 15 minutes at 0° C., the reaction mixture was raised to 23° C. for 15 minutes and a solution of the crude isochromandione glycoside from step 1 (example 16) (2.25 mmol) in 20 ml of THF was added dropwise over 7 minutes at 0° C. The reaction mixture was stirred for 20 minutes at this temperature, then 40 minutes at room temperature, worked up by adding 20 ml of a saturated NH₄Cl solution, and extracted with CH₂Cl₂. The combined organic layers were then washed with water and dried (MgSO₄). Flash chromatography (To: EtOAc; 90:10) of the crude gave 420 mg of a mixture of 1'S,1R,3S and 1'S,1S,3R diastereoisomers (24% yield). Separation of the 2 stereoisomers has been hardly achieved by HPLC.

The (1'S,1S,3R) titled diastereomer haδ: ¹H NMR (250 MHz, DMSO-d₆) δ: 1.21 (d,3H,J=6.8 Hz,CH₃), 1.86 (m,1H, 2'-CH₂), 2.27 (m,1H,2'-CH₂), 2.32 (s,3H,COCH₃), 2.50 (s,3H,CO₂CH₃), 2.76 (dd,1H,J=11.9 Hz, HCHa), 3.17 (dd, 1H,J=4.6 Hz,HCHe), 4.38 (m,2H,H-3' and H-5'), 4.75 (dd, 1H,J=4.6,11.9 Hz,CH), 5.38 (bs,1H,H-4'), 5.68 (bs,1H,H-1'), 6.12 (s,1H,O—CH—O), 7.99 (m,2H,ArH), 8.17 (m,2H, ArH), 8.28 (d,2H,ArH), 8.42 (d,2H,ArH), 9.60 (bd,1H,NH), 13.3 (s,1H,OH).

The (1'S,1R,3S) titled diastereomer haδ: ¹H NMR (250 MHz, DMSO-d₆) δ: 1.05 (d,3H,J=6.4 Hz,CH₃), 1.88 (m,1H, 2'-CH₂), 2.31 (s,3H, COCH₃), 2.34 (m,1H,2'-CH₂), 2.45 (s,3H,CO₂CH₃), 2.65 (dd,1H,H—CHa, 3.18 (dd,1H,HC He), 4.45 (m,2H,3' and 5'-CH), 4.74 (dd,1H,O—C H—COCH₃), 5.31 (bs,1H,4'-CH), 5.71 (bs,1H,1'-CH), 6.21 (s,1H,O—CH—O), 7.97 (m,2H, ArH), 8.14 (m,1H,ArH), 8.23 (m,1H,ArH), 8.27 (d,2H, ArH), 8.42 (d,2H,ArH), 9.55 (bd,1H,NH), 13.36 (s,1H,ArOH).

Step 3: (1'S,1R,3S) and (1'S,1S,3R)-Methyl-(1-(2',3',6'-trideoxy-3'-ammonium-L-lyxohexopyranose)-6,11-deoxy-5,12-dihydroxy-3,4,6,11-tetrahydroanthraceno[2,3-c]pyran-3-yl)ketone hydrochloride BCH-1130

To a stirred solution of the glycosides from step 2 (1:1 mixture) (260 mg, 0.337 mmol) in 80 ml of acetonitrile and 30 ml of THF were added, dropwise (60 minutes), 57.29 ml of a 0.1N NaOH aqueous solution at 0° C. The pH of the reaction mixture was then neutralized to 8. The intermediate was extracted with $CHCl_3$. The combined organic layers were washed successively with a mixture (1:1) of saturated $NaHCO_3$ and $NH_4Cl$ solutions, water and dried with $Na_2SO_4$. The residue was dissolved in 6 ml of $CHCl_3$ and 2 ml of MeOH anhydrous and to the solution was added, 1M HCl in $Et_2O$ (67 ml). The precipitate was formed when $Et_2O$ (40 ml) was added in. The pure solid products (82 mg) were collected by centrifugation to give a 48% yield.

The (1'S,1R,3S) titled diastereomer haδ:$^1$H NMR (250 MHz, DMSO-$d_6$) δ: 1.13 (d,3H,$CH_3$), 1.76–2.01 (m,2H,2'-$CH_2$), 2.32 (s,3H,$COCH_3$), 2.67 (dd,1H,HCHa), 3.12 (dd, 1H,HCHe), 3.56 (bs,1H,4'-CH), 4.04 (bq, 1H,5'-CH), 4.38 (m,1H,3'-CH), 4.71 (dd,1H,O—CH—$COCH_3$), 5.52 (bs,1H, 1'-CH), 6.13 (s,1H,O—CH—O), 8.02 (m,2H,ArH), 8.29 (m,2H,ArH), 13.09 (s,1H,ArOH), 13.17 (s,1H,ArOH).

The (1'S,1S,3R) titled diastereomer had: $^1$H NMR (250 MHz, DMSO-$d_6$) δ: 1.22 (d,3H,$CH_3$), 1.77–2.08 (m,2H,2'-$CH_2$), 2.31 (s,3H,$COCH_3$), 2.63 (dd,1H,HCHa), 3.04 (dd, 1H,HCHe), 3.63 (bs,1H,4'-CH), 4.37 (m, 2H,3'-CH and 5'-CH), 4.58 (dd,1H,O—CH), 5.41 (bs,1H,1'-CH), 6.12 (s,1H,O—CH—O), 7.98 (m,2H,ArH), 8.25 (m,2H,ArH), 13.03 (s,1H,ArOH), 13.19 (s,1H,ArOH). Also obtained from this reaction as a red solid was (1'S,1R,3S) and (1'S,1S,3R)-Methyl-(1-(2',3',6'-trideoxy-3'-trifluoroacetamido-L-lyxo-hexopyranose)-6,11-deoxy-5,12-dihydroxy-3,4,6,11-tetrahydroanthraceno-[2,3-c]-pyran-3-yl)-ketone.

Step 4: (1'S,1R,3S) and (1'S,1S,3R)-Methyl-(1-(2',3',6'-trideoxy-3'-morpholino-L-lyxohexopyranose)-6,11-deoxy-5,12-dihydroxy-3,4,6,11'-tetrahydroanthraceno-[2,3-c]-pyran-3-yl)ketone hydrochloride BCH-1191 and (1"S,1S,1R, 3S) and (1"R,1'S,1S,3R)-Methyl-(1-(2',3',6'-trideoxy-3'-(1"-cyanomorpholino)-L-lyxohexopyranose)-6,11-deoxy-5,12-dihydroxy-3,4,6,11'-tetrahydroanthraceno-[2,3-c]-pyran-3-yl)-ketone These compounds were obtained by applying the method reported by E. Acton et al (J. Med. Chem., 27, 638–645, 1984) to the 3'-aminoglycosides from step 3 of example 17.

The (1'S,1R,3S) titled diastereomer haδ: $^1$H NMR ($CDCl_3$, 250 MHz) δ: 1.34 (d,3H,$CH_3$), 1.69–2.03 (m, 2H,2'-$CH_2$), 2.37 (s,3H,$COCH_3$), 2.49–3.05 (overlapped multiplets,6H,2x$CH_2$N,HCHa and 3'-CH), 3.27 (dd,1H,HC He), 3.6–4.1 (overlapped multiplets, 6H,2xO$CH_2$,4'-CH and 5'-CH), 4.57 (dd,1H,O—CH—$COCH_3$), 5.61 (bs,1H,1'-CH), 6.11 (s,1H,O—CH—O), 7.83 (m,2H,ArH), 8.31 (m,2H,ArH), 13.19 (s,1H,ArOH), 13.29 (s,1H,ArOH).

The (1'S,1S,3R) titled diastereomer haδ: $^1$H NMR ($CDCl_3$, 250 MHz) δ: 1.39 (d,3H,$CH_3$), 1.69–2.03 (m,2H, 2'-$CH_2$), 2.34 (s,3H,$COCH_3$), 2.49–3.05 (overlapped multiplets, 6H,2x$CH_2$N,HCHa and 3'-CH), 3.24 (dd,1H,HC He), 3.6–4.1 (overlapped multiplets, 5H,2xO$CH_2$, 4'-CH), 4.43 (bq,1H,5'-CH), 4.54 (dd,1H,O—CH—$COCH_3$), 5.55 (bd,1H,1'-CH), 6.32 (s,1H,O—CH—O), 7.83 (m,2H,ArH), 8.31 (m,2H,ArH), 13.19 (s,ArOH), 13.37 (s,1H,ArOH). Also obtained from this reaction were the titled epimeric cyanomorpholino analogs.

Example 21

Preparation of naphtho-[2,3-c]pyran-3-yl derivatives with an ethyl side chain.

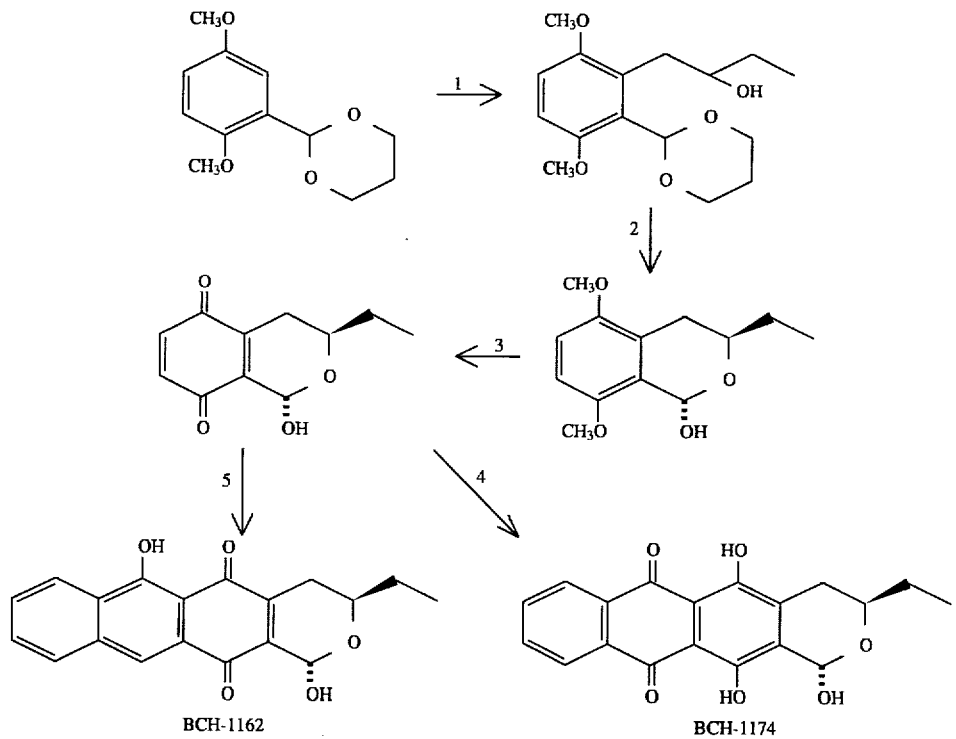

Example 21

Step 1: 2,5-Dimethoxy-6-(2-hydroxybutyl)-benzaldehyde-dioxane acetal

To a cooled (−15° C.) solution of 2,5-dimethoxybenzaldehyde dioxane acetal (13.2 g; 44.6 mmol) in 300 ml of anhydrous diethyl-ether was added dropwise under argon, n-Butyllithium (32.2 ml of a 2.5M solution in hexanes; 80.3 mmol). The mixture was warmed to −7° C. and was stirred at this temperature for 5 hours. The resulting mixture was cooled to −78° C. and was treated with boron trifluoride etherate (21.8 ml; 177 mmol) and 1,2-epoxybutane (10.2 ml; 119 mmol). After stirring at −78° C. for 60 minutes the reaction mixture was quenched with a saturated solution of bicarbonate and was extracted with ether. The organic layers were combined, washed with water, brine, and then dried over $MgSO_4$. Removal of the solvent gave a crude oil which was purified by column chromatography on silica gel, using 25% ethyl acetate in hexane, to afford 2.39 g of pure starting material (18%) and 5.21 g (52% based on S.M. recovered) of 2,5 dimethoxy-6-(2 hydroxybutyl)benzaldehydedioxane acetal as an oil.

$^1$H NMR (250 MHz, $CDCl_3$) δ:0.95 (t,J=7.3 Hz,3H,—$CH_2CH_3$), 1.35 (1H,dm, J=13.6 Hz,—$CH_2$—CH Heq—$CH_2$), 1.55 (2H,m,—$CH_2$—$CH_3$), 2.18 (1H,m,—$CH_2$—CHHax—$CH_2$—), 2.98 (1H,dd,J=2.7 and 13.7 Hz,=C—$CH_2$—CH—O—), 3.36 (1H,dd,J=10.3 and 13.6 Hz,=C—$CH_2$—CH—O), 3.65 (3H, s,—$OCH_3$), 3.66 (3H,s,—$OCH_3$), 3.60–4.10 (3H,m,—CHHeq—O—,—CH—OH), 4.16 (2H,m,—CHHax—O—), 6.16 (1H, s,—O—CH—O—), 6.61 (1H,d,J=9.0 Hz,Ar—H), 6.70 (1H,d,J=9.0 Hz,Ar—H).

Step 2: 5,8-Dimethoxy-3-ethyl-1-hydroxyisochroman

To a stirred solution of 2,5 dimethoxy-6-(2-hydroxybutyl) benzaldehydedioxane acetal (5.2 g; 17.6 mmol) in 700 ml of THF at room temperature was added dropwise 25 ml of a 1N solution of HCl. The resulting mixture was stirred for 1 hour at room temperature and then quenched with a saturated solution of sodium bicarbonate. The mixture was diluted with 1000 ml of dichloromethane and the aqueous layer, after separation, was extracted twice with dichloromethane. The combined organic layers were washed with brine and dried over $MgSO_4$. Evaporation of the solvent gave pure 5,8-dimethoxy-3-ethyl-1-hydroxyisochroman (4.1 g; 98%) which could be recrystallised in dichloromethane/hexane to give the titled compound as white crystals (M.P.: 108.9°–110.1° C.).

$^1$H NMR (250 MHz, $C_6D_6$) δ:1.02 (3H, t,J=7.4 Hz,$CH_2$—$CH_3$), 1.60 (1H,m,—CHH—$CH_3$), 1.76 (1H,m, —CHH—$CH_3$), 2.48 (1H,dd,J=11.6 and 17.3 Hz, Ar—CH—Hax—), 2.88 (1H,dd,J=3.3 and 17.3 Hz,Ar—CH—Heq), 2.98 (1H,d,J=3.9 Hz, —OH), 3.34 and 3.38 (6H,2S,—O—$CH_3$), 4.28 (1H,m,—CH—$CH_2$—$CH_3$), 6.40 (2H,m,Ar—H and —O—CH—O—), 6.46 (1H,d,J=8.8 Hz,Ar—H).

Step 3: 3-Ethyl-1-hydroxyisochroman-5,8-dione

To a stirred solution of 5,8-dimethoxy-3-ethyl-1-hydroxyisochroman (760 mg; 3.19 mmol) in 160 ml of acetonitrile at 0° C. was added dropwise a solution of CAN (5.25 g; 9.57 mmol) and sodium bicarbonate (1.45 g; 17.2 mmol) in 40 ml of water. The resulting mixture was stirred for an hour at 0° C. and then quenched by adding a saturated bicarbonate solution. The aqueous layer was extracted 3 times with dichloromethane and the combined organic layers were washed with water, brine, and then dried over $MgSO_4$. Evaporation of the solvent gave the crude titled quinone which was suitably pure to undergo further reactions (600 mg; 90%).

$^1$H NMR (250 MHz, $CDCl_3$) δ:1.02 (3H,t,J=7.4 Hz,—$CH_2$—$CH_3$), 1.70 (2H,m,—$CH_2$—$CH_3$), 2.15 (1H,ddd,J=1.1,12.4 and 19.5 Hz,Ar—CH—Hax—), 2.60 (1H, dd,J=3.2 and 19.5 Hz,Ar—CH—Heq), 3.20 (1H,br s,—OH), 4.08 (1H,m,—CH—$CH_2$—$CH_3$), 5.91 (1H, s,—O—CH—O—), 6.76 (2H,2 parts of an AB system, Ar—H).

Step 4 : (trans)-6,11-dioxo-3-ethyl-1,5,12-trihydroxy-3,4, 5,12-tetrahydroanthraceno-[2,3-c]-pyran BCH-1174

To a solution of a-acetoxyhomophtalic anhydride (694 mg, 3.15 mmol) in 65 ml of dry THF at 0° C. was added by portions sodium hydride (126 mg, 60% dispersion in oil, 3.15 mmol). The resulting mixture was stirred at room temperature for 30 minutes. A solution of 3-ethyl-1-hydroxyisochroman-5,8-dione (600 mg; 2.89 mmol) in 27 ml of THF was then added dropwise and the resulting dark red mixture was stirred for one hour at room temperature. It was then quenched with a saturated $NH_4Cl$ solution and extracted with dichloromethane. The organic layers was washed with 0.5N HCl, brine and then dried over $MgSO_4$. Evaporation of the solvent gave a crude mixture of regioisomers which was used as such for the next step (1.27 g).

Of the crude material, 403 mg were dissolved in 50 ml of THF at room temperature. To this solution was added dropwise a 0.5N NaOH solution (12.6 ml; 6.3 mmol) and the resulting mixture was stirred for 4 hours. The pH was then adjusted to ~7 by slow addition of dilute HCl and the mixture was extracted with dichloromethane. The combined organic layers were washed with brine and dried over $MgSO_4$. The crude residue was purified by column chromatography on silica gel using 1% methanol in dichloromethane affording pure 3-ethyl-1,2,3,4-tetrahydro-1,5,12-trihydroxy(2 oxygen)naphtacene-6,11-dione (41 mg; 13% overall), M.P.: 255.4°–259.7° C. (red solid).

$^1$H NMR (DMSO) δ:0.98 (3H, t,J=7.3 Hz,$CH_2$—$CH_3$), 1.61 (2H,m,—$CH_2$—$CH_3$), 2.24 (1H,dd,J=11.2 and 18.5 Hz,Ar—CH—Hax), 2.76 (1H,d,J=18.5 Hz,Ar—CH—Heq—), 4.07 (1H,m,—CH—$CH_2$—$CH_3$), 5.88 (1H,d,J=6.0 Hz,—O—CH—O—), 6.94 (1H,d,J=6.0 Hz,O—H), 7.92 and 8.18 (4H,2m,Ar—H), 13.10 and 13.18 (2H,2s,Ar—OH).

Step 5: (trans)-1,6-Dihydroxy-3-ethyl-1,2,3,4-tetrahydro-(2-oxygen) naphtacene-5,12-dione BCH-1162

To a solution of 3-ethyl-1-hydroxyisochroman-5,8-dione (106 mg; 0.51 mmol) in 6 ml of dry diethyl ether and 1 ml of dry THF at 0° C. was added 2 methoxypropene (144 mg; 2.0 mmol) and a crystal of pyridinium para-toluene sulfonate. The resulting mixture was stirred for 20 minutes at 0° C. and used as such for the next reaction.

To a stirred solution of diisopropylamine (62 mg; 0.61 mmol) in 6 ml of dry THF at 0° C. was added dropwise n-BuLi (244 ml, 0.61 mmol, 2.5M in hexanes). The resulting mixture was stirred for 20 minutes and then cooled to −78° C. A solution of homophtalic anhydride (100 mg; 0.61 mmol) in 2 ml of THF was added and the mixture was stirred for 5 minutes at −78° C. The previously prepared solution of protected hydroxy guinone was then added quickly at −78° C. The colour of the resulting solution went from green to purple. It was stirred for 20 minutes at −78° C. and 2 hours at room temperature. The mixture was quenched with a 10% solution of $NH_4Cl$ and diluted with dichloromethane. The aqueous layer was extracted with dichloromethane, and the combined organic layers were washed with brine and dried over $MgSO_4$. Evaporation of the solvent gave a crude red solid which was purified by preparative TLC on silica gel using 20% ethyl acetate in hexane as eluent affording pure 3-ethyl-6-hydroxy-1-(1-methoxy-1-methylethyl)-1,2,3,4-tetrahydro(2-oxygen)naphtacene-5,12-dione (40 mg). This material was dissolved in 5.5 ml of a 4:1.5 mixture of acetone and water at room temperature. To this mixture was added 0.5 ml of a 0.1N HCl solution and the resulting solution was stirred at room temperature for 45 minutes. It was quenched with a saturated sodium bicarbonate solution and diluted with dichloromethane. The aqueous layer was extracted with dichloromethane and the combined organic layers were washed with brine and dried over MgSO$_4$. Evaporation gave an orange solid which was triturated with dichloromethane and ethyl acetate yielding pure 1,6-dihydroxy-3-ethyl-1,2,3,4-tetrahydro(2-oxygen)naphtacene-5,12-dione (21 mg; 13% overall) as an orange solid (m.p.: 196.8°–199.1° C.).

$^1$H NMR (DMSO) δ:0.94 (3H,t,J=7.4 Hz,—CH$_2$—CH$_3$), 1.61 (2H,m,—CH$_2$—CH$_3$), 2.20 (1H,dd,J=11.2 and 18.5 Hz,Ar—CH—Hax), 2.70 (1H,J=18.5 Hz,Ar—CH—Heq), 4.02 (1H,m,—CH—CH$_2$—CH$_3$), 5.81 (1H,d,J=7.0 Hz,—O—CH—O—), 6.96 (1H,d,J=7.0 Hz, —OH), 7.81 (2H,m,Ar—H), 8.11 (1H,s,Ar—H), 8.22 and 8.37 (2H,2m, Ar—H), 13.75 (1H,brs,ArOH).

Example 22

Preparation of
(1'S,1R,3R)-5,12-dioxo-3-ethyl-6-hydroxy-1-(2',3',6'-trideoxy-3'-amino-4'-hydroxy-L-lyxohexopyranose)-3,4,5,12-tetrahydroanthraceno[2,3-c]pyran hydrochloride BCH-1614, and
(1'S,1S,3S)-5,12-dioxo-3-ethyl-6-hydroxy-1-(2',3',6'-trideoxy-3'-amino-4'-hydroxy-L-lyxohexopyranose)-3,4,5,12-tetrahydroanthraceno[2,3-c]pyran hydrochloride BCH-1610

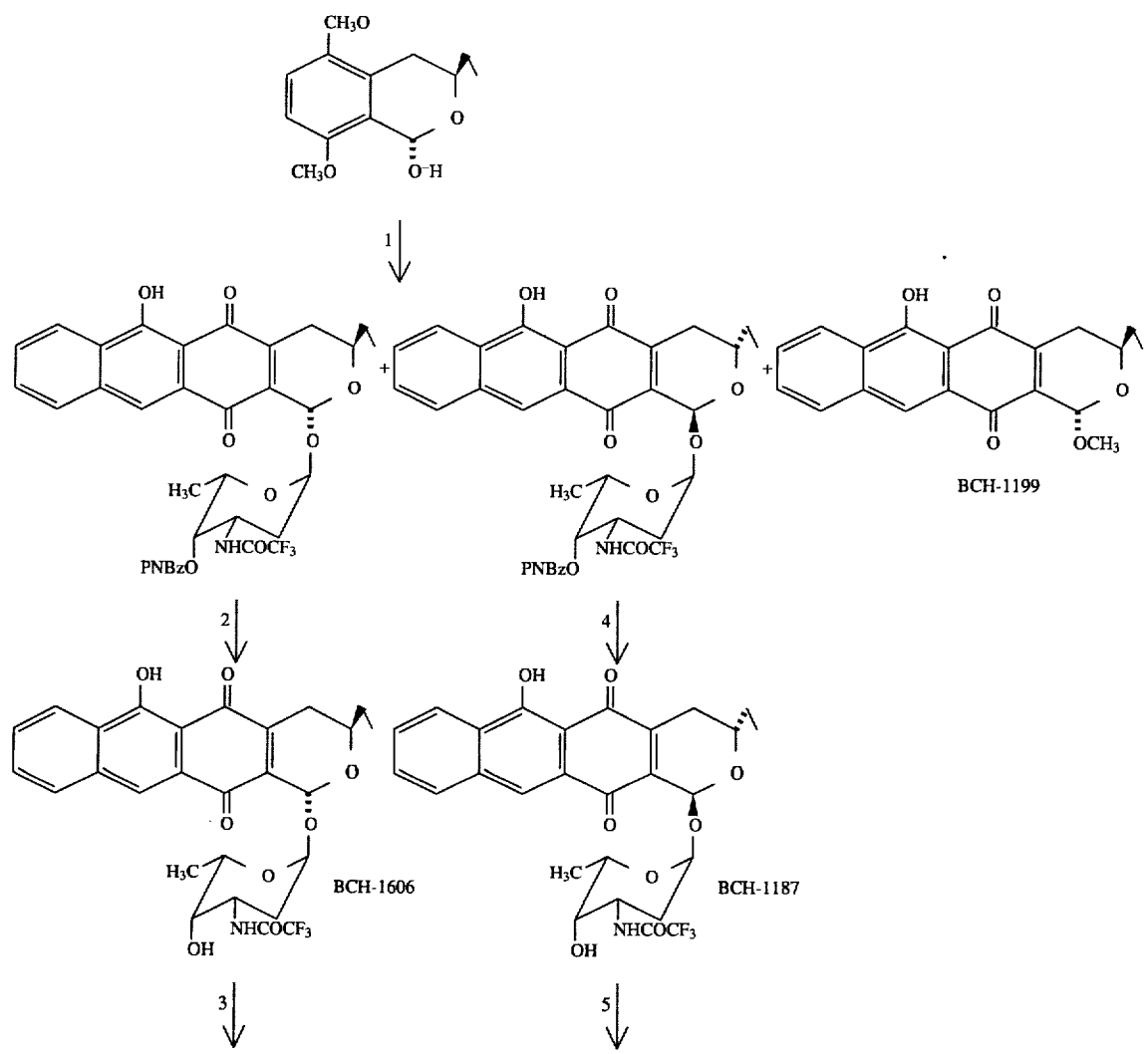

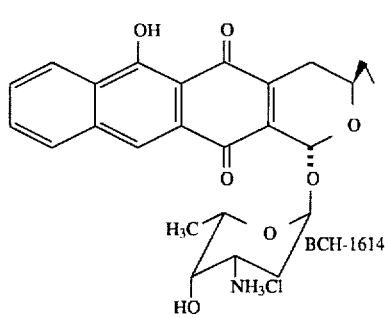

BCH-1614

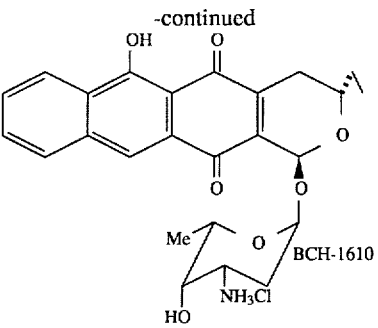

BCH-1610

Example 22

Step 1: (1'S,1R,3R) and (1'S,1S,3S)-5,12-dioxo-3-ethyl-6-hydroxy-1 -(2',3',6'-trideoxy-3'-trifluoroacetamido-4'-O-p-nitrobenzoyl-L-lyxohexopyranose)-3,4,5,12-tetrahydroanthraceno[2,3-C]pyran BCH-1199

To a solution of 5,8-dimethoxy-3-ethyl-1-hydroxyisochroman (370 mg; 1.55 mmol) in 77 ml of acetonitrile at room temperature was added dropwise a solution of CAN (2.58 g; 4.71 mmol) in 21 ml of water. The resulting mixture was stirred at room temperature for 15 minutes and then quenched by adding a saturated bicarbonate solution. The aqueous layer was extracted with dichloromethane and the combined organic layers were washed with brine and dried over $MgSO_4$. Evaporation of the solvent afforded 340 mg of crude quinone used as such for the next step.

To a solution of 2,3,6-trideoxy-3-trifluoroacetamido-1,4-di-O-p-nitrobenzoyl-a-L-lyxopyranose in 60 ml of dichloromethane and 21 ml of ether at −15° C. was added trimethylsilyl triflate (604 ml; 3.13 mmol). The mixture was warmed to 0° C. and was stirred for one hour. It was cooled to −15° C., and a solution of the freshly prepared quinone (see above) in 10 ml of dichloromethane containing 4A molecular sieves was added dropwise over a period of 10 minutes. The resulting mixture was stirred for 3 hours at −15° C. and then quenched with a saturated bicarbonate solution. The aqueous layer was extracted with dichloromethane and the combined organic layers were washed with brine and dried over $Na_2SO_4$. Evaporation gave a crude mixture (1 g) of diastereomeric quinones which was used as such for the next reaction.

To a solution of diisopropylamine (192 mg; 1.86 mmol) in tetrahydrofuran (10 ml) at 0° C. was added n-BuLi (2.5M; 744 ml; 1.86 mmol). The mixture was stirred at 0° C. for 15 minutes and was then added to a cooled (−78° C.) solution of homophtalic anhydride (296 mg; 1.86 mmol) in 16 ml of tetrahydrofuran. The resulting mixture was stirred at −78° C. for 20 minutes. A solution of the crude quinone (diastereomeric mixture, see above) in 10 ml of tetrahydrofuran was then added. The resulting mixture was stirred at −78° C. for 20 minutes and at room temperature for 2 hours. It was then quenched with a saturated $NH_4Cl$ solution and extracted with dichloromethane. The combined organic layers were washed with brine and dried over $NaSO_4$. The crude residue after evaporation of solvent was purified by column chromatography on silica gel using a 99:1 mixture of dichloromethane and acetone as eluent, affording (1'S,1S,3S)-5,12-dioxo-3-ethyl-6-hydroxy-1-(2',3',6'-trideoxy-3'-trifluoroacetamido-4'-O-p-nitrobenzoyl-L-lyxohexopyranose)-3,4,5,12-tetrahydroanthraceno[2,3-c]pyran as a red solid (180 mg, ~60% pure).

$^1$H NMR (250 MHz, $CD_2Cl_2$) δ:1.05 (3H,t,J=7.3 Hz,—$CH_2$—$CH_3$), 1.33 (3H,d, J=6.6 Hz,$CH_3$—$CH$), 1.71 (2H,q, J=7.3 Hz,—$CH_2$—$CH_3$), 1.96 (1H,dd,J=4.7 and 12.6 Hz,Heq-2'), 2.14 (1H,td,J=12.6 and 3.6 Hz,Hax-2'), 2.32 (1H,dd, J=11.0 and 19.5 Hz,Hax-4), 2.83 (1H,dd,J=3.5 and 19.5 Hz,Heq-4), 4.00 (1H,m,H-3), 4.58 (1H,m,H-3'), 4.84 (1H,q,J=6.3 Hz,H-5'), 5.43 (1H,br s,H-4'), 5.59 (1H,d,J=2.9 Hz,H-1'), 6.02 (1H,s,H-1), 6.48 (1H,br d,J=7.4 Hz,—NH), 7.70 (2H,m,Ar—H), 7.98 (1H,m,Ar—H), 8.08 (1H,s,H-11), 8.29 (4H,s,PNB), 8.42 (1H,m,Ar—H), 13.81 (1H,s,—O$H$), along with (1'S,1R,3R)-5,12-dioxo-3-ethyl-6-hydroxy-1-(2',3',6'-trideoxy-3'-trifluoroacetamido-4'-O-p-nitrobenzoyl-L-Lyxohexopyranose)-3,4,5,12-tetrahydroanthraceno [2,3-C]pyran as a red solid (82 mg; ~75% pure).

$^1$H NMR (250 MHz, $CD_2Cl_2$) δ:1.05 (3H,t,J=7.4 Hz,—$CH_2$—$CH_3$), 1.19 (3H,d, J=6.4 Hz,$CH_3$—$CH$), 1.70 (2H,m, —$CH_2$—$CH_3$), 1.90–2.50 (3H,m,H-2' and Hax-4), 2.76 (1H, dd,J=3.3 and 19.4 Hz,Heq-4), 4.05 (1H,m,H-3), 4.42 (1H, br q,J=6.6 Hz,H-5'), 4.60 (1H,m,H-3'), 5.45 (1H,br s,H-4'), 5.69 (1H,d,J=2.5 Hz,H-1'), 5.85 (1H, s,H-1), 6.66 (1H,br d,J=7.6 Hz,—N$H$), 7.67 (2H,m,Ar—H), 7.89 (1H,m,Ar—H), 7.96 (1H,s,H-11), 8.23 (4H,m, PNB), 8.37 (1H,m,Ar—H), 13.76 (1H,s,—O$H$). The corresponding methoxy aglycone trans-3-ethyl-6-hydroxy-1-methoxy-1,2,3,4-tetrahydro(2-oxygen)naphtacene-5,12-dione was obtained as a by-product (12 mg).

$^1$H NMR (250 MHz, $CD_2Cl_2$) δ:1.04 (3H,t,J=7.4 Hz,—$CH_2$—$CH_3$), 1.67 (2H,qu, J=7.5 Hz,—$CH_2$—$CH_3$), 2.24 (1H,dd,J=11.5 and 19.5 Hz,Hax-4), 2.74 (1H, dd,J=3.6 and 19.5 Hz,Heq-4), 3.51 (3H, s,O—$CH_3$), 3.94 (1H,m,H-3), 5.49 (1H,s,H-1), 7.70 (2H,m,Ar—H), 7.93 (1H,m,Ar—H), 8.03 (1H,s,H-11), 8.39 (1H,m,Ar—H), 13.80 (1H,s,—OH).

Step 2: (1'S,1R,3R)-5,12-dioxo-3-ethyl-6-hydroxy-1-(2',3', 6'-trideoxy-3'-trifluoroacetamido-4'-hydroxy-L-lyxohexopyranose)-3,4,5,12-tetrahydroanthraceno[2,3-c]pyran BCH-1606

To a cooled solution (0° C.) of (1'S,1R,3R)-5,12-dioxo-3-ethyl-6-hydroxy-1-(2',3',6'-trideoxy-3'-trifluoroacetamido-4'-O-p-nitrobenzoyl-L-lyxohexopyranose)-3,4,5,12-tetrahydroanthraceno[2,3-c]pyran (80 mg; 0.11 mmol) in a 10:4 mixture of methanol and tetrahydrofuran (14 ml) was added a solution of sodium methoxide in methanol (61 ml of 4.37M, 0.12 mmol). The mixture was stirred at 0° C. for 15 minutes and then quenched with a saturated $NH_4Cl$ solution. The compound was extracted with dichloromethane, the organic layers were washed with brine and dried over $Na_2SO_4$. The crude residue was recrystallised in a mixture of dichloromethane and hexane yielding the title compound (32 mg) as an orange solid; M.P.: 246° C. dec.

$^1$H NMR ($CD_2Cl_2$, 250 MHz) δ:1.04 (3H,t,J=7.4 Hz,—$CH_2$—$CH_3$), 1.24 (3H,d, J=6.6 Hz,$CH_3$—CH—), 1.50–2.00 (5H,m,H-4 and H-2' and —O$H$), 2.25 (1H,dd,J=11.0 and 19.5 Hz,Hax-4), 2.83 (1H,dd,J=3.2 and 19.5 Hz,Heq-4), 3.59 (1H,d,J=2.2 Hz,H-4'), 4.07 (1H,m,H-3), 4.24 (1H,q, J=6.5 Hz, H-5'), 4.28 (1H,m,H-3'), 5.53 (1H,d,J=2.9 Hz,H-1'), 5.82 (1H,s,H-1), 6.76 (1H,d,J=8.2 Hz,N$H$—), 7.69 (2H, m,Ar—H), 7.93 (1H,m,Ar—H), 8.04 (1H,s,H-11), 8.42 (1H, m,Ar—H), 13.83 (1H,s,Ar—OH).

Step 3: (1'S,1R,3R)-5,12-dioxo-3-ethyl-6-hydroxy-1-(2',3', 6'-trideoxy-3'-amino-4'-hydroxy-L-lyxohexopyranose)-3,4, 5,12-tetrahydroanthraceno[2,3-c]pyran hydrochloride BCH-1614

To a cooled solution (0° C.) of (1'S,1R,3R)-5,12-dioxo-3-ethyl-6-hydroxy-1-(2',3',6'-trideoxy-3'-trifluoroacetamido-4'-hydroxy-L-lyxohexopyranose-2,3,5,12-tetrahydroanthraceno[2,3-C]pyran (21 mg; 0.038 mmol) in 9 ml of acetonitrile was added dropwise a 0.1N aqueous NaOH solution. The resulting purple mixture was stirred at 0° C. for 2.5 hours, then quenched with 0.1N HCl, and extracted with dichloromethane. The combined organic layers were dried over $Na_2SO_4$ and evaporated to yield 3 mg of a crude product consisting essentially in starting material. The aqueous layer was neutralised to pH ~7 using dilute NaOH and was extracted with dichloromethane (6 times). The combined organic layers were evaporated to give a brown solid (15 mg; 87%). This free base was dissolved in 5 ml of methanol and then treated with 400 ml (0.04 mmol) of 0.1N HCl. To the resulting mixture was added ~50 ml of ether. The precipitated titled hydrochloride salt was collected by filtration (7.5 mg of a red-brown solid; M.P. 175° C. dec.).

$^1$H NMR (250 MHz, DMSO), δ:0.99 (3H,t,J=7.3 Hz,CH$_3$—CH$_2$—), 1.13 (3H,d, J=6.4 Hz,CH$_3$—CH), 1.67 (3H, m,—CH$_2$—CH$_3$ and Heq-2'), 1.92 (1H,td,J=12.8 and 3.2 Hz,Hax-2), 2.23 (1H,dd,J=11.1 and 19.4 Hz,Hax-4), 2.77 (1H,brd,J=19.5 Hz,Heq-4), 3.55 (1H,m,H-4'), 3.99 (2H,m, H-3 and H-5'), 5.42 (1H,d,J=2.2 Hz,H-3'), 5.53 (1H,d,J=5.9 Hz,H-1'), 5.78 (1H,s,H-1), 7.87 (5H,m,Ar—H (2) and NH$_3$), 8.15 (1H,s,H-11), 8.22 (1H,m,Ar—H), 8.40 (1H,m, Ar—H), 13.77 (1H,s,Ar—OH).

Step 4: (1'S,1S,3S)-5,12-dioxo-3-ethyl-6-hydroxy-1-(2',3', 6'-trideoxy-3'-trifluoroacetamido-4'-hydroxy-L-lyxohexopyranose)-3,4,5,12-tetrahydroanthraceno[2,3-c]pyran BCH-1187

The same procedure as described in step 2 was used and afforded the titled compound in 92% yield as an orange solid [M.P. 246° C. (dec.)];

$^1$H NMR (CD$_2$Cl$_2$, 250 MHz) δ:1.02 (3H,t,J=7.3 Hz,CH$_2$—CH$_3$), 1.37 (3H,d, J=6.6 Hz,CH$_3$—CH—), 1.69 (2H,m,CH$_2$—CH$_3$), 1.86 (2H,dd,J=3.1 and 9.5 Hz,H-2'), 2.06 (1H,br s,—OH), 2.31 (1H,dd,J=11.0 and 19.5 Hz,Hax-4), 2.83 (1H,dd,J=3.5 and 19.5 Hz,Heq-4), 3.62 (1H,br s,H-4'), 4.00 (1H,m,H-3), 4.27 (1H,m,H-3'), 4.63 (1H,q,J=6.6 Hz,H-5'), 5.41 (1H,br s,H-1'), 5.98 (1H, s,H-1), 6.79 (1H,br d,J=8.4 Hz,NH—), 7.70 (2H,m,Ar—H), 7.95 (1H, m,Ar—H), 8.07 (1H,s,H-11), 8.43 (1H,m,Ar—H), 13.83 (1H,s, Ar—OH), Step 5: (1'S,1S,3S)-5,12-dioxo-3-ethyl-6-hydroxy-1-(2',3', 6'-trideoxy-3'-amino-4'-hydroxy-L-lyxohexopyranose)-3,4, 5,12-tetrahydroanthraceno[2,3-c]pyran hydrochloride BCH-1610

Applying the same procedure as described in step 3 (except that reaction was carried out at room temperature instead 0° C.) afforded the title compound in 11% yield as an orange solid;

$^1$H NMR (250 MHz, DMSO) δ:0.98 (3H, t,J=7.2 Hz,CH$_3$—CH$_2$), 1.25 (3H,d, J=6.4 Hz,CH$_3$—CH), 1.67 (3H,m,CH$_2$—CH$_3$ and Heq-2'), 1.98 (1H,m, Hax-2'), 2.28 (1H,dd, J=10.7 and 19.5 Hz,Hax-4), 2.79 (1H,dd,J=3 and 19.3 Hz,Heq-4), 3.61 (1H,m,H-4'), 3.88 (1H,m,H-3), 4.41 (1H, m,H-5'), 5.30 (1H,s,H-3'), 5.55 (1H, d,J=6.1 Hz,H-1'), 5.85 (1H,s,H-1), 7.90 (5H,m,Ar—H (2) and NH$_3$), 8.19 (1H,s, H-11), 8.22 (1H,m,Ar—H), 8.38 (1H,m,Ar—H), 13.75 (1H, br,Ar—OH).

Example 23

Preparation of Hydroxymethyl ketone analogs

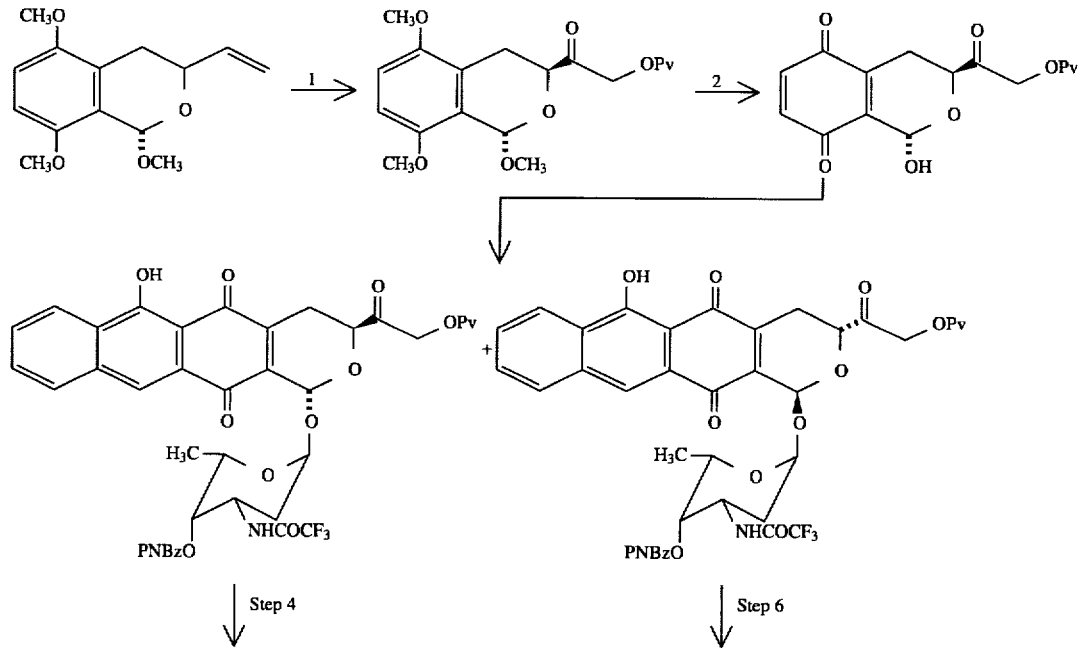

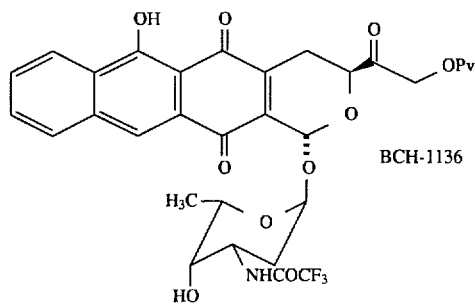

BCH-1136

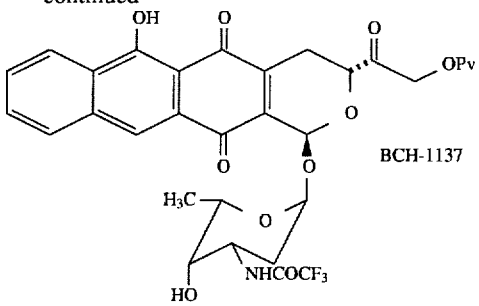

BCH-1137

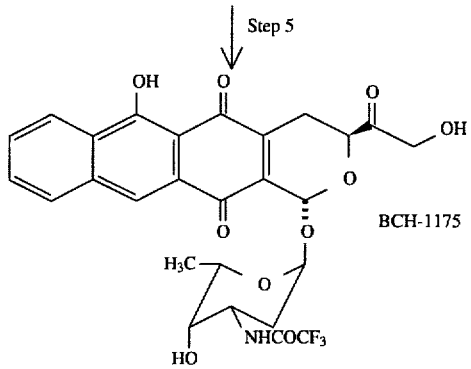

BCH-1175

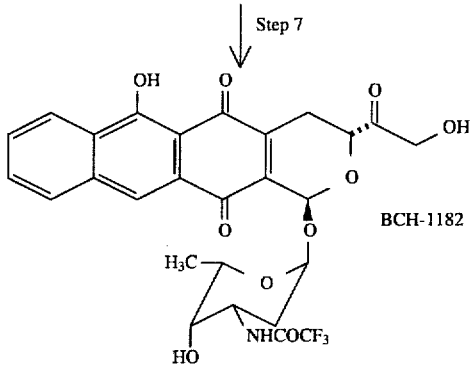

BCH-1182

Example 23

Step 1: Trans-3-(2'-trimethylacetoxy)aceto-1,5,8-trimethoxyisochroman 1,5,8-trimethoxy-3-vinylisochroman Compound I (2.159 g, 8.64 mmol) was treated with Me₃NO (1.92 g, 17.28 mmol) and a catalytic amount of OsO₄ (0.02M in t-BuOH, 10.8 ml, 0.216 mmol) in the presence of acetone (125 ml), H₂O (40 ml), and CCl₄ (3.6 ml) at room temperature for 15 hours. The mixture was quenched with 5% solution of sodium sulphite (100 ml). After the volatile were removed, the residue was extracted with CH₂Cl₂ (4×100 ml). The combined organic phases were washed with H₂O and brine, dried over MgSO₄, filtered and then concentrated to a residue (2.517 g) which was found to be pure dihydroxylated product.

The residue was then treated with trimethyl acetyl chloride (1.31 ml, 10.63 mmol) in the presence of 60 ml pyridine at room temperature for 2 hours. After quenching with 100 ml H₂O, the product was extracted with ethyl acetate. The combined organic phases were washed with H₂O, dried over Na₂SO₄, filtered, and then concentrated in vacuo to give 3.26 g of the titled monoprotected crude compound.

The crude product was dissolved in 35ml of DMSO and 35 ml of Et₃N, followed by addition of SO₃Py (7.14 g) in 20 ml of DMSO. The mixture was stirred at room temperature for about 3 hours till the starting material was consumed. After quenching with H₂O, the product was extracted with CH₂Cl₂. The combined organic phases were washed with H₂O, dried over MgSO₄, filtered and then concentrated. Purification of the crude residue by flash chromatography (hexanes/ethyl acetate,5=1) gave 2.5 g of titled compound (79% yield for three steps).

¹H NMR (300 MHz, CDCl₃) δ:1.29 (s,9H), 2.62 (dd,1H, J=18.5 Hz, 12.0 Hz), 3.05 (dd,1H,J=18.5 Hz,5.0 Hz), 3.59 (s,3H), 3.76 (s,3H), 3.81 (s,3H), 4.74 (dd,1H,J=12.0 Hz,5.0 Hz), 5.06 (d,1H,J=19.0 Hz), 5.12 (d,1H,J=19.0 Hz), 5.68 (s,1H), 6.70 (d,1H,J=7.6 Hz), 6.75 (d,1H, J=7.6 Hz). IR (neat) 2954 s, 1736 s, 1612 m, 1482 s, 1764 s, 1070 s cm⁻¹.

Step 2: 1-hydroxy-3-(2'-trimethylacetoxy)acetoisochroman-5,8-dione

The compound from step 1 (38.0 mg, 0.10 mmol) was treated with PTSA (2.0 mg) in the presence of 1.5 ml acetone, and 0.5 ml H₂O at room temperature for 8 hours. Et₃N (0.5 ml) was added and the volatiles were removed by rotavapor. The product was extracted with ethyl acetate (2×15 ml). The combined organic phases were washed with H₂O, dried over MgSO₄, filtered and then concentrated. The residue was then dissolved in 2.5 ml of CH₃CN and cooled at 0° C., and to the solution was added a CAN solution (NH₄)Ce(NO₃)6, 170 mg, 0.31 mmol, in 1 ml of H₂O). After 20 minutes, the mixture was quenched with H₂O (5 ml) and extracted with CH₂Cl₂ (3×10 ml). The combined organic phases were washed with H₂O, dried over MgSO₄, filtered, and concentrated to give the titled compound (33.5 mg, 100%) which was used for next reaction without any further purification.

¹H NMR (300 MHz, CDCl₃) δ:1.31 (s,9H), 2.15 (dd,1H, J=19.0 Hz, 12.0 Hz), 2.55 (dd,1H,J=19.0 Hz, 4.3 Hz), 4.39 (dd,1H,J=12.0 Hz,4.3 Hz), 4.83 (d,1H,J=17.5 Hz), 4.93 (d,1H,J=17.6 Hz), 5.50 (s,1H), 5.90 (m, 2H).

Step 3: (1'S,1R, 3S) and (1'S,1S,3R)-1,2,3,4,5,12-hexahydro-6-hydroxy-3-trimethylacetoxyaceto-1-(N-trifluoroacetyl-4'-O-p-nitrobenzoyl-L-daunosamine)-(2-oxo)-naphthacene-6,11-dione To a stirred mixture of 1,4-di-O-p-nitrobenzoyl-N-trifluoroacetyl daunosamine (362 mg, 0.668 mmol), and molecular sieves (250 mg), in 17 ml of CH₂Cl₂ and 7 ml of Et₂O was added TMSOTf (0.26 ml, 1.35 mmol) at −40° C. under Ar₂. The temperature was then raised to −3° C. and the mixture was stirred for 1 hour. The quinone from step 2, (196 mg crude, 0.608 mmol) in 4 ml of CH₂Cl₂ was slowly added to the mixture after cooling to −15° C. The resulting mixture was stirred at −15° C. for 6 hours and then kept in the freezer overnight. Quenching with a 5% NaHCO₃ solution, followed by extraction with CH₂Cl₂, and evaporation, gave a crude yellow residue. After dissolving in 4 ml of THF, the yellow residue was slowly added to the lithium enolate of homophthalic anhydride solution at −78° C. (the enolate was prepared by adding LDA to homophthalic anhydride at −78° C. in THF). The mixture was stirred at −78° C. for 30 minutes and then slowly warmed up to room temperature. Work up with saturated $NH_4Cl$, extraction with $CH_2Cl_2$ followed by drying, and evaporation provided a residue that was purified by flash chromatography (tol/ethyl acetate, 10:1) to give the titled compounds (198 mg, 1:1) in 40% overall yield, starting from the isochroman from step 1. $^1H$ NMR for the 1'S,1R,3S diastereomer; ($CDCl_3$, 300 MHz) δ:1.30 (s, 9H), 1.39 (d,3H,J=7.4 Hz), 1.94–2.20 (m,2H), 2.70 (dd,1H,J=18.0 Hz, 12.0 Hz), 3.15 (dd,1H,J=18.0 Hz,4.0 Hz), 4.60 (m,1H), 4.71 (dd,1H,J=12.0 Hz,4.0 Hz), 4.87 (q,1H,J=7.2 Hz), 5.20 (s,2H), 5.48 (s,1H), 5.60 (s, 1H), 6.22 (s,1H), 6.39 (d,1H,J=8.0 Hz), 7.72 (m,2H), 7.98 (d,1H, J=8.5Hz), 8.12 (s,1H), 8.30 (m,4H), 8.48 (d,1H,J=8.6 Hz), 13.78 (s, 1H).

$^1H$ NMR for the 1'S,1S,3R diastereomer; ($CDCl_3$, 300 MHz) δ:1.26 (d,3H,J=7.3 Hz), 1.30 (s,9H), 1.94–2.20 (m,2H), 2.68 (dd,1H,J=17.8 Hz,11.5 Hz), 3.19 (dd,1H,J=17.9 Hz, 4.0 Hz), 4.34 (m,1H), 4.60 (m,1H), 4.73 (dd,1H, J=11.3 Hz,4.0 Hz), 5.00 (s,2H), 5.44 (s,1H), 5.75 (s,1H), 6.07 (s,1H), 6.26 (m, 1H), 7.72 (m, 2H), 7.93 (d,1H,J=8.6 Hz), 8.10 (s,1H), 8.30 (m,4H), 8.49 (d,1H,J=8.4 Hz), 13.79 (s,1H).

Step 4: (1'S,1R,3S)-1,2,3,4,5,12-hexahydro-6-hydroxy-3-trimethylacetoxyaceto-1-N-trifluoroacetyl-L-daunosamine-(2-oxo)-naphthacene-5,12-dione BCH-1136

The 1'S,1R,3S diastereomer from step 3 (30.0 mg, 0.037 mmol) was treated $NaHCO_3$ (3.7 mg, 0.044 mmol) in the presence of 4 ml MeOH, 1 ml $H_2O$, and 1.5 ml $CH_2Cl_2$ at room temperature for about 3 hours until all the starting material was consumed. After addition of 5 ml $H_2O$, the product was extracted with $CH_2Cl_2$ (20ml×2). The combined organic phases were dried over $MgSO_4$, filtered, and concentrated. Purification of the crude residue by flash chromatography (hexanes/EOAc, 6:4) gave the title compound (21.3 mg) in 87% yield.

1H NMR ($CDCl_3$, 300 MHz) δ:1.27 (s,9H), 1.44 (d,3H, J=6.50 Hz), 1.80–2.00 (m,2H), 2.69 (dd, 1H,J=20.0 Hz,11.7 Hz, 3.15 (dd,1H,J=20.0 Hz, 3.2 Hz), 3.66 (m,1H), 4.32 (m,1H), 4.66 (m,1H), 4.95 (d,1H,J=17.70 Hz), 5.04 (d,1H, J=18.0 Hz), 5.42 (s,1H), 6.17 (s,1H), 6.70 (m,1H), 7.71 (m, 2H), 7.94 (m,1H), 8.10 (s,1H), 8.48 (m, 1H), 13.78 (s,1H).

Step 5: (1', S,1R,3S)-1,2,3,4,5,12 -hexahydro-6 -hydroxy-3 -hydroxy-aceto-1-N-trifluoroacetyl-L-daunosamine-(2-oxo) naphthacene-5, 12-dione BCH-1175

To a stirred solution of the product of step 4 (9.7 mg, 0.0146 mmol) in 2 ml of $CH_3CN$ was added 0.3 ml of aqueous NaOH (0.1N, 0.03 mmol) and the resulting mixture was stirred at room temperature for exactly 10 minutes. To the mixture was added 0.3 ml of aqueous AcOH (0.1N), and the product was extracted with $CHCl_3$ (10 ml×3). The combined organic extracts were dried over $Na_2SO_4$, filtered and concentrated. The residue was precipitated in $CH_2Cl_2$ and hexanes to give 6.1 mg of titled compound (72%).

$^1H$ NMR ($CDCl_3$, 250 MHz) δ:1.45 (d,3H,J=6.5 Hz), 1.80–2.00 (m,2H), 2.68 (dd,1H,J=18.5,11.5 Hz), 3.22 (dd, 1H,J=18.4,3.2 Hz), 3.68 (m,1H), 4.25–4.45 (m,1H), 4.50–4.80 (m,1H), 5.40 (m,1H), 6.17 (s,1H), 6.75 (m,1H), 7.73 (m,2H), 7.94 (m,1H), 8.11 (s,1H), 8.51 (m,1H), 13.78 (s,1H). IR (neat) 3414 br, 2927, 1723, 1715, 1663, 1610, 1505, 1460, 1380, 1296, 1164, 987 $cm^{31\ 1}$.

Step 6: (1'S,1S,3R)-1,2,3,4,5,12-hexahydro-6-hydroxy-3-trimethylacetoxyaceto-1-N-trifluoroacetyl-L-daunosamine-(2-oxo) naphthacene-5,12-dione BCH-1137

The procedure as described in step 4 was followed. The titled compound was obtained from the 1'S,1S,3R diastereomer of step 3 in 83% yield.

$^1H$ NMR ($CDCl_3$, 300 MHz) δ:1.27 (s,9H), 1.30 (d,3H, J=6.8 Hz), 1.80–2.05 (m,3H), 2.62 (dd, 1H,J=18.5,11.6 Hz), 3.07 (dd,1H,J=18.4,3.5 Hz), 3.63 (m,1H), 4.12 (m,1H), 4.32 (m,1H), 4.72 (dd,1H,J=11.5,3.2 Hz), 4.99 (s,2H), 5.59 (m,1H), 6.00 (s,1H), 6.62 (m,1H), 7.11 (m,2H), 7.92 (m,1H), 8.09 (s,1H), 8.49 (m,1H), 13.79 (s,1H).

Step 7: (1 'S,1S,3R)-1,2,3,4,5,12-hexahydro-6-hydroxy-3-hydroxy-aceto-1-N-trifluoroacetyl-L-daunosamine-(2-oxo) naphthacene-5,12-dione BCH-1182

The procedure as described in step 5 was followed. The title compound was obtained in 43% yield from the product of step 6 after flash chromatography ($CHC_1$/MeOH 95:5).

$^1H$ NMR ($CDCl_3$, 250 MHz) δ:1.30 (d,3H,J=6.7 Hz), 1.55–2.20 (m,3H), 2.60 (dd,1H,J=17.9,11.6 Hz), 3.24 (dd, 1H,J=17.7,3.3 Hz), 3.66 (m,1H), 4.11 (m,1H), 4.38 (m,2H), 4.54 (d,1H,J=19.0 Hz), 4.68 (d, 1H,J=19.1 Hz), 4.81 (dd, 1H,J=11.5,3.4 Hz), 5.62 (m,1H), 5.99 (s,1H), 6.74 (m,1H), 7.72 (m,2H), 7.95 (m,1H), 8.09 (s,1H), 8.50 (m,1H), 13.78 (s, 1H). IR (neat) 3424 br, 2924, 1721 br, 1665, 1609, 1574, 1455, 1300, 1166, 983 $cm^{-1}$.

EXAMPLE 24

Preparation of pyranylglucoanthraquinones

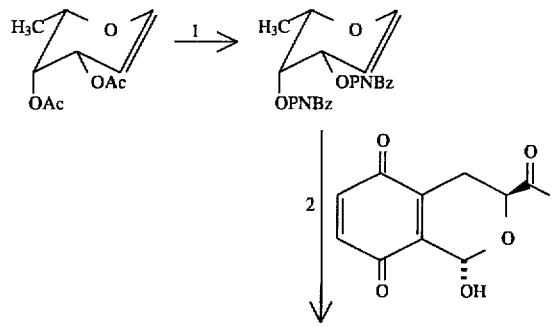

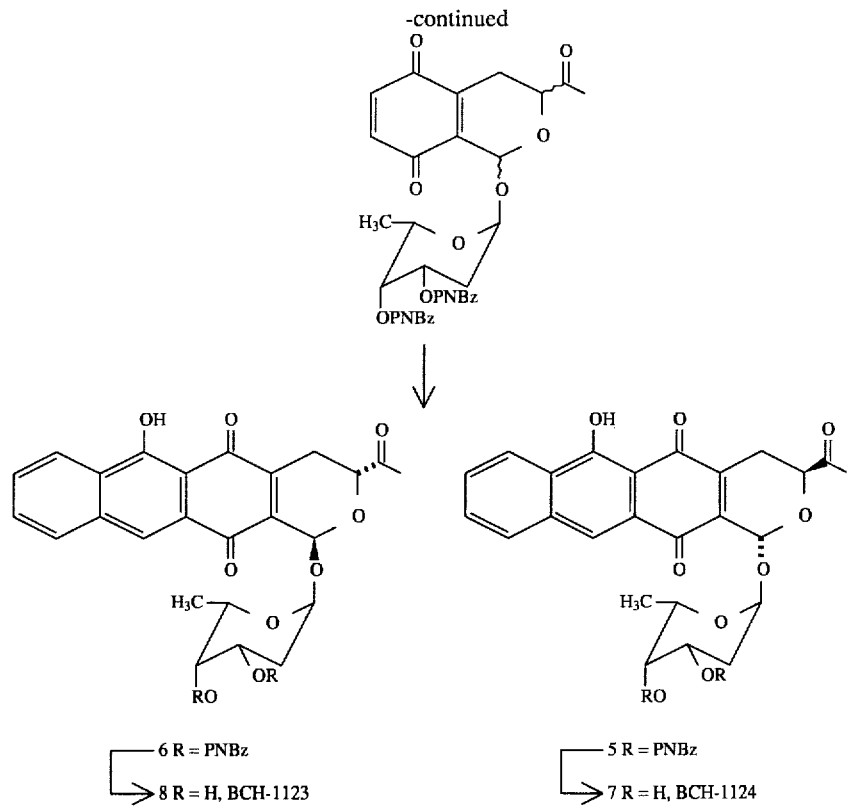

EXAMPLE 24

Step 1. Di-p-nitrobenzoyl-L-fucal

To a stirred solution of diacetyl-L-fucal (114 mg, 0.53 mmol) in methanol (2.5 ml) was added a solution of sodium methoxide in methanol (25 ml, 4.37M., 0.1 mmol). After 45 minutes, methanol was evaporated under vacuum. The crude was dissolved in CH$_2$Cl$_2$ (2.5 ml) and pyridine (1.5 ml) and at 0° C., β-nitrobenzoyl chloride (2.1 mmol, 390 mg) was added. After a few minutes at 0°, the reaction mixture was poured in CH$_2$Cl$_2$ (20 ml) and washed with water, NaHCO$_3$ 10% and then brine. The titled product was purified by flash chromatography (hexanes/AcOET-5:1) (M.P.: 130°–132° C.), (210 mg, 90%).

$^1$H NMR (250 MHz) δ:CD$_2$Cl$_2$:1.40 (d,3H,—CH$_3$), 4.40 (q,1H,H-5), 4.85 (m,1H,H-2), 5.65 (m,1H,H-4), 5.90 (m,1H, H-3), 6.6 (m,1H,H-1).

Step 2. (1'S,1S,3R) and (1'S,1R,3S)-Methyl-(6-hydroxy-1-(2',6'-dideoxy-L-lyxohexopyranose-5,12-dioxo-3,4,5,12-tetrahydroanthraceno-(2,3-c)-pyran-3-yl)-ketone BCH-1123 & BCH-1124

To a mixture of methyl (1-hydroxy-5,8-dioxo-5,8-dihydroiso-chroman-3-yl) ketone (69.8 mg, 0.31 mmol), 1,5-anhydro-3,4-di-O-paranitrobenzoyl-2,6-dideoxy-L-lyxohex-1-enitol sugar (158 mg, 0.37 mmol), and molecular sieves 4A (380 mg) in CH$_2$Cl$_2$ (15 ml) at –60° C. was added triethylamine (24 ml, 0.17 mmol) and trimethylsilyl trifluoromethanesulfonate (64 ml, 0.33 mmol) subsequently. After stirring for 40 minutes, the reaction was quenched by adding NaHCO$_3$ (10 ml) at –60° C. and gradually warmed up to room temperature. Insolubles were filtered off and the filtrate was extracted into CH$_2$Cl$_2$. The organic phase was washed with aq. HCl (0.1N, 10 ml), water and brine, dried over MgSO$_4$ and the solvent evaporated to give 236 mg of crude intermediate which was subsequently dissolved in THF/ether (4 ml/6 ml) and added slowly to a stirred solution of the lithium enolate of homophthalic anhydride, obtained by adding LDA (0.32 mmol from 44 ml diisopropylamine and 0.158 ml 2M n-BuLi, in 2 ml THF) to a solution of the homophthalic anhydride (51 mg, 0.31 mmol) in 7.5 ml of THF at –78° C. After 50 minutes the reaction mixture was quenched with aq. HCl (0.1N, 5 ml) and extracted with CH$_2$Cl$_2$. The organic phase was washed with brine, dried over MgSO$_4$ and evaporated to give 234 mg of the crude mixture of 2 and its diastereoisomer. Purifying by flash chromatography (1% ethyl acetate in CH$_1$Cl$_2$) gave 38 mg (16%) of 2 and 35 mg (15%) of its diastereoisomer. Compound 2 was then dissolved in methanol (5 ml) and treated with NaOME (23 ml, 4.373M solution in MeOH) at 0° C. The mixture was stirred for 30 minutes, quenched by adding sat. NH$_4$Cl (5 ml) and CH$_2$Cl$_2$ (5 ml) then extracted into CH$_2$Cl$_2$. The organic phase was washed with brine, dried over MgSO$_4$ and the solvent removed in vacuo to give 67 mg crude product which was purified by filtering through silica gel to give 18 mg (78%) of the pure final product BCH-1123 (1'-S,1S,3R)-Methyl-(6-hydroxy-1-(2',6'-dideoxy-L-lyxohexopyranose) -5,12-dioxo-3,4, 5,12-tetrahydroanthraceno-(2,3-c) pyran-3-yl) ketone (12.5% from 1).

$^1$H NMR (250 MHz, DMSO) δ:13.65 (s,1H,OH), 8.35 (d,6.8 Hz,1H,Ar—H), 8.19 (d,6.8 Hz,1H,Ar—H), 8.16 (s,1H,H-11), 7.28 (m,2H,Ar—H), 5.93 (s,1H,H-1), 5.27 (bs,1H,H-1'), 4.55 (m,2H,H-3,H-4'), 4.3 (m,2H,H-3',H-5'), 2.9 (bd,1H,H-4), 2.45 (bm,1H,H-4, coincides with DMSO peak), 2.2 (s,3H,COCH$_3$), 1.5–1.9 (m,2H,H-2'), 1.2 (d,6.6 Hz,3H,H-6').

Example 25

New glycosidation approach

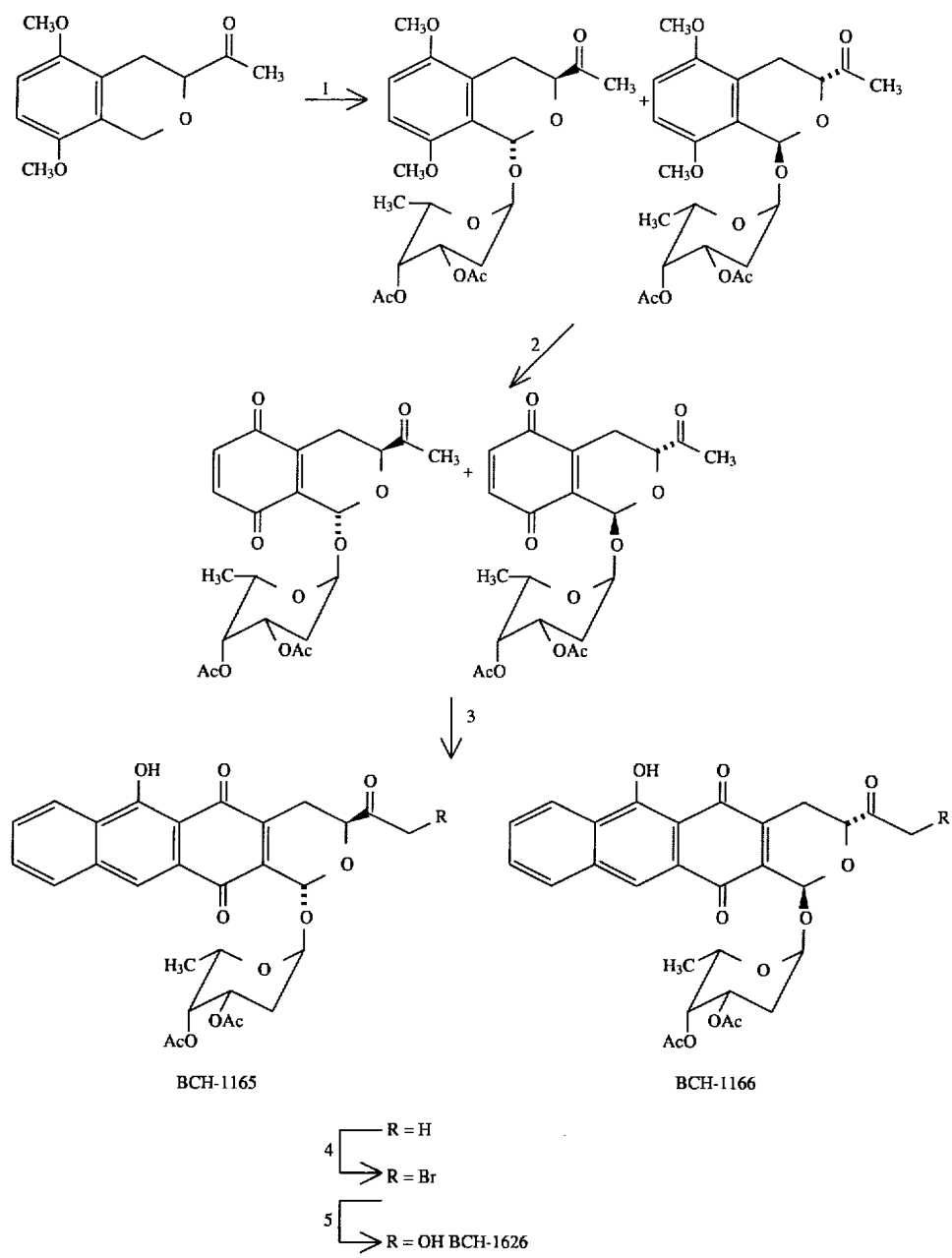

EXAMPLE 25

Step 1: (1'S,1R,3S) and (1'S,1S,3R)-3-aceto-1-O-(3',4'-di-O-acetyl-2',6'-dideoxy-a-lyxo-hexopyranosyl-5,8-dimethoxy isochroman A mixture of methyl (5,8-dimethoxy-3,4-dihydrobenzo [2,3-c] pyran-3-yl) ketone (236.0 mg, 1.0 mmol), 3,4-di-O-acetyl-2,6-dideoxy-L-lyxo-hexopyranose (α-anomer/β-anomer>1=1; 285.0 mg, 1.23 mmol), and DDQ (275 mg, 1.21 mmol) in 12 ml of $CH_2Cl_2$ was stirred at room temperature for 24 hours. After addition of a 10 ml $NaHCO_3$ solution (5%) and 30 ml $H_2O$, the products were extracted with $CH_2Cl_2$ (40ml×5). The combined organic phases were washed with $H_2O$, dried over $MgSO_4$, filtered and then concentrated. The residue was purified by flash chromatography (7:3, hexanes/EtOAc) to give the titled compound (337.4 mg) in 72% yield along with recovered starting material (17 mg) and sugar (116 mg).

$^1$H NMR ($CDCl_3$, 250 MHz) of the 1's,1R,3S diastereomer δ:1.21 (d, 3H, J=7.07 Hz), 1.70–2.20 (m,2H), 1.94 (s,3H), 2.18 (s,3H), 2.30 (s,3H), 2.55 (dd,1H,J=18.4, 12.1 Hz), 3.05 (dd,1H,J=18.5,3.5 Hz), 3.79 (s,6H), 4.56 (m,2H), 5.20 (m,2H), 5.55 (m, 1H), 6.18 (s,1H), 6.70 (d,1H,J=9.8 Hz), 6.78 (d,1H,J=9.9 Hz). The 1's,1S,3R diastereomer had δ:1.15 (d,3H,J=7.04 Hz), 1.70–2.20 (m,2H), 1.95 (s,3H), 2.16 (s,3H), 2.32 (s,3H), 2.50 (dd, 1H,J=18.6,12.2 Hz), 3.09 (dd,1H,J=18.6,3.9 Hz), 3.79 (s,6H), 4.18 (m,1H), 4.56 (m,1H), 5.21 (m,2H), 5.55 (m,1H), 5.99 (s,1H), 6.69 (d,1H, J=9.5 Hz), 6.76 (d,1H,J=9.8 Hz). IR for the mixture of diastereomers=2948, 1740, 1720, 1489, 1372, 1263, 1097, 980 $cm^{-1}$.

Step 2: (1'S,1R,3S) and (1'S,1S,3R)-3-aceto-1-O-(3',4'-di-O-acetyl-2', 6'-dideoxy-a-lyxo-hexopyranosyl)-isochroman 5,8-dione To a stirred solution of the product from step 1 (299.5 mg, 0.64 mmol) in 10 ml of $CH_3CN$ was added a solution of $NaHCO_3$ (103 mg, 1.23 mmol) in 3 ml of $H_2O$ at room temperature. After stirring for 5 minutes, a solution of CAN (1.125 g, 1.93 mmol) in 5 ml of $H_2O$ was added dropwise. After 20 minutes, the mixture was diluted with 20 ml of $H_2O$, and extracted with $CH_2Cl_2$ (50ml×2). The combined organic layers were washed with $H_2O$, dried over $MgSO_4$, filtered and then concentrated to a crude which was found to be pure titled compounds.

$^1$H NMR ($CDCl_3$, 250 MHz) of the 1'S,1R,3S-diastereomer δ:1.27 (d,3H, J=6.4 Hz), 1.70–2.25 (m,2H), 1.96 (s,3H), 2.17 (s,3H), 2.28 (s,3H), 2.41 (dd,1H,J=19.2,12.0 Hz), 2.87 (dd,1H,J=19.8,4.1 Hz), 4.48 (m,2H), 5.19 (m,2H), 5.49 (d,1H,J=3.8 Hz), 5.98 (s,1H), 6.75 (d,1H,J=10.1 Hz), 6.83 (d,1H,J=10.2 Hz) the 1'S,1S,3R-diastereomer had δ:1.15 (d,3H,J=6.5 Hz), 1.75–2.35 (m,2H), 1.96 (s,3H), 2.17 (s,3H), 2.30 (s,3H), 2.42 (dd,1H,J=19.5,11.5 Hz), 2.90 (dd, 1H,J=19.6,4.0 Hz), 4.47 (m,2H), 5.18 (m,2H), 5.57 (d,1H, J=3.7 Hz), 5.80 (s,1H), 6.73 (d,1H,J=10.2 Hz), 6.81 (d,1H, J=10.2 Hz).

Step 3: (1'S,1R, 3S) and (1'S,1S,3R)-3-aceto-1-O-(3',4'-di-O-acetyl-2', 6'-dideoxy-a-lyxo-hexopyranosyl)-1,2,3,4,5,12-hexahydro-6-hydroxy-[2-oxo]-naphthacene-5,12-dione BCH-1165 & BCH-1166

The procedure described in example 16, second part of step 1, was followed. After purification, titled compounds were obtained (207.0 mg) in 59% overall yield for step 2 and step 3.

$^1$H NMR is identical to the compounds reported previously.

Step 4: (1'S,1R,3S) and (1'S,1S,3R)-3-bromoaceto-1-O-(3', 4'-di-O-acetyl-2',6'-dideoxy-a-lyxo-hexopyranosyl)-1,2,3,4, 5,12-hexahydro-6-hydroxy-[2-oxo]-naphthacene-5,12 -dione A mixture of compounds from step 3 above (143.6 mg, 0.26 mmol) and pyridinium bromide perbromide (1000 mg, 0.3 mmol) in 15 ml of THF was stirred at room temperature under argon for 5 hours. After removal of THF by reduced pressure, the residue was dissolved in ethyl acetate (20 ml) and $H_2O$ (20 ml). The product was extracted with ethyl acetate (30 ml×2). The combined organic solvent was dried over $Na_2SO_4$, filtered and then concentrated. Flash chromatography of the residue (EtOAc/hexanes,=9) gave the two titled diastereoisomers (117.0 mg) in 71% yield. $^1$H NMR ($CDCl_3$, 250 MHz) δ: the 1'S, 1R, 3S diostereomer had 1.34 (d,3H,J=6.4 Hz), 1.90–2.30 (m,2H), 1.95 (s,3H), 2.19 (s,3H), 2.65 (dd,1H,J=19.5,12.0 Hz), 3.18 (dd,1H,J=19.5, 4.0 Hz), 3.98 (d,H,J=11.8 Hz), 4.38 (d,1H,J=11.9 Hz), 4.68 (m,1H), 4.96 (m,1H), 5.20 (m,2H), 5.70 (br s,1H), 6.21 (s,1H), 7.72 (m,2H), 8.00 (m,1H), 8.12 (s,1H), 8.48 (m,1H), 13.78 (s,1H); the 1'S, 1S, 3R diastereomer had 1.18 (d,3H, J=6.4 Hz), 1.90–2.30 (m,2H), 1.95 (s,3H), 2.19 (s,3H), 2.64 (dd,1H,J=19.5,12.0 Hz), 3.17 (dd,1H,J=19.5,4.0 Hz), 4.28 (m,1H), 5.00 (m,1H), 5.21 (m,2H), 5.70 (b s,1H), 6.02 (s,1H), 7.72 (m,2H), 8.00 (m,1H), 8.08 (s,1H), 8.48 (m,1H), 13.78 (s,1H).

Step 5: (1'S,1R,3S) and (1'S,1S,3R)-1-O-(3',4'-di-O-acetyl-2',6'-dideoxy-a-lyxo-hexopyranosyl)-1,2,3,4,5,12-hexahydro-6-hydroxy-3-hydroxyaceto-[2-oxo]-naphthacene-5,12-dione BCH-1626

The bromides from step 4 (15.0 mg, 24 mmol) were dissolved in 4 ml of acetone and 1 ml of $H_2O$. To this solution was added NaOH solid (1.1 mg, 27.5 mmol). The resulting blue solution was refluxed at 80° C. for 5 minutes when the red colour returned. The solution was concentrated to ca 2 ml, diluted with $H_2O$, extracted with 1=1 ($CHCl_3$/ MeOH). Purification of the crude residue by flash chromatography (20=1, $CHC_3$/MeOH) provided 10.2 mg of titled compounds as a mixture of diastereoisomers in 75% yield. $^1$H NMR ($CLCl_3$, 250 MHz) δ:VIa=1.36 (d,3H,J=6.5 Hz), 1.73–2.30 (m,2H), 1.98 (s,3H), 2.20 (s,3H), 2.62 (dd,1H,J= 19.8,12.1 Hz), 3.0 (m,1H), 3.21 (dd,1H,J=19.7,4.0 Hz), 4.50–4.84 (m,4H), 5.20 (m,2H), 5.50 (br s,1H), 6.20 (s,1H), 7.75 (m,2H), 7.98 (m,1H), 8.16 (s,1H), 8.50 (m,1H), 13.79 (s,1H), VIb=1.15 (d,3H,J=6.50 Hz), 1.75–2.30 (m,2H), 1.98 (s,3H), 2.20 (s,3H), 2.61 (dd,1H,J=19.7,12.0 Hz), 3.0 (m,1H), 3.21 (dd,1H,J=19.7,4.0 Hz), 4.50–4.84 (m,4H), 5.20 (m,2H), 5.68 (br s,1H), 6.01 (s,1H), 7.75 (m, 2H), 7.98 (m,1H), 8.09 (s,1H), 8.50 (m,1H), 13.79 (s,1H), ir (neat) VI=3478 br, 2940, 1744, 1662, 1460, 1371, 1302, 1252, 1023, 986, 941 $cm^{-1}$.

Example 26

Synthesis of functionalized Isochroman

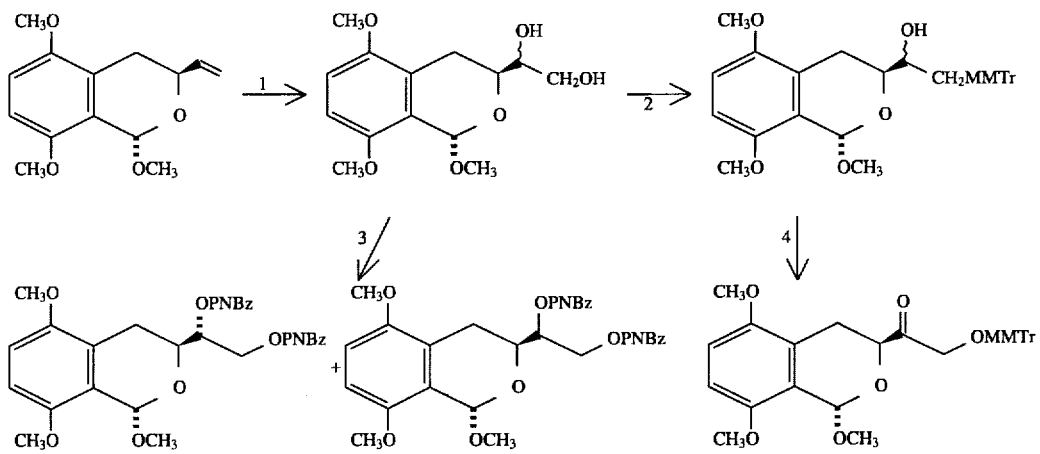

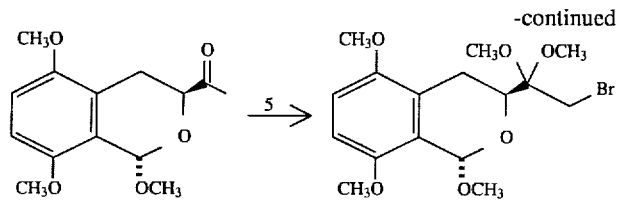

Example 26

Step 1: (trans)-3-(1',2'-dihydroxy)-ethyl-1,5,8-trimethoxy-isochroman 1,5,8-trimethoxy-3-vinylisochroman (553.0 mg, 2.21 mmol) was treated with Me₃NO—H₂O (490.5 mg, 4.41 mmol) and a catalytic amount of OsO₄ (0.02M in tBuOH, 2.8 ml, 0.056 mmol) in the presence of acetone (50 ml), H₂O (26 ml), and CCl₄ (1 ml) at room temperature for 15 hours. The mixture was quenched with a 5% sodium sulfate solution (25 ml). After the volatiles were removed by rotavapor, the residue was extracted with CH₂Cl₂ (30ml×4). The combined organic phases were washed with H₂O, brine, dried over MgSO₄, filtered, and then concentrated to a residue (630.0 mg) that was found to be the titled diastereomeric mixture. This was used without any further purification for the next step.

Step 2: (trans)-3-(1'-hydroxy-2'-p-anisyldiphenylmethoxy)-ethyl-1,5,8-trimethoxyisochroman The residue obtained from the previous step, 2.21 mmol) was treated with p-anisyldiphenyl chloromethane (3.4 g) in the presence of 42 ml of pyridine at 5° C. for 21 hours. The mixture was poured into ice water, and extracted with CH₂Cl₂. The combined organic phases were dried over MgSO₄, filtered, and then evaporated to dryness. The diastereomeric mixture was used for next step without further characterization.

Step 3: (trans)-3-(1',2'-di-O-p-nitrobenzoyl)-ethyl-1,5,8-trimethoxyisochroman

The residue obtained in step 1, 2.21 mmol was treated with p-nitrobenzyl chloride (2.05 g, 11.0 mmol) in the presence of 20 ml pyridine at room temperature for 4 hours. After addition of saturated NH₄Cl (50 ml) the products were extracted with CH₂Cl₂ (60ml×4). The combined organic phases were dried over MgSO₄, filtered, and then evaporated to dryness. Purification by flash chromatography (7:2:1, hexanes/CH₂Cl₂/EOAc) gave the 2'-R titled compound (891.0 mg, 69.2%) and the 2'-S titled compound (226.0 mg, 17.6%).

¹H NMR (CDCl₃, 250 MHz) 2'R isomer δ:2.62 (dd,1H, J=18.2,11.4 Hz), 2.93 (dd,1H,J=18.2,4.0 Hz), 3.55 (s,3H), 3.77 (s,3H), 3.82 (s,3H), 4.62 (m,1H), 4.79 (m,1H), 4.98 (m,1H), 5.62 (s,1H), 5.68 (m,1H) 6.72 (d, 1H,J=9.0 Hz), 6.77 (d, 1H,J=8.9 Hz), 8.10–8.35 (m,8H), 2'-R isomer 2.61 (dd, 1H,J=18.4,11.6 Hz, 2.82 (dd,1H,J=18.4,3.9 Hz), 3.53 (s,3H), 3.76 (s, 3H), 3.82 (s,3H), 4.62 (m,1H), 4.85 (m,2H), 5.64 (s,1H), 5.79 (m, 1H), 6.71 (d,1H,J=9.5 Hz), 6.76 (d,1H,J=9.4 Hz).

Step 4: (trans)-3-(2'-p-anisyldiphenylmethoxy)-aceto-1,5,8-trimethoxy-isochroman The residue obtained in step 2, 2.21 mmol, was treated with SO₃.Py (3.502 g, 22.0 mmol) in the presence of 20 ml DMSO, and 9.1 ml Et₃N at room temperature for 48 hours. After the mixture was diluted with 300 ml of H₂O the products were extracted with CH₂Cl₂ (150 ml×3). The combined organic phases were washed with sat. NaCl, H₂O, dried over MgSO₄, filtered and then concentrated. Flash chromatography of the residue (7:3), hexanes/ethyl acetate) gave the titled compound (1.164 g) in 95% overall yield for three steps.

¹H NMR (CDCl₃, 250 MHz)δ:2.39 (dd,1H,J=18.2,12.5 Hz), 2.98 (dd,1H, J=18.2,4.0 Hz), 3.36 (s,3H), 3.72 (s,3H), 3.74 (s,3H), 3.75 (s,3H), 4.10 (d,1H,J=17.6 Hz), 4.21 (d,1H, J=17.5 Hz), 4.62 (dd,1H,J=12.5, 4.1 Hz), 5.49 (s,1H), 6.60 (d,1H,J=9.1 Hz), 6.68 (d,1H,J=9.1 Hz), 6.78 (m,2H), 7.12–7.50 (m,2H).

Step 5: (trans) -3-(2'-bromo-1', 1'-dimethoxy)-ethyl-1,5,8-trimethoxyisochroman

3-Aceto-5,8-dimethoxyisochroman (126 mg, 0.53 mmol) was treated with Br₂ (1M in CCl₄, 1.1 ml, 1.1 mmol) in the presence of trimethylorthoformate (0.4 ml), methanol (7 ml), and dioxane (10 ml) at room temperature for 3 hours. After the volatiles were removed, the residue was purified by flash chromatography (7=3, hexanes/EoAc) to provide the titled compound (107–9 mg) in 52% yield.

¹H NMR (CDCl₃, 250 MHz) δ:2.82 (d,2H,J=8.6 Hz), 3.40 (s,3H), 3.45 (s,3H), 3.60 (s,3H), 3.67 (s,2H), 3.78 (s,3H), 3.80 (s,3H), 4.57 (t,1H,J=8.5 Hz), 5.62 (s,1H), 6.68 (d,1H, J=9.1 Hz), 6.73 (d, 1H, J=9.2 Hz).

Example 27

Preparation of
Trans-3-aceto-1,6-dihydroxy-1,2,3,4,5,12-hexahydro-2-(sulfur)naphthacene-5,12-dione and
cis-3-aceto-1,6-dihydroxy-1,2,3,4,5,12-hexahydro-2-(sulfur)naphthacene-5,12-dione BCH-1167, and
Trans-3-aceto-6-hydroxy-1-methoxy-1,2,3,4,5,12-hexahydro-2-(sulfur)naphthacene-5,12-dione

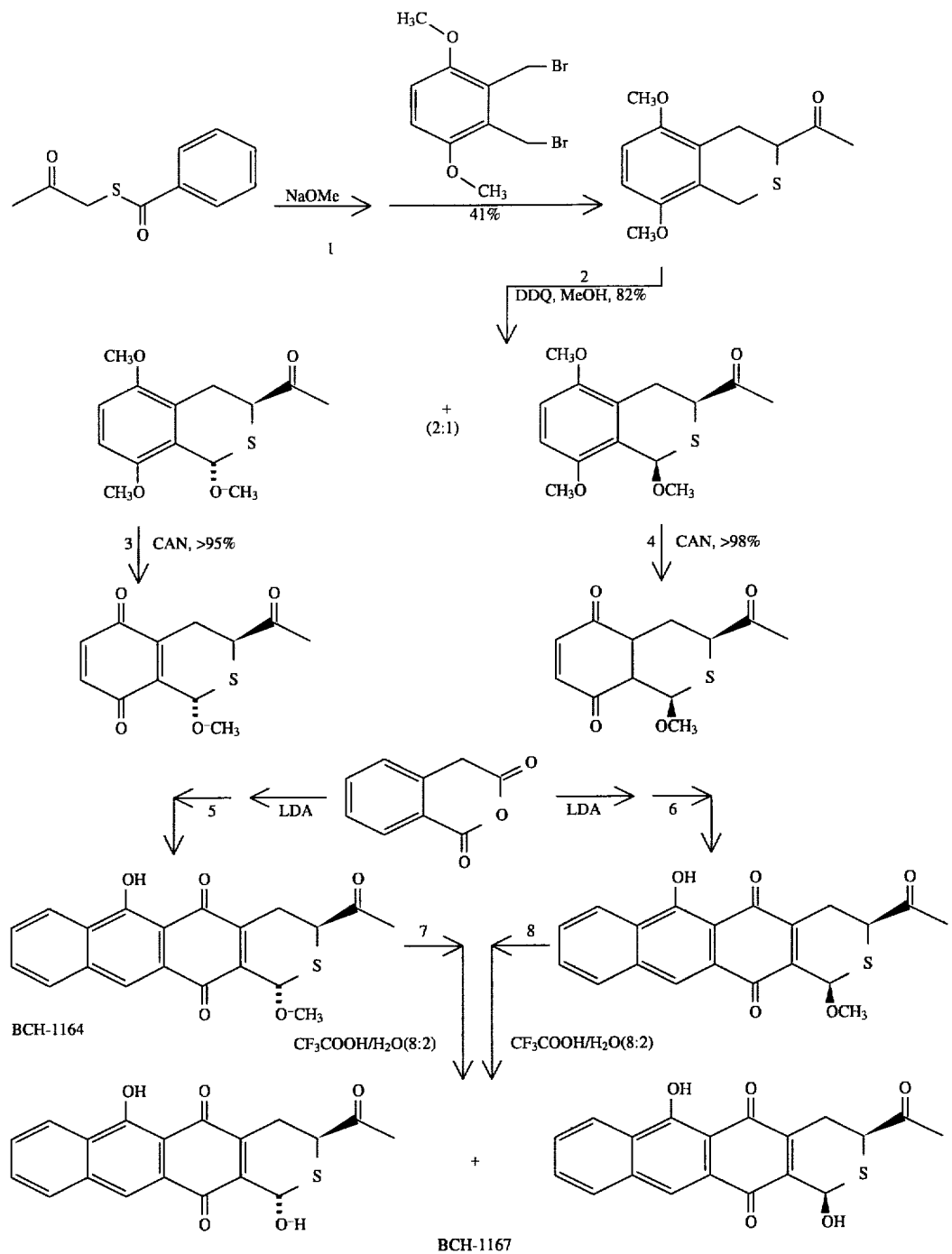

Example 27

Step 1: 3-Aceto-5,8-dimethoxythioisochroman 1-thiobenzoylpropan-2-one (10.083 g, 51.97 mole) was dissolved in MeOH (100 ml), cooled to 0° C., followed by the slow addition of NaOME (4.37M, 14.3 ml, 62.36 mmole). The resulting mixture was stirred at 0° C. for 3/4 hour. It was then cooled to −78° C. followed by the slow addition of dibromide (II, 6.74 g, 20.79 mmole) in $CH_2Cl_2$: MeOH (60.20 ml). The resulting mixture was slowly warmed to room temperature and stirred for 2½ hours. $NH_4Cl$ (saturated solution) was added and it was extracted with ethyl acetate. The combined organic phases were dried over $MgSO_4$, filtered and concentrated in vacuum. The crude obtained was flash chromatographed to give the titled compound (2.08 g, 8.25 mmol) in 41% yield.

$^1H$ NMR (250 MHz, $CD_3COCD_3$) δ:2.31 (s,3H,$CH_3$), 2.83 (dd,1H,J=1.06, 8.55 Hz,HCHaCH—S), 2.99 (dd,1H,J= 2.44,6.17 Hz,HCHeCH—S), 3.44 (m,1H, HCHa—e—S), 3.78 (2s,6H,$OCH_3$), 3.85 (m,2H,$CH_2$—S), 6.78 (dd,2H,J= 8.95, 12.58 Hz, ArH). IR ($cm^{-1}$): 2900: CH,1707:C=O.

Step 2: Trans-2-aceto-1,5,8-trimethoxythioisochroman and cis-3-aceto-1,5,8-trimethoxythioisochroman The thioisochroman from step 1 (example 24, 100.0 mg, 0.40 mmol) was dissolved in $CH_2Cl_2$ (12 ml) and MeOH (4 ml) followed by the addition of DDQ (109.0 mg, 0.48 mmol, 1.2 eq [1] at room temperature. The resulting mixture was stirred at room temperature overnight. $H_2O$ was added and it was extracted with $CH_2Cl_2$. The combined organic phases were washed with lots of water, dried over $MgSO_4$, filtered and concentrated in vacuum. The crude obtained was flash chromatographed using Tol: EE (95:5) to give the trans titled compound (65.0 mg, 0.23 mmol) in 58% yield.

$^1H$ NMR (250 MHz, $CDCl_3$) δ:2.34 (s,3H,$CH_3CO$), 2.91 (dd,1H,J=11.73, 17.78 Hz, HCHaCHC—S), 3.27 (dd,1H,J= 4.10,17.77 Hz,HCHeCHC—S), 3.54 (s,3H,$OCH_3$), 3.78 (s,3H,$OCH_3$), 3.82 (s,3H,$OCH_3$), 4.16 (dd,1H,4.23,11.79 Hz,HCHa,e—S), 5.69 (s,1H,CH—S), 6.75 (dd,2H, J=8.96, 14.36 Hz,ArH). IR ($cm^{-1}$): 2925: CH;1705.7:C=O); Cis-3-Aceto-1,5,8-trimethoxythioisochroman (32.4 mg, 0.11 mmol) was obtained in 30% yield. (Total yield if including the isolation of trans isomer is 82%).

$^1H$ NMR (250 MHz, $CDCl_3$) δ:2.34 (s,3H,$CH_3$), 3.25 (d,2H,J=6.58 Hz, HaCHeCHC—S), 3.46 (s,3H,$OCH_3$), 3.59 (dd,1H,J=6.75,13.55 Hz,HCHa,e—S), 3.79 (2s,6H,$OCH_3$), 5.73 (s,1H,CH—S), 6.76 (dd,2H,J=9.50,21.30 Hz, ArH). $^{13}C$ NMR (250 MHz, $CDCl_3$) δ:22.62 ($CH_3$), 26.50 ($CH_2$—C), 48.32 (CH—S), 55.56, 55.72, 55.76 ($OCH_3$), 77.50 (S—C—$OCH_3$), 108.75, 110.63 (C—$OCH_3$), 126.25, 126.44 (CH-aromatic), 149.65, 151.47 (C-quaternary aromatic), 203.71 (C=O,ketone). IR ($cm^{-1}$): 2900:CH,1713.2:C=O;

Step 3: Trans-3-aceto-1-methoxy-5,8-dioxoisothiochroman

The trans thioisochroman from step 2 (178.2 mg, 0.63 mole) was dissolved in acetonitrile (10 ml) and $H_2O$ (10 ml), followed by the addition of $NaHCO_3$ (100.8 mg, 1.22 mmole). The mixture was cooled to 0° C., followed by the slow addition of CAN (1.04 g, 1.89 mole). After 20 minutes of stirring, $H_2O$ was added it was extracted with $CH_2Cl_2$. The combined organic phases were washed with $H_2O$, dried over $MgSO_4$, filtered and concentrated in vacuum. The crude obtained was found to be pure titled compound (yield>95%). $^1H$ NMR (250 MHz, $CDCl_3$) δ:1.73 (s,3H, $CH_3$), 2.62 (dd,1H, J=11.32, 19.81 Hz,HCHaCH—s), 2.87 (dd,1H,J=4.28,20.10 Hz,HCHeCH—S), 3.21 (s, 3H,$OCH_3$), 3.61 (dd,1H,J=4.31,11.42 Hz,HCHa—e—S), 5.97 (m,2H, ArH).

Step 4: Cis-3-aceto-1-methoxy-5,8-dioxoisothiochroman

The titled compound was obtained by applying the procedure described in step 3 to the cis thioisochroman of step 2. The crude obtained was used in the following step, the yield being>98%.

$^1H$ NMR (250MHz, $CDCl_3$) δ:2.04 (s,3H,$CH_3$), 2.23 (dd, 1H,J=4.88, 19.49 Hz,HCHaCH—S), 2.54 (d,1H,J=5.68 Hz,HCHeCH—S), 3.56 (dd, 1H, J=2.10,19.23 Hz,HCHa, e—S), 5.09 (s,1H, CH—S), 5.96 (dd,2H, J=10.30, 12.20 Hz,ArH).

Step 5: Trans-3-aceto-1-methoxy-6-hydroxy-1,2,3,4,5,12-hexahydro-2-(sulfur)naphthacene-5,12-dione BCH-1164

To a freshly made LDA solution (0.88 mmol, 7 ml THF) at −78° C. was added dropwise a solution of homophthalic anhydride (136.2mg, 0.84 mmole) in 7 ml of THF under argon. The resulting mixture was stirred for 20 minutes before the quinone from step 3 (0.70 mmol; 7 ml THF) was added slowly. The resulting mixture was allowed to stir at −78° C. for 20 minutes and was slowly warmed to room temperature. It was quenched with $NH_4Cl$ (sat.) and extracted with $CH_2Cl_2$. The combined organic phases were dried over $MgSO_4$, filtered and concentrated in vacuum. The crude obtained was flash chromatographed using Hex:EE (7:3) to give the titled compound (90.7 mg, 0.25 mmol) in 35% yield.

$^1H$ NMR (250 MHz, $CDCl_{32}$) δ:2.41 (s,3H,$CH_3$), 2.97 (dd, 1H,J=11.48, 19.73 Hz,HCHaCH—S), 3.32 (dd,1H,J= 4.13,20.02 Hz,HCHeCH—s), 3.60 (s, 3H,$OCH_3$), 4.14 (dd, 1H,J=4.15,11.59 Hz,HCHa,e—S), 5.75 (s,1H,CH—$OCH_3$), 7.73 (m,2H,ArH), 7.97 (m,1H,ArH), 8.15 (s,1H,ArH), 8.49 (d,1H, J=9.54 Hz,ArH), 13.91 (s,1H,OH).

Step 6: Cis-3-aceto-1-methoxy-6-hydroxy-1,2,3,4,5,12-hexahydro-2-(sulfur)-naphthacene-B,12-dione Application of the procedure described in step 5 to cis-3-aceto-1-methoxy-5,8-dioxoisothiochroman gave a crude product which was flash chromatographed using Hex:EE (7:3) to give the titled compound (115.7mg, 0.31 mmol) in>37% yield.

$^1H$ NMR (250 MHz, $CDCl_3$)δ:2.39 (s,3H,$CH_3$), 2.79 (dd,1H,J=5.54, 19.31 Hz,HCHaCH—s), 3.41 (m,1H, HCHeCH—s), 3.53 (s,3H, $OCH_3$), 3.67 (m,1H,HCHa, e—S), 5.53 (s,1H,CH—$OCH_3$), 7.71 (m,1H,ArH), 7.94 (d,1H, J=7.27 Hz,ArH), 8.11 (s,1H,ArH), 8.49 (d,1H,J=6.04 Hz,ArH), 13.93 (s, 1H,OH).

Step 7: Trans-3-aceto-1,6-hydroxy-1,2,3,4,5,12-hexahydro-2-(sulfur)naphthacene-5,12-dione and cis-3-aceto-1,6-hydroxy-1,2,3,4,5,12 -hexahydro-2-(sulfur)naphthacene-5,12-dione BCH-1167

Trans-3-aceto-1-methoxy-6-hydroxy-1,2,3,4,5,12-hexahydro-2-(sulfur)naphthacene-5,12-dione (91.6 mg, 0.25 mmol) was treated with trifluoroacetic acid (6.4 ml) and water (1.6 ml) at 0° C. for 2 hours. $NaHCO_3$ (5%) was added and it was extracted with $CH_2Cl_2$. The combined organic phases were dried over $MgSO_4$, filtered and concentrated in vacuum. The crude obtained showed the presence of the titled compounds as well as some impurities recrystallization from dichloromethane and pentane yielded a mixture of titled compounds in a ratio of about 80:20%, (trans:cis).

$^1H$ NMR (250 MHz, $CDCl_3$) δ:2.38 (s,3H,$CH_3$, cis or trans), 2.40 (s, 3H,$CH_3$, cis or trans), 2.75 (m,2H,HCHaCH—S, cis and trans), 3.55 (m,1H,HCHeCH—S, cis or trans), 4.01 (m,1H,HCHa,eS, cis or trans), 4.46 (m,1H, HCHa,e—S, cis or trans), 6.073 (s,1H,CH—OH, cis or trans). 6.25 (s,1H,CH—OH, cis or trans), 7.76 (m,2H,ArH), 8.05 (m,1H,ArH), 8.37 (m,1H,ArH), 13.87 (s,1H,OH, cis or trans) 13.90 (s,1H,OH, cis or trans).

Step 8:

The products from step 7 but in cis configuration could also be obtained from the acid hydrolysis of cis-3-aceto-1-methoxy-6-hydroxy-1,2,3,4,5,12-hexahydro-2-(sulfur)naphtacene-5,12-dione.

Example 28

Preparation of (1'S,1R,3S)-6-hydroxy-1-(2',3',6'-trideoxy-3'-trifluoroacetamido-L-lyxohexopyranose)-3-(2-aza-3-acetamidothienyl)-5,12-dioxo-3,4,5,12-tetrahydroanthraceno-[2,3-c]-pyran BCH-1623

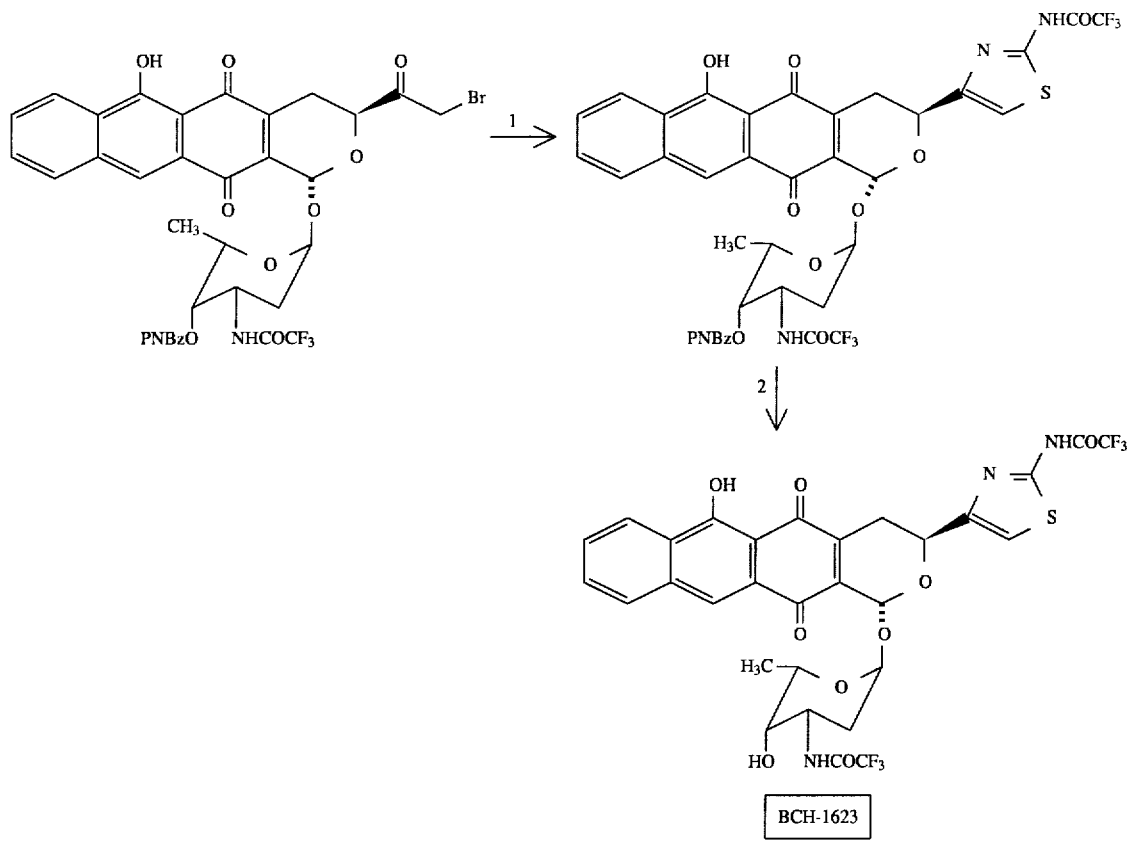

Example 28

Step 1: (1'S,1R,3S)-6-hydroxy-1-(2',3',6'-trideoxy-4'-p-nitrobenzoyl-3'-trifluoroacetamido-L-lyxohexopyranose)-3-(2-aza-3-acetamidothienyl)-5,12-dioxo-3,4,5,12-tetrahydroanthraceno-[2,3-c]-pyran A sample of (1'S,1R,3S)-bromomethyl-6-hydroxy-1-(2', 3',6'-trideoxy-4'-p-nitrobenzoyl-3'-trifluoroacetamido-L-lyxohexo pyra- nose)-5,12-dioxo-3,4,5,12-tetrahydro anthraceno-[2,3-c]-pyran-3-yl-ketone, (25 mg, 0.032 mmole) dissolved in tetrahydrofuran (2.5 ml) and dichloromethane (2.5 ml) was stirred with 1-acetylthiourea (4.8 mg, 0.04 mole) at room temperature for 1 hour then at 40° C. for 2 hours. Solvent was evaporated and the crude product was chromatographed (volume ratio, chloroform:methanol= 100:6) to allow collection of the desired product as an orange solid (12 mg). M.P. 170° C., decompose at 180° C.

$^1$H NMR (250 MHz, acetone-d$_6$) δ:1.11 (d,3H,J=7.0 Hz,6'-CH$_3$, 1.96 (bd, 1H,J=13.2'-HCHa), 2.27 (s,3H,NHCOCH$_3$), 2.44 (dt,1H,J=3.0 Hz,13 Hz, 2'-HCHe), 2.76 (dd, 1H,J=12.0 Hz,18.8 Hz,4-HCHa), 3.17 (dd,1H,J=4.0 Hz, 18.8 Hz, 4-HCHe), 4.61 (qua,1H,J=7.0 Hz,5'-CH), 4.66 (m,1H,3'-CH), 5.34 (dd,1H,J=4.0 Hz,12 Hz,3-CH), 5.48 (br s,1H,4'—CH), 5.72 (d,1H, J=2.2 Hz,1'-CH), 6.01 (s,1H,1-CH), 7.21 (s,1H, thiazole—CH), 7.81 (m, 2H,8.9-CH), 8.12 (s,1H,11-CH), 8.15 (d, 1H,J=8.9 Hz,10-CH), 8.39 (m, 4H,p-nitro-benzoyl), 8.71 (d,1H,J=8.5 Hz,7-CH), 11.08 (s,1H, NHAc), 13.89 (bs,1H,6-OH). IR (Nicolet 205 FT, film on NaCl plate): 3400–3116 (str,pk at 3273), 2950, 2924, 2861, 1729 (str), 1712 (str), 1608, 1526, 1451, 1375, 1351, 1275 (str), 1221, 1186, 1167, 1102, 1052, 952, 840, 723.

Step 2: (1'S,1R,3S)-6-hydroxy-1-(2',3',6'-trideoxy-3'-trifluoroacetamido-L-lyxohexopyranose)-3-(2-aza-3-acetamido-thienyl)-5,12-dioxo-3,4,5,12-tetrahydro- anthraceno-[2,3-c]-pyran BCH-1623

To a sample of thiazole derivative (6 mg, 0.0074 mmole) from the previous step, dissolved in methanol (761 ml), dichloromethane (285 ml), and water (176 ml and cooled to 0° C., was added a sodium bicarbonate solution (0.93 mg, 0.011 mmole, in 45 ml of water). The resulting liquid was stirred at room temperature for 1.5 h till the starting material was consumed. The purple reaction mixture was poured to HCl solution (50 ml of 1.0M HCl diluted in 10 ml of water) and extracted with methylene chloride. The organic layer was washed with brine, dried (over sodium sulfate) and then evaporated to give a crude product which was recrystalized from methylene chloride and hexane to yield the desired product as an orange solid (4.4 mg). M.P. 185~190.

$^1$H NMR (250 MHz, acetone-d$_6$) δ:1.12 (d,3H,J=6.7 Hz,6'-CH$_3$), 1.65 (d,1H,J=13.6 Hz,2'-HCHa), 2.11 (t,1H,J= 13.6 Hz,2'-HCHe), 2.26 (b,3H, NHCOCH$_3$), 2.69 (dd,1H, J=11.6 Hz,20 Hz,4-HCHa), 3.20 (dd,1H,J=4.0 Hz, 20 Hz,4-HCHe), 3.65 (bs,1H,4'-CH), 4.24 (qua,1H,J=6.7 Hz,5'-CH), 4.31 (m,1H,3'-CH), 5.26 (bs,1H,1'-CH), 5.97 (s,1H,1-CH), 7.12 (s,1H, thiazole-CH), 7.82 (m,2H, 8.9-CH), 8.14 (s,1H, 11-CH), 8.16 (d,1H, J=8.5 Hz, 10-CH), 8.47 (d,1H,J=8.5 Hz,7-CH), 11.02 (s,1H,NHAc), 13.91 (bs,1H,6-OH).

IR (Nicolet 205 FT, film on NaCl plate): 3567–3100 (str, pks at 3408.6 and 3261.9), 2958.2, 2929.6, 2856.3, 1721.0 (str) 1666.0, 1611.0 (m), 1549.8 (str), 1503.0, 1460.1, 1374.5, 1295, 1162.6, 983.23,899.66, 807.95, 756.99, 728.30.

Example 29

Preparation of
(1'S,1S,3R)-6-hydroxy-1-(2',3',6'-trideoxy-3'-trifluoro-
acetamido-L-lyxohexopyranose)-3-(2-aza-3-acetamido-
thienyl)-5,12-dioxo-3,4,5,12-tetrahydro-
anthraceno-[2,3-c]-pyran BCH-1619

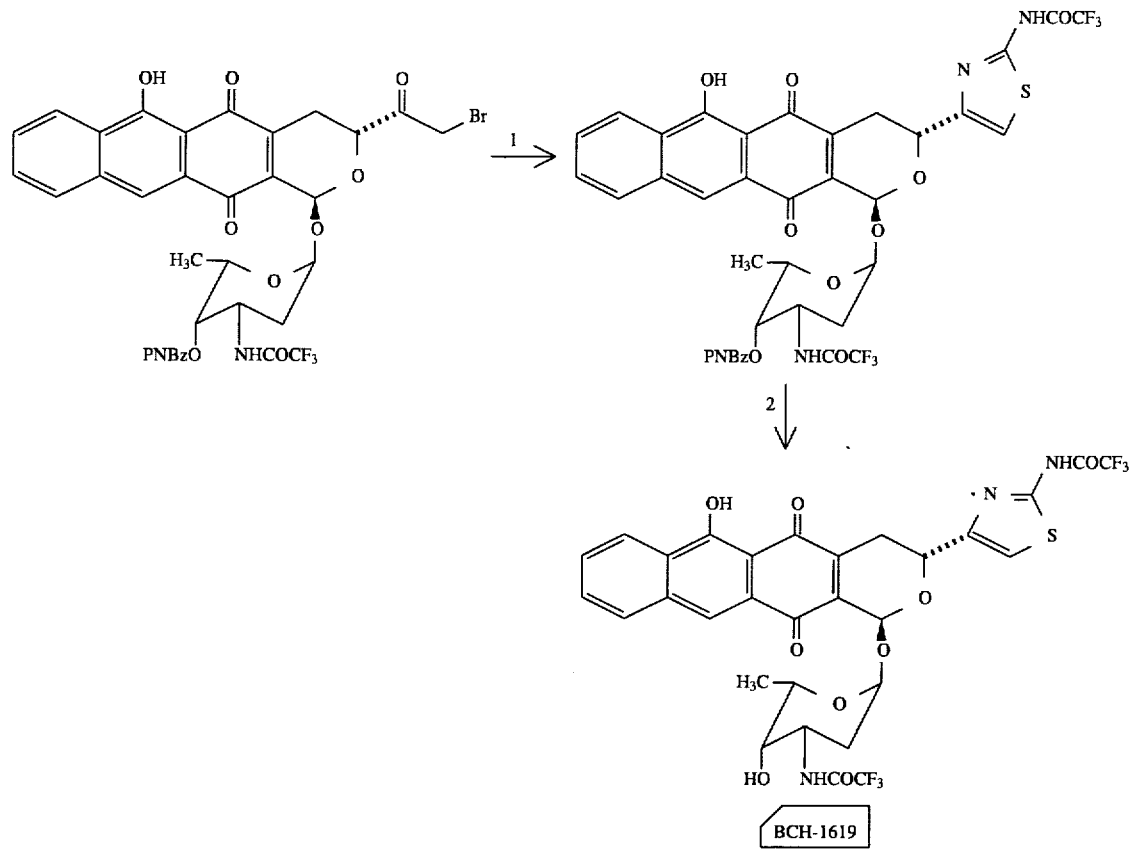

Example 29

Step 1: (1'S, 1S,3R)-6-hydroxy-1-(2',3',6'-trideoxy-4'-p-nitrobenzoyl-3'-trifluoroacetamido-L-lyxohexo pyranose)-3-(2-aza-3-acetamidothienyl)-5,12-dioxo-3,4,5,12-tetrahydroanthraceno-[2,3-c]-pyran.

A sample of (1'S,1S,3R)-bromomethyl-6-hydroxy-1-(2',3',6,-trideoxy-4'-p-nitrobenzoyl-3'-trifluoroacetamide-L-lyxohexo-pyranose) -5,12-dioxo-3,4,5,12-tetrahydroanthraceno-[2,3-c]-pyran-3-yl-ketone (25 mg, 0.032 mmole) dissolved in tetrahydrofuran (2.5 ml) and dichloromethane (2.5 ml) was stirred with 1-acetylthiourea (4.8 mg, 0.04 mmole). Sodium iodide (0.24 mg, 0.0016 mmole) and 4A-molecule sieves (3 mg) at 40° C. for one hour. More 1-acetyl thiourea (1 mg, 0.008 mmole) was added. The mixture was stirred at the same temperature for another hour. Solvent was evaporated and the crude product was chromatographed (volume ratio, chloroform:methanol-100:6) to yield the desired product as an orange solid (18 mg). M.P. 100° C.

1H NMR (250 MHz, acetone-d$_6$) δ:1.35 (d,3H,J=6.9 Hz,6'-CH$_3$), 2.0 (m,1H,2'-HCHa, partially overlapped by acetone signal), 2.28 (s,1H,NHCOCH$_3$ ), 2.50 (dt,1H,J=4.0 Hz, 13.4 Hz, 2'-HCHe), 2.75 (dd,1H, J=11.2 Hz,18.8 Hz, 4-HCHa), 3.16 (dd,1H,J=4.2 Hz,J=18.8 Hz,4-HCHe), 4.63 (m,1H,3'-CH), 4.96 (qua,1H, J=6.9 Hz,5'-CH), 5.22 (dd,1H,J=4.2 Hz, 11.2 Hz, 3-CH), 5.55 (bs,1H, 4'-CH), 5.68 (bd,1H,J=2.9 Hz,1'-CH), 6.13 (s,1H,1-CH), 7.18 (s,1H,thiazole-CH), 7.80 (m,2H,8.9-CH), 8.09 (s, 1H,11-CH), 8.15 (d,1H,8.0 Hz,10-CH), 8.40 (m,4H,p-nitrobenzoyl), 8.72 (d,J=8.0 Hz,7-CH), 11.04 (s,1H,NHAc), 13.81 (bs,1H,6-OH).

IR (Nicolet 205 FT, film or NaCl plate): 3490.3~3137.5 (str at pk at 3286.9) 3064.4 (w), 2946.8, 1729.6 (str), 1713.7 (str), 1608.9, 1532.6, 1456.3, 1373.7, 1348.3, 1272.0 (str), 1221.1, 1189.4, 1163.9, 1005.0, 975.18, 951.31, 838.00, 719.36.

Step 2: (1'S, 1S,3R)-6-hydroxy-1-(2',3',6'-trideoxy-3'-trifluoroacetamido-L-lyxohexopyranose)-3 -(2-aza-3-acetamidothienyl)-5,12 -dioxo-3,4,5,12-tetrahydro- anthraceno-[2,3-c]-pyran BCH-1619

To a sample of thiazole derivative (6 mg, 0.0074 mmol), from the previous step, dissolved in methanol (2.0 ml) and tetrahydrofuran (0.5 ml) and cooled to 0° C., was added sodium methoxide solution (4.3M methanolic solution, 1.8 ml, 0.0078 mmol). The dark purple liquid was stirred for 20 minutes at the same temperature then poured into a HCl solution (50 m at 1M HCl diluted in water to 10 ml). The mixture was extracted with methylene chloride and the organic layer was washed with brine and then dried over sodium sulfate. The solvent was evaporated to give a crude product which was recrystallized to yield the desired product as an orange solid (4.0 mg). M.P. 112~115.

$^1$H NMR (250 MHz, acetone-D$_6$), δ:1.35 (d,3H,J=6.8Hz, 6'-CH$_3$), 1.78 (dd,1H,J=4.8 Hz,13.6 Hz,2'-HCHa), 2.20 (dt, 1H,J=3.4 Hz,13.6 Hz,2'-HCHe), 2.28 (s,3H,NHCOCH$_3$), 2.80 (dd,1H,J=12.7 Hz,19.5 Hz,4-HCHa), 3.20 (dd,1H,J= 4.1 Hz, 19.5 Ha,4-HCHe), 3.75 (bs,1H,4'-CH), 4.29 (m,1H, 3'CH), 4.63 (qua,1H,J=6.8 Hz,5'-CH), 5.70 (dd,1H,J=4.1

Hz,12.7 Hz,3-CH), 5.49 (d,1H,J=4.1 Hz,1'-CH), 6.12 (s,1H, 1-CH), 7.18 (s,1H, thiazole-CH), 7.83 (m,2H,8.9-CH), 8.17 (s,1H,11-CH), 8.20 (d,1H, J=8.6 Hz,10-CH), 8.47 (d,1H,J= 8.6 Hz,7-CH), 11.12 (s,1H,NHAc), 13.91 (s,1H,6-OH).

IR (Nicolet 205 FT, film on NaCl plate): 3627.8–3150.00 (str, pks at 3421.7, 3269.0), 3072.1, 2929.6, 2856.9, 1716.1, 1664.6, 1611.2, 1550.5, 1500.8, 1460.3, 1375.7, 1296.6, 1165.9, 1119.9, 981.94, 899.14, 805.30, 759.30, 722.50.

Example 30

The following heteroanthracycline chemicals, of the invention, were synthesized using the processes described herein and biological test results are reported in the table in Example 31.

BCH-725: (1S,3S) and (1R,3R)-6-hydroxy-3-hydroxymethyl-1-methoxy-1,2,3,4-tetrahydro-(2-sulfur)-naphthacene-5,12-dione

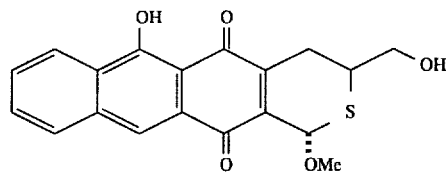

BCH-731: (1'S,1R,3S) and (1'S,1S,3R)-3-(2-acetoxy-1-trimethyleneketal) aceto-6-acetoxy-1,2,3,4,5,12-hexahydro-1-N-trifluoroacetyl-L-daunosamine(2-oxygen) naphthacene-5,12-dione and (1'S,1R,3S) and (1'S,1S,3R)-3-(2-acetoxy-1-trimethyleneketal) aceto-11-acetoxy-1,2,3,4,5,12-hexahydro-1-N-trifluoroacetyl-L-daunosamine(2-oxygen) naphthacene-5,12-dione

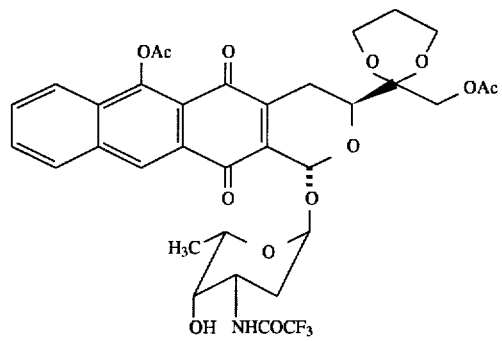

BCH-732: (1'S,1R,3S), (1'S,1S,3R), (1'S,1R,3R) and (1S, 1S,3S)-1,2,3,4,5,12-hexahydro-6-hydroxy-3-(2-methoxymethoxy) aceto-1-(4'-O-p-nitrobenzoate-N-trifluoroacetyl)-L-daunosamine(2-oxygen) naphthacene-5, 12-dione

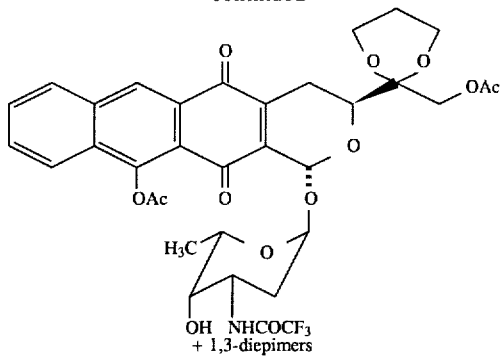

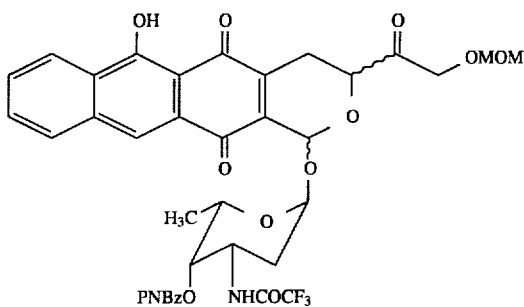

BCH-746: (1'S,1S,3R) and (1'S,1R,3S)-3-(2-acetoxy-1-trimethyleneketal) aceto-1,2,3,4,5,12-hexahydro-6-hydroxy-1-N-trifluoroacetyl-L-daunosamine(2-oxygen) naphthacene-5,12-dione and (1'S,1S,3R) and (1'S,1R,3S)-3-(2-acetoxy-1-trimethyleneketal) aceto-1,2,3,4,5,12-hexahydro-11-hydroxy-1-N-trifluoroacetyl-L-daunosamine(2-oxygen) naphthacene-5,12-dione

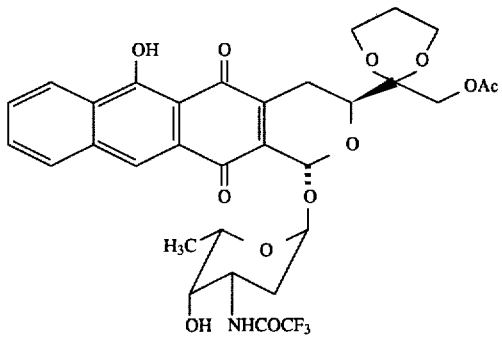

247

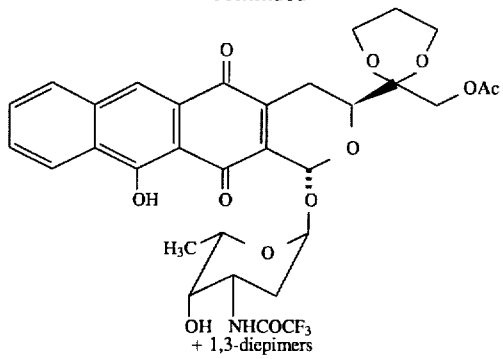

BCH-747: (1'S,1S,3R) or (1'S,1R,3S)-3-(2-acetoxy-1-trimethyleneketal) aceto-1,2,3,4,5,12-hexahydro-6-hydroxy-1-N-trifluoroacetyl-L-daunosamine(2-oxygen) naphthacene-5,12-dione

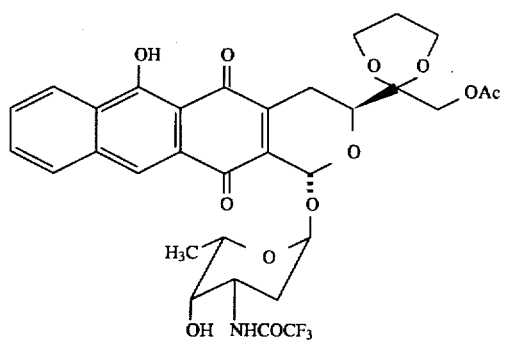

BCH-748: (1'S,1R,3S) or (1'S,1R,3S)-3-(2-acetoxy-1-trimethyleneketal) aceto-1,2,3,4,5,12-hexahydro-11-hydroxy-1-N-trifluoroacetyl-L-daunosamine(2-oxygen) naphthacene-5,12-dione

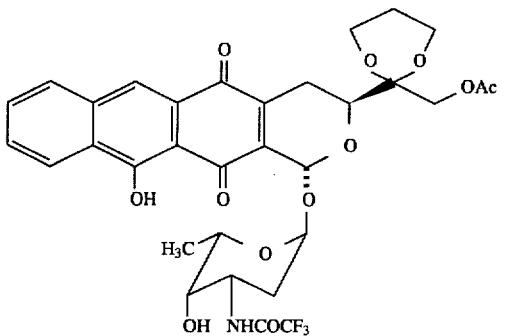

BCH-749: (1'S,1S,3R) and (1'S,1R,3S)-3-(2-hydroxy-1-trimethyleneketal) aceto-1,2,3,4,5,12-hexahydro-6-hydroxy-1-L-daunosamine(2-oxygen) naphthacene-5,12-dione-hydrochloride and
(1'S,1S,3R) and (1'S,1R,3S)-3-(2-hydroxy-1-trimethyleneketal) aceto-1,2,3,4,5,12-hexahydro-11-hydroxy-1-L-daunosamine(2-oxygen) naphthacene-5,12-dione-hydrochloride

248

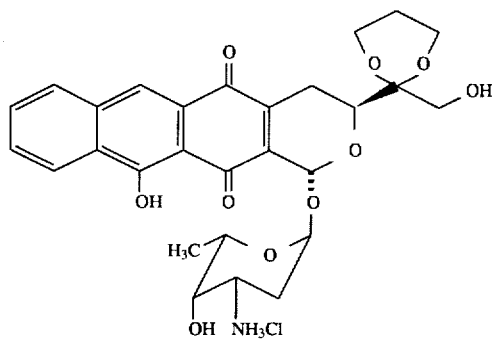

BCH-1108: 3-trimethyleneketalaceto-1,2,3,4,5,12-hexahydro-11-hydroxy-(2-oxygen) naphthacene-5,12-dione

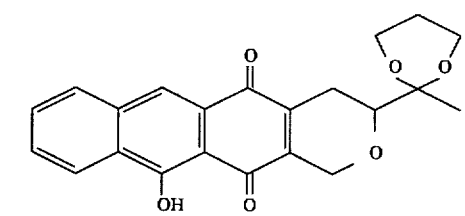

BCH-1109: 3-trimethyleneketalaceto-1,2,3,4,5,12-hexahydro-6-hydroxy-(2-oxygen) naphthacene-5,12-dione

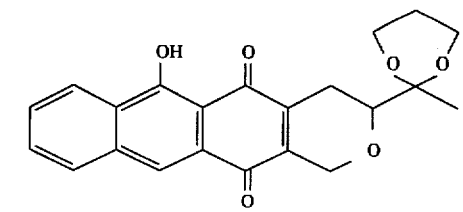

BCH-1110: 3-trimethyleneketalaceto-1, 2,3,4,5,12-hexahydro-11-hydroxy-6 -acetoxy-(2-oxygen) naphthacene-5,12-dione

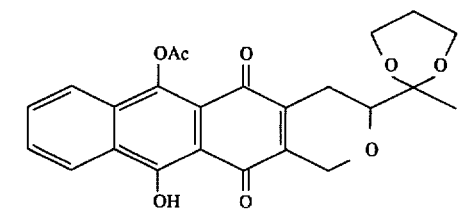

BCH-1111: 3-trimethyleneketalaceto-1,2,3,4,5,12-hexahydro-6-hydroxy-11-acetoxy-(2-oxygen) naphthacene-5,12-dione

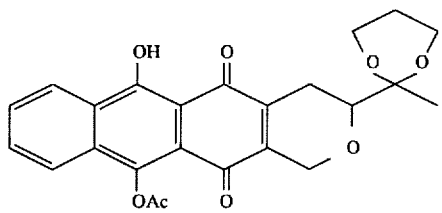

BCH-1112: 3-ethyleneketalaceto-1,2,3,4,5,12-hexahydro-11-hydroxy-(2-oxygen) naphthacene-5,12-dione

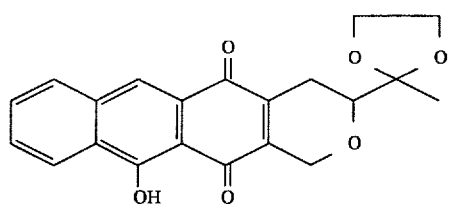

BCH-1113: 3-ethyleneketalaceto-1,2,3,4,5,12-hexahydro-6 and 11-hydroxy-(2-oxygen) naphthacene-5,12-dione

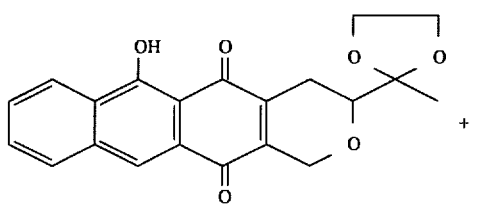

BCH-1114: 3-ethyleneketalaceto-1,2,3,4,5,6,11-hexahydro-5,12-dihydroxy-(2-oxygen) naphthacene-6,11-dione

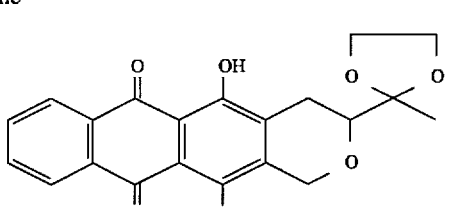

BCH-1115: 3-trimethyleneketalaceto-1,2,3,4,5,6,11-hexahydro-5,12-dihydroxy-(2-oxygen) aphthacene-6,11-dione

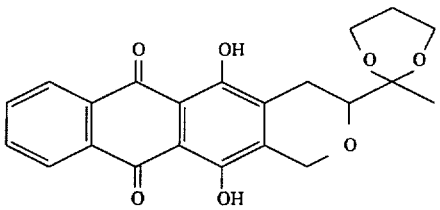

BCH-1135: 3-aceto-1,2,3,4,5,12-hexahydro-6-hydroxy-(2-sulfur) naphthacene-5,12-dione and 3-aceto-1,2,3,4,5,12-hexahydro-11-hydroxy-(2-sulfur) naphthacene-5,12-dione

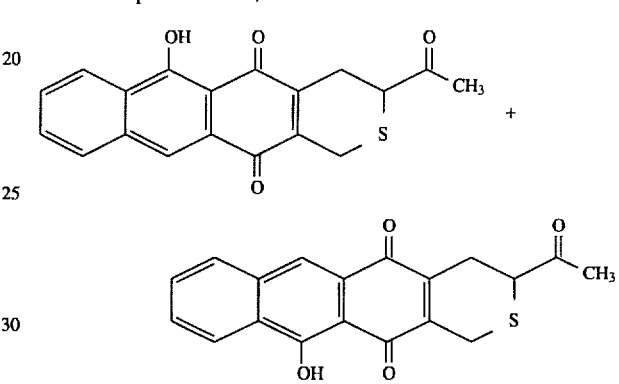

BCH-1151: 3-aceto-1,2,3,4,5,12-hexahydro-6-hydroxy-(2-sulfur) naphthacene-5,12-dione

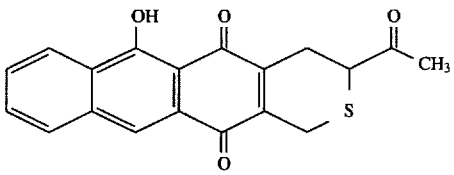

BCH-1152: 3-aceto-1,2,3,4,5,12-hexahydro-11-hydroxy-(2-sulfur) naphthacene-5,12-dione

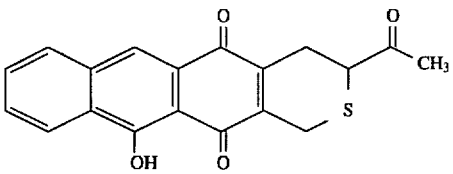

BCH-1153: (1'S,1S,3R) or (1'S,1R,3S)-3-(2-hydroxy-1-trimethyleneketal) aceto-1,2,3,4,5,12-hexahydro-6-hydroxy-1-L-daunosamine(2-oxo) naphthacene-5,12-dione-hydrochloride

251

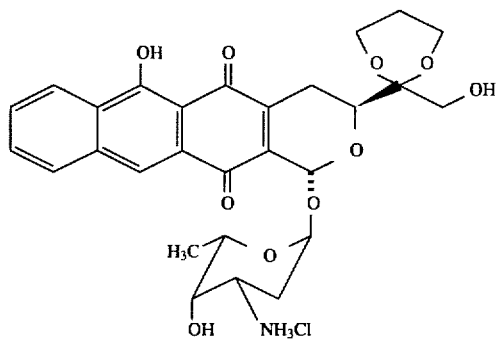

BCH-1154: (1'S,1S,3R) or (1'S,1R,3S)-3-(2-hydroxy-1-trimethyleneketal) aceto-1,2,3,4,5,12-hexahydro-6-hydroxy-1-L-daunosamine(2-oxo) naphthacene-5,12-dione-hydrochloride

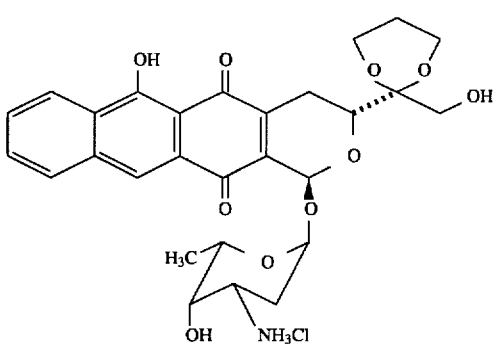

BCH-1155: (1'S, 1S, 3R) or (1'S, 1R, 3S)-1,2,3,4,5,12-hexahydro-6-hydroxy-1-(N-trifluoroacetyl-L-daunosamine)-3-vinyl(2-oxo) naphthacene-5,12-dione

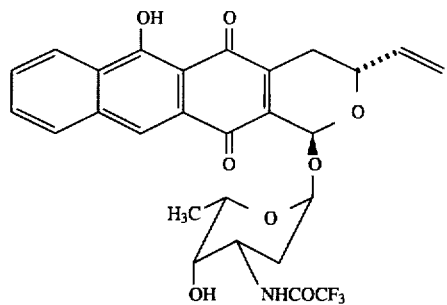

BCH-1156: (1'S,1S,3R) and (1'S,1R,3S)-Methyl-(5,12-dihydroxy-1-(2',3',4', 6'-tetradeoxy-3'-azido-4'-iodo-L-lyxohexopyranose)-6,11-dioxo-3,4,6,11-tetrahydroanthraceno[2,3-c]pyran-3-yl)ketone

252

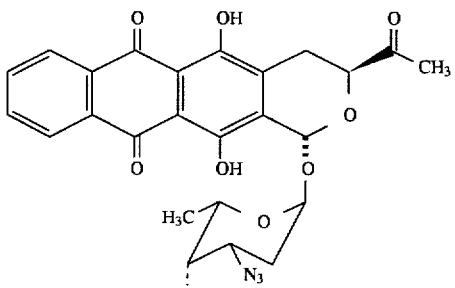

BCH-1157: (1'S, 1S, 3R)-Methyl-6-hydroxy-1-(2',3',4',6'-tetradeoxy-3'-azido-4'-iodo-L-lyxohexopyranose)-5, 12-dioxo-3,4,5,12-tetrahydroanthraceno[2,3 -c]pyran-3-yl)ketone

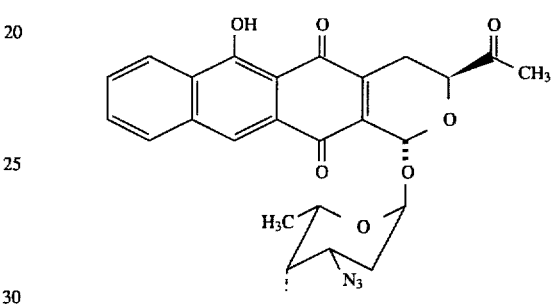

BCH-1158: (1'S, 1R, 3S)-Methyl-6-hydroxy-1-(2',3', 4', 6'-tetradeoxy-3'-azido-4'-iodo-L-lyxohexopyranose)-5, 12-dioxo-3,4,5,12-tetrahydroanthraceno[2,3-c]pyran-3-yl)ketone

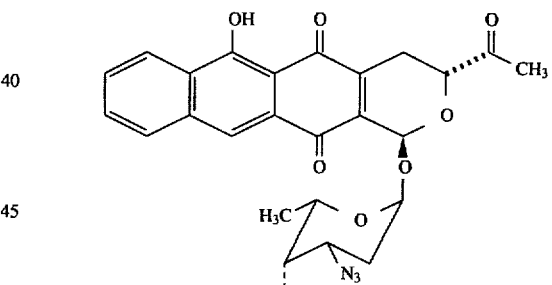

BCH-1168: (1'S,1S,3R) or (1'S,1R,3S)-1,2,3,4,5,12-hexahydro-1-(N-trifluroacetyl-L-daunosamine)-3-vinyl (2-oxo)naphthacene-5,12-dione

253

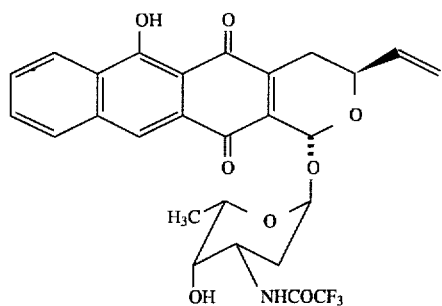

BCH-1178: (1'S,1S,3R) or (1'S,1R,3S)-3-(2-acetoxy-1-trimethyleneketal) aceto-1,2,3,4,5,12-hexahydro-6-acetoxy-1-(N-trifluoroacetyl-L-daunosamine)(2-oxo)naphthacene-5,12-dione

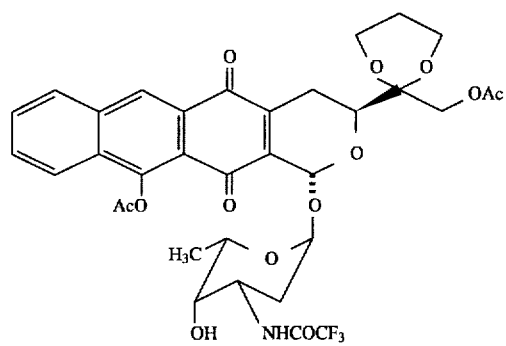

BCH-1179: (1'S, 1S, 3R) or (1'S, 1R, 3S)-3-(2-acetoxy-1-trimehtyleneketal) aceto-1,2,3,4,5,12-hexahydro-11-acetoxy-1-(N-trifluoroacetyl-L-daunosamine)(2-oxo)naphthacene-5,12-dione

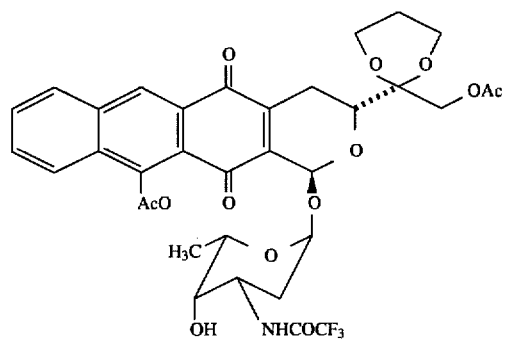

BCH-1183: (1'S, 1R, 3S) and (1'S, 1S, 3R)-3-(hydroxy) trimethylacetoxyaceto-1,2,3,4,6,11-hexahydro-5,12-dihydroxy-1-N-trifluoroacetyl-L-daunosamine(2-oxo) naphthacene-6,11-dione

254

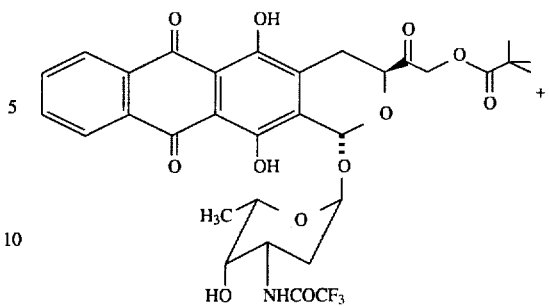

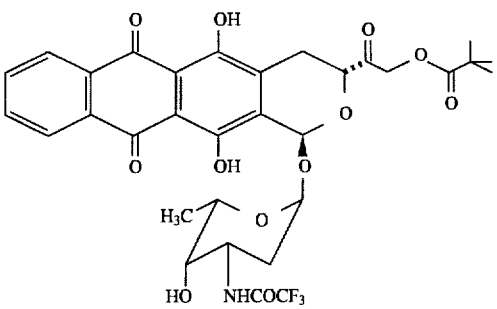

BCH-1611: (1'S,1R,3S) or (1'S,1S,3R)-1,2,3,4,5,12-hexahydro-6-hydroxy-1-L-daunosamine-3-vinyl(2-oxo)naphthacene-5,12-dione

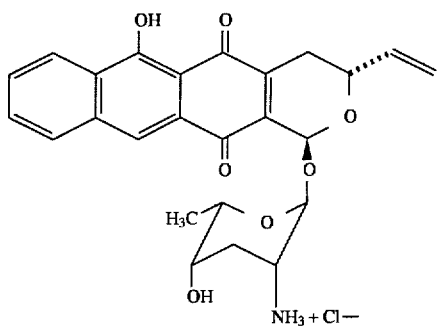

BCH-1617: (1'S, 1R, 3S)-Methyl-(6-hydroxy-1-(2', 3',4', 6'-tetradeoxy-3'-trifluoroacetamido-4'-iodo-L-lyxohexopyranose)-5,12-dioxo-3,4,5,12-tetrahydroanthraceno [2,3-c]pyran-3-yl)ketone

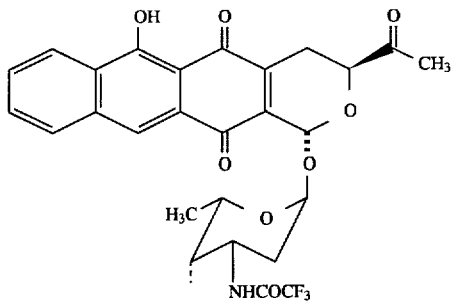

BCH-1618: (1'S,1S,3R)-Methyl-(6-hydroxy-1-(2',3',4',6'-tetradeoxy-3'-trifluoroacetamido-4'-iodo-L-lyxohexopyranose)-5,12-dioxo-3,4,5,12-tetrahydroanthraceno [2,3-c]pyran-3-yl)ketone

255

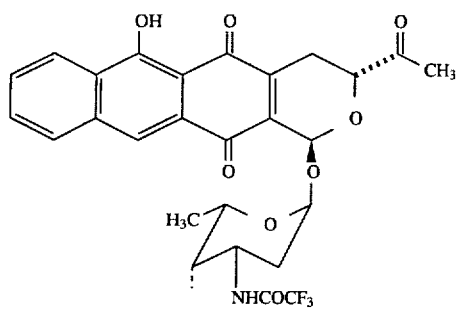

BCH-1624: (1'S,1R,3S)-Methyl-(5,12-dihydroxy-1-(2',3',6'-trideoxy-3',4'-dihydroxyl-L-lyxohexopyranose)-6,11-dioxo-3,4,6,11-tetrahydroanthraceno[2,3-c]pyran-3-yl)ketone

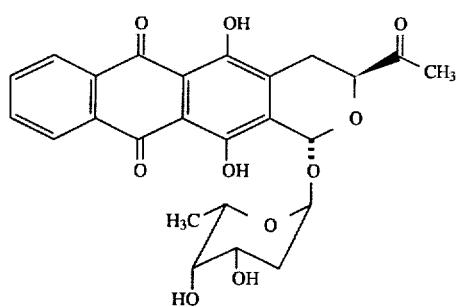

BCH-1625: (1'S,1S,3R)-Methyl-(5,12-dihydroxy-1-(2',3',6'-trideoxy-3',4'-dihydroxyl-L-lyxohexopyranose)-6,11-dioxo-3,4,6,11-tetrahydroanthraceno[2,3-c]pyran-3-yl)ketone

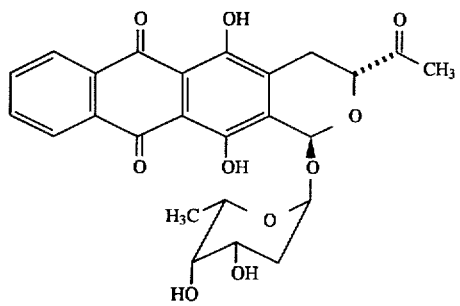

BCH-1626: (1'S, 1R, 3S) and (1'S, 1S, 3R)-1-O-(3',4'-di-O-acetyl-2',6'-dideoxy-α-lyxohexopyranosyl)-1,2,3,4,5,12-hexahydro-6-hydroxy-3-hydroxyaceto-(2-oxo)naphthacene-5,12-dione

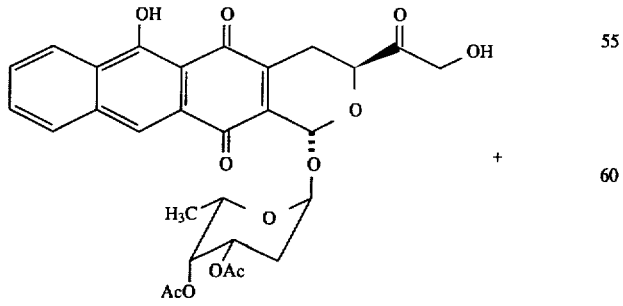

+

256
-continued

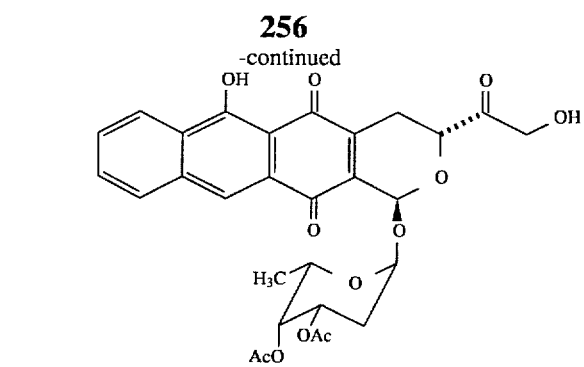

BCH-1627: 3-Aceto-1-O-(N-tert-butoxycarbonyl)ethanoamino-1,2,3,4,5,12-hexahydro-6-hydroxy-(2-sulfur)naphthacene-5,12-dione

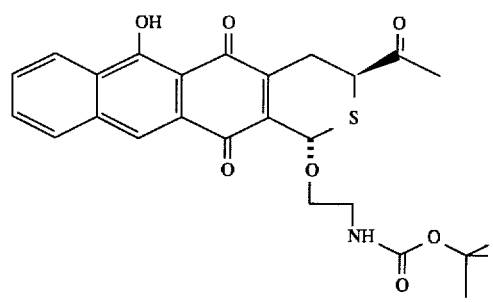

BCH-1628: 3-Aceto-1-O-(ethanoamino)-1,2,3,4,5,12-hexahydro-6-hydroxy-(2-sulfur)naphthacene-5,12-dione hydrochloride

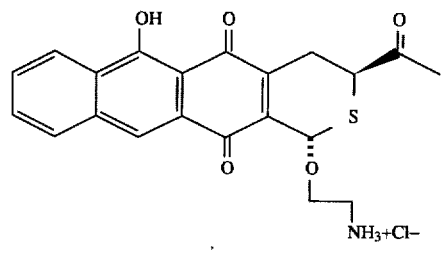

BCH-1629: (1 S, 1S, 3S)-5,12-dioxo-3-ethyl-6-hydroxy-1-(2, 6-dideoxy-L-lyxohexopyranose)-3,4,5,12-tetrahydroanthraceno[2,3-c]pyran

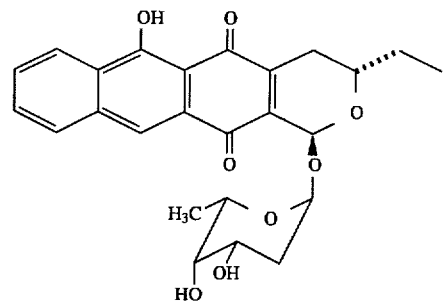

BCH-1630: (1 S,1R,3R)-5,12-dioxo-3-ethyl-6-hydroxy-1-(2, 6-dideoxy-L-lyxohexopyranose)-3,4,5,12-tetrahydroanthraceno[2,3-c]pyran

257

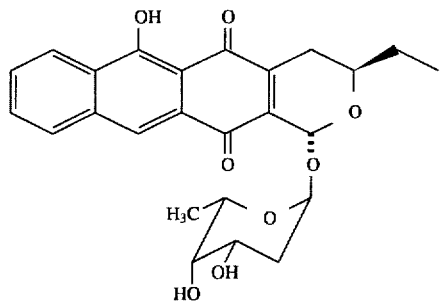

BCH-1633: (1'S,1S,3S)-3-Ethyl-5,12-dihydroxy-1-(2',3',6'-trideoxy-3'-amino-4'-hydroxy-L-lyxohexopyranose)-1,2,3,4-tetrahydro-(2-oxygen)naphthacene-6,11-dione-hydrochloride

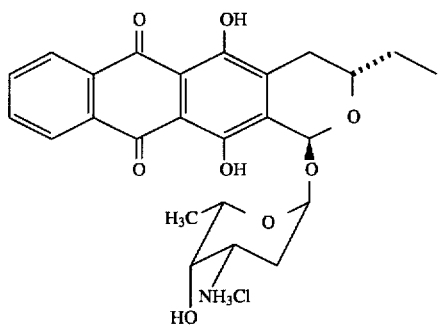

BCH-1634: (1'S, 1R, 3S) and (1'S, 1S, 3R)-1-(2',3',6'-trideoxy-3'-amino-L-lyxohexo pyranose)-3-[4-(2-acetamido)-thiazolyl]-5,12-dihydroxy-6,11-dioxo-3,4,5,12-tetrahydroanthraceno[2,3-c]pyran hydrochloride

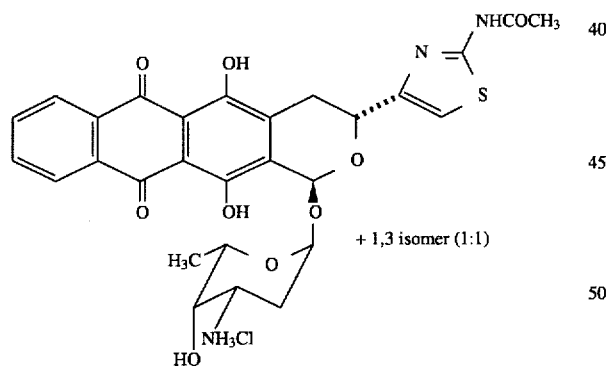

BCH-1635: (1'S, 1R, 3S) and (1'S, 1S, 3R)-3-aceto-1,2,3,4,5,12-hexahydro-6-hydroxy-1-N-trifluoroacetyl-L-daunosamine-(2-sulfur)naphthacene-5,12-dione

258

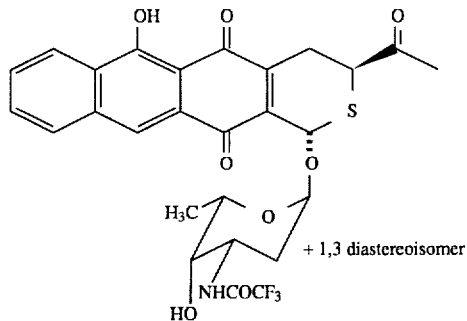

BCH-1636: (4'R, 1R, 3S) and (4'R, 1S, 3R)-3-aceto-1-(2',2'dimethyl-1',3'-dioxanyl-4'-methoxyl)-6-hydroxyl-1,2,3,4,5,12-hexahydro-(2-sulfur)naphthacene-5,12-dione

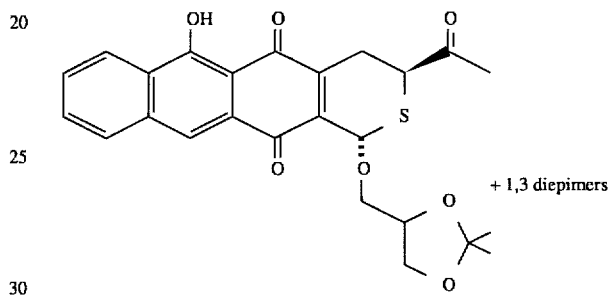

BCH-1637: (1'S,1S,3R)- and (1'S,1R,3S)-Methyl-(6-hydroxy-1-(2',3',6'trideoxy-3'-trifluoroacetamido-4-hydroxy-L-arabino-hexopyranose)-5,12-dioxo-3,4,5,12-tetrahydroanthraceno-[2,3-c]pyran-3-yl)ketone

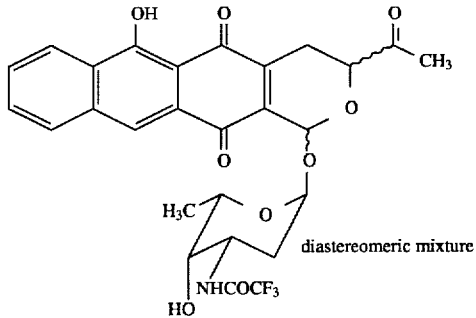

Example 31

Amino acid substituted anthracenoquinone derivatives.

BCH-1657=(1S,2'S,3R) and (1R, 2'S,3S)-Methyl-{6-hydroxyl-1[O-serine methyl ester]-5,12-dioxo-3,4,5,12-tetrahydroanthraceno-[2,3-c]pyran-3-yl}ketone hydrochloride salt

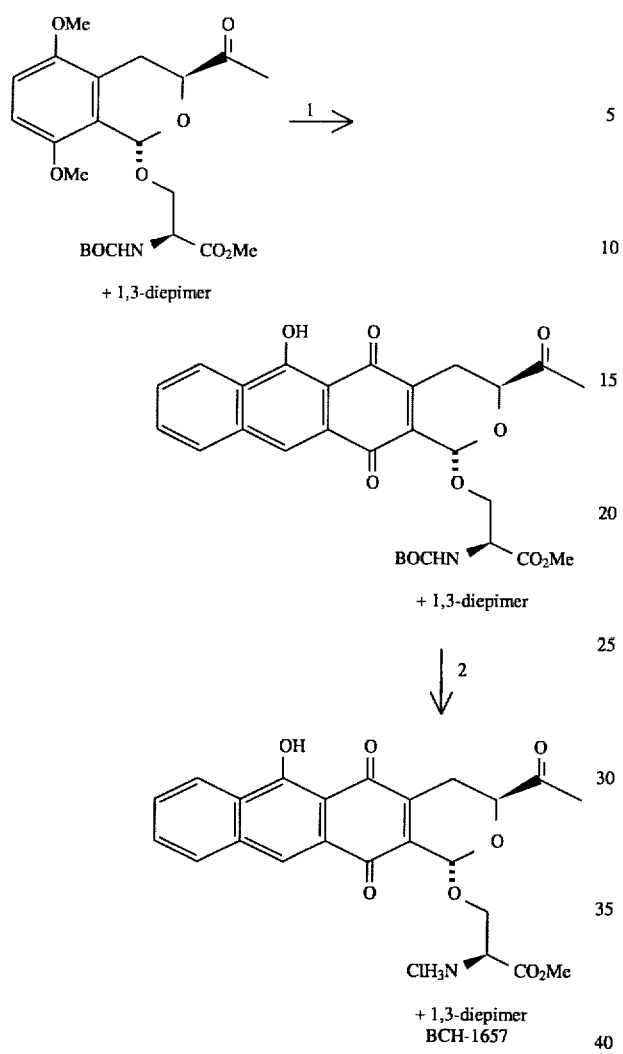

Example 32

Monoaminosugar substituted anthracenoquinone derivative

BCH-1680=(1'S,1S,3R) and (1'S, 1R, 3S)-methyl-{6-hydroxy-1(2',3',4',6'-tetradeoxy-4'-trifluoroacetamido-L-lyxohexopyranose)-5,12-dioxo-3,4,5,12-tetrahydroanthraceno-[2,3-c]pyran-3-yl}ketone

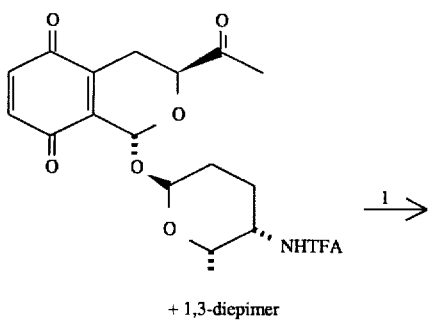

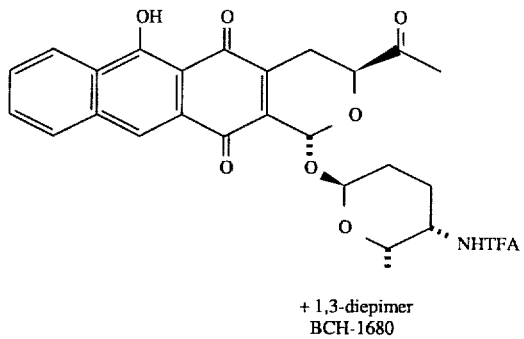

Example 33

Preparation of
(1'S)-3,3-bis-methoxycarbonyl-1-(1'-methoxycarbonyl-ethoxy)-5,12-dioxo-6-hydroxy-3,4,5,12-tetrahydro-anthraceno-[2,3-c]-pyran. (BCH-1668)

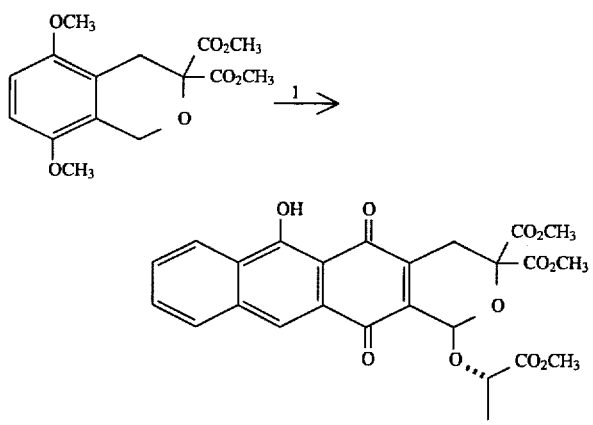

Example 34

Preparation of methoxymethyl substituted heteroanthracyclin derivatives

BCH-1694: (1'S,1R,3S)-5,12-dioxo-6-hydroxy-3-methoxymethyl-1-(2',3',6'-trideoxy-3'-trifluoroacemmido-L-lyxohexopyranose)-3,4,5,12-tetrahydroanthraceno-[2,3-c]pyran, BCH-1695: (1'S ,1R,3S)-5,12-dioxo-6-hydroxy-3-methoxymethyl-1-(2',3',6'trideoxy-3'-amino-L-lyxohexopyranose)-3,4,5,12-tetrahydroanthraceno-[2,3-c]pyran, and BCH-1696:(1'S ,1S ,3 R)-5,12-dioxo-6-hydroxy-3-methoxymethyl-1-(2',3',6'-trideoxy-3'-trifluoroacetamido-L-lyxohexopyranose)-3,4,5,12-tetrahydroanthraceno-[2,3-c]pyran.

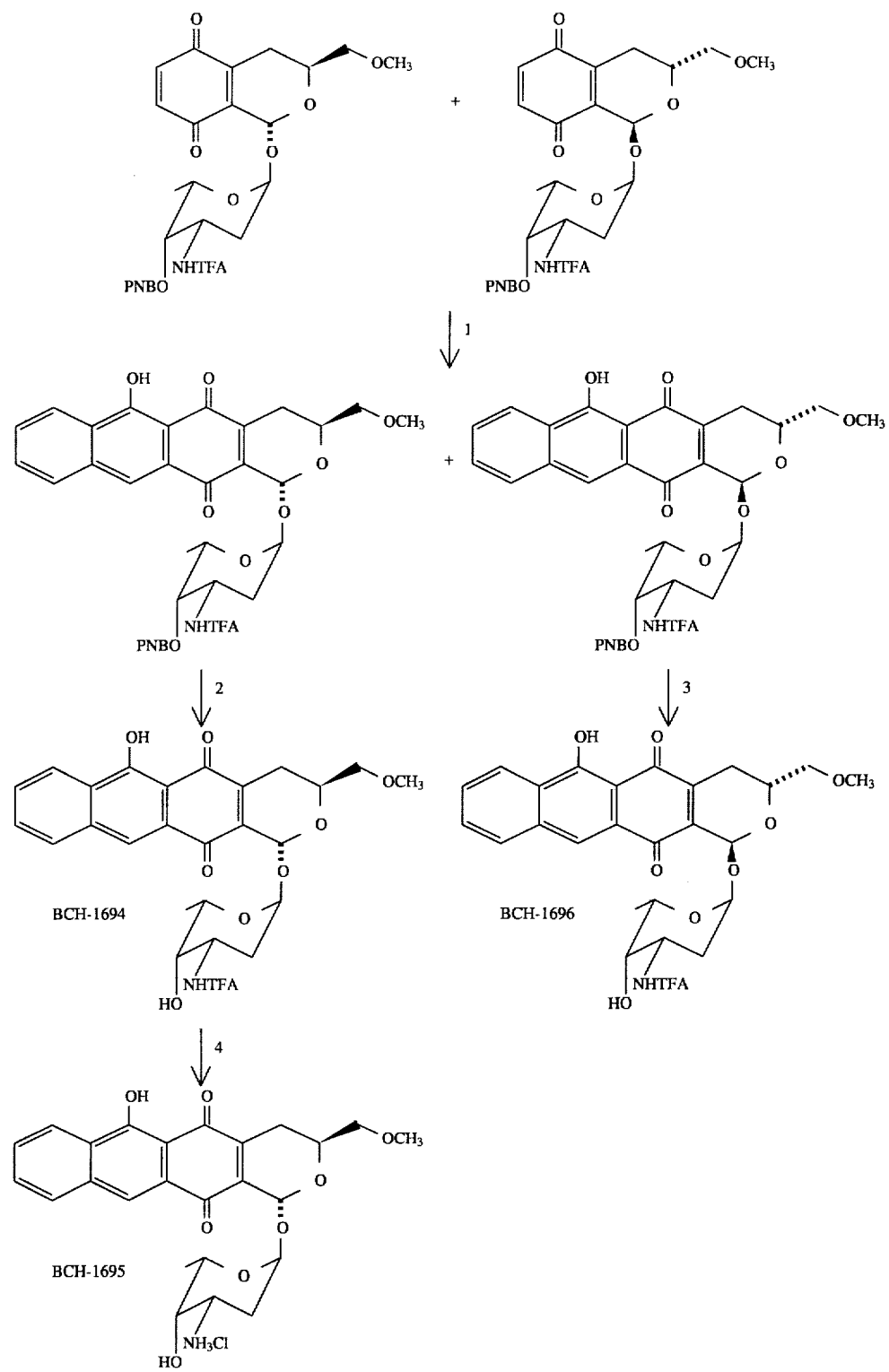

Example 35

Preparation of (1'S, 1S, 3R) and (1'S, 1R, 3S)-5,12-dihydroxy-6,11-dioxo-3-methoxymethyl-(2',3',6'-trideoxy-3'-amino-L-lyxohexopyranose)-3,4,6,11-tetrahydroanthraceno-[2,3-c]-pyran hydrochloride. (BCH-1992)

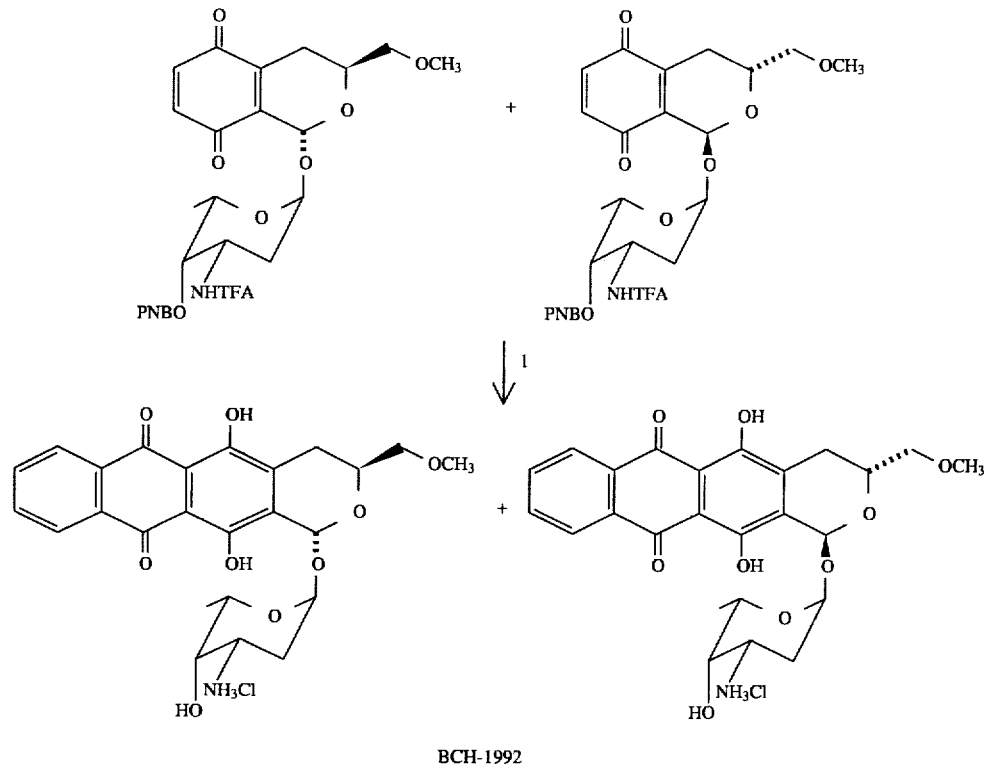

BCH-1992

Example 36

Preparation of isopropyl substituted heteroanthracyclin derivatives

BCH-2049: (1'S,1S,3R)-5,12-trihydroxy-3-isopropyl-1-(2',3',6'-trideoxy-3'-amino-L-lyxohexopyranose)-1,2,3,4-tetrahydro-(2-oxygen)-naphthacene-6,11-dione-hydrochloride;

BCH-2050: (1'S,1R,3S)-5,12-Dixydroxy-3-isopropy-1-(2',3',6'-trideoxy-3'-amino 'L-lyxohexopyranose)-1,2,3,4-tetrahydro-(2-oxygen)-naphtacene-6,11-dione-hydrochloride;

BCH-2185: (1'S,1R,3S)-5,12-dihydroxy-6,11-dioxo-3-isopropyl-1-(2',3',6'-trideoxy-3'-trifluoroacetamido-L-lyxoheoxpyranose)-3,4,5,12-tetrahydranthraceno-[2,3-c]-pyran;

BCH-2190: (1'S,1S,3R)-5,12-dihydroxy-6,11-dioxo-3-isopropyl-1-(2',3',6'-trideoxy-3'-(4-morpholinyl)-L-lyxohexopyranose)-3,4,5,12-tetrahydroanthraceno-[2,3-c]-pyran;

BCH-2192: (1'S,1S,3R)-5,12-dihydroxy-6,11-dioxo-3-isopropyl-1-(2',3',6'-trideoxy-3'(4-morpholinyl)-L-lyxohexopyranose)-3,4,5,12-tetrahydroanthraceno-[2,3-c]-pyran hydrochloride;

BCH-2195: (1'S,1S,3R)-5,12-dihydroxy-6,11-dioxo-3-isopropyl-1-(2',3',6'-trideoxy-3'(3-cyano-4-morpholinyl)-L-lyxohexopyranose)-3,4,5,12-tetrahydroanthraceno-[2,3-c]-pyran.

Example 36

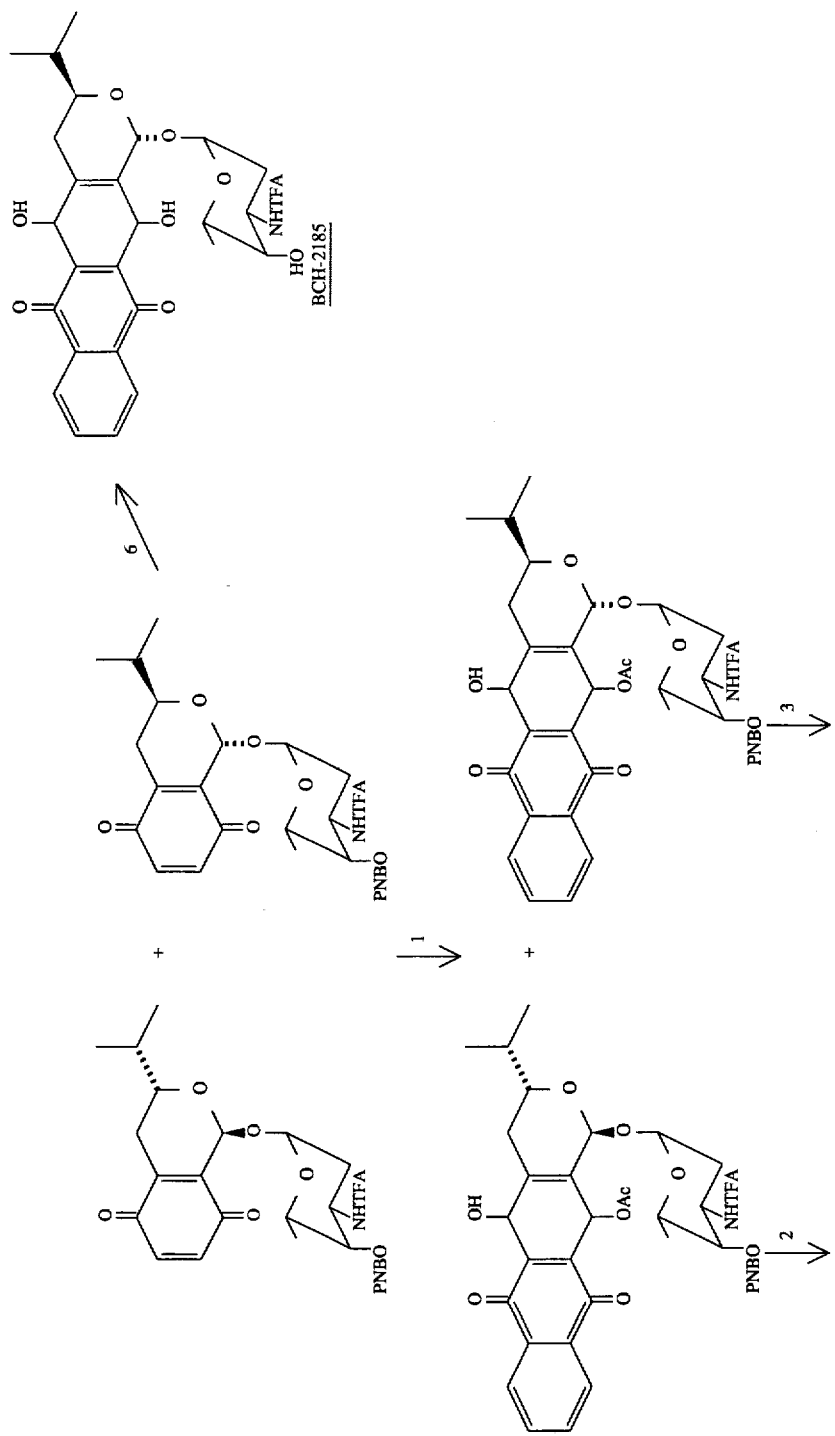

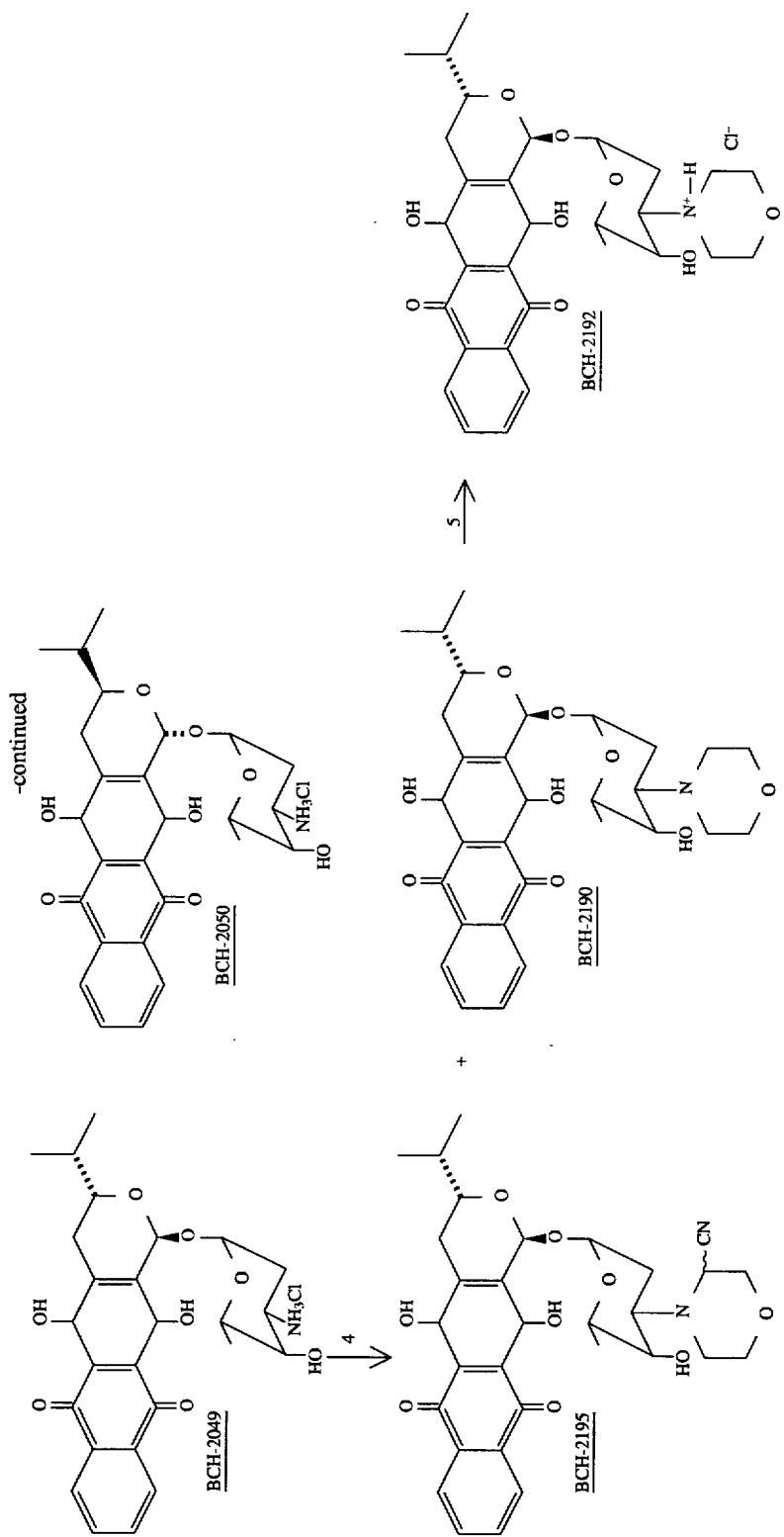

Example 37
Preparation of (1'S, 1R, 3R) and (1'S, 1S, 3S)-5,12-dihydroxy-6,11dioxo-3-pentyl-(2',3',6'-trideoxy-3'-amino-L-lyxohexopuranose)-3,4,6,11-tetrahydroanthraceno-[2,3-c]-pyran hydrochloride. (BCH-2088 and 2089)
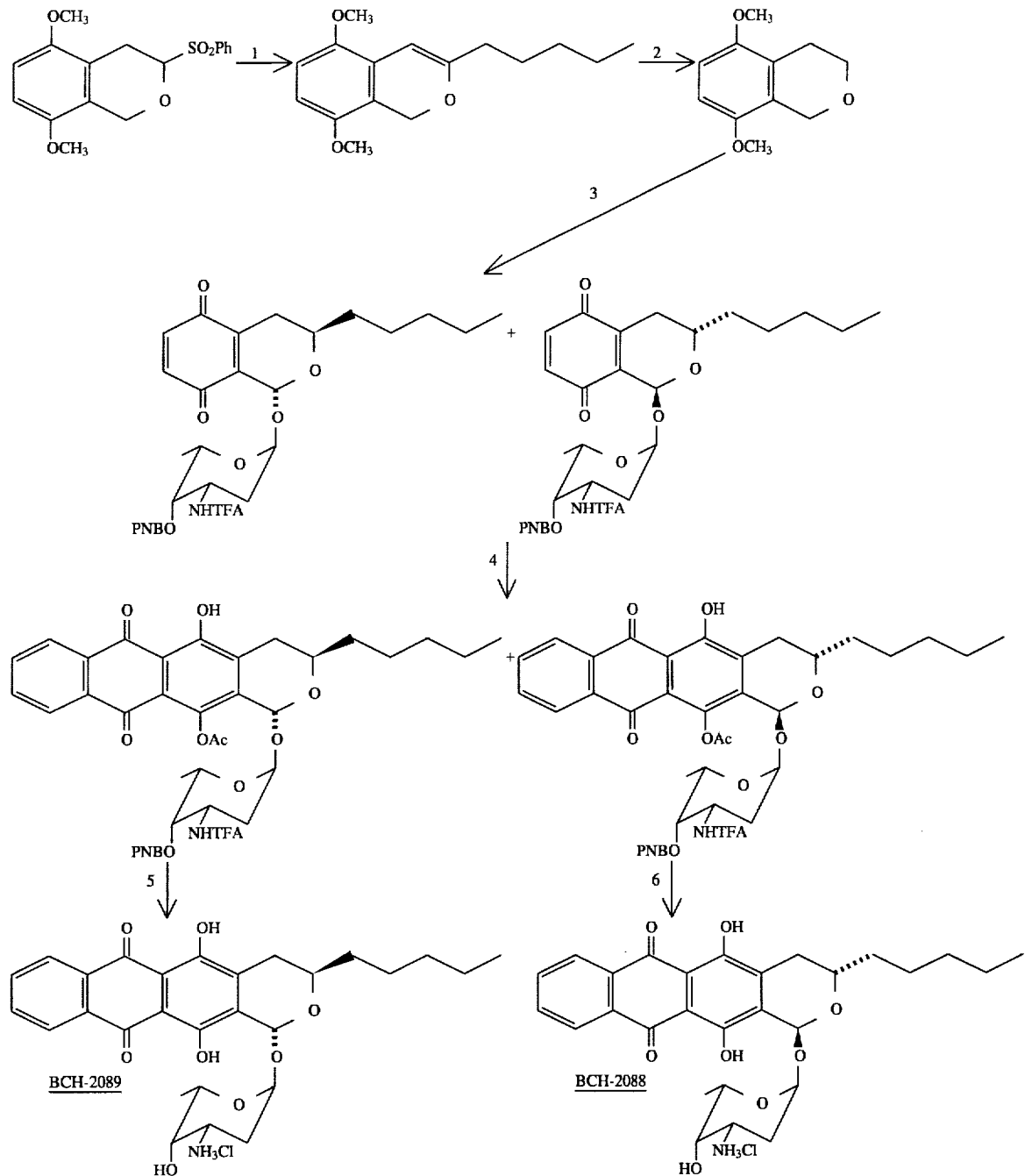

Example 38
Preparation of (1'S, 1R,3S) and (1'S, 1S,3R)-isopropyl-[5,12-dihydroxy-6,11-dioxo-1-(2',3',6'-trideoxy-3'-amino-L-lyxohexopyranose)-3,4,6,11-tetrahydroanthraceno-[2,3-c]-pyran-3-yl]-ketone hydrochloride (1:1) (BCH-2120).
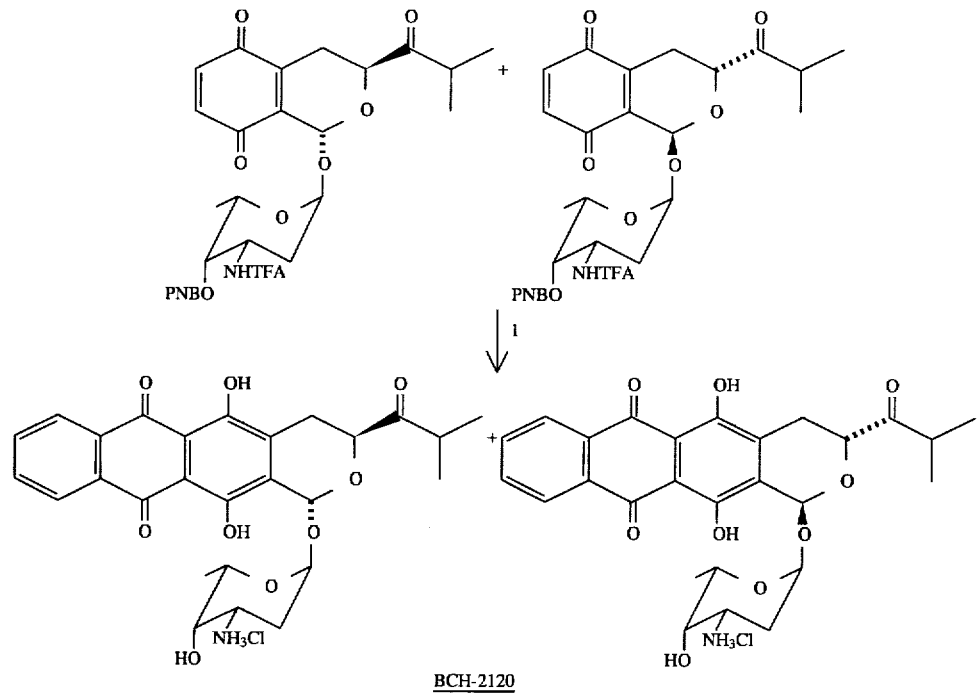
BCH-2120
Example 39
Preparation of (1'S, 1R,3S) and (1'S, 1S,3R)-5,12-dihydroxy-6,11-dioxo-3-isopropenyl-1-(2',3',6'-trideoxy-3'-amino-L-lyxohexopyranose)-3,4,6,11-tetrahydroanthraceno-[2,3-c]-pyran hydrochloride (BCH-2189 and 2188).
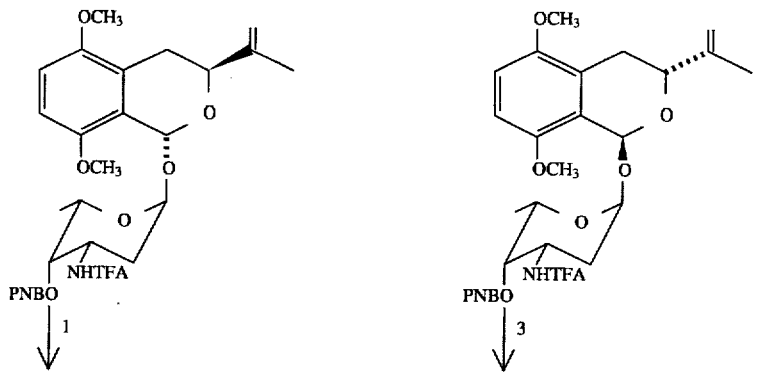

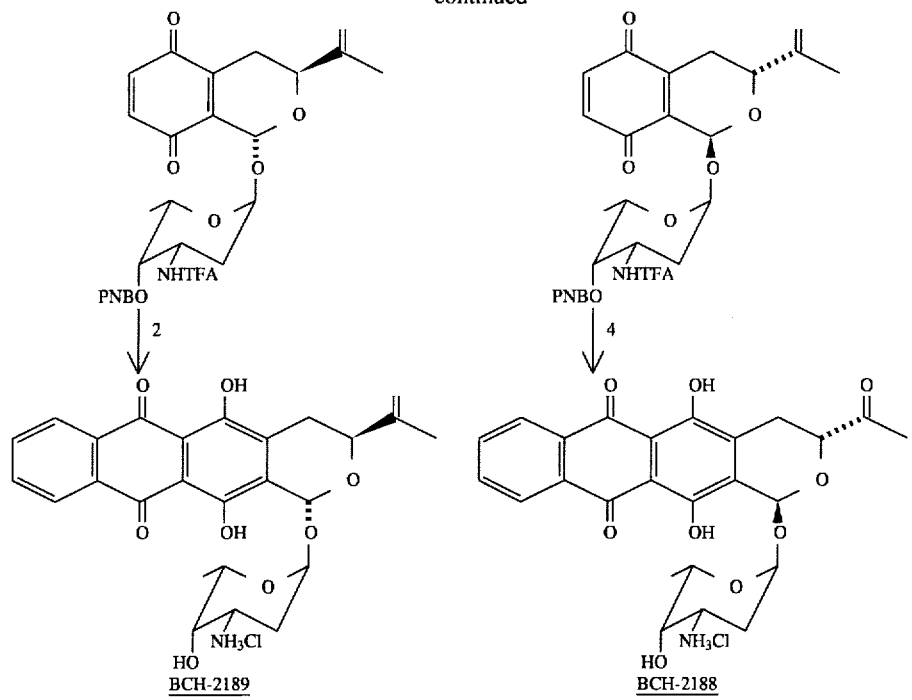

Example 40

Preparation of tetrahydroanthraceno-[2,3-c]pyran derivative with a phenyl side chain.

BCH-1686: (1S,1S,3S)-3-(6-hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-c]pyran-3-yl)propene, BCH-1687: (1S,1R,3R)-3-(6-hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-c]pyran-3-yl)propene, BCH-2005: (1'S,1R,3R)-3-(6-hydroxy-1-(2',3',6'-trideoxy-3'-amino-4'-hydroxy-L-lyxohexopyranose)-5,12-dioxo-3,4,5,12-tetrahydroanthraceno-[2,3-c]pyran-3-yl)propene hydrochloride, and BCH-2006: (1'S,1S,3S)-3-(6-hydroxy-1-(2',3',6'-trideoxy-3'-amino-4'-hydroxy-L-lyxohexopyranose)-5,12-dioxo-3,4,5,12-tetrahydroanthraceno-[2,3-c]pyran-3-yl)propene hydrochloride.

Example 40

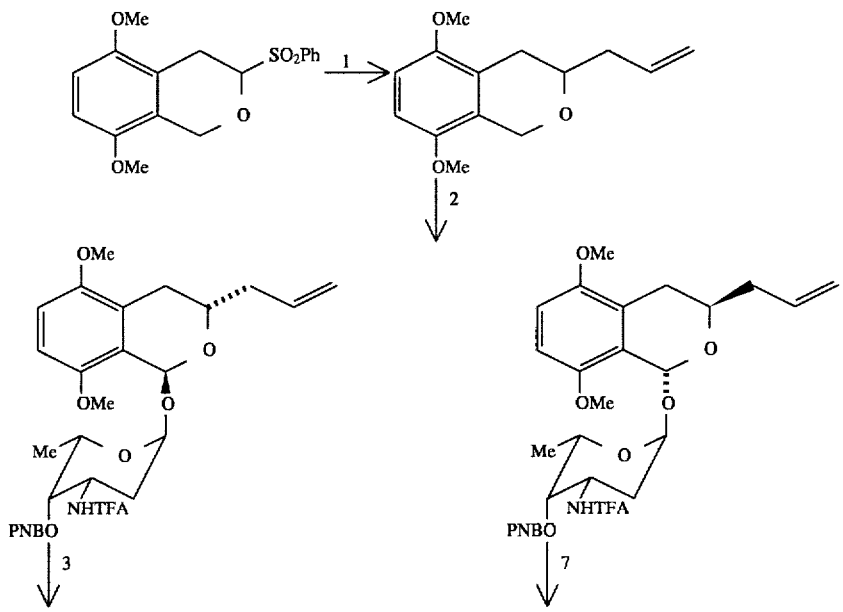

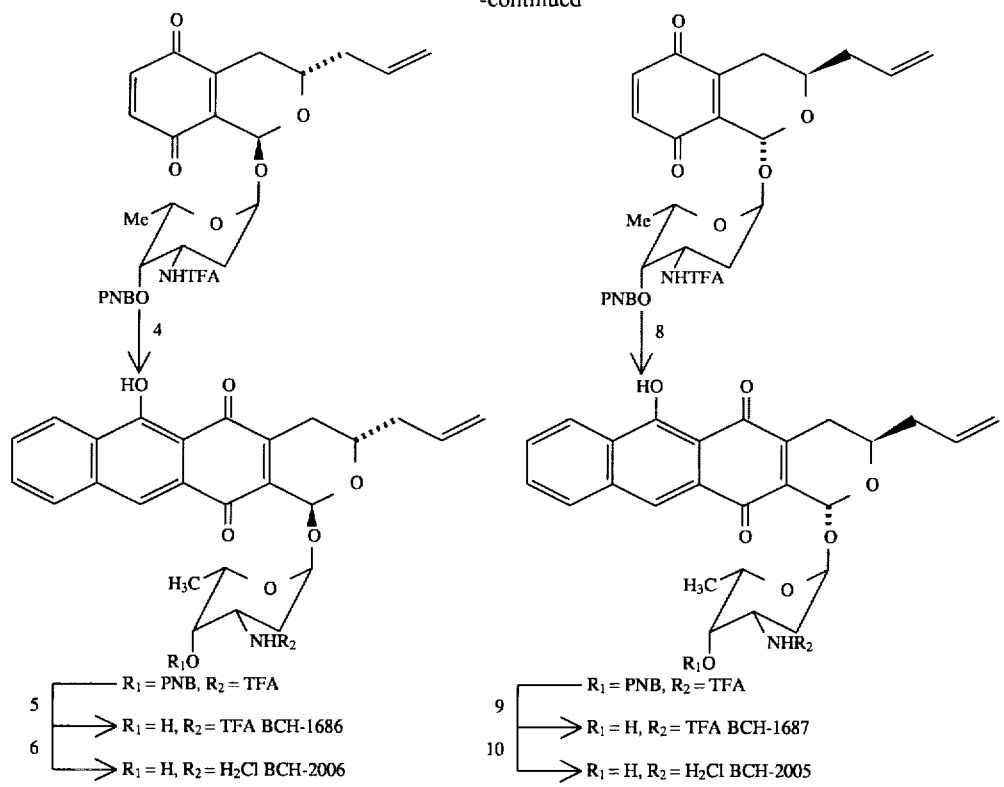
Example 41
Preparation of tetrahydroanthraceno-[2,3-c]pyran derivative with an allyl side chain
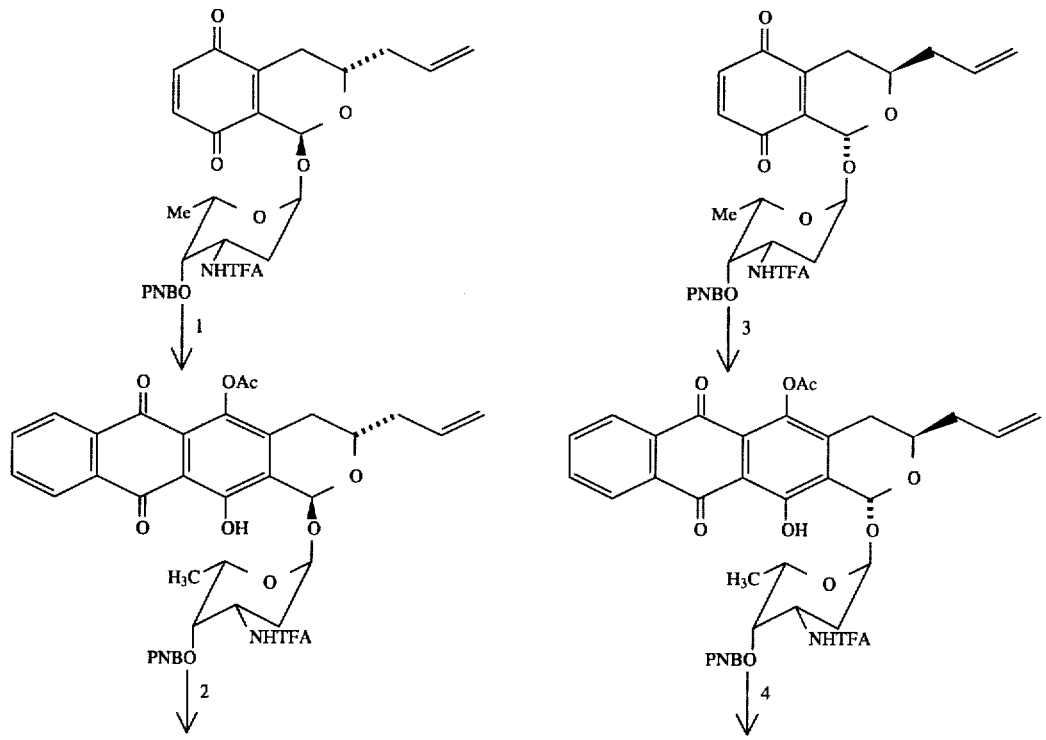

277 278

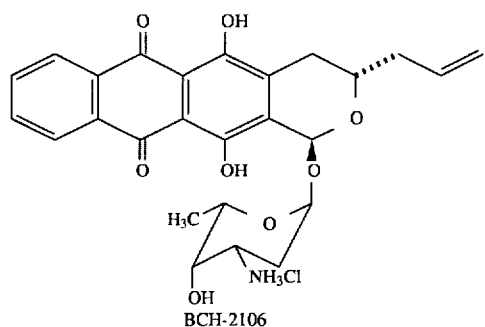
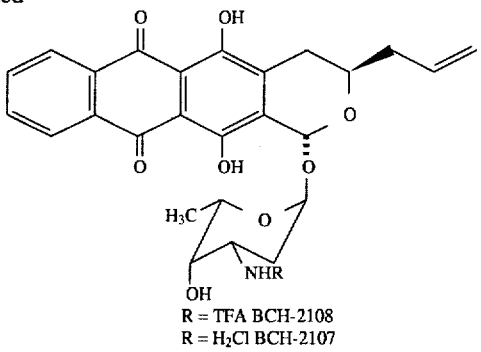

-continued

BCH-2106

R = TFA BCH-2108
R = H₂Cl BCH-2107

BCH-2106: (1'S,1S,3S)-3-(5,12-dihydroxy-1-(2',3',6'-trideoxy-3'-amino-4'-hydroxy-L-lyxohexopyranose)-6,11-dioxo-3,4,5,12-tetrahydroanthraceno-[2,3-c]pyran-3-yl)propene hydrochloride;

BCH-2107: (1'S,1R,3R)-3-(5,12-dihydroxy-1-(2',3',6'-trideoxy-3'-amino-4'-hydroxy-L-lyxohexopyranose)-6,11-dioxo-3,4,5,12-tetrahydroanthraceno-[2,3-c]pyran-3-ylpropene hydrochloride;

BCH-2108: (1'S,1R,3R)-3-(5,12-dihydroxy-1-(2',3',6'-trideoxy-3'-trifluoroacetamido-4'-hydroxy-L-lyxohexopyranose)-6,11-dioxo-3,4,5,12-tetrahydroanthraceno-[2,3-c]pyran-3-yl)propene.

Example 42

Preparation of tetrahydroanthraceno-[2,3-c]pyran derivative with a homo methyl ketone side chain

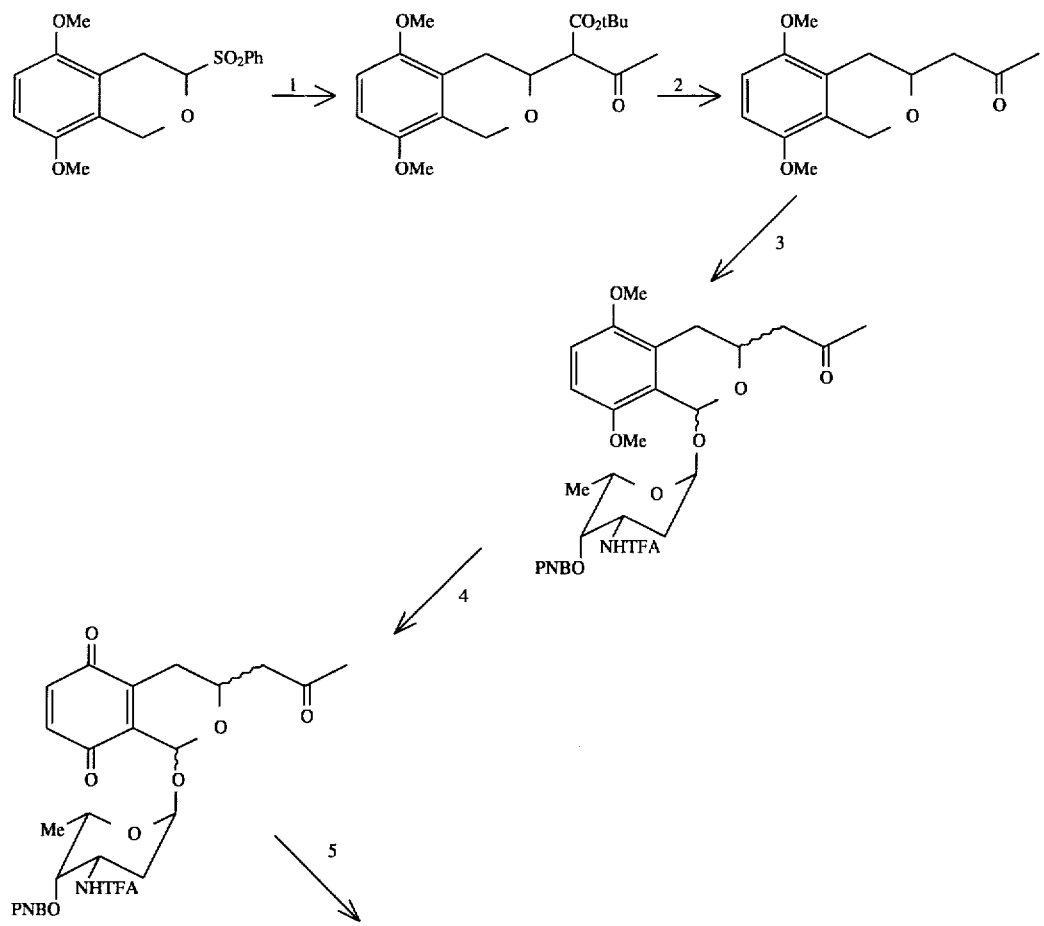

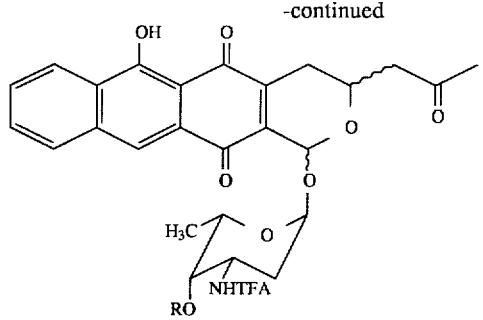

BCH-2097: (1'S,1R,3S) and (1'S,1S,3R)(6-hydroxy-1-(2', 3',6'-trideoxy-3'-trifluoroacetamido-4'-hydroxy-L-lyxohexopyranose)-5,12-dioxo-3,4,5,12-tetrahydroanthraceno[2,3-c]pyran-3-yl)propanone;

BCH-2111: (1'S,1R,3S) and (1'S,1S,3R)-3-6-hydroxy-1-(2',3',6'-trideoxy-3'-amino-4'-hydroxy-L-lyxohexopyranose-5,12-dioxo-3,4,5,12-tetrahydroanthraceno[2,3-c]pyran-3-yl)propanone hydrochloride.

Example 43

Preparation of tetrahydroanthraceno-[2,3-c]pyran derivative with a C-2' glycoside linkage

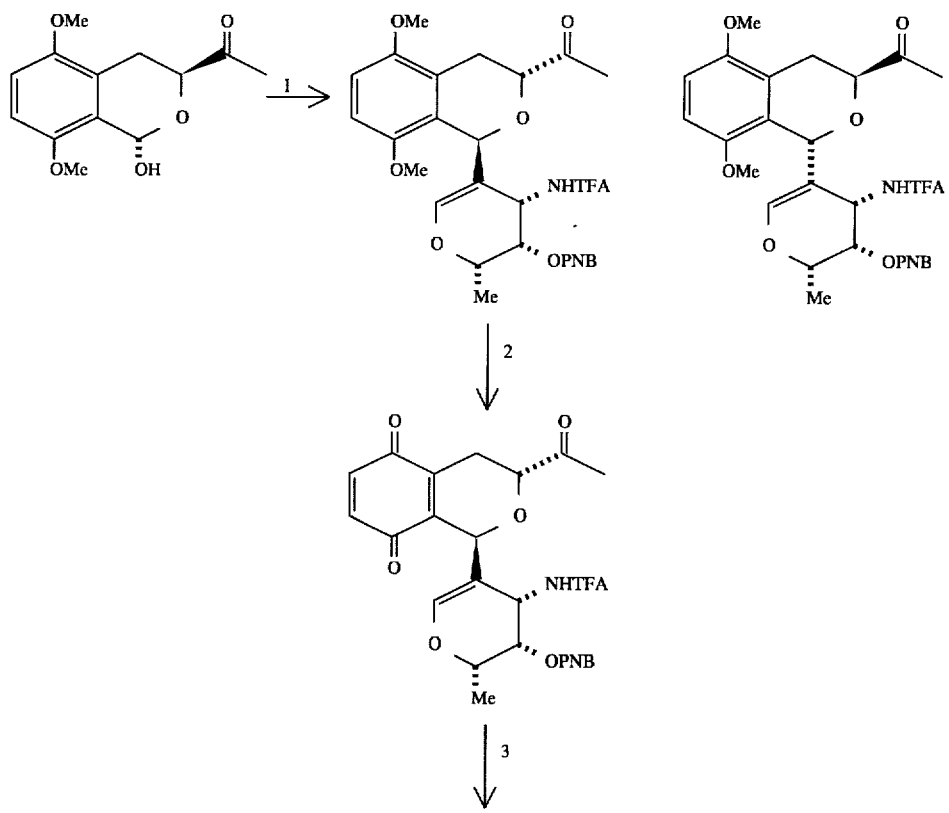

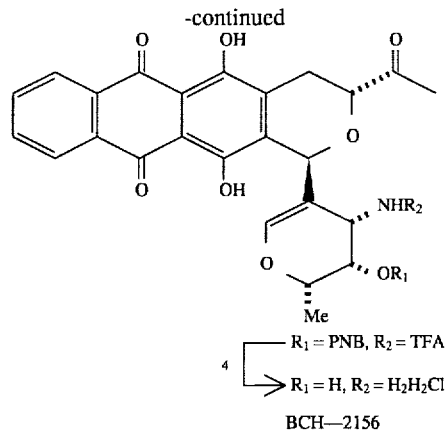
BCH—2156
BCH-2156: 1S,3R-Methyl(1-[2',3',6'-trideoxy-3'-trifluoroacetamido-4'-hydroxy-1,5-dihydro-L-lyxohexopyranose-2-yl)-6,11-dioxo-3,4,5,12-tetrahydroanthraceno[2,3-c]pyran-3-yl)ketone.
Example 44
Preparation of tetrahydroanthraceno-[2,3-c]pyran derivatives with a cyano side chain
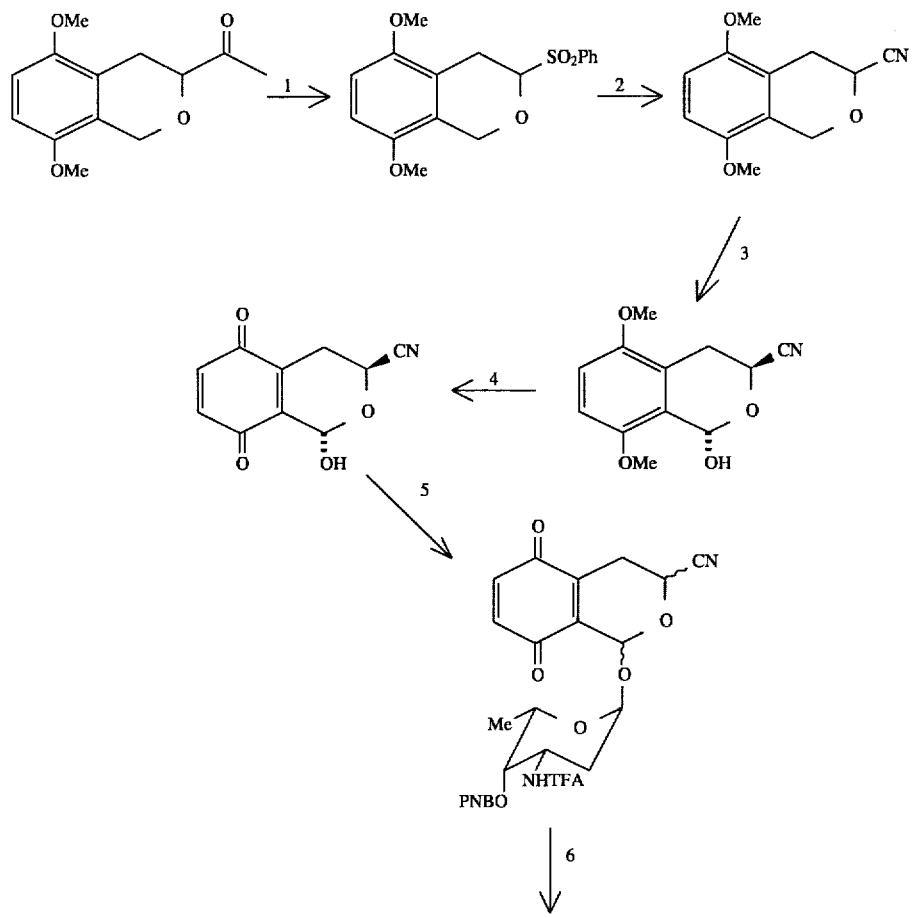

283

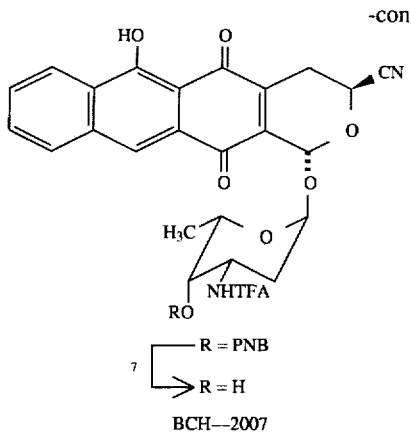

BCH—2007

284

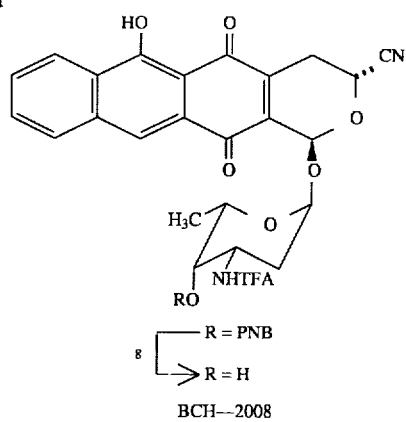

BCH—2008

BCH-2007: (1'S,1R,3S)-3-(6-hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-c]pyran-3-yl)nitrile, and BCH-2008: (1'S,1S,3R)-3-(6-hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-c]pyran-3-yl)nitrile.

Example 45

Preparation of tetrahydroanthraceno-[2,3-c]pyran derivative with a cyano side chain

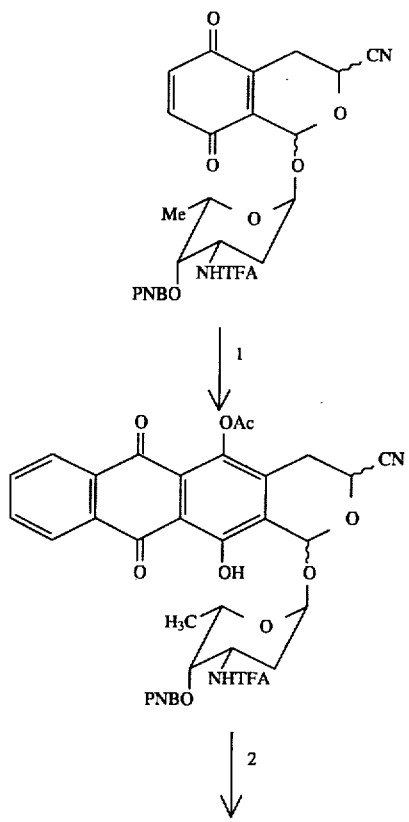

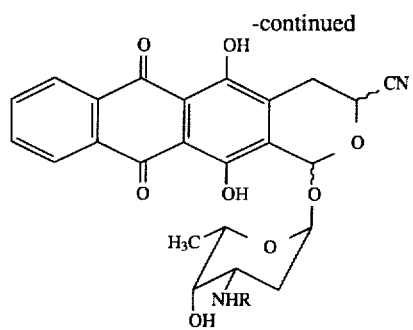

R = TFA BCH—2055
R = H₂Cl BCH—2056

BCH-2055: (1'S,1R,3S) and (1'S,1S,3R)(5,12-Dihydroxy-1-(2',3',6'-trideoxy-3'-trifluoroacetamido-4'-hydroxy-L-lyxohexopyranose)-6,11-dioxo-3,4,5,12-tetrahydroanthraceno-[2,3-c]pyran-3-yl)nitrile;

BCH-2056: (1'S,1R,3S) and (1'S,1S,3R)(5,12-Dihydroxy-1-(2',3',6'-trideoxy-3'-amino-4'-hydroxy-L-lyxohexopyranose)-6,11-dioxo-3,4,5,12-tetrahydroanthraceno-[2,3-c]pyran-3-yl)nitrile.

Example 46

Preparation of tetrahydroanthraceno-[2,3-c]pyran derivative with a phenyl side chain

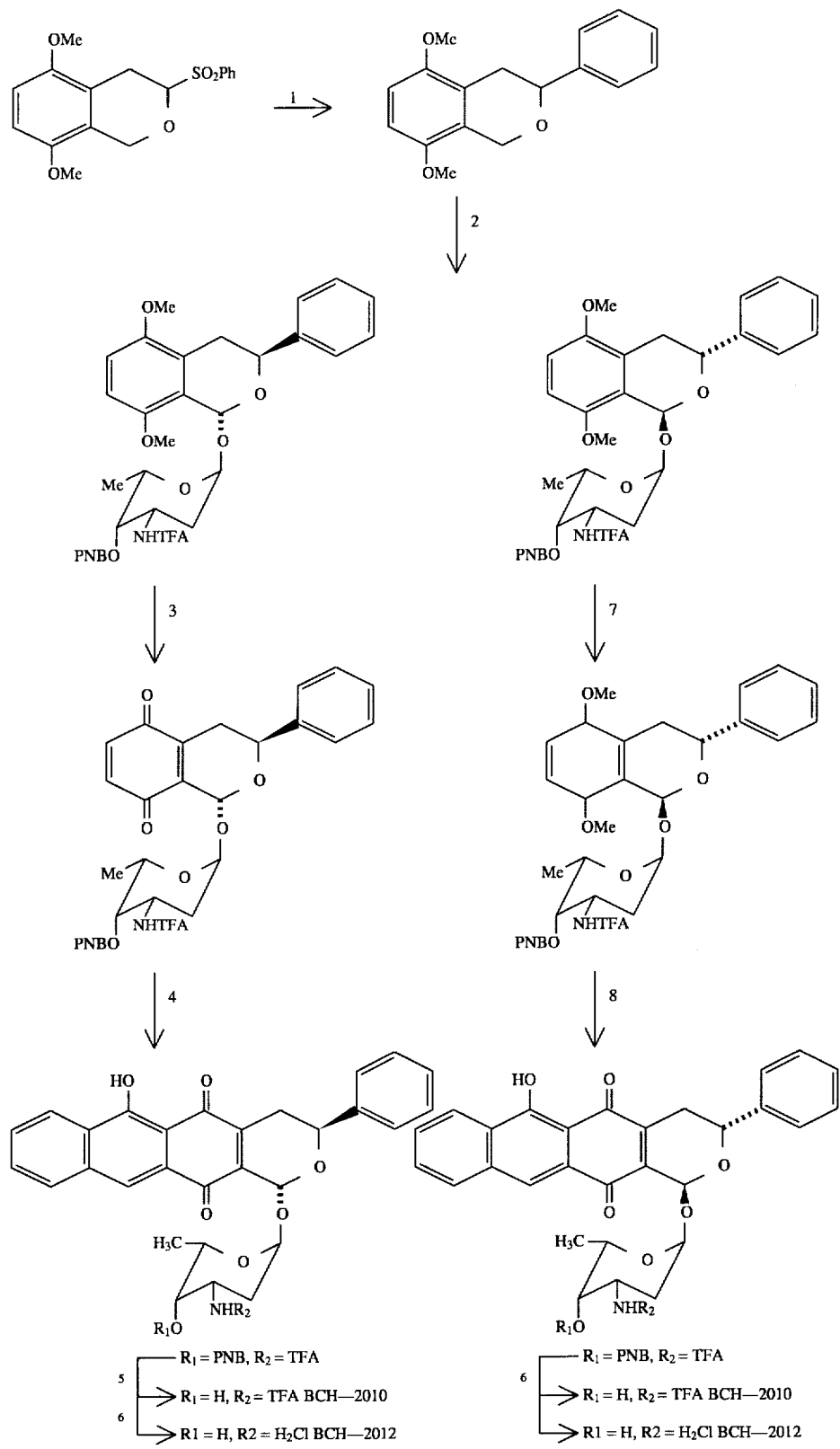
BCH-2010: (1S, 1R, 3S)-3-(6-hydroxy-1-(2',3',6'-trideoxy-3'-trifluoroacetamido-4'-hydroxy-L-lyxohexopyranose)-5,12-dioxo-3,4,5,12-tetrahydroanthraceno[2,3-c]pyran-3-yl)benzene, and BCH-2012: (1'S,1R,3S)-3-(6-hydroxy-1-(2',3',6'-trideoxy-3'-amino-4'-hydroxy-L-lyxohexopyranose)-5,12-dioxo-3,4,5,12-tetrahydroanthraceno-[2,3-c]pyran-3-yl)benzene hydrochloride.

Example 47

Preparation of tetrahydroanthraceno-[2,3-c]pyran derivative with a homo cyclopropyl ketone side chain

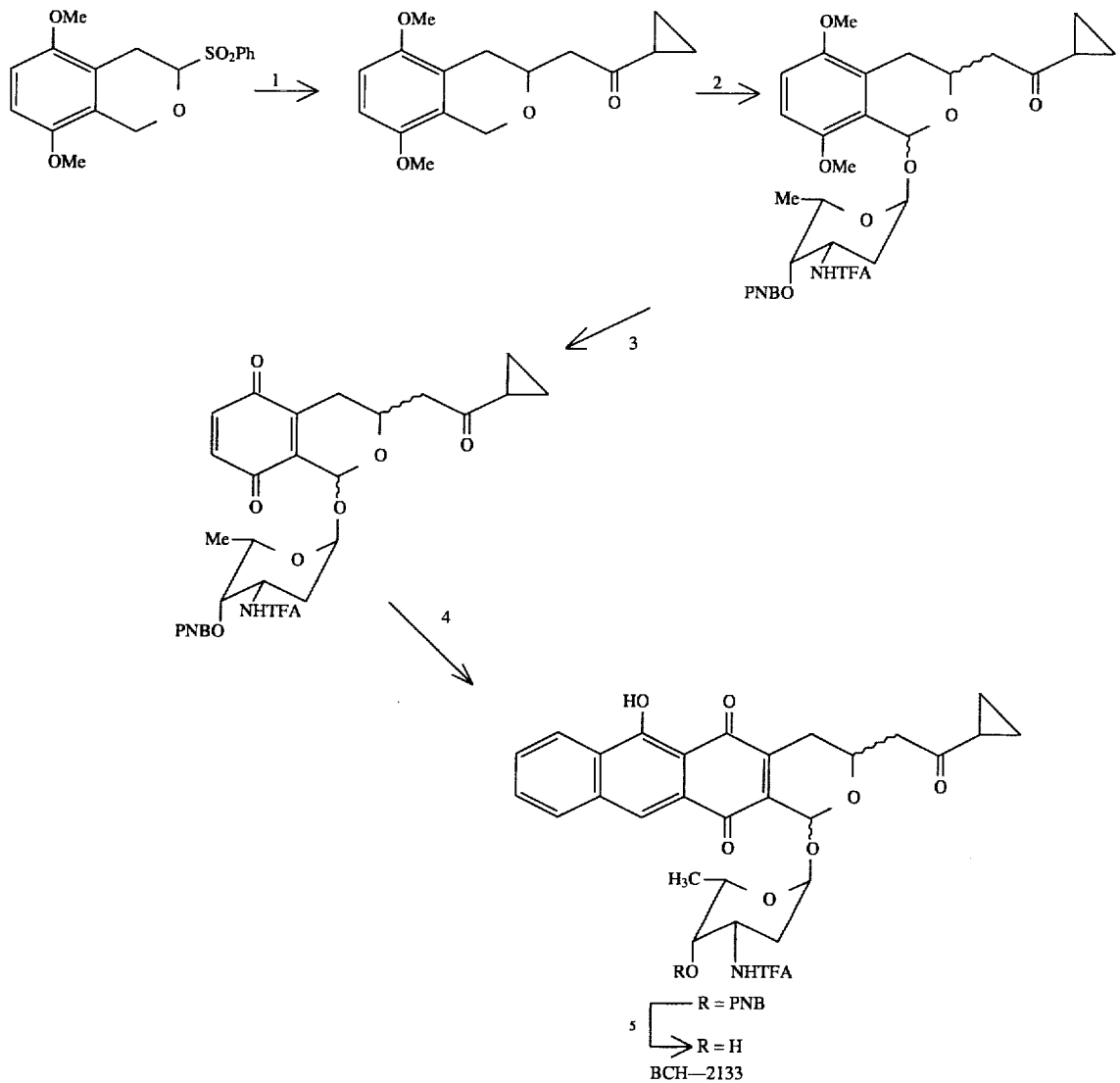

BCH-2133: (1'S,1S,3R) and (1'S,1R,3S)-cyclopropyl-(6-hydroxy-1-((2',3',6'-trideoxy-3'-trifluoroacetamido-4'-hydroxy-L-arabino-hexopyranose)-5,10-dioxo-3,4,5,12-tetrahydronaphto-[2,3-c]pyran-3-yl)methylene).

Example 48

Preparation of 5,12-dioxo-3,4-dihydroanthraceno derivatives from a bicyclic quinone aglycal

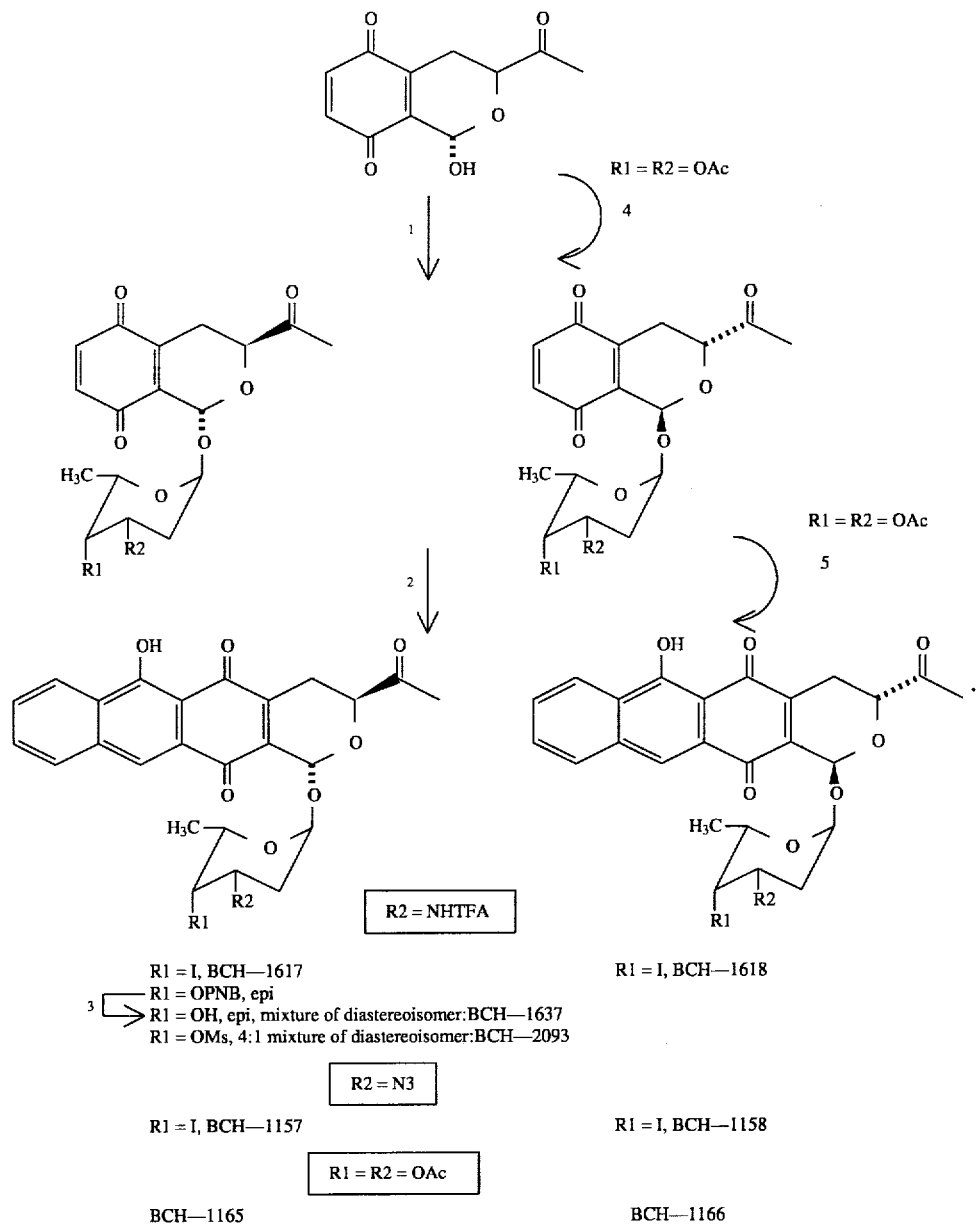

BCH-1157: (1'S,1S,3R)-methyl-6-hydroxy-1-(2',3',4',6'-tetradeoxy-3'-azido-4'-iodo-L-lyxohexopyranose)-5,12-dioxo-3,4,5,12-tetrahydroanthraceno-[2,3-c]pyran-3-yl ketone, BCH-1158: (1'S,1R,3S)-methyl-6-hydroxy-1-(2',3',4',6'-tetradeoxy-3'-azido-4'-iodo-L-lyxohexopyranose)-5,12-dioxo-3,4,5,12-tetrahydroanthraceno-[2,3-c]pyran-3-yl ketone, BCH-1165: (1'S,1R,3S)-methyl-(6-hydroxy-1-(2',3',4',6'-tetradeoxy-3',4'-diacetyl-L-lyxohexopyranose)-5,12-dioxo-3,4,5,12-tetrahydroanthraceno-[2,3-c]pyran-3-yl) ketone, and BCH-1166: (1'S,1S,3R)-methyl-(6-hydroxy-1-(2',3',4',6'-tetradeoxy-3',4'-diacetyl-L-lyxohexopyranose)-5,12-dioxo-3,4,5,12-tetrahydroanthraceno-[2,3-c]pyran-3-yl) ketone, BCH-1617: (1'S,1R,3S)-methyl-(6-hydroxy-1-(2',3',4',6'-tetradeoxy-3'-trifluoroacetamido-4'-iodo-L-lyxohexopyranose)-5,12-dioxo-3,4,5,12-tetrahydroanthraceno-[2,3-c]pyran-3-yl)ketone, BCH-1618: (1'S,1S,3R)-methyl-(6-hydroxy-1-(2',3',4',6'-tetradeoxy-3'-trifluoroacetamido-4'-iodo-L-lyxohexopyranose)-5,12-dioxo-3,4,5,12-tetrahydroanthraceno-[2,3-c]pyran-3-yl)ketone, BCH-2093: (1S,1R,3S)-Methyl-(6-hydroxy-1-(2',3',4',6'-tetradeoxy-3'-trifluoroacetamido-4'-O-methanesulfonyl-L-lyxohexopyranose)-5,12-dioxo-3,4,5,12-tetrahydroanthraceno[2,3-c]pyran-3-yl)ketone Example 49

Preparation of (1'S,1R, 3R) and (1'S,1S,3S)-5,12-dioxo-3-ethyl-6-hydroxy-1-(2,6-dideoxy-L-lyxohexopyranose)-3,4,5,12-tetrahydroantrahceno-[2,3-c]pyran BCH-1630 and BCH-1629

291 292
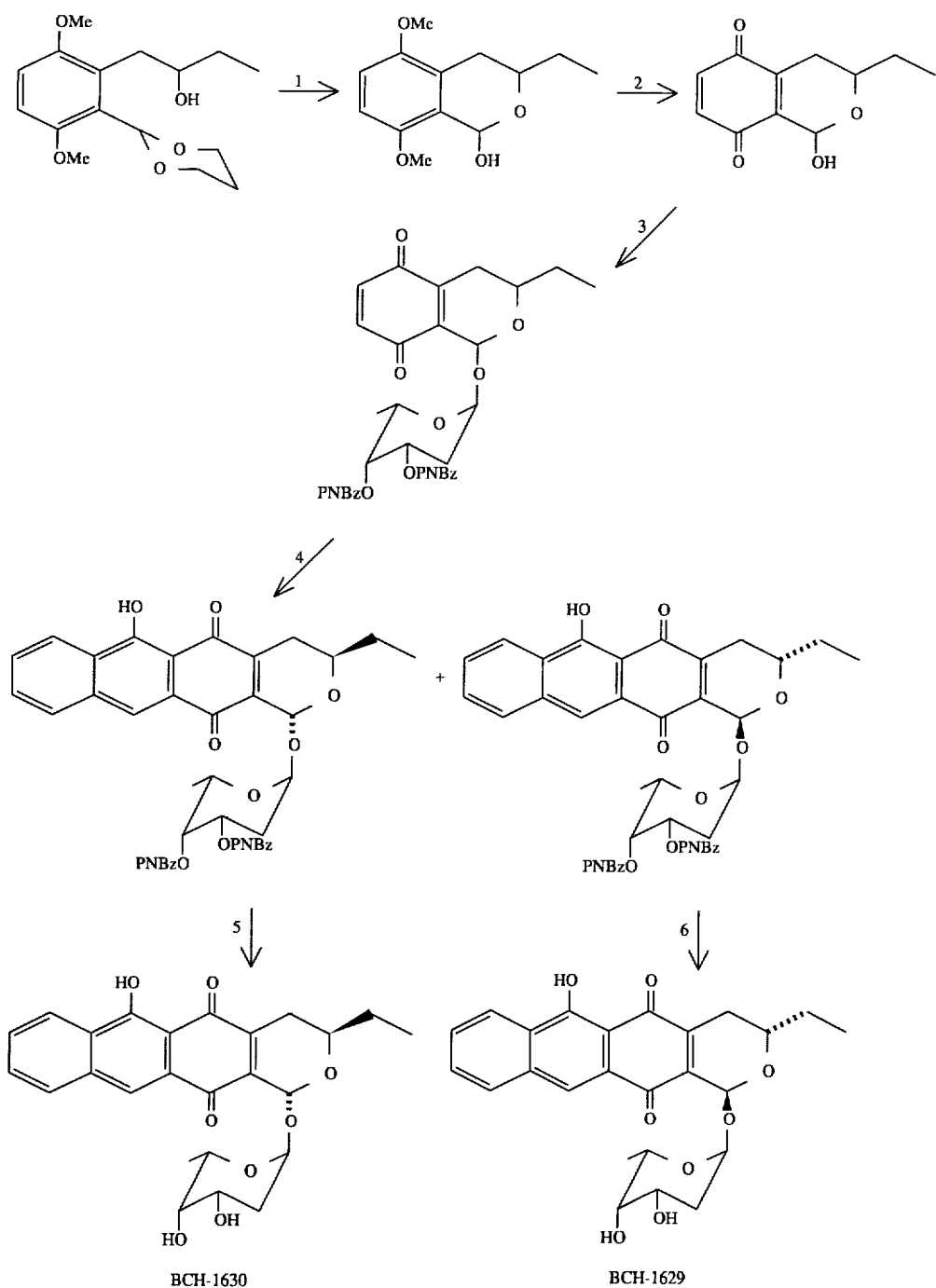
Example 50
Preparation of (1'R, 1R,3S)-3-aceto-5,12-dihydroxy-1(2-deoxy-2-amino-D-glucopyranose)-6,11-dioxo-3,4,6,11-tetrahydro-1H-anthra-[2,3 -c]pyran (BCH-1659) hydrochloride (BCH-1685)

293
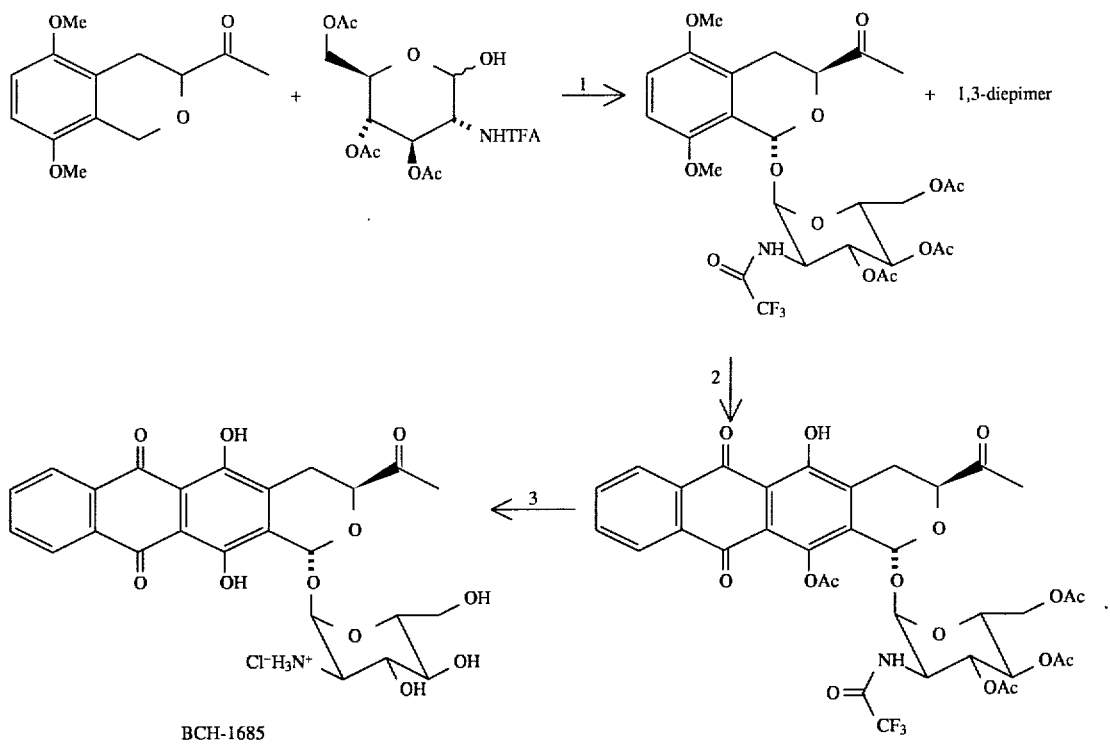
294
+ 1,3-diepimer
BCH-1685
Example 51
(1'S, 1S,3R)-3-(Oximoethyl)-5,12-dihydroxy-1(2,3,6-trideoxy-3-amino-L-lyxohexolpyranose)-6,11-dioxo-3,4,6,11-tetrahydro-1H-anthra[2,3-C]pyran hydrochloride (BCH-2074)
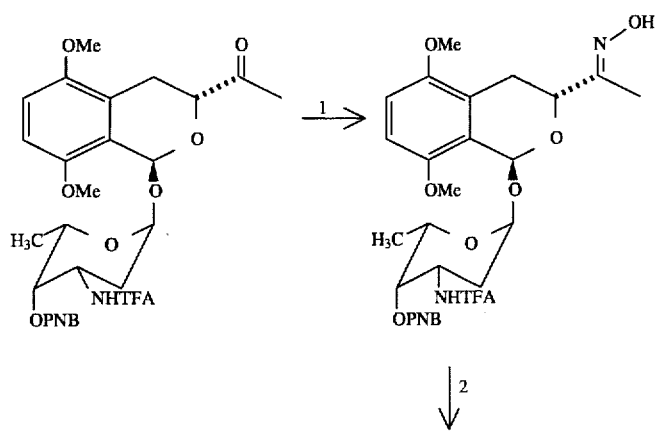

295 296
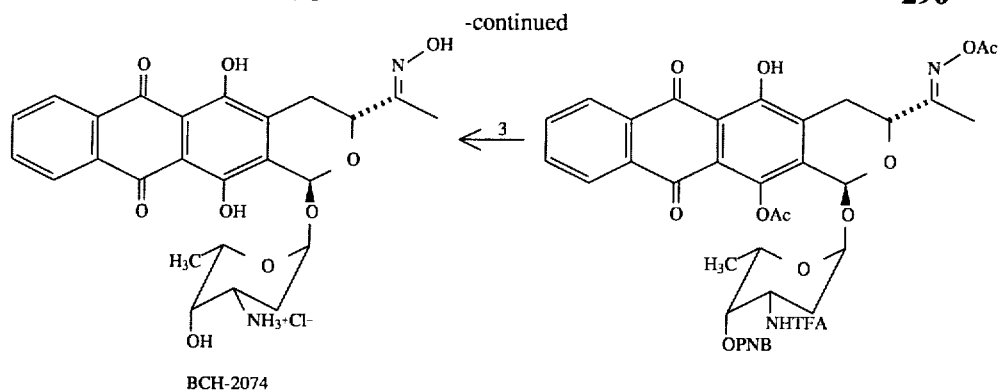
BCH-2074
Example 52
Preparation of (1'R, 1R,3S)-3-aceto-5,12-dihydroxy-1(2-deoxy-2-chloroethylnitroso ureido D-glucopyranose)-6,11-dioxo-3,4,6,11-tetrahydro-1H-anthra[2,3-c]pyran (BCH-1999)
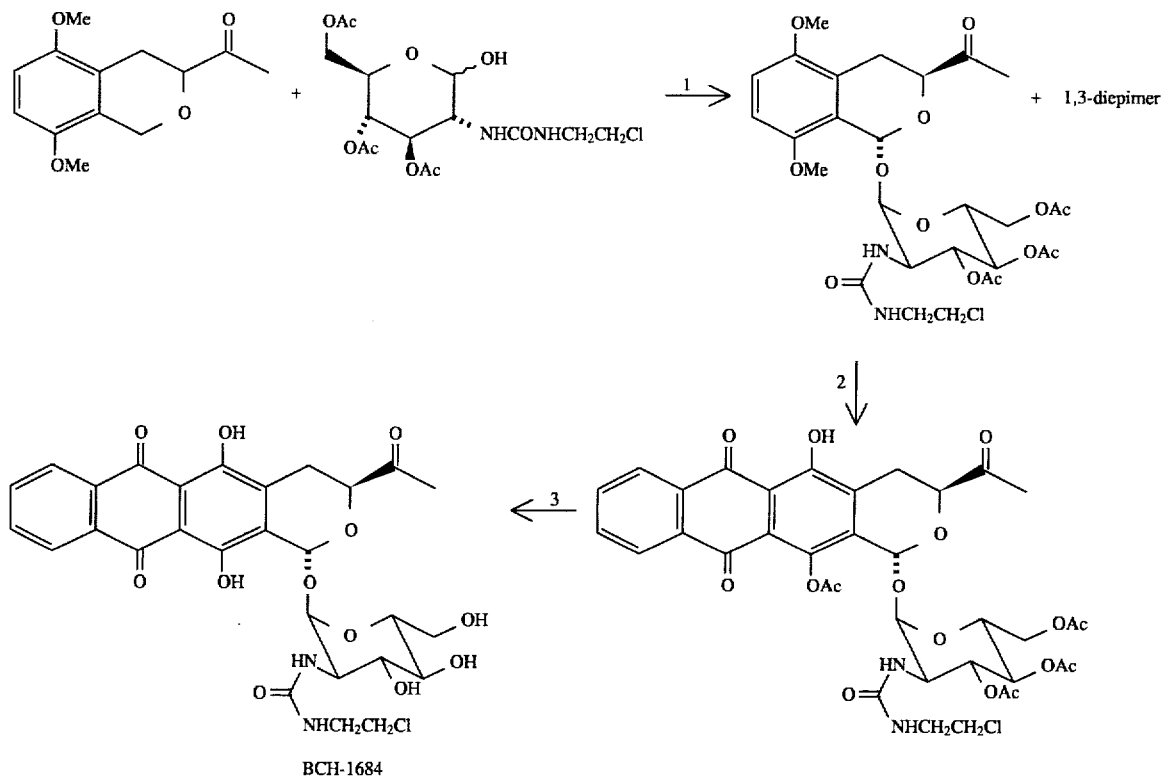
BCH-1684

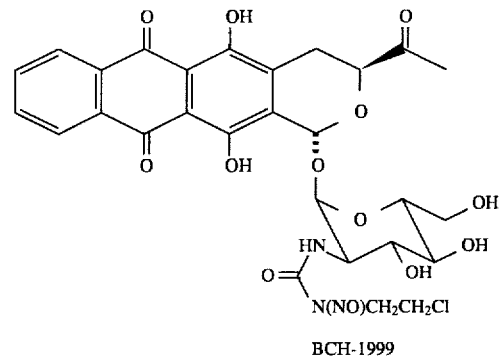
BCH-1999
Example 53
Preparation of (1R,3S) and (1S,3R)-3-aceto-6,11-dioxo-5,12-dihydroxy-1(4-chloroethylnitrosoureido-cyclohexyl-oxy)-3,4,6,11-tetrahydro-1H-anthra[2,3-C]pyran (BCH-2116)
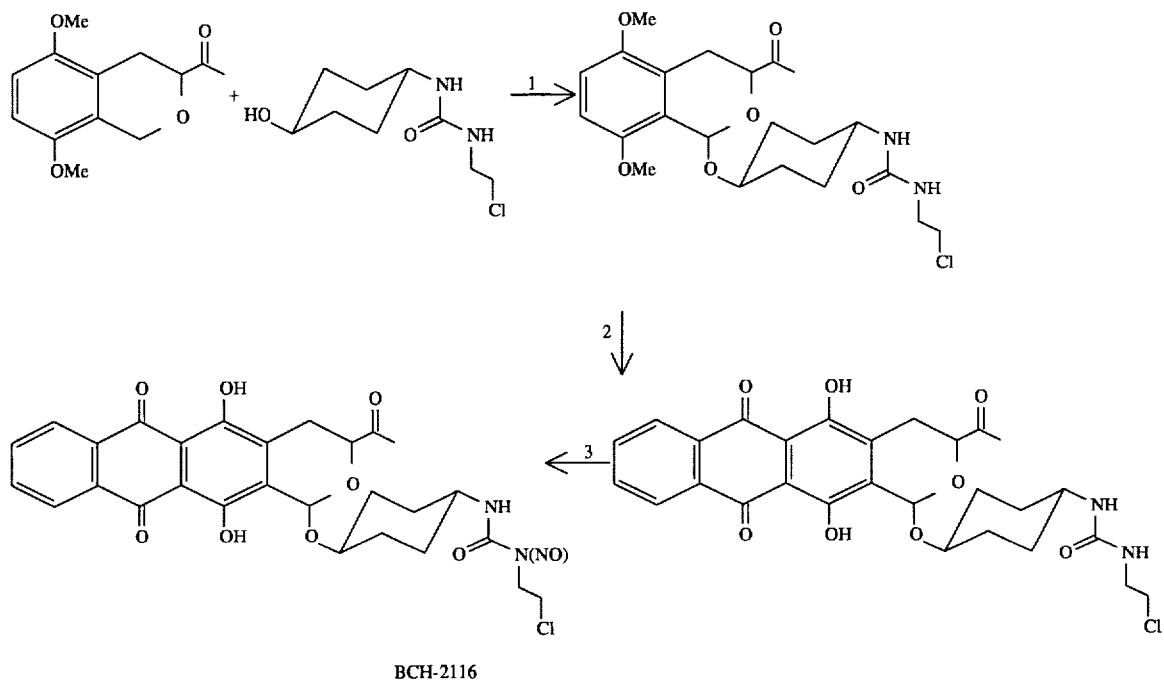
BCH-2116
Example 54
Preparation of (1'R, 1R,3S)-3-Aceto-6-hydroxy-1-(2-deoxy-2-chloroethylnitrosoureido-D-glucopyranose)-5,12-dioxo-3,4,5,12-tetrahydro-1H-anthra[2,3-C]pyran (BCH-2073) and 1,3-diepimer (BCH-2039)

299 300
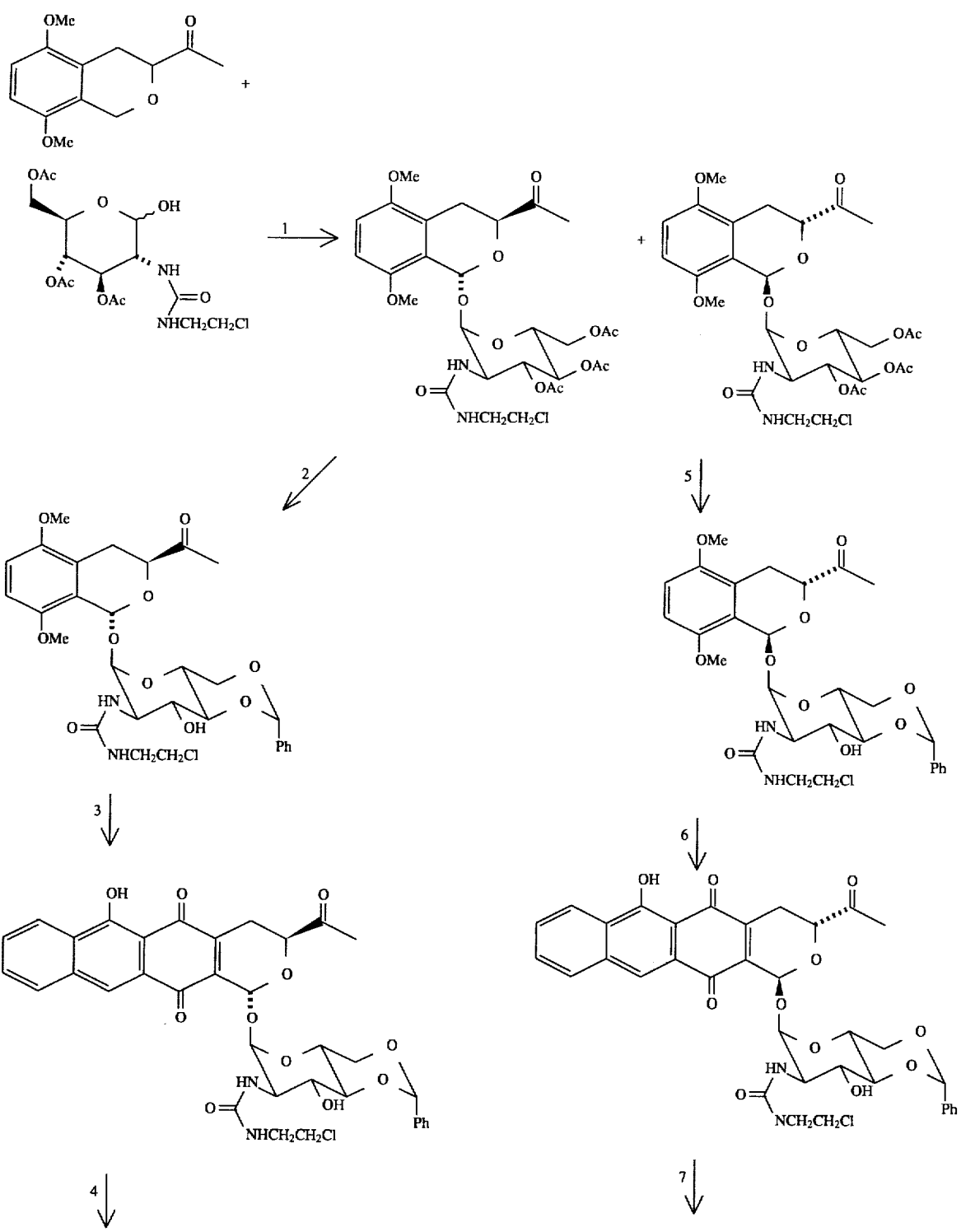

301
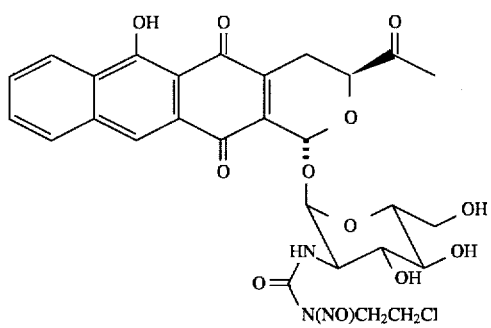
BCH-2073
302
-continued
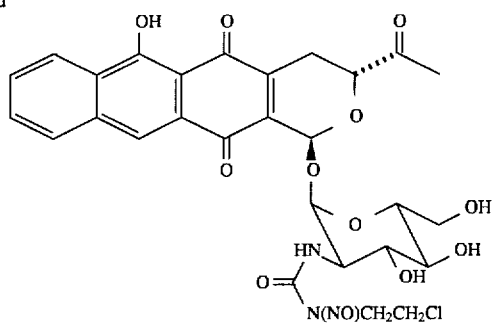
BCH-2039
Example 55
Preparation of (1'S,1S,3R)-3(aminoethyl)-5,12-dihydroxyl-1(2,3,6-trideoxy-3,4-dihydroxy-L-lyxohexopyranose)-6,11-dioxo-3,4,6,11-tetrahydro-1H-anthra[2,3-c]pyran hydrochloride(BCH-1683)
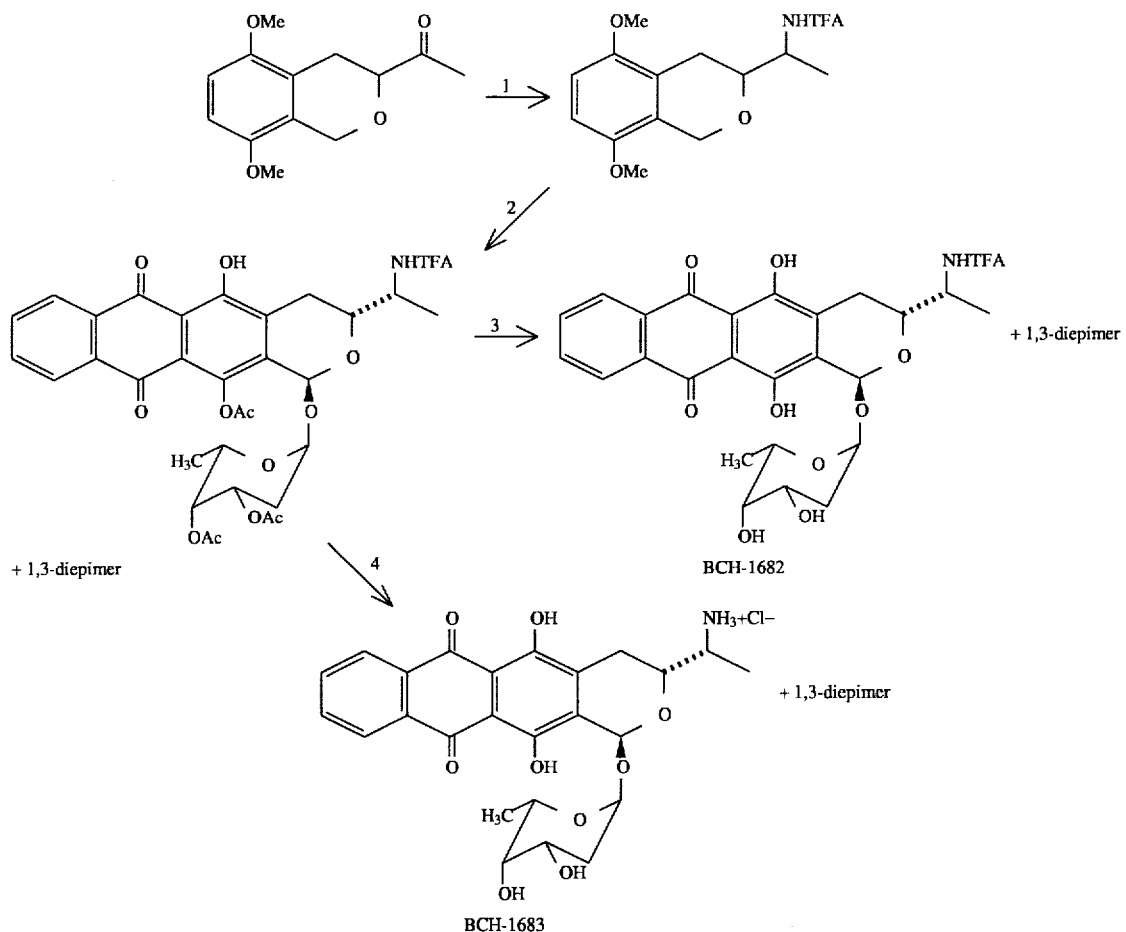

Example 56
(1'S,1R, 3R)-3-ethyl-5,12-dihydroxy-1-(2',3',6'-trideoxy-3'-amino-L-lyxohexopyranose)-1,2,3,4-tetrahydro-(2-oxygen)-naphthacene-6,11-dione-hydrochloride (BCH-2016)
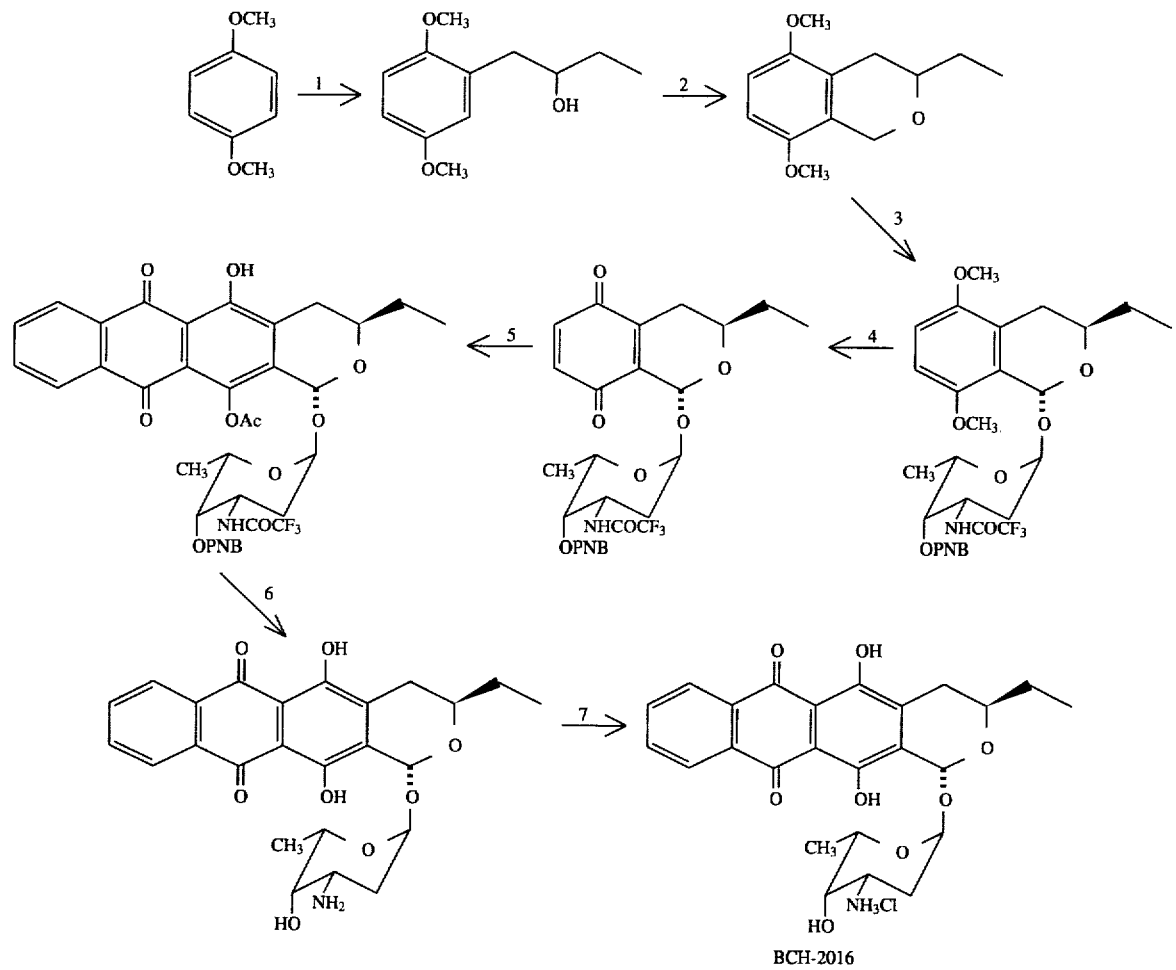
Example 57
(1'S,1S,3S)-3-ethyl-5,12-dihydroxy-1-(2',3',6'-trideoxy-3'-amino-L-lyxohexopyranose)-1,2,3,4-tetrahydro-(2-oxygen)-naphthacene-6,11-dione-hydrochloride (BCH-1633)
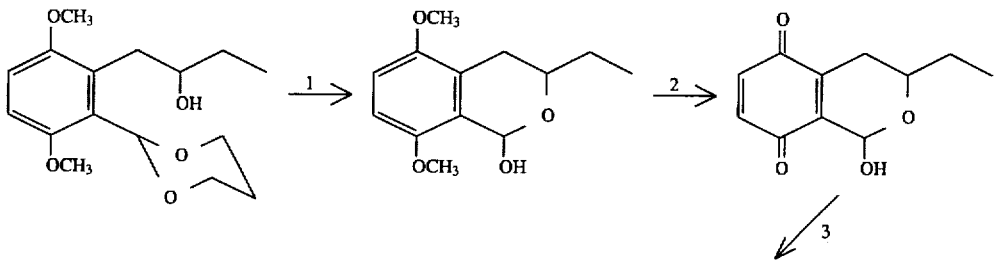

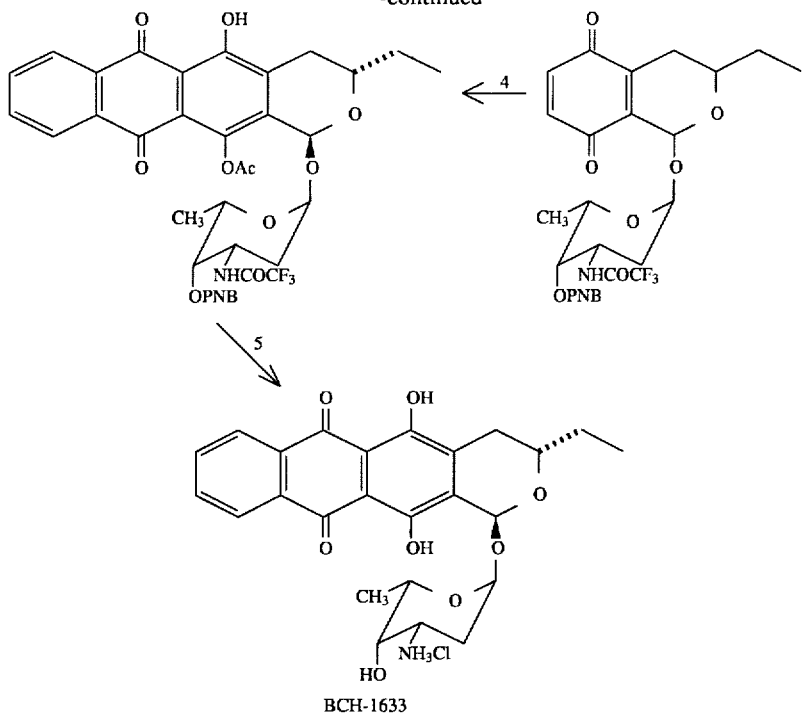
Example 58
3-(1',1'-difluoroethyl)-6 and
11-hydroxy-1,2,3,4-tetrahydro-(2-oxygen)-
naphthacene-5,12-dione (BCH-1638 & 1639)
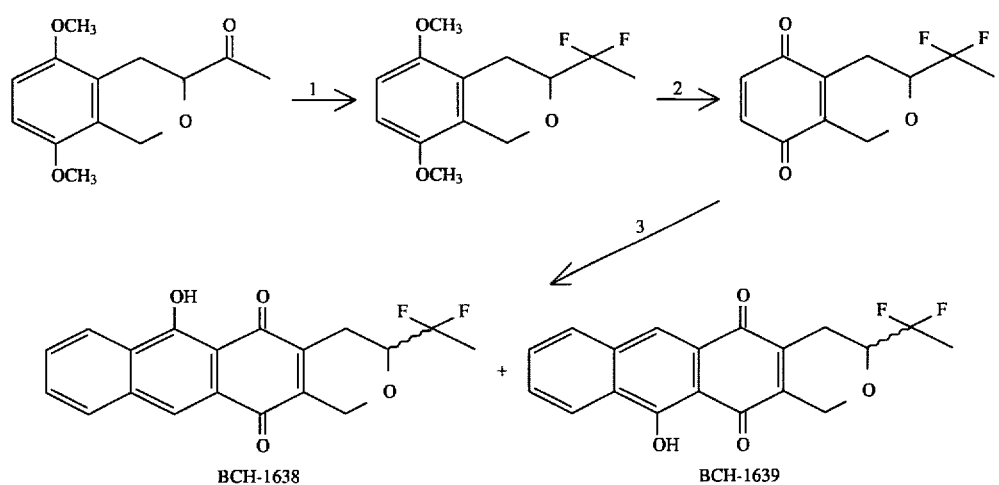
Example 59
(1'S,1S,3S) and (1'S,1R,
3R)-5,12-dioxo-3-(1,1-difluoroethyl)-6-hydroxy-1-
(2',6'-dideoxy-L-lyxohexopyranose)-3,4,5,12-
tetrahydroanthraceno-[2,3-c]-pyran (BCH-1662 &
1663).

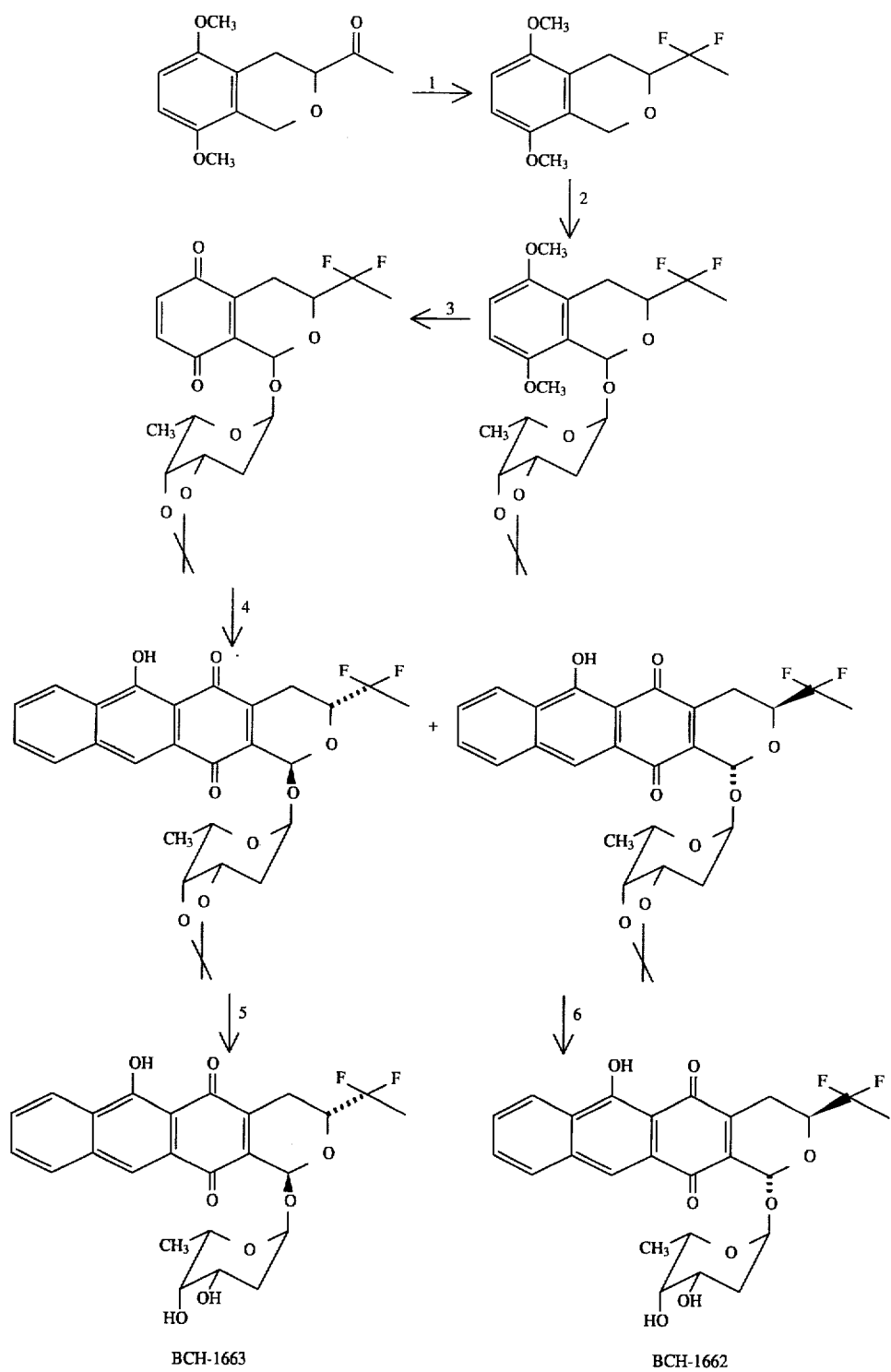
Example 60
(1'S, 1R, 3S) and
(1'S,1S,3R)-5,12-dioxo-3-(1,1-difluoroethyl)-6-
hydroxy-1-(2',3',6'-trideoxy-3'trifluoroacetamido-
L-lyxohexopyranose)-3,4,5,12-tetrahydro-
anthraceno-[2,3-c]-pyran (BCH-1676 & 1677).

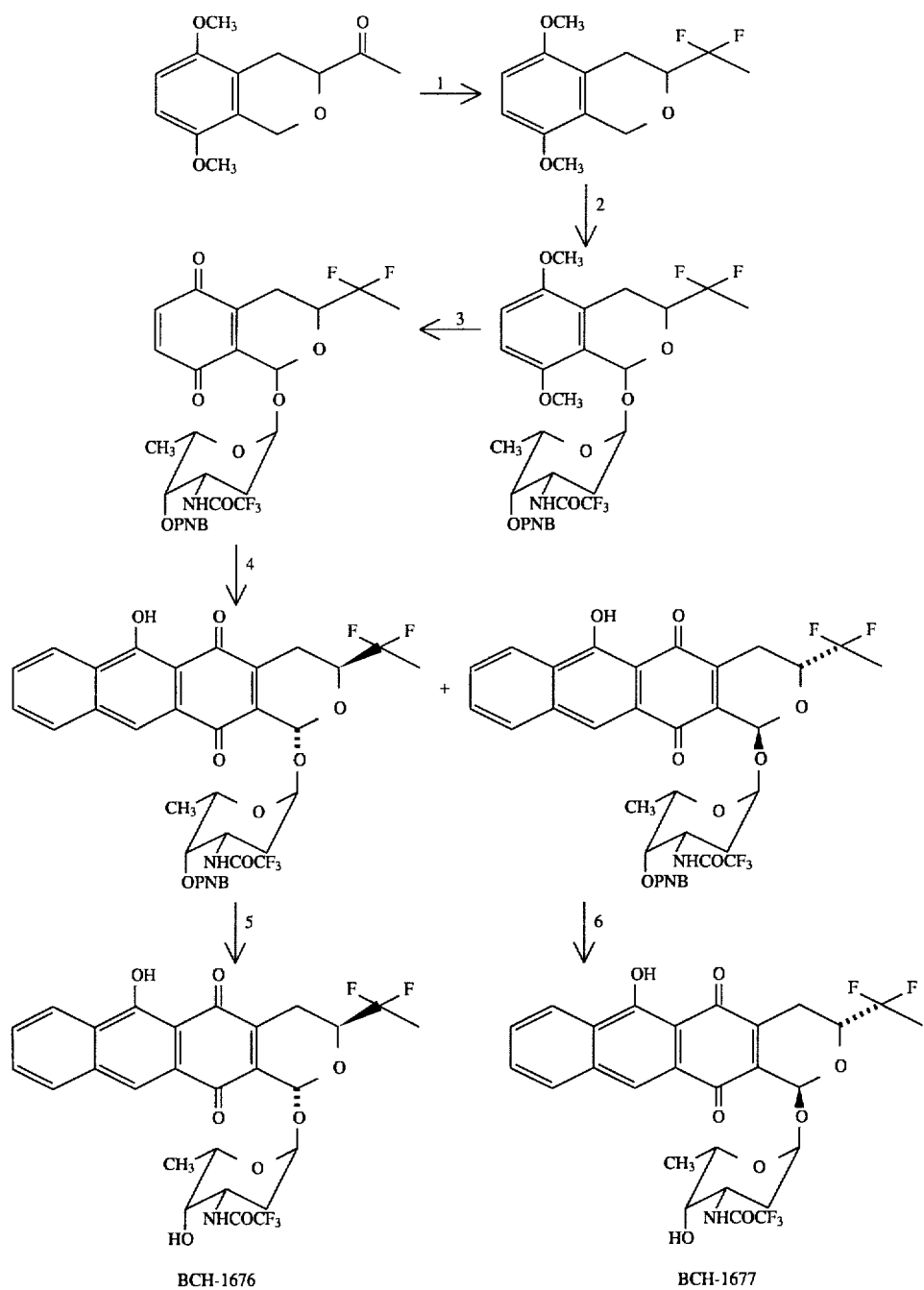
Example 61
(1'S,1S)-5,12-dioxo-6-hydroxy-3,3-bis-methoxymethyl-1-(2',3',6'-trideoxy-3'-amino-L-lyxohexo-pyranose)-3,4,5,12-tetrahydroanthraceno-[2,3-c]-pyran-hydrochloride (BCH-1991), and
(1'S,1S)-5,12-dioxo-6-hydroxy-3,3-bis-methoxymethyl-1-(2',3',6'-trideoxy-3'-trifluoroacetamido-L-lyxohexopyranose)-3,4,5,12-tetrahydroanthraceno-[2,3-c]pyran BCH-1698

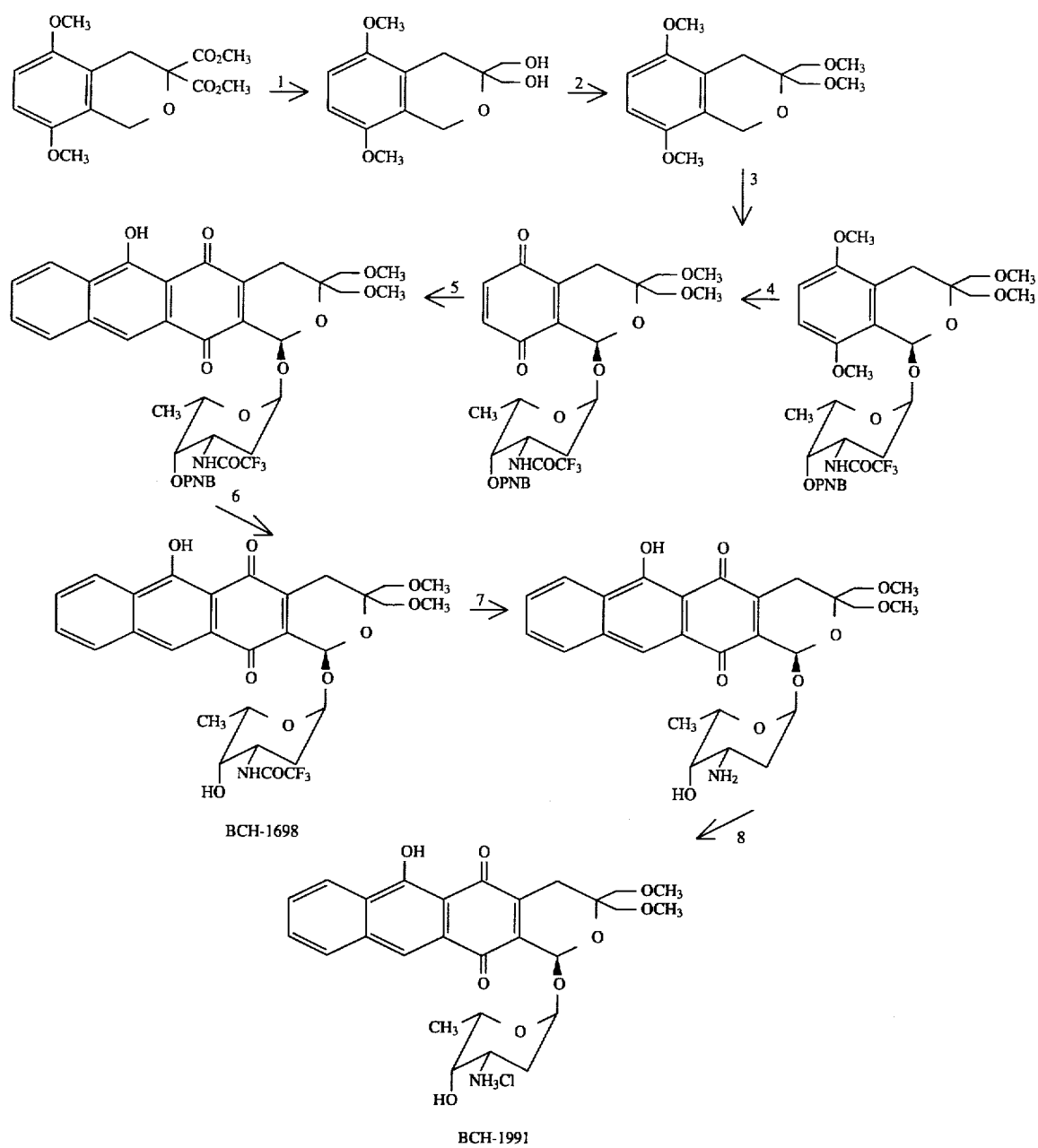
Example 62
(1'S,1R,3S) and
(1'S,1S,3R)-5,12-dioxo-6-hydroxy-3-phenyloxymethyl-
1-(2',3',6'-trideoxy-3'-trifluoroacetamido-L-
lyxohexopyranose)-3,4,5,12-tetrahydroanthraceno-
[2,3-c]-pyran (BCH-2048 & 2057).

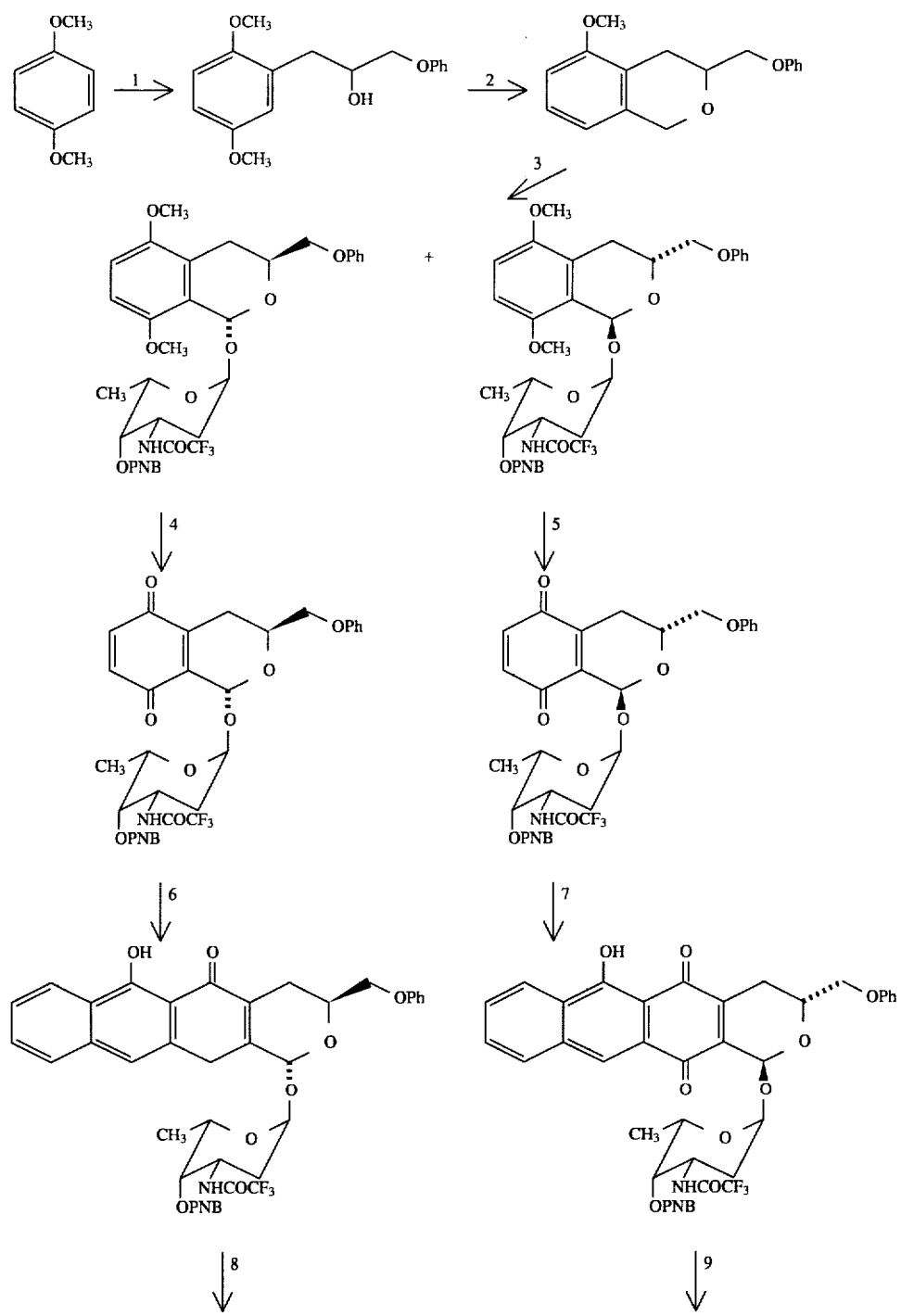

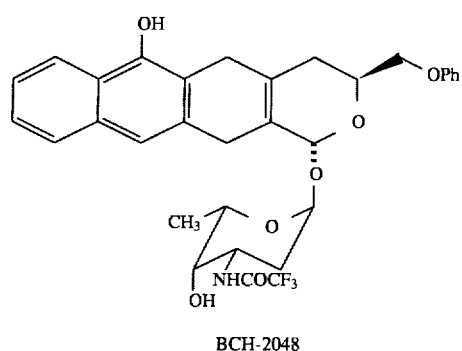
BCH-2048
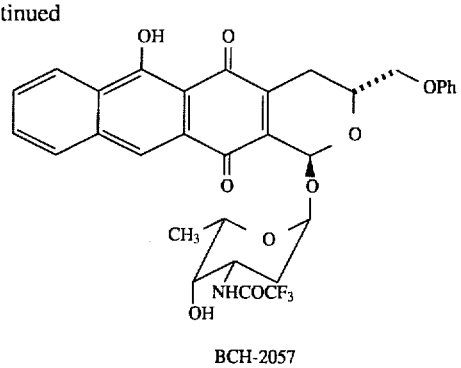
BCH-2057
Example 63
(1'S,1R,3S) and (1'S,1S,3R)-5,12-dihydroxy-3-phenyloxymethyl-1-(2',3',6'-trideoxy-3'-amino-L-lyxohexopyranose)-1,2,3,4-tetrahydro-(2-oxygen)-naphthacene-6,11-dione-hydrochloride (BCH-2058 & 2059).
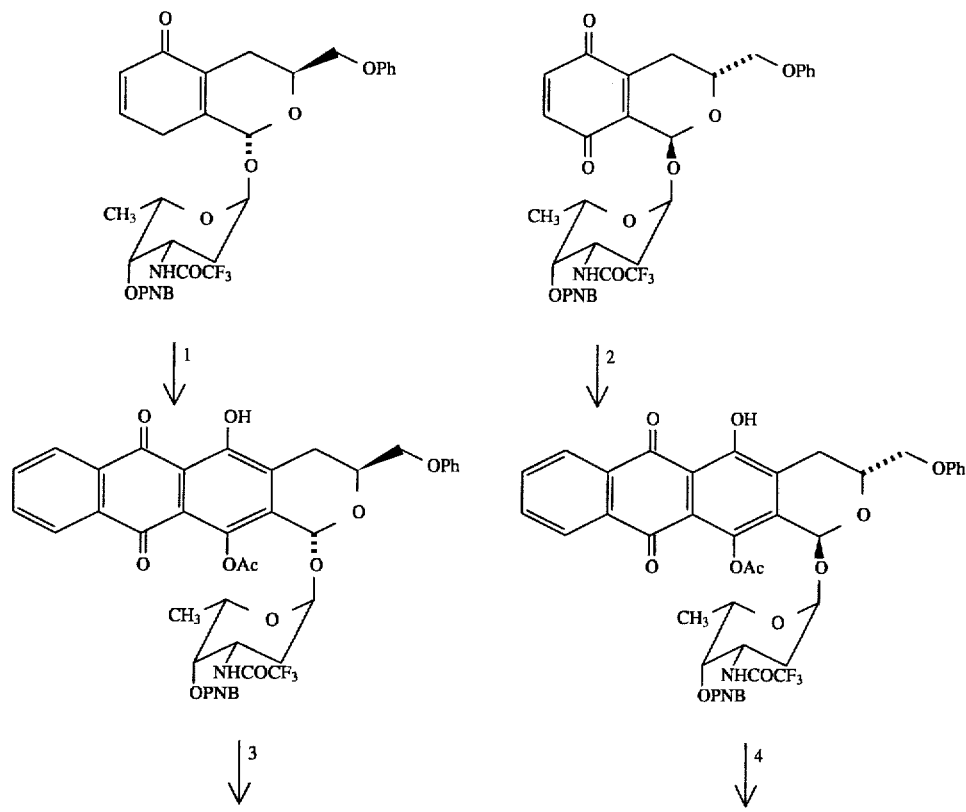

317
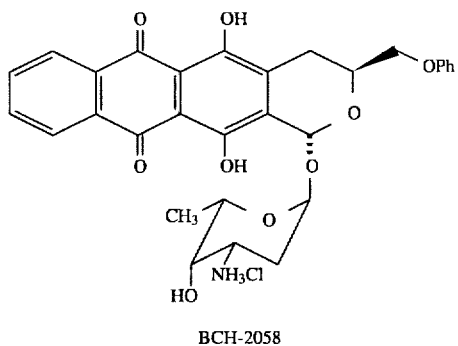
BCH-2058
-continued
318
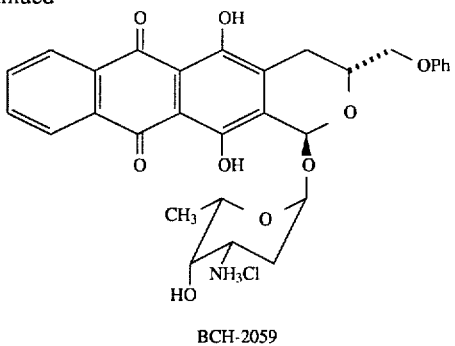
BCH-2059
Example 64
(1'S, 1S,4S) and
(1'S,1R,4R)-5,12-dioxo-4-ethyl-6-hydroxy-1-(2',3',6'-trideoxy-3'-trifluoroacetamido-L-lyxohexopyranose)-3,4,5,12-tetrahydroanthraceno-[2,3-c]-pyran (BCH-2080 &2084).
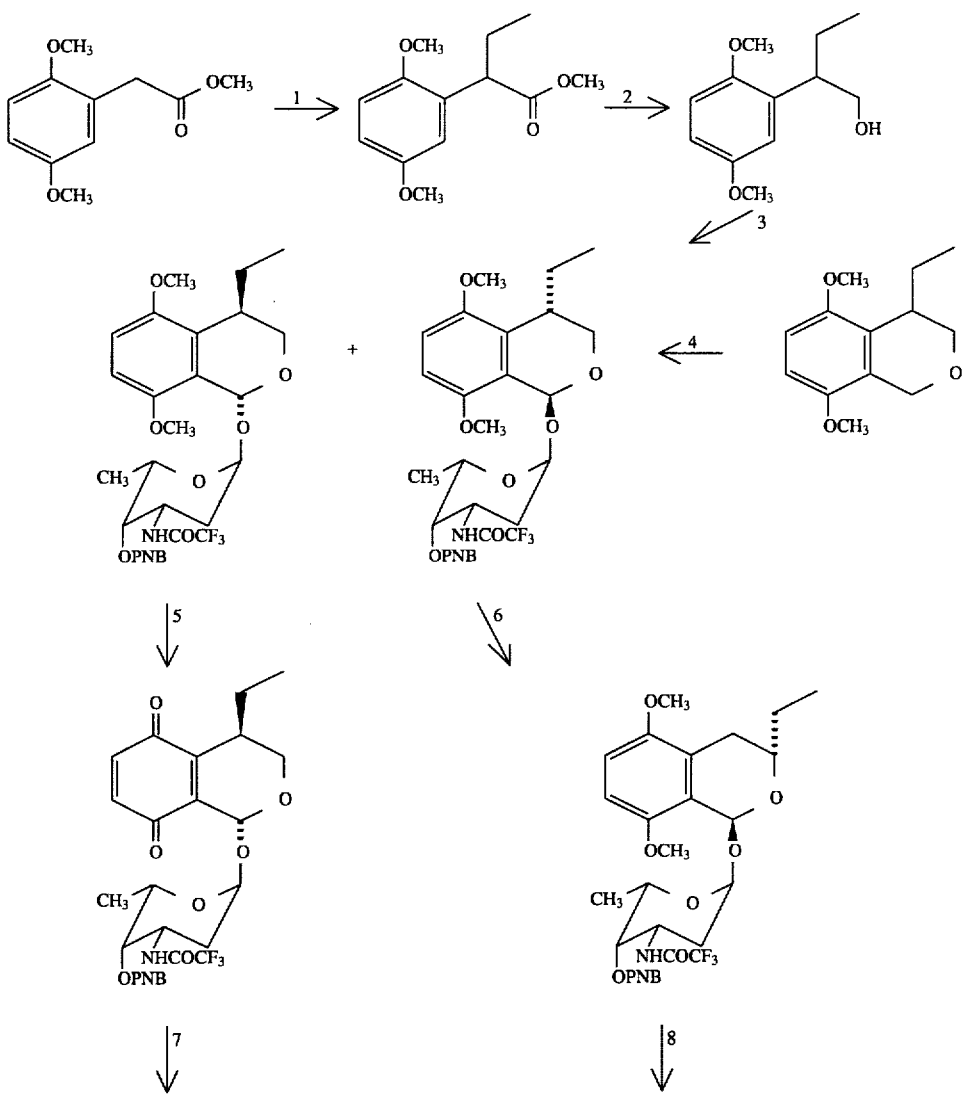

-continued
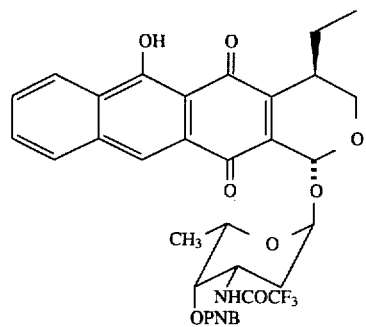
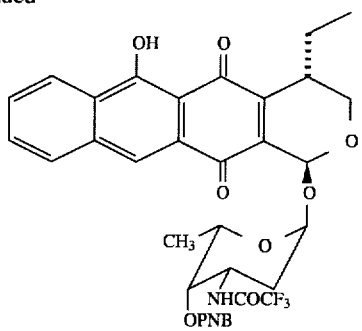
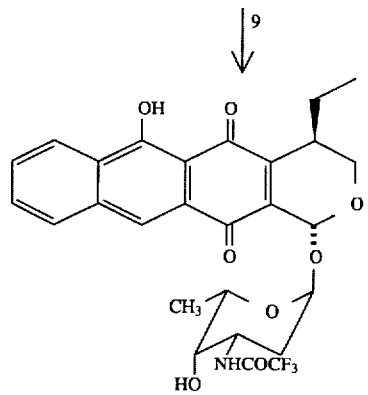
BCH-2080
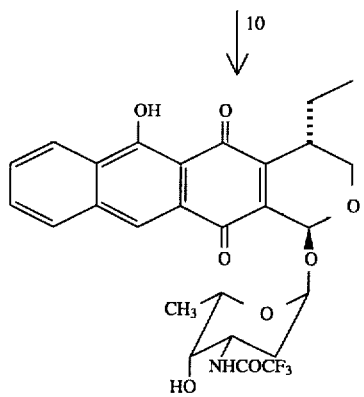
BCH-2084
Example 65
(1'S,1S,4S) and (1'S,1R,4R)-5,12-dihydroxy-4-ethyl-1-(2',3',6'-trideoxy-3'-amino-L-lyxohexopyranose)-1,2,3,4-tetrahydro-(2-oxygen)-naphthacene-6,11-dione-hydrochloride (BCH-2085 & 2086).
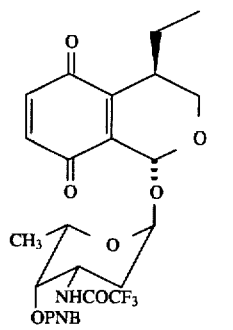
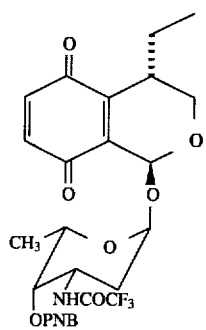

321 322
-continued
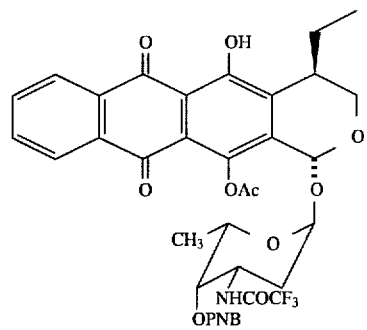 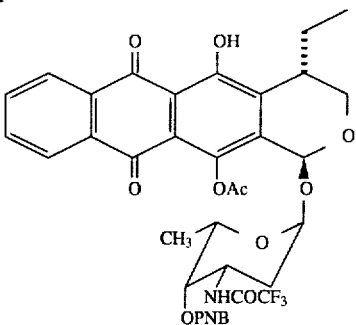
↓3 ↓4
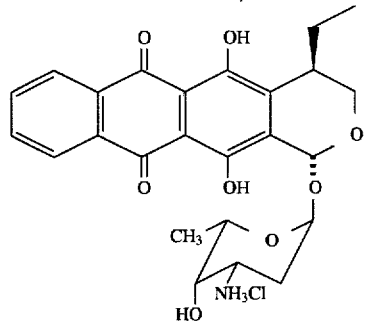 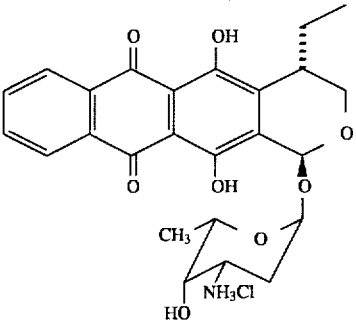
BCH-2085    BCH-2086
Example 66
(1'S, 1S,3S) and (1'S,1R, 3R)-tert-butyl-(6-hydroxy-1-(2',3',6'-trideoxy-3'-trifluoroacetamido-4-hydroxy-L-lyxohexopyranose)-5,12-dioxo-3,4,5,12-tetrahydroanthraceno-[2,3-c]-pyran-3-yl)-ketone BCH-2197 & 2198).
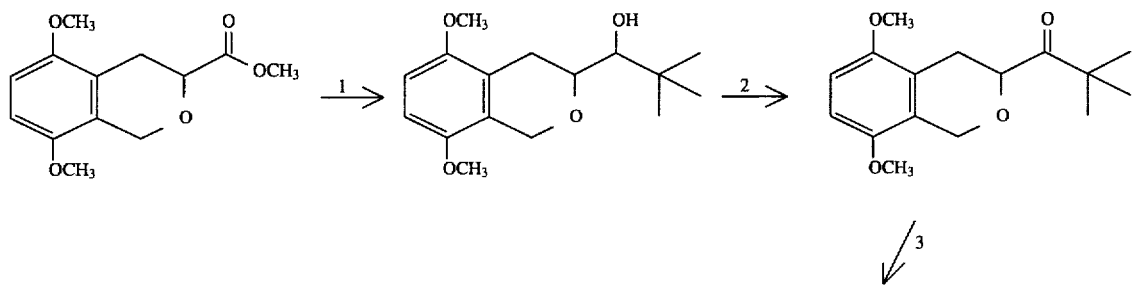

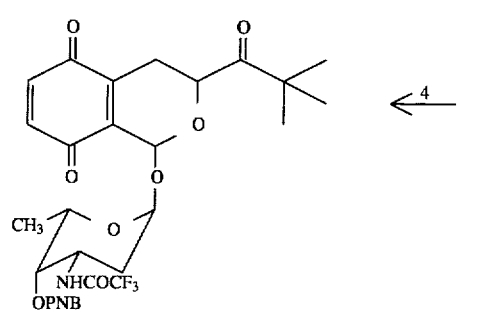

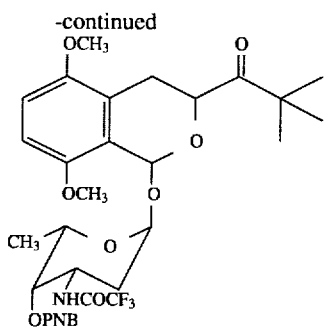
-continued

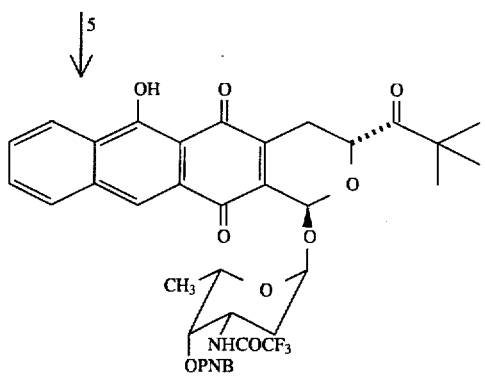

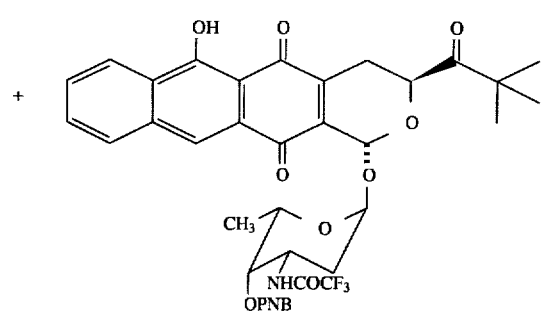

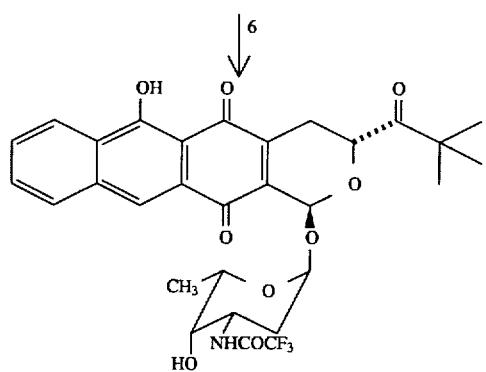

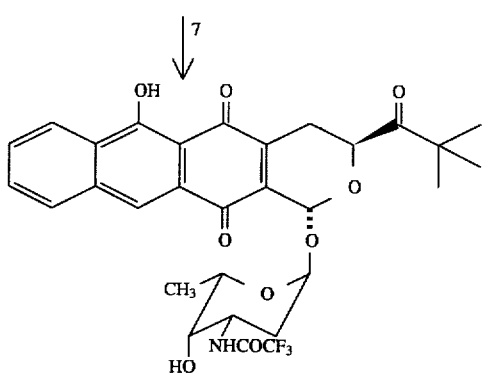

BCH-2197

BCH-2198

Example 67

The following compounds were also synthesized according to any of the above presented processes.

BCH-650: Ethyl (5,12-dihydroxy-6,11-dioxo-3,4,6,11-tetrahydroanthraceno [2,3-c]pyranyl-formate;

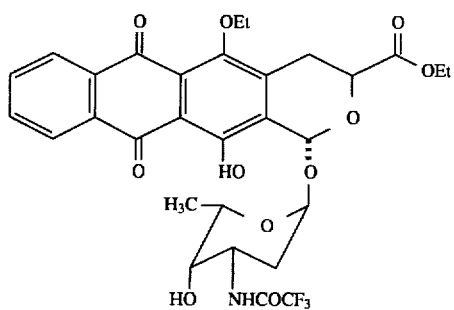

BCH-659: Ethyl(6-acetoxy-5,12-dioxo-3,4,5,12-tetrahydroanthraceno[2,3-c]pyran-3-yl)formate;

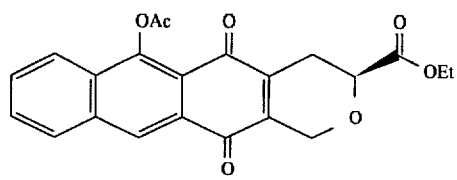

BCH-688: Methyl-(5,12-dihydroxy-6,11-dioxo-3,4,6,11-tetrahydroanthraceno-[2,3-c]pyran-3-yl)ketone;

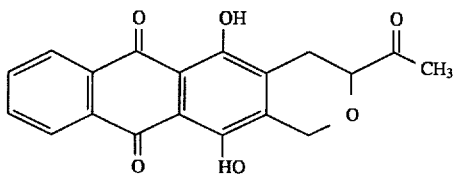

BCH-703: Methyl(1,11-dihydroxy-5,12-dioxo-3,4,5,12-tetrahydroanthraceno[2,3-c]pyran-3-yl)formate;

325

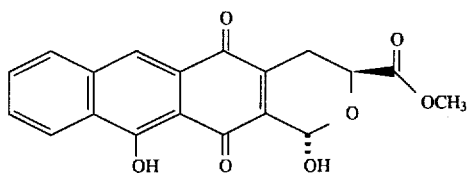

BCH-705: Ethyl(5-ethoxy-12-hydroxy-1-(2',3',6'-trideoxy-3'-trifluoroacetamido-4'-hydroxy-L-lyxohexopyranose)-6,11-dioxo-3,4,6,11-tetrahydroanthraceno[2,3-c]pyran-3-yl)formate;

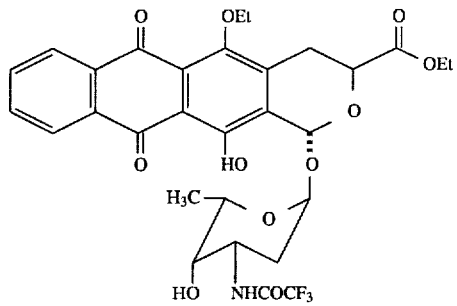

BCH-715: 6-Acetoxy-3-(methoxymethyl)-aceto-1,2,3,4-tetrahydro-(2-oxygen)-naphthacene-5,12-dione; and 11-Acetoxy-3-(methoxymethyl)-aceto-1,2,3,4-tetrahydro-(2-oxygen)-naphthacene-5,12-dione;

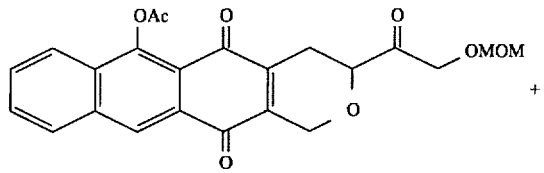

+

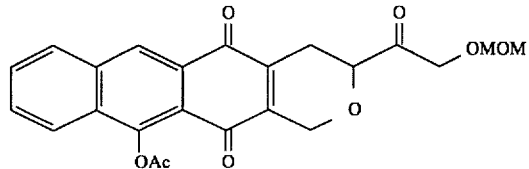

BCH-721: Methyl(11-hydroxy-6-acetoxy-5,12-dioxo-2,4,5,12-tetrahydroanthraceno[2,3-c]pyran-3-yl)ketone;

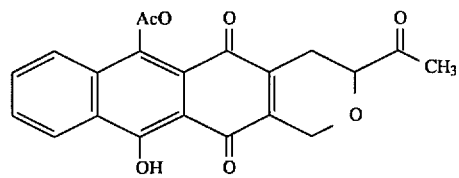

BCH-722: (1S,3S) and (1R,3R) Methyl [1,6-dihydroxy-5,12-dioxo-2,3,5,12-tetrahydroanthraceno (2,3-C)pyran-3-yl]ketone;

326

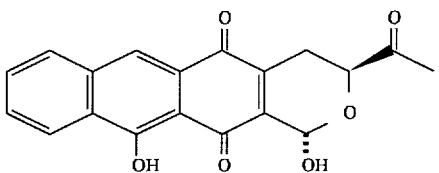

BCH-733: 3-(2-Acetoxy-1-propeneketal)aceto-11-acetoxy-1-hydroxy-1,2,3,4-tetrahydro-(2-oxygen)naphthacene-5,12-dione;

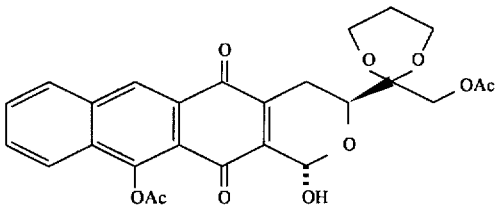

BCH-734: 3-(2-Acetoxy-1-propeneketal)aceto-6-acetoxy-1-hydroxy-1,2,3,4-tetrahydro-( 2-oxygen)naphthacene-5,12-dione;

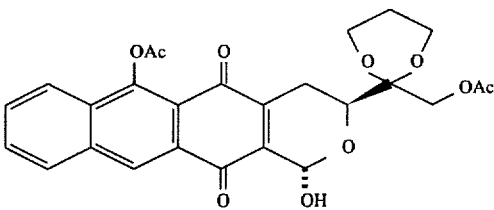

BCH-736: (1'S,3R) or (1R,3S)-t-Acetoxy-3-acetoxyaceto-1,2,3,4,5,12-hexahydro-1-hydroxy(2-oxygen) naphthacene-5,12-dione (1S,3R) or (1R,3S)-11-acetoxy-3-acetoxyaceto-1,2,3,4,5,12-hexahydro-1-hydroxy(2-oxygen)naphthacene-5,12-dione;

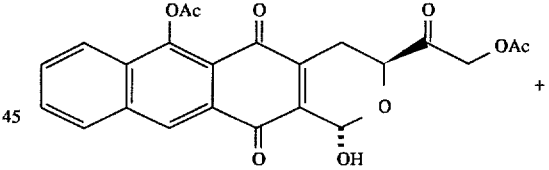

+

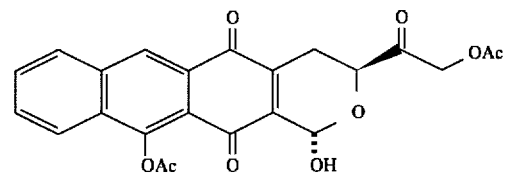

BCH-1116: 3-Aceto-1,2,3,4,5,6,11-hexahydro-1-5-12-trihydroxy-(2-oxygen)naphthacene-5,12-dione;

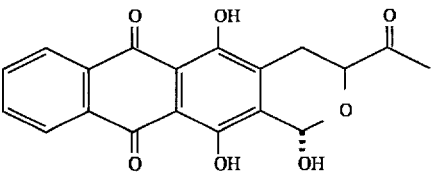

BCH-1149: 3-Carbomethoxy-1,2,3,4,5,12-hexahydro-6-hydroxy-(2-sulfur)naphthacene-5,12-dione;

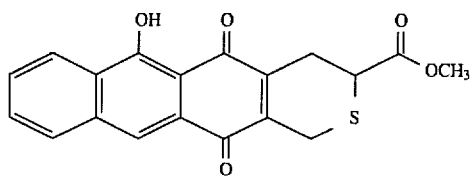

BCH-1150: 3-Carbomethoxy-1,2,3,4,5,12-hexahydro-11-hydroxy=(2-sulfur)naphthacene-5,12-dione;

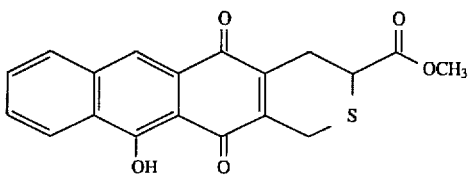

BCH-1178:

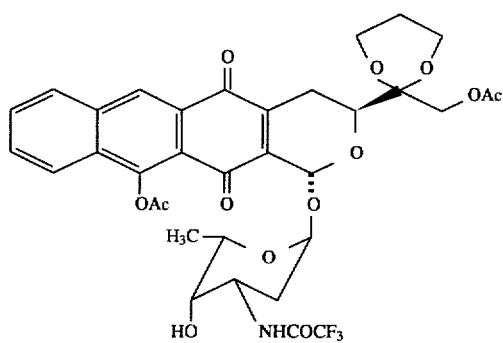

BCH-1193: (1'S, 1R, 3S) and (1'S, 1S, 3R)-Methyl(1-(2', 3',6'-trideoxy-3'-morpholino-L-lyxohexopyranose)-6,11-dioxo-5,12-dihydroxy-3,4,611-tetrahydroanthraceno[2,3-c]pyran-3-yl)ketone hydrochloride

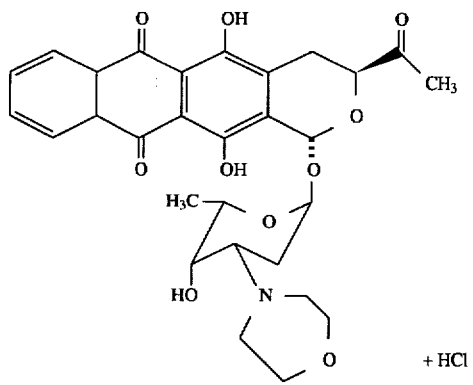

+ STEREOISOMER (1:1)

BCH-1641: (1'S, 1S, 3R)-3-Aceto-1,2,3,4,5,12-hexahydro-6-hydroxy-1-N-trifluoroacetyl-L-daunosamine-(2-sulfur)naphthacene-5,12-dione;

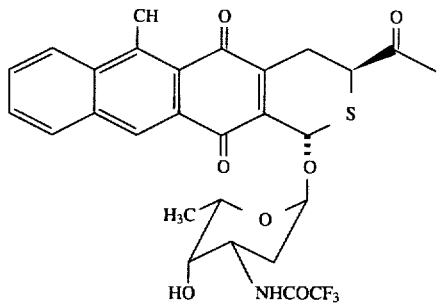

BCH-1645: (2'R, 1R,3S) and (2'R, 1S,3R)-3-Aceto-1-(2', 3'-dihydroxyl)-N-propoxy-6-hydroxyl-1,2,3,4,5,12-hexahydro-(2-sulfur)naphthacene-5,12-dione;

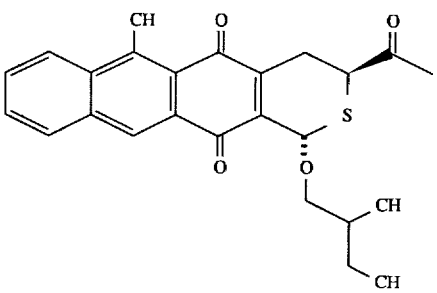

+ DIASTEREOISOMER

BCH-1646: (1'S, 1R,)-1-[(2',3',6'-Trideoxy-3'-acetamido-L-lyxohexopyranosyl)oxy]-6-hydroxy-3,4,5,12-tetrahydro-5,12-dioxo-1H-anthra[2,3-C]pyran;

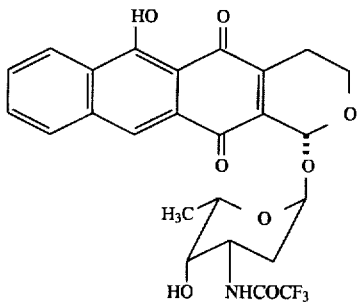

+ STEREOISOMER (88%:12%)

BCH-1647: (1'S, 1S,)-1-[(2',3',6'-Trideoxy-3'-acetamido-L-lyxohexopyranosyl)oxy]-6-hydroxy-3,4,5,12-tetrahydro-5,12-dioxo-1H-anthra[2,3-C ]pyran;

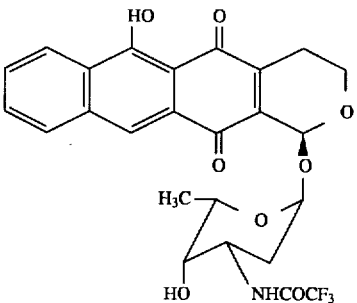

BCH-1650: 3-Dimethylphosphonoacetyl-6-hydroxy-1-methoxy-5,12-dioxo-3,4,5,12-tetrahydroanthraceno-[2,3-C]-pyran;

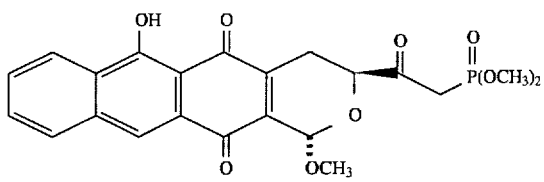

BCH-1652: 3-Phenylsulfonyl-6-hydroxy-1,2,3,4-tetrahydro-(2-oxygen)naphthacene-5,12-dione and 3-Phenylsulfonyl-11-hydroxy-1,2,3,4-tetrahydro-(2-oxygen)-naphthacene-5,12-dione;

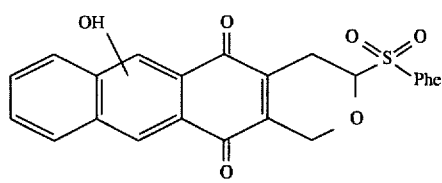

BCH-1653: (1'S, 1S, 3R)-6-Hydroxy-1-(2',3',6'-trideoxy-3'-trifluoroacetamido-L-lyxohexo pyranose)-3-diethylaminocarbonyl-5,12-dioxo-3,4,5,12-tetrahydroanthraceno-[2,3-c]-pyran;

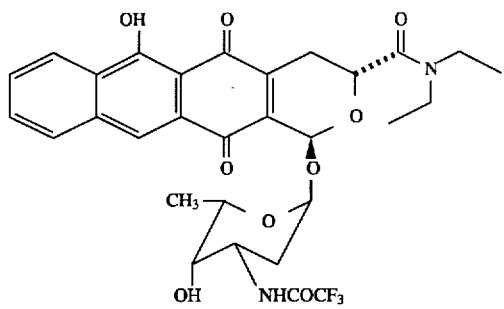

BCH-1656: (1'S,1R,3S)-6-Hydroxy-1-(2',3',6'-trideoxy-3'trifluoroacetamido-L-lyxohexo pyranose)-3-diethylaminocarbonyl-5,12-dioxo-3,4,5,12-tetrahydroanthraceno-[2,3-c]-pyran;

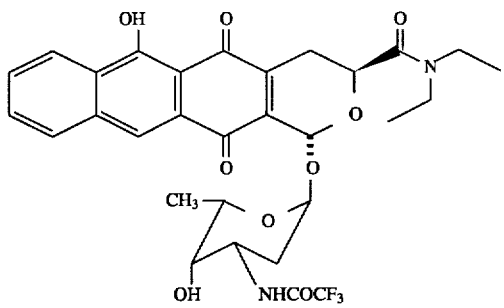

BCH-1660: (4'S,1R,3S) and (4'S,1S, 3R)-3-Aceto-1-(2', 2'-dimethyl-1',3'-dioxanyl-4'-methoxyl)-6-hydroxyl-1, 2,3,4,5,12-hexahydro-(sulfur)naphthacene-5,12-dione;

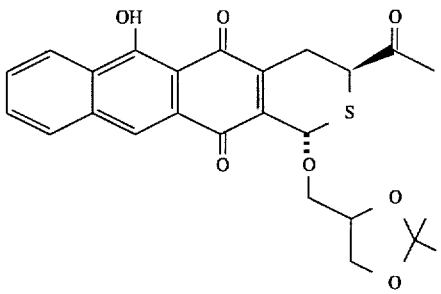

+ DIASTEREOISOMER

BCH-1661: (4'R,1R,3S) and (4'R,1S,3R)-3-Aceto-1-(2', 2'-dimethyl-1',3'-dioxanyl-4-methoxyl)-6-hydroxyl-1, 2,3,4,5,12-hexahydro-(2-oxo)naphthacene-5,12-dione;

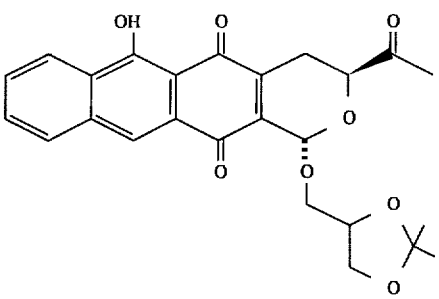

+ DIASTEREOISOMER

BCH-1669: (2'R,1R,3S) and (2'R,1S,3R)-3-Acetyl-1-(2', 3'-dihydroxyl)-n-propoxy-6-hydroxyl-1,2,3,4,5,12-hexahydro-(2-oxo)naphthacene-5,12-dione;

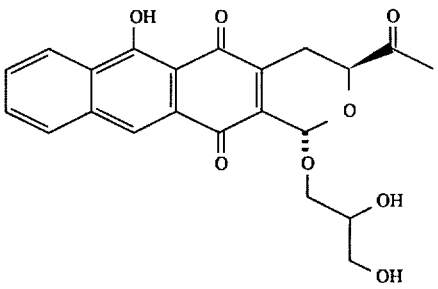

+ DIASTEREOISOMER

BCH-1670: (2'S,1R,3S) and (2'S,1S,3R)-3-Acetyl-1-(2', 3'-dihydroxyl)-n-propoxy-6-hydroxyl-1,2,3,4,5,12-hexahydro-(2-sulfur)naphthacene-5,12-dione;

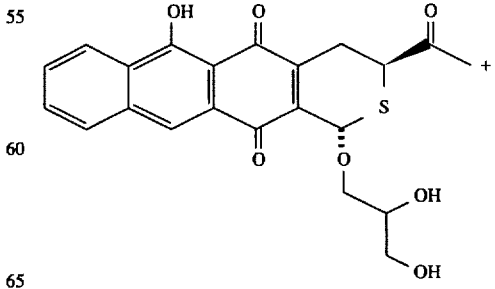

DIASTEREOISOMER

BCH-1671: (1'S,1S,3R)-3-Acetyl-1-O-(3',4'-di-O-acetyl-
2',6-dideoxy-α-lyxohexopyranosyl)-1,2,3,4,5,12-
hexahydro-6-hydroxy(2-sulfur)naphthacene-5,12-di-
one;

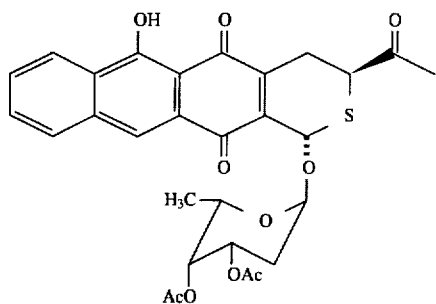

BCH-1672: (1'S,1R,3S)-Methyl-(5,12-dihydroxy-1-(2',
6'-dideoxy-3',4'-dihydroxy-2'-iodo-L-lyxohexopyra-
nose)-6,11-dioxo-3,4,6,11-dioxo-3,4,6,11-tetrahydro-
anthraceno-[2,3-C]pyran-3-yl)ketone;

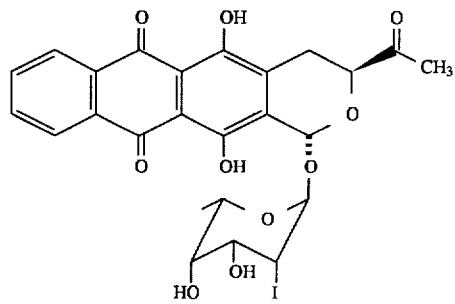

BCH-1675: (1'S,1S,3R)-Methyl-(5,12-dihydroxy-1-(2',
6'-dideoxy-3',4'-dihydroxy'2'-iodo-L-lyxohexopyra-
nose)-6,11-dioxo-3,4,6,11-tetrahydro-anthraceno-[2,3,
-C]pyran-3-yl)ketone;

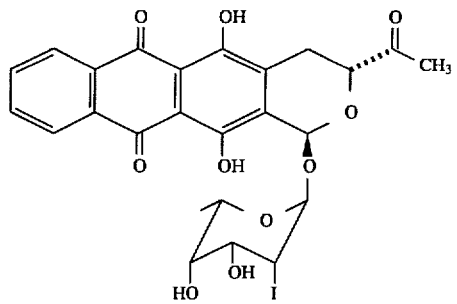

BCH-1678: (1'S,1R,3S)-6-Hydroxy-1-(2',3',6'-trideoxy-
3'-trifluoroacetamido-L-lyxohexopyranose)-3-dimeth-
ylphosphonoacetyl-5,12-dioxo-3,4,5,12-tetrahydroan-
thraceno-[2,3-c]-pyran;

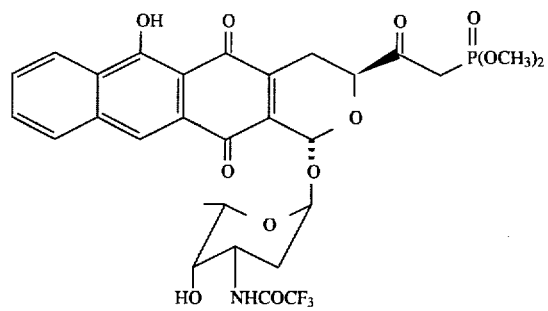

BCH-1679:(1'S, 1s, 3R)-6-Hydroxo-1-(2',3',6'-trideoxy-
3'-trifluoroacetamido-L-lyxohexo pyranose)-3-dimeth-
ylphosphonoacetyl-5,12-dioxo-3,4,5,12-tetrahydroan-
thraceno-[2,3-c]-pyran;

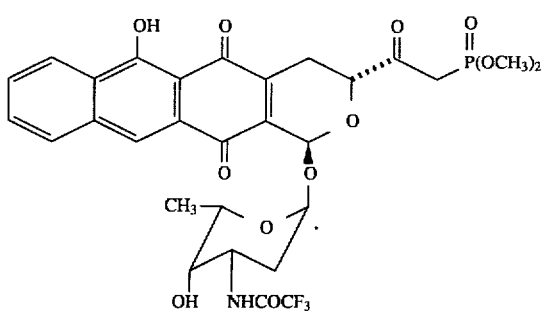

BCH-1681: (1'S,1S,3R)-Methyl-(1-[2',6'-dideoxy-3',4'-
diacetyl-2'-iodo-L-lyxohexopyranose]-6-hydroxy-3,4,
5,10-tetrahydroanthraceno[2,3-C]pyran-3-Yl)ketone;

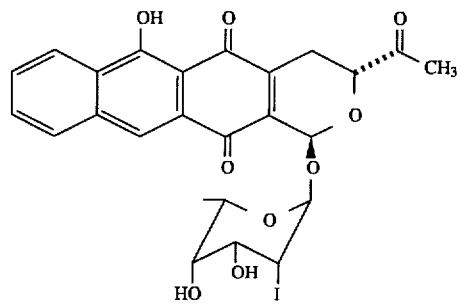

BCH-1682: (1S,1S,3R) and (1'S,1R,3S)-3-(2-Trifluoroac-
etamidoethyl)-5,12-dihydroxy-1-(2',3',6'-trideoxy-3',
4'-dihydroxy-L-lyxohexopyranose)-6,11-dioxo-3,4,6,
11-tetrahydro-1H-anthra[2,3-C]pyran;

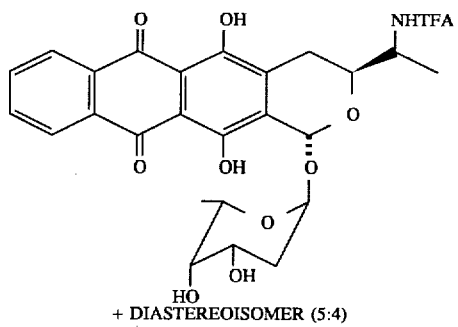

BCH-1990: (1'S,1R,3S)-Methyl-(1-[2',6'-dideoxy-3',4'-dihydroxy-2'-iodo-L-lyxohexopyranose]-5,12-dioxo-3,4,5,12-tetrahydroanthraceno[2,3-C]pyran-3-yl)ketone;

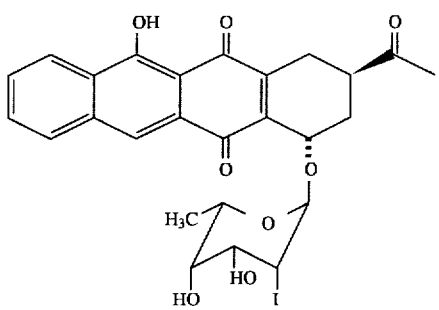

BCH-1993: (4'S,1R,3S)-3-Aceto-1-(2',2'-dimethyl-1',3'-dioxanyl-4'-methoxyl)-6-hydroxyl-1,2,3,4,5,12-hexahydro-(2-sulfur)naphthacene-5,12-dione;

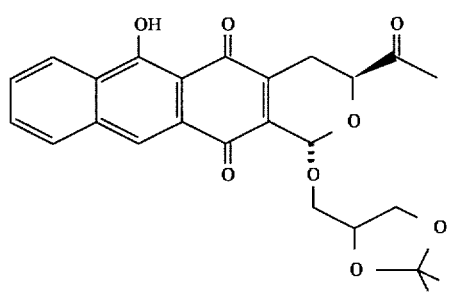

BCH-1994: (4'S,1S,3R)-3-Aceto-1-(2',2'-dimethyl-1',3'-dioxanyl-4'-methoxyl)6-hydroxyl-1,2,3,4,5,12-hexahydro-(2-sulfur)naphthacene-5,12-dione;

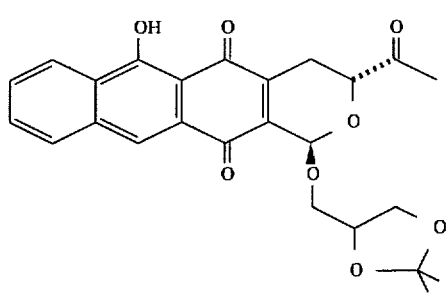

BCH-1997: (1'S,1S,3R,13R)-3-Dihydroxyethyl-6-hydroxy-1-(N-trifluoroacetyl-L-daunosamine-(2-oxo)naphthacene-5,12-dione;

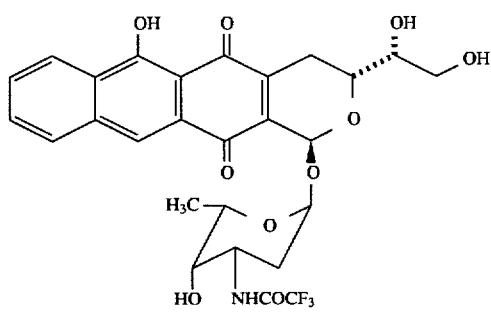

BCH-2001: (1'S, 1-R, 3-S)-3-{6-Hydroxy-1-(2',3',6'-trideoxy-3'-trifluoroacetamido-4'-hydroxy-L-lyxo-hexopyranose)-5,12-dioxo-3,4,5,12-tetrahydroanthraceno-[2,3-c]pyran-3-yl}(phenyl)sulfone;

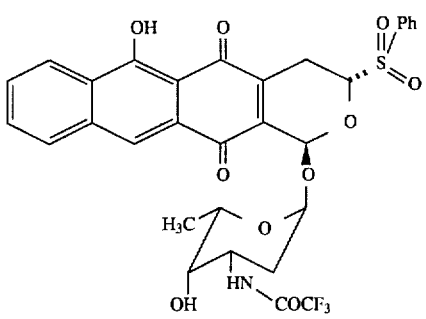

BCH-2002: (1'-S, 1-S)-6-Hydroxy-1-(2',3',6'-trideoxy-3'-trifluoroacetamido-4'-hydroxy-L-lyxo-hexopyranose)-5,12-dioxo-5,12-dihydroanthraceno-[2,3-c]pyran;

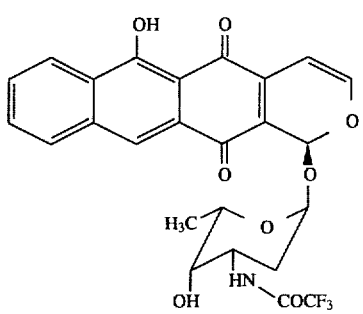

BCH-2013: (1'-S,1-S,3-R)-3-(6-Hydroxy-1-(2',3',6'-trideoxy-3'amino-4'-hydroxy-L-lyxohexopyranose)-5,12-dioxo-3,4,5,12-tetrahydroanthraceno-[2,3-c]pyran-3-yl)benzene hydrochloride;

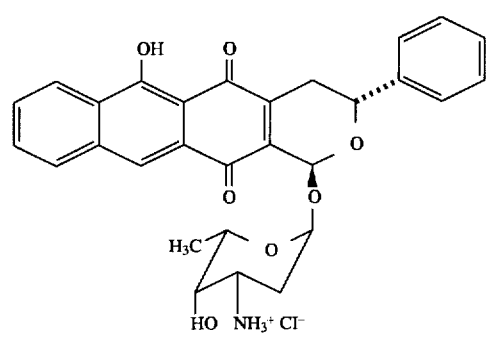

BCH-2025: (1'S,1-S, 3-R)-3-{6-Hydroxy-1-(2',3',6'-trideoxy-3'-trifluoroacetamido-4'-hydroxy-L-lyxo-hexopyranose)-5,12-dioxo-3,4,5,12-tetrahydroanthraceno-[2,3-c]pyran-3-yl}(phenyl)sulfone;

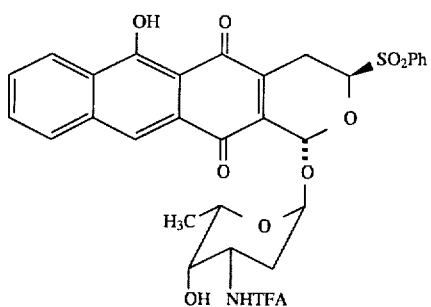

BCH-2034: (2'S,1R,3S) and (2'S,1S,3R)-3-Acetyl-(2',3'-dihydroxyl)-n-propoxy-6-hydroxyl-1,2,3,4,5,12-hexahydro-(2, oxo)naphthacene-5,12-dione;

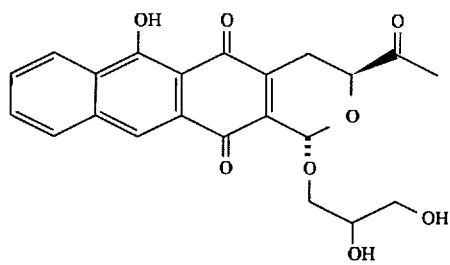

BCH-2036: Trans 3-acetyl-6-hydroxy-1-[3'-N-(vinyl carbxyl)amino propoxyl]-1,2,3,4,5,12-hexahydro(2, oxo)naphthacene-5,12-dione;

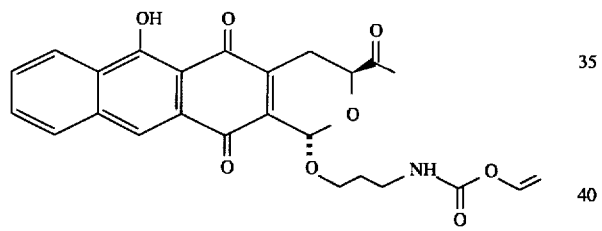

BCH-2063: (1'S,1R,3S)-Methyl-(5,12-dihydroxy-1-(2',3', 6'-trideoxy-3'-trifluoroacetamido-2'-iodo-4'-hydroxy-L-lyxohexopyranose)-6,11-dioxo-3,4,6,11-tetrahydroanthraceno-[2-3C]-pyran-3-yl)ketone;

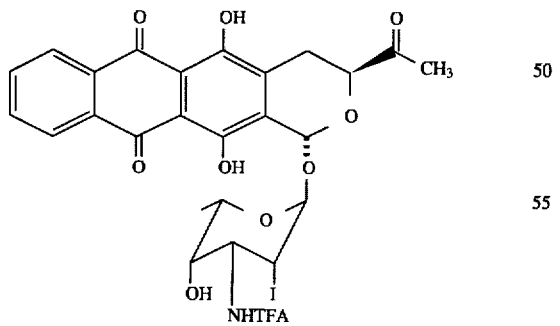

BCH-2064: (1'S,1S,3R)-Methyl-(1-[2',3',6'-trideoxy-3'-trifluoroacetamido-4'-hydroxy-2'-iodo-L-lyxohexopyranose]-5,12-dioxo-3,4,5,12-tetrahydroanthraceno[2,3-C]pyran-3-yl)ketone;

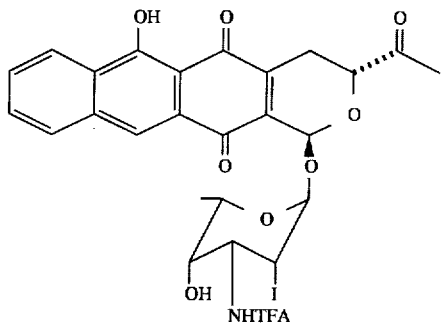

BCH-2006: (1'S,1R,3S)-Methyl-(5,12-dihydroxy-1-[2',3', 6'trideoxy-3'-amino 4'-hydroxy-2'-iodo-L-lyxohexopyranose]-6,11-dioxo-3,4,6,11-tetrahydroanthraceno-[2, 3C]-pyran-3-yl)ketone hydrochloride;

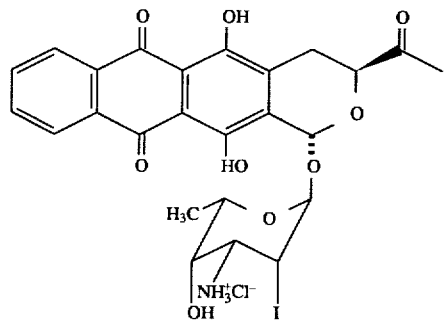

BCH-2094: A 4,5:1 diastereomeric mixture of (1'-S,1-S, 3-R) and (1'-S,1-R,3-S)-Methyl-(6-hydroxy-1-(2',3',4', 6'-tetradeoxy-3'-trifluoroacetamido-4'-O-methanesulfonyl-L-lyxohexopyranose)-5,12-dioxo-3,4,5,12-tetrahydroanthraceno[2,3-C]pyran-3-yl)ketone;

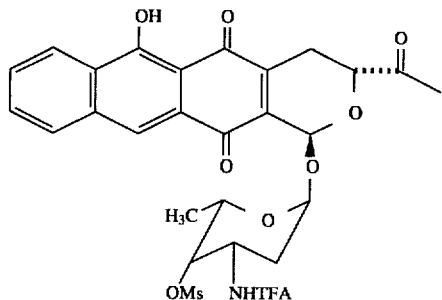

BCH-2110: (1'S,1-S,3-S)3-(5,12-dihydroxy-1-(2',3,6'-trideoxy-3'-(2-chloroethylureido ),4'-hydroxy-L-lyxohexopyranose)-6,11-dioxo-3,4,5,12-tetrahydroanthraceno-[2,3-c]pyran-3-yl )propene;

337
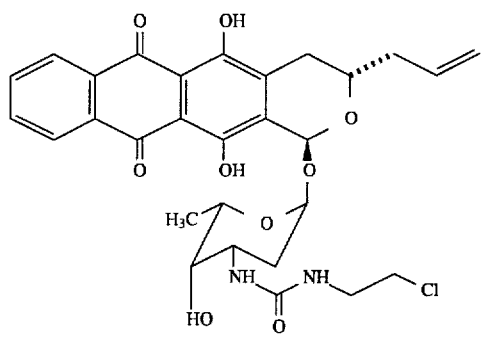
BCH-2850: (1'R,1S,3R)-6-Hydroxy-1-(3'-trifluoroacetamido-2',3',6'-trideoxy-L-lyxohexopyranose)-3-t-butoxycarbonyl-5,12-dioxo-3,4,5,12- tetrahydro-1H-anthroceno-[2,3-c]-pyran;
338
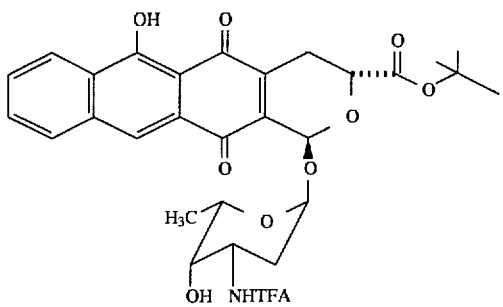
Example 68
Preparation of (1'S,2'R, 3'S,5'R, 1S,3R) and (1'S,2'R, 3'S,5'R, 1R, 3S)-1-(3-amino-2-hydroxy-1-methyl tetrahydropyran-5-yl)methyl-3-ethyl-5,12-dihydroxy-6,11-dioxo-3,4,6,11-tetrahydroanthraceno-[2,3-c]pyran hydrochloride (BCH-2817).
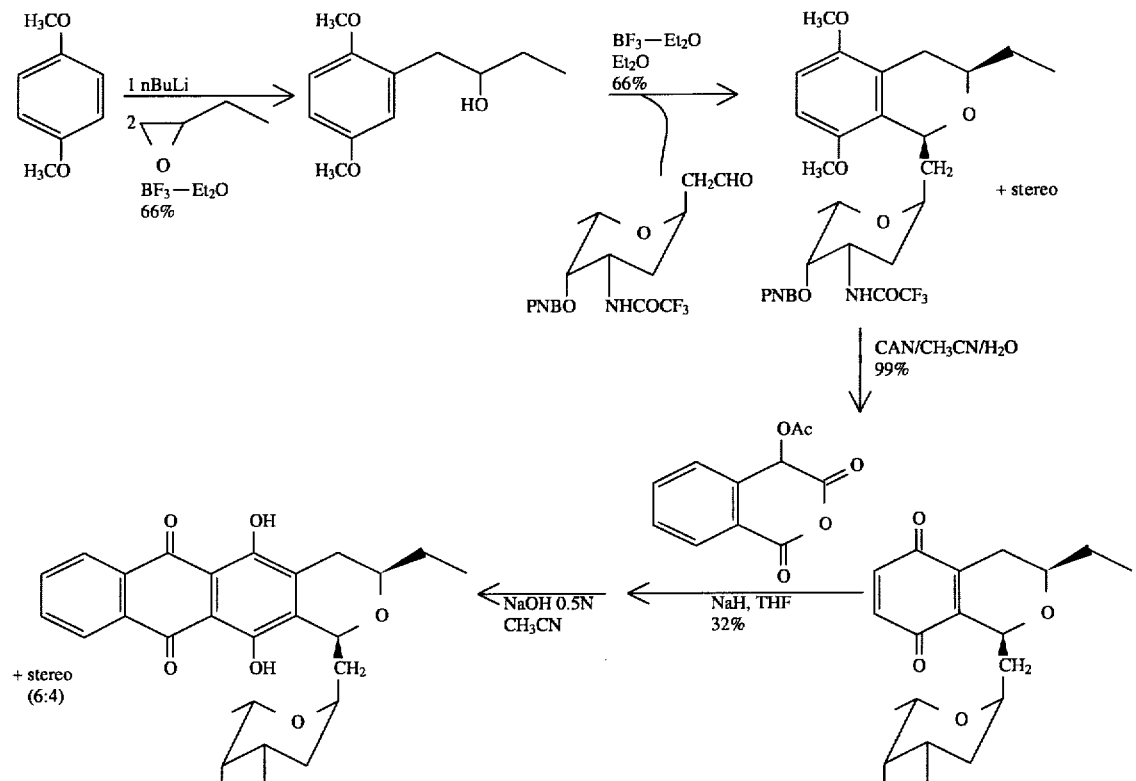

Example 69

In vitro Cytotoxicity—Microculture Tetrazolium Assay

Reference: Plumb, J. A. et al., 1989 Cancer Research 49, 4435–4440. The cytotoxicity of compounds towards tumor cells is measured in vitro using a microculture tetrazolium assay. This method is based upon the ability of live, but not dead cells to reduce the yellow water soluble dye 3-(4,5-dimethylthiazol-2-yl)-2,5-diphenyltetrazolium bromide (MTT) to its water insoluble purple formazan product.
Reagents:
Tissue Culture:

(Irvine Scientific Catalog).

a-MEM containing nucleosides (Catalog #9144).

Fetal Bovine Serum (Catalog #3000).

Non essential amino acids (Catalog #9304).

Dulbecco's phosphate buffered saline (Catalog #9240).

Sodium pyruvate (Catalog #9334).

All other tissue culture and general reagents were from Sigma Chemical Company.

The table which follows shows the antitumor activity of some of the synthetic heteroanthracyclin of the invention. A range of potency is observed. Generally the BCH's of this invention avoid multi drug resistance whereas adriamycin does not. These results suggest that certain heteroanthracyclinones should be useful in the treatment of certain resistant cancers.

TABLE 25

(MICROCULTURE TETRAZOLIUM ASSAY) $IC_{50}$ μM

| Examples | COMPOUND | SKOV3 | SKVLB | T47D | LOX | HT29 | VLB/OV3 |
|---|---|---|---|---|---|---|---|
|  | Adriamycin | 0.0572 | 4.72 | 0.0763 | 0.0437 | 0.2672 | 82.63 |
|  | Adriamycin | 0.012 | 1.49 | 0.072 | −.034 | 0.090 | 121.5 |
| 67 | BCH650 | 100.00 | 100.00 | 100.00 | 100.00 | 91.10 |  |
| 3 | BCH651 | 20.80 | 23.60 | 36.30 | 22.10 | 17.00 | 1.13 |
| 3 | BCH654 | 98.40 | 57.10 | >100 | 70.50 | 47.30 | 0.58 |
| 3 | BCH655 | >100 | >100 | >100 | >100 | >100 |  |
| 1,3 | BCH656 | 76.70 | 82.90 | 65.60 | 68.90 | 86.60 | 1.08 |
| 1,3 | BCH657 | 6.80 | 6.75 | 13.10 | 9.30 | 2.28 | 0.99 |
| 3 | BCH658 | 11.20 | >100 | >100 | 66.20 | >100 |  |
| 67 | BCH659 | 4.53 | 2.54 | 3.83 | 4.82 | 2.36 | 0.56 |
| 3 | BCH660 | 5.34 | 6.49 | 6.67 | 9.84 | 2.92 | 1.22 |
| 4 | BCH671 | 4.69 | 6.19 | 2.86 | 2.61 | 4.23 | 1.32 |
| 3 | BCH674 | 7.46 | 6.81 | 4.17 | 2.06 | 6.63 | 0.91 |
| 3 | BCH675 | 9.16 | 3.97 | 2.80 | 4.29 | 5.26 | 0.43 |
| 3 | BCH681 | 6.02 | 6.99 | 8.15 | 4.89 | 1.72 | 1.16 |
| 3 | BCH684 | 4.19 | 6.38 |  |  |  | 1.52 |
| 67 | BCH688 | 100.0 | 100.0 | 100.0 | 100.0 | 100.0 |  |
| 3 | BCH689 | 3.79 | 4.02 |  |  |  | 1.06 |
| 3 | BCH691 | 1.27 | 1.41 | 2.25 | 1.37 | 0.3010 | 1.11 |
| 3 | BCH692 | 2.84 | 1.77 | 71.00 | 3.89 | 2.18 | 0.62 |
| 8 | BCH693 | 41.60 | 44.20 | 16.30 | 48.00 | 18.90 | 1.06 |
| 7 | BCH694 | 8.22 | 17.90 | 11.30 | 15.00 | 13.40 | 2.18 |
| 7 | BCH695 | 30.80 | 15.00 | 25.20 | 21.50 | 11.40 | 0.49 |
| 7 | BCH697 | 15.50 | 10.60 | 13.00 | 12.60 | 6.04 | 0.68 |
| 67 | BCH703 | 24.80 | 18.50 | 16.40 | 12.80 | 7.38 | 0.75 |
| 6 | BCH704 | 16.40 | 13.80 | 11.80 | 28.30 | 10.70 | 0.84 |
| 67 | BCH705 | 12.90 | 14.10 |  |  |  | 1.09 |
| 7 | BCH710 | 3.98 | 5.19 | 3.57 | 3.51 | 1.79 | 1.30 |
| 11 | BCH711 | 11.10 | 13.50 | 12.40 | 11.50 | 5.68 | 1.22 |
| 67 | BCH715 | 17.90 | 25.20 | 13.40 | 12.30 | 10.50 | 1.41 |
| 10 | BCH716 | >100 | 85.50 | 70.30 | 41.60 | >100 |  |
| 14 | BCH717 | >100 | >100 | >100 | >100 | >100 |  |
| 67 | BCH721 | 55.80 | 30.70 | 47.80 | 24.90 | 23.40 | 0.55 |
| 67 | BCH722 | 19.20 | 83.00 | 12.00 | 43.70 | 7.11 | 4.32 |
| 19 | BCH724 | 3.15 | 1.64 | 3.89 | 1.49 | 0.7270 | 0.52 |
| 30 | BCH725 | 3.46 | 3.99 | 4.57 | 1.93 | 2.49 | 1.15 |
| 19 | BCH730 | 3.52 | 2.01 | 3.62 | 1.78 | 0.6370 | 0.57 |
| 19 | BCH730 | 1.62 | 2.88 | 3.08 | 1.66 | 5.30 | 1.78 |
| 30 | BCH731 | 3.36 | 2.17 | 2.70 | 2.08 | 1.57 | 0.65 |
| 30 | BCH732 | 38.50 | 100.00 | 100.00 | 48.00 | 38.40 |  |
| 67 | BCH733 | 4.30 | 6.96 | 5.51 | 6.07 | 2.01 | 1.62 |
| 67 | BCH734 | 8.82 | 8.97 | 6.41 | 9.76 | 5.77 | 1.02 |
| 67 | BCH736 | 1.52 | 1.96 | 1.97 | 1.61 | 0.5420 | 1.29 |
| 30 | BCH746 | 4.59 | 3.49 | 3.63 | 3.41 | 3.30 | 0.76 |
| 30 | BCH747 | 21.00 | 20.50 | 18.10 | 18.50 | 15.30 | 0.98 |
| 30 | BCH748 | 4.90 | 8.41 | 7.73 | 10.10 | 5.99 | 1.72 |
| 30 | BCH749 | 100.00 | 6.66 | 3.84 | 9.61 | 3.17 |  |
| 30 | BCH1108 | 1.50 | 2.31 | 3.83 | 100.00 | 2.80 | 1.5 |
| 30 | BCH1109 | 62.30 | 100.00 | 47.10 | 76.00 | 62.60 |  |
| 30 | BCH1110 | 100.00 | 100.00 | 100.00 | 100.00 | 28.90 |  |
| 30 | BCH1111 | 100.00 | 56.30 | 100.00 | 98.50 | 100.00 |  |
| 30 | BCH1112 | 5.16 | 2.83 | 9.09 | 5.32 | 5.47 | 0.55 |
| 30 | BCH1113 | 10.00 | 14.70 | 22.50 | 14.10 | 8.26 | 1.47 |
| 30 | BCH1114 | 64.60 | 100.00 | 100.00 | 100.00 | 68.90 |  |
| 30 | BCH1115 | 9.28 | 11.50 | 12.60 | 7.02 | 6.25 | 1.24 |
| 67 | BCH1116 | 26.10 | 21.30 | 11.10 | 31.30 | 7.60 | 0.82 |

TABLE 25-continued (MICROCULTURE TETRAZOLIUM ASSAY)
$IC_{50}$ μM

| Examples | COMPOUND | SKOV3 | SKVLB | T47D | LOX | HT29 | VLB/OV3 |
|---|---|---|---|---|---|---|---|
| 19 | BCH1122 | 4.27 | 14.70 | 6.79 | 2.14 | >100 | 3.44 |
| 24 | BCH1123 | 1.41 | 1.30 | 3.84 | 1.22 | 0.4360 | 0.92 |
| 24 | BCH1124 | 4.98 | 2.17 | 6.05 | 1.88 | 1.46 | 0.44 |
| 19 | BCH1127 | 2.07 | 3.87 | 2.86 | 1.31 | 0.4160 | 1.87 |
| 19 | BCH1127 | 5.21 | 16.90 | 11.50 | 3.00 | 4.78 | 3.24 |
| 19 | BCH1128 | 0.8740 | 1.40 | 1.31 | 0.8500 | 0.1450 | 1.60 |
| 19 | BCH1128 | 1.20 | 2.20 | 1.91 | 0.4930 | 0.8160 | 1.83 |
| 20 | BCH1130 | 0.0262 | 0.5730 | 0.4730 | 0.0514 | 0.1700 | 21.87 |
| 20 | BCH1130 | 0.0541 | 1.03 | 0.3790 | 0.1200 | 0.127 | 19.04 |
| 20 | BCH1130 | | | 0.1890 | | | 19.04 |
| 20 | BCH1131 | 4.58 | 11.20 | 9.48 | 4.83 | 6.93 | 2.45 |
| 30 | BCH1135 | 26.10 | 24.40 | 100.00 | 16.70 | 18.60 | 0.93 |
| 23 | BCH1136 | 18.00 | 23.10 | 18.90 | 12.30 | 11.50 | 1.28 |
| 23 | BCH1137 | 13.70 | 14.10 | 8.40 | 8.88 | 6.37 | 1.03 |
| 67 | BCH1149 | 30.00 | 41.50 | 38.50 | 25.30 | 29.70 | 1.38 |
| 67 | BCH1150 | 100.00 | 100.00 | 78.30 | 84.60 | 64.10 | |
| 30 | BCH1151 | 53.30 | 75.00 | 62.50 | 30.50 | 58.90 | 1.41 |
| 30 | BCH1152 | 100.00 | 100.00 | 100.00 | 100.00 | 100.00 | |
| 30 | BCH-1153 | 3.02 | 14.90 | 4.65 | 2.90 | 2.94 | 4.93 |
| 30 | BCH1154 | 8.94 | 28.40 | 14.20 | 3.74 | 8.55 | 3.18 |
| 30 | BCH1155 | 6.25 | 7.01 | 8.50 | 3.97 | 8.80 | 1.12 |
| 30 | BCH1156 | 26.20 | 100.00 | 100.00 | 100.00 | 36.20 | |
| 30,48 | BCH1157 | 14.70 | 21.00 | 37.60 | >100 | 13.00 | 1.43 |
| 30,48 | BCH1158 | 8.35 | 6.20 | 25.70 | >100 | 8.25 | 0.74 |
| 21 | BCH1162 | 1.16 | 2.70 | 2.57 | >100 | 4.17 | 2.33 |
| 20 | BCH1163 | 11.00 | 11.60 | 5.00 | 26.10 | 4.67 | 1.05 |
| 27 | BCH1164 | 9.36 | 9.20 | 12.20 | >100 | 6.97 | 0.98 |
| 25,48 | BCH1165 | 30.50 | 42.10 | 31.50 | 23.60 | 10.00 | 1.38 |
| 25,48 | BCH1166 | 24.40 | 50.80 | 31.40 | 30.50 | 12.50 | 2.08 |
| 27 | BCH1167 | >100 | >100 | >100 | >100 | >100 | |
| 30 | BCH1168 | 88.00 | 94.20 | 84.40 | 100.00 | 100.00 | 1.07 |
| 21 | BCH1174 | >100 | >100 | >100 | >100 | >100 | |
| 23 | BCH1175 | >100 | >100 | >100 | >100 | >100 | |
| 67 | BCH1178 | 6.93 | 12.80 | 7.06 | 12.30 | 5.64 | 1.85 |
| 30 | BCH11-79 | 5.25 | 8.31 | 4.90 | 10.90 | 4.03 | 1.58 |
| 23 | BCH1182 | 23.60 | 73.70 | 28.30 | 1.98 | 25.40 | 3.12 |
| 22 | BCH1187 | 1.20 | 3.86 | 1.03 | 0.9790 | 1.42 | 3.22 |
| 22 | BCH1187 | 1.85 | 3.88 | 2.72 | 3.60 | 1.98 | 2.10 |
| 20 | BCH1191 | 0.2940 | 1.05 | 0.8720 | 0.3790 | 0.4690 | 3.57 |
| 20 | BCH1191 | 1.16 | | 3.80 | 1.14 | 0.9450 | 3.57 |
| 67 | BCH-1193 | 1.95 | 4.79 | 2.57 | 0.8750 | 1.04 | 2.46 |
| 67 | BCH-1193 | | 4.92 | 4.16 | 2.77 | 0.9400 | 2.46 |
| 20 | BCH-1194 | 0.0056 | 1.46 | 0.0439 | 0.0623 | | 260.71 |
| 20 | BCH-1195 | 0.6720 | 3.35 | 1.41 | 0.7410 | | 4.99 |
| 22 | BCH1199 | 32.30 | >100 | 46.20 | >100 | >100 | |
| 22 | BCH-1606 | 1.13 | 3.26 | 1.33 | 0.8910 | | 2.88 |
| 22 | BCH-1610 | 0.8390 | 2.77 | 1.36 | 0.8450 | | 3.30 |
| 30 | BCH-1611 | 1.89 | 7.32 | 2.16 | 4.30 | 2.81 | 3.87 |
| 22 | BCH-1614 | 1.02 | 1.67 | 0.7420 | 1.09 | 3.58 | 1.64 |
| 30,48 | BCH1617 | 2.15 | 2.96 | 2.43 | 3.04 | 1.20 | 1.38 |
| 30,48 | BCH1618 | 3.26 | 3.21 | 3.66 | 3.75 | 3.63 | .098 |
| 29 | BCH1619 | 4.81 | 5.68 | 3.37 | 5.37 | 3.80 | 1.18 |
| 28 | BCH1623 | 49.50 | 90.20 | 42.80 | 44.20 | 32.10 | 1.82 |
| 30 | BCH1624 | 85.00 | 100.00 | 100.0 | 100.00 | 100.00 | |
| 30 | BCH1625 | 5.1 | 45.00 | 34.00 | 16.00 | 61.00 | 8.8 |
| 30 | BCH-1626 | 2.32 | 7.66 | 5.39 | 2.99 | 5.18 | 3.30 |
| 30 | BCH1627 | 7.1 | 14.00 | 7.1 | 5.0 | 11.0 | 2.0 |
| 30 | BCH-1628 | 2.71 | 5.92 | 2.89 | 3.52 | 3.43 | 2.18 |
| 30 | BCH1629 | 6.7 | 19.00 | 9.0 | 7.4 | 22.00 | 2.8 |
| 30 | BCH1630 | 12.00 | 31.00 | 18.00 | 8.5 | 66.00 | 2.6 |
| 30,57 | BCH1633 | 0.2450 | 0.4700 | 0.7350 | 0.2010 | 0.0995 | 1.92 |
| 30 | BCH1635 | 1.99 | 3.18 | 3.11 | 1.00 | 0.8760 | 1.60 |
| 30 | BCH1636 | 2.65 | 4.52 | 2.97 | 1.23 | 2.53 | 1.71 |
| 30,48 | BCH1637 | 2.28 | 3.82 | 5.24 | 2.07 | 0.6910 | 1.68 |
| 58 | BCH1638 | >100 | >100 | >100 | >100 | >100 | |
| 58 | BCH1639 | >100 | >100 | >100 | >100 | >100 | |
| 67 | BCH1641 | 1.68 | 2.74 | 2.00 | 1.35 | 0.8710 | 1.63 |
| 67 | BCH1645 | 2.02 | 3.83 | 3.73 | 1.37 | 0.5970 | 1.90 |
| 67 | BCH1646 | 4.99 | 6.56 | 2.81 | 2.96 | 5.92 | 1.31 |
| 67 | BCH1647 | 3.59 | 6.00 | 0.8710 | 3.24 | 2.50 | 1.67 |
| 67 | BCH1650 | 0.8020 | 0.8950 | 2.44 | 0.7550 | 0.6290 | 1.12 |
| 67 | BCH1652 | 2.29 | 7.55 | 4.31 | 2.59 | 1.66 | 3.30 |
| 67 | BCH1653 | 3.22 | 5.97 | 7.09 | 3.92 | 0.8850 | 1.85 |
| 67 | BCH1656 | 4.12 | 7.07 | 5.19 | 3.86 | 3.77 | 1.72 |

TABLE 25-continued

| | | (MICROCULTURE TETRAZOLIUM ASSAY) $IC_{50}$ μM | | | | | |
|---|---|---|---|---|---|---|---|
| Examples | COMPOUND | SKOV3 | SKVLB | T47D | LOX | HT29 | VLB/OV3 |
| 32 | BCH1657 | 0.5730 | 4.25 | 3.11 | 2.41 | 2.59 | 7.42 |
| 67 | BCH1660 | 2.29 | 2.02 | 4.97 | 2.81 | 6.28 | 0.88 |
| 67 | BCH1661 | 2.82 | 2.66 | 5.12 | 3.59 | 3.04 | 0.94 |
| 59 | BCH1662 | 86.60 | 89.90 | 59.70 | 38.10 | 79.60 | 1.04 |
| 59 | BCH1663 | 27.90 | 32.40 | 47.90 | 31.20 | 31.30 | 1.16 |
| 33 | BCH1668 | 6.2 | 6.2 | | 5.2 | 5.7 | |
| 67 | BCH1669 | 1.21 | 1.05 | | 0.6310 | 0.5910 | 0.87 |
| 67 | BCH1670 | 0.5470 | 0.6800 | | 0.6730 | 0.3420 | 1.24 |
| 67 | BCH1671 | 2.04 | 1.67 | | 1.76 | 1.46 | 0.82 |
| 67 | BCH1671 | 6.19 | 6.22 | | 5.22 | 5.72 | 1.00 |
| 67 | BCH1672 | 0.3430 | 0.9900 | | 0.2320 | 1.67 | 2.89 |
| 67 | BCH1675 | | | | 1.18 | 5.28 | |
| 60 | BCH1676 | 2.46 | 4.01 | | 2.31 | 3.05 | 1.63 |
| 60 | BCH1677 | 4.71 | 7.79 | | 2.48 | 5.44 | 1.65 |
| 67 | BCH1678 | 5.36 | 13.60 | | 3.77 | 5.65 | 2.54 |
| 67 | BCH1679 | 1.2 | 3.6 | | 1.1 | 1.1 | |
| 32 | BCH1680 | 2.81 | 3.83 | | 2.26 | 2.24 | 1.36 |
| 67 | BCH1681 | 0.9140 | 0.6710 | | 0.4540 | 0.1230 | 0.73 |
| 67 | BCH1682 | 24.70 | >100 | | 16.40 | 25.80 | |
| 55 | BCH1683 | 3.07 | 11.40 | | 2.29 | 1.35 | 3.71 |
| 50 | BCH1685 | 0.8100 | 53.20 | | 0.6830 | 1.93 | 65.68 |
| 40 | BCH1686 | 0.9720 | 2.53 | | 0.6840 | 1.84 | 2.60 |
| 40 | BCH1687 | 0.7910 | 1.86 | | 0.7060 | 1.24 | 2.35 |
| 34 | BCH1694 | 2.99 | 9.54 | 4.49 | 3.58 | 4.31 | 3.19 |
| 34 | BCH1695 | 5.74 | 25.60 | 12.80 | 5.23 | 14.80 | 4.46 |
| 34 | BCH1696 | 1.10 | 2.71 | 1.21 | 1.10 | 0.8230 | 2.46 |
| 61 | BCH1698 | 0.8650 | 5.82 | 0.7270 | 0.3980 | 1.12 | 6.73 |
| 67 | BCH1990 | 2.10 | 5.54 | 3.88 | 3.01 | 1.10 | 2.64 |
| 61 | BCH1991 | 1.47 | 5.54 | 0.9180 | 1.29 | 1.72 | 3.77 |
| 35 | BCH1992 | 0.5700 | 2.74 | 0.8070 | 0.6660 | 0.1830 | 4.81 |
| 67 | BCH1993 | 4.19 | 13.00 | 9.81 | 4.02 | 3.47 | 3.10 |
| 67 | BCH1994 | 2.74 | 8.62 | 4.41 | 1.91 | 1.96 | 3.15 |
| 67 | BCH1997 | 1.56 | 6.72 | 2.14 | 2.30 | 2.69 | 4.31 |
| 52 | BCH1999 | <7.74 | 1.00 | 20.00 | 4.97 | 8.06 | |
| 67 | BCH2001 | 3.06 | 5.82 | 2.59 | 2.49 | 1.38 | 1.90 |
| 67 | BCH2002 | 1.24 | 3.57 | 1.46 | 1.75 | 0.9800 | 2.88 |
| 40 | BCH2005 | 0.3410 | 0.3640 | | 0.1380 | 0.2450 | 1.07 |
| 40 | BCH2006 | 0.8820 | 3.73 | 1.92 | 0.4840 | 0.4100 | 4.23 |
| 44 | BCH2007 | 0.4330 | 2.79 | 0.5060 | 0.3790 | 0.1480 | 6.44 |
| 44 | BCH2008 | 0.3320 | 2.18 | 0.3870 | 0.1540 | 0.0625 | 6.57 |
| 46 | BCH2010 | 12.70 | 28.50 | 13.50 | 9.25 | 10.70 | 2.24 |
| 46 | BCH2012 | 2.06 | 4.03 | 0.9540 | 0.7360 | 0.5650 | 1.96 |
| 67 | BCH2013 | | 4.64 | | 0.5540 | | |
| 56 | BCH2016 | 0.0934 | 0.6700 | 0.3450 | 0.05970 | 0.1300 | 7.17 |
| 67 | BCH2025 | 1.97 | 6.20 | 3.34 | 1.11 | 0.6440 | 3.15 |
| 67 | BCH2034 | 2.95 | 7.49 | 7.87 | 1.43 | 2.05 | 2.54 |
| 67 | BCH2036 | 3.70 | 12.10 | 6.21 | 5.40 | 3.38 | 3.27 |
| 54 | BCH2039 | 13.50 | 81.20 | 12.60 | 1.55 | 4.43 | 6.01 |
| 62 | BCH2048 | 4.36 | 10.30 | 5.72 | 1.77 | 6.38 | 2.36 |
| 36 | BCH2049 | 0.2750 | 0.4720 | 0.2630 | 0.1020 | 0.0773 | 1.72 |
| 36 | BCH2050 | 0.0706 | 0.0672 | 0.4120 | 0.0384 | 0.3040 | 0.95 |
| 45 | BCH2055 | 0.8980 | 2.56 | 3.51 | 1.13 | 0.4710 | 2.85 |
| 45 | BCH2056 | 0.1710 | 0.5980 | 0.2710 | 0.1700 | 0.0832 | 3.50 |
| 62 | BCH2057 | 1.03 | 5.16 | 0.2430 | 1.49 | 2.69 | 5.01 |
| 63 | BCH2058 | 0.3920 | 0.4070 | 0.4900 | 0.2260 | 0.1630 | 1.04 |
| 63 | BCH2059 | 0.2470 | 0.3060 | 0.4420 | 0.2090 | 0.1560 | 1.24 |
| 67 | BCH2063 | 0.4470 | 1.94 | 0.1460 | 0.3140 | 2.66 | 4.34 |
| 67 | BCH2064 | 1.45 | 3.45 | 0.8780 | 10.80 | 0.4400 | 2.38 |
| 67 | BCH2066 | 0.0927 | 0.5860 | 0.5010 | 0.1050 | 0.5340 | 6.32 |
| 54 | BCH2073 | 5.14 | 13.70 | 6.12 | 0.8070 | 6.59 | 2.67 |
| 50 | BCH2074 | 0.3100 | 14.10 | 0.6930 | 0.1480 | 0.5860 | 45.48 |
| 64 | BCH2080 | 2.4 | 4.7 | 3.6 | 2.1 | 3.0 | |
| 64 | BCH2084 | 4.2 | 12.0 | 5.6 | 5.2 | 5.8 | |
| 65 | BCH2085 | 1.1 | 3.4 | 1.6 | 0.58 | 0.80 | |
| 65 | BCH2086 | 0.86 | 1.7 | 1.4 | 0.36 | 0.64 | |
| 37 | BCH2088 | 0.5730 | 1.09 | 0.1740 | 0.2010 | .02400 | 1.90 |
| 37 | BCH2089 | 0.3320 | 0.4200 | 0.2010 | 0.1040 | 0.1940 | 1.27 |
| 48 | BCH2093 | 10.30 | 39.30 | 15.90 | 4.36 | 2.80 | 3.82 |
| 67 | BCH2094 | 4.70 | 12.00 | 6.51 | 1.40 | 1.06 | 2.55 |
| 42 | BCH2097 | 6.06 | 5.36 | 4.45 | 2.51 | 2.64 | 0.88 |
| 41 | BCH2106 | 0.1480 | | | | | |
| 41 | BCH2108 | 11.40 | 14.30 | 11.90 | | 8.52 | 1.25 |
| 67 | BCH2110 | 2.48 | 2.83 | 2.46 | | 1.51 | 1.14 |
| 42 | BCH2111 | 2.14 | 11.80 | 2.42 | | 0.9540 | 5.51 |

TABLE 25-continued

| | | (MICROCULTURE TETRAZOLIUM ASSAY) $IC_{50}$ μM | | | | | |
|---|---|---|---|---|---|---|---|
| Examples | COMPOUND | SKOV3 | SKVLB | T47D | LOX | HT29 | VLB/OV3 |
| 53 | BCH2116 | 18.70 | 50.10 | 22.70 | | 23.30 | 2.68 |
| 38 | BCH2120 | 0.4320 | 0.3980 | 0.3140 | 0.1430 | 0.1680 | 0.92 |
| 47 | BCH2133 | 7.02 | 1.60 | 3.62 | 2.49 | 3.68 | 0.23 |
| 43 | BCH2156 | 3.41 | 5.36 | 2.71 | 0.3750 | 1.19 | 1.57 |
| 39 | BCH2188 | 0.3740 | 0.1980 | | | 0.2110 | 0.53 |
| 39 | BCH2188 | 0.6400 | 0.2970 | | | 0.3100 | 0.46 |
| 39 | BCH2189 | 0.2680 | 0.1040 | | | 0.1470 | 0.39 |
| 39 | BCH2189 | 0.3420 | 0.2490 | | | 0.1440 | 0.73 |
| 36 | BCH2190 | 1.65 | 3.18 | | | 3.71 | 1.93 |
| 36 | BCH2192 | 1.93 | 2.28 | | | 4.65 | 1.18 |
| 36 | BCH2195 | 4.55 | 10.10 | | | 3.40 | 2.22 |
| 66 | BCH2197 | 2.77 | 3.02 | | | 0.5200 | 1.09 |
| 66 | BCH2198 | 4.40 | 4.15 | | | 2.41 | 0.94 |
| 68 | BCH2817 | 1.67 | 11.00 | | | 3.53 | 6.59 |
| 67 | BCH2850 | 3.5 | 5.2 | | | 5.1 | 1.49 |

We claim:
1. A compound of the formula:

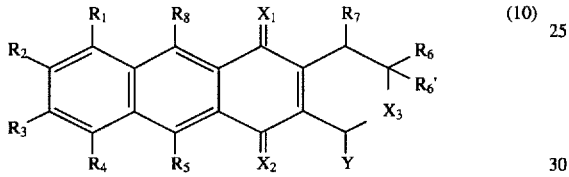

(10)

wherein $X_1$ and $X_2$ are independently O; S; unsubstituted amino; or amino which is mono- or disubstituted by alkyl groups, hydroxyl groups, acyl groups, aryl groups or other amino groups;

$X_3$ is selected from the group consisting of: O; S; SO; $SO_2$; unsubstituted amino and amino which is mono- or disubstituted by alkyl groups, acyl groups, aryl groups or other amino groups;

$R_1$, $R_2$, $R_3$, $R_4$, $R_5$ & $R_8$ are each independently selected from the group consisting of: hydrogen; hydroxy; $C_{1-16}$ alkyl; $C_{1-16}$ acyl; halogen; silane; sulfonate; ureido; unsubstituted amino; and amino which is mono- or disubstituted by alkyl groups, acyl groups, aryl groups, alkenyl groups, alkynyl groups, or other amino groups;

$R_6$ is hydrogen; $C_{1-16}$ alkyl or alkoxy, $C_{1-16}$ acyl or acyloxy, $C_{7-20}$ aryl or aryloxy; squaric acid or salts thereof; phosphonate; or a 5 or 6 membered aromatic or non-aromatic heterocycle, wherein the heteroatom is selected from the group consisting of O, S, N, SO, $SO_2$, P, PO and $NR_{28}$ wherein $R_{28}$ is selected from the group consisting of hydrogen, oxygen, hydroxyl, $C_{2-8}$ acyl, $C_{1-4}$ alkyl and $C_{6-14}$ aryl;

$R_6'$ is hydrogen; halogen; $C_{1-16}$ alkyl or alkoxy; unsubstituted amino; amino which is mono- or disubstituted by alkyl groups, acyl groups, aryl groups or other amino groups; hydroxy; thiol; cyano; sulfide; $C_{1-16}$ acyl or acyloxy;

$R_7$ is selected from the group consisting of: hydrogen; halogen; hydroxy; $C_{1-16}$ alkyl; cyano; amino; $C_{1-16}$ acyl and acyloxy; and Y is a saccharide which is a 5 or 6-membered sugar ring of natural or unnatural configuration linked to the heteroanthracycline through a carbon chain or through a heteroatom selected from the group consisting of oxygen, sulfur and amino.

2. A compound of formula according to claim 1, wherein $X_1$ and $X_2$ are independently selected from the group consisting of:
O;
S; and
$N(R_{20})$ wherein $R_{20}$ is selected from the group consisting of:
hydrogen;
hydroxyl;
$C_{1-16}$ alkyl;
$C_{1-16}$ acyl; and,
$C_{1-16}$ alkylamine;

$X_3$ is selected from the group consisting of:
O;
S;
SO;
$SO_2$; and
$NR_{21}$ wherein $R_{21}$ is selected from the group consisting of:
hydroxyl,
$C_{2-16}$ acyl,
$C_{1-16}$ alkyl,
$C_{7-16}$ aryl,
$C_{2-16}$ haloacyl, and
hydrogen;

$R_1$, $R_2$, $R_3$, $R_4$, $R_5$ and $R_8$ are independently selected from the group consisting of:
hydrogen;
hydroxyl;
$C_{1-16}$ alkyl;
$C_{1-16}$ alkoxyl;
$C_{3-8}$ cycloalkyl;
$C_{3-16}$ alkyl silane;
tosyl;
triflate;
trifluoroacetate;
halogen;
thiol;
nitro;
cyano;
$C_{2-16}$ acyl;
$C_{7-16}$ arylalkyl;
$C_{3-16}$ alkoxy silane;
$NH(CH_2)_{1-4}NH(CH_2)_{1-4}OH$;
$NH(CH_2)_{1-4}NH(CH_2)_{1-4}X$ wherein X is halogen;
amino which may be unsubstituted or mono- or di-substituted by $C_{1-8}$ alkyl, $C_{3-8}$ cycloalkyl, $C_{1-16}$ acyl, $C_{1-16}$ trifluoroacyl, $C_{7-16}$ aralkyl or $C_{7-14}$ aryl, $C_{2-8}$ alkenyl, or $C_{2-8}$ alkynyl;

$NH(CO)N(NO)(CH_2)_{0-4}CH_2X$, wherein X is halogen; and a group of the formula $-O-C(R_{22})=O$ wherein $R_{22}$ is selected from the group consisting of:
hydrogen,
$C_{1-16}$ alkyl,
$C_{3-8}$ cycloalkyl,
$C_{2-16}$ alkoxyalkyl,
$C_{7-16}$ aralkyl,
$C_{8-16}$ araloxyalkyl,
$C_{8-16}$ aryloxyalkyl and
$C_{6-14}$ aryl;

$R_6$ is selected from the group consisting of:
cyano;
hydrogen;
acetoxy;
$C_{6-14}$ aryl;
$C_{2-8}$ alkenyl;
$C_{2-8}$ alkynyl;
$C_{1-16}$ hydroxyalkyl;
phenyl;
phenylsulfone;
$C_{6-14}$ aryl sulfone;
methylsulfone;
$C_{1-16}$ alkyl;
$C_{1-16}$ dihydroxyalkyl;
$C_{3-8}$ cycloalkyl;
squaric acid;
$C_{1-16}$ alkyl squarate;
dimethylphosphonate;
an acyl of the formula $-C(R_{23})=O$, or its dioxolane or dioxane ketal wherein $R_{23}$ is selected from the group consisting of:
hydrogen,
$C_{1-16}$ alkyl,
thiomethyl,
$C_{3-8}$ cycloalkyl,
fluoromethyl,
difluoromethyl
$C_{1-16}$ hydroxyalkyl,
squaric acid,
$C_{1-4}$ alkyl squarate,
$C_{2-16}$ alkoxyalkyl,
$C_{8-16}$ araloxyalkyl,
$C_{3-16}$ acyloxyalkyl,
$C_{3-16}$ acetoxymethyl,
bromomethyl,
amino which may be unsubstituted or mono- or di-substituted by $C_{1-8}$ alkyl, $C_{3-8}$ cycloalkyl, $C_{2-8}$ acyl, $C_{2-8}$ trifluoroacyl, $C_{7-16}$ aralkyl or $C_{7-16}$ aryl, and
an amino acid selected from the group consisting of alanine, arginine, asparagine, aspartic acid, cysteine, glutamine, glutamic acid, glycine, histidine, isoleucine, leucine, lysine, methionine, ornithine, phenylalanine, proline, serine, threonine, tryptophan, tyrosine and valine;
a group of the formula $-C(R_{23})(OC_{1-5}alkyl)_2$ wherein $R_{23}$ is as defined above;
a group of the formula $-C(OR_{24})=O$ wherein $R_{24}$ is selected from the group consisting of:
hydrogen,
$C_{1-16}$ alkyl,
$C_{3-8}$ cycloalkyl,
$C_{1-16}$ hydroxyalkyl,
$C_{2-16}$ alkoxyalkyl,
$C_{7-16}$ aryloxyalkyl,
$C_{8-16}$ araloxyalkyl,
$C_{6-14}$ aryl, and
$C_{7-16}$ aralkyl;

a group of the formula $-CR_{25}R_{26}C(R_{27})=O$ wherein $R_{25}$ and $R_{26}$ are independently selected from the group consisting of hydrogen, fluorine, chlorine, and bromine, and wherein $R_{27}$ is selected from the group consisting of:
hydrogen,
hydroxy,
$C_{1-8}$ alkoxy,
$C_{1-16}$ alkyl,
$C_{3-8}$ cycloalkyl,
$C_{1-16}$ hydroxyalkyl,
$C_{2-16}$ alkoxyalkyl,
$C_{7-16}$ aryloxyalkyl,
$C_{8-16}$ araloxyalkyl,
$C_{6-14}$ aryl,
$C_{7-16}$ aralkyl, and
amino which may be unsubstituted, mono- or di-substituted by $C_{1-8}$ alkyl, $C_{3-8}$ cycloalkyl, $C_{2-8}$ acyl, $C_{1-16}$ trifluoroacyl, $C_{7-16}$ aralkyl or $C_{6-16}$ aryl;
a 5 or 6 membered aromatic or non aromatic heterocycle containing one or more heteroatom selected from the group consisting of O, S, N, SO, $SO_2$, P, PO, and $NR_{28}$ wherein $R_{28}$ is selected from the group consisting of hydrogen, oxygen, hydroxyl, $C_{2-8}$ acyl, $C_{1-4}$ alkyl and $C_{6-14}$ aryl,
said heterocycle being optionally substituted with one or more halogen, hydroxy, $C_{1-16}$ alkoxy, nitro, $C_{1-16}$ alkyl, $C_{1-16}$ hydroxyalkyl, amino which may be unsubstituted or mono- or disubstituted by $C_{1-8}$ alkyl, $C_{3-8}$ cycloalkyl, $C_{2-8}$ acyl, $C_{2-8}$ trifluoroacyl, $C_{7-16}$ aralkyl $C_{6-14}$ aryl, $C_{2-8}$ alkenyl, $C_{2-8}$ alkynyl, and hydroxy;

$R_6'$ is selected from the group consisting of:
hydrogen;
$C_{1-16}$ alkyl;
halogen;
amino;
hydroxy;
$C_{1-16}$ alkoxy;
thiol;
cyano;
sulfide;
acyl of the formula $-C(R_{29})=O$, wherein $R_{29}$ is selected from the group consisting of:
hydrogen,
$C_{1-16}$ alkyl,
$C_{3-8}$ cycloalkyl,
$C_{1-16}$ hydroxyalkyl,
$C_{2-16}$ araloxyalkyl,
$C_{2-16}$ alkoxyalkyl,
$C_{3-16}$ acyloxyalkyl,
squaric acid or $C_{5-10}$ alkyl squarate,
amino which may be unsubstituted or mono- or di-substituted by $C_{1-8}$ alkyl, $C_{3-8}$ cycloalkyl, $C_{2-8}$ acyl, cyano, trifluoroacyl, $C_{7-16}$ aralkyl or $C_{6-14}$ aryl,and
an amino acid as defined in $R_6$;
a group of the formula $-C(OR_{30})=O$ wherein $R_{30}$ is selected from the group consisting of:
hydrogen,
$C_{3-8}$ alkyl,
$C_{3-8}$ cycloalkyl, $C_{1-16}$ hydroxyalkyl,
$C_{2-16}$ alkoxyalkyl,
$C_{7-16}$ aryloxyalkyl,
$C_{8-16}$ araloxyalkyl,
$C_{6-14}$ aryl,
$C_{7-16}$ aralkyl, and
$C_{2-16}$ alkenyl;

$R_7$ is independently selected from the group consisting of:
hydrogen;
halogen;
hydroxyl;
$C_{2-16}$ trihydroxyalkyl;
$C_{1-16}$ dihydroxyalkyl;
$C_{1-16}$ alkoxy;
$C_{1-16}$ alkyl;
$C_{2-16}$ alkoxyalkylamino;
$C_{2-16}$ acetylenyl;
$C_{3-8}$ cycloalkyl;
$C_{2-16}$ alkenyl;
cyano;
amino which may be unsubstituted or mono- or di-substituted by $C_{1-8}$ alkyl, $C_{3-8}$ cycloalkyl, $C_{2-8}$ acyl, cyano, trifluoroacyl, $C_{7-16}$ aralkyl, and $C_{6-14}$ aryl;
an amino acid as defined in $R_6$;
a group of the formula —O—C($R_{31}$)=O wherein $R_{31}$ is selected from the group consisting of:
hydrogen,
$C_{1-16}$ alkyl,
$C_{3-8}$ cycloalkyl,
$C_{2-16}$ alkoxyalkyl, and
$C_{6-14}$ aryl;
an acyl of the formula —C($R_{32}$)=O wherein $R_{32}$ is selected from the group consisting of:
hydrogen,
thiol,
$C_{1-16}$ thioalkyl,
$C_{1-16}$ alkyl,
$C_{3-8}$ cycloalkyl,
$C_{1-16}$ hydroxyalkyl,
$C_{2-16}$ alkoxyalkyl,
$C_{8-16}$ araloxyalkyl, and
$C_{3-16}$ acyloxyalkyl;
a group of the formula —C(OR$_{33}$)=O wherein $R_{33}$ is selected from the group consisting of:
hydrogen,
$C_{1-16}$ alkyl, and
$C_{3-8}$ cycloalkyl;

Y is a saccharide of the formula:

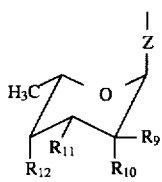

wherein
Z is selected from O; S; SO; SO$_2$; $C_{1-6}$ alkyl; or amino unsubstituted or monosubstituted with $C_{1-6}$ alkyl or acyl;

$R_9$ and $R_{10}$ are independently selected from the group consisting of:
hydrogen;
halogen;
hydroxyl;
acetoxy;
$C_{1-16}$ alkoxy;
$C_{1-16}$ alkyl;
$C_{3-8}$ cycloalkyl;
thiol;
amino;
cyano;
trifluoroacetamido;
chloroethylnitrosoureido;
chloroethylureido;
ethylnitrosoureido; and
ethylureido;

$R_{11}$ is selected from the group consisting of:
amino which may be unsubstituted or mono or di-substituted by $C_{1-8}$ acetoxy, $C_{1-8}$ alkyl, $C_{3-8}$ cycloalkyl, $C_{2-8}$ acyl, t-butylacyl, t-butyloxycarbonyl, trifluoroacyl, $C_{7-16}$ aralkyl, and $C_{6-16}$ aryl;
an amino acid as defined in $R_6$;
mono or dibenzylated amino;
azido;
$C_{2-8}$ acylated amino;
trifluoroacylated amino;
morpholino;
cyano-substituted-morpholino;
mono-, di-, tri- or tetra-methoxy-substituted morpholino;
hydroxy;
hydrogen;
halogen;
acetoxy;
$C_{1-16}$ alkoxyl;
$C_{3-8}$ cycloalkyl;
thiol;
sulfide;
a group of the formula NH(CH$_2$)$_{0-5}$CH(OR$_{34}$)$_2$ wherein each $R_{34}$ is independently selected from the group consisting of a $C_{1-16}$ alkyl, $C_{1-16}$ acyl and $C_{7-16}$ aroyl;
NH(CO)N(NO)(CH$_2$)$_{0-4}$CH$_2$Cl; and
NH(CH$_2$)$_2$OCH$_2$CH(OAc)$_2$; and $R_{12}$ is selected from the group consisting of:
hydrogen;
hydroxyl or its tetrahydropropyl ether (—OTHP);
halogen;
mono, bi, or trisaccharide;
amino;
$C_{1-16}$ mono or dialkylated amino;
trifluoroacetamido;
$C_{1-16}$ alkoxy;
$C_{3-8}$ cycloalkyl;
benzoate which may be unsubstituted or substituted with nitro;
acetoxy;
trifluoroacetoxy;
NH(CO)N(NO)(CH$_2$)$_{0-4}$CH$_2$Cl; and
NH(CH$_2$)$_2$OCH$_2$CH(OAc)$_2$.

3. A compound according to claim 1, wherein
$X_1$ and $X_2$ are independently:
O; or
NH;

$X_3$ is selected from the group consisting of
O;
S;
SO;
SO$_2$;
NH; and
NOH;

$R_1, R_2, R_3, R_4, R_5$ and $R_8$ are independently selected from the group consisting of:

hydrogen;
hydroxyl;
$C_{1-4}$ alkoxyl;
tosyl;
triflate;
fluorine;
chlorine;
$C_{3-9}$ alkoxy silane;
amino;
$NH(CH_2)_{1-3}NH(CH_2)_{1-3}OH$;
$NH(CH_2)_{1-3}NH(CH2)_{1-3}Cl$;
$NH(CO)N(NO)(CH_2)_{0-4}CH_2Cl$; and
a group of the formula $-O-C(R_{22})=O$ wherein $R_{22}$ is selected from the group consisting of:
hydrogen,
$C_{1-6}$ alkyl, and
$C_{6-10}$ aryl;

$R_6$ is selected from the group consisting of:
hydrogen;
cyano;
acetoxy;
phenylsulfone;
$C_{1-8}$ hydroxyalkyl;
$C_{1-8}$ dihydroxyalkyl;
squaric acid;
$C_{1-16}$ alkyl squarate;
$C_{1-4}$ alkyl;
acyl of the formula $-C(R_{23})=O$ wherein $R_{23}$ is selected from the group consisting of:
hydrogen,
$C_{1-8}$ alkyl,
$C_{1-8}$ hydroxyalkyl,
squaric acid,
$C_{1-4}$ alkyl squarate,
$C_{2-8}$ alkoxyalkyl,
$C_{3-8}$ acyloxyalkyl,
bromomethyl,
$C_{3-8}$ acetoxymethyl,
amino which may be unsubstituted or mono- or di-substituted with $C_{1-8}$ alkyl, $C_{3-8}$ cycloalkyl, $C_{2-8}$ acyl, trifluoroacyl, $C_{7-16}$ aralkyl or $C_{7-16}$ aryl;
a group of the formula $-C(OR_{24})=O$, wherein $R_{24}$ is selected from the group consisting of:
hydrogen,
$C_{1-8}$ alkyl,
$C_{6-14}$ aryl, and
$C_{7-16}$ aralkyl;
a group of the formula $-CH_2C(R_{27})=O$ wherein $R_{27}$ is selected from the group consisting of:
hydrogen,
hydroxy,
$C_{1-8}$ alkoxy,
$C_{1-8}$ alkyl, and
amino which may be unsubstituted or mono- or di-substituted with $C_{1-8}$ alkyl, $C_{3-8}$ cycloalkyl, $C_{2-8}$ acyl, $C_{1-8}$ trifluoroacyl, $C_{7-16}$ aralkyl or $C_{7-14}$ aryl;
a 5 or 6 membered aromatic or non aromatic heterocycle containing one or more heteroatom selected from the group consisting of O, S, N, and NH;
said heterocycle being optionally substituted with one or more halogen, hydroxy, $C_{1-8}$ alkoxy, $C_{1-8}$ alkyl, $C_{1-8}$ hydroxyalkyl, amino which may be unsubstituted or mono- or or disubstituted by $C_{1-4}$ alkyl, $C_{3-5}$ cycloalkyl, acyl, trifluoroacyl, $C_{6-14}$ aryl, and hydroxy;

$R_6'$ is selected from the group consisting of:
hydrogen;
fluorine;
$C_{1-4}$ alkyl;
$C_{1-4}$ alkoxy;
cyano;
acyl of the formula $-C(R_{29})=O$ wherein $R_{29}$ is selected from the group consisting of:
hydrogen,
$C_{1-8}$ alkyl,
$C_{1-8}$ hydroxyalkyl,
$C_{3-8}$ acyloxyalkyl, and
amino,
a group of the formula $-C(OR_{30})=O$, wherein $R_{30}$ is selected from the group consisting of:
hydrogen,
$C_{1-8}$ alkyl,
$C_{6-10}$ aryl, and
$C_{1-8}$ alkenyl;

$R_7$ is independently selected from the group consisting of:
hydrogen;
halogen;
hydroxyl;
$C_{1-8}$ alkoxy;
$C_{2-8}$ acetylenyl;
$C_{2-8}$ alkenyl;
cyano;
a group of the formula $-O-C(R_{31})=O$ wherein $R_{31}$ is selected from the group consisting of:
hydrogen, and
$C_{1-8}$ alkyl;
acyl of the formula $-C(R_{32})=O$ wherein $R_{32}$ is selected from the group consisting of:
hydrogen,
thiol,
$C_{1-8}$ alkyl,
$C_{1-8}$ hydroxyalkyl, and amino;
a group of the formula $-C(OR_{33})=O$, wherein $R_{33}$ is selected from the group consisting of:
hydrogen, and
$C_{1-8}$ alkyl; and Y is a saccharide of formula:

$$\begin{array}{c} | \\ Z \\ H_3C \diagup\!\!\!\diagdown O \diagup \\ \diagdown\!\!\!\diagup \!\!\!-R_9 \\ R_{11} \\ R_{12} \quad R_{10} \end{array}$$

wherein
Z is O; or $C_{1-6}$ alkyl;
$R_9$ and $R_{10}$ are independently selected from the group consisting of:
hydrogen;
iodine;
fluorine;
chlorine;
hydroxyl;
amino;
trifluoroacetamido;
chloroethylnitrosoureido; and
chloroethylureido;
$R_{11}$ is selected from the group consisting of:
amino which may be unsubstituted or mono- or disubstituted with $C_{1-8}$ acetoxy, $C_{1-8}$ alkyl, $C_{3-8}$ cycloalkyl, $C_{2-8}$ acyl, trifluoroacyl, $C_{7-11}$ aralkyl or $C_{7-11}$ aryl;
morpholino;
cyano-substituted morpholino;
mono-, di-, tri-, or tetra-methoxy-substituted morpholino;
hydroxy;
$C_{1-16}$ mono or dialkylated-amino;
azido;
iodine;
acetoxy;
fluorine;
$C_{1-8}$ alkoxy;
a group of the formula $NH(CH_2)_{1-5}CH(OR_{34})_2$ wherein each $R_{34}$ is independently selected from the group consisting of $C_{1-8}$ alkyl, $C_{2-8}$ acyl and $C_{7-12}$ aroyl;
$NH(CO)N(NO)(CH_2)_{0-4}CH_2Cl$; and
$NH_2(CH_2)_2OCH_2CH(OAc)_2$;

$R_{12}$ is selected from the group consisting of:
hydrogen;
hydroxy or its tetrahydopyranyl ether;
thiol;
halogen;
mono, bi, or trisaccharide selected from the group consisting of rhodosamine, cinerulose-B, L-cinerulose, D-cinerulose, cinerulose A, amicetose, aculose, rednose, rhodinose, 2-deoxyfucose, daunosamine, and trifluoroacetyldaunosamine;
amino;
trifluoroacetamido;
mono or dimethylated-amino;
$C_{1-8}$ alkoxy;
benzoate;
p-nitrobenzoate;
chloroalkylnitrosourea;
acetoxy; and
trifluoroacetoxy.

4. A compound of formula (10) according to claim 1, wherein $X_1$ and $X_2$ are independently selected from the group consisting of: O; and NH;

$X_3$ is selected from the group consisting of: O; S; and SO;

$R_1$, $R_2$, $R_3$, $R_4$, $R_5$ and $R_8$ are independently selected from the group consisting of:
hydrogen;
hydroxy;
methoxy;
$C_{1-8}$ alkyl silane;
aminoethylaminoethanol;
aminoethylaminoethylchloride;
$NH(CO)N(NO)(CH_2)_{0-2}CH_2Cl$;
amino; and
fluorine;

$R_6$ is selected from the group consisting of:
hydrogen;
$C_{1-4}$ alkyl;
$C_{1-4}$ hydroxyalkyl;
$C_{1-4}$ dihydroxyalkyl;
cyano;
acetoxy;
phenylsulfone;
acyl of the formula $—C(R_{23})=O$ wherein $R_{23}$ is selected from the group consisting of:
methyl,
hydroxymethyl,
bromomethyl,
acyloxymethyl, and
amino;
a group of the formula $—C(OR_{24})=O$ wherein $R_{24}$ is selected from the group consisting of:
hydrogen,
methyl, and
ethyl;
a group of the formula $—CH_2C(R_{27})=O$ wherein $R_{27}$ is selected from the group consisting of:
hydrogen,
methyl, and
ethyl;
a 5 or 6 membered aromatic or non aromatic heterocycle containing one or more heteroatom selected from the group consisting of O, S, N, NH,
said heterocycle being optionally substituted with one or more halogen, hydroxy, $C_{1-4}$ alkoxy, $C_{1-4}$ alkyl, $C_{1-4}$ hydroxyalkyl, amino which may be unsubstituted or mono- or disubstituted by methyl, cyclopropyl, $C_{2-8}$ acyl, and hydroxy;

$R_6'$ is selected from the group consisting of:
hydrogen;
fluorine;
methyl;
methoxy;
cyano;
acyl of the formula $—C(R_{29})=O$ wherein $R_{29}$ is selected from the group consisting of:
hydrogen,
$C_{1-5}$ alkyl,
$C_{1-4}$ hydroxyalkyl, and
amino ($NH_2$);
a group of the formula $—C(OR_{30})=O$ wherein $R_{30}$ is selected from the group consisting of:
hydrogen,
$C_{1-5}$ alkyl,
$C_{6-10}$ aryl, and
$C_{1-4}$ alkenyl;

$R_7$ is selected from the group consisting of: hydrogen;
hydroxy;
methoxy;
fluorine;
cyano;
acetate; and
acetyl;

Y is a saccharide of formula wherein
Z is O; or $CH_2$;

$R_9$ and $R_{10}$ are independently selected from the group consisting of:
hydrogen;
amino;
chloroethylnitroso;
ureido;
fluorine; and
iodine;

$R_{11}$ is selected from the group consisting of:

hydroxyl;
acetoxy;
amino;
dimethylamino;
trifluoroacetamido;
morpholino;
cyano-substituted morpholino;
mono-, di-, tri-, or tetra-methoxy-substituted morpholino;
a group of the formula $NH(CH_2)_{2-5}CH(OR_{34})_2$ wherein $R_{34}$ is selected from the group consisting of $C_{1-4}$ alkyl, $C_{1-4}$ acyl, and $C_{7-8}$ aroyl;
$NH(CO)N(NO)(CH_2)_{0-4}CH_2Cl$;
$NH(CH_2)_2OCH(OAc)_2$; and
fluorine;

$R_{12}$ is selected from the group consisting of:
hydroxy or its tetrahydopyranyl ether;
benzoate;
acetoxy;
p-nitrobenzoate;
amino;
trifluoroacetamido;
chloroethylnitrosoureido;
fluorine; and
iodine.

5. A compound of formula (10) according to claim 1, wherein
$X_1$ and $X_2$ are both oxygen;
$X_3$ is O; or S;
$R_1$, $R_2$, $R_3$ and $R_4$ are each independently selected from the group consisting of: hydrogen; fluorine; methoxy; and hydroxy;
$R_5$ and $R_8$ and independently selected from the group consisting of: hydrogen; hydroxy; amino; and fluorine;
$R_6$ is selected from the group consisting of:
methyl;
ethyl;
hydroxymethyl;
dihydroxyethyl;
cyano;
phenylsulfone;
methyl carboxylate (—$CO_2CH_3$);
ethyl carboxylate;
methyl homo carboxylate (—$CH_2CO_2CH_3$);
acyl of the formula —$C(R_{23})$=O wherein $R_{23}$ is selected from the group consisting of:
methyl,
fluoromethyl,
difluoromethyl,
hydroxymethyl,
acetoxymethyl, and
bromomethyl;
a 5 or 6 membered aromatic or non aromatic heterocycle containing one or more heteroatom selected from the group consisting of O, S, N, NH,
said heterocycle being optionally substituted with one or more fluorine, hydroxy, methoxy, methyl, hydroxymethyl, amino, and acylamino groups;

$R_6'$ is selected from the group consisting of:
hydrogen;
fluorine;
methyl; and
cyano;

$R_7$ is selected from the group consisting of:
hydrogen;
hydroxy; and
fluorine;

Y is a saccharide of the formula

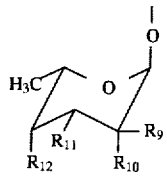

wherein $R_9$ and $R_{10}$ are independently selected from the group consisting of:
hydrogen;
fluorine; and
iodine;

$R_{11}$ is selected from the group consisting of:
amino;
hydroxy;
dimethylamino;
acetoxy;
trifluoroacetamido;
morpholino;
cyano-substituted morpholino;
methoxymorpholino;
a group of the formula $NH(CH_2)_4CH(OR_{34})_2$ wherein each $R_{34}$ is selected from a group consisting of: methyl, acyl, and benzoyl;
$NH(CO)N(NO)CH_2CH_2Cl$; and
$NH(CH_2)_2OCH_2CH(OAc)_2$; and $R_{12}$ is hydroxy; or iodine.

6. A compound according to claim 5 wherein $R_5$ and $R_8$ are both hydroxy.

7. A compound according to claim 6 wherein $X_3$ is O.

8. A compound according to claim 6 wherein $X_3$ is S.

9. A compound according to claim 7, wherein Y is a saccharide of the formula

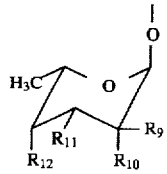

wherein $R_9$ and $R_{10}$ are independently selected from the group consisting of hydrogen, fluorine and iodine;

$R_{11}$ is selected from the group consisting of amino; hydroxy; dimethylamino; acetoxy; trifluoroacetamido; morpholino; cyano-substituted morpholino; methoxymorpholino: a group of the formula $NH(CH_2)_4CH(OR_{34})_2$ wherein each $R_{34}$ is selected from the group consisting of methyl, acyl and benzoyl;
$NH(CO)N(NO)CH_2CH_2Cl$ and
$NH(CH_2)_2OCH_2CH(OAc)_2$; and $R_{12}$ is hydroxy or iodine.

10. A compound according to claim 7, wherein Y is a saccharide of the formula

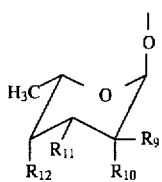

wherein $R_9$ and $R_{10}$ are independently selected from the group consisting of hydrogen, fluorine and iodine;

$R_{11}$ is selected from the group consisting of amino; hydroxy; dimethylamino; acetoxy; trifluoroacetamido; morpholino; cyano-substituted morpholino; methoxymorpholino; a group of the formula $NH(CH_2)_4CH(OR_{34})_2$ wherein each $R_{34}$ is selected from the group consisting of methyl, acyl and benzoyl; $NH(CO)N(NO)CH_2CH_2Cl$ and $NH(CH_2)_2OCH_2CH(OAc)_2$; and $R_{12}$ is hydroxy or iodine.

11. A compound according to claim 7, wherein Y is a saccharide of the formula

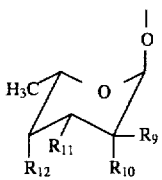

wherein $R_9$ and $R_{10}$ are independently selected from the group consisting of hydrogen, fluorine and iodine;

$R_{11}$ is selected from the group consisting of amino; hydroxy; dimethylamino; acetoxy; trifluoroacetamido; morpholino; cyano-substituted morpholino; methoxymorpholino; a group of the formula $NH(CH_2)_4CH(OR_{34})_2$ wherein each $R_{34}$ is selected from the group consisting of methyl, acyl and benzoyl; $NH(CO)N(NO)CH_2CH_2Cl$ and $NH(CH_2)_2OCH_2CH(OAc)_2$; and $R_{12}$ is hydroxy or iodine, and $R_7$ is hydrogen.

12. A compound according to claim 8, wherein Y is a saccharide of the formula

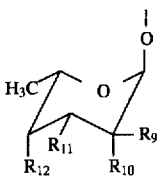

wherein $R_9$ and $R_{10}$ are independently selected from the group consisting of hydrogen, fluorine and iodine;

$R_{11}$ is selected from the group consisting of amino; hydroxy; dimethylamino; acetoxy; trifluoroacetamido; morpholino; cyano-substituted morpholino; methoxymorpholino; a group of the formula $NH(CH_2)_4CH(OR_{34})_2$ wherein each $R_{34}$ is selected from the group consisting of methyl, acyl and benzoyl; $NH(CO)N(NO)CH_2CH_2Cl$ and $NH(CH_2)_2OCH_2CH(OAc)_2$; and $R_{12}$ is hydroxy or iodine.

13. A compound according to claim 8 wherein Y is a saccharide.

14. A compound according to claim 8 wherein Y is a saccharide and $R_7$ is hydrogen.

15. A compound according to claim 5 wherein only one of $R_5$ and $R_8$ is hydroxy.

16. A compound according to claim 15 wherein $X_3$ is O.

17. A compound according to claim 16 wherein Y is a saccharide and $R_7$ is hydrogen.

18. A compound according to claim 15 wherein $X_3$ is S.

19. A compound according to claim 18 wherein Y is a saccharide and $R_7$ is hydrogen.

20. A compound according to claim 5 with the proviso that $R_6$ is not a 5 or 6 membered aromatic or non-aromatic heterocycle.

21. A compound according to claim 20 wherein Y is a saccharide and $R_7$ is H.

22. Compound according to claim 1 selected from the group consisting of:

(1'S,1R,3S) or (1'S,1S,3R)-Methyl(6-hydroxy-1-(3'-trifluoroacyl-daunosamine)-5,12-dioxo-3,4,5,12-tetrahydroanthraceno[2,3-C]pyran-3-yl)ketone, and mixture thereof;

(1S',1R,3S)Methyl(6-hydroxy-1-daunosamine)-5,12-dioxo-3,4,5,12-tetrahydroanthraceno[2,3-C]pyran-3-yl)ketone;

(1S',1S,3R)Methyl(6-hydroxy-1-daunosamine)-5,12-dioxo-3,4,5,12-tetrahydroanthraceno[2,3-C]pyran-3-yl)ketone;

(1'S,1R,3S)-methyl(1-(2',3',6'-trideoxy-3'-trifluoroacetamido-L-lyxohexopyranose)-6,11-dioxo-5,12-dihydroxy-3,4,6,11-tetrahydroanthraceno[,2,3-C]pyran-3-yl)ketone;

(1'S,1S,3R)-methyl(1-(2',3',6'-trideoxy-3'-trifluoroacetamido-L-lyxohexopyranose)-6,11-dioxo-5,12-dihydroxy-3,4,6,11-tetrahydroanthraceno[2,3-C]pyran-3-yl)ketone;

(1'S,1R,3S )-methyl(1-(2',3',6'-trideoxy-3'amino-L-lyxohexopyranose)-6,11-dioxo-5,12-dihydroxy-3,4,6,11-tetrahydroanthraceno[2,3-C]pyran-3-yl)ketonehydrochloride;

(1'S,1S,3R)-methyl(1-(2',3',6'-trideoxy-3'amino-L-lyxohexopyranose)-6,11-dioxo-5,12-dihydroxy-3,4,6,11-tetrahydroanthraceno-[2,3-C]pyran-3-yl)ketonehydrochloride;

(1'S,1R,3 S)-methyl(1-(2',3',6'-trideoxy-3'-morpholino-L-lyxohexopyranose)-6,11-dioxo-5,12-dihydroxy-3,4,6,11-tetrahydroanathraceno[2,3-C]pyran-3-yl)ketonehydrochloride;

(1'S,1S,3R)-methyl(1-(2',3',6'-trideoxy-3'-morpholino-L-lyxohexopyranose)-6,11-dioxo-5,12-dihydroxy-3,4,6,11-tetrahydroanathraceno[2,3-C]pyran-3-yl)ketonehydrochloride;

(1'S,1R,3S)-methyl(1-(2',3',6',-trideoxy-3'-(1''-cyanomorpholino)-L-lyxohexopyranose)-6,11-dioxo-5,12-dihydroxy-3,4,6,11-tetrahydroanthraceno[2,3-C]pyran-3-yl)ketone;

(1'S,1S,3R)-methyl(1-(2',3',6',-trideoxy-3'-(1''-cyanomorpholino)-L-lyxohexopyranose)-6,11-dioxo-5,12-dihydroxy-3,4,6,11-tetrahydroanthraceno[2,3-C]pyran-3-yl)ketone;

(1'S,1R,3R)-5,12-dioxo-3-ethyl-6-hydroxy-1-(2',3',6'-trideoxy-3'-trifluoroacetamido-4'-hydroxy-L-lyxohexopyranose)-3,4,5,12-tetrahydroanthraceno[2,3-c]pyran;

(1'S,1R,3R)-5,12-dioxo-3-ethyl-6-hydroxy-1-(2',3',6'-trideoxy-3'-amino-4'-hydroxy-L-lyxohexopyranose)-3,4,5,12-tetrahydroanthraceno[2,3-c]pyranhydrochloride;

(1'S,1S,3S)-5,12-dioxo-3-ethyl-6-hydroxy-1-(2',3',6'-trideoxy-3'-trifluoroacetamido-4'-hydroxy-L-lyxohexopyranose)-3,4,5,12-tetrahydroanthraceno[2,3-c]pyran;

(1'S,1S,3S)-5,12-dioxo-3-ethyl-6-hydroxy-1-(2',3',6'-trideoxy-3'-amino-4'-hydroxy-L-lyxohexopyranose)-3,4,5,12-tetrahydroanthraceno[2,3-c]pyranhydrochloride;

(1'S,1R,3S)-1,2,3,4,5,12-hexahydro-6-hydroxy-3-trimethyl-acetoxyaceto-1-N-trifluoroacetyl-L-daunosamine-(2-oxo)-naphthacene-5,12-dione;

(1',S,1R,3S)-1,2,3,4,5,12-hexahydro-6-hydroxy-3-hydroxy-a-ceto-1-N-trifluoroacetyl-L-daunosamine-(2-oxo)naphthacene-5,12-dione;

(1'S,1S,3R)-1,2,3,4,5,12-hexahydro-6-hydroxy-3-trimethyl-acetoxyaceto-1-N-trifluoroacetyl-L-daunosamine-(2-oxo)naphthacene-5,12-dione;

(1'S,1S,3R)-1,2,3,4,5,12-hexahydro-6-hydroxy-3-hydroxyaceto-1-N-trifluoroacetyl-L-daunosamine-(2-oxo)naphthacene-5,12-dione;

(1'S,1S,3R) or (1'S,1R,3S)-Methyl-(6-hydroxy-1-(2',6'-dideoxy-L-lyxohexopyranose)-5,12-dioxo-3,4,5,12-tetrahydroanthraceno(2,3-c)pyran-3-yl)ketone, and mixture thereof;

(1'S,1R,3S)-6-hydroxy-1-(2',3',6'-trideoxy-3'-trifluoroacetamido-L-lyxohexopyranose)-3-(2-aza-3-acetamidothienyl)-5,12-dioxo-3,4,5,12tetrahydroanthraceno-[2,3-C]-pyran;

(1'S,1S,3R)-6-hydroxy-1-(2',3',6'-trideoxy-3'-trifluoroacetamido-L-lyxohexopyranose)-3-(2-aza-3-acetamidothienyl)-5,12-dioxo-3,4,5,12-tetrahydroanthraceno-[2,3-C]pyran;

(1'S,1R,3S) or (1'S,1S,3R)methyl[11-hydroxy-1-(2',3',6'-trideoxy-3'-trifluoroacetamido-L-lyxohexopyranose)-5,12-dioxo-3,4,5,12-tetrahydroanthraceno[2,3-c]pyran-3-yl]formate, and mixture thereof;

(1'S,1R,3S) or (1'S,1S,3R)Ethyl[11-hydroxy-1-(2',3',6'-trideoxy-3-trifluoroacetamido-L-lyxohexopyranose)-5,12-dioxo-3,4,5,12-tetrahydroanthraceno[2,3-c]pyran-3-yl]formate, and mixture thereof;

(1'S,1R,3S) or (1'S,1S,3R)Ethyl[6-Methoxy,11-hydroxy-1-(2',3',6'-trideoxy-3'-trifluoroacetamido-L-lyxohexopyranose)-5,12-dioxo-3,4,5,12-tetrahydroanthraceno[2,3-c]pyran-3-yl]formate, and mixture thereof;

(1'S,1R,3S) or (1'S,1S,3R)Ethyl[11-Methoxy,6-hydroxy-1-(2',3',6'-trideoxy-3'-trifluoroacetamido-L-lyxohexopyranose)-5,12-dioxo-3,4,5,12-tetrahydroanthraceno[2,3-c]pyran-3-yl]formate, and mixture thereof;

(1'S,1R,3S) or (1'S,1S,3R)Ethyl[6-hydroxy-1-(2',3',6'-trideoxy-3'-trifluoroacetamido-L-lyxohexopyranose)-5,12-dioxo-3,4,5,12-tetrahydroanthraceno[2,3-c]pyran-3-yl]formate, and mixture thereof;

(1'S,1R,3S) or (1'S,1S,3R)Methyl[6-hydroxy,1-(2',3',6'-trideoxy-3'-trifluoroacetamido-L-lyxohexopyranose)-5,12-dioxo-3,4,5,12-tetrahydroanthraceno[2,3-c]pyran-3-yl]formate, and mixture thereof;

(1'S,1R,3S) or (1'S,1S,3R)methyl[1-(2',3',6'-trideoxy-3'-trifluoroacetamido-L-lyxohexopyranose)-5,12-dioxo-3,4,5,12-tetrahydroanthraceno[2,3-c]pyran-3-yl]formate, and mixture thereof;

(1'S,1S,3S) or (1'S,1R,3R)methyl[1-(2',3',6'-trideoxy-3'-trifluoroacetamido-L-lyxohexopyranose)-5,12-dioxo-3,4,5,12-tetrahydroanthraceno[2,3-c]pyran-3-yl]formate, and mixture thereof;

1'S,1S,3R) or (1'S,1R,3S)Methyl[11-acetoxy-6-hydroxy-1-(2',3',6'-trideoxy-3'-L-trifluoroacetamido-L-lyxohexopyranose)-5,12-dioxo-3,4,5,12-tetrahydroanthraceno[2,3-c]pyran-3-yl]ketone, and mixture thereof;

(1'S,1R,3S)-methyl(6-hydroxy-1-(2',3',6'-trideoxy-3'-amino-L-lyxohexopyranose)-5,12-dioxo-3,4,5,12tetrahydroanthraceno[2,3-C]pyran-3-yl)ketone;

(1'S,1S,3R)-methyl(6-hydroxy-1-(2',3',6'-trideoxy-3'-amino-L-lyxohexopyranose)-5,12-dioxo-3,4,5,12-tetrahydroanthraceno[2,3-C]pyran-3-yl)ketone;

(1'S,1R,3S)-methyl(5,12-dihydroxy-1-(2',3',6'-trideoxy-3'-amino-L-lyxohexopyranose)-6,11-dioxo-3,4,6,11-tetrahydroanthraceno[2,3-C]pyran-3-yl)ketone;

(1'S,1S,3R)-methyl(5,12-dihydroxy-1-(2',3',6'-trideoxy-3'-amino-L-lyxohexopyranose)-6,11-dioxo-3,4,6,11-tetrahydroanthraceno[2,3-C]pyran-3-yl)ketone;

(1'S,1R,3S)-3-aceto-1-(2'-iodo daunosamine)-6-hydroxy-5,12-dioxo-3,4,5,12-tetrahydroanthraceno[2,3-C]pyran;

(1'S,1S,3R)-3-aceto-1-(2'-iododaunosamine)-6-hydroxy-5,12-dioxo-3,4,5,12-tetrahydroanthraceno[2,3-C]pyran;

(1'S,1R,3S)-3-aceto-1-(2'-iododaunosamine)-5,12-dihydroxy-6,11-dioxo-3,4,6,11-tetrahydroanthraceno[2,3-C]pyran;

(1'S,1S,3R)-3-aceto-1-(2'-iododaunosamine)-5,12-dihydroxy-6,11-dioxo-3,4,6,11-tetrahydroanthraceno[2,3-C]pyran;

(1'S,1R,3S)-3-aceto-1-(2'-deoxy-2'-iodofucose)-6-hydroxy-5,12-dioxo-3,4,5,12-tetrahydroanthraceno[2,3-C]pyran;

(1'S,1S,3R)-3-aceto-1-(2'-deoxy-2'-iodofucose)-6-hydroxy-5,12-dioxo-3,4,5,12-tetrahydroanthraceno[2,3-C]pyran;

(1'S,1R,3S)-3-aceto-1-(2'-deoxy-2'-iodofucose)-5,12-dihydroxy-6,11-dioxo-3,4,6,11-tetrahydroanthraceno[2,3-C]pyran; and (1'S,1S,3R)-3-aceto-1-(2'-deoxy-2'-iodofucose)-5,12-dihydroxy-6,11-dioxo-3,4,6,11-tetrahydroanthraceno[2,3-C]pyran.

23. A compound according to claim 1 selected from the group consisting of:

BCH-671: (1'S,1R,3S)Methyl(1-[2',3',6'-trideoxyacetamido-4'-hydroxy-L-lyxohexopyranose]-5,12-dioxo-3,4,5,12-tetra-hydroanthraceno(2,3-c)pyran-3-yl)formate;

BCH-674 and BCH-675: (1'S,1S,3R) and 1'S,1R,3S) Methyl(11-hydroxy-6-methoxy-1-[2',3',6'-trideoxy-3-trifluoroacetamido-4'-hydroxy-L-lyxohexopyranose]-5,12-dioxo-3,4,5,12-tetrahydroanthra-ceno[2,3-c]pyran-3-yl) formate;

BCH-681: (1'S,1R,3S)Ethyl[6-hydroxy-5,12-dioxo-1-(3'-trifuloroacetamido-1-daunosaminyl)-3,4,5,12-tetrahydroanthraceno(2,3-C)pyran-3-yl]formate;

BCH-684: (1'S,1S,3R)Ethyl[6-hydroxy-5,12-dioxo-1-(3'-trifluoroacetamido-1-daunosaminyl)-3,4,5,12-tetrahydroanthraceno(2,3-C)pyran-3-yl]formate;

BCH-689: (1'S,1R,3S) and (1'S,1S,3R)Ethyl[6-hydroxy-11-methoxy- 5,12-dioxo-1-(3'-trifuloroacetamido-1-daunosaminyl)-3,4,5,12-tetrahydroanthraceno(2,3-C)pyran-3-yl]formate;

BCH-691: (1'S,1R,3S)-Methyl-(11-hydroxy-1-(2',3',6'-trideoxy-3'-trifluoroacetamido-4'-hydroxy-L-lyxoheoxpyranose)-5,12-dioxo-3,4,5,12-tetrahydroanthraceno[2,3-c]pyran-3-yl) formate;

3-[2-Acetoxy-1-trimethylene-ketal]-aceto-11-acetoxy-1-hydroxy-1,2,3,4-tetrahydro-(2-oxygen)-naphthacene-5,12-dione;

BCH-724: (1'S,1S,3R)-Methyl-[11-hydroxy-1-(2',3',6'-trideoxy-3'-trifluoroacetamido-4'-hydroxy-L-lyxohexopyranose)-5,12-dioxo-2,3,5,12-tetrahydroanthraceno(2,3-C)pyran-3-yl]ketone;

BCH-730: (1'S,1R,3S)Methyl(6-hydroxy-1-(2',3',6'-trideoxy-3'-trifluoroacetamido-4-hydroxy-L-lyxohexopyranose-5,12-dioxo-3,4,5,12-tetrahydroanthraceno(2,3-C) pyran-3-yl]ketone;

BCH-731: (1'S,1R,3S) and (1'S,1S,3R)-3-(2-acetoxy-1-trimethyleneketal)aceto-6-acetoxy-1,2,3,4,5,12-hexahydro-1-N-trifluoroacetyl-L-daunosamine(2-oxygen)naphthacene-5,12-dione; and
1'S,1R,3S) and (1'S,1S,3R)-3-(2-acetoxy-1-trimethyleneketal) aceto-11-acetoxy-1,2,3,4,5,12-hexahydro-1-N-trifluoroacetyl-L-daunosamine(2-oxygen) naphthacene-5,12-dione;

BCH-746: (1'S,1S,3S) and (1'S,1R,3S)-3-(2-acetoxy-1-trimethyleneketal)aceto-1,2,3,4,5,12-hexahydro-6-hydroxy-1-N-trifluoroacetyl-L-daunosamine(2-oxygen) naphthacene-5,12-dione; and
(1'S,1S,3R) and (1'S,1R,3S)-3-(2-acetoxy-1-trimethyleneketal) aceto-1,2,3,4,5,12-hexahydro-11-hydroxy-1-N-trifluoroacetyl-L-daunosamine(2-oxygen) naphthacene-5,12-dione;

BCH-1123: (1'S,1S,3R)-Methyl-[6-hydroxy-1-(2',3',6'-trideoxy-3',4'-dihydroxy-L-lyxohexopyranose)-5,12-dioxo-3,4,5,12-tetrahydroanthraceno(2,3-C)pyran-3-yl]ketone;

BCH-1124: (1'S,1R,3S)-Methyl-[6-hydroxy-1-(2',3',6'-trideoxy-3',4'-dihydroxy-L-lyxohexopyranose)-5,12-dioxo-2,3,5,12-tetrahydroanthraceno(2,3-C)pyran-3-yl]ketone;

BCH-1127: (1'S,1S,3R)-Methyl-[6-hydroxy-1-(2',3',6'-trideoxy-3'-amino-4'-hydroxy-L-lyxohexopyranose)-5,12-dioxo-3,4,5,12-tetrahydroanthraceno-(2,3-C)pyran-3-yl]ketone hydrochloride;

BCH-1128: (1'S,1R,3S)-Methyl-[6-hydroxy-1-(2',3',6'-trideoxy-3'-amino-4'-hydroxy-L-lyxohexopyranose-5,12-dioxo-3,4,5,12-tetrahydroanthraceno-(2,3-C)pyran-3-yl]ketone hydrochloride;

BCH-1130: (1'S,1S,3R) and (1,S,1R,3S)-Methyl-[5,12-dihydroxy-1-(2',3',6'-trideoxy-3'-amino-4'-hydroxy-L-lyxohexopyranose)-6,11-dioxo-3,4,6,11-tetrahydroanthraceno-(2,3-C)pyran-3-yl]ketone hydrochloride;

BCH-1131: (1'S,1S,3R) and (1S,1R,3S)-Methyl-[5,12-dihydroxy-1-(2',3',6'-trideoxy-3'-trifluoroacetamido-4'-hydroxy-L-lyxohexopyranose)-6,11-dioxo-3,4,6,11, tetrahydroanthraceno-(2,3-C)pyran-3-yl]ketone;

BCH-1153: (1'S,1S,3R) or (1'S,1R,3S)-3-(2-hydroxy-1-trimethyleneketal) aceto-1,2,3,4,5,12-hexahydro-6-hydroxy-1-L-daunosamine(2-oxo) naphthacene-5,12-dione-hydrochloride;

BCH-1179: (1'S,1S,3R) or (1'S,1R,3S)-3-(2-acetoxy-1-trimethyleneketal) aceto-1,2,3,4,5,12-hexahydro-11-acetoxy-1-(N-trifluoroacetyl-L-daunosamine)(2-oxo) naphthacene-5,12-dione;

BCH-1187: (1'S,1S,3S)-5,12-Dioxo-3-ethyl-6-hydroxy-1-(2',3',6'-trideoxy-3'-trifluoroacetamido-4'-hydroxy-L-lyxohexopyranose)-3,4,5,12-tetrahydroanthraceno(2,3-C)pyran;

BCH-1191: (1'S,1R,3S) and (1'S,1S,3R)-Methyl(1-(2',3',6'-trideoxy-3'-morpholino-L-lyxohexopyranose)-6,11-dioxo-5,12-dihydroxy-3,4,611-tetrahydroanthraceno [2,3-c]pyran-3-yl)ketone;

BCH-1193: (1'S,1R,3S) and (1'S,1S,3R)-Methyl(1-(2',3', 6'-trideoxy-3'-morpholino-L-lyxohexopyranose)-6,11-dioxo-5,12-dihydroxy-3,4,611-tetrahydroanthraceno [2,3-c]pyran-3-yl)ketone hydrochloride;

BCH-1194: (1'S,1R,3S)-Methyl-[5,12-dihydroxy-1-(2',3', 6'-trideoxy-3'-amino-4'-hydroxy-L-lyxohexopyranose)-6,11-dioxo-3,4,6,11-tetrahydroanthraceno-(2,3-C)pyran-3-yl]ketone hydrochloride;

BCH-1195: (1'S,1S,3R)-Methyl-[5,12-dihydroxy-1-(2',3', 6'-trideoxy-3'-amino-4'-hydroxy-L-lyxohexopyranose)-6,11,dioxo-3,4,6,11-tetrahydroanthraceno-(2,3-C)pyran-3-yl]ketone hydrochloride;

BCH-1606: (1'S,1R,3R)-5,12-Dioxo-3-ethyl-6-hydroxy-1-[2',3',6'-trideoxy-3'-trifluoroacetamido-4'-hydroxy-L-lyxohexopyranose]-3,4,5,12-tetrahydroanthraceno(2,3-C)pyran;

BCH-1610: (1'S,1S,3s)-5,12-Dioxo-3-ethyl-6-hydroxy-1-[2',3',6'-trideoxy-3'-amino-4'-hydroxy-L-lyxohexopyranose]-3,4,5,12-tetrahydroanthraceno(2,3-C)pyran hydrochloride;

BCH-1611: (1'S,1R,3S) or (1'S,1S,3R)-1,2,3,4,5,12-hexahydro-6-hydroxy-1-L-daunosamine -3-vinyl(2-oxo)naphthacene-5,12-dione;

BCH-1614: (1S,1R,3R)-5,12-Dioxo-3-ethyl-6-hydroxy-1-[2',3',6'-trideoxy-3'-amino-4'-hydroxy-L-lyxohexopyranose]-3,4,5,12-tetrahydroanthraceno(2,3-C)pyran hydrochloride;

BCH-1617: (1'S,1R,3S)-Methyl-(6-hydroxy-1-(2',3',4',6'-tetradeoxy-3'-trifluoroacetamido-4'-iodo-L-lyxohexopyranose)-5,12-dioxo-3,4,5,12-tetrahydroanthraceno [2,3-c]pyran-3-yl)ketone;

BCH-1618: (1'S,1S,3R)-Methyl-(6-hydroxy-1-(2',3',4',6'-tetradeoxy-3'-trifluoroacetamido-4'-iodo-L-lyxohexopyranose)-5,12-dioxo-3,4,5,12-tetrahydroanthraceno [2,3-c]pyran-3-yl)ketone;

BCH-1619: (1'S,1S,3R)-6-Hydroxy-1-[2',3',6'-trideoxy-3'-trifluoroacetamido-L-lyxohexopyranose]-3-(2-aza-3-acetamidothienyl)-5,12-dioxo-3,4,5,12-tetrahydroanthraceno(2,3-C)pyran;

BCH-1626: (1S,1R,3S) and (1S,1S,3R)-1-O-(3',4'-di-O-acetyl-2',6'-dideoxy-α-lyxohexopyranosyl)-1,2,3,4,5, 12-hexahydro-6-hydroxy-3-hydroxyaceto-(2-oxo) naphthacene-5,12-dione;

BCH-1633: (1'S,1S,3S)-3-Ethyl-5,12-dihydroxy-1-(2',3', 6'-trideoxy-3'-amino-4'-hydroxy-L-lyxohexopyranose)-1,2,3,4-tetrahydro-(2-oxygen)naphthacene-6,11-dione-hydrochloride;

BCH-1635: (1'S,1R,3S) and (1'S,1S,3R)-3-aceto-1,2,3,4, 5,12-hexahydro-6-hydroxy-1-N-trifluoroacetyl-L-daunosamine-(2-sulfur)naphthacene-5,12-dione;

BCH-1641: (1'S,1S,3R)-3-Aceto-1,2,3,4,5,12, hexahydro-6-hydroxy-1-N-trifluoroacetyl-L-daunosamine-(2-sulfur)naphthacene-5,12-dione;

BCH-1646: (1'S,1R)-1-[(2',3',6'-trideoxy-3'-acetamido-L-lyxohexopyranosyl)oxy]-6-hydroxy-3,4,5,12-tetrahydro-5,12-dioxo-1H-anthra(2,3-C)pyran;

BCH-1647: (1'S,1S)-1-[(2',3',6'-tetradeoxy-3'-acetamido-L-lyxohexopuranosyl)oxy]-6-hydroxy-3,4,5,12-tetrahydro-5,12-dioxo-1H-anthra(2,3-C)pyran;

BCH-1653: (1'S,1R,3S)-6-Hydroxy-1-(2',3',6'-trideoxy-3'-trifluoroacetamido-L-lyxohexopyranose)-3-diethylaminocarbonyl-5,12-dioxo-3,4,5,12-tetrahydroanthraceno-(2,3-C) pyran;

BCH-1656: (1'S,1R,3S)-6-hydroxy-1-(2',3',6',-trideoxy-3'-trifluoroacetamido-L-lyxohexopyranose)-3-diethylaminocarbonyl-5,12-dioxo-3,4,5,12-tetrahydroanthraceno-(2,3-C)-pyran;

BCH-1671: (1'S,1S,3R)-3-acetyl-1-O-(3',4'-di-O-acetyl-2',6'-dideoxy-α-lyxohexopyranosyl)-1,2,3,4,5,12-hexahydro-6-hydroxy(2-sulfur)naphthacene-5,12-dione;

BCH-1672: (1'S,1R,3S)-Methyl-[5,12-dihydroxy-1-(2',6'-dideoxy-3',4'-dihydroxy-2'-iodo-L-lyxohexopyranose)-6,11-dioxo-3,4,6,11-tetrahydroanthraceno-(2,-C)pyran-3-yl]ketone;

BCH-1675: (1'S,1S,3R)-Methyl-(5,12-dihydroxy-1-(2',6'-dideoxy-3',4'-dihydroxy-2'-iodo-L-lyxohexopyranose)-6,11-dioxo-3,4,6,11-tetrahydroanthraceno(2,3-C)pyran-3-yl]ketone;

BCH-1676 & 1677: (1'S,1R,3S) and (1'S,1S,3R)-5,12-dioxo-3-(1,1-difluoroethyl)-6-hydroxy-1-(2',3',6'-trideoxy-3'-trifluoroacetamido-L-lyxohexopyranose)-3,4,5,12-tetrahydroanthraceno-[2,3-c]-pyran;

BCH-1678: (1'S,1R,3S)-6-hydroxy-1-(2',3',6'-trideoxy-3'-trifluroacetamido-L-lyxohexopyranose)-3-dimethylphosphonoacetyl-5,12-dioxo-3,4,5,12-tetrahydroanthraceno[2,3-C]-pyran;

BCH-1679: (1'S,1S,3R)-6-hydroxy-1-(2',3',6'-trideoxy-3'-trifluroacetamido-L-lyxohexopyranose)-3-dimethylphosphonoacetyl-5,12-dioxo-3,4,5,12-tetrahydroanthraceno-[2,3-C]-pyran;

BCH-1680: (1'S,1S,3R) and (1'S,1R,3S)-Methyl-(6-hydroxy-1-(2',3',4',6'-tetradeoxy-4'-trifluoroacetamido-L-lyxohexopyranose)-5,12-dioxo-3,4,5,12-tetrahydroanthraceno-[2,3-C]pyran-3-yl)ketone;

BCH-1681: (1'S,1S,3R)-Methyl-(1-[2',6'-dideoxy-3',4'-diacetyl- 2'-iodo-L-lyxohexopyranose]-6-hydroxy-3,4,5,10-tetrahydroanthraceno[2,3-c]pyran-3-yl)ketone;

BCH-1683: (1'S,1S,3R) and (1S,1R,3S)-3-(2-aminoethyl)-5,12-dihydroxy-1-(2',3',6'-trideoxy-3',4'-dihydroxy-L-lyxohexopyranose)-6,11-dioxo-3,4,6,11-tetrahydro-1H-anthra[2,3-C]pyran hydrochloride;

BCH-1686: (1'S,1S,3S)-3-(6-hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl) propene;

BCH-1687: (1'S,1R,3R)-3-(6hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl) porpene;

BCH-1694: (1'S,1R,3S)-5,12-dioxo-6-hydroxy-3-methoxymethyl-1-(2',3',6'-trideoxy-3'-trifluoroacetamido-L-lyxohexopyranose)-3,4,5,12-tetrahydroanthraceno-[2,3-C]pyran;

BCH-1696: (1'S,1S,3R)-5,12-dioxo-6-hydroxy-3-methoxymethyl-1-(2',3',6'-trideoxy-3'-trifluoroacetamido-L-lyxohexopyranose)-3,4,5,12-tetrahydroanthraceno-[2,3-C]pyran;

BCH-1698: (1'S,1S)-5,12-dioxo-6-hydroxy-3,3-bis-methoxymethyl-1-(2',3',6'-trideoxy-3'-trifluoroacetamido-L-lyxohexopyranose)-3,4,5,12-tetrahydroanthraceno-[2,3-C]pyran;

BCH-1990: (1'S,1R,3S)-methyl-(1[2',6'-dideoxy-3',4'-dihydroxy-2'-iodo-L-lyxohexopyranose]-5,12-dioxo-3,4,5,12-tetrahydroanthraceno[2,3-C]pyran-3-yl)ketone;

BCH-1991:(1'S,1S)-5,12-dioxo-6-hydroxy-3,3-bis-methoxymethyl-1-(2',3',6'-trideoxy-3'-amino-L-lyxohexopyranose)-3,4,5,12-tetrahydroanthraceno-[2,3-c]-pyran-hydrochloride;

BCH-1992: (1'S,1S,3R) and (1'S,1R,3S)-5,12-dihydroxy-3-methoxymethyl-1-(2',3',6'-trideoxy-3'-amino-L-lyxohexopyranose)-1,2,3,4-tetrahydro-(2-oxygen)-naphthacene-6,11-dione hydrochloride;

BCH-1997: (1'S,1S,3R,13R)-3-dihydroxyethyl-6-hydroxy-1-(N-trifluoroacetyl-L-daunosamine-(2-oxo)naphthacene-5,12-dione;

BCH-2001: (1'S,1R,3S)-3-{6-hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl}(phenyl)sulfone;

BCH-2002: (1'S,1S)-6-hydroxy-1-(2',3',6'-trideoxy-3'-trifluoroacetamido-4'-hydroxy-L-lyxohexopyranose)-5,12-dioxo-5,12-dihydroanthraceno-[2,3-C]pyran;

BCH-2005: (1'S,1R,3R)-3-{6-Hydroxy-1-(2',3',6'-trideoxy-3'amino-4'-hydroxy-L-lyxohexopyranose)-5,12-dioxo-3,4,5,12-tetrahydroanthraceno-[2,3-C]pyran-3-yl}propene hydrochloride;

BCH-2006: (1'S,1S,3S)-3-{6-Hydroxy-1-(2',3',6'-trideoxy-3'-amino-4'-hydroxy-L-lyxohexopyranose)-5,12-dioxo-3,4,5,12-tetrahydroanthraceno-[2,3-C]pyran-3-yl}propene hydrochloride;

BCH-2007: (1'S,1R,3S)-3-{6-Hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]- 3-yl}nitrile;

BCH-2008: (1'S,1S,3R)-3-{6-Hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl}nitrile;

BCH-2012: (1'S,1R,3S)-3-{6-Hydroxy-1-(2',3',6'-trideoxy-3'-amino-4'-hydroxy-L-lyxohexopyranose)-5,12-dioxo-3,4,5,12-tetrahydroanthraceno-[2,3-C]pyran-3-yl}benzene hydrochloride;

BCH-2016: (1'S,1R, 3R)-3-Ethyl-5,12-dihydroxy-1-(2',3',6'-trideoxy-3'-amino-L-lyxohexopyranose)-1,2,3,4-tetrahydro-(2-oxygen)-naphtacene-6,11-dione hydrochloride;

BCH-2025: (1S,1S,3R)-3-{6-hydroxy-1-(2',3',6'-trideoxy-3'-trifluoroacetamido-4'-hydroxy-L-lyxohexopyranose)-5,12-dione-3,4,5,12-tetrahydroanthraceno-[2,3-c]pyran-3-yl)(phenyl)sulfone;

BCH-2048: (1'S,1R,3S)-5,12-dioxo-6-hydroxy-3-phenyloxy-1- (2',3',6'-trideoxy-3'-trifluoroacetamido-L-lyxohexopyranose)-3,4,5,12-tetrahydroanthraceno-[2,3-c] pyran;

BCH-2049: (1'S,1S,3R)-5,12-trihydroxy-3-isopropyl-1-(2',3',6'-trideoxy-3'-amino-L-lyxohexopyranose)-1,2,3,4-tetrahydro-(2-oxygen)-naphtacene-6,11-dione-hydrochloride;

BCH-2050: (1'S,1R,3S)-5,12-Dixydroxy-3-isopropy-1-(2',3',6'-trideoxy-3'-amino 'L-lyxohexopyranose)-1,2,3,4-tetrahydro-(2 -oxygen)-naphtacene-6,11-dione-hydrochloride;

BCH-2055: Diastereomeric mixture of (1'-S,1-R,3-S) and (1'-S,1-S,3-R)(5,12-dihydroxy-1-(2',3',6'-trideoxy-3'-trifluoroacetamido-4'-hydroxy-L-lyxohexopyranose)-6,11-dioxo-3,4,5,12-tetrahydroanthraceno-[2,3-c]pyran-3-yl)nitrile;

BCH-2056: Diastereomeric mixture of (1'-S,1-R,3-S) and (1'-S,3-R)(5,12-dithydroxy-1-(2',3',6'-trideoxy-3'-amino-4'-hydroxy-L-lyxohexopyranose)-6,11-dioxo-3,4,5,12-tetrahydroanthraceno-[2,3-c]pyran-3-yl)nitrile;

BCH-2057: (1'S,1S,3R)-5,12-dioxo-6-hydroxy-3-phenyloxymethyl-1-(2',3',6'-trideoxy-3'-trifluoroacetamido-L-lyxohexopyranose)-3,4,5,12-tetrahydroanthraceno-[2,3-c]pyran;

BCH-2058 & 2059: (1'S,1R,3S) and (1'S,1S,3R)-5,12-Dihydroxy-3-phenyloxymethyl-1-(2',3',6'-trideoxy-3'-amino-L-lyxohexopyranose)-1,2,3,4-tetrahydro-(2-oxygen)-naphthacene-6,11-dione-hydrochloride;

BCH-2063: (1'S,1R,3S)-Methyl-(5,12-dihydroxy-1-(2',3',6'-trideoxy-3'-trifluoroacetamido-2'-iodo-4'-hydroxy-L-lyxohexopyranose)-6,11-dioxo-3,4,6,11-tetrahydroanthraceno-[2,3C]-pyran-3-yl)-ketone;

BCH-2064: (1'S,1S,3R)-Methyl-(1-[2',3',6'-trideoxy-3'-trifluoroacetamido-4'-hydroxy-2'-iodo-L-lyxohexopyranose]-5,12-dioxo-3,4,5,12-tetrahydroanthraceno[2,3-C]pyran-3-yl)ketone;

BCH-2066: (1'S,1R,3S)-Methyl-(5,12-dihydroxy-1-[2',3',6'-trideoxy-3'-amino-4'hydroxy-2'-iodo-L-lyxohexopyranose]-6,11-dioxo-3,4,6,11-tetrahydroanthraceno-[2,3C]-pyran-3-yl)ketone hydrochloride;

BCH-2073: (1'R,1R,3S )-3-Aceto-6-hydroxy-1-(2-deoxy-2-deoxy-2-chloroethylnitrosoureido-D-glucopyranose)-5,12-dioxo-3,4,5,12-tetrahydro-1H-anthra[2,3-c]pyran;

BCH-2074: (1'S,1S,3R )-3-(2-oximoethyl)-5,12-dihydroxy-1-(2,3,6,-trideoxy-3-amino-L-lyxohexopyranose)-6,11-dioxo-3,4, 5,12-tetrahydro-1H-anthra[2,3-C]pyran hydrochloride;

BCH-2080 & 2084: (1'S,1S,4S) and (1'S,1R,4R)-5,12-Dioxo-4-ethyl-6-hydroxy-1-(2',3',6'-trideoxy-3'-trifluoroacetamido-L-lyxohexopyranose)-3,4,5,12-tetrahydroanthraceno-[2,3-c]-pyran;

BCH-2085 & 2086: (1'S,1S,4S) and (1'S,1R,4R)-5,12-Dihydroxy-4-ethyl-1-(2',3',6'-trideoxy-3'-amino-L-lyxohexopyranose)-1,2,3,4-tetrahydro-(2-oxygen)-naphthacene-6,11-dione-hydrochloride;

BCH-2088: (1'S,1S,3S)-5,12-mihydroxy-3-pentyl-1-(2',3',6'-trideoxy-3'-amino-L-lyxohexopyranose)-1,2,3,4-tetrahydro-(2-oxygen)-naphtacene-6,11-dione-hydrochloride;

BCH-2089: (1'S,1R,3R)-5,12-Dihydroxy-3-pentyl-1-(2',3',6'-trideoxy-3'-amino-L-lyxohexopyranose)-1,2,3,4-tetrahydro-(2-oxygen)-naphtacene-6,11-dione-hydrochloride along with its 1'S,1S,3S) diastereomer (4:1);

BCH-2094: A 4.5:1 diastereomeric mixture of (1'-S,1-S, 3-R) and (1'-S,1-R,3-S)-methyl-(6-hydroxy-1-(2',3',4',6'-tetradeoxy-3'-trifluoroacetamido-4'-O-methanesulfonyl-L-lyxohexopyranose)-5,12-dioxo-3,4,5,12-tetrahydroanthraceno[2,3-C]pyran-3-yl)ketone;

BCH-2097: (1'-S,1-R,3-S) and (1'-S,1-S,3-R)(6-Hydroxy-1-(2',3',6'-trideoxy, 3'-trifluoroacetamido-4'-hydroxy-L-lyxohexopyranose)-5,12-dioxo-3,4,5,12-tetrahydroanthraceno[2,3-c]pyran-3-yl)propanone;

BH-2110: (1'-S,1-S,3-S)3-(5,12-Dihydroxy-1-(2',3',6'-trideoxy-3'-(2-chloroethylureido),4'-hydroxy-L-lyxohexopyranose)-6,11-dioxo-3,4,5,12-tetrahydroanthraceno-[2,3-c]pyran-3-yl)propene;

BCH-2111: (1'-S,1-R,3-S) and (1'-S,1-S,3-R)-3-(6-ydroxy-1-(2',3',6'-trideoxy-3'amino-4'-hydrohy-L-lyxohexopyranose)-5–12-dioxo-3,4,5,12-tetrahydroanthraceno[2,3-c]pyran-3yl)propanone hydrochloride;

BCH-2120: (1'S,1R,3S) and (1'S,1R,3S)-Isopropyl-[5,12-dihydroxy-6,11-dioxo-1-(2',3',6'-trideoxy-3'-amino-L-lyxohexopyranose)-3,4,6,11-tetrahydroanthraceno-[2,3-c]-pyran-3-yl]-ketone hydrochloride;

BCH-2133: (1'S,1S,3R) and (1'S,1R,3S)-cyclopropyl-(6-hydroxy-1-((2',3',6'-trideoxy-3'-trifluoroacetamido-4'-hydroxy-L-arabino-hexopyranose)-5,10-dioxo-3,4,5, 12-tetrahydronaphto-[2,3-c]pyran-3-yl)methylene);

BCH-2156: 1S,3R-Methyl(1-[2',3',6'-trideoxy-3'-trifluoroacetamido-4'-hydroxy-1,5-dihydro-L-lyxohexopyranose-2-yl)-6,11-dioxo-3,4,5,12-tetrahydroanthraceno [2,3-c]pyran-3-yl)ketone;

BCH-2188: (1'S,1S,3R)-5,12-dihydroxy-6,11-dioxo-3-isopropenyl-1-(2',3',6'-trideoxy-3'-amino-L-lyxohexopyranose)-3,4,5,12-tetrahydroanthraceno-[2,3-c]-pyran hydrochloride;

BCH-2189: (1'S,1S,3R)-5,12-dihydroxy-6,11-dioxo-3-isopropenyl-1-(2',3',6'-trideoxy-3'-amino-L-lyxohexopyranose)-3,4,5,12-tetrahydroanthraceno-[2,3-c]-pyran hydrochloride;

BCH-2190: (1'S,1S,3R)-5,12-dihydroxy-6,11-dioxo-3-isopropyl-1-(2',3',6'-trideoxy-3'-(4-morpholinyl)-L-lyxohexolpyranose)-3,4,5,12-tetrahydroanthraceno-[2, 3-c]-pyran;

BCH-2192: (1'S,1S,3R)-5,12-dihydroxy-6,11-dioxo-3-isopropyl-1-(2',3',6'-trideoxy-3'(4-morpholinyl)-L-lyxohexopyranose)-3,4,5,12-tetrahydroanthraceno-[2, 3-c]-pyran hydrochloride;

BCH-2195: (1'S,1S,3R)-5,12-dihydroxy-6,11-dioxo-3-isopropyl-1-(2',3',6'-trideoxy-3'(3-cyano-4-morpholinyl)-L-lyxohexopyranose)-3,4,5,12-tetrahydroanthraceno-[2,3-c]-pyran;

BCH-2197 & 2198: (1'S,1S,3S) and (1'S,1R,3R)-aertbutyl-(6-hydroxy-1-(2',3',6'-trideoxy-3'-trifluoroacetamido-4-hydroxy-L-lyxohexopyranose)-5,12-dioxo-3, 4,5,12-tetrahydroanthraceno-[2,3-c]pyran-3-yl)ketone;

BCH-2850: (1'R,1S,3R)-6-Hydroxy-1-(3'-trifluoroacetamido-2',3',6'-trideoxy-L-lyxohexopyranose)-3-t-butoxycarbonyl-5,12-dioxo-3,4,5,12-tetrahydro-1H-anthroceno-[2,3-c]-pyran.

24. A compound according to claim 1 selected from the group consisting of:

BCH-671: (1'S,1R,3S) Methyl (1-[2',3',6'-trideoxyacetamido-4'-hydroxy-L-lyxohexopyranose]-5,12-dioxo-3, 4,5,12-tetra-hydroanthraceno(2,3-c)pyran-3-yl) formate;

BCH-689: (1'S,1R,3S) and (1'S,1S,3R)Ethyl[6-hydroxy-11-methoxy-5,12-dioxo-1-(3'-trifuloroacetamido-1-daunosaminyl)-3,4,5,12-tetrahydroanthraceno(2,3-C)pyran- 3-yl]formate;

BCH-691: (1'S,1R,3S)-Methyl-}11-hydroxy-1-(2',3',6'-trideoxy-3'-trifluoroacetamido-4'-hydroxy-L-lyxoheoxpyranose)-5,12-dioxo-3,4,5,12-tetrahydroanthraceno[2,3-c]pyran-3-yl)formate;

BCH-724: (1'S,1S,3R)-Methyl-[11-hydroxy-1-(2',3',6'-trideoxy-3'-trifluoroacetamido-4'-hydroxy-L-lyxohexopyranose)-5,12-dioxo-2,3,5,12-tetrahydroanthraceno(2,3-C)pyran-3-yl]ketone;

BCH-730: (1'S,1R,3S)Methyl(6-hydroxy-1-(2',3',6'-trideoxy-3'-trifluoroacetamido-4-hydroxy-L-lyxohexopyranose-5,12-dioxo-3,4,5,12-tetrahydroanthraceno(2,3-C) pyran-3-yl]ketone;

BCH-731: (1'S,1R,3S) and (1'S,1S,3R)-3-(2-acetoxy-1-trimethyleneketal)aceto-6-acetoxy-1,2,3,4,5,12-hexahydro-1-N-trifluoroacetyl-L-daunosamine(2-oxygen) naphthacene-5,12-dione; and (1'S,1R,3S) and (1'S,1S,3R)-3-(2-acetoxy-1-trimethyleneketal) aceto-11-acetoxy-1,2,3,4,5,12-hexahydro-1-N-trifluoroacetyl-L-daunosamine(2-oxygen) naphthacene-5,12-dione;

BCH-746: (1'S,1S,3S) and (1'S,1R,3S)-3-(2-acetoxy-1-trimethyleneketal)aceto-1,2,3,4,5,12-hexahydro-6-hydroxy-1-N-trifluoroacetyl-L-daunosamine(2-oxygen) naphthacene-5,12-dione; and (1'S,1S,3R) and (1'S,1R,3S)-3-(2-acetoxy-1-trimethyleneketal) aceto-1,2,3,4,5,12-hexahydro-11-hydroxy-1-N-trifluoroacetyl-L-daunosamine(2-oxygen) naphthacene-5,12-dione;

BCH-1123: (1'S,1S,3R)-Methyl-[6-hydroxy-1-(2',3',6'-trideoxy-3',4'-dihydroxy-L-lyxohexopyranose)-5,12-dioxo-3,4,5,12-tetrahydroanthraceno(2,3-C)pyran-3-yl]ketone;

BCH-1124: (1'S,1R,3S)-Methyl-[6-hydroxy-1-(2',3',6'-trideoxy-3',4'-dihydroxy-L-lyxohexopyranose)-5,12-dioxo-2,3,5,12-tetrahydroxyanthraceno(2,3-C)pyran-3-yl]ketone;

BCH-1127: (1'S,1S,3R)-Methyl-[6-hydroxy-1-(2',3',6'-trideoxy-3'-amino-4'-hydroxy-L -lyxohexopyranose)-5,12-dioxo-3,4,5,12-tetrahydroanthraceno-(2,3-C)pyran-3-yl]ketone hydrochloride;

BCH-1128: (1'S,1R,3S)-Methyl-[6-hydroxy-1-(2',3',6'-trideoxy-3'-amino-4'-hydroxy-L-lyxohexopyranose-5,12-dioxo-3,4,5,12-tetrahydroanthraceno-(2,3-C)pyran-3-yl]ketone hydrochloride;

BCH-1130: (1'S,1S,3R) and (1'S,1R,3S)-Methyl-[5,12-dihydroxy-1-(2',3',6'-trideoxy-3'-amino-4'-hydroxy-L-lyxohexopyranose)-6,11-dioxo-3,4,6,11-tetrahydroanthraceno-( 2,3-C)pyran-3-yl]ketone hydrochloride;

BCH-1187: (1'S,1S,3S)-5,12-Dioxo-3-ethyl-6-hydroxy-1-(2',3',6'-trideoxy-3'-trifluoroacetamido-4'-hydroxy-L-lyxohexopyranose)-3,4,5,12-tetrahydroanthraceno(2,3-C)pyran;

BCH-1191: (1'S,1R,3S) and (1'S,1S,3R)-Methyl(1-(2',3',6'-trideoxy-3'-morpholino-L-lyxohexopyranose)-6,11-dioxo-5,12-dihydroxy-3,4,611tetrahydroanthraceno[2,3-c]pyran-3-yl)ketone;

BCH-1193: (1'S,1R,3S) and (1'S,1S,3R)-Methyl(1-(2',3',6'-trideoxy-3'-morpholino-L-lyxohexopyranose)-6,11-dioxo-5,12-dihydroxy-3,4,611-tetrahydroanthraceno[2,3-c]pyran-3-yl)ketone hydrochloride;

BCH-1194: (1'S,1R,3S)-Methyl-[5,12-dihydroxy-1-(2',3',6'-trideoxy-3'-amino-4'-hydroxy-L-lyxohexopyranose)-6,11-dioxo-3,4,6,11-tetrahydroanthraceno-(2,3-C)pyran-3-yl]ketone hydrochloride;

BCH-1195: (1'S,1S,3R)-Methyl-[5,12-dihydroxy-1-(2',3',6'-trideoxy-3'-amino-4'-hydroxy-L-lyxohexopyranose)-6,11,dioxo-3,4,6,11-tetrahydroanthraceno-(2,3-C)pyran-3-yl]ketone hydrochloride;

BCH-1606: (1'S,1R,3R)-5,12-Dioxo-3-ethyl-6-hydroxy-1-[2',3',6'-trideoxy-3'-trifluoroacetamido-4'-hydroxy-L-lyxohexopyranose]-3,4,5,12-tetrahydroanthraceno(2,3-C)pyran;

BCH-1610: (1'S,1S,3s)-5,12-Dioxo-3-ethyl-6-hydroxy-1-[2',3',6'-trideoxy-3'-amino-4'-hydroxy-L-lyxohexopyranose]-3,4,5,12-tetrahydroanthraceno (2,3-C)pyran hydrochloride;

BCH-1611: (1'S,1R,3S) or (1'S,1S,3R)-1,2,3,4,5,12-hexahydro-6-hydroxy-1-L-daunosamine-3-vinyl(2-oxo)naphthacene- 5,12-dione;

BCH-1614: (1'S,1R,3R)-5,12-Dioxo-3-ethyl-6-hydroxy-1-[2',3',6'-trideoxy-3'-amino-4'-hydroxy-L-lyxohexopyranose]-3,4,5,12-tetrahydroanthraceno (2,3-C)pyran hydrochloride;

BCH-1617: (1'S,1R,3S)-Methyl-(6-hydroxy-1-(2',3',4',6'-tetradeoxy-3'-trifluoroacetamido-4'-iodo-L-lyxohexopyranose)-5,12-dioxo-3,4,5,12-tetrahydroanthraceno[2,3-c]pyran-3-yl)ketone;

BCH-1618: (1'S,1S,3R)-Methyl-(6-hydroxy-1-(2',3',4',6'-tetradeoxy-3'-trifluoroacetamido-4'-iodo-L-lyxohexopyranose)-5,12-dioxo-3,4,5,12-tetrahydroanthraceno[2,3-c]pyran-3-yl)ketone;

BCH-1619: (1'S,1S,3R)-6-Hydroxy-1-[2',3',6'-trideoxy-3'-trifluoroacetamido-L-lyxohexopyranose]-3-(2-aza-3-acetamidothienyl)-5,12-dioxo-3,4,5,12-tetrahydroanthraceno(2,3-C)pyran;

BCH-1626: (1'S,1R,3S) and (1'S,1S,3R)-1-O-(3',4'-di-O-acetyl-2',6'-dideoxy-α-lyxohexopyranosyl)-1,2,3,4,5,12-hexahydro-6-hydroxy-3-hydroxyaceto-(2-oxo)naphthacene-5,12-dione;

BCH-1633: (1'S,1S,3S)-3-Ethyl-5,12-dihydroxy-1-(2',3',6'-trideoxy-3'-amino-4'-hydroxy-L-lyxohexopyranose)-1,2,3,4-tetrahydro-(2-oxygen)naphthacene-6,11-dione-hydrochloride;

BCH-1635: (1'S,1R,3S) and 1'S,1S,3R)-3-aceto-1,2,3,4,5,12-hexahydro-6-hydroxy-1-N-trifluoroacetyl-L-daunosamine-(2-sulfur)naphthacene-5,12-dione;

BCH-1637: (1'S,1S,3R)- and (1'S,1R,3S)-Methyl-(6-hydroxy-1-(2',3',6'-trideoxy-3'-trifluoroacetamido-4-hydroxy-L-arabino-hexopyranose)-5,12-dioxo-3,4,5,12-tetrahydroanthraceno-[2,3-c]pyran-3-yl)ketone;

BCH-1641: (1'S,1S,3R)-3-Aceto-1,2,3,4,5,12,hexahydro-6-hydroxy-1-N-trifluoroacetyl-L-daunosamine-(2-sulfur)naphthacene-5,12-dione;

BCH-1646: (1'S,1R)-1-[(2',3',6'-trideoxy-3'-acetamido-L-lyxohexopyranosyl)oxy]-6-hydroxy-3,4,5,12-tetrahydro-5,12-dioxo-1H-anthra(2,3-C)pyran;

BCH-1647: (1'S,1S)-1-[(2',3',6'-tetradeoxy-3'-acetamido-L-lyxohexopyranosyl)oxy]-6-hydroxy-3,4,5,12-tetrahydro-5,12-dioxo-1H-anthra(2,3-C)pyran;

BCH-1653: (1'S,1R,3S)-6-Hydroxy-1-(2',3',6'-trideoxy-3'-trifluoroacetamido-L-lyxohexopyranose)-3-diethylaminocarbonyl-5,12-dioxo-3,4,5,12-tetrahydroanthraceno-(2,3-C)pyran;

BCH-1656: (1'S,1R,3S)-6-hydroxy-1-(2',3',6',-trideoxy-3'-trifluoroacetamido-L-lyxohexopyranose)-3-diethylaminocarbonyl-5,12-dioxo-3,4,5,12-tetrahydroanthraceno-(2,3-C)-pyran;

BCH-1671: (1'S,1S,3R )-3-acetyl-1-O-(3',4'-di-O-acetyl-2',6'-dideoxy-α-lyxohexopyranosyt)-1,2,3,4,5,12-hexahydro-6-hydroxy(2-sulfur)naphthacene-5,12-dione;

BCH-1672: (1'S,1R,3S)-Methyl-[5,12-dihydroxy-1-(2',6'-dideoxy-3',4'-dihydroxy-2'-iodo-L-lyxohexopyranose)-6,11-dioxo-3,4,6,11-tetrahydroanthraceno-(2,-C)pyran-3-yl]ketone;

BCH-1675: (1'S,1S,3R)-Methyl-(5,12-dihydroxy-1-(2',6'-dideoxy-3',4'-dihydroxy-2'-iodo-L-lyxohexopyranose)-6,11-dioxo-3,4,6,11-tetrahydroanthraceno(2,3-C)pyran-3-yl]ketone;

BCH-1676: (1'S,1R,3S)-5,12-dioxo-3-(1,1-difluoroethyl)-6-hydroxy-1-(2',3',6'-trideoxy-3'-trifluoroacetamido-L-lyxohexopyranose)-3,4,5,12-tetrahydroanthraceno-[2,3-c]-pyran;

BCH-1679: (1'S,1S,3R)-6-hydroxy-1-(2',3',6'-trideoxy-3'-trifluroacetamido-L-lyxohexopyranose)-3-dimethylphosphonoacetyl-5,12-dioxo-3,4,5,12-tetrahydroanthraceno-[2,3-C]-pyran;

BCH-1680: (1'S,1S,3R) and (1'S,1R,3S)-Methyl-(6-hydroxy-1-(2',3',4',6'-tetradeoxy-4'-trifluoroacetamido-L- lyxohexopyranose)-5,12-dioxo-3,4,5,12-tetrahydroanthraceno-[2,3-C]pyran-3-yl)ketone;

BCH-1681: (1'S,1S,3R)-Methyl-(1-[2',6'-dideoxy-3',4'-diacetyl-2'-iodo-L-lyxohexopyranose]-6-hydroxy-3,4,5,10-tetrahydroanthraceno[2,3-c]pyran-3-yl)ketone;

BCH-1683: (1'S,1S,3R) and (1'S,1R,3S)-3-(2-aminoethyl)-5,12-dihydroxy-1-(2',3',6'-trideoxy-3',4'-dihydroxy-L-lyxohexopyranose)-6,11-dioxo-3,4,6,11-tetrahydro-1H-anthra[2,3-C]pyran hydrochloride;

BCH-1686: (1'S,1S,3S)-3-(6-hydroxy-1-(2',3',6'-trideoxy-3'-trifluoroacetamido-4'-hydroxy-L-lyxohexopyranose)-5,12-dioxo-3,4,5,12-tetrahydroanthraceno[2,3-C]pyran-3-yl)propene;

BCH-1687: (1'S,1R,3R)-3-(6hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl)porpene;

BCH-1694: (1'S,1R,3S)-5,12-dioxo-6-hydroxy-3-methoxymethyl-1-(2',3',6'-trideoxy-3'-trifluoroacetamido-L-lyxohexopyranose)-3,4,5,12-tetrahydroanthraceno-[2,3-C]pyran;

BCH-1696: (1'S,1S,3R)-5,12-dioxo-6-hydroxy-3-methoxymethyl-1-(2',3',6'-trideoxy-3'-trifluoroacetamido-L-lyxohexopyranose)-3,4,5,12-tetrahydroanthraceno-[2,3-C]pyran;

BCH-1698: (1'S,1S)-5,12-dioxo-6-hydroxy-3,3-bismethoxymethyl-1-(2',3',6'-trideoxy-3'-trifluoroacetamido-L-lyxohexopyranose)-3,4,5,12-tetrahydroanthraceno-[2,3-C]pyran;

BCH-1990: (1'S,1R,3S)-methyl-(1[2',6'-dideoxy-3',4'-dihydroxy-2'-iodo-L-lyxohexopyranose]-5,12-dioxo-3,4,5,12-tetrahydroanthraceno[2,3-C]pyran-3-yl)ketone;

BCH-1991:(1'S,1S)-5,12-dioxo-6-hydroxy-3,3-bis-methoxymethyl-1-(2',3',6'-trideoxy-3'-amino-L-lyxohexopyranose)-3,4,5,12-tetrahydroanthraceno-[2,3-c]-pyran-hydrochloride;

BCH-1992: (1'S,1S,3R) and (1'S,1R,3S)-5,12-dihydroxy-3-methoxymethyl-1-(2',3',6'-trideoxy-3'-amino-L-lyxohexopyranose)-1,2,3,4-tetrahydro-(2-oxygen)-naphthacene-6,11-dione hydrochloride;

BCH-1997: (1'S,1S,3R,13R)-3-dihydroxyethyl-6-hydroxy-1-(N-trifluoroacetyl-L-daunosamine-(2-oxo)naphthacene-5,12-dione (tent ass);

BCH-2001: (1'S,1R,3S)-3-{6-hydroxy-1-(2',3',6'-trideoxy-3'trifluoroacetamido-4'-hydroxy-L-lyxohexopyranose)-5,12-dioxo-3,4,5,12-tetrahydroanthraceno-[2,3-C]pyran-3-yl}(phenyl)sulfone;

BCH-2002: (1'S,1S)-6-hydroxy-1-(2',3',6'-trideoxy-3'-trifluoroacetamido-4'-hydroxy-L-lyxohexopyranose)-5,12-dioxo-5,12-dihydroanthraceno-[2,3-C]pyran;

BCH-2005: (1'S,1R,3R)-3-{6-Hydroxy-1-(2',3',6'-trideoxy-3'amino-4'-hydroxy-L-lyxohexopyranose)-5,12-dioxo-3,4,5,12-tetrahydroanthraceno-[2,3-C]pyran-3-yl}propene hydrochloride;

BCH-2006: (1'S,1S,3S)-3-{6-Hydroxy-1-(2',3',6'-trideoxy-3'-amino-4'-hydroxy-L-lyxohexopyranose)-5,12-dioxo-3,4,5,12-tetrahydroanthraceno-[2,3-C]pyran-3-yl}propene hydrochloride;

BCH-2007: (1'S,1R,3S)-3-{6-Hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]-yran-3-yl}nitrile;

BCH-2008: (1'S,1S,3R)-3-{6-Hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl}nitrile;

BCH-2012: (1'S,1R,3S)-3-{6-Hydroxy-1-(2',3',6'-trideoxy-3'-amino-4'-hydroxy-L-lyxohexopyranose)-5,12-dioxo-3,4,5,12-tetrahydroanthraceno-[2,3-C]pyran-3-yl}benzene hydrochloride;

BCH-2016: (1'S,1R,3R)-3-Ethyl-5,12-dihydroxy-1-(2',3',6'-trideoxy-3'-amino-L-lyxohexopyranose)-1,2,3,4-tetrahydro-(2-oxygen)-naphtacene-6,11-dione hydrochloride;

BCH-2025: (1'S,1S,3R)-3-{6-hydroxy-1-(2',3',6'-trideoxy-3'-trifluoroacetamido-4'-hydroxy-L-lyxohexopyranose)-5,12-dione-3,4,5,12-tetrahydroanthraceno-[2,3-c]pyran-3-yl}(phenyl)sulfone;

BCH-2049: (1'S,1S,3R)-5,12-rihydroxy-3-isopropyl-1-(2',3',6'-trideoxy-3'-amino-L-lyxohexopyranose)-1,2,3,4-tetrahydro-(2-oxygen)-naphtacene-6,11-dione-hydrochloride;

BCH-2050: (1'S,1R,3S)-5,12-Dixydroxy-3-isopropy-1-(2',3',6'-trideoxy- 3'-amino 'L-lyxohexopyranose)-1,2,3,4-tetrahydro-(2-oxygen)-naphtacene-6,11-dione-hydrochloride;

BCH-2055: Diastereomeric mixture of (1'-S,1-R,3-S) and (1'-S,1-S,3-R)(5,12-dihydroxy-1-(2',3',6'-trideoxy-3'-trifluoroacetamido-4'hydroxy-L-lyxohexopyranose)-6,11-dioxo-3,4,5,12-tetrahydroanthraceno-[2,3-c]pyran-3-yl)nitrile;

BCH-2056: Diastereomeric mixture of (1'-S,1-R,3-S) and (1'-S,3-R)(5,12-dithydroxy-1-(2',3',6'-trideoxy-3'-amino-4'-hydroxy-L-lyxohexopyranose)-6,11-dioxo-3,4,5,12-tetrahydroanthraceno-[2,3-c]pyran-3-yl)nitrile;

BCH-2057: (1'S,1S,3R)-5,12-dioxo-6-hydroxy-3-phenyloxymethyl-1-(2',3',6'-trideoxy-3'-trifluoroacetamido-L-lyxohexopyranose)-3,4,5,12-tetrahydroanthraceno-[2,3-c]pyran;

BCH-2058 & 2059: (1'S,1R,3S) and (1'S,1S,3R)-5,12-Dihydroxy-3-phenyloxymethyl-1-(2',3',6'-trideoxy-3'-amino-L-lyxohexopyranose)-1,2,3,4-tetrahydro-(2-oxygen)-naphthacene-6,11-dione-hydrochloride;

BCH-2063: (1'S,1R,3S)-Methyl-(5,12-dihydroxy-1-(2',3',6'-trideoxy-3'-trifluoroacetamido-2'-iodo-4'-hydroxy-L-lyxohexopyranose)-6,11-dioxo-3,4,6,11-tetrahydroanthraceno-[2,3C]-pyran-3-yl)-ketone;

BCH-2064: (1'S,1S,3R)-Methyl-(1-[2',3',6'-trideoxy-3'-trifluoroacetamido-4'-hydroxy-2'-iodo-L-lyxohexopyranose]-5,12-dioxo-3,4,5,12-tetrahydroanthraceno[2,3-C]pyran-3-yl)ketone;

BCH-2066: (1'S,1R,3S)-Methyl-(5,12-dihydroxy-1-[2',3',6'-trideoxy-3'-amino-4'hydroxy-2'-iodo-L-lyxohexopyranose]-6,11-dioxo-3,4,6,11-tetrahydroanthraceno-[2,3C]-pyran-3-yl)ketone hydrochloride;

BCH-2074: (1'S,1S,3R)-3-(2-oximoethyl)-5,12-dihydroxy-1-(2,3,6,-trideoxy-3-amino-L-lyxohexopyranose)-6,11-dioxo-3,4,5,12-tetrahydro-1H-anthra[2,3-C]pyran hydrochloride;

BCH-2080: (1'S,1S,4S)-5,12-Dioxo-4-ethyl-6-hydroxy-1-(2',3',6'-trideoxy-3'-trifluoroacetamido-L-lyxohexopyranose)-3,4,5,12-tetrahydroanthraceno-[2,3-c]-pyran;

BCH-2085 & 2086: (1'S,1S,4S) and (1'S,1R,4R)-5,12-Dihydroxy-4-ethyl-1-(2',3',6'-trideoxy-3'-amino-L-lyxohexopyranose)-1,2,3,4-tetrahydro-(2-oxygen)-naphthacene-6,11-dione-hydrochloride;

BCH-2088: (1'S,1S,3S)-5,12-mihydroxy-3-pentyl-1-(2',3',6'-trideoxy-3'-amino-L-lyxohexopyranose)-1,2,3,4- tetrahydro-(2-oxygen)-naphtacene-6,11-dione-hydrochloride;

BCH-2089: (1'S,1R,3R)-5,12-Dihydroxy-3-pentyl-1-(2',3',6'-trideoxy-3'-amino-L-lyxohexopyranose)-1,2,3,4-tetrahydro-(2-oxygen)-naphtacene-6,11-dione-hydrochloride along with its 1'S,1S,3S) diastereomer (4:1);

BCH-2097: (1'-S,1-R,3-S) and (1'-S,1-S,3-R)(6-Hydroxy-1-(2',3',6'-trideoxy, 3'-trifluoroacetamido-4'-hydroxy-L-lyxohexopyranose)-5,12-dioxo-3,4,5,12-tetrahydroanthrceno[2,3-c]pyran-3-yl)propanone;

BH-2110: (1'-S,1-S,3-S)3-(5,12-Dihydroxy-1-(2',3',6'-trideoxy-3'-(2-chloroethylureido),4'-hydroxy-L-lyxohexopyranose)-6,11-dioxo-3,4,5,12-tetrahydroanthraceno-[2,3-c]pyran-3-yl)propene;

BCH-2111: (1'-S,1-R,3-S) and (1'-S,1-S,3-R)-3-(6-ydroxy-1-(2',3',6'-trideoxy-3'amino-4'-hydrohy-L-lyxohexopyranose)-5–12-dioxo-3,4,5,12 -tetrahydroanthraceno[2,3-c]pyran-3yl)propanone hydrochloride;

BCH-2120: (1'S,1R,3S) and (1'S,1R,3S)-Isopropyl-[5,12-dihydroxy-6,11-dioxo-1-(2',3',6'-trideoxy-3'-amino-L-lyxohexopyranose)-3,4,6,11-tetrahydroanthraceno-[2,3-c]-pyran-3-yl]-ketone hydrochloride;

BCH-2133: (1'S,1S,3R) and (1'S,1R,3S)-cyclopropyl-(6-hydroxy-1-((2',3',6'-trideoxy-3'-trifluoroacetamido-4'-hydroxy-L-arabino-hexopyranose)-5,10-dioxo- 3,4,5,12-tetrahydronaphto-[2,3-c]pyran-3-yl)methylene);

BCH-2156 : 1S,3R-Methyl(1-[2',3',6'-trideoxy-3'-trifluoroacetamido-4'-hydroxy-1,5-dihydro-L-lyxohexopyranose-2-yl)-6,11-dioxo-3,4,5,12-tetrahydroanthraceno [2,3-c]pyran-3-yl)ketone;

BCH-2188: (1'S,1S,3R)-5,12-dihydroxy-6,11-dioxo-3-isopropenyl-1-(2',3',6'-trideoxy-3'-amino-L-lyxohexopyranose)-3,4,5,12-tetrahydroanthraceno-[2,3-c]-pyran hydrochloride;

BCH-2189: (1'S,1R,3S)-5,12-dihydroxy-6,11-dioxo-3-isopropenyl-1-(2',3',6'-trideoxy-3'-amino-L-lyxohexopyranose)-3,4,5,12-tetrahydroanthraceno-[2,3-c]-pyran hydrochloride;

BCH-2190: (1'S,1S,3R)-5,12-dihydroxy-6,11-dioxo-3-isopropyl-1-(2',3',6-trideoxy-3'-(4-morpholinyl)-L-lyxohexopyranose)-3,4,5,12-tetrahydroanthraceno-[2,3-c]-pyran;

BCH-2192: (1'S,1S,3R)-5,12-dihydroxy-6,11-dioxo-3-isopropyl-1-(2',3',6'-trideoxy-3'(4-morpholinyl)-L-lyxohexopyranose)-3,4,5,12-tetrahydroanthraceno-[2,3-c]-pyran hydrochloride;

BCH-2197 & 2198: (1'S,1S,3S) and (1'S,1R,3R)-aert-butyl-(6-hydroxy-1-(2',3',6'-trideoxy-3'-trifluoroacetamido-4 -hydroxy-L-lyxohexopyranose)-5,12-dioxo-3,4,5,12-tetrahydroanthraceno-[2,3-c]pyran-3-yl)ketone; and BCH-2850: (1'R,1S,3R)-6-Hydroxy-1-(3'-trifluoroacetamido-2',3',6'-trideoxy-L-lyxohexopyranose)-3-t-butoxycarbonyl-5,12-dioxo-3,4,5,12-tetrahydroanthroceno-[2,3-c]-pyran.

25. A compound according to claim 1 selected from the group consisting of:

BCH-691: (1'S,1R,3S)-Methyl-{11-hydroxy-1-(2',3',6'-trideoxy-3'-trifluoroacetamido-4'-hydroxy-L-lyxoheoxpyranose)-5,12-dioxo-3,4,5,12-tetrahydroanthraceno[2,3-c]pyran-3-yl}formate;

BCH-724: (1'S,1S,3R)-Methyl-[11-hydroxy-1-(2',3',6'-trideoxy-3'-trifluoroacetamido-4'-hydroxy-L-lyxohexopyranose)-5,12-dioxo-2,3,5,12-tetrahydroanthraceno(2,3-C)pyran-3-yl]ketone;

BCH-731: (1'S,1R,3S) and (1'S,1S,3R)-3-(2-acetoxy-1-trimethyleneketal)aceto-6-acetoxy-1,2,3,4,5,12-hexahydro-1-N-trifluoroacetyl-L-daunosamine(2-oxygen)naphthacene-5,12-dione; and
(1'S,1R,3S) and (1'S,1S,3R)-3-(2-acetoxy-1-trimethyleneketal) aceto-11-acetoxy-1,2,3,4,5,12-hexahydro-1-N-trifluoroacetyl-L-daunosamine(2-oxygen) naphthacene-5,12-dione;

BCH-1123: (1'S,1S,3R)-Methyl-[6-hydroxy-1-(2',3',6'-trideoxy-3',4'-dihydroxy-L-lyxohexopyranose)-5,12-dioxo-3,4,5,12 -tetrahydroanthraceno(2,3-C )pyran-3-yl]ketone;

BCH-1127: (1'S,1S,3R)-Methyl-[6-hydroxy-1-(2',3',6'-trideoxy-3'-amino-4'-hydroxy-L-lyxohexopyranose)-5,12-dioxo-3,4,5,12-tetrahydroanthraceno-(2,3-C)pyran-3-yl]ketone hydrochloride;

BCH-1128: (1'S,1R,3S)-Methyl-[6-hydroxy-1-(2',3',6'-trideoxy-3'-amino-4'-hydroxy-L-lyxohexopyranose-5,12-dioxo-3,4,5,12-tetrahydroanthraceno-(2,3-C)pyran-3-yl]ketone hydrochloride;

BCH-1130: (1'S,1S,3R) and 1'S,1R,3S)-Methyl-[5,12-dihydroxy-1-(2',3',6 '-trideoxy-3 '-amino-4'-hydroxy-L-lyxohexopyranose)-6,11-dioxo-3,4,6,11-tetrahydroanthraceno-(2,3-C )pyran-3-yl]ketone hydrochloride;

BCH-1187: (1'S,1S,3S)-5,12-Dioxo-3-ethyl-6-hydroxy-1-(2',3',6'-trideoxy-3'-trifluoroacetamido-4'-hydroxy-L-lyxohexopyranose)-3,4,5,12-tetrahydroanthraceno(2,3 -C)pyran;

BCH-1191: (1'S,1R,3S) and (1'S,1S,3R)-Methyl(1-(2',3',6'-trideoxy-3'-morpholino-L-lyxohexopyranose)-6,11-dioxo-5,12-dihydroxy-3,4,611-tetrahydroanthraceno [2,3-c]pyran-3-yl)ketone;

BCH-1194: (1'S,1R,3S)-Methyl-[5,12-dihydroxy-1-(2',3',6'-trideoxy-3'-amino-4'-hydroxy-L-lyxohexopyranose)-6,11-dioxo-3,4,6,11-tetrahydroanthraceno-(2,3-C)pyran-3-yl]ketone hydrochloride;

BCH-1195: (1'S,1S,3R)-Methyl-[5,12-dihydroxy-1-(2',3',6'-trideoxy-3'-amino-4'-hydroxy-L-lyxohexopyranose)-6,11,dioxo-3,4,6,11-tetrahydroanthraceno-(2,3-C)pyran-3-yl]ketone hydrochloride;

BCH-1606: (1'S,1R,3R)-5,12-Dioxo-3-ethyl-6-hydroxy-1-[2',3',6'-trideoxy-3'-trifluoroacetamido-4'-hydroxy-L-lyxohexopyranose]-3,4,5,12-tetrahydroanthraceno(2,3-C)pyran;

BCH-1610: (1'S,1S,3s)-5,12-Dioxo-3-ethyl-6-hydroxy-1-[2',3',6'-trideoxy-3'-amino-4'-hydroxy-L-lyxohexopyranose]-3,4,5,12-tetrahydroanthraceno (2,3-C)pyran hydrochloride;

BCH-1614: (1'S,1R,3R)-5,12-Dioxo-3-ethyl-6-hydroxy-1-[2',3',6'-trideoxy-3'-amino-4'-hydroxy-L-lyxohexopyranose]-3,4,5,12-tetrahydroanthraceno (2,3-C)pyran hydrochloride;

BCH-1617: (1'S,1R,3S)-Methyl-(6-hydroxy-1-(2',3',4',6'-tetradeoxy-3'-trifluoroacetamido-4'-iodo-L-lyxohexopyranose)-5,12-dioxo-3,4,5,12-tetrahydroanthraceno [2,3-c]pyran-3-yl]ketone;

BCH-1633: (1'S,1S,3S)-3-Ethyl-5,12-dihydroxy-1-(2',3',6'-trideoxy-3'-amino-4'-hydroxy-L-lyxohexopyranose)-1,2,3,4-tetrahydro-(2-oxygen)naphthacene-6,11-dione-hydrochloride;

BCH-1641: (1'S,1S,3R)-3-Aceto-1,2,3,4,5,12, hexahydro-6-hydroxy-1-N-trifluoroacetyl-L-daunosamine-(2-sulfur)naphthacene-5,12-dione;

BCH-1672: (1'S,1R,3S)-Methyl-[5,12-dihydroxy-1-(2',6'-dideoxy-3',4'-dihydroxy-2'-iodo-L-lyxohexopyranose)-6,11-dioxo-3,4,6,11-tetrahydroanthraceno-(2,-C)pyran-3-yl]ketone;

BCH-1679: (1'S,1S,3R)-6-hydroxy-1-(2',3',6'-trideoxy-3'-trifluroacetamido-L-lyxohexopyranose)-3-dimethylphosphonoacetyl-5,12-dioxo-3,4,5,12-tetrahydroanthraceno-[2,3-C]-pyran;

BCH-1681: (1'S,1S,3R)-Methyl-(1-[2',6'-dideoxy-3',4'-diacetyl-2'-iodo-L-lyxohexopyranose]-6-hydroxy-3,4,5,10-tetrahydroanthraceno[2,3-c]pyran-3-yl)ketone;

BCH-1686: (1'S,1S,3S)-3-(6-hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl)propene;

BCH-1687: (1'S,1R,3R)-3-(6hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl)porpene;

BCH-1696: (1'S,1S,3R)-5,12-dioxo-6-hydroxy-3-methoxymethyl-1-(2',3',6'-trideoxy-3'-trifluoroacetamido-L-lyxohexopyranose)-3,4,5,12-tetrahydroanthraceno-[2,3-C]pyran;

BCH-1698: (1'S,1S)-5,12-dioxo-6-hydroxy-3,3-bis methoxymethyl-1-(2',3',6'-trideoxy-3'-trifluoroacetamido-L-lyxohexopyranose)-3,4,5,12-tetrahydroanthraceno-[2,3-C]pyran;

BCH-1991: (1'S,1S)-5,12-dioxo-6-hydroxy-3,3-bis methoxymethyl-1-(2',3',6'-trideoxy-3'-amino-L-lyxohexopyranose)-3,4,5,12-tetrahydroanthraceno-[2,3-c]-pyran-hydrochloride;

BCH-1992: (1'S,1S,3R) and (1'S,1R,3S)-5,12-dihydroxy-3-methoxymethyl-1-(2',3',6'-trideoxy-3'-amino-L-lyxohexopyranose)- 1,2,3,4-tetrahydro-(2-oxygen)-naphthacene-6,11-dione hydrochloride;

BCH-2002: (1'S,1S)-6-hydroxy-1-(2',3',6'-trideoxy-3'-trifluoroacetamido-4'-hydroxy-L-lyxohexopyranose)-5,12-dioxo-5,12-dihydroanthraceno-[2,3-C]pyran;

BCH-2006: (1'S,1S,3S)-3-{6-Hydroxy-1-(2',3',6'-trideoxy-3'-amino-4'-hydroxy-L-lyxohexopyranose)-5,12-dioxo-3,4,5,12-tetrahydroanthraceno-[2,3-C]pyran-3-yl}propene hydrochloride;

BCH-2007: (1'S,1R,3S)-3-{6-Hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]-yran-3-yl}nitrile;

BCH-2008: (1'S,1S,3R)-3-{6-Hydroxy-1-(2',3',6'-trideoxy-3'trifluoroacetamido-4'-hydroxy-L-lyxohexopyranose)-5,12-dioxo-3,4,5,12-tetrahydroanthraceno-[2,3-C]pyran-3-yl}nitrile;

BCH-2012: (1'S,1R,3S)-3-{6-Hydroxy-1-(2',3',6'-trideoxy-3'-amino-4'-hydroxy-L-lyxohexopyranose)-5,12-dioxo-3,4,5,12-tetrahydroanthraceno-[2,3-C]pyran-3-yl}benzene hydrochloride;

BCH-2016: (1'S,1R,3R)-3-Ethyl-5,12-dihydroxy-1-(2',3',6'-trideoxy-3'-amino-L-lyxohexopyranose)-1,2,3,4-tetrahydro-(2-oxygen)-naphtacene-6,11-dione hydrochloride;

BCH-2049: (1'S,1S,3R)-5,12-rihydroxy-3-isopropyl-1-(2',3',6'trideoxy-3'-amino-L-lyxohexopyranose)-1,2,3,4-tetrahydro-(2-oxygen)-naphtacene-6,11-dione-hydrochloride;

BCH-2050: (1'S,1R,3S)-5,12-Dixydroxy-3-isopropy-1-(2',3',6'-trideoxy- 3'-amino 'L-lyxohexopyranose)-1,2,3,4-tetrahydro-(2-oxygen)-naphtacene-6,11-dione-hydrochloride;

BCH-2055: Diastereomeric mixture of (1'-S,1-R,3-S) and (1'-S,1-S,3-R)(5,12-dihydroxy-1-(2',3',6'-trideoxy-3'-trifluoroacetamido-4'hydroxy-L-lyxohexopyranose)-6,11-dioxo-3,4,5,12-tetrahydroanthraceno-[2,3-c]pyran-3-yl)nitrile;

BCH-2056: Diastereomeric mixture of (1'-S,1-R,3-S) and (1'-S,3-R)(5,12-dithydroxy-1-(2',3',6'-trideoxy-3'-amino-4'-hydroxy-L-lyxohexopyranose)-6,11-dioxo-3,4,5,12-tetrahydroanthraceno-[2,3-c]pyran-3-yl)nitrile;

BCH-2057: (1'S,1S,3R)-5,12-dioxo-6-hydroxy-3-phenyloxymethyl-1-(2',3',6'-trideoxy-3'-trifluoroacetamido-L-lyxohexopyranose)-3,4,5,12-tetrahydroanthraceno-[2,3-c]pyran;

BCH-2058 & 2059: (1'S,1R,3S) and (1'S,1S,3R)-5,12-Dihydroxy-3-phenyloxymethyl-1-(2',3',6'-trideoxy-3'-amino-L-lyxohexopyranose)-1,2,3,4-tetrahydro-(2-oxygen)-naphthacene-6,11-dione-hydrochloride;

BCH-2063: (1'S,1R,3S)-Methyl-(5,12-dihydroxy-1-(2',3',6'-trideoxy-3'-trifluoroacetamido-2'-iodo-4'-hydroxy-L-lyxohexopyranose)-6,11-dioxo-3,4,6,11-tetrahydroanthraceno-[2,3C]-pyran-3-yl)-ketone;

BCH-2066: (1'S,1R,3S)-Methyl-(5,12-dihydroxy-1-[2',3',6'-trideoxy-3'-amino-4'hydroxy-2'-iodo-L-lyxohexopyranose]-6,11-dioxo-3,4,6,11-tetrahydroanthraceno-[2,3C]-pyran-3-yl)ketone hydrochloride;

BCH-2085 & 2086: (1'S,1S,4S) and (1'S,1R,4R)-5,12-Dihydroxy-4-ethyl-1-(2',3',6'-trideoxy-3'-amino-L-lyxohexopyranose)-1,2,3,4-tetrahydro-(2-oxygen)-napthacene- 6,11-dione-hydrochloride;

BCH-2088: (1'S,1S,3S)-5,12-mihydroxy-3-pentyl-1-(2',3',6'-trideoxy-3'-amino-L-ilyxohexopyranose)-1,2,3,4-tetrahydro-(2-oxygen)-naphtacene-6,11-dione-hydrochloride;

BCH-2089: (1'S,1R,3R)-5,12-Dihydroxy-3-pentyl-1-(2',3',6'-trideoxy-3'-amino-L-lyxohexopyranose)-1,2,3,4-tetrahydro-(2-oxygen)-naphtacene-6,11-dione-hydrochloride along with its (1'S,1S,3S) diastereomer (4:1);

BH-2110: (1'-S,1-S,3-S)3-(5,12-Dihydroxy-1-(2',3',6'-trideoxy-3'-(2-chloroethylureido),4'-hydroxy-L-lyxohexopyranose)-6,11-dioxo-3,4,5,12-tetrahydroanthraceno-[2,3-c]pyran-3-yl)propene;

BCH-2120: (1'S,1R,3S) and (1'S,1R,3S)-Isopropyl-[5,12-dihydroxy-6,11-dioxo-1-(2',3',6'-trideoxy-3'-amino-L-lyxohexopyranose)-3,4,6,11-tetrahydroanthraceno-[2,3-c]-pyran-3-yl]-ketone hydrochloride;

BCH-2188: (1'S,1S,3R)-5,12-dihydroxy-6,11-dioxo-3-isopropenyl-1-(2',3',6'-trideoxy-3'-amino-L-lyxohexopyranose)-3,4,5,12-tetrahydroanthraceno-[2,3-c]-pyran hydrochloride; and BCH-2189: (1'S,1R,3S)-5,12-dihydroxy-6,11-dioxo-3-isopropenyl-1-(2',3',6'-trideoxy-3'-amino-L-lyxohexopyranose)-3,4,5,12-tetrahydroanthraceno-[2,3-c]-pyran hydrochloride.

26. A compound according to claim 1 selected from the group consisting of:

BCH-1128: (1'S,1R,3S)-Methyl-[6-hydroxy-1-(2',3',6'-trideoxy-3'-amino-4'-hydroxy-L-lyxohexopyranose-5,12-dioxo-3,4,5,12-tetrahydroanthraceno-(2,3-C)pyran-3-yl]ketone hydrochloride;

BCH-1130: (1'S,1S,3R) and (1'S,1R,3S)-Methyl-[5,12-dihydroxy-1-(2',3',6'-trideoxy-3'-amino-4'-hydroxy-L-lyxohexopyranose)-6,11-dioxo-3,4,6,11-tetrahydroanthraceno-(2,3-C)pyran-3-yl]ketone hydrochloride;

BCH-1194: (1'S,1R,3S)-Methyl-[5,12-dihydroxy-1-(2',3', 6'-trideoxy-3'-amino-4'-hydroxy-L-lyxohexopyranose)-6,11-dioxo-3,4,6,11-tetrahydroanthraceno-(2,3-C)pyran-3-yl]ketone hydrochloride;

BCH-1633: (1'S,1S,3S)-3-Ethyl-5,12-dihydroxy-1-(2',3', 6'-trideoxy-3'-amino-4'-hydroxy-L-lyxohexopyranose)-1,2,3,4-tetrahydro-(2-oxygen)naphthacene-6,11-dione-hydrochloride;

BCH-1672: (1'S,1R,3S)-Methyl-[5,12-dihydroxy-1-(2', 6'-trideoxy-3',4'-dihydroxy-2'-iodo-L-lyxohexopyranose)-6,11-dioxo-3,4,6,11-tetrahydroanthraceno-(2,-C)pyran-3-yl]ketone;

BCH-1681: (1'S,1S,3R)-Methyl-(1-[2',6'-dideoxy-3',4'-diacetyl-2'-iodo-L-lyxohexopyranose]-6-hydroxy-3,4, 5,10-tetrahydroanthraceno[2,3-c]pyran-3-yl)ketone;

BCH-1992: (1'S,1S,3R) and (1'S,1R,3S)-5,12-dihydroxy-3-methoxymethyl-1-(2',3',6'-trideoxy-3'-amino-L-lyxohexopyranose)-1,2,3,4-tetrahydro-(2-oxygen)-naphthacene-6,11-dione hydrochloride;

BCH-2007: (1'S,1R,3S)-3-{6-Hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]-yran-3-yl}nitrile;

BCH-2008: (1'S,1S,3R)-3-{6-Hydroxy-1-(2',3',6'-trideoxy-3'-trifluoroacetamido-4'-hydroxy-L-lyxohexopyranose)-5,12-dioxo-3,4,5,12-tetrahydroanthraceno-[2,3-C]pyran-3-yl}nitrile;

BCH-2016: (1'S,1R,3R)-3-Ethyl-5,12-dihydroxy-1-(2',3', 6'-trideoxy-3'-amino-L-lyxohexopyranose)-1,2,3,4-tetrahydro-(2-oxygen)-naphtacene-6,11-dione hydrochloride;

BCH-2049: (1'S,1S,3R)-5,12-rihydroxy-3-isopropyl-1-(2',3',6'-trideoxy-3'-amino-L-lyxohexopyranose)-1,2,3, 4-tetrahydro-(2-oxygen)-naphtacene-6,11-dione-hydrochloride;

BCH-2050: (1'S,1R,3S)-5,12-Dixydroxy-3-isopropy-1-(2',3',6'-trideoxy-3'-amino 'L-lyxohexopyranose)-1,2,3, 4-tetrahydro-(2-oxygen)-naphtacene-6,11-dione-hydrochloride;

BCH-2056: Diastereomeric mixture of (1'-S,1-R,3-S) and (1'-S,3-R)(5,12-dithydroxy-1-(2',3',6'-trideoxy-3'-amino-4'-hydroxy-L-lyxohexopyranose)-6,11-dioxo-3, 4,5,12-tetrahydroanthraceno-[2,3-c]pyran-3-yl)nitrile;

BCH-2058 & 2059: (1'S,1R,3S) and (1'S,1S,3R)-5,12-Dihydroxy-3-phenyloxymethyl-1-(2',3',6'-trideoxy-3'-amino-L-lyxohexopyranose)-1,2,3,4-tetrahydro-(2-oxygen)-naphthacene-6,11-dione-hydrochloride;

BCH-2066: (1'S,1R,3S)-Methyl-(5,12-dihydroxy-1-[2',3', 6'-trideoxy-3'-amino-4'hydroxy-2'-iodo-L-lyxohexopyranose]-6,11-dioxo-3,4,6,11-tetrahydroanthraceno-[2, 3C]-pyran-3-yl) ketone hydrochloride;

BCH-2086: (1'S,1R,4R)-5,12-Dihydroxy-4-ethyl-1-(2',3', 6'-trideoxy-3'-amino-L-lyxohexopyranose)-1,2,3,4-tetrahydro-(2-oxygen)-naphthacene-6,11-dione-hydrochloride;

BCH-2088: (1'S,1S,3S)-5,12-mihydroxy-3-pentyl-1-(2', 3',6'-trideoxy-3'-amino-L-lyxohexopyranose)-1,2,3,4-tetrahydro-(2-oxygen)-naphtacene-6,11-dione-hydrochloride;

BCH-2089: (1'S,1R,3R)-5,12-Dihydroxy-3-pentyl-1-(2', 3',6'-trideoxy-3'-amino-L-lyxohexopyranose)-1,2,3,4-tetrahydro-(2-oxygen)-naphtacene-6,11-dione-hydrochloride along with its (1'S,1S,3S) diastereomer (4:1);

BCH-2120: (1'S,1R,3S) and (1'S,1R,3S)-Isopropyl-[5,12-dihydroxy-6,11-dioxo-1-(2',3',6'-trideoxy-3'-amino-L-lyxohexopyranose)-3,4,6,11-tetrahydroanthraceno-[2, 3-c]-pyran-3-yl]-ketone hydrochloride;

BCH-2188: (1'S,1S,3R)-5,12-dihydroxy-6,11-dioxo-3-isopropenyl-1-(2',3',6'-trideoxy-3'-amino-L-lyxohexopyranose)-3,4,5,12-tetrahydroanthraceno-[2,3-c]-pyran hydrochloride; and BCH-2189: (1'S,1R,3S)-5,12-dihydroxy-6,11-dioxo-3-isopropenyl-1-(2',3',6'-trideoxy-3'-amino-L-lyxohexopyranose)-3,4,5,12-tetrahydroanthraceno-[2,3-c]-pyran hydrochloride.

27. A compound according to claim 1 selected from the group consisting of:

(1S',1R,3S)-methyl(6-hydroxy-1-(2',3',6'-trideoxy-3'trifluoroacetamido-L-4'-O-p-nitrobenzoyl-L-lyxohexopyranose)-6-hydroxy-5,12-dioxo-3,4,5,12-tetrahydroanthraceno[2,3-C]pyran-3-yl)ketone;

(1'S,1S,3R)-methyl(6-hydroxy-1-(2',3',6'-trideoxy-3'-trifluoroacetamido-L-4'-O-p-nitrobenzoyl-L-lyxohexopyranose)-6-hydroxy-5,12-dioxo-3,4,5,12-tetrahydroanthraceno[2,3-C]pyran-3-yl)ketone;

(1'S,1R,3S)-methyl(1-(2',3'6'-trideoxy-3'-trifluoroacetamido-4'-O-lyxohexopyranose)-6,11-dioxo-5-hydroxy-12-acetoxy-3,4,6,11-tetrahydroanthraceno[2,3-C]pyran-3-yl)ketone;

(1'S,1S,3R)-methyl(1-(2',3',6'-trideoxy-3'-trifluoroacetamido-4'-O-p-nitrobenzoyl-L-lyxohexopyranose)-6,11-dioxo-5-hydroxy-12-acetoxy-3,4,6,11-tetrahydroanthraceno[2,3-C]pyran-3-yl)ketone;

(1'S,1R,3R)-5,12-dioxo-3-ethyl-6-hydroxy-1-(2',3',6'-trideoxy-3'trifluoroacetamido-4'-O-p-nitrobenzoyl-L-lyxohexopyranose)-3,4,5,12-tetrahydroanthraceno[2,3-C]pyran;

(1'S,1S,3S)-5,12-dioxo-3-ethyl-6-hydroxy-1-(2',3',6'-trideoxy-3'-trifluoroacetamido-4'-O-p-nitrobenzoyl-L-lyxohexopyranose)-3,4,5,12-tetrahydroanthraceno[2,3-C]pyran;

(1'S,1R,3S)-1,2,3,4,5,12-hexahydro-6-hydroxy-3-trimethylacetoxyaceto-1-(N-trifluoroacetyl-4'-O-p-nitrobenzoyl-L-daunosamine)-(2-oxo)-naphthacene-6,11-dione;

(1'S,1S,3R)-1,2,3,4,5,12-hexahydro-6-hydroxy-3-trimethylacetoxyaceto-1-(N-trifluoroacetyl-4'-O-p-nitrobenzoyl-L-daunosamine)-(2-oxo)-naphthacene-6,11-dione;

(1'S,1R,3S)-3-bromoaceto-1-O-(3,4-di-O-acetyl-2',6'-dideoxy-2-lyxohexopyranosyl)-1,2,3,4,5,12-hexahydro-6-hydroxy(2-OXO)naphthacene-5,12-dione;

(1'S,1S,3R)-3-bromoaceto-1-O-(3',4'-di-O-acetyl-2',6'-dideoxy-a-lyxohexopyranosyl)-1,2,3,4,5,12-hexahydro-6-hydroxy-(2-oxo)naphthacene-5,12-dione;

(1'S,1R,3S)-3-aceto-1-O-(3',4'-di-O-acetyl-2',6'-dideoxy-a-lyxohexopyranosyl)-1,2,3,4,5,12-hexahydro-6-hydroxy[2-oxo]naphthacene-5,12-dione;

(1'S,1S,3R)-3-aceto-1-O-(3',4'-di-O-acetyl-2',6'-dideoxy-a-lyxohexopyranosyl)-1,2,3,4,5,12-hexahydro-6-hydroxy[2-oxo]naphthacene-5,12-dione;

(1'S,1R,3S)-6-hydroxy-1-(2',3', 6'-trideoxy-4'-p-nitrobenzoyl-3'trifluoroacetamido-L-lyxohexopyranose)-3-(2-aza-3-acetamidothienyl)-5,-12-dioxo-3,4,5,12-tetrahydroanthraceno-[2,3-C]-pyran;

(1'S,1R,3S)-6-hydroxy-1-(2',3',6'-trideoxy-4'-p-nitrobenzoyl-3'-trifluoroacetamido-L-lyxohexopyranose)-3-(2-aza-3-acetamidothienyl)-5,-12-dioxo-3,4,5,12-tetrahydroanthraceno-[2,3-C]-pyran;

[(1R,3R) or (1S,3S)cis-p-nitrobenzyl(5,12-dioxo-1-methyl-3,4,5,12-tetrahydroanthraceno[2,3-c]pyran-3-yl)formate;and]

(1'S,1S,3R) or (1'S,1R,3S)Methyl[11-acetoxy-6-hydroxy-1-(2',3',6'-trideoxy-3'-trifluoroacetamido-4'-O-p-nitrobenzoyl-L-lyxohexopyranose )-5,12-dioxo-3,4,5,12-tetrahydroanthraceno[2,3-c]pyran-3-yl]ketone;

[(1S,3S) or (1R,3S)trans-p-nitrobenzyl(5,12-dioxo-1-methyl-3,4,5,12-tetrahydroanthraceno[2,3-c]pyran-3-yl)formate;]

[(1R,3R) or (1S,3S)cis-p-nitrobenzyl(5,12-dioxo-7,10-dimethoxy-1-methyl-3,4,5,12-tetrahydroanthraceno[2,3-c]pyran-3-yl)formate;]

[(1S,3R) or (1R,3S)trans-p-nitrobenzyl(5,12-dioxo-7,10-dimethoxy-1-methyl-3,4,5,12-tetrahydroanthraceno[2,3-c]pyran-3-yl)formate;]

(1'S,1R,3S) or (1'S,1S,3R)Ethyl[11-acetoxy-1-(2',3',6'-trideoxy-3'-trifluoroacetamido-4'-O-p-nitrobenzoyl-L-lyxohexopyranose)-5,12-dioxo-3,4,5,12-tetrahydroanthraceno[2,3-c]pyran-3-yl]formate;

(1'S,1R,3S) or (1'S,1S,3R)Methyl[6-acetoxy-1-(2',3',6'-trideoxy-3'-trifluoroacetamido-4'-O-p-nitrobenzoyl-L-lyxohexopyranose)-5,12-dioxo-3,4,5,12-tetrahydroanthraceno[2,3-c]pyran-3-yl]formate;

(1'S,1R,3S) or (1'S,1S,3R)Ethyl[6-acetoxy-1-(2',3',6'-trideoxy-3'-trifluoroacetamido-4'-O-p-nitrobenzoyl-L-lyxohexopyranose)-5,12-dioxo-3,4,5,12-tetrahydroanthraceno[2,3-c]pyran-3-yl]formate;

(1'S,1S,3R) or (1'S,1R,3S)ethyl[11-acetoxy-6-hydroxy-1-(2',3',6'-trifluoroacetamido-4'-O-p-nitrobenzyl-L-lyxohexopyranose)-5,12-dioxo-3,4,5,12-tetrahydroanthraceno[2,3-c]pyran-3-yl]formate; and (1'S,1R,3S) or (1'S,1S,3R)P-nitrobenzyl[-1-(2',3',6'-trideoxy-3'-trifluoroacetamido-4'-O-p-nitrobenzoyl-L-lyxohexopyranose)-5,12-dioxo-3,4,5,12-tetrahydroanthraceno[2,3-c]pyran-3-yl]formate.

28. A compound according to claim 1, selected from the group consisting of (1'S,1R,3S)methyl(11-hydroxy-1-(2',3',6'-trideoxy-3'-trifluoroacetamido-4'-hydroxy-L-lyxohexopyranose)-5,12-dioxo-3,4,5,12-tetrahydroanthraceno[2,3-C]pyran-3-yl) ketone;

(1'S,1S,3R)methyl(11-hydroxy-1-(2',3',6'-trideoxy-3'-trifluoroacetamido-4'-hydroxy-L-lyxohexopyranose)-5,12-dioxo-3,4,5,12-tetrahydroanthraceno[2,3-C]pyran-3-yl) ketone;

(1'S,1R,3S)methyl(11-hydroxy-1-(2',3',6'-trideoxy-3'-amino-4'-hydroxy-L-lyxohexopyranose)-5,12-dioxo-3,4,5,12-tetrahydroanthraceno[2,3-C]pyran-3-yl) ketone;

(1'S,1S,3R)methyl(11-hydroxy-1-(2',3',6'-trideoxy-3'-amino-4'-hydroxy-L-lyxohexopyranose)-5,12-dioxo-3,4,5,12-tetrahydroanthraceno [2,3-C]pyran-3-yl) ketone;

(1'S,1R,3S)methyl(6-hydroxy-10-methoxy-1-(2',3',6'-trideoxy-3'-trifluoroacetamido-4'-hydroxy-L-lyxohexopyranose)-5,12-dioxo-3,4,5,12-tetrahydroanthraceno[2,3-C]pyran-3-yl)ketone;

(1'S,1S,3R)methyl(6-hydroxy-10-methoxy-1-(2',3',6'-trideoxy-3'-trifluoroacetamido-4'-hydroxy-L-lyxohexopyranose)-5,12-dioxo-3,4,5,12 -tetrahydroanthraceno[2,3-C]pyran-3-yl)ketone;

(1'S,1R,3S)methyl(6-hydroxy-10-methoxy-1-(2',3',6'-trideoxy-3'-amino-4'-hydroxy-L-lyxohexopyranose)-5,12-dioxo-3,4,5,12-tetrahydroanthraceno[2,3-C]pyran-3-yl) ketone;

(1'S,1S,3R)methyl(6-hydroxy-10-methoxy-1-(2',3',6'-trideoxy-3'-amino-4'-hydroxy-L-lyxohexopyranose)-5,12-dioxo-3,4,5,12-tetrahydroanthraceno[2,3-C]pyran-3-yl) ketone;

(1'S,1R,3S)methyl(5,12-dihydroxy-10-methoxy-1-(2',3',6'-trideoxy-3'-amino-4'-hydroxy-L-lyxohexopyranose)-6,11-dioxo-3,4,6,11-tetrahydroanthraceno [2,3-C]pyran-3-yl) ketone;

(1'S,1S,3R)methyl(5,12-dihydroxy-10-methoxy-1-(2',3',6'-trideoxy-3'-amino-4'-hydroxy-L-lyxohexopyranose)-6,11-dioxo-3,4,6,11-tetrahydroanthraceno[2,3-C]pyran-3-yl) ketone;

(1'S,1R,3S)-3-aceto-1,2,3,4,5,12-hexahydro-6-hydroxy-1-daunosamine-(2-sulfur)naphthacene-5,12-dione;

(1'S,1S,3R)-3-aceto-1,2,3,4,5,12-hexahydro-6-hydroxy-1-daunosamine-(2-sulfur)naphthacene-5,12-dione;

(1'S,1R,3S)-3-aceto-1,2,3,4,5,12-hexahydro-6-hydroxy-10-methoxy-1-daunosamine-(2-sulfur)naphthacene-5,12-dione;

(1'S,1S,3R)-3-aceto-1,2,3,4,5,12-hexahydro-6-hydroxy-10-methoxy-1-daunosamine-(2-sulfur)naphthacene-5,12-dione;

(1'S,1R,3S)-3-aceto-1,2,3,4,5,12-hexahydro-6-hydroxy-10-methoxy-1-(N-trifluoroacetyl-L-daunosamine)-(2-sulfur) naphthacene-5,12-dione;

(1'S,1S,3R)-3-aceto-1,2,3,4,5,12-hexahydro-6-hydroxy-10-methoxy-1-(N-trifluoroacetyl-L-daunosamine)-(2-sulfur) naphthacene-5,12-dione;

(1'S,1R,3S)-3-aceto-1,2,3,4,6,11-hexahydro-5,12-dihydroxy-1 -(N-trifluoroacetyl-L-daunosamine)-(2-sulfur) naphthacene-6,11-dione;

(1'S,1S,3R)-3-aceto-1,2,3,4,6,11-hexahydro-5,12-dihydroxy-1-(N-trifluoroacetyl-L-daunosamine)-(2-sulfur) naphthacene-6,11-dione;

(1'S,1R,3S)-3-aceto-1,2,3,4,6,11-hexahydro-5,12-dihydroxy-1-L-daunosamine)-(2-sulfur) naphthacene-6,11-dione;

(1'S,1S,3R)-3-aceto-1,2,3,4,6,11-hexahydro-5,12-dihydroxy-1-L-daunosamine)-(2-sulfur)naphthacene-6,11-dione;

(1'S,1R,3S)-3-aceto-1,2,3,4,6,11-hexahydro-5,12-dihydroxy-10-methoxy-1-L-daunosamine)-(2-sulfur) naphthacene-6,11-dione;

(1'S,1S,3R)-3-aceto-1,2,3,4,6,11-hexahydro-5,12-dihydroxy-10-methoxy-1-L-daunosamine)-(2-sulfur)naphthacene-6,11-dione;

(1'S,1R,3S)-3-ethyl-1,2,3,4,6,11-hexahydro-5,12-dihydroxy-10-methoxy-1-L-daunosamine)-(2-sulfur) naphthacene-6,11-dione;

(1'S,1S,3R)-3-ethyl-1,2,3,4,6,11-hexahydro-5,12-dihydroxy-10-methoxy-1-L-daunosamine)-(2-sulfur) naphthacene-6,11-dione;

(1'S,1R,3S)-3-ethyl-1,2,3,4,6,11-hexahydro-5,12-dihydroxy-1-L-daunosamine)-(2-sulfur)naphthacene-6,11-dione;

(1'S,1S,3R)-3-ethyl-1,2,3,4,6,11-hexahydro-5,12-dihydroxy-1-L-daunosamine)-(2-sulfur)naphthacene-6,11-dione;

(1'S,1R,3S)-3-difluoroethyl-1,2,3,4,6,11-hexahydro-5,12-dihydroxy-1-L-daunosamine)-naphthacene-6,11-dione;

(1'S,1S,3R)-3-difluoroethyl-1,2,3,4,6,11-hexahydro-5,12-dihydroxy-1-L-daunosamine)-naphthacene-6,11-dione;

(1'S,1R,3S)-3-difluoroethyl-1,2,3,4,5,12-hexahydro-6-hydroxy-1-L-daunosamine)-naphthacene-5,12-dione;

(1'S,1S,3R)-3-difluoroethyl-1,2,3,4,5,12-hexahydro-6-hydroxy-1-L-daunosamine)-naphthacene-5,12-dione;

(1'S,1R,3S)-3-ethyl-1,2,3,4,6,11-hexahydro-5,12-dihydroxy-1-(2'-deoxyfucose)-naphthacene-5,12-dione;

(1'S,1S,3R)-3-ethyl-1,2,3,4,6,11-hexahydro-5,12-dihydroxy-1-(2'-deoxyfucose)-naphthacene-5,12-dione;

(1'S,1R,3S)-3-ethyl-1,2,3,4,5,12-hexahydro6-hydroxy-1-(2'deoxyfucose)-naphthacene-5,12-dione;

(1'S,1S,3R)-3-ethyl-1,2,3,4,5,12-hexahydro6-hydroxy-1-(2'deoxyfucose)-naphthacene-5,12-dione;

(1'S,1R,3S)-1-(2',3',6'-trideoxy-3'-amino-L-lyxohexopyranose)-3-oxazole-5,12-dihydroxy-6,11-dioxo-3,4,6,11-tetrahydroanthraceno [2,3-C]pyran;

(1'S,1S,3R)-1-(2',3',6'-trideoxy-3'-amino -L-lyxohexopyranose)-3-oxazole-5,12-dihydroxy-6,11-dioxo-3,4,6,11-tetrahydroanthraceno [2,3-C]pyran;

(1'S,1R,3S)-1-(2',3',6'-trideoxy-3'-amino -L-lyxohexopyranose)-3-oxazole-6-hydroxy-5,12-dioxo-3,4,5,12-tetrahydroanthraceno [2,3-C]pyran;

(1'S,1S,3R)-1-(2',3',6'-trideoxy-3'-amino-L-lyxohexopyranose)-3-oxazole-6-hydroxy-5,12-dioxo-3,4,5,12-tetrahydroanthraceno [2,3-C]pyran;

(1'S,1R,3S)-3-aceto-1,2,3,4,5,12-hexahydro-6-hydroxy-1-(2',3',4',6'-tetradeoxy-4'-amino-L-lyxohexopyranose)-naphthacene-5,12-dione;

(1'S,1S,3R)-3-aceto-1,2,3,4,5,12-hexahydro-6-hydroxy-1-(2',3',4',6'-tetradeoxy-4'-amino-L-lyxohexopyranose)-naphthacene-5,12-dione;

(1'S,1R,3S)-3-aceto-1,2,3,4,6,11-hexahydro-5,12-dihydroxy-1-(2',3',4',6'-tetradeoxy-4'-amino-L-lyxohexopyranose)-naphthacene-6,11-dione;

(1'S,1S,3R)-3-aceto-1,2,3,4,6,11-hexahydro-5,12-dihydroxy-1-(2',3',4',6'-tetradeoxy-4'-amino-L-lyxohexopyranose)-naphthacene-6,11-dione;

(1'S,1R,3S)-3-aceto-1,2,3,4,5,12-hexahydro-6-hydroxy-1-(2',3',4',6'-tetradeoxy-4'-amino-L-arabinohexopyranose)-naphthacene-5,12-dione;

(1'S,1S,3R)-3-aceto-1,2,3,4,5,12-hexahydro-6-hydroxy-1-(2',3',4',6'-tetradeoxy-4'-amino-L-arabinohexopyranose)-naphthacene-5,12 -dione;

(1'S,1R,3S)-3-aceto-1,2,3,4,6,11-hexahydro-5,12-dihydroxy-1-(2',3',4',6'-tetradeoxy-4'-amino-L-arabinohexopyranose)-naphthacene-6,11-dione;

(1'S,1S,3R)-3-aceto-1,2,3,4,6,11-hexahydro-5,12-dihydroxy-1-(2',3',4',6'-tetradeoxy-4'-amino-L-arabinohexopyranose)-naphthacene-6,11-dione;

(1S,1R,3S)-6-hydroxy-1-(2',3',6'-trideoxy-3'-amino-4'hydroxy-L-lyxohexopyranose)-5,12-dioxo-3,4,5,12-tetrahydroanthraceno[2,3-C]pyran-3-acetic acid;

(1S,1S,3R)-6-hydroxy-1-(2',3',6'-trideoxy-3'-amino-4'hydroxy-L-lyxohexopyranose)-5,12-dioxo-3,4,5,12-tetrahydroanthraceno[2,3-C]pyran-3-acetic acid;

(1S,1R,3S)-5,12-dihydroxy-1-(2',3',6'-trideoxy-3'-amino-4'hydroxy-L-lyxohexopyranose)-6,11-dioxo-3,4,6,11-tetrahydroanthraceno[2,3-C]pyran-3-acetic acid;

(1S,1S,3R)-5,12-dihydroxy-1-(2',3',6'-trideoxy-3'-amino-4'hydroxy-L-lyxohexopyranose)-6,11-dioxo-3,4,6,11-tetrahydroanthraceno[2,3-C]pyran-3-acetic acid;

(1S,1R)-6-hydroxy-1-(2',3',6',-trideoxy-3'-trifluoroacetamido-4'-hydroxy-L-lyxohexopyranose)-5,12-dioxo-3,4,5,12-tetrahydroanthraceno[2,3-C]pyran;

(1S,1S)-6-hydroxy-1-(2',3',6',-trideoxy-3'-trifluoroacetamido-4'-hydroxy-L-lyxohexopyranose)-5,12-dioxo-3,4,5,12-tetrahydroanthraceno[2,3-C]pyran;

1'S,1R)-6-hydroxy-1-(2',3',6',-trideoxy-3'-amino-4'-hydroxy-L-lyxohexopyranose)-6,11-dioxo-3,4,6,11-tetrahydroanthraceno[2,3-C]pyran;

(1'S,1S)-6-hydroxy-1-(2',3',6',-trideoxy-3'-amino-4'-hydroxy-L-lyxohexopyranose)-6,11-dioxo-3,4,6,11-tetrahydroanthraceno[2,3-C]pyran;

(1'S,1R)-5,12-dihydroxy-1-(2',3',6',-trideoxy-3'-amino-4'-hydroxy-L-lyxohexopyranose)-6,11-dioxo-3,4,6,11-tetrahydroanthraceno[2,3-C]pyran;

(1'S, 1S)-5,12-dihydroxy-1-(2',3',6',-trideoxy -3'-amino-4'-hydroxy-L-lyxohexopyranose)-6,11-dioxo-3,4,6,11-tetrahydroanthraceno[2,3-C]pyran;

(1'S,1R)-5,12-dihydroxy-1-(2',3',6',-trideoxy-3'-trifluoroacetamido-4'-hydroxy-L-lyxohexopyranose)-6,11-dioxo-3,4,6,11-tetrahydroanthraceno [2,3-C]pyran; and (1'S,1S)-5,12-dihydroxy-1-(2',3',6',-trideoxy-3'-trifluoroacetamido-4'-hydroxy-L-lyxohexopyranose)-6,11-dioxo-3,4,6,11-tetrahydroanthraceno [2,3-C]pyran.

29. A pharmaceutical composition possessing anti-tumor activity, comprising an effective amount of at least one compound according to claim 1, and a pharmaceutically acceptable carrier.

30. A pharmaceutical composition possessing anti-tumor activity, comprising an effective amount of at least one compound according to claim 3 in admixture with a pharmaceutically acceptable carrier.

31. A pharmaceutical composition possessing anti-tumor activity, comprising an effective amount of at least one compound according to claim 22 and a pharmaceutically acceptable carrier.

32. A method of treating a tumor in an animal or human in need of such treatment, which method comprises the step of administering to said animal or human a therapeutically effective amount of at least one compound of claim 1.

33. A method of treating a tumor in an animal or human in need of such treatment, which method comprises the step of administering to said human or animal a therapeutically effective amount of at least one compound of claim 5.

34. A method of treating a tumor in an animal or human, which method comprises the step of administering to said human or animal a therapeutically effective amount of at least one compound of claim 22.

* * * * *